US011352426B2

(12) United States Patent
Tan et al.

(10) Patent No.: US 11,352,426 B2
(45) Date of Patent: Jun. 7, 2022

(54) CD3 BINDING POLYPEPTIDES

(71) Applicant: Aptevo Research and Development LLC, Seattle, WA (US)

(72) Inventors: Philip Tan, Edmonds, WA (US); John W. Blankenship, Seattle, WA (US)

(73) Assignee: APTEVO RESEARCH AND DEVELOPMENT LLC, Seattle, WA (US)

(*) Notice: Subject to any disclaimer, the term of this patent is extended or adjusted under 35 U.S.C. 154(b) by 678 days.

(21) Appl. No.: 15/761,499

(22) PCT Filed: Sep. 21, 2016

(86) PCT No.: PCT/US2016/052942
§ 371 (c)(1),
(2) Date: Mar. 20, 2018

(87) PCT Pub. No.: WO2017/053469
PCT Pub. Date: Mar. 30, 2017

(65) Prior Publication Data
US 2018/0273622 A1 Sep. 27, 2018

Related U.S. Application Data

(60) Provisional application No. 62/221,190, filed on Sep. 21, 2015.

(51) Int. Cl.
*C07K 16/28* (2006.01)
*C07K 16/30* (2006.01)
*A61P 35/00* (2006.01)
*A61K 39/00* (2006.01)

(52) U.S. Cl.
CPC .......... *C07K 16/2809* (2013.01); *A61P 35/00* (2018.01); *C07K 16/2803* (2013.01); *C07K 16/2896* (2013.01); *C07K 16/30* (2013.01); *C07K 16/3069* (2013.01); *A61K 2039/505* (2013.01); *C07K 2317/24* (2013.01); *C07K 2317/31* (2013.01); *C07K 2317/33* (2013.01); *C07K 2317/524* (2013.01); *C07K 2317/526* (2013.01); *C07K 2317/56* (2013.01); *C07K 2317/565* (2013.01); *C07K 2317/567* (2013.01); *C07K 2317/622* (2013.01); *C07K 2317/64* (2013.01); *C07K 2317/72* (2013.01); *C07K 2317/76* (2013.01); *C07K 2317/90* (2013.01); *C07K 2317/92* (2013.01); *C07K 2317/94* (2013.01); *C07K 2319/00* (2013.01); *C07K 2319/33* (2013.01)

(58) Field of Classification Search
None
See application file for complete search history.

(56) References Cited

U.S. PATENT DOCUMENTS

| | | |
|---|---|---|
| 3,927,193 A | 12/1975 | Hansen et al. |
| 4,179,337 A | 12/1979 | Davis et al. |
| 4,301,144 A | 11/1981 | Iwashita et al. |
| 4,331,647 A | 5/1982 | Goldenberg |
| 4,348,376 A | 9/1982 | Goldenberg |
| 4,361,544 A | 11/1982 | Goldenberg |
| 4,444,744 A | 4/1984 | Goldenberg |
| 4,460,459 A | 7/1984 | Shaw et al. |
| 4,460,559 A | 7/1984 | Goldenberg |
| 4,460,561 A | 7/1984 | Goldenberg |
| 4,468,457 A | 8/1984 | Goldenberg et al. |
| 4,496,689 A | 1/1985 | Mitra |
| 4,624,846 A | 11/1986 | Goldenberg |
| 4,640,835 A | 2/1987 | Shimizu et al. |
| 4,670,417 A | 6/1987 | Iwasaki et al. |
| 4,704,692 A | 11/1987 | Ladner |
| 4,769,330 A | 9/1988 | Paoletti et al. |
| 4,782,840 A | 11/1988 | Martin, Jr. et al. |
| 4,791,192 A | 12/1988 | Nakagawa et al. |
| 4,816,567 A | 3/1989 | Cabilly et al. |
| 4,818,709 A | 4/1989 | Primus et al. |
| 4,861,579 A | 8/1989 | Meyer, Jr. et al. |
| 4,897,268 A | 1/1990 | Tice et al. |
| 4,906,562 A | 3/1990 | Hellstrom et al. |

(Continued)

FOREIGN PATENT DOCUMENTS

| | | |
|---|---|---|
| CA | 2 379 586 A1 | 10/2003 |
| CA | 2 414 148 A1 | 6/2004 |

(Continued)

OTHER PUBLICATIONS

Thakur et al. (Curr Opin Mol Ther, 12(3):340-349, 2010).*
Kussie et al (Journal of Immunology, 152:146-152, 1994.*
Chen et al, (The EMBO Journal, 14(12):2784-2794, 1995).*
Rudikoff et al PNAS 79:1979-1983, 1982.*
Bendig (Methods: A Companion to Methods in Enzymology 1995; 8:83-93).*
Paul, Fundamental Immunology, 3rd Edition, 1993, pp. 292-295.*
Colman P. M. (Research in Immunology, 145:33-36, 1994.*
Anasetti, C. et al., "Induction of Specific Nonresponsiveness in Unprimed Human T Cells by Anti-CD3 Antibody and Alloantigen," J. Exp. Med 172:1691-1700, The Rockefeller University Press, United States (1990).

(Continued)

*Primary Examiner* — Patricia Duffy
(74) *Attorney, Agent, or Firm* — Cooley LLP

(57) ABSTRACT

The present disclosure relates to protein molecules that specifically bind to CD3, which may have at least one humanized CD3-binding domain. Such molecules are useful for the treatment of cancer. The protein molecule binding to CD3 may have a second binding domain that binds to another target. In one embodiment, multispecific polypeptide molecules bind both tumor antigen-expressing cells and the CD3 subunit of a T-cell receptor complex on T-cells to induce target-dependent T-cell cytotoxicity, activation, and proliferation. The disclosure also provides pharmaceutical compositions comprising the CD3-binding poypeptide molecules, nucleic acid molecules encoding these polypeptides and methods of making these molecules.

37 Claims, 19 Drawing Sheets

Specification includes a Sequence Listing.

(56) References Cited

U.S. PATENT DOCUMENTS

| | | |
|---|---|---|
| 4,932,412 A | 6/1990 | Goldenberg |
| 4,935,495 A | 6/1990 | Hellstrom et al. |
| 4,946,778 A | 8/1990 | Ladner et al. |
| 5,017,487 A | 5/1991 | Stunnenberg et al. |
| 5,075,109 A | 12/1991 | Tice et al. |
| 5,091,177 A | 2/1992 | Hellstrom et al. |
| 5,098,833 A | 3/1992 | Lasky et al. |
| 5,141,736 A | 8/1992 | Iwasa et al. |
| 5,217,713 A | 6/1993 | Iwasa et al. |
| 5,225,539 A | 7/1993 | Winter |
| 5,260,203 A | 11/1993 | Ladner et al. |
| 5,434,131 A | 7/1995 | Linsley et al. |
| 5,455,030 A | 10/1995 | Ladner et al. |
| 5,500,362 A | 3/1996 | Robinson et al. |
| 5,521,288 A | 5/1996 | Linsley et al. |
| 5,530,101 A | 6/1996 | Queen et al. |
| 5,580,756 A | 12/1996 | Linsley et al. |
| 5,585,089 A | 12/1996 | Queen et al. |
| 5,591,828 A | 1/1997 | Bosslet et al. |
| 5,595,721 A | 1/1997 | Kaminski et al. |
| 5,597,707 A | 1/1997 | Marken et al. |
| 5,601,819 A | 2/1997 | Wong et al. |
| 5,605,690 A | 2/1997 | Jacobs et al. |
| 5,637,481 A | 6/1997 | Ledbetter et al. |
| 5,645,835 A | 7/1997 | Fell, Jr. et al. |
| 5,677,180 A | 10/1997 | Robinson et al. |
| 5,677,425 A | 10/1997 | Bodmer et al. |
| 5,693,762 A | 12/1997 | Queen et al. |
| 5,709,859 A | 1/1998 | Aruffo et al. |
| 5,714,147 A | 2/1998 | Capon et al. |
| 5,721,108 A | 2/1998 | Robinson et al. |
| 5,736,137 A | 4/1998 | Anderson et al. |
| 5,770,197 A | 6/1998 | Linsley et al. |
| 5,773,253 A | 6/1998 | Linsley et al. |
| 5,776,456 A | 7/1998 | Anderson et al. |
| 5,795,572 A | 8/1998 | Diegel et al. |
| 5,807,734 A | 9/1998 | Diegel et al. |
| 5,834,597 A | 11/1998 | Tso et al. |
| 5,837,243 A | 11/1998 | Deo et al. |
| 5,843,398 A | 12/1998 | Kaminski et al. |
| 5,843,439 A | 12/1998 | Anderson et al. |
| 5,844,093 A | 12/1998 | Kettleborough et al. |
| 5,844,095 A | 12/1998 | Linsley et al. |
| 5,849,898 A | 12/1998 | Seed et al. |
| 5,869,049 A | 2/1999 | Noelle et al. |
| 5,869,620 A | 2/1999 | Whitlow et al. |
| 5,876,718 A | 3/1999 | Noelle et al. |
| 5,876,950 A | 3/1999 | Siadak et al. |
| 5,885,793 A | 3/1999 | Griffiths et al. |
| 5,888,773 A | 3/1999 | Jost et al. |
| 5,892,019 A | 4/1999 | Schlom et al. |
| 5,897,861 A | 4/1999 | Fanger et al. |
| 5,916,560 A | 6/1999 | Larsen et al. |
| 5,922,845 A | 7/1999 | Deo et al. |
| 5,929,212 A | 7/1999 | Jolliffe et al. |
| 5,932,448 A | 8/1999 | Tso et al. |
| 5,955,315 A | 9/1999 | Lee et al. |
| 5,959,083 A | 9/1999 | Bosslet et al. |
| 5,980,896 A | 11/1999 | Hellstrom et al. |
| 6,015,542 A | 1/2000 | Kaminski et al. |
| 6,015,695 A | 1/2000 | Casterman et al. |
| 6,072,035 A | 6/2000 | Hardman et al. |
| 6,074,644 A | 6/2000 | Pastan et al. |
| 6,074,655 A | 6/2000 | Fowler et al. |
| 6,087,329 A | 7/2000 | Armitage et al. |
| 6,090,365 A | 7/2000 | Kaminski et al. |
| 6,090,914 A | 7/2000 | Linsley et al. |
| 6,105,542 A | 8/2000 | Efford |
| 6,120,767 A | 9/2000 | Robinson et al. |
| 6,129,914 A | 10/2000 | Weiner et al. |
| 6,132,992 A | 10/2000 | Ledbetter et al. |
| 6,133,426 A | 10/2000 | Gonzalez et al. |
| 6,136,313 A | 10/2000 | Stevenson |
| 6,147,203 A | 11/2000 | Pastan et al. |
| 6,150,508 A | 11/2000 | Murphy et al. |
| 6,150,584 A | 11/2000 | Kucherlapati et al. |
| 6,171,586 B1 | 1/2001 | Lam et al. |
| 6,180,370 B1 | 1/2001 | Queen et al. |
| 6,193,966 B1 | 2/2001 | Deo et al. |
| 6,194,551 B1 | 2/2001 | Idusogie et al. |
| 6,197,294 B1 | 3/2001 | Tao et al. |
| 6,224,866 B1 | 5/2001 | Barbera-Guillem |
| 6,242,195 B1 | 6/2001 | Idusogie et al. |
| 6,262,244 B1 | 7/2001 | Houchins et al. |
| 6,264,951 B1 | 7/2001 | Armitage et al. |
| 6,270,765 B1 | 8/2001 | Deo et al. |
| 6,284,536 B1 | 9/2001 | Morrison et al. |
| 6,287,537 B1 | 9/2001 | Kaminski et al. |
| 6,303,755 B1 | 10/2001 | Deo et al. |
| 6,306,393 B1 | 10/2001 | Goldenberg |
| 6,312,692 B1 | 11/2001 | Noelle et al. |
| 6,312,694 B1 | 11/2001 | Thorpe et al. |
| 6,352,694 B1 | 3/2002 | June et al. |
| 6,368,596 B1 | 4/2002 | Ghetie et al. |
| 6,376,459 B1 | 4/2002 | Aruffo et al. |
| 6,379,966 B2 | 4/2002 | Monahan et al. |
| 6,379,967 B1 | 4/2002 | Meredith et al. |
| 6,380,169 B1 | 4/2002 | Adams et al. |
| 6,380,170 B1 | 4/2002 | Muller et al. |
| 6,380,362 B1 | 4/2002 | Watson et al. |
| 6,380,369 B1 | 4/2002 | Adams et al. |
| 6,380,371 B1 | 4/2002 | Sassetti et al. |
| 6,380,382 B1 | 4/2002 | Khodadoust |
| 6,383,138 B1 | 5/2002 | Sen et al. |
| 6,383,478 B1 | 5/2002 | Prokop et al. |
| 6,383,481 B1 | 5/2002 | Ikehara et al. |
| 6,383,512 B1 | 5/2002 | Ciccarelli et al. |
| 6,383,522 B1 | 5/2002 | Dupont |
| 6,383,733 B1 | 5/2002 | Beug et al. |
| 6,383,737 B2 | 5/2002 | Olsen et al. |
| 6,383,738 B1 | 5/2002 | Bruni et al. |
| 6,383,743 B1 | 5/2002 | Kinzler et al. |
| 6,383,746 B1 | 5/2002 | Guignard et al. |
| 6,383,753 B1 | 5/2002 | Thiele et al. |
| 6,383,785 B1 | 5/2002 | Mueller et al. |
| 6,383,794 B1 | 5/2002 | Mountz et al. |
| 6,383,795 B1 | 5/2002 | Carrion et al. |
| 6,383,811 B2 | 5/2002 | Wolff et al. |
| 6,383,814 B1 | 5/2002 | Lee et al. |
| 6,384,018 B1 | 5/2002 | Content et al. |
| 6,384,198 B1 | 5/2002 | Diegel et al. |
| 6,384,202 B1 | 5/2002 | Sedlacek et al. |
| 6,384,203 B1 | 5/2002 | Anderson et al. |
| 6,384,210 B1 | 5/2002 | Blanchard |
| 6,395,272 B1 | 5/2002 | Deo et al. |
| 6,399,061 B1 | 6/2002 | Anderson et al. |
| 6,403,769 B1 | 6/2002 | Larochelle et al. |
| 6,410,319 B1 | 6/2002 | Raubitschek et al. |
| 6,410,391 B1 | 6/2002 | Zelsacher |
| 6,410,690 B1 | 6/2002 | Deo et al. |
| 6,423,498 B1 | 7/2002 | Markland et al. |
| 6,444,792 B1 | 9/2002 | Gray et al. |
| 6,455,043 B1 | 9/2002 | Grillo-Lopez |
| 6,472,179 B2 | 10/2002 | Stahl et al. |
| 6,472,510 B1 | 10/2002 | Aruffo et al. |
| 6,476,198 B1 | 11/2002 | Kang |
| 6,482,919 B2 | 11/2002 | Ledbetter et al. |
| 6,515,110 B1 | 2/2003 | Whitlow et al. |
| 6,518,277 B1 | 2/2003 | Sadhu et al. |
| 6,528,624 B1 | 3/2003 | Idusogie et al. |
| 6,538,124 B1 | 3/2003 | Idusogie et al. |
| 6,551,592 B2 | 4/2003 | Lindhofer et al. |
| 6,586,428 B2 | 7/2003 | Geroni et al. |
| 6,589,527 B1 | 7/2003 | Winter et al. |
| 6,623,940 B1 | 9/2003 | Ledbetter et al. |
| 6,641,809 B1 | 11/2003 | Linsley et al. |
| 6,696,290 B2 | 2/2004 | Fitzpatrick et al. |
| 6,761,889 B2 | 7/2004 | Lowman et al. |
| 6,800,620 B2 | 10/2004 | Sadhu et al. |
| 6,809,185 B1 | 10/2004 | Schoonjans et al. |
| 6,815,540 B1 | 11/2004 | Pluckthun et al. |
| 6,818,213 B1 | 11/2004 | Thorpe et al. |
| 6,828,422 B1 | 12/2004 | Achim et al. |
| 6,881,557 B2 | 4/2005 | Foote |

(56) References Cited

U.S. PATENT DOCUMENTS

| | | |
|---|---|---|
| 6,893,625 B1 | 5/2005 | Robinson et al. |
| 6,896,885 B2 | 5/2005 | Hanna |
| 6,962,981 B1 | 11/2005 | Murphy et al. |
| 7,052,872 B1 | 5/2006 | Hansen et al. |
| 7,074,403 B1 | 7/2006 | Goldenberg et al. |
| 7,122,646 B2 | 10/2006 | Holliger et al. |
| 7,129,330 B1 | 10/2006 | Little et al. |
| 7,148,321 B2 | 12/2006 | Gillies et al. |
| 7,166,707 B2 | 1/2007 | Feige |
| 7,183,076 B2 | 2/2007 | Arathoon et al. |
| 7,201,900 B2 | 4/2007 | Murphy et al. |
| 7,381,803 B1 | 6/2008 | Weiner et al. |
| 7,405,288 B2 | 7/2008 | Galanis et al. |
| 7,476,513 B2 | 1/2009 | Murphy et al. |
| 7,507,796 B2 | 3/2009 | Little et al. |
| 7,612,181 B2 | 11/2009 | Wu et al. |
| 7,635,472 B2 | 12/2009 | Kufer et al. |
| 7,695,936 B2 | 4/2010 | Carter et al. |
| 7,713,524 B2 | 5/2010 | Bourel et al. |
| 7,754,208 B2 | 7/2010 | Ledbetter et al. |
| 7,754,209 B2 | 7/2010 | Ledbetter et al. |
| 7,776,311 B1 | 8/2010 | McBride et al. |
| 7,811,564 B2 | 10/2010 | Cuello et al. |
| 7,820,166 B2 | 10/2010 | Lanzavecchia |
| 7,829,056 B2 | 11/2010 | Lee |
| 7,829,084 B2 | 11/2010 | Ledbetter et al. |
| 7,833,528 B2 | 11/2010 | Griffiths et al. |
| 7,875,278 B2 | 1/2011 | Cardarelli et al. |
| 8,003,774 B2 | 8/2011 | Stavenhagen et al. |
| 8,066,989 B2 | 11/2011 | Lindhofer et al. |
| 8,101,722 B2 | 1/2012 | Kufer et al. |
| 8,106,161 B2 | 1/2012 | Ledbetter et al. |
| 8,114,965 B2 | 2/2012 | Maddon et al. |
| 8,147,835 B2 | 4/2012 | Ledbetter et al. |
| 8,158,573 B2 | 4/2012 | McBride et al. |
| 8,188,237 B2 | 5/2012 | Ledbetter et al. |
| 8,188,239 B2 | 5/2012 | Hansen et al. |
| 8,197,810 B2 | 6/2012 | Ledbetter et al. |
| 8,236,308 B2 | 8/2012 | Kischel et al. |
| 8,333,966 B2 | 12/2012 | Tan et al. |
| 8,409,577 B2 | 4/2013 | Thompson et al. |
| 8,470,330 B2 | 6/2013 | Maddon et al. |
| 8,518,403 B2 | 8/2013 | Hoffmann et al. |
| 8,629,247 B2 | 1/2014 | Moffett et al. |
| 8,632,777 B2 | 1/2014 | Elsasser-Beile et al. |
| 8,663,638 B2 | 3/2014 | Lindhofer et al. |
| 8,709,421 B2 | 4/2014 | Heiss et al. |
| 8,734,791 B2 | 5/2014 | Lazar et al. |
| 8,759,496 B2 | 6/2014 | Govindan et al. |
| 9,782,478 B1 | 10/2017 | Blankenship et al. |
| 2001/0044135 A1 | 11/2001 | Stahi et al. |
| 2002/0004587 A1 | 1/2002 | Miller et al. |
| 2002/0006404 A1 | 1/2002 | Hanna et al. |
| 2002/0009444 A1 | 1/2002 | Grillo-Lopez |
| 2002/0012665 A1 | 1/2002 | Hanna |
| 2002/0031510 A1 | 3/2002 | Larsen et al. |
| 2002/0039557 A1 | 4/2002 | White |
| 2002/0041847 A1 | 4/2002 | Goldenberg |
| 2002/0103345 A1 | 8/2002 | Zhu |
| 2002/0128448 A1 | 9/2002 | Reff |
| 2002/0128488 A1 | 9/2002 | Yamakawa et al. |
| 2002/0150559 A1 | 10/2002 | DeBoer et al. |
| 2002/0155604 A1 | 10/2002 | Ledbetter et al. |
| 2002/0192223 A1 | 12/2002 | Hellstrom et al. |
| 2002/0197255 A1 | 12/2002 | Anderson et al. |
| 2002/0197256 A1 | 12/2002 | Grewal |
| 2003/0021781 A1 | 1/2003 | Anderson et al. |
| 2003/0026780 A1 | 2/2003 | Hood et al. |
| 2003/0026801 A1 | 2/2003 | Weiner et al. |
| 2003/0031667 A1 | 2/2003 | Deo et al. |
| 2003/0044423 A1 | 3/2003 | Gillies et al. |
| 2003/0078385 A1 | 4/2003 | Arathoon et al. |
| 2003/0088074 A1 | 5/2003 | Hamers et al. |
| 2003/0108548 A1 | 6/2003 | Bluestone et al. |
| 2003/0115614 A1 | 6/2003 | Kanda et al. |
| 2003/0118592 A1 | 6/2003 | Ledbetter et al. |
| 2003/0133930 A1 | 7/2003 | Goldenberg et al. |
| 2003/0133939 A1 | 7/2003 | Ledbetter et al. |
| 2003/0166868 A1 | 9/2003 | Presta et al. |
| 2003/0219433 A1 | 11/2003 | Hansen et al. |
| 2003/0219436 A1 | 11/2003 | Ledbetter et al. |
| 2003/0219446 A1 | 11/2003 | Linsley et al. |
| 2003/0219876 A1 | 11/2003 | Ledbetter et al. |
| 2004/0018557 A1 | 1/2004 | Qu et al. |
| 2004/0024188 A1 | 2/2004 | Murphy et al. |
| 2004/0043029 A1 | 3/2004 | Hellstrom et al. |
| 2004/0044182 A1 | 3/2004 | Hunt et al. |
| 2004/0058445 A1 | 3/2004 | Ledbetter et al. |
| 2004/0071696 A1 | 4/2004 | Adams et al. |
| 2004/0110290 A1 | 6/2004 | June et al. |
| 2004/0120958 A1 | 6/2004 | Bander et al. |
| 2004/0126793 A1 | 7/2004 | Segal et al. |
| 2004/0191248 A1 | 9/2004 | Goldenberg et al. |
| 2005/0031617 A1 | 2/2005 | Ma et al. |
| 2005/0054000 A1 | 3/2005 | Dubel |
| 2005/0084933 A1 | 4/2005 | Schilling et al. |
| 2005/0118164 A1 | 6/2005 | Herman et al. |
| 2005/0136049 A1 | 6/2005 | Ledbetter et al. |
| 2005/0158829 A1 | 7/2005 | Fandl et al. |
| 2005/0163782 A1 | 7/2005 | Glaser et al. |
| 2005/0164307 A1 | 7/2005 | Kojima et al. |
| 2005/0175614 A1 | 8/2005 | Ledbetter et al. |
| 2005/0180970 A1 | 8/2005 | Ledbetter et al. |
| 2005/0186203 A1 | 8/2005 | Singh et al. |
| 2005/0186216 A1 | 8/2005 | Ledbetter et al. |
| 2005/0202012 A1 | 9/2005 | Ledbetter et al. |
| 2005/0202023 A1 | 9/2005 | Ledbetter et al. |
| 2005/0202028 A1 | 9/2005 | Ledbetter et al. |
| 2005/0202534 A1 | 9/2005 | Ledbetter et al. |
| 2005/0238646 A1 | 10/2005 | Ledbetter et al. |
| 2005/0261317 A1 | 11/2005 | Sadhu et al. |
| 2006/0008415 A1 | 1/2006 | Kaisheva et al. |
| 2006/0051844 A1 | 3/2006 | Heavner et al. |
| 2006/0063715 A1 | 3/2006 | Whitlow et al. |
| 2006/0088529 A1 | 4/2006 | Leung et al. |
| 2006/0088539 A1 | 4/2006 | Bander |
| 2006/0099205 A1 | 5/2006 | Adams et al. |
| 2006/0104971 A1 | 5/2006 | Garber et al. |
| 2006/0153837 A1 | 7/2006 | Black et al. |
| 2006/0210564 A1 | 9/2006 | Kumagai et al. |
| 2006/0263367 A1 | 11/2006 | Fey et al. |
| 2006/0286030 A1 | 12/2006 | Boumsell et al. |
| 2007/0014794 A1 | 1/2007 | Carter et al. |
| 2007/0041967 A1 | 2/2007 | Jung et al. |
| 2007/0059306 A1 | 3/2007 | Grosmaire et al. |
| 2007/0071675 A1 | 3/2007 | Wu et al. |
| 2007/0128671 A1 | 6/2007 | Murphy et al. |
| 2007/0160617 A1 | 7/2007 | Ma et al. |
| 2007/0237779 A1 | 10/2007 | Ledbetter et al. |
| 2008/0176247 A1 | 7/2008 | Chou et al. |
| 2008/0213256 A1 | 9/2008 | Kufer et al. |
| 2008/0213273 A1 | 9/2008 | Burge |
| 2008/0241884 A1 | 10/2008 | Shitara et al. |
| 2008/0260738 A1 | 10/2008 | Moore et al. |
| 2008/0279850 A1 | 11/2008 | Brady et al. |
| 2009/0041765 A1 | 2/2009 | Espling et al. |
| 2009/0053225 A1 | 2/2009 | Marzari et al. |
| 2009/0088346 A1 | 4/2009 | Enzelberger et al. |
| 2009/0148447 A1 | 6/2009 | Ledbetter et al. |
| 2009/0162380 A1 | 6/2009 | Glaser et al. |
| 2009/0175867 A1 | 7/2009 | Thompson et al. |
| 2009/0196870 A1 | 8/2009 | Ledbetter et al. |
| 2009/0214539 A1 | 8/2009 | Grosmaire et al. |
| 2009/0252729 A1 | 10/2009 | Farrington et al. |
| 2009/0258005 A1 | 10/2009 | Gill et al. |
| 2009/0274649 A1 | 11/2009 | Qu et al. |
| 2009/0274692 A1 | 11/2009 | Tan et al. |
| 2009/0298195 A1 | 12/2009 | Ruker et al. |
| 2009/0324589 A1 | 12/2009 | Igawa et al. |
| 2010/0034820 A1 | 2/2010 | Ledbetter et al. |
| 2010/0135900 A1 | 6/2010 | Cerveny et al. |
| 2010/0203052 A1 | 8/2010 | Ledbetter et al. |
| 2010/0279932 A1 | 11/2010 | Ledbetter et al. |
| 2011/0033483 A1 | 2/2011 | Thompson et al. |

(56) References Cited

U.S. PATENT DOCUMENTS

| | | |
|---|---|---|
| 2011/0081345 A1 | 4/2011 | Moore et al. |
| 2011/0091461 A1 | 4/2011 | Ledbetter et al. |
| 2011/0105729 A1 | 5/2011 | Ledbetter et al. |
| 2011/0142851 A1 | 6/2011 | Misher et al. |
| 2011/0152173 A1 | 6/2011 | Lofguist et al. |
| 2011/0158995 A1 | 6/2011 | Tan et al. |
| 2011/0171208 A1 | 7/2011 | Tan et al. |
| 2011/0177070 A1 | 7/2011 | Lofquist et al. |
| 2011/0189209 A1 | 8/2011 | Neville, Jr. et al. |
| 2011/0217302 A1 | 9/2011 | Odegard et al. |
| 2011/0223164 A1 | 9/2011 | Ledbetter et al. |
| 2011/0250216 A1 | 10/2011 | Ma et al. |
| 2011/0262439 A1 | 10/2011 | Kufer et al. |
| 2011/0275787 A1 | 11/2011 | Kufer et al. |
| 2011/0293619 A1 | 12/2011 | Kufer et al. |
| 2012/0034245 A9 | 2/2012 | Thompson et al. |
| 2012/0100139 A1 | 4/2012 | Thompson et al. |
| 2012/0171115 A1 | 7/2012 | Hudson et al. |
| 2012/0195900 A1 | 8/2012 | Ghayur et al. |
| 2012/0213773 A1 | 8/2012 | Ledbetter et al. |
| 2012/0244162 A1 | 9/2012 | Kufer et al. |
| 2012/0301400 A1 | 11/2012 | Williams et al. |
| 2012/0321626 A1 | 12/2012 | Zhou |
| 2013/0052195 A1 | 2/2013 | Misher et al. |
| 2013/0078249 A1 | 3/2013 | Ast et al. |
| 2013/0089554 A1 | 4/2013 | Blankenship et al. |
| 2013/0095106 A1 | 4/2013 | Lindhofer |
| 2013/0129723 A1 | 5/2013 | Blankenship et al. |
| 2013/0129729 A1 | 5/2013 | Kischel et al. |
| 2013/0129730 A1 | 5/2013 | Kufer et al. |
| 2013/0165389 A1 | 6/2013 | Schellenberger et al. |
| 2013/0189261 A1 | 7/2013 | Odegard et al. |
| 2013/0196377 A1 | 8/2013 | Lee et al. |
| 2013/0224205 A1 | 8/2013 | Hofmeister et al. |
| 2013/0253172 A1 | 9/2013 | Gurney et al. |
| 2013/0295121 A1 | 11/2013 | Johnson et al. |
| 2013/0309234 A1 | 11/2013 | Lindhofer |
| 2013/0323204 A1 | 12/2013 | Rossi et al. |
| 2013/0336977 A1 | 12/2013 | Thompson et al. |
| 2014/0050660 A1 | 2/2014 | Chang et al. |
| 2014/0056895 A1 | 2/2014 | Baurin et al. |
| 2014/0056897 A1 | 2/2014 | Buelow et al. |
| 2014/0081002 A1 | 3/2014 | Lee et al. |
| 2014/0088295 A1 | 3/2014 | Smith et al. |
| 2014/0099254 A1 | 4/2014 | Chang et al. |
| 2014/0099318 A1 | 4/2014 | Huang et al. |
| 2014/0112914 A1 | 4/2014 | Nezu et al. |
| 2014/0127203 A1 | 5/2014 | Thompson et al. |
| 2014/0127210 A1 | 5/2014 | Kim et al. |
| 2014/0141022 A1 | 5/2014 | Thompson et al. |
| 2014/0147382 A1 | 5/2014 | Goldenberg et al. |
| 2014/0154250 A1 | 6/2014 | Thompson et al. |
| 2014/0154252 A1 | 6/2014 | Thompson et al. |
| 2014/0161800 A1 | 6/2014 | Blankenship et al. |
| 2014/0178388 A1 | 6/2014 | Chou et al. |
| 2015/0232557 A1 | 8/2015 | Tan et al. |
| 2015/0274844 A1 | 10/2015 | Blankenship et al. |
| 2017/0008960 A1 | 1/2017 | Odegard et al. |
| 2018/0022819 A1 | 1/2018 | Blankenship et al. |
| 2018/0100021 A1 | 4/2018 | Blankenship et al. |

FOREIGN PATENT DOCUMENTS

| | | |
|---|---|---|
| CN | 1421459 A | 6/2003 |
| EP | 0 274 394 A2 | 7/1988 |
| EP | 0 330 191 A2 | 8/1989 |
| EP | 0 332 865 A2 | 9/1989 |
| EP | 0 555 880 A2 | 8/1993 |
| EP | 0 586 002 A2 | 3/1994 |
| EP | 0 682 039 A1 | 11/1995 |
| EP | 0 330 191 B1 | 10/1996 |
| EP | 0 757 099 A2 | 2/1997 |
| EP | 1 186 300 A1 | 3/2002 |
| EP | 1 444 268 B1 | 8/2004 |
| EP | 1 654 358 | 2/2005 |
| EP | 0 610 046 B1 | 12/2005 |
| EP | 1 666 500 A1 | 6/2006 |
| EP | 1210374 B1 | 10/2006 |
| EP | 1726650 A1 | 11/2006 |
| EP | 1 746 162 A2 | 1/2007 |
| EP | 2006381 A1 | 12/2008 |
| EP | 1629011 B1 | 1/2010 |
| EP | 1691833 B1 | 3/2010 |
| EP | 1587837 B1 | 6/2012 |
| EP | 2326350 B1 | 9/2013 |
| EP | 1912677 B1 | 10/2013 |
| EP | 1940881 B1 | 11/2016 |
| JP | 11-506310 A | 6/1999 |
| JP | 2002-518041 A | 6/2005 |
| JP | 2006-512407 A | 4/2006 |
| RU | 2179862 C1 | 2/2002 |
| WO | WO 88/04936 A1 | 7/1988 |
| WO | WO 89/01973 A2 | 3/1989 |
| WO | WO 89/01974 A1 | 3/1989 |
| WO | WO 89/07142 A1 | 8/1989 |
| WO | WO 90/07936 A1 | 7/1990 |
| WO | WO 91/00360 A1 | 1/1991 |
| WO | WO 91/02805 A2 | 3/1991 |
| WO | WO 91/04329 A1 | 4/1991 |
| WO | WO 91/09967 A1 | 7/1991 |
| WO | WO 91/11456 A1 | 8/1991 |
| WO | WO 91/13166 A1 | 9/1991 |
| WO | WO 92/00092 A1 | 1/1992 |
| WO | WO 92/08802 A1 | 5/1992 |
| WO | WO 92/21755 A1 | 12/1992 |
| WO | WO 93/00431 A1 | 1/1993 |
| WO | WO 93/03709 A1 | 3/1993 |
| WO | WO 93/25234 A1 | 12/1993 |
| WO | WO 93/25698 A1 | 12/1993 |
| WO | WO 94/03622 A1 | 2/1994 |
| WO | WO 94/04678 A1 | 3/1994 |
| WO | WO 94/05690 A1 | 3/1994 |
| WO | WO 94/09034 A1 | 4/1994 |
| WO | WO 94/11026 A2 | 5/1994 |
| WO | WO 94/13804 A1 | 6/1994 |
| WO | WO 94/25591 A1 | 11/1994 |
| WO | WO 1994/028027 A1 | 12/1994 |
| WO | WO 95/03770 A1 | 2/1995 |
| WO | WO 95/08577 A1 | 3/1995 |
| WO | WO 95/09917 A1 | 4/1995 |
| WO | WO 95/24220 A1 | 9/1995 |
| WO | WO 95/30014 A1 | 11/1995 |
| WO | WO 96/34103 A1 | 10/1996 |
| WO | WO 96/40789 A1 | 12/1996 |
| WO | WO 97/09433 A1 | 3/1997 |
| WO | WO 97/35616 A1 | 10/1997 |
| WO | WO 1997/044362 A1 | 11/1997 |
| WO | WO 98/02462 A1 | 1/1998 |
| WO | WO 98/02463 A1 | 1/1998 |
| WO | WO 98/23646 A2 | 6/1998 |
| WO | WO 98/56418 A1 | 12/1998 |
| WO | WO 98/58964 A1 | 12/1998 |
| WO | WO 99/02711 A2 | 1/1999 |
| WO | WO 99/10494 A2 | 3/1999 |
| WO | WO 99/22764 A1 | 5/1999 |
| WO | WO 99/37791 A1 | 7/1999 |
| WO | WO 99/42077 A2 | 8/1999 |
| WO | WO 99/43713 A1 | 9/1999 |
| WO | WO 99/47554 A1 | 9/1999 |
| WO | WO 99/51642 A1 | 10/1999 |
| WO | WO 99/57150 A2 | 11/1999 |
| WO | WO 99/57266 A2 | 11/1999 |
| WO | WO 99/66951 A2 | 12/1999 |
| WO | WO 00/06605 A2 | 2/2000 |
| WO | WO 00/09160 A1 | 2/2000 |
| WO | WO 00/20864 A1 | 4/2000 |
| WO | WO 00/27428 A1 | 5/2000 |
| WO | WO 00/27433 A1 | 5/2000 |
| WO | WO 00/27885 A1 | 5/2000 |
| WO | WO 00/42072 A2 | 7/2000 |
| WO | WO 00/44777 A1 | 8/2000 |
| WO | WO 00/44788 A1 | 8/2000 |
| WO | WO 00/67795 A1 | 11/2000 |
| WO | WO 00/67796 A1 | 11/2000 |

(56) References Cited

FOREIGN PATENT DOCUMENTS

| | | |
|---|---|---|
| WO | WO 00/69913 A1 | 11/2000 |
| WO | WO 00/74718 A1 | 12/2000 |
| WO | WO 00/76542 A1 | 12/2000 |
| WO | WO 01/03734 A1 | 1/2001 |
| WO | WO 01/09186 A2 | 2/2001 |
| WO | WO 01/09187 A2 | 2/2001 |
| WO | WO 01/09192 A1 | 2/2001 |
| WO | WO 01/10460 A1 | 2/2001 |
| WO | WO 01/10461 A1 | 2/2001 |
| WO | WO 01/10462 A1 | 2/2001 |
| WO | WO 01/13945 A1 | 3/2001 |
| WO | WO 01/34194 A1 | 5/2001 |
| WO | WO 01/72333 A1 | 10/2001 |
| WO | WO 01/74388 A1 | 10/2001 |
| WO | WO 01/77342 A1 | 10/2001 |
| WO | WO 01/80884 A1 | 11/2001 |
| WO | WO 01/85798 A2 | 11/2001 |
| WO | WO 01/97858 A2 | 12/2001 |
| WO | WO 02/02773 A2 | 1/2002 |
| WO | WO 02/02781 A1 | 1/2002 |
| WO | WO 02/04021 A1 | 1/2002 |
| WO | WO 02/08773 A2 | 1/2002 |
| WO | WO 02/34790 A1 | 5/2002 |
| WO | WO 2002/040545 A2 | 5/2002 |
| WO | WO 2002/056910 A1 | 7/2002 |
| WO | WO 02/060955 A2 | 8/2002 |
| WO | WO 02/064634 A2 | 8/2002 |
| WO | WO 02/072141 A2 | 9/2002 |
| WO | WO 02/072605 A2 | 9/2002 |
| WO | WO 02/079255 A1 | 10/2002 |
| WO | WO 02/096948 A2 | 12/2002 |
| WO | WO 02/098897 A2 | 12/2002 |
| WO | WO 02/100348 A2 | 12/2002 |
| WO | WO 02/102312 A2 | 12/2002 |
| WO | WO 03/020906 A2 | 3/2003 |
| WO | WO 03/025018 A2 | 3/2003 |
| WO | WO 03/026490 A2 | 4/2003 |
| WO | WO 03/030835 A2 | 4/2003 |
| WO | WO 03/034903 A2 | 5/2003 |
| WO | WO 03/042231 A2 | 5/2003 |
| WO | WO 03/048209 A1 | 6/2003 |
| WO | WO 2013/092001 A1 | 6/2003 |
| WO | WO 03/057829 A2 | 7/2003 |
| WO | WO 03/064606 A2 | 8/2003 |
| WO | WO 03/074569 A2 | 9/2003 |
| WO | WO 03/083069 A2 | 10/2003 |
| WO | WO 03/106622 A2 | 12/2003 |
| WO | WO 2004/003019 A2 | 1/2004 |
| WO | WO 2004/016750 A2 | 2/2004 |
| WO | WO 2004/029207 A2 | 4/2004 |
| WO | WO 2004/032857 A2 | 4/2004 |
| WO | WO 2004/032961 A1 | 4/2004 |
| WO | WO 2004/035537 A2 | 4/2004 |
| WO | WO 2004/035607 A2 | 4/2004 |
| WO | WO 2004/058171 A2 | 7/2004 |
| WO | WO 2004/058191 A2 | 7/2004 |
| WO | WO 2004/076489 A1 | 9/2004 |
| WO | WO 2004/106380 A2 | 12/2004 |
| WO | WO 2004/106381 A1 | 12/2004 |
| WO | WO 2005/000899 A2 | 1/2005 |
| WO | WO 2005/004809 A2 | 1/2005 |
| WO | WO 2005/014618 A2 | 2/2005 |
| WO | WO 2005/017148 A1 | 2/2005 |
| WO | WO 2005/021710 A2 | 3/2005 |
| WO | WO 2005/035586 A1 | 4/2005 |
| WO | WO 2005/037989 A2 | 4/2005 |
| WO | WO 2005/040220 A1 | 5/2005 |
| WO | WO 2005/061547 A2 | 7/2005 |
| WO | WO 2005/063816 A2 | 7/2005 |
| WO | WO 2005/070456 A2 | 8/2005 |
| WO | WO 2005/070966 A2 | 8/2005 |
| WO | WO 2005/077981 A2 | 8/2005 |
| WO | WO 2005/077982 A1 | 8/2005 |
| WO | WO 2005/095460 A2 | 10/2005 |
| WO | WO 2005/100404 A1 | 10/2005 |
| WO | WO 2005/103081 A2 | 11/2005 |
| WO | WO 2005/123129 A2 | 12/2005 |
| WO | WO 2006/002438 A2 | 1/2006 |
| WO | WO 2006/008548 A2 | 1/2006 |
| WO | WO 2006/020258 A2 | 2/2006 |
| WO | WO 2006/028936 A2 | 3/2006 |
| WO | WO 2006/063150 A2 | 6/2006 |
| WO | WO 2006/074399 A2 | 7/2006 |
| WO | WO 2006/089230 A2 | 8/2006 |
| WO | WO 2006/089231 A2 | 8/2006 |
| WO | WO 2006/095164 A1 | 9/2006 |
| WO | WO 2006/106905 A1 | 10/2006 |
| WO | WO 2006/117782 A2 | 11/2006 |
| WO | WO 2007/011363 A2 | 1/2007 |
| WO | WO 2007/014238 A2 | 2/2007 |
| WO | WO 2007/014278 A2 | 2/2007 |
| WO | WO 2007/024715 A2 | 3/2007 |
| WO | WO 2007/042261 A2 | 4/2007 |
| WO | WO 2007/048037 A2 | 4/2007 |
| WO | WO 2007/095338 A2 | 8/2007 |
| WO | WO 2007/113172 A2 | 10/2007 |
| WO | WO 2007/114319 A1 | 10/2007 |
| WO | WO 2007/145941 A2 | 12/2007 |
| WO | WO 2007/146968 A2 | 12/2007 |
| WO | WO 2008/051448 A2 | 5/2008 |
| WO | WO 2008/052030 A2 | 5/2008 |
| WO | WO 2008/079713 A2 | 7/2008 |
| WO | WO 2008/138834 A1 | 11/2008 |
| WO | WO 2008/152387 A1 | 12/2008 |
| WO | WO 2008/152390 A2 | 12/2008 |
| WO | WO 2008/152394 A1 | 12/2008 |
| WO | WO 2008/153636 A1 | 12/2008 |
| WO | WO 2009/019312 A2 | 2/2009 |
| WO | WO 2009/023386 A2 | 2/2009 |
| WO | WO 2009/036082 A2 | 3/2009 |
| WO | WO 2009/039140 A1 | 3/2009 |
| WO | WO 2009/040552 A2 | 4/2009 |
| WO | WO 2009/042607 A1 | 4/2009 |
| WO | WO 2009/045174 A1 | 4/2009 |
| WO | WO 2009/045175 A1 | 4/2009 |
| WO | WO 2009/046294 A2 | 4/2009 |
| WO | WO 2009/046448 A1 | 4/2009 |
| WO | WO 2009/052145 A1 | 4/2009 |
| WO | WO 2009/053715 A1 | 4/2009 |
| WO | WO 2009/053716 A1 | 4/2009 |
| WO | WO 2009/055418 A1 | 4/2009 |
| WO | WO 2009/058361 A1 | 5/2009 |
| WO | WO 2009/059030 A1 | 5/2009 |
| WO | WO 2009/064802 A2 | 5/2009 |
| WO | WO 2009/066084 A1 | 5/2009 |
| WO | WO 2009/068482 A1 | 6/2009 |
| WO | WO 2009/070524 A1 | 6/2009 |
| WO | WO 2009/080251 A1 | 7/2009 |
| WO | WO 2009/080254 A1 | 7/2009 |
| WO | WO 2009/126944 A1 | 10/2009 |
| WO | WO 2009/127046 A1 | 10/2009 |
| WO | WO 2009/130575 A2 | 10/2009 |
| WO | WO 2010/014629 A1 | 2/2010 |
| WO | WO 2010/034441 A1 | 4/2010 |
| WO | WO 2010/037836 A2 | 4/2010 |
| WO | WO 2010/040105 A2 | 4/2010 |
| WO | WO 2010/040508 A1 | 4/2010 |
| WO | WO 2010/042904 A2 | 4/2010 |
| WO | WO 2010/057047 A1 | 5/2010 |
| WO | WO 2010/118522 A1 | 10/2010 |
| WO | WO 2010/136172 A1 | 12/2010 |
| WO | WO 2011/000054 A1 | 1/2011 |
| WO | WO 2011/090754 A1 | 7/2011 |
| WO | WO 2011/090761 A1 | 7/2011 |
| WO | WO 2011/090762 A1 | 7/2011 |
| WO | WO 2011/121110 A1 | 10/2011 |
| WO | WO 2012/125850 A1 | 9/2012 |
| WO | WO 2012/145714 A2 | 10/2012 |
| WO | WO 2012/156429 A1 | 11/2012 |
| WO | WO 2013/026839 A1 | 2/2013 |
| WO | WO 2013/104804 A2 | 7/2013 |
| WO | WO 2013/121175 A1 | 8/2013 |
| WO | WO 2013/128027 A1 | 9/2013 |
| WO | WO 2013/128194 A1 | 9/2013 |

(56) References Cited

FOREIGN PATENT DOCUMENTS

| | | |
|---|---|---|
| WO | WO 2013/132268 A1 | 9/2013 |
| WO | WO 2013/158856 A2 | 10/2013 |
| WO | WO 2013/172961 A1 | 11/2013 |
| WO | WO 2013/173820 A2 | 11/2013 |
| WO | WO 2014/012085 A2 | 1/2014 |
| WO | WO 2014/043208 A1 | 3/2014 |
| WO | WO 2014/056783 A1 | 4/2014 |
| WO | WO 2014/072888 A1 | 5/2014 |
| WO | WO 2014/079000 A1 | 5/2014 |
| WO | WO 2014/100490 A1 | 6/2014 |
| WO | WO 2014/106602 A1 | 7/2014 |
| WO | WO 2014/108483 A1 | 7/2014 |
| WO | WO 2014/110601 A1 | 7/2014 |
| WO | WO 2014/143807 A2 | 9/2014 |
| WO | WO 2014/151438 A1 | 9/2014 |
| WO | WO 2016/014974 A2 | 1/2016 |
| WO | WO 2016/094873 A2 | 6/2016 |
| WO | WO 2016/130819 A2 | 8/2016 |

OTHER PUBLICATIONS

"IUPAC-IUB commission on biochemical nomenclature rules for naming synthetic modification of natural peptides tentative rules," J. Biol. Chem. 242:555-557, 1967.
Adlersberg, J.B, "The immunoglobulin hinge (interdomain) region," Ric. Clin. Lab. 6:191-205, 1976.
Afanasieva, T.A., et al., "Single-chain antibody and its derivatives directed against vascular endothelial growth factor: application for antiangiogenic gene therapy," Gene Ther. 10:1850-1859, 2003.
AFINITOR (everolimus) tablets for oral administration, Highlights of Prescribing Information, retrieved from http://www.miochol.org/product/pi/pdf/afinitor.pdf, 2009, 12 pages.
Aicher, A., et al., "Characterization of human inducible costimulator ligand expression and function," J. Immunol. 164:4689-4696, 2000.
Alberola-Ila et al., "Stimulation through the TCR/CD3 complex up-regulates the CD2 surface expression on human T Lymphocytes," J. Immunol. 146(4):1085-1092 (1991).
Albrecht, H., et al., "Monospecific bivalent scFv-SH: Effects of linker length and location of an engineered cysteine on production, antigen binding activity and free SH accessibility," J. Immunol. Meth. 310:100-116, 2006.
Altschuler et al., "Generation of Recombinant Antibodies and Means for Increasing Their Affinity," Biochemistry (Moscow) 75:1584-1605 (2010) originally published in Uspekhi Biologicheskoi Khimii, 50:203-258 (2010).
Amit, A.G., et al., "Three-Dimensional Structure of an Antigen-Antibody Complex at 2.8 angstrom Resolution," Science 233(4765):747-753, 1986.
Anderson, D.R., et al., "Targeting Cytotoxic Immunotherapy: Targeted anti-cancer therapy using rituximab, a chimaeric anti-CD20 antibody (IDEC-C2B8) in the treatment of non-Hodgkin's B-cell lymphoma," Biochem. Soc. Transactions, pp. 705-708, 1997.
Andritsos, L., et al., "A phase I trial of TRU-016, an anti-CD37 small modular immunopharmaceutical (SMIP) in relapsed and refractory CLL," 2009 Annual Meeting, American Society of Clinical Oncology (ASCO), J. Clin. Oncol. 27(suppl.):15s (Abstract #3017), 2009.
Angal, S., et al., "A single amino acid substitution abolishes the heterogeneity of chimeric mouse/human (IgG4) antibody," Mol. Immunol. 30(1):105-108, 1993.
Anthony, K., Ed., "Selective inhibitors gain traction," Nat. Rev. Cancer 10:160, 2010.
Bander et al., "Targeting Metastatic Prostate Cancer with Radiolabeled Monoclonal Antibody J591 to the Extracellular Domain of Prostate Specific Membrane Antigen," J. Urology 170:1717-1721 (2003).
Barone, D., et al., "Efficacy of SMIP-016, a novel CD37-directed biologic therapy, in human NHL tumor xenograft models," J. Clin. Oncol. 24(18S)(Jun. 20 Suppl.):Abstract #2565, 2006.
Barone, D., et al., "Prolonged Depletion of Circulating B Cells in Cynomolgus Monkeys after a Single Dose of TRU-015, a Novel CD20 Directed Therapeutic," Ann. Rheum. Dis. 64(Suppl. III):159 (Abstract #THU0169), 2005.
Barone, D., et al., "TRU-015, a novel CD20-directed biologic therapy, demonstrates significant anti-tumor activity in human tumor xenograft models," J. Clin. Oncol. 23(16S):178s (Abstract #2549) Jun. 1, 2005.
Batra, J.K., et al., "Single-Chain Immunotoxins Directed at the Human Transferrin Receptor Containing Pseudomonas Exotoxin A or Diphtheria Toxin: Anti-TFR(Fv)-PE40 and DT388-Anti-TFR(Fv)," Mol. Cell. Biol. 11 (4):2200-2205, 1991.
Baum, P.R., et al., "Evaluation of the effect of TRU-016, an anti-CD37 directed SMIP™, in combination with other therapeutic drugs in models of Non-Hodgkin's Lymphoma," 2009 Annual Meeting, American Society of Clinical Oncology (ASCO), J. Clin. Oncol. 27(May 20 Suppl.):15S (Abstract 8571), 2009.
Beavil, A.J., et al., "α-Helical coiled-coil stalks in the low-affinity receptor for IgE (FcεRII/CD23) and related C-type lectins," Proc. Natl. Acad. Sci. USA 89:753-757, 1992.
Beiske, K., et al., "Triggering of neoplastic B cells via surface IgM and the cell surface antigens CD20 and CDw40. Responses differ from normal blood B cells and are restricted to certain morphologic subsets," Int. J. Cancer 42:521-528, 1988.
Belov, L., et al., "Immunophenotyping of Leukemias Using a Cluster of Differentiation Antibody Microarray," Canc. Res. 61:4483-4489, 2001.
Benoist, C., and Mathis, D., "A revival of the B cell paradigm for rheumatoid arthritis pathogenesis?" Arthritis Res. 2(2):90-94, 2000.
Berenbaum, M.C., "What is Synergy?," Pharmacological Reviews 41:93-141, The American Society for Pharmacology and Experimental Therapeutics, United States (1989).
Bernstein, I.D., et al., "High Dose Radiolabeled Antibody Therapy of Lymphoma," Canc. Res. 50(Suppl.):1017s-1021s, 1990.
Berzofsky, J.A., and Berkower, I.J., "Immunogenicity and Antigen Structure," in Fundamental Immunology, Third Edition, William E. Paul, Ed., Chap. 8, pp. 235-282, Raven Press, Ltd., New York, 1993.
Best, W.R., et al., "Development of a Crohn's Disease Activity Index. National Cooperative Crohn's Disease Study," Gastroenterology 70(3):439-444, 1976.
Better, M., et al., "*Escherichia coli* Secretion of an Active Chimeric Antibody Fragment," Science 240:1041-1043, 1988.
Bezouska et al., "Rat Natural Killer Cell Antigen, NKR-P1, Related to C-type Animal Lectins is a Carbohydrate-binding Protein,", J. Biol. Chem. 269(24):16945-16952 (1994).
biocrawler.com/encyclopedia/glycosylation, "Glycosylation", 3 pages, retrieved on May 20, 2006.
Bloom, J.W., et al., "Intrachain disulfide bond in the core hinge region of human lgG4," Protein Sci. 6:407-415, 1997.
Boehm, M.K., et al., "The Fab and Fc fragments of IgA1 exhibit a different arrangement from that in IgG: a study by X-ray and neutron solution scattering and homolgy modelling," J. Mol. Biol. 286:1421-1447, 1999.
Boerman et al., "Tumour targetting of the anti-ovarian carcinoma X anti-CD3/TCR bispesific monoclonal antibody OC/TR and its parental MOv18 antibody in experimental ovarian cancer," Anticancer Res. 15(5B):2169-2174 (1995).
Bongini, L., et al., "Freezing immunoglobulins to see them move," Proc. Natl. Acad. Sci. USA 101(17):6466-6471, 2004.
Bortoletto et al., "Optimizing anti-CD3 affinity for effective T cell targeting against tumor cells," Eur. J. Immunol. 32(11):3102-3107 (2002).
Boussif, O., et al., "A versatile vector for gene and oligonucleotide transfer into cells in culture and in vivo: Polyethylenimine," Proc. Natl. Acad. Sci. USA 92:7297-7301, 1995.
Brandl et al., "Bispecific antibody fragments with CD20 X CD28 specificity allow effective autologous and allogeneic T-cell activation against malignant cells in peripheral blood and bone marrow cultures from patients with B-cell lineage leukemia and lymphoma," Exp. Hematol. 27:1264-1270 (1999).
Braslawsky, G.R., et al., "Adriamycin(hydrazone)-antibody conjugates require internalization and intracellular acid hydrolysis for antitumor activity," Cancer Immunol. Immunother. 33:367-374, 1991.
Brekke, O.H., et al., "The structural requirements for complement activation by IgG: does it hinge on the hinge?" Immunol. Today 16(2):85-90, 1995.

(56) References Cited

OTHER PUBLICATIONS

Brinkmann, U., et al., "Recombinant immunotoxins containing the VH or VL domain of monoclonal antibody B3 fused to Pseudomonas exotoxin," J. Immunol. 150(7):2774-2782, 1993.

Brok, H.P.M., et al., "Prophylactic and therapeutic effects of a humanized monoclonal antibody against the IL-2 receptor (DACLIZUMAB) on collagen-induced arthritis (CIA) in rhesus monkeys," Clin. Exp. Immunol. 124:134-141, 2001.

Brorson, K., et al., "Mutational analysis of avidity and fine specificity of anti-levan antibodies," J. Immunol. 163:6694-6701, 1999.

Brown et al., "A novel monoclonal antibody 107-1A4 with high prostate specificity: generation, characterization of antigen expression, and targeting of human prostate cancer xenografts," Prostate Canc. Prostatic Dis. 1:208-215 (1998).

Brown, R.S., et al., "Intratumoral Microdistribution of [131I]MB-1 in Patients with B-Cell Lymphoma Following Radioimmunotheraphy," Nucl. Med. Biol. 24:657-663, 1997.

Brown, S.L., et al., "Treatment of B-Cell Lymphomas with Anti-idiotype Antibodies Alone and in Combination with Alpha Interferon," Blood 73(3):651-661, 1989.

Bruenke, et al., "A recombinant bispecific single-chain Fv antibody against HLA class II and FcγRIII (CD16) triggers effective lysis of lymphoma cells." British Journal of Haematology (2004); 125(2): 167-169.

Brummell, D.A., et al., "Probing the Combining Site of an Anti-Carbohydrate Antibody by Saturation-Mutagenesis: Role of the Heavy-Chain CDR3 Residues," Biochemistry 32:1180-1187, 1993.

Buchsbaum, D.J., et al., "Therapy with Unlabeled and 131I-labeled Pan-B-Cell Monoclonal Antibodies in Nude Mice Bearing Raji Burkitt's Lymphoma Xenografts," Canc. Res. 52:6476-6481, 1992.

Buhler et al., "A bispecific diabody directed against prostate-specific membrane antigen and CD3 induces T-cell mediated lysis of prostate cancer cells," Canc. Immunol. Immunother. 57(1):43-52 (2008).

Burgess, W.H., et al., "Possible dissociation of the heparin-binding and mitogenic activities of heparin-binding (acidic fibroblast) growth factor-1 from its receptor-binding activities by site-directed mutagenesis of a single lysine residue," J. Cell Biol. 111:2129-2138, 1990.

Burke, J.M., et al., "Radioimmunotherapy for acute leukemia," Cancer Control 9(2):106-113, 2002.

Burks, E.A., et al., "In vitro scanning saturation mutagenesis of an antibody binding pocket," Proc. Natl. Acad. Sci. USA 94:412-417, 1997.

Bussel, J.B., "Overview of Idiopathic Thrombocytopenia Purpura: New Approach to Refractory Patients," Semin. Oncol. 27(6 Suppl 12):91-98, 2000.

Byrd, J.C., et al., "Effect of CD37 small modular immuno-pharmaceutical (SMIP) on direct apoptosis in chronic lymphocytic leukemia cells via transcriptional up-regulation of the BH3 family member BIM," 2009 Annual Meeting, American Society of Clinical Oncology (ASCO), J. Clin. Oncol. 27(May 20 Suppl.):15S (Abstract 3035), 2009.

Cai, X., and Garen, A., "Comparison of fusion phage libraries displaying VH or single-chain Fv antibody fragments derived from the antibody repertoire of a vaccinated melanoma patient as a source of melanoma-specific targeting molecules," Proc. Natl. Acad. Sci. USA 94:9261-9266, 1997.

Caldas et al., "Humanization of the anti-CD18 antibody 6.7: an unexpected effect of a framework residue in binding to antigen," Mol. Immunol. 39:941-952 (2003).

Calistoga Pharmaceuticals, "About Calistoga," 7 pages, 2009.

Calistoga Pharmaceuticals, "Preliminary evidence of clinical activity in a phase 1 study of CAL-101, a potent selective inhibitor of the p110δ isoform of phosphatidylinositol 3-kinase, in patients with B-cell malignancies," European Hematology Association, Jun. 4-7, 2009, Poster Session, 17 pages.

Cambridge, G., et al., "Serologic Changes Following B Lymphocyte Depletion Therapy for Rheumatoid Arthritis," Arthritis Rheum. 48(8):2146-2154, 2003.

Campbell, N.A., et al., Biology, 5th Ed., p. 856, Benjamin-Cummings Publ. Co., Menlo Park, CA (1999).

Capaldi, R.A., et al., "Changes in Order of Migration of Polypeptides in Complex III and Cytochrome c Oxidase under Different Condtions of SDS Polyacrylamide Gel Electrophoresis," Biochem. Biophys. Res. Commun. 74(2):425-433, 1977.

Capon, D.J., et al., "Designing CD4 immunoadhesins for AIDS therapy," Nature 337:525-531, 1989.

Carpenter, P.A., et al., "A humanized non-FcR-binding anti-CD3 antibody, visilizumab, for treatment of steroid-refractory acute graft-versus-host disease," Blood 99:2712-2719, American Society of Hematology, United States (2002).

Carpenter, P.A., et al., "Non-Fc Receptor-Binding Humanized Anti-CD3 Antibodies Induce Apoptosis of Activated Human T Cells", The Journal of Immunology 165: 6205-6213 (2000).

Carter, "Bispecific human IgG by design," J. Immunol. Methods 248:7-15 (2001).

Carter, P., "Antibody Engineering—IBC's Tenth International Conference, Dec. 6-9, 1999, La Jolla, CA, USA," IDrugs 3(3):259-261, 2000. PubMed Abstract only, PMID: 16103927.

Carter, P., "Improving the efficacy of antibody-based cancer therapies," Nature Reviews Cancer 1:118-129, 2001.

Casset et al., "A peptide mimetic of an anti-CD4 monoclonal antibody by rational design," Biochem. Biophys. Res. Commun. 307:198-205 (2003).

Catley et al., "Monoclonal antibodies for the treatment of asthma," Pharmacol. Ther. 132:333-351 (2011).

Cephalon Oncology, "Treanda Prescribing Information," 6 pages, 2008.

Chakraborti, T., et al., "Complement activation in heart disease: Role of oxidants," Cell. Signal. 12:607-617, 2000.

Chakravarty, et al., "The oestrogen receptor alpha-regulated lncRNA NEAT1 is a critical modulator of prostate cancer." Nat Commun. (2014); 5: 5383, 16 pages.

Chan, O.T.M., et al., "A Novel Mouse with B Cells but Lacking Serum Antibody Reveals an Antibody-Independent Role for B Cells in Murine Lupus," J. Exp. Med. 189(10):1639-1647, 1999.

Chang et al., "Loop-Sequence Features and Stability Determinants in Antibody Variable Domains by High Throughput Experiments," Structure 22: 9-21 (2014).

Chang, S.H. and Dong, C., "A novel heterodimeric cytokine consisting of IL-17 and IL-17F regulates inflammatory responses," Cell Research 17: 435-440 (2007).

Chang, S.S. et al., "Metastatic renal cell carcinoma neovasculature expresses prostate-specific membrane antigen," Urology. (2001); 57(4): 801-805.

Chatenoud, L., "CD3-Specific Antibody-Induced Active Tolerance: From Bench to Bedside," Nature Reviews Immunology 3:123-132 (2003).

Chatenoud, L., et al., "Restriction of the Human In Vivo Immune Response Against the Mouse Monoclonal Antibody OKT3," The Journal of Immunology 137(3):830-838 (1986).

Chatterjee, M.B., et al., "Idiotypic antibody immunotherapy of cancer," Cancer Immunol. Immunother. 38:75-82, 1994.

Chaudhary, V.K., et al., "A recombinant immunotoxin consisting of two antibody variable domains fused to Pseudomonas exotoxin," Nature 339:394-397, 1989.

Chen, Y., et al., "Selection and Analysis of an Optimized Anti-VEGF Antibody: Crystal Structure of an Affinity-matured Fab in Complex with Antigen," J. Mol. Biol. 293:865-881, 1999.

Cheson, B.D., "CLL Response Criteria," Clin. Adv. Hematol. Oncol. 4(5)(Suppl. 12):4-5, 2006.

Cheson, B.D., et al., "Report of an international working group to standardize response criteria for myelodysplastic syndromes," Blood 96:3671-3674, 2000.

Cheson, B.D., et al., "Report of an International Workshop to Standardize Response Criteria for Non-Hodgkin's Lymphomas," J. Clin. Oncol. 17:1244-1253, 1999.

Cheson, B.D., et al., "Revised Recommendations of the International Working Group for Diagnosis, Standardization of Response Criteria, Treatment Outcomes, and Reporting Standards for Therapeutic Trials in Acute Myeloid Leukemia," J. Clin. Oncol. 21(24):4642-4649, 2003.

(56) References Cited

OTHER PUBLICATIONS

Chien et al., "Significant structural and functional change of an antigen-binding site by a distant amino acid substitution: Proposal of a structural mechanism," Proc. Natl. Acad. Sci. USA 86: 5532-5536 (1989).
Choi, I., et al., "Recombinant chimeric OKT3 scFv IgM antibodies mediate immune suppression while reducing T cell activation in vitro," European Journal of Immunology, 31: 94-106 (2001).
Chothia, C., and Lesk, A.M., "Canonical Structures for the Hypervariable Regions of Immunoglobulins," J. Mol. Biol. 196:901-917, 1987.
Chothia, C., et al., "Conformations of immunoglobulin hypervariable regions," Nature 342:877-883, 1989.
Chothia, C., et al., "Domain association in immunoglobulin molecules. The packing of variable domains," J. Mol. Biol. 186(3):651-663, 1985.
Chou, "Drug Combination Studies and Their Synergy Quantification Using the Chou-Talalay Method." Cancer Research (2010); 70(2): 440-446. Published OnlineFirst Jan. 12, 2010.
Chowdhury, P.S., and Pastan, I., "Improving antibody affinity by mimicking somatic hypermutation in vitro," Nat. Biotechnol. 17:568-572, 1999.
Clackson, T., et al., "Making antibody fragments using phage display libraries," Nature 352:624-628, 1991.
Clark, E.A., and Einfeld, D, "Human B Cell Surface Molecules Defined by an International Workshop Panel of Monoclonal Antibodies," in Leukocyte Typing II (1986), vol. 2, Reinherz, E.L., et al., Eds., pp. 155-167, Springer Verlag, New York, 1986.
Clark, E.A., and Ledbetter, J.A., "Activation of human B cells mediated through two distinct cell surface differentiation antigens, Bp35 and Bp50," Proc. Natl. Acad. Sci. USA 83:4494-4498, 1986.
Clark, E.A., and Ledbetter, J.A., "Structure, function, and genetics of human B cell-associated surface molecules," Adv. Cancer Res. 52:81-149, 1989.
Clark, E.A., et al., "Role of the Bp35 cell surface polypeptide in human B-cell activation," Proc. Natl. Acad. Sci. USA 82:1766-1770, 1985.
Classon et al., "The hinge region of the CD8α chain: structure, antigenicity, and utility in expression of immunoglobulin superfamily domains," Int. Immunol. 4(2):215-225 (1992).
Co, M.S., et al., "Chimeric and Humanized Antibodies with Specificity for the CD33 Antigen," J. Immunol. 148(4): 1149-1154, 1992.
Co, M.S., et al., "Genetically Engineered Deglycosylation of the Variable Domain Increases the Affinity of an Anti-CD33 Monoclonal Antibody," Mol. Immunol. 30(15):1361-1367, 1993.
Co, M.S., et al., "Humanized antibodies for antiviral therapy," Proc. Natl. Acad. Sci. USA 88:2869-2873, 1991.
Coffin, J.M., et al., Eds., Retroviruses, Cold Spring Harbor Laboratory Press, Plainview, NY, 1997.
Coiffier, B., et al., "Rituximab (Anti-CD-20 Monoclonal Antibody) for the Treatment of Patients With Relapsing or Refractory Aggressive Lymphoma: A Multicenter Phase II Study," Blood 92(6): 1927-1932, 1998.
Colman, P.M., "Effects of amino acid sequence changes on antibody-antigen interactions," Res. Immunol. 145:33-36, 1994.
Coloma, M.J., and Morrison, S.L., "Design and production of novel tetravalent bispecific antibodies," Nat. Biotechnol. 15:159-163, 1997.
Coloma, M.J., et al., "The hinge as a spacer contributes to covalent assembly and is required for function of IgG," J. Immunol. 158:733-740, 1997.
Cooke, S.P., et al., "A strategy for antitumor vascular therapy by targeting the vascular endothelial growth factor: receptor complex," Cancer Res. 61:3653-3659, 2001.
Cote, R.J., et al., "Generation of human monoclonal antibodies reactive with cellular antigens," Proc. Natl. Acad. Sci. USA 80:2026-2030, 1983.
Cotten, M., et al., "High-efficiency receptor-mediated delivery of small and large (48 kilobase gene constructs using the endosome-disruption activity of defective or chemically inactivated adenovirus particles," Proc. Natl. Acad. Sci. USA 89:6094-6098, 1992.
Cragg, M.S., and Glennie, M.J., "Antibody specificity controls in vivo effector mechanisms of anti-CD20 reagents," Blood 103(7):2738-2743, 2004.
Crawford and Hou, "The role of LHRH antagonists in the treatment of prostate cancer." Oncology (2009); 23(7): 626-630.
Cree, B., et al., "Tolerability and Effects of Rituximab (Anti-CD20 Antibody) in Neuromyelitis Optica (NMO) and Rapidly Worsening Multiple Sclerosis (MS)," Neurology 62(Suppl 5):A492 (Abstract P06.090), Apr. 2004.
Crunkhorn, S., "Designing selective PI3K inhibitors," Nat. Rev. Drug Discovery 9:105, 2010.
Cruse, J.M., and Lewis, R.E., Illustrated Dictionary of Immunology, p. 157, CRC Press, Inc., 1995.
Curiel, D.T., et al., "High-efficiency gene transfer mediated by adenovirus coupled to DNA-polylysine complexes," Hum. Gene Ther. 3(2):147-154, 1992. PubMed Abstract only, PMID: 1391034.
Dall'Acqua, W.F., et al., "Modulation of the Effector Functions of a Human IgG1 through Engineering of it Hinge Region," J. Immunol. 177:1129-1138, 2006.
Damle, N.K., et al., "Direct helper T cell-induced B cell differentiation involves interaction between T cell antigen CD28 and B cell activation antigen B7," Eur. J. Immunol. 21:1277-1282, 1991.
Davies J., and Riechmann, L., "Single antibody domains as small recognition units: design and in vitro antigen selection of camelized, human VH domains with improved protein stability," Protein Eng. 9(6):531-537, 1996.
Davies, J., "Hematological malignancies," American Society of Hematology—45th Annual Meeting and Exposition, Dec. 5-9, 2003, San Diego, CA, USA; iDrugs 7(1):1-3, 2004.
Davies, J., and Riechmann, L., "Camelising human antibody fragments: NMR studies on VH domains," FEBS Lett. 339:285-290, 1994.
Davis, S.J., et al., "High Level Expression in Chinese Hamster Ovary Cells of Soluble Forms of CD4 T Lymphocyte Glycoprotein Including Glycosylation Variants," J. Biol. Chem. 265(18):10410-10418, 1990.
De Kruif, J. and Logtenberg, T., "Leucine Zipper Dimerized Bivalent and Bispecific scFv Antibodies from a Semi-synthetic Antibody Phage Display Library," The Journal of Biological Chemistry 271 (13):7630-7634, The American Society for Biochemistry and Molecular Biology, Inc., United States (1996).
De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," J. Immunol. 169(6):3076-3084 (2002).
De Vita, S., et al., "Efficacy of Selective B Cell Blockade in the Treatment of Rheumatoid Arthritis. Evidence for a Pathogenic Role of B Cells," Arthritis Rheum. 46(8):2029-2033, 2002.
Deans, J.P., et al., "Association of tyrosine and serine kinases with the B cell surface antigen CD20. Induction via CD20 of tyrosine phosphorylation and activation of phospholipase C-γ1 and PLC phospholipase C-γ2," J. Immunol. 151(9):4494-4504, 1993.
Dechant, M., et al., "Chimeric IgA antibodies against HLA class II effectively trigger lymphoma cell killing," Blood 100(13):4574-4580, 2002.
Decker, T., et al., "A pilot trial of the mTOR (mammalian target of rapamycin) inhibitor RAD001 in patients with advanced B-CLL," Ann. Hematol. 88:221-227, 2009.
Dermer, G.B., "Another Anniversary for the War on Cancer," Bio/Technology 12:320, 1994.
Desmyter, A., et al., "Crystal structure of a camel single-domain VH antibody fragment in complex with lysozyme," Nat. Struct. Biol. 3(9):803-811, 1996.
Dietsch, M.T., et al., "Bispecific receptor globulins, novel tools for the study of cellular interactions. Preparation and characterization of an E-selectin/P-selectin bispecific receptor globulin," J. Immunol. Methods 162:123-132, 1993.

(56) References Cited

OTHER PUBLICATIONS

Dietsch, M.T., et al., "Coengagement of CD2 with LFA-1 pr VLA-4 by bispecific ligand fusion proteins primes T cells to respond more effectively to T cell receptor-dependent signals," J. Leukoc. Biol. 56:444-452, 1994.
Dillman, R.O., et al., "Continuous infusion of T101 monoclonal antibody in chronic lymphocytic leukemia and cutaneous T-cell lymphoma," J. Biol. Response Mod. 5:394-410, 1986.
Divgi, C.R. et al., "Phase I/II radioimmunotherapy trial with iodine-131-labeled monoclonal antibody G250 in metastatic renal cell carcinoma," Clin Cancer Res. (1998); 4(11): 2729-2739.
Dong, H., et al., "B7-H1, a third member of the B7 family, co-stimulates T-cell proliferation and interleukin-10 secretion," Nat. Med. 5(12):1365-1369, 1999.
Dorai, H., et al., "Role of inter-heavy and light chain disulfide bonds in the effector functions of human immunoglobulin IgG1," Mol. Immunol. 29(12):1487-1491, 1992.
Dorrington, K.J., and Klein, M., "Aspects of immunoglobulin G structure relevant to its interaction with Fc receptors," Arch. Immunol. Ther. Exp. (Warsz.) 29:275-282, 1981.
Dufner, P., et al., "Harnessing phage and ribosome display for antibody optimisation," Trends Biotechnol. 24(11):523-529, 2006.
Duncan, A.R., and Winter, G., "The binding site for C1q on IgG," Nature 332:738-740, 1988.
Durie, F.H., et al., "Prevention of collagen-induced arthritis with an antibody to gp39, the ligand for CD40," Science 261:1328-1330, 1993.
Dyer, M.J., et al., "Effects of CAMPATH-1 antibodies in vivo in patients with lymphoid malignancies: influence of antibody isotype," Blood 73(6):1431-1439, 1989.
Edwards, et al., Arthritis Rheum. 46:S197 (Abstract 446), 2002.
Edwards, J.C.W., "Importance of T cells in Rheumatoid Synovitis: Comment on the Review by Firestein and Zvaifler," Arthritis Rheum. 46(11):3105-3106, 2002.
Edwards, J.C.W., and Cambridge, G., "Rheumatoid Arthritis: The Predictable Effect of Small Immune Complexes in which Antibody is Also Antigen," Br. J. Rheumatol. 37:126-130, 1998.
Edwards, J.C.W., and Cambridge, G., "Sustained improvement in rheumatoid arthritis following a protocol designed to deplete B lymphocytes," Rheumatology 40:205-211, 2001.
Edwards, J.C.W., et al., "B-lymphocyte depletion therapy in rheumatoid arthritis and other autoimmune disorders," Biochem. Soc. Trans. 30(4):824-828, 2002.
Edwards, J.C.W., et al., "Do self-perpetuating B lymphocytes drive human autoimmune disease?" Immunology 97:188-196, 1999.
Edwards, J.C.W., et al., "Efficacy of B-Cell-Targeted Therapy with Rituximab in Patients with Rheumatoid Arthritis," New Engl. J. Med. 350:2572-2581, 2004.
Einfeld, D.A., et al., "Molecular cloning of the human B cell CD20 receptor predicts a hydrophobic protein with multiple transmembrane domains," EMBO J. 7(3):711-717, 1988.
Elsässer, D., et al., "HLA Class II as Potential Target Antigen on Malignant B Cells for Therapy with Bispecific Antibodies in Combination with Granulocyte Colony-Stimulating Factor," Blood 87(9):3803-3812, 1996.
Endo, K., "Current status of nuclear medicine in Japan," Gan To Kagaku Ryoho 26(6):744-748, 1999. PubMed Abstract only, PMID: 10410141 (Article in Japanese).
Engelhard, E.K., et al., "The insect tracheal system: A conduit for the systemic spread of Autographa californica M nuclear polyhedrosis virus," Proc. Natl. Acad. Sci. USA 91:3224-3227, 1994.
European Patent No. 1940881 in the name of Amgen Research (Munich) GmbH, Notice of Opposition filed by Aptevo Research & Development LLC on Aug. 30, 2017, 27 pages.
European Patent No. 1940881 in the name of Amgen Research (Munich) GmbH, Reply to Notice of Opposition filed Feb. 19, 2018, 28 pages.
European Search Report, EP appl. No. 11182404.1, 11 pages (dated Dec. 19, 2012).
Evazalipour et al., "Camel Heavy Chain Antibodies Against Prostate-Specific Membrane Antigen," Hybridoma 31(6):424-429 (2012).
Examination Report, European Patent Office appl. No. 12773598.3, 4 pages (dated Jun. 29, 2016).
Fang et al., "Characterization of an anti-human ovarian carcinoma x anti-human CD3 bispecific single-chain antibody with an albumin-original interlinker," Gynecologic Oncology 92:135-146 (2004).
Faure, P., et al., "Immunohistochemical Profile of Cutaneous B-Cell Lymphoma on Cryostat and Paraffin Sections," Amer. J. Dermatopathol. 12(3):122-133, 1990.
Feldman, M.E., et al., "Active-Site Inhibitors of mTOR Target Rapamycin-Resistant Outputs of mTORC1 and mTORC2," PLoS Biol. 7(2):0371-0383, 2009.
Felgner, P.L., et al., "Lipofection: A highly efficient, lipid-mediated DNA-transfection procedure," Proc. Natl. Acad. Sci. USA 84:7413-7417, 1987.
Fell, H.P., et al., "Chimeric L6 Anti-tumor Antibody. Genomic construction, expression, and characterization of the antigen binding site," J. Biol. Chem. 267(22):15552-15558, 1992.
Fell, H.P., et al., "Genetic construction and characterization of a fusion protein consisting of a chimeric F(ab') with specificity for carcinomas and human IL-2," J. Immunol. 146(7):2446-2452, 1991.
Felson, D.T., et al., "American College of Rheumatology Preliminary Definition of Improvement in Rheumatoid Arthritis," Arthritis Rheum. 38(6):727-735, 1995.
Filpula, et al., "Single-chain Fv designs for protein, cell and gene therapeutics," Exp. Opin. Ther. Patents 9(3):231-245, 1999.
Fischer, K., et al., "Bendamustine in Combination with Rituximab (BR) for Patients with Relapsed Chronic Lymphocytic Leukemia (CLL): A Multicentre Phase II Trial of the German CLL Study Group (GCLLSG)," Blood (ASH Annual Meeting Abstracts) 112:Abstract #330, 2008, 2 pages.
Fix, J.A., "Strategies for Delivery of Peptides Utilizing Absorption-Enhancing Agents," J. Pharmaceut. Sci. 85(12):1282-1285, 1996.
Fonseca, R., et al., "Myeloma and the t(11;14)(q13;q32); evidence for a biologically defined unique subset of patients," Blood 99(10):3735-3741, 2002.
Fortmuller et al., "Effective Targeting of Prostate Cancer by Lymphocytes Redirected by a PSMA x CD3 Bispecific Single-Chain Diabody," Prostate 71:588-596 (2011).
Foster, F.M., et al., "The phosphoinositide (PI) 3-kinase family," J. Cell Sci. 116(15):3037-3040, 2003.
Francisco, J.A., et al., "Activity of a Single-Chain Immunotoxin That Selectively Kills Lymphoma and Other B-Lineage Cells Expressing the CD40 Antigen," Canc. Res. 55:3099-3104, 1995.
Frankel et al., "Characterization of diphtheria fusion proteins targeted to the human interleukin-3 receptor," Protein Eng. 13(8):575-581 (2000).
Funakoshi, S., et al., "Differential in Vitro and in Vivo Antitumor Effects Mediated by Anti-CD40 and Anti-CD20 Monoclonal Antibodies Against Human B-Cell Lymphomas," J. Immunother. 19(2):93-101, 1996.
Funakoshi, S., et al., "Inhibition of Human B-Cell Lymphoma Growth by CD40 Stimulation," Blood 83(10):2787-2794, 1994.
Genbank Accession No. L07414, *Homo sapiens* CD40 surface protein mRNA, complete cds, Apr. 27, 1993.
Genbank Accession No. M17953, Mouse Ig rearranged H-chain V-region mRNA VJ1, Apr. 27, 1993.
Genbank Accession No. M17954, Mouse Ig rearranged kappa-chain mRNA VJ5, Apr. 27, 1993.
Genbank Accession No. M62541, Mouse CD20 cell surface protein mRNA, complete cds, Jul. 26, 1993.
Genbank Accession No. M62542, Mouse CD19 gene, complete cds, Apr. 27, 1993.
Genbank Accession No. M83312, Mouse CD40 mRNA, complete cds, Apr. 27, 1993.
Genbank Accession No. M83312, Mouse CD40 mRNA, complete cds, Sep. 23, 1996.
Genbank Accession No. M84371, Human CD19 gene, complete cds, Apr. 27, 1993.
Genbank Accession No. M84371, Human CD19 gene, complete cds, Jul. 18, 1995.

(56) References Cited

OTHER PUBLICATIONS

Genbank Accession No. U15637, *Homo sapiens* CD40 binding protein (CD40BP) mRNA, complete cds, Dec. 7, 1994.
Genbank Accession No. X14046, Human mRNA for leukocyte antigen CD37, Apr. 21, 1993.
Genbank Accession No. X53517, R. norvegicus mRNA for antigen CD37, Apr. 21, 1993.
Genbank Accession No. X65453, M. musculus mRNA for CD40 ligand, Apr. 21, 1993.
Genbank Accession No. X65453, M. musculus mRNA for CD40 ligand, Apr. 27, 2001.
Genbank Accession No. X67878, *H. sapiens* mRNA for CD40 ligand, Apr. 21, 1993.
Genbank Accession No. X96710, *H. sapiens* mRNA for CD40 ligand, Apr. 5, 1996.
Genbank Accession No. Y10507, *H. sapiens* mRNA for CD40 protein, Sep. 9, 1997.
George et al., "An analysis of protein domain linkers: their classification and role in protein folding," Prot. Eng. 15(11):871-879 (2002).
George et al., "Differential Effects of Anti-$\beta_2$-Glycoprotein I Antibodies on Endothelial Cells and on the Manifestations of Experimental Antiphospholipid Syndrome," Circulation 97:900-906 (1998).
Gillies, S.D., and Wesolowski, J.S., "Antigen binding and biological activities of engineered mutant chimeric antibodies with human tumor specificities," Hum. Antibod. Hybridomas 1(1):47-54, 1990.
Gillies, S.D., et al., "Improving the efficacy of antibody-interleukin 2 fusion proteins by reducing their interaction with Fc receptors," Cancer Res. 59:2159-2166, 1999.
Gilliland, L.K., et al., "Elimination of the Immunogenicity of Therapeutic Antibodies," J. Immunol. 162:3663-3671, 1999.
Gilliland, L.K., et al., "Rapid and reliable cloning of antibody variable regions and generation of recombinant single chain antibody fragments," Tissue Antigens 47:1-20, 1996.
Giusti et al., "Somatic diversification of S107 from an antiphosphocholine to an anti-DNA autoantibody is due to a single base change in its heavy chain variable region," Proc. Natl. Acad. Sci. USA 84:2926-2930 (1987).
Gladman, D.D., et al., "Sensitivity to Change of 3 Systemic Lupus Erythematosus Disease Activity Indices: International Validation," J. Rheumatol. 21:1468-1471, 1994.
Gluzman, Y., "SV40-Transformed Simian Cells Support the Replication of Early SV40 Mutants," Cell 23:175-182, 1981.
Gottdiener, J.S., et al., "Cardiac Manifestations in Poliomyositis," Amer. J. Cardiol. 41:1141-1149, 1978.
Graff, C.P., et al., "Directed evolution of an anti-carcinoembryonic antigen scFv with a 4-day monovalent dissociation half-time at 37° C.," Prot. Eng. Des. Sel. 17(4):293-304, 2004.
Griffiths, A.D., et al., "Isolation of high affinity human antibodies directly from large synthetic repertoires," EMBO J. 13(14):3245-3260, 1994.
Grillo-Lopez, A.J., et al., "Response criteria for NHL: Importance of 'normal' lymph node size and correlations with response rates," Ann. Oncol. 11:399-408, 2000.
Grossbard, M.L., et al., "Monoclonal Antibody-Based Therapies of Leukemia and Lymphoma," Blood 80(4):863-878, 1992.
Gura, T., "Cancer Models. Systems for Identifying New Drugs Are Often Faulty," Science 278(5340):1041-1042, 1997.
Güssow and Seemann, "Humanization of Monoclonal Antibodies," Meth. Enzymol. 203:99-121 (1991).
Halin, C., et al., "Tumor-targeting properties of antibody-vascular endothelial growth factor fusion proteins," Int. J. Cancer 102:109-116, 2002.
Hamers-Casterman, C., et al., "Naturally occurring antibodies devoid of light chains," Nature 363:446-448, 1993.
Haritunians, T., et al., "Antiproliferative activity of RAD001 (everolimus) as a single agent and combined with other agents in mantle cell lymphoma," Leukemia 21:333-339, 2007.
Harris, C.L. et al., "Tumor cell killing using chemically engineered antibody constructs specific for tumor cells and the complement inhibitor CD59." Clin Exp Immunol 107; 364-371, 1997.
Harrison, "Phosphoinositide 3-kinase inhibitors," Nat. Rev. Drug Discovery 8:607, 2009.
Hayden, M.S., et al., "Antibody engineering," Curr. Opin. Immunol. 9:201-212, 1997.
Hayden, M.S., et al., "Costimulation by CD28 sFv expressed on the tumor cell surface or as a soluble bispecific molecule targeted to the L6 carcinoma antigen," Tissue Antigens 48:242-254, 1996.
Hayden, M.S., et al., "Single-chain mono- and bispecific antibody derivatives with novel biological properties and antitumour activity from a COS cell transient expression system," Ther. Immunol. 1:3-15, 1994.
Hayden-Ledbetter, M., et al., "Induction of Apoptosis in B Lymphoma Cell Lines by CytoxB37G, a Small Modular ImmunoPharmaceutical (SMIP) That Binds CD37," Blood 102(11):Abstract #1572, 2003, and Poster (19 pages).
Hekman, A., et al., "Initial experience with treatment of human B cell lymphoma with anti-CD19 monoclonal antibody," Cancer Immunol. Immunother. 32:364-372, 1991.
Hellström, I., et al., "Monoclonal Mouse Antibodies Raised against Human Lung Carcinoma," Canc. Res. 46:3917-3923, 1986.
Hemler, M.E., "Targeting of tetraspanin proteins—potential benefits and strategies," Nat. Rev. Drug Discovery 7:747-758, 2008.
Herold, K.C., et al., "Activation of human T cells by FcR nonbinding anti-CD3 mAb, hOKT3γ1 (Ala-Ala)," J. Clin. Invest. 111 (3):409-418, American Society for Clinical Investigation, United States (2003).
Higashida, et al., "Treatment of DMARD-Refractory Rheumatoid Arthritis With Rituximab," Annual Scientific Meeting of the American College of Rheumatology (Abstract #LB11), New Orleans, LA (Oct. 2002). (Best available copy).
Hinek, A., et al., "The Elastin Receptor: A Galactoside-Binding Protein," Science 239:1539-1541, 1988.
Hinkle, G.H. et al., "Multicenter radioimmunoscintigraphic evaluation of patients with prostate carcinoma using indium-111 capromab pendetide," Cancer. (1998); 83(4): 739-747.
Hirsch, R., et al., "Effects of In Vivo Administration of ANTI-T3 Monoclonal Antibody on T Cell Function in Mice," The Journal of Immunology 140(11):3766-3772, The American Association of Immunologists, United States, (1988).
Hirsch, R., et al., "Effects of In Vivo Administration of Anti-CD3 Monoclonal Antibody on T Cell Function in Mice: II. In Vivo Activation of T Cells", The Journal of Immunology 142(3):737-743 (1989).
Hoet, R.M., et al., "Generation of high-affinity human antibodies by combining donor-derived and synthetic complementarity-determining-region diversity," Nature Biotechnology 23:344-348 (2005).
Hollenbaugh, D., et al., "The human T cell antigen gp39, a member of the TNF gene family, is a ligand for the CD40 receptor: expression of a soluble form of gp39 with B cell co-stimulatory activity," EMBO J. 11:4313-4321, 1992.
Holliger and Hudson, "Engineered antibody fragments and the rise of single domains," Nat. Biotechnol. 23(9):1126-1136(2005).
Holm et al., "Functional mapping and single chain construction of the anti-cytokeratin 8 monoclonal antibody TS1," Mol. Immunol. 44:1075-1084 (2007).
Hoogenboom, H.R., and Winter, G., "By-passing Immunisation. Human Antibodies from Synthetic Repertoires of Germline VH Gene Segments Rearranged in Vitro," J. Mol. Biol. 227:381-388, 1992.
Hu et al., "Minibody: A Novel Engineered Anti-Carcinoembryonic Antigen Antibody Fragment (Single-Chain FVC$_H$3) Which Exhibits Rapoid, High-Level Targeting of Xenografts," Cancer Res. 36:3055-3061 (1996).
Hudson, P.J., "Recombinant antibodies: a novel approach to cancer diagnosis and therapy," Expert Opin. Investig. Drugs 9(6):1231-1242, 2000.
Hudson, P.J., "Recombinant antibody fragments," Curr. Opin. Biotechnol. 9:395-402, 1998.

(56) References Cited

OTHER PUBLICATIONS

Huls, G., et al., "Antitumor Immune Effector Mechanisms Recruited by Phage Display-derived Fully Human IgG1 and IgA1 Monoclonal Antibodies," Cancer Res. 59:5778-5784, 1999.

Humphreys et al., "F(ab')2 molecules made from *Escherichia coli* produced Fab' with hinge sequences conferring increased serum survival in an animal model," J. Immunol. Methods 217:1-10 (1998).

Huret, J.-L., "t(11;14)(q13;q32)," Atlas Genet. Cytogenet. Oncol. Haematol., May 1998. URL: http://atlasgeneticsoncology.org/Anomalies/t1114ID2021.html.

Huston et al., "Protein engineering of antibody binding sites: Recovery of specific activity in an anti-digoxin single-chain Fv analogue produced in *Escherichia coli*," Proc. Natl. Acad. Sci. USA 85:5879-5883 (1988).

Huston, J.S., et al., "Medical applications of single-chain antibodies," Int. Rev. Immunol. 10:195-217, 1993.

Hwang, W.Y.K., et al., "Use of human germline genes in a CDR homology-based approach to antibody humanization," Methods 36:35-42, 2005.

Igawa et al., "Reduced elimination of IgG antibodies by engineering the variable region," Prot. Eng. Design Select. 23(5):385-392 (2010).

Inoue et al., "Efficient production of a functional mouse/human chimeric Fab' against human urokinase-type plasminogen activator by Bacillus brevis," Appl. Microbiol. Biotechnol. 48:487-492 (1997).

International Non-Hodgkin's Lymphoma Prognostic Factors Project, "A Predictive Model for Aggressive Non-Hodgkin's Lymphoma," New Engl. J. Med. 329:987-994, 1993.

International Preliminary Examination Report, dated Aug. 4, 2006, for PCTAN PCT/US03/41600, 5 pages.

International Preliminary Examination Report, dated Feb. 26, 2003, for PCTAN PCT/US02/01487, 4 pages.

International Preliminary Examination Report, dated Nov. 28, 2007, for PCTAN PCT/US03/24918, 5 pages.

International Preliminary Report on Patentability for International Application No. PCT/US2012/034575 dated Oct. 23, 2013, 7 pages.

International Preliminary Report on Patentability for International Application No. PCT/US2016/017568 dated Aug. 15, 2017, 17 pages.

International Preliminary Report on Patentability, PCT appl. no. PCT/US2013/037135, 8 pages (dated Oct. 21, 2014).

International Preliminary Report on Patentability, PCT Application No. PCT/US2009/060286, 14 pages, dated Apr. 12, 2011.

International Search Report and Written Opinion for International Application No. PCT/US2016/017568 dated Jul. 22, 2016, 23 pages.

International Search Report and Written Opinion for International Application No. PCT/US2016/052942 dated Mar. 17, 2017, 11 pages.

International Search Report for International Application PCT/US2010/062436, European Patent Office, Netherlands, dated Apr. 28, 2011.

International Search Report for International Patent Application No. PCT/US2009/060286, dated Jul. 7, 2010.

International Search Report, dated Apr. 17, 2008, and Written Opinion for PCTAN PCT/US2007/071052, 29 pages.

International Search Report, dated Jan. 22, 2007, for PCTAN PCT/US03/24918, 4 pages.

International Search Report, dated Jul. 16, 2007, for PCTAN PCT/US2006/029038, 10 pages.

International Search Report, dated Mar. 2, 2010, for PCTAN PCT/US2009/064470, 4 pages.

International Search Report, dated May 9, 2002, for PCTAN PCT/US02/01487, 3 pages.

International Search Report, dated Nov. 2, 2004, for PCTAN PCT/US03/41600, 4 pages.

International Search Report, dated Oct. 1, 2009, and Written Opinion for PCTAN PCT/US2008/069378, 13 pages.

International Search Report, dated Sep. 18, 2002, for PCTAN PCT/US02/07011, 3 pages.

International Search Report, dated Sep. 23, 2009, and Written Opinion for PCTAN PCT/US2009/040288, 15 pages.

International Search Report, PCT Appl. No. PCT/US2012/034575, 6 pages (dated Nov. 2, 2012).

Isaacs, J.D., et al., "Therapy with monoclonal antibodies. II. The contribution of Fcγ receptor binding and the influence of CH1 and CH3 domains on in vivo effector function," J. Immunol. 161:3862-3869, 1998.

Isenman, D.E., et al., "Correlation between the exposure of aromatic chromophores at the surface of the Fc domains of immunoglobulin G and their ability to bind complement," Biochemistry 16(2):233-240, 1977.

Israeli, R.S. et al., "Expression of the prostate-specific membrane antigen," Cancer Res. (1994); 54(7): 1807-11.

Jacquemin, M., et al., "Variable region heavy chain glycosylation determines the anticoagulant activity of a factor VIII antibody," J. Thromb. Haemost. 4:1047-1055, 2006.

Jain, R.K., "Barriers to drug delivery in solid tumors," Scientific American, pp. 58-65, 1994.

Jain, R.K., "Physiological barriers to delivery of monoclonal antibodies and other macromolecules in tumors," Cancer Res. 50(Suppl.):814s-819s, 1990.

Janeway, C.A., et al., Eds., Immunobiology: The Immune System in Health and Disease, 4th ed., Chap. 3, p. 92, Elsevier Science Ltd., London, and Garland Publishing, New York, 1999.

Jang, Y.-J., et al., "The structural basis for DNA binding by an anti-DNA autoantibody," Mol. Immunol. 35:1207-1217, 1998.

Jendreyko, N., et al., "Intradiabodies, Bispecific, Tetravalent Antibodies for the Simultaneous Functional Knockout of Two Cell Surface Receptors," J. Biol. Chem. 278(48):47812-47819, 2003.

Jendreyko, N., et al., "Phenotypic knockout of VEGF-R2 and Tie-2 with an intradiabody reduces tumor growth and angiogenesis in vivo," Proc. Natl. Acad. Sci. USA 102(23):8293-8298, 2005.

Jermutus, L., et al., "Tailoring in vitro evolution for protein affinity of stability," Proc. Natl. Acad. Sci. USA 98(1):75-80, 2001.

Jin, H., et al., "MetMAb, the One-Armed 5D5 Anti-c-Met Antibody, Inhibits Orthotopic Pancreatic Tumor Growth and Improves Survival," Cancer Research 68(11):4360-4368, American Association for Cancer Research, United States (2008).

Johnson, G., and Wu, T.T., "Kabat Database and its applications: 30 years after the first variability plot," Nucl. Acids Res. 28(1):214-218, 2000.

Jones, P.T., et al., "Replacing the complementarity-determining regions in a human antibody with those from a mouse," Nature 321:522-525, 1986.

Joosten, L.A.B., et al., "Protection against cartilage and bone destruction by systemic interleukin-4 treatment in established murine type II collagen-induced arthritis," Arthritis Res. 1:81-91, 1999.

Jost, C.R., et al., "Mammalian Expression and Secretion of Functional Single-chain Fv Molecules," J. Biol. Chem. 269(42):26267-26273, 1994.

Kalergis, A.M., et al., "Efficient T cell activation requires an optimal dwell-time of interaction between the TCR and the pMHC complex," Nat. Immunol. 2(3):229-234, 2001.

Kaminski, M.S., et al., "Imaging, Dosimetry, and Radioimmunotherapy With Iodine 131-Labeled Anti-CD37 Antibody in B-Cell Lymphoma," J. Clin. Oncol. 10(11):1696-1711, 1992.

Kaminski, M.S., et al., "Radioimmunotherapy of B-Cell Lymphoma with [131I]Anti-B1 (Anti-CD20) Antibody," N. Engl. J. Med. 329(7):459-465, 1993.

Kato, K., et al., "A conformational change in the Fc precludes the binding of two Fcγ receptor molecules to one IgG," Immunol. Today 21:310-312, 2000.

Kersh, E.N., et al., "Fidelity of T Cell Activation Through Multistep T Cell Receptor ζ Phosphorylation," Science 281:572-575, 1998.

Keystone, E., "B cell targeted therapies," Arthritis Res. Ther. 7(Suppl. 3):S13-S18, 2005.

Kiel, C., et al., "Electrostatically optimized Ras-binding Ralf guanine dissociation stimulator mutants increase the rate of association by stabilizing the encounter complex," Proc. Natl. Acad. Sci. USA 101(25):9223-9228, 2004.

Kienberger, F., et al., "Following single antibody binding to purple membranes in real time," EMBO Rep. 5(6):579-583, 2004.

(56) References Cited

OTHER PUBLICATIONS

Kiesel, S., et al., "Removal of Cells from a Malignant B-Cell Line from Bone Marrow with Immunomagnetic Beads and with Complement and Immunoglobulin Switch Variant Mediated Cytolysis," Leukemia Res. 11:1119-1125, 1987.
Kim et al., "Anti-CD30 diabody-drug conjugates with potent antitumor activity," Mol. Cancer Ther. 7:2486-2497 (2008).
Kipriyanov et al., "Two amino acid mutations in an anti-human CD3 single-chain Fv antibody fragment that affect the yield on bacterial secretion but not the affinity," Protein Eng. 4(10):445-453 (1997).
Kirschfink, M., "Targeting complement in therapy," Immunol. Rev. 180:177-189, 2001.
Klein, M., et al., "Expression of biological effector functions by immunoglobulin G molecules lacking the hinge region," Proc. Natl. Acad. Sci. USA 78(1):524-528, 1981.
Knobeloch, K.-P., et al., "Targeted Inactivation of the Tetraspanin CD37 Impairs T-Cell-Dependent B-Cell Response under Suboptimal Costimulatory Conditions," Mol. Cell. Biol. 20(15):5363-5369, 2000.
Kobayashi et al., "The Pharmacokinetic Characteristics of Glycolated Humanized Anti-Tac Fabs Are Determined by Their Isoelectric Points," Cancer Res. 59:422-430 (1999).
Kobayashi, H., et al., "Tryptophan H33 plays an important role in pyrimidine (6-4) pyrimidone photoproduct binding by a high-affinity antibody," Protein Eng. 12(10):879-884, 1999.
Köhl, J., and Gessner, J.E., "On the role of complement and Fc γ-receptors in the Arthus reaction," Mol. Immunol. 36:893-903, 1999.
Kolls, J., et al., "Prolonged and effective blockade of tumor necrosis factor activity through adenovirus-mediated gene transfer," Proc. Natl. Acad. Sci. USA 91:215-219, 1994.
Konterman, R., and Dübel, S., Eds., "Antibody Engineering," Springer-Verlag, Berlin, 2001 (title pages and Table of Contents only).
Koolwijk, P., et al., "Interaction between hybrid mouse monoclonal antibodies and the human high-affinity IgG FcR, huFc gamma RI, on U937. Involvement of only one of the mIgG heavy chains in receptor binding," J. Immunol. 143(5):1656-1662, 1989.
Kortt, A.A., et al., "Dimeric and trimeric antibodies: high avidity scFvs for cancer targeting," Biomol. Eng. 18:95-108, 2001.
Kortt, A.A., et al., "Recombinant anti-sialidase single-chain variable fragment antibody. Characterization, formation of dimer and higher-molecular-mass multimers and the solution of the crystal structure of the single-chain variable fragment/sialidase complex," Eur. J. Biochem. 221:151-157, 1994.
Kost et al., "Production of a urokinase plasminogen activator-IgG fusion protein (uPA-IgG) in the baculovirus expression system," Gene 190:139-144 (1997).
Kozbor, D., and Roder, J.C., "The production of monoclonal antibodies from human lymphocytes," Immunol. Today 4(3):72-79, 1983. (misspelled in 406C1 spec).
Kumar, S., et al., "Molecular Cloning and Expression of the Fabs of Human Autoantibodies in *Escherichia coli*," J. Biol. Chem. 275(45):35129-35136, 2000.
Kunkel, T.A., "Rapid and efficient site-specific mutagenesis without phenotypic selection," Proc. Natl. Acad. Sci. USA 82:488-492, 1985.
Kurtzke, J.F., "Rating neurologic impairment in multiple sclerosis: An expanded disability status scale (EDSS)," Neurology 33:1444-1452, 1983.
Kusumi, A., et al., "Confined Lateral Diffusion of Membrane Receptors as Studied by Single Particle Tracking (Nanovid Microscopy). Effects of Calcium-Induced Differentiation in Cultured Epithelial Cells," Biophys. J. 65:2021-2040, 1993.
Ladetto, M., et al., "Rituximab anti-CD20 monoclonal antibody induces marked but transient reductions of peripheral blood lymphocytes in chronic lymphocytic leukaemia patients," Med. Oncol. 17:203-210, 2000.

Lamminmäki, U., and Kankare, J.A., "Crystal Structure of a Recombinant Anti-estradiol Fab Fragment in Complex with 17β-Estradiol," J. Biol. Chem. 276(39):36687-36694, 2001.
Lavasani, S., et al., "Monoclonal Antibody against T-Cell Receptor αβ Induces Self Tolerance in Chronic Experimental Autoimmune Encephalomyelitis," Scandinavian Journal of Immunology 65: 39-47 (2007).
Law, C.-L., et al., "Expression and characterization of recombinant soluble human CD3 molecules: presentation of antigenic epitopes defined on the native TCR-CD3 complex," Int. Immunol. 14(4):389-400, 2002.
Layios, N., et al., "Remission of severe cold agglutinin disease after Rituximab therapy," Leukemia, pp. 187-188, 2000.
Lazar, E., et al., "Transforming growth factor α: mutation of aspartic acid 47 and leucine 48 results in different biological activities," Mol. Cell. Biol. 8(3):1247-1252, 1988.
Lazar, G.A., et al., "Engineered antibody Fc variants with enhanced effector function," Proc. Natl. Acad. Sci. USA 103(11):4005-4010, 2006.
Le Gall, F., et al. "Immunosuppressive properties of anti-CD3 single-chain Fv and diabody," Journal of Immunological Methods 285:111-127 (2004).
Leandro, M.J., et al., "An Open Study of B Lymphocyte Depletion in Systemic Lupus Erythematosus," Arthritis Rheum. 46(10):2673-2677, 2002.
Leandro, M.J., et al., "B Lymphocyte Depletion in Rheumatoid Arthritis: Early Evidence for Safety, Efficacy, and Dose Response," Arthritis Rheum. 44(9):S370 (Abstract #1905), 2001.
Leandro, M.J., et al., "Clinical outcome in 22 patients with rheumatoid arthritis treated with B lymphocyte depletion," Ann. Rheum. Dis. 61:883-888, 2002.
Leatherbarrow, R.J., et al., "Effector Functions of a Monoclonal Aglycosylated Mouse IgG2a: Binding and Activation of Complement Component C1 and Interaction with Human Monocyte Fc Receptor," Mol. Immunol. 22(4):407-415, 1985.
Ledbetter, J.A., et al., "Antibodies to Tp67 and Tp44 Augment and Sustain Proliferative Responses of Activated T Cells," J. Immunol. 135(4):2331-2336, 1985.
Ledbetter, J.A., et al., "Augmentation of normal and malignant B cell proliferation by monoclonal antibody to the B cell-specific antigen BP50 (CDW40)," J. Immunol. 138(3):788-794, 1987.
Ledbetter, J.A., et al., "Binding Constructs and Methods for Use Thereof," Office Action dated Dec. 8, 2006, for U.S. Appl. No. 10/627,556, 38 pages.
Ledbetter, J.A., et al., "Binding Constructs and Methods for Use Thereof," Office Action dated Feb. 14, 2008, for U.S. Appl. No. 10/627,556, 22 pages.
Ledbetter, J.A., et al., "Binding Constructs and Methods for Use Thereof," Office Action dated Feb. 20, 2009, for U.S. Appl. No. 10/566,409, 13 pages.
Ledbetter, J.A., et al., "Binding Constructs and Methods for Use Thereof," Office Action dated Jul. 10, 2008, for U.S. Appl. No. 10/566,409, 8 pages.
Ledbetter, J.A., et al., "Binding Constructs and Methods for Use Thereof," Office Action dated Jun. 24, 2009, for U.S. Appl. No. 10/627,556, 14 pages.
Ledbetter, J.A., et al., "Binding Constructs and Methods for Use Thereof," Office Action dated Jun. 9, 2009, for U.S. Appl. No. 10/566,409, 32 pages.
Ledbetter, J.A., et al., "Binding Constructs and Methods for Use Thereof," Office Action dated Nov. 26, 2008, for U.S. Appl. No. 10/627,556, 25 pages.
Ledbetter, J.A., et al., "Binding Constructs and Methods for Use Thereof," Office Action dated Nov. 27, 2009, for U.S. Appl. No. 10/566,409, 12 pages.
Ledbetter, J.A., et al., "Binding Constructs and Methods for Use Thereof," Office Action dated Nov. 29, 2010, for U.S. Appl. No. 12/371,467, 17 pages.
Ledbetter, J.A., et al., "Binding Constructs and Methods for Use Thereof," Office Action dated Nov. 6, 2009, for U.S. Appl. No. 10/627,556, 15 pages.

(56) References Cited

OTHER PUBLICATIONS

Ledbetter, J.A., et al., "Binding Constructs and Methods for Use Thereof," Office Action dated Sep. 11, 2007, for U.S. Appl. No. 10/627,556, 19 pages.
Ledbetter, J.A., et al., "Binding Domain-lmmunoglobulin Fusion Proteins," Office Action dated Apr. 19, 2007, for U.S. Appl. No. 10/053,530, 17 pages.
Ledbetter, J.A., et al., "Binding Domain-Immunoglobulin Fusion Proteins," Office Action dated Apr. 2, 2007, for U.S. Appl. No. 10/207,655, 22 pages.
Ledbetter, J.A., et al., "Binding Domain-Immunoglobulin Fusion Proteins," Office Action dated Apr. 5, 2007, for U.S. Appl. No. 11/089,367, 11 pages.
Ledbetter, J.A., et al., "Binding Domain-Immunoglobulin Fusion Proteins," Office Action dated Aug. 27, 2004, for U.S. Appl. No. 10/053,530, 15 pages.
Ledbetter, J.A., et al., "Binding Domain-Immunoglobulin Fusion Proteins," Office Action dated Dec. 13, 2010, for U.S. Appl. No. 12/541,062, 12 pages.
Ledbetter, J.A., et al., "Binding Domain-Immunoglobulin Fusion Proteins," Office Action dated Dec. 5, 2007, for U.S. Appl. No. 10/053,530, 11 pages.
Ledbetter, J.A., et al., "Binding Domain-Immunoglobulin Fusion Proteins," Office Action dated Feb. 28, 2008, for U.S. Appl. No. 11/088,569, 26 pages.
Ledbetter, J.A., et al., "Binding Domain-Immunoglobulin Fusion Proteins," Office Action dated Jan. 14, 2008, for U.S. Appl. No. 10/207,655, 27 pages.
Ledbetter, J.A., et al., "Binding Domain-Immunoglobulin Fusion Proteins," Office Action dated Jan. 14, 2008, for U.S. Appl. No. 11/089,511, 30 pages.
Ledbetter, J.A., et al., "Binding Domain-Immunoglobulin Fusion Proteins," Office Action dated Jan. 14, 2010, for U.S. Appl. No. 11/088,693, 13 pages.
Ledbetter, J.A., et al., "Binding Domain-Immunoglobulin Fusion Proteins," Office Action dated Jan. 17, 2006, for U.S. Appl. No. 10/053,530, 18 pages.
Ledbetter, J.A., et al., "Binding Domain-Immunoglobulin Fusion Proteins," Office Action dated Jan. 18, 2011, for U.S. Appl. No. 11/088,693, 8 pages.
Ledbetter, J.A., et al., "Binding Domain-Immunoglobulin Fusion Proteins," Office Action dated Jan. 2, 2004, for U.S. Appl. No. 10/053,530, 15 pages.
Ledbetter, J.A., et al., "Binding Domain-Immunoglobulin Fusion Proteins," Office Action dated Jul. 12, 2010, for U.S. Appl. No. 12/541,062, 9 pages.
Ledbetter, J.A., et al., "Binding Domain-Immunoglobulin Fusion Proteins," Office Action dated Jul. 13, 2006, for U.S. Appl. No. 11/089,511, 7 pages.
Ledbetter, J.A., et al., "Binding Domain-Immunoglobulin Fusion Proteins," Office Action dated Jul. 25, 2006, for U.S. Appl. No. 10/207,655, 29 pages.
Ledbetter, J.A., et al., "Binding Domain-Immunoglobulin Fusion Proteins," Office Action dated Jun. 2, 2010, for U.S. Appl. No. 12/724,333, 7 pages.
Ledbetter, J.A., et al., "Binding Domain-Immunoglobulin Fusion Proteins," Office Action dated Jun. 4, 2007, for U.S. Appl. No. 11/088,569, 24 pages.
Ledbetter, J.A., et al., "Binding Domain-Immunoglobulin Fusion Proteins," Office Action dated Jun. 4, 2007, for U.S. Appl. No. 11/088,737, 27 pages.
Ledbetter, J.A., et al., "Binding Domain-Immunoglobulin Fusion Proteins," Office Action dated Jun. 4, 2007, for U.S. Appl. No. 11/089,190, 27 pages.
Ledbetter, J.A., et al., "Binding Domain-Immunoglobulin Fusion Proteins," Office Action dated Jun. 6, 2007, for U.S. Appl. No. 11/088,570, 27 pages.
Ledbetter, J.A., et al., "Binding Domain-Immunoglobulin Fusion Proteins," Office Action dated Jun. 8, 2007, for U.S. Appl. No. 11/089,368, 29 pages.
Ledbetter, J.A., et al., "Binding Domain-Immunoglobulin Fusion Proteins," Office Action dated Mar. 1, 2005, for U.S. Appl. No. 10/053,530, 11 pages.
Ledbetter, J.A., et al., "Binding Domain-Immunoglobulin Fusion Proteins," Office Action dated Mar. 22, 2010, for U.S. Appl. No. 12/541,062, 9 pages.
Ledbetter, J.A., et al., "Binding Domain-Immunoglobulin Fusion Proteins," Office Action dated Mar. 23, 2007, for U.S. Appl. No. 10/053,530, 22 pages.
Ledbetter, J.A., et al., "Binding Domain-Immunoglobulin Fusion Proteins," Office Action dated Mar. 26, 2007, for U.S. Appl. No. 11/089,511, 34 pages.
Ledbetter, J.A., et al., "Binding Domain-Immunoglobulin Fusion Proteins," Office Action dated Mar. 28, 2008, for U.S. Appl. No. 11/088,693, 16 pages.
Ledbetter, J.A., et al., "Binding Domain-Immunoglobulin Fusion Proteins," Office Action dated Mar. 3, 2008, for U.S. Appl. No. 11/088,570, 28 pages.
Ledbetter, J.A., et al., "Binding Domain-Immunoglobulin Fusion Proteins," Office Action dated Mar. 3, 2008, for U.S. Appl. No. 11/088,737, 29 pages.
Ledbetter, J.A., et al., "Binding Domain-Immunoglobulin Fusion Proteins," Office Action dated Mar. 3, 2008, for U.S. Appl. No. 11/089,190, 26 pages.
Ledbetter, J.A., et al., "Binding Domain-Immunoglobulin Fusion Proteins," Office Action dated Mar. 4, 2009, for U.S. Appl. No. 11/088,693, 10 pages.
Ledbetter, J.A., et al., "Binding Domain-Immunoglobulin Fusion Proteins," Office Action dated Mar. 5, 2008, for U.S. Appl. No. 11/089,368, 30 pages.
Ledbetter, J.A., et al., "Binding Domain-Immunoglobulin Fusion Proteins," Office Action dated May 14, 2007, for U.S. Appl. No. 11/088,693, 11 pages.
Ledbetter, J.A., et al., "Binding Domain-Immunoglobulin Fusion Proteins," Office Action dated May 18, 2009, for U.S. Appl. No. 10/207,655, 7 pages.
Ledbetter, J.A., et al., "Binding Domain-Immunoglobulin Fusion Proteins," Office Action dated May 22, 2003, for U.S. Appl. No. 10/053,530, 17 pages.
Ledbetter, J.A., et al., "Binding Domain-Immunoglobulin Fusion Proteins," Office Action dated Nov. 20, 2009, for U.S. Appl. No. 10/207,655, 10 pages.
Ledbetter, J.A., et al., "Binding Domain-Immunoglobulin Fusion Proteins," Office Action dated Nov. 30, 2007, for U.S. Appl. No. 11/089,367, 15 pages.
Ledbetter, J.A., et al., "Binding Domain-Immunoglobulin Fusion Proteins," Office Action dated Nov. 4, 2008, for U.S. Appl. No. 10/207,655, 20 pages.
Ledbetter, J.A., et al., "Binding Domain-Immunoglobulin Fusion Proteins," Office Action dated Oct. 12, 2006, for U.S. Appl. No. 10/053,530, 16 pages.
Ledbetter, J.A., et al., "Binding Domain-Immunoglobulin Fusion Proteins," Office Action dated Sep. 11, 2009, for U.S. Appl. No. 11/088,693, 12 pages.
Ledbetter, J.A., et al., "Binding Domain-Immunoglobulin Fusion Proteins," Office Action dated Sep. 12, 2006, for U.S. Appl. No. 11/089,368, 8 pages.
Ledbetter, J.A., et al., "Binding Domain-Immunoglobulin Fusion Proteins," Office Action dated Sep. 14, 2006, for U.S. Appl. No. 11/088,569, 8 pages.
Ledbetter, J.A., et al., "Binding Domain-Immunoglobulin Fusion Proteins," Office Action dated Sep. 14, 2006, for U.S. Appl. No. 11/088,570, 7 pages.
Ledbetter, J.A., et al., "Binding Domain-Immunoglobulin Fusion Proteins," Office Action dated Sep. 14, 2006, for U.S. Appl. No. 11/088,737, 7 pages.
Ledbetter, J.A., et al., "Binding Domain-Immunoglobulin Fusion Proteins," Office Action dated Sep. 14, 2006, for U.S. Appl. No. 11/089,190, 7 pages.
Ledbetter, J.A., et al., "Binding Domain-Immunoglobulin Fusion Proteins," Office Action dated Sep. 2, 2010, for U.S. Appl. No. 12/724,333, 11 pages.

(56) References Cited

OTHER PUBLICATIONS

Ledbetter, J.A., et al., "Monoclonal antibodies to a new gp40-45 (CD37) B-cell-associated cluster group modulate B-cell proliferation," in Leucocyte Typing III: White Cell Differentiation Antigens, A.J. McMichael, Ed., pp. 339-340, Oxford University Press, Oxford (1987).
Lee, E.J., and Kueck, B., "Rituxan in the Treatment of Cold Agglutinin Disease," Blood 92(9):3490-3491, 1998.
Lee, H.S., et al., "Generation and characterization of a novel single-gene-encoded single-chain immunoglobulin molecule with antigen binding activity and effector functions," Mol. Immunol. 36:61-71, 1999.
Leget, G.A., and Czuczman, M.S., "Use of rituximab, the new FDA-approved antibody," Curr. Opin. Oncol. 10:548-551, 1998.
Lehninger, A.L., et al., Principles of Biochemistry, 2nd Ed., Figure 5-6, Worth Publishers, New York (1993).
Leigh, B.R., et al., "Preclinical evaluation of chimeric L6 antibody for the treatment of Kaposi's sarcoma with radioimmunotherapy," Cancer Biother. Radiopharm. 14(2):113-119, 1999.
Leonard, P., et al., "High throughput ranking of recombinant avian scFv antibody fragments from crude lysates using the Biacore A100," J. Immunol. Meth. 323:172-179, 2007.
Levine, T.D., "Rituximab in the Treatment of Dermatomyositis," Arthritis Rheum. 52(2):601-607, 2005.
Levine, T.D., and Pestronk, A., "IgM antibody-related polyneuropathies: B-cell depletion chemotherapy using Rituximab," Neurology 52:1701-1704, 1999.
Li, J.-Y., et al., "Detection of Translocation t(11;14)(q13;q32) in Mantle Cell Lymphoma by Fluorescence in Situ Hybridization," Amer. J. Pathol. 154(5):1449-1452, 1999.
Li, Q., et al., "Assessment of Recombinant Adenoviral Vectors for Hepatic Gene Therapy," Hum. Gene Ther. 4:403-409, 1993.
Li, S.L., et al., "Single-chain antibodies against human insulin-like growth factor I receptor: expression, purification, and effect on tumor growth," Cancer Immunol. Immunother. 49:243-252, 2000.
Lin, M.C, et al., "Structure-Function Relationships in Glucagon: Properties of Highly Purified Des-His1-, Monoiodo-, and [Des-Asn28, Thr29](homoserine lactone27)-glucagon," Biochemistry 14(8):1559-1563, 1975.
Lin, T.S., et al., "Rituximab in B-Cell Chronic Lymphocytic Leukemia," Sem. Oncol. 30(4):483-492, 2003.
Link, M.P., et al., "A Unique Antigen on Mature B Cells Defined by a Monoclonal Antibody," J. Immunol. 137(9):3013-3018, 1986.
Linsley, P.S., et al., "T-cell antigen CD28 mediates adhesion with B cells by interacting with activation antigen B7/BB-1," Proc. Natl. Acad. Sci. USA 87:5031-5035, 1990.
Liu H, et al., "Monoclonal antibodies to the extracellular domain of prostate-specific membrane antigen also react with tumor vascular endothelium," Cancer Res. (1997); 57(17): 3629-3634.
Liu, A.Y., et al., "Production of a Mouse-Human Chimeric Monoclonal Antibody to CD20 with Potent Fc-Dependent Biologic Activity," J. Immunol. 139(10):3521-3526, 1987.
Liu, H. et al., "Constitutive and antibody-induced internalization of prostate-specific membrane antigen," Cancer Res. (1998); 58(18): 4055-4060.
Lohwasser et al., "Cloning of murine NKG2A, B and C: second family of C-type lectin receptors on murine NK cells," Eur. J. Immunol. 29:755-761 (1999).
Looney, R.J., et al., "B Cell Depletion as a Novel Treatment for Systemic Lupus Erythematosus," Arthritis Rheum. 50(8):2580-2589, 2004.
Lu, D., et al., "A Fully Human Recombinant IgG-like Bispecific Antibody to Both the Epidermal Growth Factor Receptor and the Insulin-like Growth Factor Receptor for Enhanced Antitumor Activity," J. Biol. Chem. 280(20):19665-19672, 2005.
Lu, D., et al., "Di-diabody: a novel tetravalent bispecific antibody molecule by design," J. Immunol. Meth. 279:219-232, 2003.
Lv, Ming et al., "Structured to reduce the mitogenicity of anti-CD3 antibody based on computer-guided molecular design," International Journal of Biochemistry & Cell Biology 39:1142-1155 (2007).

Lyons, D.S., et al., "A TCR Binds to Antagonist Ligands with Lower Affinities and Faster Dissociation Rates Than to Agonists," Immunity 5:53-61, 1996.
MacCallum et al., "Antibody-antigen Interactions: Contact Analysis and Binding Site Topography," J. Mol. Biol. 262:732-745 (1996).
Mallender and Voss, Jr., "Construction, expression, and activity of a bivalent bispecific single-chain antibody." The Journal of Biological Chemistry (1994); 269: 199-206.
Maloney, D.G., et al., "IDEC-C2B8 (Rituximab) Anti-CD20 Monoclonal Antibody Therapy in Patients with Relapsed Low-Grade Non-Hodgkin's Lymphoma," Blood 90(6):2188-2195, 1997.
Maloney, D.G., et al., "IDEC-C2B8: results of a phase I multiple-dose trial in patients with relapsed non-Hodgkin's lymphoma," J. Clin. Oncol. 15(10):3266-3274, 1997.
Maloney, D.G., et al., "Phase I Clinical Trial Using Escalating Single-Dose Infusion of Chimeric Anti-CD20 Monoclonal Antibody (IDEC-C2B8) in Patients With Recurrent B-Cell Lymphoma," Blood 84(8):2457-2466, 1994.
Mariuzza et al., "The Structural Basis of Antigen-Antibody Recognition," Ann. Rev. Biophys. Biophys. Chem. 16:139-159 (1987).
Marks, J.D., et al., "By-passing Immunization. Human Antibodies from V-gene Libraries Displayed on Phage," J. Mol. Biol. 222:581-597, 1991.
Marsh, J.E., et al., "Targeting the complement system," Curr. Opin. Nephrol. Hypertens. 8:557-562, 1999.
Martens, C.L., et al., "Heavy chain genes of rabbit IgG: Isolation of a cDNA encoding γ heavy chain and identification of two genomic Cγ genes," Proc. Natl. Acad. Sci. USA 79:6018-6022, 1982.
Martin, A.C.R., et al., "Modeling antibody hypervariable loops: A combined algorithm," Proc. Natl. Acad. Sci. USA 86:9268-9272, 1989.
Martin, S., et al., "Efficient Neutralization and Disruption of Rhinovirus by Chimeric ICAM-1/Immunoglobulin Molecules," J. Virol. 67(6):3561-3568, 1993.
Marvin and Zhu, "Recombinant approaches to IgG-like bispecific antibodies," Acta Pharmacol. Sin. 26:649-658 (2005).
Matsui, K., et al., "Kinetics of T-cell receptor binding to peptide/I-Ek complexes: Correlation of the dissociation rate with T-cell responsiveness," Proc. Natl. Acad. Sci. USA 91:12862-12866, 1994.
Matthews, R., "Medical Heretics," New Scientist, pp. 34-37, Apr. 7, 2001.
Mattu, T.S., et al., "The Glycosylation and Structure of Human Serum IgA1, Fab, and Fc Regions and the Role of N-Glycosylation on Fcα Receptor Interactions," J. Biol. Chem. 273(4):2260-2272, 1998.
McFarland et al., "Symmetry Recognizing Asymmetry: Analysis of the Interactions between the C-Type Lectin-like Immunoreceptor NKG2D and MHC Class l=like Ligands," Structure 11:411-422 (2003).
McLaughlin, P., et al., "Clinical Status and Optimal Use of Rituximab for B-Cell Lymphomas," Oncology 12(12):1763-1769, 1998; review by Grossbard, M.L., and Multani, P.S., pp. 1769-1770; review by Raubitschek, A., pp. 1775-1776; review by Molina, A., pp. 1776-1777, 1781.
McLaughlin, P., et al., "IDEC-C2B8 Anti-CD20 Antibody: Final Report on a Phase III Pivotal Trial in Patients (PTS) with Relapsed Low-Grade or Follicular Lymphoma (LG/F NHL)," Blood 88(Suppl. 1):90a (Abstract 349), 1996.
McLaughlin, P., et al., "Pharmacokinetics (PK) and Pharmacodynamics (PD) of the Anti-CD20 Antibody (Mab) IDEC-C2B8 in Patients (Pts) with Relapsed Low-Grade or Follicular Lymphoma (LG/F NHL)," Blood 88(10)(Suppl. 1):90a (Abstract 350), 1996.
Merson, A., and Brochier, J., "Phenotypic heterogeneity of B cell chronic lymphocytic leukaemia," Immunol. Lett. 19:269-272, 1988.
Michaelsen, T.E., et al., "Antibody dependent cell-mediated cytotoxicity induced by chimeric mouse-human IgG subclasses and IgG3 antibodies with altered hinge region," Mol. Immunol. 29(3):319-326, 1992.
Michaelsen, T.E., et al., "Enhancement of complement activation and cytolysis of human IgG3 by deletion of hinge exons," Scand. J. Immunol. 32:517-528, 1990.

(56) References Cited

OTHER PUBLICATIONS

Michaelsen, T.E., et al., "One disulfide bond in front of the second heavy chain constant region is necessary and sufficient for effector functions of human IgG3 without a genetic hinge," Proc. Natl. Acad. Sci. USA 91:9243-9247, 1994.

Miller, A.D., "Retrovirus Packaging Cells," Hum. Gene Ther. 1:5-14, 1990.

Miller, F.W., "Classification and Prognosis of Inflammatory Muscle Disease," Rheum. Dis. Clin. North Amer. 20(4):811-826, 1994.

Miller, F.W., "Inflammatory Myopathies: Polymyositis, Dermatomyositis, and Related Conditions," in Arthritis and Allied Conditions: A Textbook of Rheumatology, 15th ed., Koopman, W.J., and Moreland, L.W., Eds., Chap. 75, pp. 1593-1620, Lippincott Williams & Wilkins, Philadelphia, 2005.

Minsavage, G.D., and Dillman III, J.F., "Bifunctional Alkylating Agent-Induced p53 and Nonclassical Nuclear Factor κB Responses and Cell Death Are Altered by Caffeic Acid Phenethyl Ester: A Potential Role for Antioxidant/Electrophilic Response-Element Signaling," J. Pharmacol. Exp. Ther. 321(1):202-212, 2007.

Moldenhauer, G., "CD37," J. Biol. Regul. Homeost. Agents 14:281-283, 2000.

Monson, N.L., et al., "Effect of Rituximab on the Peripheral Blood and Cerebrospinal Fluid B Cells in Patients With Primary Progressive Multiple Sclerosis," Arch. Neurol. 62:258-264, 2005.

Moore, K., et al., "Use of the Monoclonal Antibody WR17, Identifying the CD37 gp40-45 Kd Antigen Complex, in the Diagnosis of B-Lymphoid Malignancy," J. Pathol. 152:13-21, 1987.

Mukai, Y., et al., "Optimization of anti-tumor necrosis factor-α single chain Fv displayed on phages for creation of functional antibodies," Pharmazie 61:889-890, 2006.

Mullinax, R.L., et al., "Identification of human antibody fragment clones specific for tetanus toxoid in a bacteriophage λ immunoexpression library," Proc. Natl. Acad. Sci. USA 87:8095-8099, 1990.

Multani, P.S., and Grossbard, M.L., "Monoclonal antibody-based therapies for hematologic malignancies," J. Clin. Oncol. 16(11):3691-3710, 1998.

Munoz et al., "Binding of Anti-CD23 Monoclonal Antibody to the Leucine Zipper Motif of FcεRII/CD23 on B Cell Membrane Promotes Its Proteolytic Cleavage," J. Biol. Chem. 273(48):21975-21800 (1998).

Muñoz, E., et al., "The CH1 domain of IgG is not essential for C3 covalent binding: importance of the other constant domains as targets for C3," Int. Immunol. 10(2):97-106, 1998.

Muraoka, S., and Shulman, M.J., "Structural Requirements for IgM Assembly and Cytolytic Activity. Effects of Mutations in the Oligosaccharide Acceptor Site at Asn 402," J. Immunol. 142(2):695-701, 1989.

Muyldermans, "Single domain camel antibodies: current status," Rev. Mol. Biotechnol. 74:277-302 (2001).

Muyldermans, S., et al., "Sequence and structure of VH domain from naturally occurring camel heavy chain immunoglobulins lacking light chains," Protein Eng. 7(9):1129-1135, 1994.

Müller et al., "The first constant domain ($C_H1$ and $C_L$) of an antibody used as heterodimerization domain for bispecific miniantibodies," FEBS Lett. 422:259-264 (1998).

Nadler, L.M., "B Cell/Leukemia Panel Workshop: Summary and Comments," in Leukocyte Typing II, vol. 2, Reinherz, E.L., et al., Eds., pp. 3-21, Springer Verlag, New York, 1986.

NCBI Reference Sequence NP_001765.1 for Leukocyte Surface Antigen CD37, Oct. 31, 2000.

Neve, R.M., et al., "Biological effects of anti-ErbB2 single chain antibodies selected for internalizing function," Biochem. Biophys. Res. Commun. 280:274-279, 2001.

Nguyen, D.T., et al., "IDEC-C2B8 anti-CD20 (Rituximab) immunotherapy in patients with low-grade non-Hodgkin's lymphoma and lymphoproliferative disorders: evaluation of response on 48 patients," Eur. J. Haematol. 62:76-82, 1999.

Nguyen, V.K., et al., "Heavy-chain antibodies in Camelidae; a case of evolutionary innovation," Immunogenetics 54:39-47, 2002.

Nguyen, V.K., et al., "The specific variable domain of camel heavy-chain antibodies is encoded in the germline," J. Mol. Biol. 275:413-418, 1998.

Nieba, L., et al., "Disrupting the hydrophobic patches at the antibody variable/constant domain interface: improved in vivo folding and physical characterization of an engineered scFv fragment," Protein Eng. 10(4):435-444, 1997.

Nielsen, U.B., et al., "Targeting of Bivalent Anti-ErbB2 Diabody Antibody Fragments to Tumor Cells is Independent of the Intrinsic Antibody Affinity," Cancer Res. 60:6434-6440, 2000.

Nikula, T.K., et al., "Impact of the high tyrosine fraction in complementarity determining regions: measured and predicted effects of radioiodination on IgG immunoreactivity," Mol. Immunol. 32(12):865-872, 1995.

Novak, H., et al., "Selective antibody-mediated targeting of class I Mhc to EGFR-expressing tumor cells induces potent antitumor CTL activity in vitro and in vivo," Int. J. Cancer 120:329-336, 2007.

Nuttall, S.D., et al., "Immunoglobulin VH domains and beyond: design and selection of single-domain binding and targeting reagents," Curr. Pharm. Biotechnol. 1:253-263, 2000.

Office Action, Japanese Application Serial No. 2009-515618, dated Jul. 10, 2012, 7 pages.

Oganesyan, V., et al., "Structural characterization of a human Fc fragment engineered for lack of effector functions," Acta Crystallographica Section D, 64:700-704 (2008).

Ogoshi, M., et al., "In Situ Hybridization Analysis of the Expression of Human Telomerase RNA in Normal and Pathologic Conditions of the Skin," J. Invest. Dermatol. 110:818-823, 1998.

Okazaki, T., et al., "PD-1 immunoreceptor inhibits B cell receptor-mediated signaling by recruiting src homology 2-domain-containing tyrosine phosphatase 2 to phosphotyrosine," Proc. Natl. Acad. Sci. USA 98(24):13866-13871, 2001.

Oki, S., et al., "Augmentation of CTLA-4 expression by wortmannin: involvement of lysosomal sorting properties of CTLA-4," Int. Immunol. 11(9):1563-1571, 1999.

Oliyai, R., and Stella, V.J., et al., "Prodrugs of Peptides and Proteins for Improved Formulation and Delivery," Annu. Rev. Pharmacol. Toxicol. 32:521-544, 1993.

Omidfar et al., "Production and Characterization of a New Antibody Specific for the Mutant EGF Receptor, EGFRvIII, in Camelus bactrianus," Tumor Biol. 25:179-187 (2004).

Onda et al, "Lowering the Isoelectric Point of the Fv Portion of Recombinant Immunotoxins Leads to Decreased Nonspecific Animal Toxicity without Affecting Antitumor Activity," Cancer Res. 61:5070-5077 (2001).

Orcutt et al., "A modular IgG-scFv bispecific antibody topology," Prot. Eng. Des. Select. 23(4):221-228 (published online Dec. 17, 2009).

Ortho Multicenter Transplant Study Group, "A Randomized Clinical Trial of OKT3 Monoclonal Antibody for Acute Rejection of Cadaveric Renal Transplants," The New England Journal of Medicine 313(6):337-342 (1985).

Paar, J.M., et al., "Bivalent Ligands with Rigid Double-Stranded DNA Spacers Reveal Structural Constraints on Signaling by FcεRI," J. Immunol. 169:856-864, 2002.

Padlan, E.A., "A Possible Procedure for Reducing the Immunogenicity of Antibody Variable Domains While Preserving Their Ligand-Binding Properties," Mol. Immunol. 28(4/5):489-498, 1991.

Padlan, E.A., "Anatomy of the Antibody Molecule," Mol. Immunol. 31(3):169-217, 1994.

Pakula et al., "Genetic analysis of protein stability and function," Annu. Rev. Genet. 23:289-310 (1989).

Pallesen, G., and Hager, H., "The expression of the 40-45 kDa pan-B cluster (CD37) in normal human tissues and in haematopoietic neoplasms as defined by immunohistology," in Leukocyte Typing III: White Cell Differentiation Antigens, A.J. McMichael, Ed., pp. 337-339, Oxford University Press, Oxford (1987).

Panka, D.J., et al., "Variable Region Framework Differences Result in Decreased or Increased Affinity of Variant Anti-Digoxin Antibodies," Proc. Natl. Acad. Sci. USA 85(9):3080-3084, 1988.

(56) References Cited

OTHER PUBLICATIONS

Papadakis, K., et al., "Anti-CD20 Chimeric Monoclonal Antibody (Rituximab) Treatment of Immune-Mediated Thrombocytopenia Associated With Crohn's Disease," Gastroenterology 124(2):583, Feb. 2003.
Park, S.S., et al., "Generation and characterization of a novel tetravalent bispecific antibody that binds to hepatitis B virus surface antigens," Mol. Immunol. 37:1123-1130, 2000.
Pawson, R., et al., "Treatment of T-cell prolymphocytic leukemia with human CD52 antibody," J. Clin. Oncol. 15(7):2667-2672, 1997.
Pelat, T., et al., "Germline Humanization of a Non-human Primate Antibody that Neutralizes the Anthrax Toxin, by in Vitro and in Silico Engineering," J. Mol. Biol. 384:1400-1407, 2008.
Peter, K. et al., "Construction and functional evaluation of a single-chain antibody fusion protein with fibrin targeting and thrombin inhibition after activation by factor Xa," Circulation 101:1158-1164, 2000.
Petri, M.A., et al., "Effects of Prasterone on Disease Activity and Symptoms in Women With Active Systemic Lupus Erythematosus. Results of a Multicenter Randomized, Double-Blind, Placebo-Controlled Trial," Arthritis Rheum. 50(9):2858-2868, 2004.
Pezzutto, A., et al., "CD19 Monoclonal Antibody HD37 Inhibits Anti-Immunoglobulin-Induced B Cell Activation and Proliferation," J. Immunol. 138(9):2793-2799, 1987.
Plevy, S., et al., "A Phase I Study of Visilizumab, a Humanized Anti-CD3 Monoclonal Antibody, in Severe Steroid-Refractory Ulcerative Colitis," Gastroenterology 133:1414-1422 (2007).
Poljak, R.J., et al., "Three-Dimensional Structure of the Fab' Fragment of a Human Immunoglobulin at 2.8-Å Resolution," Proc. Natl. Acad. Sci. USA 70(12):3305-3310, 1973.
Pollard, H., et al., "Polyethylenimine but Not Cationic Lipids Promotes Transgene Delivery to the Nucleus in Mammalian Cells," J. Biol. Chem. 273(13):7507-7511, 1998.
Portolano, S., et al., "Lack of promiscuity in autoantigen-specific H and L chain combinations as revealed by human H and L chain 'roulette'," J. Immunol. 150(3):880-887, 1993.
Press, O.W., et al., "High-Dose Radioimmunotherapy of B Cell Lymphomas," in The Present and Future Role of Monoclonal Antibodies in Management of Cancer. Front. Radiat. Ther. Oncol., Vaeth, J.M., and Meyer, J.L., Eds., Karger, Basel, Switzerland, 24:204-213, 225-227 (discussion), 1990.
Press, O.W., et al., "Monoclonal Antibody 1F5 (Anti-CD20) Serotherapy of Human B Cell Lymphomas," Blood 69(2):584-591, 1987.
Press, O.W., et al., "Radiolabeled Antibody Therapy of Human B Cell Lymphomas," in Immunobiology of Proteins and Peptides VI, Atassi, M.Z., Ed., Plenum Press, New York, pp. 91-96, 1991.
Press, O.W., et al., "Radiolabeled-Antibody Therapy of B-Cell Lymphoma with Autologous Bone Marrow Support," N. Engl. J. Med. 329(17):1219-1224, 1993.
Press, O.W., et al., "Treatment of refractory non-Hodgkin's lymphoma with radiolabeled MB-1 (anti-CD37) antibody," J. Clin. Oncol. 7(8):1027-1038, 1989.
Presta, L.G., et al., "Engineering therapeutic antibodies for improved function," Biochem. Soc. Trans. 30(4):487-490, 2002.
Protheroe, A., et al., "Remission of inflammatory arthropathy in association with anti-CD20 therapy for non-Hodgkin's lymphoma," Rheumatology 38:1150-1152, 1999.
Prous, J.R., Ed., "Annual Update 2004/2005—Treatment of Musculoskeletal Disorders," Drugs Fut. 30(2):181-232, 2005.
PubMed (NCBI) search for "des-leucine", 1 page, Nov. 14, 2006.
Queen, C., et al., "A humanized antibody that binds to the interleukin 2 receptor," Proc. Natl. Acad. Sci. USA 86:10029-10033, 1989.
Radaev, S., and Sun, P.D., "Recognition of IgG by Fcγ receptor. The role of Fc glycosylation and the binding of peptide inhibitors," J. Biol. Chem. 276(19):16478-16483, 2001.
Radaev, S., et al., "The Structure of a Human Type III Fcγ Receptor in Complex with Fc," J. Biol. Chem. 276(19):16469-16477, 2001.
Rader, C., et al., "A phage display approach for rapid antibody humanization: Designed combinatorial V gene libraries," Proc. Nat. Acad. Sci. USA 95:8910-8915, 1998.
Rai, K.R., et al., "Fludarabine Compared with Chlorambucil as Primary Therapy for Chronic Lymphocytic Leukemia," New Engl. J. Med. 343(24):1750-1757, 2000.
Rapamune (sirolimus) Oral Solution and Tablets, Highlights of Prescribing Information (1 page) and Full Prescribing Information (47 pages), retrieved from http://www.wyeth.com/content/showlabeling.asp?id=139, 2009, 48 pages.
Rastetter, W., et al., "Rituximab: Expanding Role in Therapy for Lymphomas and Autoimmune Diseases," Annu. Rev. Med. 55:477-503, 2004.
Ratanatharathorn, V., et al., "Anti-CD20 Chimeric Monoclonal Treatment of Refractory Immune-Mediated Thrombocytopenia in a Patient with Chronic Graft-versus-Host Disease," Ann. Intern. Med. 133(4):275-279, 2000.
Redpath, S., et al., "The influence of the hinge region length in binding of human IgG to human Fcγ receptors," Hum. Immunol. 59:720-727, 1998.
Reff, M.E., et al., "Depletion of B Cells in Vivo by a Chimeric Mouse Human Monoclonal Antibody to CD20," Blood 83(2):435-445, 1994.
Rider, L.G., et al., "International Consensus on Preliminary Definitions of Improvement in Adult and Juvenile Myositis," Arthritis Rheum. 50(7):2281-2290, 2004.
Riechmann, L., "Rearrangement of the former VL interface in the solution structure of a camelised, single antibody VH domain," J. Mol. Biol. 259:957-969, 1996.
Riechmann, L., et al., "Reshaping human antibodies for therapy," Nature 332:323-327, 1988.
Roguska, M.A., et al., "A comparison of two murine monoclonal antibodies humanized by CDR-grafting and variable domain resurfacing," Protein Eng. 9(10):895-904, 1996.
Rothe, C., et al., "The human combinatorial antibody library HuCAL GOLD combines diversification of all six CDRs according to the natural immune system with a novel display method for efficient selection of high-affinity antibodies," J. Mol. Biol. 376:1182-1200, 2008. PubMed Abstract only, PMID: 18191144.
Roux, K.H., et al., "Comparisons of the ability of human IgG3 hinge mutants, IgM, IgE, and IgA2, to form small immune complexes: a role for flexibility and geometry," J. Immunol. 161:4083-4090, 1998.
Roux, K.H., et al., "Flexibility of Human IgG Subclasses," J. Immunol. 159:3372-3382, 1997.
Roux, K.H., et al., "Structural analysis of the nurse shark (new) antigen receptor (NAR): Molecular convergence of NAR and unusual mammalian immunoglobulins," Proc. Natl. Acad. Sci. USA 95:11804-11809, 1998.
Rudick, R.A., et al., "Impact of interferon beta-1a on neurologic disability in relapsing multiple sclerosis," Neurology 49:358-363, 1997.
Rudikoff et al., "Single amino acid substitution altering antigen-binding specificity," Proc. Natl. Acad. Sci. USA 79:1979-1983 (1982).
Rummel, M.J., "German Experience With Bendamustine Treating Relapsed/Refractory Indolent B-Cell and Mantle Cell Lymphomas," Semin. Hematol. 44:S22-S26, 2007.
Rummel, M.J., et al., "Bendamustine Plus Rituximab Versus CHOP Plus Rituximab in the First-Line Treatment of Patients with Indolent and Mantle Cell Lymphomas—First Interim Results of a Randomized Phase III Study of the StiL (Study Group Indolent Lymphomas, Germany)," Blood (ASH Annual Meeting Abstracts) 110:Abstract #385, 2007, 2 pages.
Saldanha, J.W., et al., "A single backmutation in the human kIV framework of a previously unsuccessfully humanized antibody restores the binding activity and increases the secretion in cos cells," Mol. Immunol. 36:709-719, 1999.
Saleh, M.N., et al., A Pilot Study of the Anti-CD20 Monoclonal Antibody Rituximab in Patients With Refractory Immune Thrombocytopenia, Semin. Oncol. 27(6)(Suppl 12):99-103, 2000.

(56) References Cited

OTHER PUBLICATIONS

Samelson, L. et al., "Monoclonal antibodies against the antigen receptor on a cloned T-cell hybrid", Proc. Natl. Acad. Sci. USA. (1983); 80 (22): 6972-6976.
Santos, L., et al., "Role of macrophage migration inhibitory factor (MIF) in murine antigen-induced arthritis: interaction with glucocorticoids," Clin. Exp. Immunol. 123:309-314, 2001.
Scheinberg, D.A., et al., "A phase I toxicity, pharmacology, and dosimetry trial of monoclonal antibody OKB7 in patients with non-Hodgkin's lymphoma: effects of tumor burden and antigen expression," J. Clin. Oncol. 8(5):792-803, 1990.
Schmidt, M., et al., "Suppression of metastasis formation by a recombinant single chain antibody-toxin targeted to full-length and oncogenic variant EGF receptors," Oncogene 18:1711-1721, 1999.
Schuster, M., et al., "Improved Effector Functions of a Therapeutic Monoclonal Lewis Y-Specific Antibody by Glycoform Engineering," Cancer Res. 65(17):7934-7941, 2005.
Schwartz, G.P., et al., "A superactive insulin: [B10-aspartic acid]insulin(human)," Proc. Natl. Acad. Sci. USA 84:6408-6411, 1987.
Schwartz-Albiez, R., et al., "The B Cell-Associated CD37 Antigen (gp40-52). Structure and Subcellular Expression of an Extensively Glycosylated Glycoprotein," J. Immunol. 140(3):905-914, 1988.
Search Output from ATCC Website for Hybridomas: 2H7 (pp. 1-2), 1D8 (p. 1), HD37 (p. 1), G28-1 (p. 1), 4.4.220 (p. 1), Fc2-2 (p. 1), UCHL-1 (p. 1), 5B9 (p. 1), L6 (p. 1), 10A8 (p. 1), 2e12 (p. 1). 40.2.36 (p. 1) and G19-4 (p. 1).
Search Report in United Arab Emirates Patent Application No. 1130/2013, received Mar. 26, 2018, no mail date provided, 5 pages.
Search Report, SG appl. No. 11201406346S, 6 pages (dated Sep. 16, 2015).
Search Report and Written Opinion, SG appl. No. 2013077086, 15 pages (dated Jan. 7, 2015).
Seaver, S.S., "Monoclonal Antibodies in Industry: More Difficult Than Originally Thought," Genet. Eng. News 14(14):10, 21, 1994.
Segal, D.M., et al., "Introduction: bispecific antibodies," J. Immunol. Methods 248:1-6, 2001.
Selzer, T., et al., "Rational design of faster associating and tighter binding protein complexes," Nat. Struct. Biol. 7(7):537-541, 2000.
Sensel, M.G., et al., "Engineering novel antibody molecules," Chem. Immunol. 65:129-158, 1997.
Serpieri et al., "Comparison of Humanized IgG and FvFc Anti-CD3 Monoclonal Antibodies Expressed in CHO Cells," Mol. Biotechnol. 45(3):218-225 (2010).
Shahied, L.S., et al., "Bispecific Minibodies Targeting HER2/neu and CD16 Exhibit Improved Tumor Lysis When Placed in a Divalent Tumor Antigen Binding Format," J. Biol. Chem. 279(52):53907-53914, 2004.
Shan, D., et al., "Apoptosis of Malignant Human B Cells by Ligation of CD20 with Monoclonal Antibody," Blood 91(5):1644-1652, 1998.
Shan, D., et al., "Characterization of scFv-Ig Constructs from the Anti-CD20 mAb 1F5 Using Linker Peptides of Varying Lengths," J. Immunol. 162:6589-6595, 1999.
Shankar, S., et al., "Antiepidermal growth factor variant III scFv fragment: effect of radioiodination method on tumor targeting and normal tissue clearance," Nucl. Med. Biol. 33:101-110, 2006.
Shegogue, D., and Trojanowska, M., "Mammalian Target of Rapamycin Positively Regulates Collagen Type I Production via a Phosphatidylinositol 3-Kinase-independent Pathway," J. Biol. Chem. 279(22):23166-23175, 2004.
Shen et al., "Single Variable Domain-IgG Fusion. A Novel Recombinant Approach to Fc Domain-Containing Bispecific Antibodies," J. Biol. Chem. 281(16):10706-10714 (2006).
Shimoni, A., et al., "Autologous T Cells Control B-Chronic Lymphocytic Leukemia Tumor Progression in Human → Mouse Radiation Chimera," Cancer Res. 59:5968-5974, 1999.
Shin, S.-U., et al., "Genetically-Engineered Antibodies: Tools for the Study of Diverse Properties of the Antibody Molecule," Immunol. Rev. 130:87-107 (1992).
Shin, S.-U., et al., "Hybrid antibodies," Int. Rev. Immunol. 10:177-186 (1993).
Shipp, M.A., et al., "A Predictive Model for Aggressive Non-Hodgkin's Lymphoma," New Engl. J. Med. 329:987-994, 1993.
Shlomchik, M.J., et al., "The Role of B Cells in lpr/lpr-induced Autoimmunity," J. Exp. Med. 180:1295-1306, 1994.
Shu, L., et al., Secretion of a single-gene-encoded immunoglobulin from myeloma cells, Proc. Natl. Acad. Sci. USA 90:7995-7999, 1993.
Simonds, H.M., and Miles, D., "Adjuvant treatment of breast cancer: impact of monoclonal antibody therapy directed against the HER2 receptor," Expert Opin. Biol. Ther. 7(4):487-491, 2007.
Simonis, B., et al., "Evaluation and Validation of a Crohn's Disease Inflammatory Activity Index Reflecting Pattern of Endoscopic Severity," Scand. J. Gastroenterol. 33(3):283-288, 1998.
Smellie, W.J.B., et al., "Radioimmunotherapy of breast cancer xenografts with monoclonal antibody ICR12 against c-erbB2 p185: comparison of iodogen and N-succinimidyl 4-methyl-3-(tri-n-butylstannyl)benzoate radioiodination methods," Cancer Res. 55(Suppl):5842s-5846s, 1995.
Smith, G.E., et al., "Molecular Engineering of the Autographa californica Nuclear Polyhedrosis Virus Genome: Deletion Mutations Within the Polyhedrin Gene," J. Virol. 46(2):584-593, 1983.
Smith, K.A., et al., "Isolation and characterization of vascular endothelial growth factor-165 specific scFv fragments by phage display," Int. J. Oncol. 22:333-338, 2003 (Abstract).
Smith-Gill, S.J., et al., "Contributions of immunoglobulin heavy and light chains to antibody specificity for lysozyme and two haptens," J. Immunol. 139:4135-4144, 1987.
Sonderman, P., et al., "The 3.2-Å crystal structure of the human IgG1 Fc fragment-FcγRIII complex," Nature 406:267-273, 2000.
Song, M.-K., et al., "Light chain of natural antibody plays a dominant role in protein antigen binding," Biochem. Biophys. Res. Commun. 268:390-394, 2000.
Souriau, C., and Hudson, P.J., "Recombinant antibodies for cancer diagnosis and therapy," Expert Opin. Biol. Ther. 3(2):305-318, 2003.
Speth, C., et al., "The complement system: Pathophysiology and clinical relevance," Wien. Klin. Wochenschr. 111(10):378-391, 1999.
Spiro, R.G., "Protein glycosylation: nature, distribution, enzymatic formation, and disease implications of glycopeptide bonds," Glycobiology 12(4):43R-56R, 2002.
Sporici, R.A., et al., "ICOS ligand costimulation is required for T-cell encephalitogenicity," Clin. Immunol. 100(3):277-288, 2001.
Stamenkovic, I., and Seed, B., "Analysis of Two cDNA Clones Encoding the B Lymphocyte Antigen CD20 (B1, Bp35), A Type III Integral Membrane Protein," J. Exp. Med. 167:1975-1980, 1988.
Stasi, R. et al., "Rituximab chimeric anti-CD20 monoclonal antibody treatment for adults with chronic idiopathic thrombocytopenic purpura," Blood 98:952-957, 2001.
Stein, et al., "Androgen synthesis inhibitors in the treatment of castration-resistant prostate cancer." Asian J Androl. (2014); 16(3): 387-400.
Steukers, M., et al., "Rapid kinetic-based screening of human Fab fragments," J. Immunol. Meth. 310:126-135, 2006.
Stevenson, G.T., et al., "Conjugation of Human Fcγ in Closed-Hinge or Open-Hinge Configuration to Fab'γ and Analogous Ligands," J. Immunol. 158:2242-2250, 1997.
Stevenson, G.T., et al., "Mechanisms in Removal of Tumor by Antibody," Cell Biophys. 24/25:45-50, 1994.
Su, B., et al., "Automated high-throughput purification of antibody fragments to facilitate evaluation in functional and kinetic based assays," J. Immunol. Meth. 322:94-103, 2007.
Su, S.L. et al., "Alternatively spliced variants of prostate-specific membrane antigen RNA: ratio of expression as a potential measurement of progression," Cancer Res. (1995); 55(7):1441-3.
Supplementary European Search Report, EP appl. No. 12773598.3, 9 pages (dated Dec. 12, 2014).
Supplementary European Search Report, EP appl. No. 13778209.0, 12 pages (dated Feb. 25, 2016).
Sweat, S.D. et al., "Prostate-specific membrane antigen expression is greatest in prostate adenocarcinoma and lymph nodemetastases," Urology. (1998); 52(4): 637-40.

(56) References Cited

OTHER PUBLICATIONS

Tagawa, S.T. et al., "Anti-prostate-specific membrane antigen-based radioimmunotherapy for prostate cancer," Cancer. (2010); 116(4Suppl): 1075-1083.
Tamburini, J., et al., "Mammalian target of rapamycin (mTOR) inhibition activates phosphatidylinositol 3-kinase/Akt by up-regulating insulin-like growth factor-1 receptor signaling in acute myeloid leukemia: rationale for therapeutic inhibition of both pathways," Blood 111:379-382, 2008.
Tamura, H., et al., "B7-H1 costimulation preferentially enhances CD28-independent T-helper cell function," Blood 97(6):1809-1816, 2001.
Tan, E.M., et al., "The 1982 Revised Criteria for the Classification of System Lupus Erythematosus," Arthritis Rheum. 25(11):1271-1277, 1982.
Tan, L.K., et al., "Influence of the hinge region on complement activation, C1q binding, and segmental flexibility in chimeric human immunoglobulins," Proc. Natl. Acad. Sci. USA 87:162-166, 1990.
Tan, P., et al., "'Superhumanized' Antibodies: Reduction of Immunogenic Potential by Complementarity-Determining Region Grafting with Human Germline Sequences: Application to an Anti-CD28," J. Immunol. 169:1119-1125, 2002.
Tao, M.H., and Morrison, S.L., "Studies of aglycosylated chimeric mouse-human IgG. Role of carbohydrate in the structure and effector functions mediated by the human IgG constant region," J. Immunol. 143(8):2595-2601, 1989.
Targoff, I.N., "Dermatomyositis and Polymyositis," Curr. Probl. Dermatol., pp. 134-180, Sep./Oct. 1991.
Taylor, A.K., and Wall, R., "Selective Removal of α Heavy-Chain Glycosylation Sites Causes Immunoglobulin A Degradation and Reduced Secretion," Mol. Cell. Biol. 8(10):4197-4203, 1988.
Tedder, T.F., et al., "Cloning of a Complementary DNA Encoding a New Mouse B Lymphocyte Differentiation Antigen, Homologous to the Human B1 (CD20) Antigen, and Localization of the Gene to Chromosome 19," J. Immunol. 141(12):4388-4394, 1988.
Tempest, P.R., et al., "Reshaping a Human Monoclonal Antibody to Inhibit Human Respiratory Syncytial Virus Infection in Vivo," Bio/Technology 9:266-271, 1991.
Terry, L.A., et al., "The monoclonal antibody, UCHL1, recognizes a 180,000 MW component of the human leucocyte-common antigen, CD45," Immunol. 64:331-336, 1988.
Thommesen, J.E., et al., "Lysine 322 in the human IgG3 C(H)2 domain is crucial for antibody dependent complement activation," Mol. Immunol. 37:995-1004, 2000.
Thompson et al., "Single-Chain Multivalent Binding Proteins With Effector Function," Office Action dated Dec. 16, 2011, for U.S. Appl. No. 12/304,562, 23 pages.
Thompson et al., "Single-Chain Multivalent Binding Proteins With Effector Function," Office Action dated Jun. 1, 2012, for U.S. Appl. No. 12/304,562, 24 pages.
Thompson et al., "Single-Chain Multivalent Binding Proteins With Effector Function," Office Action dated Jun. 24, 2011, for U.S. Appl. No. 12/304,562, 7 pages.
Thompson, P.A., et al., "Single-Chain Multivalent Binding Proteins with Effector Function," Office Action dated May 5, 2011, for U.S. Appl. No. 12/041,590, 8 pages.
Traunecker, A., et al., "Bispecific single chain molecules (Janusins) target cytotoxic lymphocutes on HIV infected cells," EMBO J. 10(12):3655-3659, 1991.
Treon, S.P., and Anderson, K.C., "The Use of Rituximab in the Treatment of Malignant and Nonmalignant Plasma Cell Disorders," Semin. Oncol. 27(Suppl 12):79-85, 2000.
Treon, S.P., et al., "CD20-Directed Antibody-Mediated Immunotherapy Induces Responses and Facilitates Hematologic Recovery in Patients With Waldenstrom's Macroglobulinemia," J. Immunother. 24(3):272-279, 2001.
Troyer, J.K. et al., "Biochemical characterization and mapping of the 7E11-C5.3 epitope of the prostate-specific membrane antigen," Urol Oncol. (1995); 1(1): 29-37.

Troyer, J.K. et al., "Location of prostate-specific membrane antigen in the LNCaP prostate carcinoma cell line," Prostate. (1997); 30(4): 232-42.
Trubion, "Trubion Pharmaceuticals Announces Upcoming Presentations at the 2006 American Society of Hematology (ASH) Annual Meeting," PR Newswire, Dec. 4, 2006, 2 pages.
Trubion, "Data on Trubion's Drug Candidate TRU-016 Presented at ASCO 2006," Trubion Pharmaceuticals Press Release dated Jun. 4, 2006, 1 page.
Trubion, "Trubion Announces Positive Data for Two Product Candidates at Upcoming American Society of Hematology Meeting; Abstracts to be Published in Nov. 16, 2003 Issue of Blood," PR Newswire, Nov. 20, 2003, 2 pages.
Trubion, "Trubion Announces Presentation of Positive TRU-016 Data at ASCO," PR Newswire, Jun. 2, 2008, 2 pages.
Trubion, "Trubion Announces Upcoming Presentation at the 2007 American Society of Hematology (ASH) Annual Meeting," PR Newswire, Dec. 6, 2007, 2 pages.
Trubion, "Trubion Initiates Phase 1/2 Study of TRU-016 in CLL, Announces Next-Generation Product Candidate for RA and Provides Product Pipeline Update," PR Newswire, Mar. 27, 2008, 3 pages.
Trubion, "Trubion Pharmaceuticals, Inc. Announces Upcoming Presentation at the 2007 ASCO Annual Meeting," PR Newswire, May 31, 2007, 2 pages.
Tuscano, J.M., "Successful Treatment of Infliximab-Refractory Rheumatoid Arthritis with Rituximab," Annual Scientific Meeting of the American College of Rheumatology, New Orleans, LA (Oct. 24-29, 2002), Abstract #LB11, 1 page.
Vajdos, et al., "Comprehensive Functional Maps of the Antigen-binding Site of an Anti-ErbB2 Antibody Obtained with Shotgun Scanning Mutagenesis," Journal of Molecular Biology (2002); 320(2): 415-428.
Van den Abbeele, A.D., et al., "Antigen-binding site protection during radiolabeling leads to a higher immunoreactive fraction," J. Nucl. Med. 32(1):116-122, 1991.
Van den Beucken, T., et al., "Building novel binding ligands of B7.1 and B7.2 based on human antibody single variable light chain domains," J. Mol. Biol. 310:591-601, 2001.
Van Spriel, A.B., et al., "A Regulatory Role for CD37 in T Cell Proliferation," J. Immunol. 172:2953-2961, 2004.
Vanhove et al., "Selective blockade of CD28 and not CTLA-4 with a single-chain Fv-α1-antitrypsin fusion antibody," Blood 102:564-570 (2003).
Vaswani, S.K., and Hamilton, R.G., "Humanized antibodies as potential therapeutic drugs," Ann. Allergy Asthma Immunol. 81:105-119, 1998.
Verhoeyen, M., et al., "Reshaping Human Antibodies: Grafting an Antilysozyme Activity," Science 239:1534-1536, 1988.
Vincent, N., et al., "Long-term correction of mouse dystrophic degeneration by adenovirus-mediated transfer of a minidystrophin gene," Nat. Genet. 5:130-134, 1993.
Vitaliti, A., et al., "Inhibition of tumor angiogenesis by a single-chain antibody directed against vascular endothelial growth factor," Cancer Res. 60:4311-4314, 2000.
Vlasveld, L.T., et al., "Treatment of low-grade non-Hodgkin's lymphoma with continuous infusion of low-dose recombinant interleukin-2 in combination with the B-cell-specific monoclonal antibody CLB-CD19," Cancer Immunol. Immunother. 40:37-47, 1995.
Walker, M.R., et al., "Aglycosylation of human IgG1 and IgG3 monoclonal antibodies can eliminate recognition by human cells expressing Fcγ RI and/or Fcγ RII receptors," Biochem. J. 259:347-353, 1989.
Walther, W., and Stein, U., Eds., Gene Therapy of Cancer: Methods and Protocols, Humana Press, Totowa, NJ, 2000.
Wang et al., "Identification of Prostate Specific Membrane Antigen (PSMA) as the Target of Monoclonal Antibody 107-1A4 by Proteinchip; Array, Surface-Enhanced Laser Desorption/Ionization (SELDI) Technology," Int. J. Cancer 92(6):871-876 (2001).
Wang, B., et al., "Human single-chain Fv immunoconjugates targeted to a melanoma-associated chondroitin sulfate proteoglycan

(56) References Cited

OTHER PUBLICATIONS mediate specific lysis of human melanoma cells by natural killer cells and complement," Proc. Natl. Acad. Sci. USA 96:1627-1632, 1999.
Wang, C.-Y., and Huang, L., "pH-sensitive immunoliposomes mediate target-cell-specific delivery and controlled expression of a foreign gene in mouse," Proc. Natl. Acad. Sci. USA 84:7851-7855, 1987.
Wang, J., et al., "Generation and Characterization of CD20-Specific CD8+Cytotoxic T Lymphocytes (CTL) Genetically Modified by Introduction of an scFvFc:zeta Chimeric T Cell Receptor Gene: Preclinical Studies Prior to a Phase I Trial of Cellular Immunotherapy of Follicular Lymphoma," 44th Annual Meeting of the American Society of Hematology, Blood 100(11), Abstract No. 755, Nov. 16, 2002, 1 page.
Ward, E.S., and Ghetie, V., "The effector functions of immunoglobulins: implications for therapy," Ther. Immunol. 2:77-94, 1995.
Ward, E.S., et al., "Binding activities of a repertoire of single immunoglobulin variable domains secreted from *Escherichia coli*," Nature 341:544-546, 1989.
Warnock, D., et al., "In Vitro Galactosylation of Human IgG at 1 kg Scale Using Recombinant Galactosyltransferase," Biotechnol. Bioeng. 92(7):831-842, 2005.
Weisel, J.W., et al., "A Model for Fibrinogen: Domains and Sequence," Science 230:1388-1391 (1985).
Welschof, M., et al., "The Antigen Binding Domain of Non-idiotypic Human Anti-F(ab')2 Autoantibodies: Study of their Interaction with IgG Hinge Region Epitopes," Hum. Immunol. 60:282-290, 1999.
Weston, K.M., et al., "In vivo binding of mouse IgG via polyreactive surface IgM abrogates progressive lymphocytosis in prolymphocytic leukemia," Leuk. Lymphoma 29:361-373, 1998.
White, C.A., et al., "Anti-CD20 monoclonal antibodies as novel treatments for non-Hodgkin's lymphoma," Pharm. Sci. Technol. Today 2(3):95-101, 1999.
White, M.W., et al., "Activation of Dense Human Tonsilar B Cells. Induction of c-myc Gene Expression via Two Distinct Signal Transduction," J. Immunol. 146(3):846-853, 1991.
Willems et al., "CD3 x CD28 cross-interacting bispecific antibodies improve tumor cell dependent T-cell activation," Cancer Immunol. Immunother. 54:1059-1071 (2005).
Wilson, I.A., and Stanfield, R.L., "A Trojan horse with a sweet tooth," Nat. Struct. Biol. 2:433-436, 1995. Abstract only.
Winberg, G., et al., "Surface Expression of CD28 Single Chain Fv for Costimulation by Tumor Cells," Immunol. Rev. 153:209-223, 1996.
Winkler et al., "Changing the Antigen Binding Specificity by Single Point Mutations of an Anti-p24 (HIV-1) Antibody," J. Immunol. 165: 4505-4514 (2000).
Wolf et al., "BiTEs: bispecific antibody constructs with unique anti-tumor activity," Drug Discov. Today 10(18):1237-1244 (2005).
Wörn, A., and Plückthun, A., "Stability engineering of antibody single-chain Fv fragments," J. Mol. Biol. 305(5):989-1010, 2001.
Wriggers et al., "Control of Protein Functional Dynamics by Peptide Linkers," Biopolymers 80(6):736-746 (2005).
Wright, G.L. et al., "Expression of prostate-specific membrane antigen in normal, benign, and malignant prostate tissues," Urol Oncol. (1995); 1(1): 18-28.
Wright, G.L. et al., "Upregulation of prostate-specific membrane antigen after androgen-deprivation therapy," Urology. (1996); 48(2): 326-34.
Written Opinion and International Search Report for International Patent Application No. PCT/US2009/060286, dated Jul. 7, 2010, 23 pages.
Written Opinion of the International Searching Authority, PCT appl. No. PCT/US2013/037135, 7 pages (dated Jul. 5, 2013).
Written Opinion, dated Aug. 19, 2005, for PCTAN PCT/US03/41600, 4 pages.
Written Opinion, dated Jul. 16, 2007, for PCTAN PCT/US2006/029038, 11 pages.
Written Opinion, dated Nov. 20, 2002, for PCTAN PCT/US02/01487, 4 pages.
Written Opinion, SG appl. No. 11201406346S, 11 pages (dated Sep. 18, 2015).
Written Opinion, SG appl. No. 2013077086, 15 pages (dated Jan. 7, 2015).
Wu et al., "Humanization of a Murine Monoclonal Antibody by Simultaneous Optimization of Framework and CDR Residues," J. Mol. Biol. 294:151-162 (1999).
Wu S. et al., "Use of Bispecific Heteroconjugated Antibodies (Anti-T Cell Antigen Receptor x Anti-MHC Class II) to Study Activation of T Cells with a Full Length or Truncated Antigen Receptor Chain", Journal of Immunology (1993); 150 (6): 2211-2221.
Wu, A.M., et al., "Multimerization of a chimeric anti-CD20 single-chain Fv-Fc fusion protein is mediated through variable domain exchange," Protein Eng. 14(12):1025-1033, 2001.
Wu, C.H., et al., "Targeting Genes: Delivery and Persistent Expression of a Foreign Gene Driven by Mammalian Regulatory Elements in Vivo," J. Biol. Chem. 264(29):16985-16987, 1989.
Xavier, K.A., and Willson, R.C., "Association and Dissociation Kinetics of Anti-Hen Egg Lysozyme Monoclonal Antibodies HyHEL-5 and HyHEL-10," Biophys. J. 74:2036-2045, 1998.
Ye, Z., et al., "Gene therapy for cancer using single-chain Fv fragments specific for 4-1BB," Nat. Med. 8(4):343-348, 2002.
Yokota, T., et al., "Rapid Tumor Penetration of a Single-Chain Fv and Comparison with Other Immunoglobulin Forms," Canc. Res. 52:3402-3408, 1992.
Yokoyama et al., "Immune Functions Encoded by the Natural Killer Gene Complex," Nature Reviews Immunology 3:304-316 (2003).
Yoshida, et al., "T-cell activation and cytokine production via a bispecific single-chain antibody fragment targeted to blood-stage malaria parasites." Blood (2003); 101 (6) :2300-2306. Epub Oct. 31, 2002.
Yoshinaga, S.K., et al., "Characterization of a new human B7-related protein: B7RP-1 is the ligand to the co-stimulatory protein ICOS," Int. Immunol. 12(10):1439-1447, 2000.
Yu et al., "Interaction between Bevacizumab and Murine VEGF-A: A Reassessment," Invest. Ophthalmol. Vis. Sci. 49(2):522-527 (2008).
Yu et al., "Rationalization and Design of the Complementarity Determining Region Sequences in an Antibody-Antigen Recognition Interface," PLoS ONE 7(3):e33340, 15 pages (2012).
Yu, "Coiled-coils: stability, specificity, and drug delivery potential," Adv. Drug Deliv. Rev. 54:1113-1129 (2002).
Zaja, F., et al., "Rituximab for myasthenia gravis developing after bone marrow transplant," Neurology 55:1062-1063, 2000.
Zarling, J.M., et al., "Lysis of Cells Infected with HIV-1 by Human Lymphocytes Targeted with Monoclonal Antibody Heteroconjugates," J. Immunol. 140(8):2609-2613, 1988.
Zelensky and Gready, "The C-type lectin-like domain superfamily," FEBS Journal 272: 6179-6217 (2005).
Zhang et al., "A Human Monoclonal Antimelanoma Single-Chain Fv Antibody Derived from Tumor-infiltrating Lymphocytes," Cancer Res. 55:3584-3591 (1995).
Zhao, X., et al., "Targeting CD37-positive lymphoid malignancies with a novel engineered small modular immunopharmaceutical," Blood 110(7):2569-2577, 2007.
Zhao, X.B., et al., "Novel Anti-CD37 Small Modular Immunopharmaceutical (SMIP) Induces B-Cell-Specific, Caspase-Independent Apoptosis in Human CLL Cells," Blood (ASH Annual Meeting Abstracts) 104:Abstract #2515, 2004, 1 page.
Zhorov, O.V., et al., "Oxidative iodination of rabbit IgG: localization of markers in an Fc-fragment and effects of modification," Biokhimiia 56(5):828-838, 1991 (with PubMed Abstract, PMID: 1747412).
Zhou et al., "Some characteristics and purification of anti-(human ovarian carcinoma) x anti-(human CD3) single chain bispecific antibody," Biotechnol. Appl. Biochem. 47(1):39-47 (2007).
Zhou, "Quantitative Account of the Enhanced Affinity of Two Linked scFvs Specific for Different Epitopes on the Same Antigen." Journal of Molecular Biology (2003); 329 (1): 1-8.

(56) References Cited

OTHER PUBLICATIONS

Hsu et al., "Antibody Variable Domain Interface and Framework Sequence Requirements for Stability and Function by High-Throughput Experiments," Structure, Jan. 7, 2014, 22, 22-34.

Kumagai, I., et al., "Humanized bispecific antibodies retargeting of lymphocytes against tumor cells," Drug Delivery System, 2008, 23-5, pp. 518-525 (English abstract only).

Li, N., et al., "HDAC inhibitor reduces cytokine storm and facilitates induction of chimerism that reverses lupus in anti-CD3 conditioning regimen," PNAS, Mar. 2008, vol. 105, No. 12, pp. 4796-4801.

\* cited by examiner

```
              (1)    1         10        20        30        40        50        60        70        82
DRA222 scFv   (1)    QVQLVESGGGVVQPGRSLRLSCKASGYTFTRSTMHWVRQAPGQGLEWIGYINPSSAYTNYNQKFKDRFTISADKSKSTAFLQ
TSC455 scFv   (1)    QVQLVQSGPEVKKPGSSVKVSCKASGYTFSRSTMHWVRQAPGQGLEWIGYINPSSAYTNYNQKFKDRVTITADKSTSTAYME
TSC456 scFv   (1)    QVQLVQSGPEVKKPGSSVKVSCKASGYTFSRSTMHWVRQAPGQGLEWIGYINPSSAYTNYNQKFKDRVTITADKSTSTAYME
                                                                                                  Section 2

(83)   83        90        100       110       120       130       140       150       164
DRA222 scFv   (83)   MESLRPEDTGVYFCARPQVHYDYNGFPYWGQGTPVTVSSGKGGSGGGGSGGGGS---AQDIQMTQSPSSLSASVGDRVTMTC
TSC455 scFv   (83)   LSSLRSEDTAVYYCARPQVHYDYNGFPYWGQGTPVTVSSGKGGSGGGGSGGGGSGGGGSDIQMTQSPSSLSASVGDRVTMTC
TSC456 scFv   (83)   LSSLRSEDTAVYYCARPQVHYDYNGFPYWGQGTPVTVSSGGGGSGGGGSGGGGSGGGGSDIQMTQSPSSLSASVGDRVTMTC
                                                                                                  Section 3

(165)  165       170       180       190       200       210       220       230       246
DRA222 scFv   (162)  SASSSVSYMNWYQQKPGKAPKRWIYDSSKLASGVPARFSGSGSGTDYTLTISSLQPEDFATYYCQQWSRNPPTFGGGTKLQI
TSC455 scFv   (165)  SASSSVSYMNWYQQKPGKAPKRWIYDSSKLASGVPSRFSGSGSGTEYTLTISSLQPDDFATYYCQQWSRNPPTFGGGTKLEI
TSC456 scFv   (165)  SASSSVSYMNWYQQKPGKAPKRWIYDSSKLASGVPSRFSGSGSGTDYTLTISSLQPDDFATYYCQQWSRNPPTFGGGTKLEI
                                                                                                  Section 4

(247)  247  251
DRA222 scFv   (244)  TSSS-
TSC455 scFv   (247)  KRSSS
TSC456 scFv   (247)  KRSSS
```

| NCA Parameter | Units | TSC471 | TSC266 |
|---|---|---|---|
| HL_Lambda_z | hr | 83.631 | 41.5 |
| Cmax (Tmax) | ug/mL | 144.0 (at 0.25 hr) | 114.33 (at 2 hrs) |
| AUCall | hr*ug/mL | 8561 | 2673.7 |
| AUCINF_obs | hr*ug/mL | 8668 | 2671 |
| Vz_obs | mL/kg | 150.5 | 238.7 |
| Cl_obs | mL/hr/kg | 1.247 | 3.9872 |
| Vss_obs | mL/kg | 137.70 | 197.8 |

Figure 17A

| Parameter Estimate | HL | Cmax | AUC all | AUC inf | Volume | Clearance |
|---|---|---|---|---|---|---|
| Units | hr | ug/mL | hr*ug/mL | hr*ug/mL | mL/kg | mL/hr/kg |
| ROR206a | 116.8 | 306.3 | 16306 | 16920 | 100.1 | 0.594 |
| ROR207a | 128.5 | 280.6 | 22617 | 24113 | 78.1 | 0.421 |
| ROR208a | 112.1 | 278.7 | 18545 | 19279 | 87.4 | 0.540 |
| ROR209a | 163.3 | 198.2 | 20941 | 23252 | 107.8 | 0.458 |

Figure 17B

| Parameter Estimate | CL | CLD2 | V1 | V2 | Alpha HL | Beta HL | AUC |
|---|---|---|---|---|---|---|---|
| Units | mL/hr/kg | mL/hr/kg | mL/kg | mL/kg | hr | hr | hr*ug/mL |
| ROR206a | 0.635 | 4.197 | 29.9 | 70.3 | 3.22 | 117.8 | 15818 |
| ROR207a | 0.440 | 6.165 | 35.6 | 44.6 | 2.18 | 129.2 | 23042 |
| ROR208a | 0.581 | 3.940 | 35.6 | 49.9 | 3.48 | 107.3 | 17926 |
| ROR209a | 0.469 | 3.069 | 53.5 | 56.0 | 5.93 | 168.3 | 22666 |

```
SEQUENCE LISTING

<160> NUMBER OF SEQ ID NOS: 222

<210> SEQ ID NO 1
<211> LENGTH: 1560
<212> TYPE: DNA
<213> ORGANISM: Artificial Sequence
<220> FEATURE:
<223> OTHER INFORMATION: Fc DRA222 (TSC311 or TSC312) CD3-binding domain

<400> SEQUENCE: 1
atggaagcac cagcgcagct tctcttcctc ctgctactct ggctcccaga taccaccggt      60
```

```
gagcccaaat cttctgacaa aactcacaca tgcccaccgt gcccagcacc tgaagccgcg      120
ggtgcaccgt cagtcttcct cttccccca  aaacccaagg acaccctcat gatctcccgg      180 accctgagg  tcacatgcgt ggtggtggac gtgagccacg aagaccctga ggtcaagttc      240
aactggtacg tggacggcgt ggaggtgcat aatgccaaga caaagccgcg ggaggagcag      300
tacaacagca cgtaccgtgt ggtcagcgtc ctcaccgtcc tgcaccagga ctggctgaat      360
ggcaaggcat acgcgtgcgc ggtctccaac aaagccctcc cagcccccat cgagaaaacc      420
atctccaaag ccaaagggca gccccgagaa ccacaggtgt acaccctgcc cccatcccgg      480
gatgagctga ccaagaacca ggtcagcctg acctgcctgg tcaaaggctt ctatccaagc      540
gacatcgccg tggagtggga gagcaatggg cagccggaga caactacaa  gaccacgcct      600 cccgtgctgg actccgacgg ctccttcttc ctctacagca agctcaccgt ggacaagagc      660
aggtggcagc aggggaacgt cttctcatgc tccgtgatgc atgaggctct gcacaaccac      720
tacacgcaga agagcctctc cctgtctccg ggtcagaggc acaacaattc ttccctgaat      780
acaggaactc agatggcagg tcattctccg aattctcagg tccagctggt ggagtctggg      840
ggcggagtgg tgcagcctgg gcggtcactg aggctgtcct gcaaggcttc tggctacacc      900
tttactagat ctacgatgca ctgggtaagg caggcccctg gacaaggtct ggaatggatt      960
ggatacatta atcctagcag tgcttatact aattacaatc agaaattcaa ggacaggttc     1020
acaatcagcg cagacaaatc caagagcaca gccttcctgc agatggacag cctgaggccc     1080
gaggacaccg cgtctatttt ctgtgcacgg ccccaagtcc actatgatta caacgggttt     1140
ccttactggg gccaagggac tcccgtcact gtctctagcg gtggcggagg gtctgggggt     1200
ggcggatccg gaggtggtgg ctctgcacaa gacatccaga tgacccagtc tccaagcagc     1260
ctgtctgcaa gcgtggggga cagggtcacc atgacctgca gtgccagctc aagtgtaagt     1320
tacatgaact ggtaccagca gaagccgggc aaggccccca aaagatggat ttatgactca     1380
tccaaactgg cttctggagt ccctgctcgc ttcagtggca gtgggtctgg gaccgactat     1440
accctcacaa tcagcagcct gcagcccgaa gatttcgcca cttattactg ccagcagtgg     1500
agtcgtaacc cacccacgtt cggaggggg  accaagctac aaattacatc ctccagctaa     1560
```

<210> SEQ ID NO 2
<211> LENGTH: 499
<212> TYPE: PRT
<213> ORGANISM: Artificial Sequence
<220> FEATURE:
<223> OTHER INFORMATION: Fc DRA222 (TSC311 or TSC312) CD3-binding domain

<400> SEQUENCE: 2

Glu Pro Lys Ser Ser Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr P

```
            100                 105                 110
Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Gln Arg His Asn Asn Ser Ser Leu Asn
225                 230                 235                 240

Thr Gly Thr Gln Met Ala Gly His Ser Pro Asn Ser Gln Val Gln Leu
                245                 250                 255

Val Glu Ser Gly Gly Val Val Gln Pro Gly Arg Ser Leu Arg Leu
                260                 265                 270

Ser Cys Lys Ala Ser Gly Tyr Thr Phe Thr Arg Ser Thr Met His Trp
            275                 280                 285

Val Arg Gln Ala Pro Gly Gln Gly Leu Glu Trp Ile Gly Tyr Ile Asn
            290                 295                 300

Pro Ser Ser Ala Tyr Thr Asn Tyr Asn Gln Lys Phe Lys Asp Arg Phe
305                 310                 315                 320

Thr Ile Ser Ala Asp Lys Ser Lys Ser Thr Ala Phe Leu Gln Met Asp
                325                 330                 335

Ser Leu Arg Pro Glu Asp Thr Gly Val Tyr Phe Cys Ala Arg Pro Gln
                340                 345                 350

Val His Tyr Asp Tyr Asn Gly Phe Pro Tyr Trp Gly Gln Gly Thr Pro
            355                 360                 365

Val Thr Val Ser Ser Gly Gly Gly Ser Gly Gly Gly Ser Gly
            370                 375                 380

Gly Gly Gly Ser Ala Gln Asp Ile Gln Met Thr Gln Ser Pro Ser Ser
385                 390                 395                 400

Leu Ser Ala Ser Val Gly Asp Arg Val Thr Met Thr Cys Ser Ala Ser
                405                 410                 415

Ser Ser Val Ser Tyr Met Asn Trp Tyr Gln Gln Lys Pro Gly Lys Ala
            420                 425                 430

Pro Lys Arg Trp Ile Tyr Asp Ser Ser Lys Leu Ala Ser Gly Val Pro
            435                 440                 445

Ala Arg Phe Ser Gly Ser Gly Ser Gly Thr Asp Tyr Thr Leu Thr Ile
450                 455                 460

Ser Ser Leu Gln Pro Glu Asp Phe Ala Thr Tyr Tyr Cys Gln Gln Trp
465                 470                 475                 480

Ser Arg Asn Pro Pro Thr Phe Gly Gly Gly Thr Lys Leu Gln Ile Thr
                485                 490                 495

Ser Ser Ser

<210> SEQ ID NO 3
<211> LENGTH: 1569
```

```
<212> TYPE: DNA
<213> ORGANISM: Artificial Sequence
<220> FEATURE:
<223> OTHER INFORMATION: Fc H7L1 (TSC313) CD3-binding domain

<400> SEQUENCE: 3
atggaagcac cagcgcagct tctcttcctc ctgctactct ggctcccaga taccaccggt      60
gagcccaaat cttctgacaa aactcacaca tgcccaccgt gcccagcacc tgaagccgcg     120
ggtgcaccgt cagtcttcct cttcccccca aacccaagg acaccctcat gatctcccgg      180
acccctgagg tcacatgcgt ggtggtggac gtgagccacg aagaccctga ggtcaagttc     240
aactggtacg tggacggcgt ggaggtgcat aatgccaaga caaagccgcg ggaggagcag     300
tacaacagca cgtaccgtgt ggtcagcgtc ctcaccgtcc tgcaccagga ctggctgaat     360
ggcaaggcat acgcgtgcgc ggtctccaac aaagccctcc cagcccccat cgagaaaacc     420
atctccaaag ccaaagggca gccccgagaa ccacaggtgt acaccctgcc cccatcccgg     480
gatgagctga ccaagaacca ggtcagcctg acctgcctgg tcaaaggctt ctatccaagc     540
gacatcgccg tggagtggga gagcaatggg cagccggaga caactacaa gaccacgcct       600
cccgtgctgg actccgacgg ctccttcttc ctctacagca agctcaccgt ggacaagagc     660
aggtggcagc aggggaacgt cttctcatgc tccgtgatgc atgaggctct gcacaaccac     720
tacacgcaga gagcctctc cctgtctccg ggtcagaggc acaacaattc ttccctgaat      780
acaggaactc agatggcagg tcattctccg aattctcagg tgcagctggt gcagtctggg     840
gctgaggtga agaagcctgg ggcctcagtg aaggtctcct gcaaggcttc tggatacacc     900
ttcaccagat ctacgatgca ctgggtgcga caggcccctg acaagggct tgagtggatg      960
ggatacatta tcctagcag tgcttatact aattacaatc agaaattcaa ggacagggtc     1020
accatgacca gggacacgtc catcagcaca gcctacatgg agctgagcag gctgagatct    1080
gacgacacgg ccgtgtatta ctgtgcgaga cccccaagtcc actatgatta caacgggttt    1140
ccttactggg gccaaggaac cctggtcacc gtctcctcag gtggaggcgg ttcaggcgga    1200
ggtggatccg gcggtggcgg atcggtggc ggcggatctg acatccagat gacccagtct     1260
ccaagcagcc tgtctgcaag cgtggggac agggtcacca tgacctgcag tgccagctca    1320
agtgtaagtt acatgaactg gtaccagcag aagccgggca aggcccccaa agatggatt     1380
tatgactcat ccaaactggc ttctggagtc cctgctcgct tcagtggcag tgggtctggg    1440
accgactata ccctcacaat cagcagcctg cagcccgaag atttcgccac ttattactgc    1500
cagcagtgga gtcgtaaccc acccacgttc ggagggggga ccaagctaca aattacatcc    1560
tccagctaa                                                            1569

<210> SEQ ID NO 4
<211> LENGTH: 502
<212> TYPE: PRT
<213> ORGANISM: Artificial Sequence
<220> FEATURE:
<223> OTHER INFORMATION: Fc H7L1 (TSC313) CD3-binding domain

<400> SEQUENCE: 4

Glu Pro Lys Ser Ser Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45
```

```
Val Asp Val Ser His Glu Asp Pro Glu Val Lys Phe Asn Trp Tyr Val
     50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Ala Tyr Ala Cys Ala Val Ser Asn Lys Ala
                100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Gln Arg His Asn Asn Ser Ser Leu Asn
225                 230                 235                 240

Thr Gly Thr Gln Met Ala Gly His Ser Pro Asn Ser Gln Val Gln Leu
                245                 250                 255

Val Gln Ser Gly Ala Glu Val Lys Lys Pro Gly Ala Ser Val Lys Val
            260                 265                 270

Ser Cys Lys Ala Ser Gly Tyr Thr Phe Thr Arg Ser Thr Met His Trp
        275                 280                 285

Val Arg Gln Ala Pro Gly Gln Gly Leu Glu Trp Met Gly Tyr Ile Asn
290                 295                 300

Pro Ser Ser Ala Tyr Thr Asn Tyr Asn Gln Lys Phe Lys Asp Arg Val
305                 310                 315                 320

Thr Met Thr Arg Asp Thr Ser Ile Ser Thr Ala Tyr Met Glu Leu Ser
                325                 330                 335

Arg Leu Arg Ser Asp Asp Thr Ala Val Tyr Tyr Cys Ala Arg Pro Gln
            340                 345                 350

Val His Tyr Asp Tyr Asn Gly Phe Pro Tyr Trp Gly Gln Gly Thr Leu
        355                 360                 365

Val Thr Val Ser Gly Gly Gly Gly Ser Gly Gly Gly Gly Ser Gly Gly
370                 375                 380

Gly Gly Ser Gly Gly Gly Gly Ser Asp Ile Gln Met Thr Gln Ser
385                 390                 395                 400

Pro Ser Ser Leu Ser Ala Ser Val Gly Asp Arg Val Thr Met Thr Cys
                405                 410                 415

Ser Ala Ser Ser Ser Val Ser Tyr Met Asn Trp Tyr Gln Gln Lys Pro
            420                 425                 430

Gly Lys Ala Pro Lys Arg Trp Ile Tyr Asp Ser Ser Lys Leu Ala Ser
        435                 440                 445

Gly Val Pro Ala Arg Phe Ser Gly Ser Gly Ser Gly Thr Asp Tyr Thr
450                 455                 460
```

```
Leu Thr Ile Ser Ser Leu Gln Pro Glu Asp Phe Ala Thr Tyr Tyr Cys
465                 470                 475                 480

Gln Gln Trp Ser Arg Asn Pro Pro Thr Phe Gly Gly Gly Thr Lys Leu
            485                 490                 495

Gln Ile Thr Ser Ser Ser
            500

<210> SEQ ID NO 5
<211> LENGTH: 1572
<212> TYPE: DNA
<213> ORGANISM: Artificial Sequence
<220> FEATURE:
<223> OTHER INFORMATION: H7L4 (TSC314) CD3-binding domain

<400> SEQUENCE: 5
```

| | | | | | |
|---|---|---|---|---|---|
| atggaagcac | cagcgcagct | tctcttcctc | ctgctactct | ggctcccaga | taccaccggt | 60 |
| gagcccaaat | cttctgacaa | aactcacaca | tgcccaccgt | gcccagcacc | tgaagccgcg | 120 |
| ggtgcaccgt | cagtcttcct | cttcccccca | aaacccaagg | acaccctcat | gatctcccgg | 180 |
| acccctgagg | tcacatgcgt | ggtggtggac | gtgagccacg | aagaccctga | ggtcaagttc | 240 |
| aactggtacg | tggacggcgt | ggaggtgcat | aatgccaaga | caaagccgcg | ggaggagcag | 300 |
| tacaacagca | cgtaccgtgt | ggtcagcgtc | ctcaccgtcc | tgcaccagga | ctggctgaat | 360 |
| ggcaaggcat | acgcgtgcgc | ggtctccaac | aaagccctcc | cagcccccat | cgagaaaacc | 420 |
| atctccaaag | ccaaagggca | gccccgagaa | ccacaggtgt | acaccctgcc | cccatcccgg | 480 |
| gatgagctga | ccaagaacca | ggtcagcctg | acctgcctgg | tcaaaggctt | ctatccaagc | 540 |
| gacatcgccg | tggagtggga | gagcaatggg | cagccggaga | caactacaa | gaccacgcct | 600 |
| cccgtgctgg | actccgacgg | ctccttcttc | ctctacagca | agctcaccgt | ggacaagagc | 660 |
| aggtggcagc | aggggaacgt | cttctcatgc | tccgtgatgc | atgaggctct | gcacaaccac | 720 |
| tacacgcaga | agagcctctc | cctgtctccg | ggtcagaggc | acaacaattc | ttccctgaat | 780 |
| acaggaactc | agatggcagg | tcattctccg | aattctcagg | tgcagctggt | gcagtctggg | 840 |
| gctgaggtga | agaagcctgg | ggcctcagtg | aaggtctcct | gcaaggcttc | tggatacacc | 900 |
| ttcaccagat | ctacgatgca | ctgggtgcga | caggcccctg | gacaagggct | tgagtggatg | 960 |
| ggatacatta | atcctagcag | tgcttatact | aattacaatc | agaaattcaa | ggacagggtc | 1020 |
| accatgacca | gggacacgtc | catcagcaca | gcctacatgg | agctgagcag | gctgagatct | 1080 |
| gacgacacgg | ccgtgtatta | ctgtgcgaga | ccccaagtcc | actatgatta | caacgggttt | 1140 |
| ccttactggg | gccaaggaac | cctggtcacc | gtctcctcag | gtggaggcgg | ttcaggcgga | 1200 |
| ggtggatccg | gcggtggcgg | atcgggtggc | ggcggatctg | aaattgtgtt | gacacagtct | 1260 |
| ccagccaccc | tgtctttgtc | tcaggggaaa | gagccaccc | tctcctgcag | tgccagctca | 1320 |
| agtgtaagtt | acatgaactg | gtaccaacag | aaacctggcc | aggctcccag | gctcctcatc | 1380 |
| tatgactcat | ccaaactggc | ttctggcatc | ccagccaggt | tcagtggcag | tgggtctggg | 1440 |
| acagacttca | ctctcaccat | cagcagccta | gagcctgaag | attttgcagt | ttattactgt | 1500 |
| cagcagtgga | gtcgtaaccc | acccactttc | ggcggaggga | ccaaggtgga | gatcaaacgg | 1560 |
| tcctccagct | aa | | | | | 1572 |

```
<210> SEQ ID NO 6
<211> LENGTH: 503
<212> TYPE: PRT
<213> ORGANISM: Artificial Sequence
<220> FEATURE:
```

<223> OTHER INFORMATION: Fc H7L4 (TSC314) CD3-binding domain

<400> SEQUENCE: 6

```
Glu Pro Lys Ser Ser Asp Lys Thr His Thr Cys Pro Pro Cys Pro Ala
1               5                   10                  15
Pro Glu Ala Ala Gly Ala Pro Ser Val Phe Leu Phe Pro Pro Lys Pro
            20                  25                  30
Lys Asp Thr Leu Met Ile Ser Arg Thr Pro Glu Val Thr Cys Val Val
        35                  40                  45
Val Asp Val Ser His Glu Asp Pro Glu Val Lys Phe Asn Trp Tyr Val
    50                  55                  60
Asp Gly Val Glu Val His Asn Ala Lys Thr Lys Pro Arg Glu Glu Gln
65                  70                  75                  80
Tyr Asn Ser Thr Tyr Arg Val Val Ser Val Leu Thr Val Leu His Gln
                85                  90                  95
Asp Trp Leu Asn Gly Lys Ala Tyr Ala Cys Ala Val Ser Asn Lys Ala
            100                 105                 110
Leu Pro Ala Pro Ile Glu Lys Thr Ile Ser Lys Ala Lys Gly Gln Pro
        115                 120                 125
Arg Glu Pro Gln Val Tyr Thr Leu Pro Pro Ser Arg Asp Glu Leu Thr
    130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Tyr
            180                 185                 190
Ser Lys Leu Thr Val Asp Lys Ser Arg Trp Gln Gln Gly Asn Val Phe
        195                 200                 205
Ser Cys Ser Val Met His Glu Ala Leu His Asn His Tyr Thr Gln Lys
    210                 215                 220
Ser Leu Ser Leu Ser Pro Gly Gln Arg His Asn Asn Ser Ser Leu Asn
225                 230                 235                 240
Thr Gly Thr Gln Met Ala Gly His Ser Pro Asn Ser Gln Val Gln Leu
                245                 250                 255
Val Gln Ser Gly Ala Glu Val Lys Lys Pro Gly Ala Ser Val Lys Val
            260                 265                 270
Ser Cys Lys Ala Ser Gly Tyr Thr Phe Thr Arg Ser Thr Met His Trp
        275                 280                 285
Val Arg Gln Ala Pro Gly Gln Gly Leu Glu Trp Met Gly Tyr Ile Asn
    290                 295                 300
Pro Ser Ser Ala Tyr Thr Asn Tyr Asn Gln Lys Phe Lys Asp Arg Val
305                 310                 315                 320
Thr Met Thr Arg Asp Thr Ser Ile Ser Thr Ala Tyr Met Glu Leu Ser
                325                 330                 335
Arg Leu Arg Ser Asp Asp Thr Ala Val Tyr Tyr Cys Ala Arg Pro Gln
            340                 345                 350
Val His Tyr Asp Tyr Asn Gly Phe Pro Tyr Trp Gly Gln Gly Thr Leu
        355                 360                 365
Val Thr Val Ser Ser Gly Gly Gly Gly Ser Gly Gly Gly Gly Ser Gly
    370                 375                 380
Gly Gly Gly Ser Gly Gly Gly Gly Ser Glu Ile Val Leu Thr Gln Ser
385                 390                 395                 400
```

```
Pro Ala Thr Leu Ser Leu Ser Pro Gly Glu Arg Ala Thr Leu Ser Cys
            405                 410                 415

Ser Ala Ser Ser Ser Val Ser Tyr Met Asn Trp Tyr Gln Gln Lys Pro
            420                 425                 430

Gly Gln Ala Pro Arg Leu Leu Ile Tyr Asp Ser Ser Lys Leu Ala Ser
            435                 440                 445

Gly Ile Pro Ala Arg Phe Ser Gly Ser Gly Ser Gly Thr Asp Phe Thr
            450                 455                 460

Leu Thr Ile Ser Ser Leu Glu Pro Glu Asp Phe Ala Val Tyr Tyr Cys
465                 470                 475                 480

Gln Gln Trp Ser Arg Asn Pro Pro Thr Phe Gly Gly Gly Thr Lys Val
            485                 490                 495

Glu Ile Lys Arg Ser Ser Ser
            500

<210> SEQ ID NO 7
<211> LENGTH: 1572
<212> TYPE: DNA
<213> ORGANISM: Artificial Sequence
<220> FEATURE:
<223> OTHER INFORMATION: Fc H7L5 (TSC315) CD3-binding domain

<400> SEQUENCE: 7
atggaagcac cagcgcagct tctcttcctc ctgctactct ggctcccaga taccaccggt      60
gagcccaaat cttctgacaa aactcacaca tgcccaccgt gcccagcacc tgaagccgcg     120
ggtgcaccgt cagtcttcct cttccccca aaacccaagg acaccctcat gatctcccgg      180 accctgagg tcacatgcgt ggtggtggac gtgagccacg aagaccctga ggtcaagttc      240
aactggtacg tggacggcgt ggaggtgcat aatgccaaga caaagccgcg ggaggagcag     300
tacaacagca cgtaccgtgt ggtcagcgtc ctcaccgtcc tgcaccagga ctggctgaat     360
ggcaaggcat acgcgtgcgc ggtctccaac aaagccctcc cagcccccat cgagaaaacc     420
atctccaaag ccaaagggca gccccgagaa ccacaggtgt acaccctgcc cccatcccgg     480
gatgagctga ccaagaacca ggtcagcctg acctgcctgg tcaaaggctt ctatccaagc     540
gacatcgccg tggagtggga gagcaatggg cagccggaga caactacaa gaccacgcct      600 cccgtgctgg actccgacgg ctccttcttc ctctacagca agctcaccgt ggacaagagc     660
aggtggcagc aggggaacgt cttctcatgc tccgtgatgc atgaggctct gcacaaccac     720
tacacgcaga agagcctctc cctgtctccg ggtcagaggc acaacaattc ttccctgaat     780
acaggaactc agatggcagg tcattctccg aattctcagg tgcagctggt gcagtctggg     840
gctgaggtga agaagcctgg ggcctcagtg aaggtctcct gcaaggcttc tggatacacc     900
ttcaccagat ctacgatgca ctgggtgcga caggcccctg gacaagggct gagtggatg      960 ggatacatta atcctagcag tgcttatact aattacaatc agaaattcaa ggacagggtc    1020
accatgacca gggacacgtc catcagcaca gcctacatgg agctgagcag gctgagatct    1080
gacgacacgg ccgtgtatta ctgtgcgaga ccccaagtcc actatgatta acgggtttt    1140 ccttactggg gccaaggaac cctggtcacc gtctcctcag gtggaggcgg ttcaggcgga    1200
ggtggatccg gcggtggcgg atcgggtggc ggcggatctg acatccagat gacccagtct    1260
ccatcctccc tgtctgcatc tgtaggagac agagtcacca tcacttgcag tgccagctca    1320
agtgtaagtt acatgaactg gtatcagcag aaaccaggga agcccctaa gctcctgatc    1380 tatgactcat ccaaactggc ttctggggtc ccatcaaggt tcagtggcag tggatctggg    1440
```

-continued

```
acagatttca ctctcaccat cagcagtctg caacctgaag attttgcaac ttactactgt      1500
caacagtgga gtcgtaaccc acccactttc ggcggaggga ccaaggtgga gatcaaacgg      1560
tcctccagct aa                                                         1572
```

<210> SEQ ID NO 8
<211> LENGTH: 503
<212> TYPE: PRT
<213> ORGANISM: Artificial Sequence
<220> FEATURE:
<223> OTHER INFORMATION: Fc H7L5 (TSC315) CD3-binding domain

<400> SEQUENCE: 8

```
Glu Pro Lys Ser Ser Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Ala Tyr Ala Cys Ala Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gln Arg His Asn Asn Ser Ser Leu Asn
225                 230                 235                 240

Thr Gly Thr Gln Met Ala Gly His Ser Pro Asn Ser Gln Val Gln Leu
                245                 250                 255

Val Gln Ser Gly Ala Glu Val Lys Lys Pro Gly Ala Ser Val Lys Val
            260                 265                 270

Ser Cys Lys Ala Ser Gly Tyr Thr Phe Thr Arg Ser Thr Met His Trp
        275                 280                 285

Val Arg Gln Ala Pro Gly Gln Gly Leu Glu Trp Met Gly Tyr Ile Asn
    290                 295                 300

Pro Ser Ser Ala Tyr Thr Asn Tyr Asn Gln Lys Phe Lys Asp Arg Val
305                 310                 315                 320

Thr Met Thr Arg Asp Thr Ser Ile Ser Thr Ala Tyr Met Glu Leu Ser
                325                 330                 335
```

```
Arg Leu Arg Ser Asp Asp Thr Ala Val Tyr Tyr Cys Ala Arg Pro Gln
            340                 345                 350

Val His Tyr Asp Tyr Asn Gly Phe Pro Tyr Trp Gly Gln Gly Thr Leu
        355                 360                 365

Val Thr Val Ser Ser Gly Gly Gly Gly Ser Gly Gly Gly Gly Ser Gly
    370                 375                 380

Gly Gly Gly Ser Gly Gly Gly Ser Asp Ile Gln Met Thr Gln Ser
385                 390                 395                 400

Pro Ser Ser Leu Ser Ala Ser Val Gly Asp Arg Val Thr Ile Thr Cys
                405                 410                 415

Ser Ala Ser Ser Ser Val Ser Tyr Met Asn Trp Tyr Gln Gln Lys Pro
            420                 425                 430

Gly Lys Ala Pro Lys Leu Leu Ile Tyr Asp Ser Ser Lys Leu Ala Ser
        435                 440                 445

Gly Val Pro Ser Arg Phe Ser Gly Ser Gly Ser Gly Thr Asp Phe Thr
    450                 455                 460

Leu Thr Ile Ser Ser Leu Gln Pro Glu Asp Phe Ala Thr Tyr Tyr Cys
465                 470                 475                 480

Gln Gln Trp Ser Arg Asn Pro Pro Thr Phe Gly Gly Gly Thr Lys Val
                485                 490                 495

Glu Ile Lys Arg Ser Ser Ser
            500

<210> SEQ ID NO 9
<211> LENGTH: 1569
<212> TYPE: DNA
<213> ORGANISM: Artificial Sequence
<220> FEATURE:
<223> OTHER INFORMATION: Fc H8L1 (TSC316) CD3-binding domain

<400> SEQUENCE: 9
atggaagcac cagcgcagct tctcttcctc ctgctactct ggctcccaga taccaccggt      60
gagcccaaat cttctgacaa aactcacaca tgcccaccgt gcccagcacc tgaagccgcg     120
ggtgcaccgt cagtcttcct cttcccccca aaacccaagg acaccctcat gatctcccgg     180
acccctgagg tcacatgcgt ggtggtggac gtgagccacg aagaccctga ggtcaagttc     240
aactggtacg tggacggcgt ggaggtgcat aatgccaaga caaagccgcg ggaggagcag     300
tacaacagca cgtaccgtgt ggtcagcgtc ctcaccgtcc tgcaccagga ctggctgaat     360
ggcaaggcat acgcgtgcgc ggtctccaac aaagccctcc cagcccccat cgagaaaacc     420
atctccaaag ccaagggca gccccgagaa ccacaggtgt acaccctgcc cccatcccgg     480
gatgagctga ccaagaacca ggtcagcctg acctgcctgg tcaaaggctt ctatccaagc     540
gacatcgccg tggagtggga gagcaatggg cagccggaga acaactacaa gaccacgcct     600
cccgtgctgg actccgacgg ctccttcttc ctctacagca agctcaccgt ggacaagagc     660
aggtggcagc aggggaacgt cttctcatgc tccgtgatgc atgaggctct gcacaaccac     720
tacacgcaga agagcctctc cctgtctccg ggtcagaggc acaacaattc ttccctgaat     780
acaggaactc agatggcagg tcattctccg aattctcagg tgcagctggt gcagtctggg     840
gctgaggtga agaagcctgg ggcctcagtg aaggtttcct gcaaggcatc tggatacacc     900
ttcaccagat ctacgatgca ctgggtgcga caggcccctg acaagggct gagtggatg     960 ggatacatta atcctagcag tgcttatact aattacaatc agaaattcaa ggacagagtc    1020
accatgacca gggacacgtc cacgagcaca gtctacatgg agctgagcag cctgagatct    1080
```

-continued

```
gaggacacgg ccgtgtatta ctgtgctaga ccccaagtcc actatgatta caacgggttt    1140
ccttactggg gccaaggaac cctggtcacc gtctcctcag gtggaggcgg ttcaggcgga    1200
ggtggatccg gcggtggcgg atcgggtggc ggcggatctg acatccagat gacccagtct    1260
ccaagcagcc tgtctgcaag cgtggggac  agggtcacca tgacctgcag tgccagctca    1320
agtgtaagtt acatgaactg gtaccagcag aagccgggca aggcccccaa agatggatt    1380 tatgactcat ccaaactggc ttctggagtc cctgctcgct tcagtggcag tgggtctggg    1440
accgactata ccctcacaat cagcagcctg cagcccgaag atttcgccac ttattactgc    1500
cagcagtgga gtcgtaaccc acccacgttc ggagggggga ccaagctaca aattacatcc    1560
tccagctaa                                                            1569
```

<210> SEQ ID NO 10
<211> LENGTH: 502
<212> TYPE: PRT
<213> ORGANISM: Artificial Sequence
<220> FEATURE:
<223> OTHER INFORMATION: Fc H8L1 (TSC316) CD3-binding domain

<400> SEQUENCE: 10

```
Glu Pro Lys Ser Ser Asp Lys Thr His Thr Cys Pro Pro Cys Pro Ala
1               5                  10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Ala Tyr Ala Cys Ala Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gln Arg His Asn Asn Ser Ser Leu Asn
225                 230                 235                 240

Thr Gly Thr Gln Met Ala Gly His Ser Pro Asn Ser Gln Val Gln Leu
                245                 250                 255

Val Gln Ser Gly Ala Glu Val Lys Lys Pro Gly Ala Ser Val Lys Val
            260                 265                 270
```

```
Ser Cys Lys Ala Ser Gly Tyr Thr Phe Thr Arg Ser Thr Met His Trp
            275                 280                 285

Val Arg Gln Ala Pro Gly Gln Gly Leu Glu Trp Met Gly Tyr Ile Asn
    290                 295                 300

Pro Ser Ser Ala Tyr Thr Asn Tyr Asn Gln Lys Phe Lys Asp Arg Val
305                 310                 315                 320

Thr Met Thr Arg Asp Thr Ser Thr Ser Thr Val Tyr Met Glu Leu Ser
                325                 330                 335

Ser Leu Arg Ser Glu Asp Thr Ala Val Tyr Tyr Cys Ala Arg Pro Gln
            340                 345                 350

Val His Tyr Asp Tyr Asn Gly Phe Pro Tyr Trp Gly Gln Gly Thr Leu
    355                 360                 365

Val Thr Val Ser Ser Gly Gly Gly Gly Ser Gly Gly Gly Gly Ser Gly
370                 375                 380

Gly Gly Ser Gly Gly Gly Gly Ser Asp Ile Gln Met Thr Gln Ser
385                 390                 395                 400

Pro Ser Ser Leu Ser Ala Ser Val Gly Asp Arg Val Thr Met Thr Cys
                405                 410                 415

Ser Ala Ser Ser Ser Val Ser Tyr Met Asn Trp Tyr Gln Gln Lys Pro
            420                 425                 430

Gly Lys Ala Pro Lys Arg Trp Ile Tyr Asp Ser Ser Lys Leu Ala Ser
    435                 440                 445

Gly Val Pro Ala Arg Phe Ser Gly Ser Gly Ser Gly Thr Asp Tyr Thr
    450                 455                 460

Leu Thr Ile Ser Ser Leu Gln Pro Glu Asp Phe Ala Thr Tyr Tyr Cys
465                 470                 475                 480

Gln Gln Trp Ser Arg Asn Pro Pro Thr Phe Gly Gly Gly Thr Lys Leu
                485                 490                 495

Gln Ile Thr Ser Ser Ser
            500

<210> SEQ ID NO 11
<211> LENGTH: 1572
<212> TYPE: DNA
<213> ORGANISM: Artificial Sequence
<220> FEATURE:
<223> OTHER INFORMATION: Fc H8L4 (TSC317) CD3-binding domain

<400> SEQUENCE: 11
atggaagcac cagcgcagct tctcttcctc ctgctactct ggctcccaga taccaccggt      60
gagcccaaat cttctgacaa aactcacaca tgcccaccgt gcccagcacc tgaagccgcg     120
ggtgcaccgt cagtcttcct cttccccca aaacccaagg acaccctcat gatctcccgg     180
acccctgagg tcacatgcgt ggtggtggac gtgagccacg aagaccctga ggtcaagttc     240
aactggtacg tggacggcgt ggaggtgcat aatgccaaga caaagccgcg ggaggagcag     300
tacaacagca cgtaccgtgt ggtcagcgtc ctcaccgtcc tgcaccagga ctggctgaat     360
ggcaaggcat acgcgtgcgc ggtctccaac aaagccctcc cagcccccat cgagaaaacc     420
atctccaaag ccaaagggca gccccgagaa ccacaggtgt acaccctgcc cccatcccgg     480
gatgagctga ccaagaacca ggtcagcctg acctgcctgg tcaaaggctt ctatccaagc     540
gacatcgccg tggagtggga gagcaatggg cagccggaga caactacaa gaccacgcct     600 cccgtgctgg actccgacgg ctccttcttc tcctacagca agctcaccgt ggacaagagc     660
aggtggcagc aggggaacgt cttctcatgc tccgtgatgc atgaggctct gcacaaccac     720
```

```
tacacgcaga agagcctctc cctgtctccg ggtcagaggc acaacaattc ttccctgaat    780
acaggaactc agatggcagg tcattctccg aattctcagg tgcagctggt gcagtctggg    840
gctgaggtga agaagcctgg ggcctcagtg aaggtttcct gcaaggcatc tggatacacc    900
ttcaccagat ctacgatgca ctgggtgcga caggcccctg acaagggcct gagtggatg     960
ggatacatta atcctagcag tgcttatact aattacaatc agaaattcaa ggacagagtc   1020
accatgacca gggacacgtc cacgagcaca gtctacatgg agctgagcag cctgagatct   1080
gaggacacgg ccgtgtatta ctgtgctaga ccccaagtcc actatgatta acgggtttt    1140
ccttactggg gccaaggaac cctggtcacc gtctcctcag gtggaggcgg ttcaggcgga   1200
ggtggatccg gcggtggcgg atcgggtggc ggcggatctg aaattgtgtt gacacagtct   1260
ccagccaccc tgtctttgtc tccaggggaa agagccaccc tctcctgcag tgccagctca   1320
agtgtaagtt acatgaactg gtaccaacag aaacctggcc aggctcccag gctcctcatc   1380
tatgactcat ccaaactggc ttctggcatc ccagccaggt tcagtggcag tgggtctggg   1440
acagacttca ctctcaccat cagcagccta gagcctgaag attttgcagt ttattactgt   1500
cagcagtgga gtcgtaaccc acccactttc ggcggaggga ccaaggtgga gatcaaacgg   1560
tcctccagct aa                                                       1572

<210> SEQ ID NO 12
<211> LENGTH: 503
<212> TYPE: PRT
<213> ORGANISM: Artificial Sequence
<220> FEATURE:
<223> OTHER INFORMATION: Fc H8L4 (TSC317) CD3-binding domain

<400> SEQUENCE: 12

Glu Pro Lys Ser Ser Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Ala Tyr Ala Cys Ala Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205
```

Ser Cys Ser Val Met His Glu Ala Leu His Asn His Tyr Thr Gln Lys
210                 215                 220

Ser Leu Ser Leu Ser Pro Gly Gln Arg His Asn Asn Ser Ser Leu Asn
225                 230                 235                 240

Thr Gly Thr Gln Met Ala Gly His Ser Pro Asn Ser Gln Val Gln Leu
            245                 250                 255

Val Gln Ser Gly Ala Glu Val Lys Lys Pro Gly Ala Ser Val Lys Val
            260                 265                 270

Ser Cys Lys Ala Ser Gly Tyr Thr Phe Thr Arg Ser Thr Met His Trp
            275                 280                 285

Val Arg Gln Ala Pro Gly Gln Gly Leu Glu Trp Met Gly Tyr Ile Asn
290                 295                 300

Pro Ser Ser Ala Tyr Thr Asn Tyr Asn Gln Lys Phe Lys Asp Arg Val
305                 310                 315                 320

Thr Met Thr Arg Asp Thr Ser Thr Ser Thr Val Tyr Met Glu Leu Ser
            325                 330                 335

Ser Leu Arg Ser Glu Asp Thr Ala Val Tyr Tyr Cys Ala Arg Pro Gln
            340                 345                 350

Val His Tyr Asp Tyr Asn Gly Phe Pro Tyr Trp Gly Gln Gly Thr Leu
            355                 360                 365

Val Thr Val Ser Ser Gly Gly Gly Gly Ser Gly Gly Gly Gly Ser Gly
370                 375                 380

Gly Gly Ser Gly Gly Gly Gly Ser Glu Ile Val Leu Thr Gln Ser
385                 390                 395                 400

Pro Ala Thr Leu Ser Leu Ser Pro Gly Glu Arg Ala Thr Leu Ser Cys
            405                 410                 415

Ser Ala Ser Ser Ser Val Ser Tyr Met Asn Trp Tyr Gln Gln Lys Pro
            420                 425                 430

Gly Gln Ala Pro Arg Leu Leu Ile Tyr Asp Ser Ser Lys Leu Ala Ser
            435                 440                 445

Gly Ile Pro Ala Arg Phe Ser Gly Ser Gly Ser Gly Thr Asp Phe Thr
            450                 455                 460

Leu Thr Ile Ser Ser Leu Glu Pro Glu Asp Phe Ala Val Tyr Tyr Cys
465                 470                 475                 480

Gln Gln Trp Ser Arg Asn Pro Pro Thr Phe Gly Gly Gly Thr Lys Val
            485                 490                 495

Glu Ile Lys Arg Ser Ser Ser
            500

<210> SEQ ID NO 13
<211> LENGTH: 1572
<212> TYPE: DNA
<213> ORGANISM: Artificial Sequence
<220> FEATURE:
<223> OTHER INFORMATION: Fc H8L5 (TSC318) CD3-binding domain

<400> SEQUENCE: 13
atggaagcac cagcgcagct tctcttcctc ctgctactct ggctcccaga taccaccggt     60
gagcccaaat cttctgacaa aactcacaca tgcccaccgt gcccagcacc tgaagccgcg    120
ggtgcaccgt cagtcttcct cttccccccc aaacccaagg acaccctcat gatctcccgg    180 accccctgagg tcacatgcgt ggtggtggac gtgagccacg aagaccctga ggtcaagttc    240
aactggtacg tggacggcgt ggaggtgcat aatgccaaga caaagccgcg ggaggagcag    300
tacaacagca cgtaccgtgt ggtcagcgtc ctcaccgtcc tgcaccagga ctggctgaat    360

```
ggcaaggcat acgcgtgcgc ggtctccaac aaagccctcc cagcccccat cgagaaaacc    420
atctccaaag ccaaagggca gccccgagaa ccacaggtgt acaccctgcc cccatcccgg    480
gatgagctga ccaagaacca ggtcagcctg acctgcctgg tcaaaggctt ctatccaagc    540
gacatcgccg tggagtggga gagcaatggg cagccggaga caactacaa gaccacgcct     600 cccgtgctgg actccgacgg ctccttcttc ctctacagca agctcaccgt ggacaagagc    660
aggtggcagc aggggaacgt cttctcatgc tccgtgatgc atgaggctct gcacaaccac    720
tacacgcaga gagcctctc cctgtctccg ggtcagaggc acaacaattc ttccctgaat     780
acaggaactc agatggcagg tcattctccg aattctcagg tgcagctggt gcagtctggg    840
gctgaggtga agaagcctgg ggcctcagtg aaggtttcct gcaaggcatc tggatacacc    900
ttcaccagat ctacgatgca ctgggtgcga caggcccctg acaagggct tgagtggatg      960 ggatacatta atcctagcag tgcttatact aattacaatc agaaattcaa ggacagagtc   1020
accatgacca gggacacgtc cacgagcaca gtctacatgg agctgagcag cctgagatct   1080
gaggacacgg ccgtgtatta ctgtgctaga ccccaagtcc actatgatta caacgggttt   1140
ccttactggg gccaaggaac cctggtcacc gtctcctcag gtggaggcgg ttcaggcgga   1200
ggtggatccg gcggtggcgg atcgggtggc ggcggatctg acatccagat gacccagtct   1260
ccatcctccc tgtctgcatc tgtaggagac agagtcacca tcacttgcag tgccagctca   1320
agtgtaagtt acatgaactg gtatcagcag aaaccaggga agcccctaa gctcctgatc    1380 tatgactcat ccaaactggc ttctggggtc ccatcaaggt tcagtggcag tggatctggg   1440
acagatttca ctctcaccat cagcagtctg caacctgaag attttgcaac ttactactgt   1500
caacagtgga gtcgtaaccc acccactttc ggcggaggga ccaaggtgga gatcaaacgg   1560
tcctccagct aa                                                        1572
```

<210> SEQ ID NO 14
<211> LENGTH: 503
<212> TYPE: PRT
<213> ORGANISM: Artificial Sequence
<220> FEATURE:
<223> OTHER INFORMATION: Fc H8L5 (TSC318) CD3-binding domain

<400> SEQUENCE: 14

```
Glu Pro Lys Ser Ser Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Ala Tyr Ala Cys Ala Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140
```

-continued

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gln Arg His Asn Asn Ser Ser Leu Asn
225                 230                 235                 240

Thr Gly Thr Gln Met Ala Gly His Ser Pro Asn Ser Gln Val Gln Leu
                245                 250                 255

Val Gln Ser Gly Ala Glu Val Lys Lys Pro Gly Ala Ser Val Lys Val
            260                 265                 270

Ser Cys Lys Ala Ser Gly Tyr Thr Phe Thr Arg Ser Thr Met His Trp
        275                 280                 285

Val Arg Gln Ala Pro Gly Gln Gly Leu Glu Trp Met Gly Tyr Ile Asn
    290                 295                 300

Pro Ser Ser Ala Tyr Thr Asn Tyr Asn Gln Lys Phe Lys Asp Arg Val
305                 310                 315                 320

Thr Met Thr Arg Asp Thr Ser Thr Ser Thr Val Tyr Met Glu Leu Ser
                325                 330                 335

Ser Leu Arg Ser Glu Asp Thr Ala Val Tyr Tyr Cys Ala Arg Pro Gln
            340                 345                 350

Val His Tyr Asp Tyr Asn Gly Phe Pro Tyr Trp Gly Gln Gly Thr Leu
        355                 360                 365

Val Thr Val Ser Ser Gly Gly Gly Ser Gly Gly Gly Ser Gly
    370                 375                 380

Gly Gly Gly Ser Gly Gly Gly Ser Asp Ile Gln Met Thr Gln Ser
385                 390                 395                 400

Pro Ser Ser Leu Ser Ala Ser Val Gly Asp Arg Val Thr Ile Thr Cys
                405                 410                 415

Ser Ala Ser Ser Val Ser Tyr Met Asn Trp Tyr Gln Gln Lys Pro
            420                 425                 430

Gly Lys Ala Pro Lys Leu Leu Ile Tyr Asp Ser Ser Lys Leu Ala Ser
        435                 440                 445

Gly Val Pro Ser Arg Phe Ser Gly Ser Gly Ser Gly Thr Asp Phe Thr
    450                 455                 460

Leu Thr Ile Ser Ser Leu Gln Pro Glu Asp Phe Ala Thr Tyr Tyr Cys
465                 470                 475                 480

Gln Gln Trp Ser Arg Asn Pro Pro Thr Phe Gly Gly Gly Thr Lys Val
                485                 490                 495

Glu Ile Lys Arg Ser Ser Ser
            500

<210> SEQ ID NO 15
<211> LENGTH: 1569
<212> TYPE: DNA
<213> ORGANISM: Artificial Sequence
<220> FEATURE:
<223> OTHER INFORMATION: Fc H9L1 (TSC319) CD3-binding domain

<400> SEQUENCE: 15

```
atggaagcac cagcgcagct tctcttcctc ctgctactct ggctcccaga taccaccggt    60
gagcccaaat cttctgacaa aactcacaca tgcccaccgt gcccagcacc tgaagccgcg   120
ggtgcaccgt cagtcttcct cttcccccca aacccaagg acaccctcat gatctcccgg    180
accctgagg tcacatgcgt ggtggtggac gtgagccacg aagaccctga ggtcaagttc    240
aactggtacg tggacggcgt ggaggtgcat aatgccaaga caaagccgcg ggaggagcag    300
tacaacagca cgtaccgtgt ggtcagcgtc ctcaccgtcc tgcaccagga ctggctgaat    360
ggcaaggcat acgcgtgcgc ggtctccaac aaagccctcc cagcccccat cgagaaaacc    420
atctccaaag ccaaagggca gccccgagaa ccacaggtgt acaccctgcc cccatcccgg    480
gatgagctga ccaagaacca ggtcagcctg acctgcctgg tcaaaggctt ctatccaagc    540
gacatcgccg tggagtggga gagcaatggg cagccggaga caactacaa gaccacgcct    600
cccgtgctgg actccgacgg ctccttcttc ctctacagca agctcaccgt ggacaagagc    660
aggtggcagc aggggaacgt cttctcatgc tccgtgatgc atgaggctct gcacaaccac    720
tacacgcaga agagcctctc cctgtctccg ggtcagaggc acaacaattc ttccctgaat    780
acaggaactc agatggcagg tcattctccg aattctcagg tccagcttgt gcagtctggg    840
gctgaggtga agaagcctgg ggcctcagtg aaggtttcct gcaaggcttc tggctacacc    900
tttactagat ctacgatgca ttgggtgcgc caggccccg acaaaggct gagtggatg    960
ggatacatta atcctagcag tgcttatact aattacaatc agaaattcaa ggacagggtc   1020
accattacca gggacacatc cgcgagcaca gcctacatgg agctgagcag cctgagatct   1080
gaagacacg ctgtgtatta ctgtgcgaga ccccaagtcc actatgatta caacgggttt   1140
ccttactggg gccaaggaac cctggtcacc gtctcctcag gtggaggcgg ttcaggcgga   1200
ggtggatccg gcggtggcgg atcgggtggc ggcggatctg acatccagat gacccagtct   1260
ccaagcagcc tgtctgcaag cgtgggggac agggtcacca tgacctgcag tgccagctca   1320
agtgtaagtt acatgaactg gtaccagcag aagccgggca aggcccccaa agatgatt    1380
tatgactcat ccaaactggc ttctggagtc cctgctcgct tcagtggcag tgggtctggg   1440
accgactata ccctcacaat cagcagcctg cagcccgaag atttcgccac ttattactgc   1500
cagcagtgga gtcgtaaccc acccacgttc ggaggggga ccaagctaca aattacatcc   1560
tccagctaa                                                          1569
```

<210> SEQ ID NO 16
<211> LENGTH: 502
<212> TYPE: PRT
<213> ORGANISM: Artificial Sequence
<220> FEATURE:
<223> OTHER INFORMATION: Fc H9L1 (TSC319) CD3-binding domain

<400> SEQUENCE: 16

```
Glu Pro Lys Ser Ser Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp P

-continued

Tyr Asn Ser Thr Tyr Arg Val Val Ser Val Leu Thr Val Leu His Gln
            85                  90                  95

Asp Trp Leu Asn Gly Lys Ala Tyr Ala Cys Ala Val Ser Asn Lys Ala
        100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
            165                 170                 175

Lys Thr Thr Pro Pro Val Leu Asp Ser Asp Gly Ser Phe Phe Leu Tyr
        180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
        210                 215                 220

Ser Leu Ser Leu Ser Pro Gly Gln Arg His Asn Asn Ser Ser Leu Asn
225                 230                 235                 240

Thr Gly Thr Gln Met Ala Gly His Ser Pro Asn Ser Gln Val Gln Leu
            245                 250                 255

Val Gln Ser Gly Ala Glu Val Lys Lys Pro Gly Ala Ser Val Lys Val
            260                 265                 270

Ser Cys Lys Ala Ser Gly Tyr Thr Phe Thr Arg Ser Thr Met His Trp
        275                 280                 285

Val Arg Gln Ala Pro Gly Gln Arg Leu Glu Trp Met Gly Tyr Ile Asn
        290                 295                 300

Pro Ser Ser Ala Tyr Thr Asn Tyr Asn Gln Lys Phe Lys Asp Arg Val
305                 310                 315                 320

Thr Ile Thr Arg Asp Thr Ser Ala Ser Thr Ala Tyr Met Glu Leu Ser
            325                 330                 335

Ser Leu Arg Ser Glu Asp Thr Ala Val Tyr Tyr Cys Ala Arg Pro Gln
        340                 345                 350

Val His Tyr Asp Tyr Asn Gly Phe Pro Tyr Trp Gly Gln Gly Thr Leu
        355                 360                 365

Val Thr Val Ser Ser Gly Gly Gly Ser Gly Gly Gly Gly Ser Gly
        370                 375                 380

Gly Gly Gly Ser Gly Gly Gly Gly Ser Asp Ile Gln Met Thr Gln Ser
385                 390                 395                 400

Pro Ser Ser Leu Ser Ala Ser Val Gly Asp Arg Val Thr Met Thr Cys
            405                 410                 415

Ser Ala Ser Ser Ser Val Ser Tyr Met Asn Trp Tyr Gln Gln Lys Pro
        420                 425                 430

Gly Lys Ala Pro Lys Arg Trp Ile Tyr Asp Ser Ser Lys Leu Ala Ser
        435                 440                 445

Gly Val Pro Ala Arg Phe Ser Gly Ser Gly Ser Gly Thr Asp Tyr Thr
        450                 455                 460

Leu Thr Ile Ser Ser Leu Gln Pro Glu Asp Phe Ala Thr Tyr Tyr Cys
465                 470                 475                 480

Gln Gln Trp Ser Arg Asn Pro Pro Thr Phe Gly Gly Gly Thr Lys Leu
            485                 490                 495

Gln Ile Thr Ser Ser Ser

<210> SEQ ID NO 17
<211> LENGTH: 1572
<212> TYPE: DNA
<213> ORGANISM: Artificial Sequence
<220> FEATURE:
<223> OTHER INFORMATION: Fc H9L4 (TSC320) CD3-binding domain

<400> SEQUENCE: 17

```
atggaagcac cagcgcagct tctcttcctc ctgctactct ggctcccaga taccaccggt      60
gagcccaaat cttctgacaa aactcacaca tgcccaccgt gcccagcacc tgaagccgcg     120
ggtgcaccgt cagtcttcct cttccccca aacccaagg acaccctcat gatctcccgg       180
accctgagg tcacatgcgt ggtggtggac gtgagccacg aagaccctga ggtcaagttc      240
aactggtacg tggacggcgt ggaggtgcat aatgccaaga caaagccgcg ggaggagcag     300
tacaacagca cgtaccgtgt ggtcagcgtc ctcaccgtcc tgcaccagga ctggctgaat     360
ggcaaggcat acgcgtgcgc ggtctccaac aaagccctcc cagcccccat cgagaaaacc     420
atctccaaag ccaaagggca gccccgagaa ccacaggtgt acaccctgcc cccatcccgg     480
gatgagctga ccaagaacca ggtcagcctg acctgcctgg tcaaaggctt ctatccaagc     540
gacatcgccg tggagtggga gagcaatggg cagccggaga caactacaa gaccacgcct      600
cccgtgctgg actccgacgg ctccttcttc ctctacagca agctcaccgt ggacaagagc     660
aggtggcagc aggggaacgt cttctcatgc tccgtgatgc atgaggctct gcacaaccac     720
tacacgcaga agagcctctc cctgtctccg ggtcagaggc acaacaattc ttccctgaat     780
acaggaactc agatggcagg tcattctccg aattctcagg tccagcttgt gcagtctggg     840
gctgaggtga agaagcctgg ggcctcagtg aaggtttcct gcaaggcttc tggctacacc     900
tttactagat ctacgatgca ttgggtgcgc caggccccg acaaaggct gagtggatg        960
ggatacatta atcctagcag tgcttatact aattacaatc agaaattcaa ggacagggtc    1020
accattacca gggacacatc cgcgagcaca gcctacatgg agctgagcag cctgagatct    1080
gaagacacgc tgtgtatta ctgtgcgaga ccccaagtcc actatgatta acgggttt      1140
ccttactggg gccaaggaac cctggtcacc gtctcctcag gtggaggcgg ttcaggcgga    1200
ggtggatccg gcggtggcgg atcgggtggc ggcggatctg aaattgtgtt gacacagtct    1260
ccagccaccc tgtctttgtc tccaggggaa agagccaccc tctcctgcag tgccagctca    1320
agtgtaagtt acatgaactg gtaccaacag aaacctggcc aggctcccag gctcctcatc    1380
tatgactcat ccaaactggc ttctggcatc ccagccaggt tcagtggcag tgggtctggg    1440
acagacttca ctctcaccat cagcagccta gagcctgaag attttgcagt ttattactgt    1500
cagcagtgga gtcgtaaccc acccactttc ggcggaggga ccaaggtgga gatcaaacgg    1560
tcctccagct aa                                                        1572
```

<210> SEQ ID NO 18
<211> LENGTH: 503
<212> TYPE: PRT
<213> ORGANISM: Artificial Sequence
<220> FEATURE:
<223> OTHER INFORMATION: Fc H9L4 (TSC320) CD3-binding domain

<400> SEQUENCE: 18

```
Glu Pro Lys Ser Ser Asp Lys Thr His Thr Cys Pro Pro Cys Pro Ala
1               5                  10                  15
```

-continued

```
Pro Glu Ala Ala Gly Ala Pro Ser Val Phe Leu Phe Pro Pro Lys Pro
             20                  25                  30
Lys Asp Thr Leu Met Ile Ser Arg Thr Pro Glu Val Thr Cys Val Val
         35                  40                  45
Val Asp Val Ser His Glu Asp Pro Glu Val Lys Phe Asn Trp Tyr Val
     50                  55                  60
Asp Gly Val Glu Val His Asn Ala Lys Thr Lys Pro Arg Glu Glu Gln
 65                  70                  75                  80
Tyr Asn Ser Thr Tyr Arg Val Val Ser Val Leu Thr Val Leu His Gln
                 85                  90                  95
Asp Trp Leu Asn Gly Lys Ala Tyr Ala Cys Ala Val Ser Asn Lys Ala
            100                 105                 110
Leu Pro Ala Pro Ile Glu Lys Thr Ile Ser Lys Ala Lys Gly Gln Pro
        115                 120                 125
Arg Glu Pro Gln Val Tyr Thr Leu Pro Pro Ser Arg Asp Glu Leu Thr
    130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Tyr
            180                 185                 190
Ser Lys Leu Thr Val Asp Lys Ser Arg Trp Gln Gln Gly Asn Val Phe
        195                 200                 205
Ser Cys Ser Val Met His Glu Ala Leu His Asn His Tyr Thr Gln Lys
    210                 215                 220
Ser Leu Ser Leu Ser Pro Gly Gln Arg His Asn Asn Ser Ser Leu Asn
225                 230                 235                 240
Thr Gly Thr Gln Met Ala Gly His Ser Pro Asn Ser Gln Val Gln Leu
                245                 250                 255
Val Gln Ser Gly Ala Glu Val Lys Lys Pro Gly Ala Ser Val Lys Val
            260                 265                 270
Ser Cys Lys Ala Ser Gly Tyr Thr Phe Thr Arg Ser Thr Met His Trp
        275                 280                 285
Val Arg Gln Ala Pro Gly Gln Arg Leu Glu Trp Met Gly Tyr Ile Asn
    290                 295                 300
Pro Ser Ser Ala Tyr Thr Asn Tyr Asn Gln Lys Phe Lys Asp Arg Val
305                 310                 315                 320
Thr Ile Thr Arg Asp Thr Ser Ala Ser Thr Ala Tyr Met Glu Leu Ser
                325                 330                 335
Ser Leu Arg Ser Glu Asp Thr Ala Val Tyr Tyr Cys Ala Arg Pro Gln
            340                 345                 350
Val His Tyr Asp Tyr Asn Gly Phe Pro Tyr Trp Gly Gln Gly Thr Leu
        355                 360                 365
Val Thr Val Ser Ser Gly Gly Gly Gly Ser Gly Gly Gly Gly Ser Gly
    370                 375                 380
Gly Gly Ser Gly Gly Gly Gly Ser Glu Ile Val Leu Thr Gln Ser
385                 390                 395                 400
Pro Ala Thr Leu Ser Leu Ser Pro Gly Glu Arg Ala Thr Leu Ser Cys
                405                 410                 415
Ser Ala Ser Ser Ser Val Ser Tyr Met Asn Trp Tyr Gln Gln Lys Pro
            420                 425                 430
Gly Gln Ala Pro Arg Leu Leu Ile Tyr Asp Ser Ser Lys Leu Ala Ser
```

```
                 435                 440                 445
Gly Ile Pro Ala Arg Phe Ser Gly Ser Gly Ser Gly Thr Asp Phe Thr
        450                 455                 460

Leu Thr Ile Ser Ser Leu Glu Pro Glu Asp Phe Ala Val Tyr Tyr Cys
465                 470                 475                 480

Gln Gln Trp Ser Arg Asn Pro Pro Thr Phe Gly Gly Gly Thr Lys Val
                485                 490                 495

Glu Ile Lys Arg Ser Ser Ser
            500
```

<210> SEQ ID NO 19
<211> LENGTH: 1572
<212> TYPE: DNA
<213> ORGANISM: Artificial Sequence
<220> FEATURE:
<223> OTHER INFORMATION: Fc H9L5 (TSC321) CD3-binding domain

<400> SEQUENCE: 19

| | | | | |
|---|---|---|---|---|
| atggaagcac | cagcgcagct | tctcttcctc | ctgctactct | ggctcccaga | taccaccggt | 60 |
| gagcccaaat | cttctgacaa | aactcacaca | tgcccaccgt | gcccagcacc | tgaagccgcg | 120 |
| ggtgcaccgt | cagtcttcct | cttcccccca | aaacccaagg | acaccctcat | gatctcccgg | 180 |
| accccctgagg | tcacatgcgt | ggtggtggac | gtgagccacg | aagaccctga | ggtcaagttc | 240 |
| aactggtacg | tggacggcgt | ggaggtgcat | aatgccaaga | caaagccgcg | ggaggagcag | 300 |
| tacaacagca | cgtaccgtgt | ggtcagcgtc | ctcaccgtcc | tgcaccagga | ctggctgaat | 360 |
| ggcaaggcat | acgcgtgcgc | ggtctccaac | aaagccctcc | cagcccccat | cgagaaaacc | 420 |
| atctccaaag | ccaaagggca | gccccgagaa | ccacaggtgt | acaccctgcc | cccatcccgg | 480 |
| gatgagctga | ccaagaacca | ggtcagcctg | acctgcctgg | tcaaaggctt | ctatccaagc | 540 |
| gacatcgccg | tggagtggga | gagcaatggg | cagccggaga | acaactacaa | gaccacgcct | 600 |
| cccgtgctgg | actccgacgg | ctccttcttc | ctctacagca | agctcaccgt | ggacaagagc | 660 |
| aggtggcagc | aggggaacgt | cttctcatgc | tccgtgatgc | atgaggctct | gcacaaccac | 720 |
| tacacgcaga | agagcctctc | cctgtctccg | ggtcagaggc | acaacaattc | ttccctgaat | 780 |
| acaggaactc | agatggcagg | tcattctccg | aattctcagg | tccagcttgt | gcagtctggg | 840 |
| gctgaggtga | agaagcctgg | ggcctcagtg | aaggtttcct | gcaaggcttc | tggctacacc | 900 |
| tttactagat | ctacgatgca | ttgggtgcgc | caggccccccg | acaaaggct | gagtggatg | 960 |
| ggatacatta | atcctagcag | tgcttatact | aattacaatc | agaaattcaa | ggacagggtc | 1020 |
| accattacca | gggacacatc | cgcgagcaca | gcctacatgg | agctgagcag | cctgagatct | 1080 |
| gaagacacgg | ctgtgtatta | ctgtgcgaga | ccccaagtcc | actatgatta | caacgggttt | 1140 |
| ccttactggg | gccaaggaac | cctggtcacc | gtctcctcag | gtggaggcgg | ttcaggcgga | 1200 |
| ggtggatccg | gcggtggcgg | atcgggtggc | ggcggatctg | acatccagat | gacccagtct | 1260 |
| ccatcctccc | tgtctgcatc | tgtaggagac | agagtcacca | tcacttgcag | tgccagctca | 1320 |
| agtgtaagtt | acatgaactg | gtatcagcag | aaaccaggga | agcccctaa | gctcctgatc | 1380 |
| tatgactcat | ccaaactggc | ttctggggtc | ccatcaaggt | tcagtggcag | tggatctggg | 1440 |
| acagatttca | ctctcaccat | cagcagtctg | caacctgaag | attttgcaac | ttactactgt | 1500 |
| caacagtgga | gtcgtaaccc | acccactttc | ggcggaggga | ccaaggtgga | gatcaaacgg | 1560 |
| tcctccagct | aa | | | | | 1572 |

<210> SEQ ID NO 20
<211> LENGTH: 503
<212> TYPE: PRT
<213> ORGANISM: Artificial Sequence
<220> FEATURE:
<223> OTHER INFORMATION: Fc H9L5 (TSC321) CD3-binding domain

<400> SEQUENCE: 20

```
Glu Pro Lys Ser Ser Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Ala Tyr Ala Cys Ala Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gln Arg His Asn Asn Ser Ser Leu Asn
225                 230                 235                 240

Thr Gly Thr Gln Met Ala Gly His Ser Pro Asn Ser Gln Val Gln Leu
                245                 250                 255

Val Gln Ser Gly Ala Glu Val Lys Lys Pro Gly Ala Ser Val Lys Val
            260                 265                 270

Ser Cys Lys Ala Ser Gly Tyr Thr Phe Thr Arg Ser Thr Met His Trp
        275                 280                 285

Val Arg Gln Ala Pro Gly Gln Arg Leu Glu Trp Met Gly Tyr Ile Asn
    290                 295                 300

Pro Ser Ser Ala Tyr Thr Asn Tyr Asn Gln Lys Phe Lys Asp Arg Val
305                 310                 315                 320

Thr Ile Thr Arg Asp Thr Ser Ala Ser Thr Ala Tyr Met Glu Leu Ser
                325                 330                 335

Ser Leu Arg Ser Glu Asp Thr Ala Val Tyr Tyr Cys Ala Arg Pro Gln
            340                 345                 350

Val His Tyr Asp Tyr Asn Gly Phe Pro Tyr Trp Gly Gln Gly Thr Leu
        355                 360                 365

Val Thr Val Ser Ser Gly Gly Gly Gly Ser Gly Gly Gly Gly Ser Gly
```

Gly Gly Gly Ser Gly Gly Gly Ser Asp Ile Gln Met Thr Gln Ser
385                 390                 395                 400

Pro Ser Ser Leu Ser Ala Ser Val Gly Asp Arg Val Thr Ile Thr Cys
            405                 410                 415

Ser Ala Ser Ser Ser Val Ser Tyr Met Asn Trp Tyr Gln Gln Lys Pro
        420                 425                 430

Gly Lys Ala Pro Lys Leu Leu Ile Tyr Asp Ser Ser Lys Leu Ala Ser
        435                 440                 445

Gly Val Pro Ser Arg Phe Ser Gly Ser Gly Ser Gly Thr Asp Phe Thr
    450                 455                 460

Leu Thr Ile Ser Ser Leu Gln Pro Glu Asp Phe Ala Thr Tyr Tyr Cys
465                 470                 475                 480

Gln Gln Trp Ser Arg Asn Pro Pro Thr Phe Gly Gly Gly Thr Lys Val
                485                 490                 495

Glu Ile Lys Arg Ser Ser Ser
            500

<210> SEQ ID NO 21
<211> LENGTH: 1569
<212> TYPE: DNA
<213> ORGANISM: Artificial Sequence
<220> FEATURE:
<223> OTHER INFORMATION: Fc H10L1 (TSC322) CD3-binding domain

<400> SEQUENCE: 21

| | | |
|---|---|---|
| atggaagcac cagcgcagct tctcttcctc ctgctactct ggctcccaga taccaccggt | 60 |
| gagcccaaat cttctgacaa aactcacaca tgcccaccgt gcccagcacc tgaagccgcg | 120 |
| ggtgcaccgt cagtcttcct cttccccccc aaacccaagg acaccctcat gatctcccgg | 180 |
| acccctgagg tcacatgcgt ggtggtggac gtgagccacg aagaccctga ggtcaagttc | 240 |
| aactggtacg tggacggcgt ggaggtgcat aatgccaaga caaagccgcg ggaggagcag | 300 |
| tacaacagca cgtaccgtgt ggtcagcgtc ctcaccgtcc tgcaccagga ctggctgaat | 360 |
| ggcaaggcat acgcgtgcgc ggtctccaac aaagccctcc cagcccccat cgagaaaacc | 420 |
| atctccaaag ccaaagggca gccccgagaa ccacaggtgt acaccctgcc cccatcccgg | 480 |
| gatgagctga ccaagaacca ggtcagcctg acctgcctgg tcaaaggctt ctatccaagc | 540 |
| gacatcgccg tggagtggga gagcaatggg cagccggaga caactacaa gaccacgcct | 600 |
| cccgtgctgg actccgacgg ctccttcttc ctctacagca agctcaccgt ggacaagagc | 660 |
| aggtggcagc aggggaacgt cttctcatgc tccgtgatgc atgaggctct gcacaaccac | 720 |
| tacacgcaga agagcctctc cctgtctccg ggtcagaggc acaacaattc ttccctgaat | 780 |
| acaggaactc agatggcagg tcattctccg aattctcagg tccagctggt gcaatctggg | 840 |
| gctgaggtga agaagcctgg gtcctcggtg aaggtctcct gcaaggcttc tggaggcacc | 900 |
| ttcagcagat ctacgatgca ctgggtgcga caggccctg acaagggct gagtggatg | 960 |
| ggatacatta tcctagcag tgcttatact aattacaatc agaaattcaa ggacagagtc | 1020 |
| acgattaccg cggacaaatc cacgagcaca gcctacatgg agctgagcag cctgagatct | 1080 |
| gaggacacgg ccgtgtatta ctgtgcgaga ccccaagtcc actatgatta acgggttt | 1140 |
| ccttactggg gccaaggaac cctggtcacc gtctcctcag gtggaggcgg ttcaggcgga | 1200 |
| ggtggatccg gcggtggcgg atcgggtggc ggcggatctg acatccagat gacccagtct | 1260 |
| ccaagcagcc tgtctgcaag cgtggggac agggtcacca tgacctgcag tgccagctca | 1320 |

```
agtgtaagtt acatgaactg gtaccagcag aagccgggca aggcccccaa aagatggatt    1380
tatgactcat ccaaactggc ttctggagtc cctgctcgct tcagtggcag tgggtctggg    1440
accgactata ccctcacaat cagcagcctg cagcccgaag atttcgccac ttattactgc    1500
cagcagtgga gtcgtaaccc acccacgttc ggaggggga ccaagctaca aattacatcc    1560
tccagctaa                                                            1569
```

<210> SEQ ID NO 22
<211> LENGTH: 502
<212> TYPE: PRT
<213> ORGANISM: Artificial Sequence
<220> FEATURE:
<223> OTHER INFORMATION: Fc H10L1 (TSC322) CD3-binding domain

<400> SEQUENCE: 22

```
Glu Pro Lys Ser Ser Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Ala Tyr Ala Cys Ala Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gln Arg His Asn Asn Ser Ser Leu Asn
225                 230                 235                 240

Thr Gly Thr Gln Met Ala Gly His Ser Pro Asn Ser Gln Val Gln Leu
                245                 250                 255

Val Gln Ser Gly Ala Glu Val Lys Lys Pro Gly Ser Ser Val Lys Val
            260                 265                 270

Ser Cys Lys Ala Ser Gly Gly Thr Phe Ser Arg Ser Thr Met His Trp
        275                 280                 285

Val Arg Gln Ala Pro Gly Gln Gly Leu Glu Trp Met Gly Tyr Ile Asn
    290                 295                 300

Pro Ser Ser Ala Tyr Thr Asn Tyr Asn Gln Lys Phe Lys Asp Arg Val
```

| | | | | 305 | | | | 310 | | | | 315 | | | | 320 |
|---|---|---|---|---|---|---|---|---|---|---|---|---|---|---|---|---|
Thr Ile Thr Ala Asp Lys Ser Thr Ser Thr Ala Tyr Met Glu Leu Ser
                        325                 330                 335

Ser Leu Arg Ser Glu Asp Thr Ala Val Tyr Tyr Cys Ala Arg Pro Gln
                340                 345                 350

Val His Tyr Asp Tyr Asn Gly Phe Pro Tyr Trp Gly Gln Gly Thr Leu
                355                 360                 365

Val Thr Val Ser Ser Gly Gly Gly Gly Ser Gly Gly Gly Ser Gly
        370                 375                 380

Gly Gly Gly Ser Gly Gly Gly Ser Asp Ile Gln Met Thr Gln Ser
385                 390                 395                 400

Pro Ser Ser Leu Ser Ala Ser Val Gly Asp Arg Val Thr Met Thr Cys
                405                 410                 415

Ser Ala Ser Ser Ser Val Ser Tyr Met Asn Trp Tyr Gln Gln Lys Pro
                420                 425                 430

Gly Lys Ala Pro Lys Arg Trp Ile Tyr Asp Ser Ser Lys Leu Ala Ser
                435                 440                 445

Gly Val Pro Ala Arg Phe Ser Gly Ser Gly Ser Gly Thr Asp Tyr Thr
        450                 455                 460

Leu Thr Ile Ser Ser Leu Gln Pro Glu Asp Phe Ala Thr Tyr Tyr Cys
465                 470                 475                 480

Gln Gln Trp Ser Arg Asn Pro Pro Thr Phe Gly Gly Gly Thr Lys Leu
                485                 490                 495

Gln Ile Thr Ser Ser Ser
                500

<210> SEQ ID NO 23
<211> LENGTH: 1572
<212> TYPE: DNA
<213> ORGANISM: Artificial Sequence
<220> FEATURE:
<223> OTHER INFORMATION: Fc H10L4 (TSC323) CD3-binding domain

<400> SEQUENCE: 23

```
atggaagcac cagcgcagct tctcttcctc ctgctactct ggctcccaga taccaccggt      60
gagcccaaat cttctgacaa aactcacaca tgcccaccgt gcccagcacc tgaagccgcg     120
ggtgcaccgt cagtcttcct cttccccccca aaacccaagg acaccctcat gatctcccgg    180
acccctgagg tcacatgcgt ggtggtggac gtgagccacg aagaccctga ggtcaagttc     240
aactggtacg tggacggcgt ggaggtgcat aatgccaaga caaagccgcg ggaggagcag     300
tacaacagca cgtaccgtgt ggtcagcgtc ctcaccgtcc tgcaccagga ctggctgaat     360
ggcaaggcat acgcgtgcgc ggtctccaac aaagccctcc cagcccccat cgagaaaacc     420
atctccaaag ccaaagggca gccccgagaa ccacaggtgt acaccctgcc cccatcccgg     480
gatgagctga ccaagaacca ggtcagcctg acctgcctgg tcaaaggctt ctatccaagc     540
gacatcgccg tggagtggga gagcaatggg cagccggaga caactacaa gaccacgcct     600
cccgtgctgg actccgacgg ctccttcttc ctctacagca agctcaccgt ggacaagagc     660
aggtggcagc aggggaacgt cttctcatgc tccgtgatgc atgaggctct gcacaaccac    720
tacacgcaga agagcctctc cctgtctccg ggtcagaggc acaacaattc ttccctgaat    780
acaggaactc agatggcagg tcattctccg aattctcagg tccagctggt gcaatctggg    840
gctgaggtga agaagcctgg gtcctcgtgt aaggtctcct gcaaggcttc tggaggcacc    900
ttcagcagat ctacgatgca ctgggtgcga caggcccctg gacaagggct tgagtggatg    960
```

-continued

```
ggatacatta atcctagcag tgcttatact aattacaatc agaaattcaa ggacagagtc    1020
acgattaccg cggacaaatc cacgagcaca gcctacatgg agctgagcag cctgagatct    1080
gaggacacgg ccgtgtatta ctgtgcgaga ccccaagtcc actatgatta acgggttt     1140 ccttactggg gccaaggaac cctggtcacc gtctcctcag gtggaggcgg ttcaggcgga    1200
ggtggatccg gcggtggcgg atcgggtggc ggcggatctg aaattgtgtt gacacagtct    1260
ccagccaccc tgtctttgtc tccaggggaa agagccaccc tctcctgcag tgccagctca    1320
agtgtaagtt acatgaactg gtaccaacag aaacctggcc aggctcccag gctcctcatc    1380
tatgactcat ccaaactggc ttctggcatc ccagccaggt tcagtggcag tgggtctggg    1440
acagacttca ctctcaccat cagcagccta gagcctgaag attttgcagt ttattactgt    1500
cagcagtgga gtcgtaaccc acccactttc ggcggaggga ccaaggtgga gatcaaacgg    1560
tcctccagct aa                                                       1572
```

<210> SEQ ID NO 24
<211> LENGTH: 503
<212> TYPE: PRT
<213> ORGANISM: Artificial Sequence
<220> FEATURE:
<223> OTHER INFORMATION: Fc H10L4 (TSC323) CD3-binding domain

<400> SEQUENCE: 24

```
Glu Pro Lys Ser Ser Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Ala Tyr Ala Cys Ala Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gln Arg His Asn Asn Ser Ser Leu Asn
225                 230                 235                 240

Thr Gly Thr Gln Met Ala Gly His Ser Pro Asn Ser Gln Val Gln Leu
```

```
                245                 250                 255
Val Gln Ser Gly Ala Glu Val Lys Lys Pro Gly Ser Ser Val Lys Val
            260                 265                 270

Ser Cys Lys Ala Ser Gly Gly Thr Phe Ser Arg Ser Thr Met His Trp
        275                 280                 285

Val Arg Gln Ala Pro Gly Gln Gly Leu Glu Trp Met Gly Tyr Ile Asn
    290                 295                 300

Pro Ser Ser Ala Tyr Thr Asn Tyr Asn Gln Lys Phe Lys Asp Arg Val
305                 310                 315                 320

Thr Ile Thr Ala Asp Lys Ser Thr Ser Thr Ala Tyr Met Glu Leu Ser
                325                 330                 335

Ser Leu Arg Ser Glu Asp Thr Ala Val Tyr Tyr Cys Ala Arg Pro Gln
            340                 345                 350

Val His Tyr Asp Tyr Asn Gly Phe Pro Tyr Trp Gly Gln Gly Thr Leu
        355                 360                 365

Val Thr Val Ser Ser Gly Gly Gly Gly Ser Gly Gly Gly Gly Ser Gly
    370                 375                 380

Gly Gly Ser Gly Gly Gly Gly Ser Glu Ile Val Leu Thr Gln Ser
385                 390                 395                 400

Pro Ala Thr Leu Ser Leu Ser Pro Gly Glu Arg Ala Thr Leu Ser Cys
                405                 410                 415

Ser Ala Ser Ser Val Ser Tyr Met Asn Trp Tyr Gln Gln Lys Pro
            420                 425                 430

Gly Gln Ala Pro Arg Leu Leu Ile Tyr Asp Ser Ser Lys Leu Ala Ser
        435                 440                 445

Gly Ile Pro Ala Arg Phe Ser Gly Ser Gly Ser Gly Thr Asp Phe Thr
    450                 455                 460

Leu Thr Ile Ser Ser Leu Glu Pro Glu Asp Phe Ala Val Tyr Tyr Cys
465                 470                 475                 480

Gln Gln Trp Ser Arg Asn Pro Pro Thr Phe Gly Gly Gly Thr Lys Val
                485                 490                 495

Glu Ile Lys Arg Ser Ser Ser
            500

<210> SEQ ID NO 25
<211> LENGTH: 1572
<212> TYPE: DNA
<213> ORGANISM: Artificial Sequence
<220> FEATURE:
<223> OTHER INFORMATION: Fc H10L5 (TSC324) CD3-binding domain

<400> SEQUENCE: 25
atggaagcac cagcgcagct tctcttcctc ctgctactct ggctcccaga taccaccggt      60
gagcccaaat cttctgacaa aactcacaca tgcccaccgt gcccagcacc tgaagccgcg     120
ggtgcaccgt cagtcttcct cttccccca aacccaagg acaccctcat gatctcccgg      180
acccctgagg tcacatgcgt ggtggtggac gtgagccacg aagaccctga ggtcaagttc     240
aactggtacg tggacggcgt ggaggtgcat aatgccaaga caaagccgcg ggaggagcag     300
tacaacagca cgtaccgtgt ggtcagcgtc ctcaccgtcc tgcaccagga ctggctgaat     360
ggcaaggcat acgcgtgcgc ggtctccaac aaagccctcc cagcccccat cgagaaaacc     420
atctccaaag ccaaagggca gccccgagaa ccacaggtgt acaccctgcc cccatcccgg     480
gatgagctga ccaagaacca ggtcagcctg acctgcctgg tcaaaggctt ctatccaagc     540
gacatcgccg tggagtggga gagcaatggg cagccggaga acaactacaa gaccacgcct     600
```

```
cccgtgctgg actccgacgg ctccttcttc ctctacagca agctcaccgt ggacaagagc    660
aggtggcagc aggggaacgt cttctcatgc tccgtgatgc atgaggctct gcacaaccac    720
tacacgcaga agagcctctc cctgtctccg ggtcagaggc acaacaattc ttccctgaat    780
acaggaactc agatggcagg tcattctccg aattctcagg tccagctggt gcaatctggg    840
gctgaggtga agaagcctgg gtcctcggtg aaggtctcct gcaaggcttc tggaggcacc    900
ttcagcagat ctacgatgca ctgggtgcga caggcccctg gacaagggct tgagtggatg    960
ggatacatta atcctagcag tgcttatact aattacaatc agaaattcaa ggacagagtc   1020
acgattaccg cggacaaatc cacgagcaca gcctacatgg agctgagcag cctgagatct   1080
gaggacacgg ccgtgtatta ctgtgcgaga ccccaagtcc actatgatta caacgggttt   1140
ccttactggg gccaaggaac cctggtcacc gtctcctcag gtggaggcgg ttcaggcgga   1200
ggtggatccg gcggtggcgg atcgggtggc ggcggatctg acatccagat gacccagtct   1260
ccatcctccc tgtctgcatc tgtaggagac agagtcacca tcacttgcag tgccagctca   1320
agtgtaagtt acatgaactg gtatcagcag aaaccaggga agcccctaa gctcctgatc   1380 tatgactcat ccaaactggc ttctggggtc ccatcaaggt tcagtggcag tggatctggg   1440
acagatttca ctctcaccat cagcagtctg caacctgaag attttgcaac ttactactgt   1500
caacagtgga gtcgtaaccc acccactttc ggcggaggga ccaaggtgga gatcaaacgg   1560
tcctccagct aa                                                       1572
```

<210> SEQ ID NO 26
<211> LENGTH: 503
<212> TYPE: PRT
<213> ORGANISM: Artificial Sequence
<220> FEATURE:
<223> OTHER INFORMATION: Fc H10L5 (TSC324) CD3-binding domain

<400> SEQUENCE: 26

```
Glu Pro Lys Ser Ser Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Ala Tyr Ala Cys Ala Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
```

```
            180                 185                 190
Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Gln Arg His Asn Asn Ser Ser Leu Asn
225                 230                 235                 240

Thr Gly Thr Gln Met Ala Gly His Ser Pro Asn Ser Gln Val Gln Leu
                    245                 250                 255

Val Gln Ser Gly Ala Glu Val Lys Lys Pro Gly Ser Ser Val Lys Val
            260                 265                 270

Ser Cys Lys Ala Ser Gly Gly Thr Phe Ser Arg Ser Thr Met His Trp
            275                 280                 285

Val Arg Gln Ala Pro Gly Gln Gly Leu Glu Trp Met Gly Tyr Ile Asn
            290                 295                 300

Pro Ser Ser Ala Tyr Thr Asn Tyr Asn Gln Lys Phe Lys Asp Arg Val
305                 310                 315                 320

Thr Ile Thr Ala Asp Lys Ser Thr Ser Thr Ala Tyr Met Glu Leu Ser
                    325                 330                 335

Ser Leu Arg Ser Glu Asp Thr Ala Val Tyr Tyr Cys Ala Arg Pro Gln
            340                 345                 350

Val His Tyr Asp Tyr Asn Gly Phe Pro Tyr Trp Gly Gln Gly Thr Leu
            355                 360                 365

Val Thr Val Ser Ser Gly Gly Gly Gly Ser Gly Gly Gly Gly Ser Gly
            370                 375                 380

Gly Gly Ser Gly Gly Gly Gly Ser Asp Ile Gln Met Thr Gln Ser
385                 390                 395                 400

Pro Ser Ser Leu Ser Ala Ser Val Gly Asp Arg Val Thr Ile Thr Cys
                    405                 410                 415

Ser Ala Ser Ser Ser Val Ser Tyr Met Asn Trp Tyr Gln Gln Lys Pro
            420                 425                 430

Gly Lys Ala Pro Lys Leu Leu Ile Tyr Asp Ser Ser Lys Leu Ala Ser
            435                 440                 445

Gly Val Pro Ser Arg Phe Ser Gly Ser Gly Ser Gly Thr Asp Phe Thr
            450                 455                 460

Leu Thr Ile Ser Ser Leu Gln Pro Glu Asp Phe Ala Thr Tyr Tyr Cys
465                 470                 475                 480

Gln Gln Trp Ser Arg Asn Pro Pro Thr Phe Gly Gly Gly Thr Lys Val
                    485                 490                 495

Glu Ile Lys Arg Ser Ser Ser
            500

<210> SEQ ID NO 27
<211> LENGTH: 1572
<212> TYPE: DNA
<213> ORGANISM: Artificial Sequence
<220> FEATURE:
<223> OTHER INFORMATION: Fc H7L6 (TSC334) CD3-binding domain

<400> SEQUENCE: 27
atggaagcac cagcgcagct tctcttcctc ctgctactct ggctcccaga taccaccggt      60
gagcccaaat cttctgacaa aactcacaca tgcccaccgt gcccagcacc tgaagccgcg     120
ggtgcaccgt cagtcttcct cttccccccca aaacccaagg acaccctcat gatctcccgg     180
acccctgagg tcacatgcgt ggtggtggac gtgagccacg aagaccctga ggtcaagttc     240
```

```
aactggtacg tggacggcgt ggaggtgcat aatgccaaga caaagccgcg ggaggagcag    300
tacaacagca cgtaccgtgt ggtcagcgtc ctcaccgtcc tgcaccagga ctggctgaat    360
ggcaaggcat acgcatgcgc ggtctccaac aaagccctcc cagcccccat cgagaaaacc    420
atctccaaag ccaaagggca gccccgagaa ccacaggtgt acaccctgcc cccatcccgg    480
gatgagctga ccaagaacca ggtcagcctg acctgcctgg tcaaaggctt ctatccaagc    540
gacatcgccg tggagtggga gagcaatggg cagccggaga caactacaa gaccacgcct    600 cccgtgctgg actccgacgg ctccttcttc ctctacagca agctcaccgt ggacaagagc    660
aggtggcagc aggggaacgt cttctcatgc tccgtgatgc atgaggctct gcacaaccac    720
tacacgcaga agagcctctc cctgtctccg ggtcagaggc acaacaattc ttccctgaat    780
acaggaactc agatggcagg tcattctccg aattctcagg tgcagctggt gcagtctggg    840
gctgaggtga agaagcctgg ggcctcagtg aaggtctcct gcaaggcttc tggatacacc    900
ttcaccagat ctacgatgca ctgggtgcga caggcccctg gacaagggct gagtggatg    960 ggatacatta atcctagcag tgcttatact aattacaatc agaaattcaa ggacagggtc   1020
accatgacca gggacacgtc catcagcaca gcctacatgg agctgagcag gctgagatct   1080
gacgacacgg ccgtgtatta ctgtgcgaga ccccaagtcc actatgatta acgggttt    1140 ccttactggg gccaaggaac cctggtcacc gtctcctcag gtggaggcgg ttcaggcgga   1200
ggtggatccg gcggtggcgg atcgggtggc ggcggatctg acatccagat gacccagtct   1260
ccatcctccc tgtctgcatc tgtaggagac agagtcacca tcacttgcag tgccagctca   1320
agtgtaagtt acatgaactg gtatcagcag aaaccaggga agcccctaa gagatggatt   1380 tatgactcat ccaaactggc ttctggggtc ccatcaaggt tcagtggcag tggatctggg   1440
acagatttca ctctcaccat cagcagtctg caacctgaag attttgcaac ttactactgt   1500
caacagtgga gtcgtaaccc acccactttc ggcggaggga ccaaggtgga gatcaaacgg   1560
tcctccagct aa                                                       1572
```

<210> SEQ ID NO 28
<211> LENGTH: 503
<212> TYPE: PRT
<213> ORGANISM: Artificial Sequence
<220> FEATURE:
<223> OTHER INFORMATION: Fc H7L6 (TSC334) CD3-binding domain

<400> SEQUENCE: 28

```
Glu Pro Lys Ser Ser Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Ala Tyr Ala Cys Ala Val Ser Asn Lys Ala
                100                 105                 110

Leu Pro Ala Pro Ile Glu Lys Thr Ile Ser Lys Ala Lys Gly Gln Pro
```

```
                115                 120                 125
Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Gln Arg His Asn Asn Ser Ser Leu Asn
225                 230                 235                 240

Thr Gly Thr Gln Met Ala Gly His Ser Pro Asn Ser Gln Val Gln Leu
                245                 250                 255

Val Gln Ser Gly Ala Glu Val Lys Lys Pro Gly Ala Ser Val Lys Val
            260                 265                 270

Ser Cys Lys Ala Ser Gly Tyr Thr Phe Thr Arg Ser Thr Met His Trp
        275                 280                 285

Val Arg Gln Ala Pro Gly Gln Gly Leu Glu Trp Met Gly Tyr Ile Asn
290                 295                 300

Pro Ser Ser Ala Tyr Thr Asn Tyr Asn Gln Lys Phe Lys Asp Arg Val
305                 310                 315                 320

Thr Met Thr Arg Asp Thr Ser Ile Ser Thr Ala Tyr Met Glu Leu Ser
                325                 330                 335

Arg Leu Arg Ser Asp Asp Thr Ala Val Tyr Tyr Cys Ala Arg Pro Gln
            340                 345                 350

Val His Tyr Asp Tyr Asn Gly Phe Pro Tyr Trp Gly Gln Gly Thr Leu
        355                 360                 365

Val Thr Val Ser Ser Gly Gly Gly Ser Gly Gly Gly Ser Gly
370                 375                 380

Gly Gly Gly Ser Gly Gly Gly Ser Asp Ile Gln Met Thr Gln Ser
385                 390                 395                 400

Pro Ser Ser Leu Ser Ala Ser Val Gly Asp Arg Val Thr Ile Thr Cys
                405                 410                 415

Ser Ala Ser Ser Ser Val Ser Tyr Met Asn Trp Tyr Gln Gln Lys Pro
            420                 425                 430

Gly Lys Ala Pro Lys Arg Trp Ile Tyr Asp Ser Ser Lys Leu Ala Ser
        435                 440                 445

Gly Val Pro Ser Arg Phe Ser Gly Ser Gly Ser Gly Thr Asp Phe Thr
450                 455                 460

Leu Thr Ile Ser Ser Leu Gln Pro Glu Asp Phe Ala Thr Tyr Tyr Cys
465                 470                 475                 480

Gln Gln Trp Ser Arg Asn Pro Pro Thr Phe Gly Gly Gly Thr Lys Val
                485                 490                 495

Glu Ile Lys Arg Ser Ser Ser
            500

<210> SEQ ID NO 29
<211> LENGTH: 1572
<212> TYPE: DNA
<213> ORGANISM: Artificial Sequence
```

<220> FEATURE:
<223> OTHER INFORMATION: Fc H7L7 (TSC335) CD3-binding domain

<400> SEQUENCE: 29

```
atggaagcac cagcgcagct tctcttcctc ctgctactct ggctcccaga taccaccggt      60
gagcccaaat cttctgacaa aactcacaca tgcccaccgt gcccagcacc tgaagccgcg     120
ggtgcaccgt cagtcttcct cttcccccca aacccaagg acaccctcat gatctcccgg     180
acccctgagg tcacatgcgt ggtggtggac gtgagccacg aagaccctga ggtcaagttc     240
aactggtacg tggacggcgt ggaggtgcat aatgccaaga caaagccgcg ggaggagcag     300
tacaacagca cgtaccgtgt ggtcagcgtc ctcaccgtcc tgcaccagga ctggctgaat     360
ggcaaggcat acgcatgcgc ggtctccaac aaagccctcc cagcccccat cgagaaaacc     420
atctccaaag ccaaagggca gccccgagaa ccacaggtgt acaccctgcc cccatcccgg     480
gatgagctga ccaagaacca ggtcagcctg acctgcctgg tcaaaggctt ctatccaagc     540
gacatcgccg tggagtggga gagcaatggg cagccggaga caactacaa gaccacgcct     600
cccgtgctgg actccgacgg ctccttcttc ctctacagca agctcaccgt ggacaagagc     660
aggtggcagc aggggaacgt cttctcatgc tccgtgatgc atgaggctct gcacaaccac     720
tacacgcaga agagcctctc cctgtctccg ggtcagaggc acaacaattc ttccctgaat     780
acaggaactc agatggcagg tcattctccg aattctcagg tgcagctggt gcagtctggg     840
gctgaggtga agaagcctgg ggcctcagtg aaggtctcct gcaaggcttc tggatacacc     900
ttcaccagat ctacgatgca ctgggtgcga caggcccctg gacaagggct gagtggatg     960
ggatacatta atcctagcag tgcttatact aattacaatc agaaattcaa ggacagggtc    1020
accatgacca gggacacgtc catcagcaca gcctacatgg agctgagcag gctgagatct    1080
gacgacacgg ccgtgtatta ctgtgcgaga ccccaagtcc actatgatta acgggttt     1140
ccttactggg gccaaggaac cctggtcacc gtctcctcag gtggaggcgg ttcaggcgga    1200
ggtggatccg gcggtggcgg atcgggtggc ggcggatctg aaattgtgtt gacgcagtct    1260
ccagccaccc tgtctttgtc tccaggggaa agagccaccc tctcctgcag tgccagctca    1320
agtgtaagtt acatgaactg gtaccagcag aaacctggcc tggcgcccag agatggatt    1380
tatgactcat ccaaactggc ttctggcatc ccagacaggt tcagtggcag tgggtctggg    1440
acagacttca ctctcaccat cagcagactg gagcctgaag attttgcagt gtattactgt    1500
cagcagtgga gtcgtaaccc acccactttc ggcggaggga ccaaggtgga gatcaaacgg    1560
tcctccagct aa                                                        1572
```

<210> SEQ ID NO 30
<211> LENGTH: 503
<212> TYPE: PRT
<213> ORGANISM: Artificial Sequence
<220> FEATURE:
<223> OTHER INFORMATION: Fc H7L7 (TSC335) CD3-binding domain

<400> SEQUENCE: 30

Glu Pro Lys Ser Ser Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val

```
            50                  55                  60
Asp Gly Val Glu Val His Asn Ala Lys Thr Lys Pro Arg Glu Gln
65                  70                  75                  80

Tyr Asn Ser Thr Tyr Arg Val Val Ser Val Leu Thr Val Leu His Gln
                    85                  90                  95

Asp Trp Leu Asn Gly Lys Ala Tyr Ala Cys Ala Val Ser Asn Lys Ala
                100                 105                 110

Leu Pro Ala Pro Ile Glu Lys Thr Ile Ser Lys Ala Lys Gly Gln Pro
                115                 120                 125

Arg Glu Pro Gln Val Tyr Thr Leu Pro Pro Ser Arg Asp Glu Leu Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
                195                 200                 205

Ser Cys Ser Val Met His Glu Ala Leu His Asn His Tyr Thr Gln Lys
        210                 215                 220

Ser Leu Ser Leu Ser Pro Gly Gln Arg His Asn Asn Ser Ser Leu Asn
225                 230                 235                 240

Thr Gly Thr Gln Met Ala Gly His Ser Pro Asn Ser Gln Val Gln Leu
                245                 250                 255

Val Gln Ser Gly Ala Glu Val Lys Lys Pro Gly Ala Ser Val Lys Val
                260                 265                 270

Ser Cys Lys Ala Ser Gly Tyr Thr Phe Thr Arg Ser Thr Met His Trp
        275                 280                 285

Val Arg Gln Ala Pro Gly Gln Gly Leu Glu Trp Met Gly Tyr Ile Asn
        290                 295                 300

Pro Ser Ser Ala Tyr Thr Asn Tyr Asn Gln Lys Phe Lys Asp Arg Val
305                 310                 315                 320

Thr Met Thr Arg Asp Thr Ser Ile Ser Thr Ala Tyr Met Glu Leu Ser
                325                 330                 335

Arg Leu Arg Ser Asp Asp Thr Ala Val Tyr Tyr Cys Ala Arg Pro Gln
                340                 345                 350

Val His Tyr Asp Tyr Asn Gly Phe Pro Tyr Trp Gly Gln Gly Thr Leu
        355                 360                 365

Val Thr Val Ser Ser Gly Gly Gly Ser Gly Gly Gly Ser Gly
        370                 375                 380

Gly Gly Gly Ser Gly Gly Gly Ser Glu Ile Val Leu Thr Gln Ser
385                 390                 395                 400

Pro Ala Thr Leu Ser Leu Ser Pro Gly Glu Arg Ala Thr Leu Ser Cys
                405                 410                 415

Ser Ala Ser Ser Ser Val Ser Tyr Met Asn Trp Tyr Gln Gln Lys Pro
                420                 425                 430

Gly Leu Ala Pro Arg Arg Trp Ile Tyr Asp Ser Ser Lys Leu Ala Ser
                435                 440                 445

Gly Ile Pro Asp Arg Phe Ser Gly Ser Gly Ser Gly Thr Asp Phe Thr
        450                 455                 460

Leu Thr Ile Ser Arg Leu Glu Pro Glu Asp Phe Ala Val Tyr Tyr Cys
465                 470                 475                 480
```

Gln Gln Trp Ser Arg Asn Pro Pro Thr Phe Gly Gly Gly Thr Lys Val
            485                 490                 495

Glu Ile Lys Arg Ser Ser Ser
            500

<210> SEQ ID NO 31
<211> LENGTH: 1572
<212> TYPE: DNA
<213> ORGANISM: Artificial Sequence
<220> FEATURE:
<223> OTHER INFORMATION: Fc H7L8 (TSC336) CD3-binding domain

<400> SEQUENCE: 31

| | | |
|---|---|---|
| atggaagcac cagcgcagct tctcttcctc ctgctactct ggctcccaga taccaccggt | 60 |
| gagcccaaat cttctgacaa aactcacaca tgcccaccgt gcccagcacc tgaagccgcg | 120 |
| ggtgcaccgt cagtcttcct cttccccca aacccaagg acaccctcat gatctcccgg | 180 |
| acccctgagg tcacatgcgt ggtggtggac gtgagccacg aagaccctga ggtcaagttc | 240 |
| aactggtacg tggacggcgt ggaggtgcat aatgccaaga caaagccgcg ggaggagcag | 300 |
| tacaacagca cgtaccgtgt ggtcagcgtc ctcaccgtcc tgcaccagga ctggctgaat | 360 |
| ggcaaggcat acgcatgcgc ggtctccaac aaagccctcc cagcccccat cgagaaaacc | 420 |
| atctccaaag ccaaagggca gccccgagaa ccacaggtgt acaccctgcc cccatcccgg | 480 |
| gatgagctga ccaagaacca ggtcagcctg acctgcctgg tcaaaggctt ctatccaagc | 540 |
| gacatcgccg tggagtggga gagcaatggg cagccggaga acaactacaa gaccacgcct | 600 |
| cccgtgctgg actccgacgg ctccttcttc ctctacagca agctcaccgt ggacaagagc | 660 |
| aggtggcagc aggggaacgt cttctcatgc tccgtgatgc atgaggctct gcacaaccac | 720 |
| tacacgcaga agagcctctc cctgtctccg ggtcagaggc acaacaattc ttccctgaat | 780 |
| acaggaactc agatggcagg tcattctccg aattctcagg tgcagctggt gcagtctggg | 840 |
| gctgaggtga agaagcctgg ggcctcagtg aaggtctcct gcaaggcttc tggatacacc | 900 |
| ttcaccagat ctacgatgca ctgggtgcga caggcccctg acaagggct gagtggatg | 960 |
| ggatacatta atcctagcag tgcttatact aattacaatc agaaattcaa ggacagggtc | 1020 |
| accatgacca gggacacgtc catcagcaca gcctacatgg agctgagcag gctgagatct | 1080 |
| gacgacacgg ccgtgtatta ctgtgcgaga ccccaagtcc actatgatta acgggttt | 1140 |
| ccttactggg gccaaggaac cctggtcacc gtctcctcag gtggaggcgg ttcaggcgga | 1200 |
| ggtggatccg gcggtggcgg atcgggtggc ggcggatctg acatccagat gacccagtct | 1260 |
| ccttccaccc tgtctgcatc tgtaggagac agagtcacca tcacttgcag tgccagctca | 1320 |
| agtgtaagtt acatgaactg gtatcagcag aaaccaggga agcccctaa gagatggatt | 1380 |
| tatgactcat ccaaactggc ttctggggtc ccatcaaggt tcagcggcag tggatctggg | 1440 |
| acagaattca ctctcaccat cagcagcctg cagcctgatg attttgcaac ttattactgc | 1500 |
| caacagtgga gtcgtaaccc acccactttc ggcggaggga ccaaggtgga gatcaaacgg | 1560 |
| tcctccagct aa | 1572 |

<210> SEQ ID NO 32
<211> LENGTH: 503
<212> TYPE: PRT
<213> ORGANISM: Artificial Sequence
<220> FEATURE:
<223> OTHER INFORMATION: Fc H7L8 (TSC336) CD3-binding domain

```
<400> SEQUENCE: 32

Glu Pro Lys Ser Ser Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Ala Cys Ala Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
    195                 200                 205

Ser Cys Ser Val Met His Glu Ala Leu His Asn His Tyr Thr Gln Lys
210                 215                 220

Ser Leu Ser Leu Ser Pro Gly Gln Arg His Asn Asn Ser Ser Leu Asn
225                 230                 235                 240

Thr Gly Thr Gln Met Ala Gly His Ser Pro Asn Ser Gln Val Gln Leu
                245                 250                 255

Val Gln Ser Gly Ala Glu Val Lys Lys Pro Gly Ala Ser Val Lys Val
            260                 265                 270

Ser Cys Lys Ala Ser Gly Tyr Thr Phe Thr Arg Ser Thr Met His Trp
            275                 280                 285

Val Arg Gln Ala Pro Gly Gln Gly Leu Glu Trp Met Gly Tyr Ile Asn
    290                 295                 300

Pro Ser Ser Ala Tyr Thr Asn Tyr Asn Gln Lys Phe Lys Asp Arg Val
305                 310                 315                 320

Thr Met Thr Arg Asp Thr Ser Ile Ser Thr Ala Tyr Met Glu Leu Ser
                325                 330                 335

Arg Leu Arg Ser Asp Asp Thr Ala Val Tyr Tyr Cys Ala Arg Pro Gln
            340                 345                 350

Val His Tyr Asp Tyr Asn Gly Phe Pro Tyr Trp Gly Gln Gly Thr Leu
            355                 360                 365

Val Thr Val Ser Ser Gly Gly Gly Ser Gly Gly Gly Ser
370                 375                 380

Gly Gly Gly Ser Gly Gly Gly Ser Asp Ile Gln Met Thr Gln Ser
385                 390                 395                 400

Pro Ser Thr Leu Ser Ala Ser Val Gly Asp Arg Val Thr Ile Thr Cys
            405                 410                 415
```

```
Ser Ala Ser Ser Val Ser Tyr Met Asn Trp Tyr Gln Gln Lys Pro
        420                 425                 430

Gly Lys Ala Pro Lys Arg Trp Ile Tyr Asp Ser Ser Lys Leu Ala Ser
            435                 440                 445

Gly Val Pro Ser Arg Phe Ser Gly Ser Gly Ser Gly Thr Glu Phe Thr
450                 455                 460

Leu Thr Ile Ser Ser Leu Gln Pro Asp Asp Phe Ala Thr Tyr Tyr Cys
465                 470                 475                 480

Gln Gln Trp Ser Arg Asn Pro Pro Thr Phe Gly Gly Gly Thr Lys Val
                485                 490                 495

Glu Ile Lys Arg Ser Ser Ser
            500
```

```
<210> SEQ ID NO 33
<211> LENGTH: 1572
<212> TYPE: DNA
<213> ORGANISM: Artificial Sequence
<220> FEATURE:
<223> OTHER INFORMATION: Fc H8L6 (TSC337) CD3-binding domain

<400> SEQUENCE: 33
atggaagcac cagcgcagct tctcttcctc ctgctactct ggctcccaga taccaccggt      60
gagcccaaat cttctgacaa aactcacaca tgcccaccgt gcccagcacc tgaagccgcg     120
ggtgcaccgt cagtcttcct cttccccca aaacccaagg acaccctcat gatctcccgg     180 accccctgagg tcacatgcgt ggtggtggac gtgagccacg aagaccctga ggtcaagttc     240
aactggtacg tggacggcgt ggaggtgcat aatgccaaga caaagccgcg ggaggagcag     300
tacaacagca cgtaccgtgt ggtcagcgtc ctcaccgtcc tgcaccagga ctggctgaat     360
ggcaaggcat acgcatgcgc ggtctccaac aaagccctcc cagcccccat cgagaaaacc     420
atctccaaag ccaaagggca gccccgagaa ccacaggtgt acaccctgcc cccatcccgg     480
gatgagctga ccaagaacca ggtcagcctg acctgcctgg tcaaaggctt ctatccaagc     540
gacatcgccg tggagtggga gagcaatggg cagccggaga caactacaa gaccacgcct      600 cccgtgctgg actccgacgg ctccttcttc ctctacagca agctcaccgt ggacaagagc     660
aggtggcagc aggggaacgt cttctcatgc tccgtgatgc atgaggctct gcacaaccac     720
tacacgcaga agagcctctc cctgtctccg ggtcagaggc acaacaattc ttccctgaat     780
acaggaactc agatggcagg tcattctccg aattctcagg tgcagctggt gcagtctggg     840
gctgaggtga agaagcctgg ggcctcagtg aaggtttcct gcaaggcatc tggatacacc     900
ttcaccagat ctacgatgca ctgggtgcga caggcccctg acaagggct gagtggatg      960 ggatacatta atcctagcag tgcttatact aattacaatc agaaattcaa ggacagagtc    1020
accatgacca gggacacgtc cacgagcaca gtctacatgg agctgagcag cctgagatct    1080
gaggacacgg ccgtgtatta ctgtgctaga ccccaagtcc actatgatta acgggttt     1140 ccttactggg gccaaggaac cctggtcacc gtctcctcag gtggaggcgg ttcaggcgga    1200
ggtggatccg gcggtggcgg atcgggtggc ggcggatctg acatccagat gacccagtct    1260
ccatcctccc tgtctgcatc tgtaggagac agagtcacca tcacttgcag tgccagctca    1320
agtgtaagtt acatgaactg gtatcagcag aaaccaggga agcccctaa gagatggatt     1380 tatgactcat ccaaactggc ttctggggtc ccatcaaggt tcagtggcag tggatctggg    1440
acagatttca ctctcaccat cagcagtctg caacctgaag attttgcaac ttactactgt    1500
```

```
caacagtgga gtcgtaaccc acccactttc ggcggaggga ccaaggtgga gatcaaacgg    1560
tcctccagct aa                                                        1572
```

<210> SEQ ID NO 34
<211> LENGTH: 503
<212> TYPE: PRT
<213> ORGANISM: Artificial Sequence
<220> FEATURE:
<223> OTHER INFORMATION: Fc H8L6 (TSC337) CD3-binding domain

<400> SEQUENCE: 34

```
Glu Pro Lys Ser Ser Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Ala Tyr Ala Cys Ala Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gln Arg His Asn Asn Ser Ser Leu Asn
225                 230                 235                 240

Thr Gly Thr Gln Met Ala Gly His Ser Pro Asn Ser Gln Val Gln Leu
                245                 250                 255

Val Gln Ser Gly Ala Glu Val Lys Lys Pro Gly Ala Ser Val Lys Val
            260                 265                 270

Ser Cys Lys Ala Ser Gly Tyr Thr Phe Thr Arg Ser Thr Met His Trp
        275                 280                 285

Val Arg Gln Ala Pro Gly Gln Gly Leu Glu Trp Met Gly Tyr Ile Asn
    290                 295                 300

Pro Ser Ser Ala Tyr Thr Asn Tyr Asn Gln Lys Phe Lys Asp Arg Val
305                 310                 315                 320

Thr Met Thr Arg Asp Thr Ser Thr Ser Thr Val Tyr Met Glu Leu Ser
                325                 330                 335

Ser Leu Arg Ser Glu Asp Thr Ala Val Tyr Tyr Cys Ala Arg Pro Gln
            340                 345                 350
```

```
Val His Tyr Asp Tyr Asn Gly Phe Pro Tyr Trp Gly Gln Gly Thr Leu
        355                 360                 365
Val Thr Val Ser Ser Gly Gly Gly Ser Gly Gly Gly Ser
    370                 375                 380
Gly Gly Gly Ser Gly Gly Gly Ser Asp Ile Gln Met Thr Gln Ser
385                 390                 395                 400
Pro Ser Ser Leu Ser Ala Ser Val Gly Asp Arg Val Thr Ile Thr Cys
                405                 410                 415
Ser Ala Ser Ser Ser Val Ser Tyr Met Asn Trp Tyr Gln Gln Lys Pro
            420                 425                 430
Gly Lys Ala Pro Lys Arg Trp Ile Tyr Asp Ser Ser Lys Leu Ala Ser
        435                 440                 445
Gly Val Pro Ser Arg Phe Ser Gly Ser Gly Ser Gly Thr Asp Phe Thr
    450                 455                 460
Leu Thr Ile Ser Ser Leu Gln Pro Glu Asp Phe Ala Thr Tyr Tyr Cys
465                 470                 475                 480
Gln Gln Trp Ser Arg Asn Pro Pro Thr Phe Gly Gly Gly Thr Lys Val
                485                 490                 495
Glu Ile Lys Arg Ser Ser Ser
            500
```

<210> SEQ ID NO 35
<211> LENGTH: 1572
<212> TYPE: DNA
<213> ORGANISM: Artificial Sequence
<220> FEATURE:
<223> OTHER INFORMATION: Fc H8L7 (TSC338) CD3-binding domain

<400> SEQUENCE: 35

| | | |
|---|---|---|
| atggaagcac cagcgcagct tctcttcctc ctgctactct ggctcccaga taccaccggt | 60 |
| gagcccaaat cttctgacaa aactcacaca tgcccaccgt gcccagcacc tgaagccgcg | 120 |
| ggtgcaccgt cagtcttcct cttcccccca aaacccaagg acaccctcat gatctcccgg | 180 |
| acccctgagg tcacatgcgt ggtggtggac gtgagccacg aagaccctga ggtcaagttc | 240 |
| aactggtacg tggacggcgt ggaggtgcat aatgccaaga caaagccgcg ggaggagcag | 300 |
| tacaacagca cgtaccgtgt ggtcagcgtc ctcaccgtcc tgcaccagga ctggctgaat | 360 |
| ggcaaggcat acgcatgcgc ggtctccaac aaagccctcc cagcccccat cgagaaaacc | 420 |
| atctccaaag ccaaagggca gccccgagaa ccacaggtgt acaccctgcc cccatcccgg | 480 |
| gatgagctga ccaagaacca ggtcagcctg acctgcctgg tcaaaggctt ctatccaagc | 540 |
| gacatcgccg tggagtggga gagcaatggg cagccggaga acaactacaa gaccacgcct | 600 |
| cccgtgctgg actccgacgg ctccttcttc ctctacagca agctcaccgt ggacaagagc | 660 |
| aggtggcagc aggggaacgt cttctcatgc tccgtgatgc atgaggctct gcacaaccac | 720 |
| tacacgcaga agagcctctc cctgtctccg ggtcagaggc acaacaattc ttccctgaat | 780 |
| acaggaactc agatggcagg tcattctccg aattctcagg tgcagctggt gcagtctggg | 840 |
| gctgaggtga agaagcctgg ggcctcagtg aaggtttcct gcaaggcatc tggatacacc | 900 |
| ttcaccagat ctacgatgca ctgggtgcga caggccctg acaagggct gagtggatg | 960 |
| ggatacatta atcctagcag tgcttatact aattacaatc agaaattcaa ggacagagtc | 1020 |
| accatgacca gggacacgtc cacgagcaca gtctacatgg agctgagcag cctgagatct | 1080 |
| gaggacacgg ccgtgtatta ctgtgctaga ccccaagtcc actatgatta caacgggttt | 1140 |

-continued

```
ccttactggg gccaaggaac cctggtcacc gtctcctcag gtggaggcgg ttcaggcgga    1200
ggtggatccg gcggtggcgg atcgggtggc ggcggatctg aaattgtgtt gacgcagtct    1260
ccagccaccc tgtctttgtc tccaggggaa agagccaccc tctcctgcag tgccagctca    1320
agtgtaagtt acatgaactg gtaccagcag aaacctggcc tggcgcccag agatggatt    1380 tatgactcat ccaaactggc ttctggcatc ccagacaggt tcagtggcag tgggtctggg    1440
acagacttca ctctcaccat cagcagactg gagcctgaag attttgcagt gtattactgt    1500
cagcagtgga gtcgtaaccc acccactttc ggcggaggga ccaaggtgga gatcaaacgg    1560
tcctccagct aa                                                        1572
```

<210> SEQ ID NO 36
<211> LENGTH: 503
<212> TYPE: PRT
<213> ORGANISM: Artificial Sequence
<220> FEATURE:
<223> OTHER INFORMATION: Fc H8L7 (TSC338) CD3-binding domain

<400> SEQUENCE: 36

```
Glu Pro Lys Ser Ser Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Ala Tyr Ala Cys Ala Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gln Arg His Asn Asn Ser Ser Leu Asn
225                 230                 235                 240

Thr Gly Thr Gln Met Ala Gly His Ser Pro Asn Ser Gln Val Gln Leu
                245                 250                 255

Val Gln Ser Gly Ala Glu Val Lys Lys Pro Gly Ala Ser Val Lys Val
            260                 265                 270

Ser Cys Lys Ala Ser Gly Tyr Thr Phe Thr Arg Ser Thr Met His Trp
        275                 280                 285
```

Val Arg Gln Ala Pro Gly Gln Gly Leu Glu Trp Met Gly Tyr Ile Asn
    290                 295                 300

Pro Ser Ser Ala Tyr Thr Asn Tyr Asn Gln Lys Phe Lys Asp Arg Val
305                 310                 315                 320

Thr Met Thr Arg Asp Thr Ser Ser Thr Val Tyr Met Glu Leu Ser
                325                 330                 335

Ser Leu Arg Ser Glu Asp Thr Ala Val Tyr Tyr Cys Ala Arg Pro Gln
            340                 345                 350

Val His Tyr Asp Tyr Asn Gly Phe Pro Tyr Trp Gly Gln Gly Thr Leu
        355                 360                 365

Val Thr Val Ser Ser Gly Gly Gly Gly Ser Gly Gly Gly Gly Ser Gly
    370                 375                 380

Gly Gly Ser Gly Gly Gly Gly Ser Glu Ile Val Leu Thr Gln Ser
385                 390                 395                 400

Pro Ala Thr Leu Ser Leu Ser Pro Gly Glu Arg Ala Thr Leu Ser Cys
                405                 410                 415

Ser Ala Ser Ser Ser Val Ser Tyr Met Asn Trp Tyr Gln Gln Lys Pro
            420                 425                 430

Gly Leu Ala Pro Arg Arg Trp Ile Tyr Asp Ser Ser Lys Leu Ala Ser
        435                 440                 445

Gly Ile Pro Asp Arg Phe Ser Gly Ser Gly Ser Gly Thr Asp Phe Thr
    450                 455                 460

Leu Thr Ile Ser Arg Leu Glu Pro Glu Asp Phe Ala Val Tyr Tyr Cys
465                 470                 475                 480

Gln Gln Trp Ser Arg Asn Pro Pro Thr Phe Gly Gly Gly Thr Lys Val
                485                 490                 495

Glu Ile Lys Arg Ser Ser Ser
            500

<210> SEQ ID NO 37
<211> LENGTH: 1572
<212> TYPE: DNA
<213> ORGANISM: Artificial Sequence
<220> FEATURE:
<223> OTHER INFORMATION: Fc H8L8 (TSC339) CD3-binding domain

<400> SEQUENCE: 37
atggaagcac cagcgcagct tctcttcctc ctgctactct ggctcccaga taccaccggt        60
gagcccaaat cttctgacaa aactcacaca tgcccaccgt gcccagcacc tgaagccgcg       120
ggtgcaccgt cagtcttcct cttccccccca aaacccaagg acaccctcat gatctcccgg      180
acccctgagg tcacatgcgt ggtggtggac gtgagccacg aagaccctga ggtcaagttc       240
aactggtacg tggacggcgt ggaggtgcat aatgccaaga caaagccgcg ggaggagcag       300
tacaacagca cgtaccgtgt ggtcagcgtc ctcaccgtcc tgcaccagga ctggctgaat       360
ggcaaggcat acgcatgcgc ggtctccaac aaagccctcc cagcccccat cgagaaaacc       420
atctccaaag ccaaagggca gccccgagaa ccacaggtgt acaccctgcc cccatcccgg       480
gatgagctga ccaagaacca ggtcagcctg acctgcctgg tcaaaggctt ctatccaagc       540
gacatcgccg tggagtggga gagcaatggg cagccggaga caactacaa gaccacgcct        600 ccgtgctgg actccgacgg ctccttcttc ctctacagca agctcaccgt ggacaagagc        660
aggtggcagc aggggaacgt cttctcatgc tccgtgatgc atgaggctct gcacaaccac       720
tacacgcaga gagcctctc cctgtctccg ggtcagaggc acaacaattc ttccctgaat       780

```
acaggaactc agatggcagg tcattctccg aattctcagg tgcagctggt gcagtctggg    840
gctgaggtga agaagcctgg ggcctcagtg aaggtttcct gcaaggcatc tggatacacc    900
ttcaccagat ctacgatgca ctgggtgcga caggcccctg gacaagggct tgagtggatg    960
ggatacatta atcctagcag tgcttatact aattacaatc agaaattcaa ggacagagtc   1020
accatgacca gggacacgtc cacgagcaca gtctacatgg agctgagcag cctgagatct   1080
gaggacacgg ccgtgtatta ctgtgctaga ccccaagtcc actatgatta caacgggttt   1140
ccttactggg gccaaggaac cctggtcacc gtctcctcag gtggaggcgg ttcaggcgga   1200
ggtggatccg gcggtggcgg atcgggtggc ggcggatctg acatccagat gacccagtct   1260
ccttccaccc tgtctgcatc tgtaggagac agagtcacca tcacttgcag tgccagctca   1320
agtgtaagtt acatgaactg gtatcagcag aaaccaggga agcccctaa gagatggatt    1380 tatgactcat ccaaactggc ttctggggtc ccatcaaggt tcagcggcag tggatctggg   1440
acagaattca ctctcaccat cagcagcctg cagcctgatg attttgcaac ttattactgc   1500
caacagtgga gtcgtaaccc acccactttc ggcggaggga ccaaggtgga gatcaaacgg   1560
tcctccagct aa                                                       1572
```

<210> SEQ ID NO 38
<211> LENGTH: 503
<212> TYPE: PRT
<213> ORGANISM: Artificial Sequence
<220> FEATURE:
<223> OTHER INFORMATION: Fc H8L8 (TSC339) CD3-binding domain

<400> SEQUENCE: 38

```
Glu Pro Lys Ser Ser Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Ala Tyr Ala Cys Ala Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220
```

```
Ser Leu Ser Leu Ser Pro Gly Gln Arg His Asn Asn Ser Ser Leu Asn
225                 230                 235                 240

Thr Gly Thr Gln Met Ala Gly His Ser Pro Asn Ser Gln Val Gln Leu
            245                 250                 255

Val Gln Ser Gly Ala Glu Val Lys Lys Pro Gly Ala Ser Val Lys Val
        260                 265                 270

Ser Cys Lys Ala Ser Gly Tyr Thr Phe Thr Arg Ser Thr Met His Trp
    275                 280                 285

Val Arg Gln Ala Pro Gly Gln Gly Leu Glu Trp Met Gly Tyr Ile Asn
290                 295                 300

Pro Ser Ser Ala Tyr Thr Asn Tyr Asn Gln Lys Phe Lys Asp Arg Val
305                 310                 315                 320

Thr Met Thr Arg Asp Thr Ser Thr Ser Thr Val Tyr Met Glu Leu Ser
            325                 330                 335

Ser Leu Arg Ser Glu Asp Thr Ala Val Tyr Tyr Cys Ala Arg Pro Gln
        340                 345                 350

Val His Tyr Asp Tyr Asn Gly Phe Pro Tyr Trp Gly Gln Gly Thr Leu
    355                 360                 365

Val Thr Val Ser Ser Gly Gly Gly Gly Ser Gly Gly Gly Gly Ser Gly
370                 375                 380

Gly Gly Ser Gly Gly Gly Gly Ser Asp Ile Gln Met Thr Gln Ser
385                 390                 395                 400

Pro Ser Thr Leu Ser Ala Ser Val Gly Asp Arg Val Thr Ile Thr Cys
            405                 410                 415

Ser Ala Ser Ser Ser Val Ser Tyr Met Asn Trp Tyr Gln Gln Lys Pro
        420                 425                 430

Gly Lys Ala Pro Lys Arg Trp Ile Tyr Asp Ser Ser Lys Leu Ala Ser
    435                 440                 445

Gly Val Pro Ser Arg Phe Ser Gly Ser Gly Ser Gly Thr Glu Phe Thr
450                 455                 460

Leu Thr Ile Ser Ser Leu Gln Pro Asp Asp Phe Ala Thr Tyr Tyr Cys
465                 470                 475                 480

Gln Gln Trp Ser Arg Asn Pro Pro Thr Phe Gly Gly Gly Thr Lys Val
            485                 490                 495

Glu Ile Lys Arg Ser Ser Ser
            500
```

<210> SEQ ID NO 39
<211> LENGTH: 1572
<212> TYPE: DNA
<213> ORGANISM: Artificial Sequence
<220> FEATURE:
<223> OTHER INFORMATION: Fc H10L6 (TSC340) CD3-binding domain

<400> SEQUENCE: 39

```
atggaagcac cagcgcagct tctcttcctc ctgctactct ggctcccaga taccaccggt      60
gagcccaaat cttctgacaa aactcacaca tgcccaccgt gcccagcacc tgaagccgcg     120
ggtgcaccgt cagtcttcct cttcccccca aaacccaagg acaccctcat gatctcccgg     180
acccctgagg tcacatgcgt ggtggtggac gtgagccacg aagaccctga ggtcaagttc     240
aactggtacg tggacggcgt ggaggtgcat aatgccaaga caaagccgcg ggaggagcag     300
tacaacagca cgtaccgtgt ggtcagcgtc ctcaccgtcc tgcaccagga ctggctgaat     360
ggcaaggcat acgcatgcgc ggtctccaac aaagccctcc cagcccccat cgagaaaacc     420
```

-continued

```
atctccaaag ccaaagggca gccccgagaa ccacaggtgt acaccctgcc cccatcccgg      480
gatgagctga ccaagaacca ggtcagcctg acctgcctgg tcaaaggctt ctatccaagc      540
gacatcgccg tggagtggga gagcaatggg cagccggaga caactacaa gaccacgcct       600 cccgtgctgg actccgacgg ctccttcttc ctctacagca agctcaccgt ggacaagagc      660
aggtggcagc aggggaacgt cttctcatgc tccgtgatgc atgaggctct gcacaaccac      720
tacacgcaga gagcctctc cctgtctccg ggtcagaggc acaacaattc ttccctgaat       780
acaggaactc agatggcagg tcattctccg aattctcagg tccagctggt gcaatctggg      840
gctgaggtga agaagcctgg gtcctcggtg aaggtctcct gcaaggcttc tggaggcacc      900
ttcagcagat ctacgatgca ctgggtgcga caggcccctg gacaagggct tgagtggatg      960
ggatacatta atcctagcag tgcttatact aattacaatc agaaattcaa ggacagagtc     1020
acgattaccg cggacaaatc cacgagcaca gcctacatgg agctgagcag cctgagatct     1080
gaggacacgg ccgtgtatta ctgtgcgaga ccccaagtcc actatgatta caacgggttt     1140
ccttactggg gccaaggaac cctggtcacc gtctcctcag gtggaggcgg ttcaggcgga     1200
ggtggatccg gcggtggcgg atcgggtggc ggcggatctg acatccagat gacccagtct     1260
ccatcctccc tgtctgcatc tgtaggagac agagtcacca tcacttgcag tgccagctca     1320
agtgtaagtt acatgaactg gtatcagcag aaaccaggga agcccctaa gagatggatt       1380 tatgactcat ccaaactggc ttctggggtc ccatcaaggt tcagtggcag tggatctggg     1440
acagatttca ctctcaccat cagcagtctg caacctgaag attttgcaac ttactactgt     1500
caacagtgga gtcgtaaccc acccactttc ggcggaggga ccaaggtgga gatcaaacgg     1560
tcctccagct aa                                                          1572
```

<210> SEQ ID NO 40
<211> LENGTH: 503
<212> TYPE: PRT
<213> ORGANISM: Artificial Sequence
<220> FEATURE:
<223> OTHER INFORMATION: Fc H10L6 (TSC340) CD3-binding domain

<400> SEQUENCE: 40

```
Glu Pro Lys Ser Ser Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Ala Tyr Ala Cys Ala Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160
```

```
Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gln Arg His Asn Asn Ser Ser Leu Asn
225                 230                 235                 240

Thr Gly Thr Gln Met Ala Gly His Ser Pro Asn Ser Gln Val Gln Leu
                245                 250                 255

Val Gln Ser Gly Ala Glu Val Lys Lys Pro Gly Ser Ser Val Lys Val
            260                 265                 270

Ser Cys Lys Ala Ser Gly Gly Thr Phe Ser Arg Ser Thr Met His Trp
        275                 280                 285

Val Arg Gln Ala Pro Gly Gln Gly Leu Glu Trp Met Gly Tyr Ile Asn
    290                 295                 300

Pro Ser Ser Ala Tyr Thr Asn Tyr Asn Gln Lys Phe Lys Asp Arg Val
305                 310                 315                 320

Thr Ile Thr Ala Asp Lys Ser Thr Ser Thr Ala Tyr Met Glu Leu Ser
                325                 330                 335

Ser Leu Arg Ser Glu Asp Thr Ala Val Tyr Tyr Cys Ala Arg Pro Gln
            340                 345                 350

Val His Tyr Asp Tyr Asn Gly Phe Pro Tyr Trp Gly Gln Gly Thr Leu
        355                 360                 365

Val Thr Val Ser Ser Gly Gly Gly Gly Ser Gly Gly Gly Gly Ser Gly
    370                 375                 380

Gly Gly Ser Gly Gly Gly Gly Ser Asp Ile Gln Met Thr Gln Ser
385                 390                 395                 400

Pro Ser Ser Leu Ser Ala Ser Val Gly Asp Arg Val Thr Ile Thr Cys
                405                 410                 415

Ser Ala Ser Ser Ser Val Ser Tyr Met Asn Trp Tyr Gln Gln Lys Pro
            420                 425                 430

Gly Lys Ala Pro Lys Arg Trp Ile Tyr Asp Ser Ser Lys Leu Ala Ser
        435                 440                 445

Gly Val Pro Ser Arg Phe Ser Gly Ser Gly Ser Gly Thr Asp Phe Thr
    450                 455                 460

Leu Thr Ile Ser Ser Leu Gln Pro Glu Asp Phe Ala Thr Tyr Tyr Cys
465                 470                 475                 480

Gln Gln Trp Ser Arg Asn Pro Pro Thr Phe Gly Gly Gly Thr Lys Val
                485                 490                 495

Glu Ile Lys Arg Ser Ser Ser
            500

<210> SEQ ID NO 41
<211> LENGTH: 1572
<212> TYPE: DNA
<213> ORGANISM: Artificial Sequence
<220> FEATURE:
<223> OTHER INFORMATION: Fc H10L7 (TSC341) CD3-binding domain

<400> SEQUENCE: 41
atggaagcac cagcgcagct tctcttcctc ctgctactct ggctcccaga taccaccggt    60
```

```
gagcccaaat cttctgacaa aactcacaca tgcccaccgt gcccagcacc tgaagccgcg    120
ggtgcaccgt cagtcttcct cttcccccca aacccaagg cacccctcat gatctcccgg     180
accctgagg tcacatgcgt ggtggtggac gtgagccacg aagaccctga ggtcaagttc     240
aactggtacg tggacggcgt ggaggtgcat aatgccaaga caaagccgcg ggaggagcag    300
tacaacagca cgtaccgtgt ggtcagcgtc ctcaccgtcc tgcaccagga ctggctgaat    360
ggcaaggcat acgcatgcgc ggtctccaac aaagccctcc cagcccccat cgagaaaacc    420
atctccaaag ccaaagggca gccccgagaa ccacaggtgt acaccctgcc cccatcccgg    480
gatgagctga ccaagaacca ggtcagcctg acctgcctgg tcaaaggctt ctatccaagc    540
gacatcgccg tggagtggga gagcaatggg cagccggaga caactacaa gaccacgcct      600
cccgtgctgg actccgacgg ctccttcttc ctctacagca agctcaccgt ggacaagagc    660
aggtggcagc aggggaacgt cttctcatgc tccgtgatgc atgaggctct gcacaaccac    720
tacacgcaga agagcctctc cctgtctccg ggtcagaggc acaacaattc ttccctgaat    780
acaggaactc agatggcagg tcattctccg aattctcagg tccagctggt gcaatctggg    840
gctgaggtga agaagcctgg gtcctcggtg aaggtctcct gcaaggcttc tggaggcacc    900
ttcagcagat ctacgatgca ctgggtgcga caggcccctg gacaagggct gagtggatg     960
ggatacatta atcctagcag tgcttatact aattacaatc agaaattcaa ggacagagtc   1020
acgattaccg cggacaaatc cacgagcaca gcctacatgg agctgagcag cctgagatct   1080
gaggacacgg ccgtgtatta ctgtgcgaga ccccaagtcc actatgatta caacgggttt   1140
ccttactggg gccaaggaac cctggtcacc gtctcctcag gtggaggcgg ttcaggcgga   1200
ggtggatccg gcggtggcgg atcgggtggc ggcggatctg aaattgtgtt gacgcagtct   1260
ccagccaccc tgtctttgtc tcaggggaa agagccaccc tctcctgcag tgccagctca   1320
agtgtaagtt acatgaactg gtaccagcag aaacctggcc tggcgcccag agatggatt    1380
tatgactcat ccaaactggc ttctggcatc ccagacaggt tcagtggcag tgggtctggg   1440
acagacttca ctctcaccat cagcagactg gagcctgaag attttgcagt gtattactgt   1500
cagcagtgga gtcgtaaccc acccactttc ggcggaggga ccaaggtgga gatcaaacgg   1560
tcctccagct aa                                                      1572
```

<210> SEQ ID NO 42
<211> LENGTH: 503
<212> TYPE: PRT
<213> ORGANISM: Artificial Sequence
<220> FEATURE:
<223> OTHER INFORMATION: Fc H10L7 (TSC341) CD3-binding domain

<400> SEQUENCE: 42

```
Glu Pro Lys Ser Ser Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95
```

```
Asp Trp Leu Asn Gly Lys Ala Tyr Ala Cys Ala Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gln Arg His Asn Asn Ser Ser Leu Asn
225                 230                 235                 240

Thr Gly Thr Gln Met Ala Gly His Ser Pro Asn Ser Gln Val Gln Leu
                245                 250                 255

Val Gln Ser Gly Ala Glu Val Lys Lys Pro Gly Ser Ser Val Lys Val
            260                 265                 270

Ser Cys Lys Ala Ser Gly Gly Thr Phe Ser Arg Ser Thr Met His Trp
        275                 280                 285

Val Arg Gln Ala Pro Gly Gln Gly Leu Glu Trp Met Gly Tyr Ile Asn
    290                 295                 300

Pro Ser Ser Ala Tyr Thr Asn Tyr Asn Gln Lys Phe Lys Asp Arg Val
305                 310                 315                 320

Thr Ile Thr Ala Asp Lys Ser Thr Ser Thr Ala Tyr Met Glu Leu Ser
                325                 330                 335

Ser Leu Arg Ser Glu Asp Thr Ala Val Tyr Tyr Cys Ala Arg Pro Gln
            340                 345                 350

Val His Tyr Asp Tyr Asn Gly Phe Pro Tyr Trp Gly Gln Gly Thr Leu
        355                 360                 365

Val Thr Val Ser Ser Gly Gly Gly Gly Ser Gly Gly Gly Gly Ser Gly
    370                 375                 380

Gly Gly Ser Gly Gly Gly Gly Ser Glu Ile Val Leu Thr Gln Ser
385                 390                 395                 400

Pro Ala Thr Leu Ser Leu Ser Pro Gly Glu Arg Ala Thr Leu Ser Cys
                405                 410                 415

Ser Ala Ser Ser Val Ser Tyr Met Asn Trp Tyr Gln Gln Lys Pro
            420                 425                 430

Gly Leu Ala Pro Arg Arg Trp Ile Tyr Asp Ser Ser Lys Leu Ala Ser
        435                 440                 445

Gly Ile Pro Asp Arg Phe Ser Gly Ser Gly Ser Gly Thr Asp Phe Thr
    450                 455                 460

Leu Thr Ile Ser Arg Leu Glu Pro Glu Asp Phe Ala Val Tyr Tyr Cys
465                 470                 475                 480

Gln Gln Trp Ser Arg Asn Pro Pro Thr Phe Gly Gly Gly Thr Lys Val
                485                 490                 495

Glu Ile Lys Arg Ser Ser Ser
            500
```

<210> SEQ ID NO 43
<211> LENGTH: 1572
<212> TYPE: DNA
<213> ORGANISM: Artificial Sequence
<220> FEATURE:
<223> OTHER INFORMATION: Fc H10L8 (TSC342) CD3-binding domain

<400> SEQUENCE: 43

| | |
|---|---:|
| atggaagcac cagcgcagct tctcttcctc ctgctactct ggctcccaga taccaccggt | 60 |
| gagcccaaat cttctgacaa aactcacaca tgcccaccgt gcccagcacc tgaagccgcg | 120 |
| ggtgcaccgt cagtcttcct cttcccccca aaacccaagg acaccctcat gatctcccgg | 180 |
| acccctgagg tcacatgcgt ggtggtggac gtgagccacg aagaccctga ggtcaagttc | 240 |
| aactggtacg tggacggcgt ggaggtgcat aatgccaaga caaagccgcg ggaggagcag | 300 |
| tacaacagca cgtaccgtgt ggtcagcgtc ctcaccgtcc tgcaccagga ctggctgaat | 360 |
| ggcaaggcat acgcatgcgc ggtctccaac aaagccctcc cagcccccat cgagaaaacc | 420 |
| atctccaaag ccaaagggca gccccgagaa ccacaggtgt acaccctgcc cccatcccgg | 480 |
| gatgagctga ccaagaacca ggtcagcctg acctgcctgg tcaaaggctt ctatccaagc | 540 |
| gacatcgccg tggagtggga gagcaatggg cagccggaga caactacaa gaccacgcct | 600 |
| cccgtgctgg actccgacgg ctccttcttc ctctacagca agctcaccgt ggacaagagc | 660 |
| aggtggcagc aggggaacgt cttctcatgc tccgtgatgc atgaggctct gcacaaccac | 720 |
| tacacgcaga agagcctctc cctgtctccg ggtcagaggc acaacaattc ttccctgaat | 780 |
| acaggaactc agatggcagg tcattctccg aattctcagg tccagctggt gcaatctggg | 840 |
| gctgaggtga agaagcctgg gtcctcggtg aaggtctcct gcaaggcttc tggaggcacc | 900 |
| ttcagcagat ctacgatgca ctgggtgcga caggcccctg acaagggct gagtggatg | 960 |
| ggatacatta atcctagcag tgcttatact aattacaatc agaaattcaa ggacagagtc | 1020 |
| acgattaccg cggacaaatc cacgagcaca gcctacatgg agctgagcag cctgagatct | 1080 |
| gaggacacgg ccgtgtatta ctgtgcgaga ccccaagtcc actatgatta acgggttt | 1140 |
| ccttactggg gccaaggaac cctggtcacc gtctcctcag gtggaggcgg ttcaggcgga | 1200 |
| ggtggatccg gcggtggcgg atcgggtggc ggcggatctg acatccagat gacccagtct | 1260 |
| ccttccaccc tgtctgcatc tgtaggagac agagtcacca tcacttgcag tgccagctca | 1320 |
| agtgtaagtt acatgaactg gtatcagcag aaaccaggga agcccctaa gagatggatt | 1380 |
| tatgactcat ccaaactggc ttctggggtc ccatcaaggt tcagcggcag tggatctggg | 1440 |
| acagaattca ctctcaccat cagcagcctg cagcctgatg attttgcaac ttattactgc | 1500 |
| caacagtgga gtcgtaaccc acccactttc ggcggaggga ccaaggtgga gatcaaacgg | 1560 |
| tcctccagct aa | 1572 |

<210> SEQ ID NO 44
<211> LENGTH: 503
<212> TYPE: PRT
<213> ORGANISM: Artificial Sequence
<220> FEATURE:
<223> OTHER INFORMATION: Fc H10L8 (TSC342) CD3-binding domain

<400> SEQUENCE: 44

Glu Pro Lys Ser Ser Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

```
Lys Asp Thr Leu Met Ile Ser Arg Thr Pro Glu Val Thr Cys Val Val
         35                  40                  45
Val Asp Val Ser His Glu Asp Pro Glu Val Lys Phe Asn Trp Tyr Val
 50                  55                  60
Asp Gly Val Glu Val His Asn Ala Lys Thr Lys Pro Arg Glu Glu Gln
 65                  70                  75                  80
Tyr Asn Ser Thr Tyr Arg Val Val Ser Val Leu Thr Val Leu His Gln
                 85                  90                  95
Asp Trp Leu Asn Gly Lys Ala Tyr Ala Cys Ala Val Ser Asn Lys Ala
                100                 105                 110
Leu Pro Ala Pro Ile Glu Lys Thr Ile Ser Lys Ala Lys Gly Gln Pro
             115                 120                 125
Arg Glu Pro Gln Val Tyr Thr Leu Pro Pro Ser Arg Asp Glu Leu Thr
         130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                 165                 170                 175
Lys Thr Thr Pro Pro Val Leu Asp Ser Asp Gly Ser Phe Phe Leu Tyr
             180                 185                 190
Ser Lys Leu Thr Val Asp Lys Ser Arg Trp Gln Gln Gly Asn Val Phe
         195                 200                 205
Ser Cys Ser Val Met His Glu Ala Leu His Asn His Tyr Thr Gln Lys
     210                 215                 220
Ser Leu Ser Leu Ser Pro Gly Gln Arg His Asn Asn Ser Ser Leu Asn
225                 230                 235                 240
Thr Gly Thr Gln Met Ala Gly His Ser Pro Asn Ser Gln Val Gln Leu
                 245                 250                 255
Val Gln Ser Gly Ala Glu Val Lys Lys Pro Gly Ser Ser Val Lys Val
             260                 265                 270
Ser Cys Lys Ala Ser Gly Gly Thr Phe Ser Arg Ser Thr Met His Trp
         275                 280                 285
Val Arg Gln Ala Pro Gly Gln Gly Leu Glu Trp Met Gly Tyr Ile Asn
     290                 295                 300
Pro Ser Ser Ala Tyr Thr Asn Tyr Asn Gln Lys Phe Lys Asp Arg Val
305                 310                 315                 320
Thr Ile Thr Ala Asp Lys Ser Thr Ser Thr Ala Tyr Met Glu Leu Ser
                 325                 330                 335
Ser Leu Arg Ser Glu Asp Thr Ala Val Tyr Tyr Cys Ala Arg Pro Gln
             340                 345                 350
Val His Tyr Asp Tyr Asn Gly Phe Pro Tyr Trp Gly Gln Gly Thr Leu
         355                 360                 365
Val Thr Val Ser Ser Gly Gly Gly Ser Gly Gly Gly Ser Gly
     370                 375                 380
Gly Gly Gly Ser Gly Gly Gly Ser Asp Ile Gln Met Thr Gln Ser
385                 390                 395                 400
Pro Ser Thr Leu Ser Ala Ser Val Gly Asp Arg Val Thr Ile Thr Cys
                 405                 410                 415
Ser Ala Ser Ser Ser Val Ser Tyr Met Asn Trp Tyr Gln Gln Lys Pro
             420                 425                 430
Gly Lys Ala Pro Lys Arg Trp Ile Tyr Asp Ser Ser Lys Leu Ala Ser
         435                 440                 445
```

```
Gly Val Pro Ser Arg Phe Ser Gly Ser Gly Ser Gly Thr Glu Phe Thr
        450                 455                 460

Leu Thr Ile Ser Ser Leu Gln Pro Asp Asp Phe Ala Thr Tyr Tyr Cys
465                 470                 475                 480

Gln Gln Trp Ser Arg Asn Pro Pro Thr Phe Gly Gly Gly Thr Lys Val
                485                 490                 495

Glu Ile Lys Arg Ser Ser Ser
            500
```

```
<210> SEQ ID NO 45
<211> LENGTH: 1572
<212> TYPE: DNA
<213> ORGANISM: Artificial Sequence
<220> FEATURE:
<223> OTHER INFORMATION: TSC370 CD3-binding domain

<400> SEQUENCE: 45
```

| | | | | |
|---|---|---|---|---|
| atggaagcac | cagcgcagct | tctcttcctc | ctgctactct | ggctcccaga | taccaccggt | 60 |
| gagcccaaat | cttctgacaa | aactcacaca | tgcccaccgt | gcccagcacc | tgaagccgcg | 120 |
| ggtgcaccgt | cagtcttcct | cttccccca | aaacccaagg | acaccctcat | gatctcccgg | 180 |
| accctgagg | tcacatgcgt | ggtggtggac | gtgagccacg | aagaccctga | ggtcaagttc | 240 |
| aactggtacg | tggacggcgt | ggaggtgcat | aatgccaaga | caaagccgcg | ggaggagcag | 300 |
| tacaacagca | cgtaccgtgt | ggtcagcgtc | ctcaccgtcc | tgcaccagga | ctggctgaat | 360 |
| ggcaaggcat | acgcatgcgc | ggtctccaac | aaagccctcc | cagccccat | cgagaaaacc | 420 |
| atctccaaag | ccaaagggca | gccccgagaa | ccacaggtgt | acaccctgcc | ccatcccgg | 480 |
| gatgagctga | ccaagaacca | ggtcagcctg | acctgcctgg | tcaaaggctt | ctatccaagc | 540 |
| gacatcgccg | tggagtggga | gagcaatggg | cagccggaga | acaactacaa | gaccacgcct | 600 |
| cccgtgctgg | actccgacgg | ctccttcttc | ctctacagca | agctcaccgt | ggacaagagc | 660 |
| aggtggcagc | aggggaacgt | cttctcatgc | tccgtgatgc | atgaggctct | gcacaaccac | 720 |
| tacacgcaga | agagcctctc | cctgtctccg | ggtcagaggc | acaacaattc | ttccctgaat | 780 |
| acaggaactc | agatggcagg | tcattctccg | aattctcagg | tccagctggt | gcaatctggg | 840 |
| gctgaggtga | agaagcctgg | gtcctcggtg | aaggtctcct | gcaaggcttc | tggatatacc | 900 |
| ttcagcagat | ctacgatgca | ctgggtgcga | caggccctg | acaagggct | gagtggatg | 960 |
| ggatacatta | tcctagcag | tgcttatact | aattacaatc | agaaattcaa | ggacagagtc | 1020 |
| acgattaccg | cggacaaatc | cacgagcaca | gcctacatgg | agctgagcag | cctgagatct | 1080 |
| gaggacacgg | ccgtgtatta | ctgtgcgaga | ccccaagtcc | actatgatta | caacgggttt | 1140 |
| ccttactggg | gccaaggaac | cctggtcacc | gtctcctcag | gtggaggcgg | ttcaggcgga | 1200 |
| ggtggatccg | gcggtggcgg | atcgggtggc | ggcggatctg | acatccagat | gacccagtct | 1260 |
| ccttccaccc | tgtctgcatc | tgtaggagac | agagtcacca | tcacttgcag | tgccagctca | 1320 |
| agtgtaagtt | acatgaactg | gtatcagcag | aaaccaggga | agcccctaa | gagatggatt | 1380 |
| tatgactcat | ccaaactggc | ttctggggtc | ccatcaaggt | tcagcggcag | tggatctggg | 1440 |
| acagaattca | ctctcaccat | cagcagcctg | cagcctgatg | attttgcaac | ttattactgc | 1500 |
| caacagtgga | gtcgtaaccc | acccactttc | ggcggaggga | ccaaggtgga | gatcaaacgg | 1560 |
| tcctccagct | aa | | | | | 1572 |

```
<210> SEQ ID NO 46
<211> LENGTH: 503
```

```
<212> TYPE: PRT
<213> ORGANISM: Artificial Sequence
<220> FEATURE:
<223> OTHER INFORMATION: TSC370 CD3-binding domain

<400> SEQUENCE: 46

Glu Pro Lys Ser Ser Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Ala Tyr Ala Cys Ala Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
210                 215                 220

Ser Leu Ser Leu Ser Pro Gly Gln Arg His Asn Asn Ser Ser Leu Asn
225                 230                 235                 240

Thr Gly Thr Gln Met Ala Gly His Ser Pro Asn Ser Gln Val Gln Leu
                245                 250                 255

Val Gln Ser Gly Ala Glu Val Lys Lys Pro Gly Ser Ser Val Lys Val
            260                 265                 270

Ser Cys Lys Ala Ser Gly Tyr Thr Phe Ser Arg Ser Thr Met His Trp
            275                 280                 285

Val Arg Gln Ala Pro Gly Gln Gly Leu Glu Trp Met Gly Tyr Ile Asn
290                 295                 300

Pro Ser Ser Ala Tyr Thr Asn Tyr Asn Gln Lys Phe Lys Asp Arg Val
305                 310                 315                 320

Thr Ile Thr Ala Asp Lys Ser Thr Ser Thr Ala Tyr Met Glu Leu Ser
                325                 330                 335

Ser Leu Arg Ser Glu Asp Thr Ala Val Tyr Tyr Cys Ala Arg Pro Gln
            340                 345                 350

Val His Tyr Asp Tyr Asn Gly Phe Pro Tyr Trp Gly Gln Gly Thr Leu
            355                 360                 365

Val Thr Val Ser Ser Gly Gly Gly Ser Gly Gly Gly Gly Ser Gly
370                 375                 380
```

Gly Gly Gly Ser Gly Gly Gly Ser Asp Ile Gln Met Thr Gln Ser
385                 390                 395                 400

Pro Ser Thr Leu Ser Ala Ser Val Gly Asp Arg Val Thr Ile Thr Cys
            405                 410                 415

Ser Ala Ser Ser Ser Val Ser Tyr Met Asn Trp Tyr Gln Gln Lys Pro
                420                 425                 430

Gly Lys Ala Pro Lys Arg Trp Ile Tyr Asp Ser Ser Lys Leu Ala Ser
        435                 440                 445

Gly Val Pro Ser Arg Phe Ser Gly Ser Gly Ser Gly Thr Glu Phe Thr
    450                 455                 460

Leu Thr Ile Ser Ser Leu Gln Pro Asp Asp Phe Ala Thr Tyr Tyr Cys
465                 470                 475                 480

Gln Gln Trp Ser Arg Asn Pro Pro Thr Phe Gly Gly Gly Thr Lys Val
                485                 490                 495

Glu Ile Lys Arg Ser Ser Ser
            500

<210> SEQ ID NO 47
<211> LENGTH: 1572
<212> TYPE: DNA
<213> ORGANISM: Artificial Sequence
<220> FEATURE:
<223> OTHER INFORMATION: TSC371 CD3-binding domain

<400> SEQUENCE: 47

| | |
|---|---|
| atggaagcac cagcgcagct tctcttcctc ctgctactct ggctcccaga taccaccggt | 60 |
| gagcccaaat cttctgacaa aactcacaca tgcccaccgt gcccagcacc tgaagccgcg | 120 |
| ggtgcaccgt cagtcttcct cttccccca aaacccaagg acaccctcat gatctcccgg | 180 |
| accccctgagg tcacatgcgt ggtggtggac gtgagccacg aagaccctga ggtcaagttc | 240 |
| aactggtacg tggacggcgt ggaggtgcat aatgccaaga caaagccgcg ggaggagcag | 300 |
| tacaacagca cgtaccgtgt ggtcagcgtc ctcaccgtcc tgcaccagga ctggctgaat | 360 |
| ggcaaggcat acgcatgcgc ggtctccaac aaagccctcc cagccccat cgagaaaacc | 420 |
| atctccaaag ccaaagggca gccccgagaa ccacaggtgt acaccctgcc cccatcccgg | 480 |
| gatgagctga ccaagaacca ggtcagcctg acctgcctgg tcaaaggctt ctatccaagc | 540 |
| gacatcgccg tggagtggga gagcaatggg cagccggaga caactacaa gaccacgcct | 600 |
| cccgtgctgg actccgacgg ctccttcttc ctctacagca agctcaccgt ggacaagagc | 660 |
| aggtggcagc aggggaacgt cttctcatgc tccgtgatgc atgaggctct gcacaaccac | 720 |
| tacacgcaga agagcctctc cctgtctccg ggtcagaggc acaacaattc ttccctgaat | 780 |
| acaggaactc agatggcagg tcattctccg aattctcagg tccagctggt gcaatctggg | 840 |
| gctgaggtga agaagcctgg gtcctcggtg aaggtctcct gcaaggcttc tggaggcacc | 900 |
| ttcagcagat ctacgatgca ctgggtgcga caggcccctg acaagggct gagtggata | 960 |
| ggatacatta atcctagcag tgcttatact aattacaatc agaaattcaa ggacagagtc | 1020 |
| acgattaccg cggacaaatc cacgagcaca gcctacatgg agctgagcag cctgagatct | 1080 |
| gaggacacgg ccgtgtatta ctgtgcgaga ccccaagtcc actatgatta acgggttt | 1140 |
| ccttactggg gccaaggaac cctggtcacc gtctcctcag gtggaggcgg ttcaggcgga | 1200 |
| ggtggatccg gcggtggcgg atcgggtggc ggcggatctg acatccagat gacccagtct | 1260 |
| ccttccaccc tgtctgcatc tgtaggagac agagtcacca tcacttgcag tgccagctca | 1320 |
| agtgtaagtt acatgaactg gtatcagcag aaaccaggga agcccctaa gagatggatt | 1380 |

-continued

```
tatgactcat ccaaactggc ttctggggtc ccatcaaggt tcagcggcag tggatctggg   1440
acagaattca ctctcaccat cagcagcctg cagcctgatg attttgcaac ttattactgc   1500
caacagtgga gtcgtaaccc acccactttc ggcggaggga ccaaggtgga gatcaaacgg   1560
tcctccagct aa                                                       1572
```

```
<210> SEQ ID NO 48
<211> LENGTH: 503
<212> TYPE: PRT
<213> ORGANISM: Artificial Sequence
<220> FEATURE:
<223> OTHER INFORMATION: TSC371 CD3-binding domain

<400> SEQUENCE: 48
```

Glu Pro Lys Ser Ser Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Ala Tyr Ala Cys Ala Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gln Arg His Asn Asn Ser Ser Leu Asn
225                 230                 235                 240

Thr Gly Thr Gln Met Ala Gly His Ser Pro Asn Ser Gln Val Gln Leu
                245                 250                 255

Val Gln Ser Gly Ala Glu Val Lys Lys Pro Gly Ser Ser Val Lys Val
            260                 265                 270

Ser Cys Lys Ala Ser Gly Gly Thr Phe Ser Arg Ser Thr Met His Trp
        275                 280                 285

Val Arg Gln Ala Pro Gly Gln Gly Leu Glu Trp Ile Gly Tyr Ile Asn
    290                 295                 300

Pro Ser Ser Ala Tyr Thr Asn Tyr Asn Gln Lys Phe Lys Asp Arg Val
305                 310                 315                 320

```
Thr Ile Thr Ala Asp Lys Ser Thr Ser Thr Ala Tyr Met Glu Leu Ser
            325                 330                 335

Ser Leu Arg Ser Glu Asp Thr Ala Val Tyr Tyr Cys Ala Arg Pro Gln
        340                 345                 350

Val His Tyr Asp Tyr Asn Gly Phe Pro Tyr Trp Gly Gln Gly Thr Leu
            355                 360                 365

Val Thr Val Ser Ser Gly Gly Gly Gly Ser Gly Gly Gly Gly Ser Gly
370                 375                 380

Gly Gly Ser Gly Gly Gly Gly Ser Asp Ile Gln Met Thr Gln Ser
385                 390                 395                 400

Pro Ser Thr Leu Ser Ala Ser Val Gly Asp Arg Val Thr Ile Thr Cys
                405                 410                 415

Ser Ala Ser Ser Ser Val Ser Tyr Met Asn Trp Tyr Gln Gln Lys Pro
            420                 425                 430

Gly Lys Ala Pro Lys Arg Trp Ile Tyr Asp Ser Ser Lys Leu Ala Ser
        435                 440                 445

Gly Val Pro Ser Arg Phe Ser Gly Ser Gly Ser Gly Thr Glu Phe Thr
    450                 455                 460

Leu Thr Ile Ser Ser Leu Gln Pro Asp Asp Phe Ala Thr Tyr Tyr Cys
465                 470                 475                 480

Gln Gln Trp Ser Arg Asn Pro Pro Thr Phe Gly Gly Gly Thr Lys Val
                485                 490                 495

Glu Ile Lys Arg Ser Ser Ser
            500
```

```
<210> SEQ ID NO 49
<211> LENGTH: 1572
<212> TYPE: DNA
<213> ORGANISM: Artificial Sequence
<220> FEATURE:
<223> OTHER INFORMATION: TSC372 CD3-binding domain

<400> SEQUENCE: 49
atggaagcac cagcgcagct tctcttcctc ctgctactct ggctcccaga taccaccggt      60
gagcccaaat cttctgacaa aactcacaca tgcccaccgt gcccagcacc tgaagccgcg     120
ggtgcaccgt cagtcttcct cttcccccca aaacccaagg acaccctcat gatctcccgg     180
acccctgagg tcacatgcgt ggtggtggac gtgagccacg aagaccctga ggtcaagttc     240
aactggtacg tggacggcgt ggaggtgcat aatgccaaga caaagccgcg ggaggagcag     300
tacaacagca cgtaccgtgt ggtcagcgtc ctcaccgtcc tgcaccagga ctggctgaat     360
ggcaaggcat acgcatgcgc ggtctccaac aaagccctcc cagcccccat cgagaaaacc     420
atctccaaag ccaaagggca gccccgagaa ccacaggtgt acaccctgcc cccatcccgg     480
gatgagctga ccaagaacca ggtcagcctg acctgcctgg tcaaaggctt ctatccaagc     540
gacatcgccg tggagtggga gagcaatggg cagccggaga acaactacaa gaccacgcct     600
cccgtgctgg actccgacgg ctccttcttc ctctacagca agctcaccgt ggacaagagc     660
aggtggcagc aggggaacgt cttctcatgc tccgtgatgc atgaggctct gcacaaccac     720
tacacgcaga agagcctctc cctgtctccg ggtcagaggc acaacaattc ttccctgaat     780
acaggaactc agatggcagg tcattctccg aattctcagg tccagctggt gcaatctggg     840
gctgaggtga agaagcctgg gtcctcggtg aaggtctcct gcaaggcttc tggaggcacc     900
ttcagcagat ctacgatgca ctgggtgcga caggcccctg gacaagggct gagtggatg     960 ggatacatta tcctagcag tgcttatact aattacaatc agaaattcaa ggacagagtc    1020
```

```
acgattaccg cggacaaatc cacgagcaca gcctacatgg agctgagcag cctgagatct    1080
gaggacacgg ccgtgtatta ctgtgcgaga ccccaagtcc actatgatta caacgggttt    1140
ccttactggg gccaaggaac cctggtcacc gtctcctcag gtggaggcgg ttcaggcgga    1200
ggtggatccg gcggtggcgg atcgggtggc ggcggatctg acatccagat gacccagtct    1260
ccttccaccc tgtctgcatc tgtaggagac agagtcacca tgacttgcag tgccagctca    1320
agtgtaagtt acatgaactg gtatcagcag aaaccaggga agcccctaa gagatggatt    1380 tatgactcat ccaaactggc ttctggggtc ccatcaaggt tcagcggcag tggatctggg    1440
acagaattca ctctcaccat cagcagcctg cagcctgatg attttgcaac ttattactgc    1500
caacagtgga gtcgtaaccc acccactttc ggcggaggga ccaaggtgga gatcaaacgg    1560
tcctccagct aa                                                        1572
```

<210> SEQ ID NO 50
<211> LENGTH: 503
<212> TYPE: PRT
<213> ORGANISM: Artificial Sequence
<220> FEATURE:
<223> OTHER INFORMATION: TSC372 CD3-binding domain

<400> SEQUENCE: 50

```
Glu Pro Lys Ser Ser Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Ala Tyr Ala Cys Ala Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gln Arg His Asn Asn Ser Ser Leu Asn
225                 230                 235                 240

Thr Gly Thr Gln Met Ala Gly His Ser Pro Asn Ser Gln Val Gln Leu
                245                 250                 255
```

```
Val Gln Ser Gly Ala Glu Val Lys Lys Pro Gly Ser Ser Val Lys Val
            260                 265                 270

Ser Cys Lys Ala Ser Gly Gly Thr Phe Ser Arg Ser Thr Met His Trp
        275                 280                 285

Val Arg Gln Ala Pro Gly Gln Gly Leu Glu Trp Met Gly Tyr Ile Asn
    290                 295                 300

Pro Ser Ser Ala Tyr Thr Asn Tyr Asn Gln Lys Phe Lys Asp Arg Val
305                 310                 315                 320

Thr Ile Thr Ala Asp Lys Ser Thr Ser Thr Ala Tyr Met Glu Leu Ser
                325                 330                 335

Ser Leu Arg Ser Glu Asp Thr Ala Val Tyr Tyr Cys Ala Arg Pro Gln
            340                 345                 350

Val His Tyr Asp Tyr Asn Gly Phe Pro Tyr Trp Gly Gln Gly Thr Leu
        355                 360                 365

Val Thr Val Ser Ser Gly Gly Gly Gly Ser Gly Gly Gly Gly Ser Gly
    370                 375                 380

Gly Gly Gly Ser Gly Gly Gly Gly Ser Asp Ile Gln Met Thr Gln Ser
385                 390                 395                 400

Pro Ser Thr Leu Ser Ala Ser Val Gly Asp Arg Val Thr Met Thr Cys
                405                 410                 415

Ser Ala Ser Ser Ser Val Ser Tyr Met Asn Trp Tyr Gln Gln Lys Pro
            420                 425                 430

Gly Lys Ala Pro Lys Arg Trp Ile Tyr Asp Ser Ser Lys Leu Ala Ser
        435                 440                 445

Gly Val Pro Ser Arg Phe Ser Gly Ser Gly Ser Gly Thr Glu Phe Thr
    450                 455                 460

Leu Thr Ile Ser Ser Leu Gln Pro Asp Asp Phe Ala Thr Tyr Tyr Cys
465                 470                 475                 480

Gln Gln Trp Ser Arg Asn Pro Pro Thr Phe Gly Gly Gly Thr Lys Val
                485                 490                 495

Glu Ile Lys Arg Ser Ser Ser
            500

<210> SEQ ID NO 51
<211> LENGTH: 1572
<212> TYPE: DNA
<213> ORGANISM: Artificial Sequence
<220> FEATURE:
<223> OTHER INFORMATION: TSC390 CD3-binding domain

<400> SEQUENCE: 51
atggaagcac cagcgcagct tctcttcctc ctgctactct ggctcccaga taccaccggt      60
gagcccaaat cttctgacaa aactcacaca tgcccaccgt gcccagcacc tgaagccgcg     120
ggtgcaccgt cagtcttcct cttccccccca aaacccaagg acaccctcat gatctcccgg     180 accctgagg tcacatgcgt ggtggtggac gtgagccacg aagaccctga ggtcaagttc      240
aactggtacg tggacggcgt ggaggtgcat aatgccaaga caaagccgcg ggaggagcag     300
tacaacagca cgtaccgtgt ggtcagcgtc ctcaccgtcc tgcaccagga ctggctgaat     360
ggcaaggcat acgcatgcgc ggtctccaac aaagcccctcc cagcccccat cgagaaaacc     420
atctccaaag ccaaagggca gccccgagaa ccacaggtgt acaccctgcc cccatcccgg     480
gatgagctga ccaagaacca ggtcagcctg acctgcctgg tcaaaggctt ctatccaagc     540
gacatcgccg tggagtggga gagcaatggg cagccggaga caactacaa gaccacgcct      600 cccgtgctgg actccgacgg ctccttcttc ctctacagca agctcaccgt ggacaagagc     660
```

-continued

```
aggtggcagc aggggaacgt cttctcatgc tccgtgatgc atgaggctct gcacaaccac    720
tacacgcaga agagcctctc cctgtctccg ggtcagaggc acaacaattc ttccctgaat    780
acaggaactc agatggcagg tcattctccg aattctcagg tccagctggt gcaatctggg    840
cctgaggtga agaagcctgg gtcctcggtg aaggtctcct gcaaggcttc tggatatacc    900
ttcagcagat ctacgatgca ctgggtgcga caggcccctg gacaagggct gagtggatg    960
ggatacatta atcctagcag tgcttatact aattacaatc agaaattcaa ggacagagtc   1020
acgattaccg cggacaaatc cacgagcaca gcctacatgg agctgagcag cctgagatct   1080
gaggacacgg ccgtgtatta ctgtgcgaga ccccaagtcc actatgatta acgggttt    1140
ccttactggg gccaaggaac cctggtcacc gtctcctcag gtggaggcgg ttcaggcgga   1200
ggtggatccg gcggtggcgg atcgggtggc ggcggatctg acatccagat gacccagtct   1260
ccttccaccc tgtctgcatc tgtaggagac agagtcacca tcacttgcag tgccagctca   1320
agtgtaagtt acatgaactg gtatcagcag aaaccaggga agcccctaa gagatggatt   1380
tatgactcat ccaaactggc ttctggggtc ccatcaaggt tcagcggcag tggatctggg   1440
acagagttca ctctcaccat cagcagcctg cagcctgatg attttgcaac ttattactgc   1500
caacagtgga gtcgtaaccc acccactttc ggcggaggga ccaaggtgga gatcaaacgg   1560
tcctccagct aa                                                       1572
```

<210> SEQ ID NO 52
<211> LENGTH: 503
<212> TYPE: PRT
<213> ORGANISM: Artificial Sequence
<220> FEATURE:
<223> OTHER INFORMATION: TSC390 CD3-binding domain

<400> SEQUENCE: 52

```
Glu Pro Lys Ser Ser Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Ala Tyr Ala Cys Ala Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190
```

```
Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gln Arg His Asn Asn Ser Ser Leu Asn
225                 230                 235                 240

Thr Gly Thr Gln Met Ala Gly His Ser Pro Asn Ser Gln Val Gln Leu
                245                 250                 255

Val Gln Ser Gly Pro Glu Val Lys Lys Pro Gly Ser Ser Val Lys Val
            260                 265                 270

Ser Cys Lys Ala Ser Gly Tyr Thr Phe Ser Arg Ser Thr Met His Trp
        275                 280                 285

Val Arg Gln Ala Pro Gly Gln Gly Leu Glu Trp Met Gly Tyr Ile Asn
    290                 295                 300

Pro Ser Ser Ala Tyr Thr Asn Tyr Asn Gln Lys Phe Lys Asp Arg Val
305                 310                 315                 320

Thr Ile Thr Ala Asp Lys Ser Ser Thr Ala Tyr Met Glu Leu Ser
                325                 330                 335

Ser Leu Arg Ser Glu Asp Thr Ala Val Tyr Tyr Cys Ala Arg Pro Gln
            340                 345                 350

Val His Tyr Asp Tyr Asn Gly Phe Pro Tyr Trp Gly Gln Gly Thr Leu
        355                 360                 365

Val Thr Val Ser Ser Gly Gly Gly Gly Ser Gly Gly Gly Gly Ser Gly
    370                 375                 380

Gly Gly Ser Gly Gly Gly Gly Ser Asp Ile Gln Met Thr Gln Ser
385                 390                 395                 400

Pro Ser Thr Leu Ser Ala Ser Val Gly Asp Arg Val Thr Ile Thr Cys
                405                 410                 415

Ser Ala Ser Ser Ser Val Ser Tyr Met Asn Trp Tyr Gln Gln Lys Pro
            420                 425                 430

Gly Lys Ala Pro Lys Arg Trp Ile Tyr Asp Ser Ser Lys Leu Ala Ser
        435                 440                 445

Gly Val Pro Ser Arg Phe Ser Gly Ser Gly Ser Gly Thr Glu Phe Thr
    450                 455                 460

Leu Thr Ile Ser Ser Leu Gln Pro Asp Asp Phe Ala Thr Tyr Tyr Cys
465                 470                 475                 480

Gln Gln Trp Ser Arg Asn Pro Pro Thr Phe Gly Gly Gly Thr Lys Val
                485                 490                 495

Glu Ile Lys Arg Ser Ser Ser
            500
```

<210> SEQ ID NO 53
<211> LENGTH: 1572
<212> TYPE: DNA
<213> ORGANISM: Artificial Sequence
<220> FEATURE:
<223> OTHER INFORMATION: TSC391 CD3-binding domain

<400> SEQUENCE: 53

```
atggaagcac cagcgcagct tctcttcctc ctgctactct ggctcccaga taccaccggt      60
gagcccaaat cttctgacaa aactcacaca tgcccaccgt gcccagcacc tgaagccgcg     120
ggtgcaccgt cagtcttcct cttcccccca aaacccaagg acaccctcat gatctcccgg     180 accccctgagg tcacatgcgt ggtggtggac gtgagccacg aagaccctga ggtcaagttc     240
aactggtacg tggacggcgt ggaggtgcat aatgccaaga caaagccgcg ggaggagcag     300
```

```
tacaacagca cgtaccgtgt ggtcagcgtc ctcaccgtcc tgcaccagga ctggctgaat      360
ggcaaggcat acgcatgcgc ggtctccaac aaagccctcc cagcccccat cgagaaaacc      420
atctccaaag ccaaagggca gccccgagaa ccacaggtgt acaccctgcc cccatcccgg      480
gatgagctga ccaagaacca ggtcagcctg acctgcctgg tcaaaggctt ctatccaagc      540
gacatcgccg tggagtggga gagcaatggg cagccggaga caactacaa gaccacgcct       600 cccgtgctgg actccgacgg ctccttcttc ctctacagca agctcaccgt ggacaagagc      660
aggtggcagc aggggaacgt cttctcatgc tccgtgatgc atgaggctct gcacaaccac      720
tacacgcaga gagcctctc cctgtctccg ggtcagaggc acaacaattc ttccctgaat       780
acaggaactc agatggcagg tcattctccg aattctcagg tccagctggt gcaatctggg      840
cctgaggtga agaagcctgg gtcctcggtg aaggtctcct gcaaggcttc tggatatacc      900
ttcagcagat ctacgatgca ctgggtgcga caggcccctg gacaagggct tgagtggata      960
ggatacatta atcctagcag tgcttatact aattacaatc agaaattcaa ggacagagtc     1020
acgattaccg cggacaaatc cacgagcaca gcctacatgg agctgagcag cctgagatct     1080
gaggacacgg ccgtgtatta ctgtgcgaga ccccaagtcc actatgatta caacgggttt     1140
ccttactggg gccaaggaac cctggtcacc gtctcctcag gtggaggcgg ttcaggcgga     1200
ggtggatccg gcggtggcgg atcgggtggc ggcggatctg acatccagat gacccagtct     1260
ccttccaccc tgtctgcatc tgtaggagac agagtcacca tcacttgcag tgccagctca     1320
agtgtaagtt acatgaactg gtatcagcag aaaccaggga agcccctaa gagatggatt      1380 tatgactcat ccaaactggc ttctggggtc ccatcaaggt tcagcggcag tggatctggg     1440
acagagttca ctctcaccat cagcagcctg cagcctgatg attttgcaac ttattactgc     1500
caacagtgga gtcgtaaccc acccactttc ggcggaggga ccaaggtgga gatcaaacgg     1560
tcctccagct aa                                                        1572
```

<210> SEQ ID NO 54
<211> LENGTH: 503
<212> TYPE: PRT
<213> ORGANISM: Artificial Sequence
<220> FEATURE:
<223> OTHER INFORMATION: TSC391 CD3-binding domain

<400> SEQUENCE: 54

```
Glu Pro Lys Ser Ser Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Ala Tyr Ala Cys Ala Val Ser Asn Lys Ala
            100                 105                 110

Leu Pro Ala Pro Ile Glu Lys Thr Ile Ser Lys Ala Lys Gly Gln Pro
        115                 120                 125
```

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Gln Arg His Asn Asn Ser Ser Leu Asn
225                 230                 235                 240

Thr Gly Thr Gln Met Ala Gly His Ser Pro Asn Ser Gln Val Gln Leu
                245                 250                 255

Val Gln Ser Gly Pro Glu Val Lys Lys Pro Gly Ser Ser Val Lys Val
            260                 265                 270

Ser Cys Lys Ala Ser Gly Tyr Thr Phe Ser Arg Ser Thr Met His Trp
        275                 280                 285

Val Arg Gln Ala Pro Gly Gln Gly Leu Glu Trp Ile Gly Tyr Ile Asn
290                 295                 300

Pro Ser Ser Ala Tyr Thr Asn Tyr Asn Gln Lys Phe Lys Asp Arg Val
305                 310                 315                 320

Thr Ile Thr Ala Asp Lys Ser Thr Ser Thr Ala Tyr Met Glu Leu Ser
                325                 330                 335

Ser Leu Arg Ser Glu Asp Thr Ala Val Tyr Tyr Cys Ala Arg Pro Gln
            340                 345                 350

Val His Tyr Asp Tyr Asn Gly Phe Pro Tyr Trp Gly Gln Gly Thr Leu
        355                 360                 365

Val Thr Val Ser Ser Gly Gly Gly Gly Ser Gly Gly Gly Gly Ser Gly
370                 375                 380

Gly Gly Ser Gly Gly Gly Gly Ser Asp Ile Gln Met Thr Gln Ser
385                 390                 395                 400

Pro Ser Thr Leu Ser Ala Ser Val Gly Asp Arg Val Thr Ile Thr Cys
                405                 410                 415

Ser Ala Ser Ser Ser Val Ser Tyr Met Asn Trp Tyr Gln Gln Lys Pro
            420                 425                 430

Gly Lys Ala Pro Lys Arg Trp Ile Tyr Asp Ser Ser Lys Leu Ala Ser
        435                 440                 445

Gly Val Pro Ser Arg Phe Ser Gly Ser Gly Ser Gly Thr Glu Phe Thr
450                 455                 460

Leu Thr Ile Ser Ser Leu Gln Pro Asp Asp Phe Ala Thr Tyr Tyr Cys
465                 470                 475                 480

Gln Gln Trp Ser Arg Asn Pro Pro Thr Phe Gly Gly Gly Thr Lys Val
                485                 490                 495

Glu Ile Lys Arg Ser Ser Ser
            500

<210> SEQ ID NO 55
<211> LENGTH: 1572
<212> TYPE: DNA
<213> ORGANISM: Artificial Sequence
<220> FEATURE:
<223> OTHER INFORMATION: TSC392 CD3-binding domain

<400> SEQUENCE: 55

```
atggaagcac cagcgcagct tctcttcctc ctgctactct ggctcccaga taccaccggt      60
gagcccaaat cttctgacaa aactcacaca tgcccaccgt gcccagcacc tgaagccgcg     120
ggtgcaccgt cagtcttcct cttccccca aaacccaagg acaccctcat gatctcccgg     180
accccctgagg tcacatgcgt ggtggtggac gtgagccacg aagaccctga ggtcaagttc     240
aactggtacg tggacggcgt ggaggtgcat aatgccaaga caaagccgcg ggaggagcag     300
tacaacagca cgtaccgtgt ggtcagcgtc ctcaccgtcc tgcaccagga ctggctgaat     360
ggcaaggcat acgcatgcgc ggtctccaac aaagccctcc cagcccccat cgagaaaacc     420
atctccaaag ccaaagggca gccccgagaa ccacaggtgt acaccctgcc cccatcccgg     480
gatgagctga ccaagaacca ggtcagcctg acctgcctgg tcaaaggctt ctatccaagc     540
gacatcgccg tggagtggga gagcaatggg cagccggaga caactacaa gaccacgcct     600
cccgtgctgg actccgacgg ctccttcttc ctctacagca agctcaccgt ggacaagagc     660
aggtggcagc aggggaacgt cttctcatgc tccgtgatgc atgaggctct gcacaaccac     720
tacacgcaga agagcctctc cctgtctccg ggtcagaggc acaacaattc ttccctgaat     780
acaggaactc agatggcagg tcattctccg aattctcagg tccagctggt gcaatctggg     840
cctgaggtga agaagcctgg gtcctcggtg aaggtctcct gcaaggcttc tggatatacc     900
ttcagcagat ctacgatgca ctgggtgcga caggcccctg gacaagggct gagtggatg     960
ggatacatta atcctagcag tgcttatact aattacaatc agaaattcaa ggacagagtc    1020
acgattaccg cggacaaatc cacgagcaca gcctacatgg agctgagcag cctgagatct    1080
gaggacacgg ccgtgtatta ctgtgcgaga cccaagtcc actatgatta caacgggttt    1140
ccttactggg gccaaggaac cctggtcacc gtctcctcag gtggaggcgg ttcaggcgga    1200
ggtggatccg gcggtggcgg atcgggtggc ggcggatctg acatccagat gacccagtct    1260
ccttccaccc tgtctgcatc tgtaggagac agagtcacca tgacttgcag tgccagctca    1320
agtgtaagtt acatgaactg gtatcagcag aaaccaggga agcccctaa gagatggatt    1380
tatgactcat ccaaactggc ttctggggtc ccatcaaggt tcagcggcag tggatctggg    1440
acagagttca ctctcaccat cagcagcctg cagcctgatg attttgcaac ttattactgc    1500
caacagtgga gtcgtaaccc acccactttc ggcggaggga ccaaggtgga gatcaaacgg    1560
tcctccagct aa                                                        1572
```

<210> SEQ ID NO 56
<211> LENGTH: 503
<212> TYPE: PRT
<213> ORGANISM: Artificial Sequence
<220> FEATURE:
<223> OTHER INFORMATION: TSC392 CD3-binding domain

<400> SEQUENCE: 56

```
Glu Pro Lys Ser Ser Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60
```

```
Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Ala Tyr Ala Cys Ala Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gln Arg His Asn Asn Ser Ser Leu Asn
225                 230                 235                 240

Thr Gly Thr Gln Met Ala Gly His Ser Pro Asn Ser Gln Val Gln Leu
                245                 250                 255

Val Gln Ser Gly Pro Glu Val Lys Lys Pro Gly Ser Ser Val Lys Val
            260                 265                 270

Ser Cys Lys Ala Ser Gly Tyr Thr Phe Ser Arg Ser Thr Met His Trp
        275                 280                 285

Val Arg Gln Ala Pro Gly Gln Gly Leu Glu Trp Met Gly Tyr Ile Asn
    290                 295                 300

Pro Ser Ser Ala Tyr Thr Asn Tyr Asn Gln Lys Phe Lys Asp Arg Val
305                 310                 315                 320

Thr Ile Thr Ala Asp Lys Ser Thr Ser Thr Ala Tyr Met Glu Leu Ser
                325                 330                 335

Ser Leu Arg Ser Glu Asp Thr Ala Val Tyr Tyr Cys Ala Arg Pro Gln
            340                 345                 350

Val His Tyr Asp Tyr Asn Gly Phe Pro Tyr Trp Gly Gln Gly Thr Leu
        355                 360                 365

Val Thr Val Ser Ser Gly Gly Gly Ser Gly Gly Gly Ser Gly Ser Gly
    370                 375                 380

Gly Gly Ser Gly Gly Gly Ser Asp Ile Gln Met Thr Gln Ser
385                 390                 395                 400

Pro Ser Thr Leu Ser Ala Ser Val Gly Asp Arg Val Thr Met Thr Cys
                405                 410                 415

Ser Ala Ser Ser Ser Val Ser Tyr Met Asn Trp Tyr Gln Gln Lys Pro
            420                 425                 430

Gly Lys Ala Pro Lys Arg Trp Ile Tyr Asp Ser Ser Lys Leu Ala Ser
        435                 440                 445

Gly Val Pro Ser Arg Phe Ser Gly Ser Gly Ser Gly Thr Glu Phe Thr
    450                 455                 460

Leu Thr Ile Ser Ser Leu Gln Pro Asp Asp Phe Ala Thr Tyr Tyr Cys
465                 470                 475                 480

Gln Gln Trp Ser Arg Asn Pro Pro Thr Phe Gly Gly Gly Thr Lys Val
```

Glu Ile Lys Arg Ser Ser Ser
        500

<210> SEQ ID NO 57
<211> LENGTH: 1572
<212> TYPE: DNA
<213> ORGANISM: Artificial Sequence
<220> FEATURE:
<223> OTHER INFORMATION: TSC393 CD3-binding domain

<400> SEQUENCE: 57

```
atggaagcac cagcgcagct tctcttcctc ctgctactct ggctcccaga taccaccggt     60
gagcccaaat cttctgacaa aactcacaca tgcccaccgt gcccagcacc tgaagccgcg    120
ggtgcaccgt cagtcttcct cttcccccca aaacccaagg acaccctcat gatctcccgg    180
accccctgagg tcacatgcgt ggtggtggac gtgagccacg aagaccctga ggtcaagttc    240
aactggtacg tggacggcgt ggaggtgcat aatgccaaga caaagccgcg ggaggagcag    300
tacaacagca cgtaccgtgt ggtcagcgtc ctcaccgtcc tgcaccagga ctggctgaat    360
ggcaaggcat acgcatgcgc ggtctccaac aaagccctcc cagcccccat cgagaaaacc    420
atctccaaag ccaaagggca gccccgagaa ccacaggtgt acaccctgcc cccatcccgg    480
gatgagctga ccaagaacca ggtcagcctg acctgcctgg tcaaaggctt ctatccaagc    540
gacatcgccg tggagtggga gagcaatggg cagccggaga caactacaa gaccacgcct    600
cccgtgctgg actccgacgg ctccttcttc ctctacagca agctcaccgt ggacaagagc    660
aggtggcagc aggggaacgt cttctcatgc tccgtgatgc atgaggctct gcacaaccac    720
tacacgcaga gagcctctc cctgtctccg ggtcagaggc acaacaattc ttccctgaat    780
acaggaactc agatggcagg tcattctccg aattctcagg tccagctggt gcaatctggg    840
gctgaggtga agaagcctgg gtcctcggtg aaggtctcct gcaaggcttc tggatatacc    900
ttcagcagat ctacgatgca ctgggtgcga caggcccctg gacaagggct gagtggata    960
ggatacatta atcctagcag tgcttatact aattacaatc agaaattcaa ggacagagtc   1020
acgattaccg cggacaaatc cacgagcaca gcctacatgg agctgagcag cctgagatct   1080
gaggacacgg ccgtgtatta ctgtgcgaga ccccaagtcc actatgatta caacgggttt   1140
ccttactggg gccaaggaac cctggtcacc gtctcctcag gtggaggcgg ttcaggcgga   1200
ggtggatccg gcggtggcgg atcgggtggc ggcggatctg acatccagat gacccagtct   1260
ccttccaccc tgtctgcatc tgtaggagac agagtcacca tgacttgcag tgccagctca   1320
agtgtaagtt acatgaactg gtatcagcag aaaccaggga agcccctaa gagatggatt   1380
tatgactcat ccaaactggc ttctggggtc ccatcaaggt tcagcggcag tggatctggg   1440
acagagttca ctctcaccat cagcagcctg cagcctgatg attttgcaac ttattactgc   1500
caacagtgga gtcgtaaccc acccactttc ggcggaggga ccaaggtgga gatcaaacgg   1560
tcctccagct aa                                                       1572
```

<210> SEQ ID NO 58
<211> LENGTH: 503
<212> TYPE: PRT
<213> ORGANISM: Artificial Sequence
<220> FEATURE:
<223> OTHER INFORMATION: TSC393 CD3-binding domain

<400> SEQUENCE: 58

```
Glu Pro Lys Ser Ser Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
            130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
210                 215                 220

Ser Leu Ser Leu Ser Pro Gly Gln Arg His Asn Asn Ser Ser Leu Asn
225                 230                 235                 240

Thr Gly Thr Gln Met Ala Gly His Ser Pro Asn Ser Gln Val Gln Leu
                245                 250                 255

Val Gln Ser Gly Ala Glu Val Lys Lys Pro Gly Ser Ser Val Lys Val
            260                 265                 270

Ser Cys Lys Ala Ser Gly Tyr Thr Phe Ser Arg Ser Thr Met His Trp
            275                 280                 285

Val Arg Gln Ala Pro Gly Gln Gly Leu Glu Trp Ile Gly Tyr Ile Asn
            290                 295                 300

Pro Ser Ser Ala Tyr Thr Asn Tyr Asn Gln Lys Phe Lys Asp Arg Val
305                 310                 315                 320

Thr Ile Thr Ala Asp Lys Ser Thr Ser Thr Ala Tyr Met Glu Leu Ser
                325                 330                 335

Ser Leu Arg Ser Glu Asp Thr Ala Val Tyr Tyr Cys Ala Arg Pro Gln
            340                 345                 350

Val His Tyr Asp Tyr Asn Gly Phe Pro Tyr Trp Gly Gln Gly Thr Leu
            355                 360                 365

Val Thr Val Ser Ser Gly Gly Gly Gly Ser Gly Gly Gly Gly Ser Gly
            370                 375                 380

Gly Gly Gly Ser Gly Gly Gly Gly Ser Asp Ile Gln Met Thr Gln Ser
385                 390                 395                 400

Pro Ser Thr Leu Ser Ala Ser Val Gly Asp Arg Val Thr Met Thr Cys
            405                 410                 415

Ser Ala Ser Ser Ser Val Ser Tyr Met Asn Trp Tyr Gln Gln Lys Pro
```

|   |   | 420 |   |   |   | 425 |   |   |   | 430 |   |
|---|---|---|---|---|---|---|---|---|---|---|---|
| Gly | Lys | Ala | Pro | Lys | Arg | Trp | Ile | Tyr | Asp | Ser | Ser | Lys | Leu | Ala | Ser |
|   |   |   | 435 |   |   |   |   | 440 |   |   |   |   | 445 |   |   |

Gly Val Pro Ser Arg Phe Ser Gly Ser Gly Ser Gly Thr Glu Phe Thr
          450                 455                 460

Leu Thr Ile Ser Ser Leu Gln Pro Asp Asp Phe Ala Thr Tyr Tyr Cys
465                 470                 475                 480

Gln Gln Trp Ser Arg Asn Pro Pro Thr Phe Gly Gly Gly Thr Lys Val
              485                 490                 495

Glu Ile Lys Arg Ser Ser Ser
          500

<210> SEQ ID NO 59
<211> LENGTH: 1572
<212> TYPE: DNA
<213> ORGANISM: Artificial Sequence
<220> FEATURE:
<223> OTHER INFORMATION: TSC394 CD3-binding domain

<400> SEQUENCE: 59

```
atggaagcac cagcgcagct tctcttcctc ctgctactct ggctcccaga taccaccggt     60
gagcccaaat cttctgacaa aactcacaca tgcccaccgt gcccagcacc tgaagccgcg    120
ggtgcaccgt cagtcttcct cttcccccca aaacccaagg acaccctcat gatctcccgg    180
acccctgagg tcacatgcgt ggtggtggac gtgagccacg aagaccctga ggtcaagttc    240
aactggtacg tggacggcgt ggaggtgcat aatgccaaga caaagccgcg ggaggagcag    300
tacaacagca cgtaccgtgt ggtcagcgtc ctcaccgtcc tgcaccagga ctggctgaat    360
ggcaaggcat acgcatgcgc ggtctccaac aaagccctcc cagcccccat cgagaaaacc    420
atctccaaag ccaaagggca gccccgagaa ccacaggtgt acaccctgcc cccatcccgg    480
gatgagctga ccaagaacca ggtcagcctg acctgcctgg tcaaaggctt ctatccaagc    540
gacatcgccg tggagtggga gagcaatggg cagccggaga caactacaa gaccacgcct    600
cccgtgctgg actccgacgg ctccttcttc ctctacagca agctcaccgt ggacaagagc    660
aggtggcagc aggggaacgt cttctcatgc tccgtgatgc atgaggctct gcacaaccac    720
tacacgcaga gagcctctc cctgtctccg ggtcagaggc acaacaattc ttccctgaat    780
acaggaactc agatggcagg tcattctccg aattctcagg tccagctggt gcaatctggg    840
cctgaggtga agaagcctgg gtcctcggtg aaggtctcct gcaaggcttc tggatatacc    900
ttcagcagat ctacgatgca ctgggtgcga caggcccctg gacaagggct gagtggata    960
ggatacatta tcctagcag tgcttatact aattacaatc agaaattcaa ggacagagtc   1020
acgattaccg cggacaaatc cacgagcaca gcctacatgg agctgagcag cctgagatct   1080
gaggacacgg ccgtgtatta ctgtgcgaga ccccaagtcc actatgatta acgggttt   1140
ccttactggg gccaaggaac cctggtcacc gtctcctcag gtggaggcgg ttcaggcgga   1200
ggtggatccg gcggtggcgg atcgggtggc ggcggatctg acatccagat gacccagtct   1260
ccttccaccc tgtctgcatc tgtaggagac agagtcacca tgacttgcag tgccagctca   1320
agtgtaagtt acatgaactg gtatcagcag aaaccaggga agcccctaa gagatggatt   1380
tatgactcat ccaaactggc ttctggggtc ccatcaaggt tcagcggcag tggatctggg   1440
acagagttca ctctcaccat cagcagcctg cagcctgatg attttgcaac ttattactgc   1500
caacagtgga gtcgtaaccc acccactttc ggcggaggga ccaaggtgga gatcaaacgg   1560
```
tcctccagct aa 1572

<210> SEQ ID NO 60
<211> LENGTH: 503
<212> TYPE: PRT
<213> ORGANISM: Artificial Sequence
<220> FEATURE:
<223> OTHER INFORMATION: TSC394 CD3-binding domain

<400> SEQUENCE: 60

| Glu | Pro | Lys | Ser | Ser | Asp | Lys | Thr | His | Thr | Cys | Pro | Pro | Cys | Pro | Ala |
|---|---|---|---|---|---|---|---|---|---|---|---|---|---|---|---|
| 1 | | | | 5 | | | | | 10 | | | | | 15 | |

| Pro | Glu | Ala | Ala | Gly | Ala | Pro | Ser | Val | Phe | Leu | Phe | Pro | Pro | Lys | Pro |
|---|---|---|---|---|---|---|---|---|---|---|---|---|---|---|---|
| | | | 20 | | | | | 25 | | | | | 30 | | |

| Lys | Asp | Thr | Leu | Met | Ile | Ser | Arg | Thr | Pro | Glu | Val | Thr | Cys | Val | Val |
|---|---|---|---|---|---|---|---|---|---|---|---|---|---|---|---|
| | | | 35 | | | | | 40 | | | | | 45 | | |

| Val | Asp | Val | Ser | His | Glu | Asp | Pro | Glu | Val | Lys | Phe | Asn | Trp | Tyr | Val |
|---|---|---|---|---|---|---|---|---|---|---|---|---|---|---|---|
| | 50 | | | | | 55 | | | | | 60 | | | | |

| Asp | Gly | Val | Glu | Val | His | Asn | Ala | Lys | Thr | Lys | Pro | Arg | Glu | Glu | Gln |
|---|---|---|---|---|---|---|---|---|---|---|---|---|---|---|---|
| 65 | | | | | 70 | | | | | 75 | | | | | 80 |

| Tyr | Asn | Ser | Thr | Tyr | Arg | Val | Val | Ser | Val | Leu | Thr | Val | Leu | His | Gln |
|---|---|---|---|---|---|---|---|---|---|---|---|---|---|---|---|
| | | | | 85 | | | | | 90 | | | | | 95 | |

| Asp | Trp | Leu | Asn | Gly | Lys | Ala | Tyr | Ala | Cys | Ala | Val | Ser | Asn | Lys | Ala |
|---|---|---|---|---|---|---|---|---|---|---|---|---|---|---|---|
| | | | 100 | | | | | 105 | | | | | 110 | | |

| Leu | Pro | Ala | Pro | Ile | Glu | Lys | Thr | Ile | Ser | Lys | Ala | Lys | Gly | Gln | Pro |
|---|---|---|---|---|---|---|---|---|---|---|---|---|---|---|---|
| | | | 115 | | | | | 120 | | | | | 125 | | |

| Arg | Glu | Pro | Gln | Val | Tyr | Thr | Leu | Pro | Pro | Ser | Arg | Asp | Glu | Leu | Thr |
|---|---|---|---|---|---|---|---|---|---|---|---|---|---|---|---|
| | 130 | | | | | 135 | | | | | 140 | | | | |

| Lys | Asn | Gln | Val | Ser | Leu | Thr | Cys | Leu | Val | Lys | Gly | Phe | Tyr | Pro | Ser |
|---|---|---|---|---|---|---|---|---|---|---|---|---|---|---|---|
| 145 | | | | | 150 | | | | | 155 | | | | | 160 |

| Asp | Ile | Ala | Val | Glu | Trp | Glu | Ser | Asn | Gly | Gln | Pro | Glu | Asn | Asn | Tyr |
|---|---|---|---|---|---|---|---|---|---|---|---|---|---|---|---|
| | | | | 165 | | | | | 170 | | | | | 175 | |

| Lys | Thr | Thr | Pro | Pro | Val | Leu | Asp | Ser | Asp | Gly | Ser | Phe | Phe | Leu | Tyr |
|---|---|---|---|---|---|---|---|---|---|---|---|---|---|---|---|
| | | | 180 | | | | | 185 | | | | | 190 | | |

| Ser | Lys | Leu | Thr | Val | Asp | Lys | Ser | Arg | Trp | Gln | Gln | Gly | Asn | Val | Phe |
|---|---|---|---|---|---|---|---|---|---|---|---|---|---|---|---|
| | | | 195 | | | | | 200 | | | | | 205 | | |

| Ser | Cys | Ser | Val | Met | His | Glu | Ala | Leu | His | Asn | His | Tyr | Thr | Gln | Lys |
|---|---|---|---|---|---|---|---|---|---|---|---|---|---|---|---|
| | 210 | | | | | 215 | | | | | 220 | | | | |

| Ser | Leu | Ser | Leu | Ser | Pro | Gly | Gln | Arg | His | Asn | Asn | Ser | Ser | Leu | Asn |
|---|---|---|---|---|---|---|---|---|---|---|---|---|---|---|---|
| 225 | | | | | 230 | | | | | 235 | | | | | 240 |

| Thr | Gly | Thr | Gln | Met | Ala | Gly | His | Ser | Pro | Asn | Ser | Gln | Val | Gln | Leu |
|---|---|---|---|---|---|---|---|---|---|---|---|---|---|---|---|
| | | | | 245 | | | | | 250 | | | | | 255 | |

| Val | Gln | Ser | Gly | Pro | Glu | Val | Lys | Lys | Pro | Gly | Ser | Ser | Val | Lys | Val |
|---|---|---|---|---|---|---|---|---|---|---|---|---|---|---|---|
| | | | 260 | | | | | 265 | | | | | 270 | | |

| Ser | Cys | Lys | Ala | Ser | Gly | Tyr | Thr | Phe | Ser | Arg | Ser | Thr | Met | His | Trp |
|---|---|---|---|---|---|---|---|---|---|---|---|---|---|---|---|
| | | | 275 | | | | | 280 | | | | | 285 | | |

| Val | Arg | Gln | Ala | Pro | Gly | Gln | Gly | Leu | Glu | Trp | Ile | Gly | Tyr | Ile | Asn |
|---|---|---|---|---|---|---|---|---|---|---|---|---|---|---|---|
| | 290 | | | | | 295 | | | | | 300 | | | | |

| Pro | Ser | Ser | Ala | Tyr | Thr | Asn | Tyr | Asn | Gln | Lys | Phe | Lys | Asp | Arg | Val |
|---|---|---|---|---|---|---|---|---|---|---|---|---|---|---|---|
| 305 | | | | | 310 | | | | | 315 | | | | | 320 |

| Thr | Ile | Thr | Ala | Asp | Lys | Ser | Thr | Ser | Thr | Ala | Tyr | Met | Glu | Leu | Ser |
|---|---|---|---|---|---|---|---|---|---|---|---|---|---|---|---|
| | | | | 325 | | | | | 330 | | | | | 335 | |

| Ser | Leu | Arg | Ser | Glu | Asp | Thr | Ala | Val | Tyr | Tyr | Cys | Ala | Arg | Pro | Gln |
|---|---|---|---|---|---|---|---|---|---|---|---|---|---|---|---|
| | | | 340 | | | | | 345 | | | | | 350 | | |

| Val | His | Tyr | Asp | Tyr | Asn | Gly | Phe | Pro | Tyr | Trp | Gly | Gln | Gly | Thr | Leu |

```
             355                 360                 365
Val Thr Val Ser Ser Gly Gly Gly Ser Gly Gly Gly Ser Gly
            370                 375                 380
Gly Gly Gly Ser Gly Gly Gly Ser Asp Ile Gln Met Thr Gln Ser
385                 390                 395                 400
Pro Ser Thr Leu Ser Ala Ser Val Gly Asp Arg Val Thr Met Thr Cys
                    405                 410                 415
Ser Ala Ser Ser Ser Val Ser Tyr Met Asn Trp Tyr Gln Gln Lys Pro
                420                 425                 430
Gly Lys Ala Pro Lys Arg Trp Ile Tyr Asp Ser Ser Lys Leu Ala Ser
            435                 440                 445
Gly Val Pro Ser Arg Phe Ser Gly Ser Gly Ser Gly Thr Glu Phe Thr
        450                 455                 460
Leu Thr Ile Ser Ser Leu Gln Pro Asp Asp Phe Ala Thr Tyr Tyr Cys
465                 470                 475                 480
Gln Gln Trp Ser Arg Asn Pro Pro Thr Phe Gly Gly Gly Thr Lys Val
                485                 490                 495
Glu Ile Lys Arg Ser Ser Ser
            500
```

<210> SEQ ID NO 61
<211> LENGTH: 2301
<212> TYPE: DNA
<213> ORGANISM: Artificial Sequence
<220> FEATURE:
<223> OTHER INFORMATION: TSC408 Anti-PSMA X anti-CD3 bispecific molecule

<400> SEQUENCE: 61

```
atggaagcac cagcgcagct tctcttcctc ctgctactct ggctcccaga taccaccggt      60
gatatccaga tgacccagtc tccatccgcc atgtctgcat ctgtaggaga cagagtcacc     120
atcacttgcc gggcgagtaa gagcattagc aaatatttag cctggtttca gcagaaacca     180
gggaaagttc ctaagctccg catccattct ggatctactt tgcaatcagg ggtcccatct     240
cggttcagtg gcagtggatc tgggacagaa tttactctca ccatcagcag cctgcagcct     300
gaagattttg caacttatta ctgtcaacag catattgaat acccgtggac gttcggccaa     360
gggaccaagg tggaaatcaa acgaggtggc ggagggtctg ggggtggcgg atccggaggt     420
ggtggctctc aggtccagct ggtacagtct ggggctgagg tgaagaagcc tggggcttca     480
gtgaaggtct cctgcaaggc ttctggatac acattcactg actactacat gcactgggtg     540
cgacaggccc ctggacaagg gcttgagtgg atgggatatt ttaatcctta taatgattat     600
actagatacg cacagaagtt ccagggcaga gtcaccatga ccagggacac gtctatcagc     660
acagcctaca tggagctgag cagcctgaga tctgacgaca cggccgtgta ttactgtgca     720
agatcggatg gttactacga tgctatggac tactggggtc aaggaaccac agtcaccgtc     780
tcctcgagtg agcccaaatc ttctgacaaa actcacacat gcccaccgtg cccagcacct     840
gaagccgcgg gtgcaccgtc agtcttcctc ttccccccaa aacccaagga caccctcatg     900
atctcccgga cccctgaggt cacatgcgtg gtggtggacg tgagccacga agaccctgag     960
gtcaagttca actggtacgt ggacggcgtg gaggtgcata atgccaagac aaagccgcgg    1020
gaggagcagt acaacagcac gtaccgtgtg gtcagcgtcc tcaccgtcct gcaccaggac    1080
tggctgaatg gcaaggcgta cgcgtgcgcg gtctccaaca aagccctccc agcccccatc    1140
gagaaaacca tctccaaagc caagggcagc cccgagaac cacaggtgta caccctgccc    1200
```

```
ccatcccggg atgagctgac caagaaccag gtcagcctga cctgcctggt caaaggcttc    1260
tatccaagcg acatcgccgt ggagtgggag agcaatgggc agccggagaa caactacaag    1320
accacgcctc ccgtgctgga ctccgacggc tccttcttcc tctacagcaa gctcaccgtg    1380
gacaagagca ggtggcagca ggggaacgtc ttctcatgct ccgtgatgca tgaggctctg    1440
cacaaccact acacgcagaa gagcctctcc ctgtctccgg gtcagaggca acaattct     1500 tccctgaata caggaactca gatggcaggt cattctccga attctcaggt ccagctggtg    1560
caatctgggc ctgaggtgaa gaagcctggg tcctcggtga aggtctcctg caaggcttct    1620
ggatatacct tcagcagatc tacgatgcac tgggtgcgac aggcccctgg acaagggctt    1680
gagtggatag gatacattaa tcctagcagt gcttatacta attacaatca gaaattcaag    1740
gacagagtca cgattaccgc ggacaaatcc acgagcacag cctacatgga gctgagcagc    1800
ctgagatctg aggacacggc cgtgtattac tgtgcgagac cccaagtcca ctatgattac    1860
aacgggtttc cttactgggg ccaaggaacc ctggtcaccg tctcctcagg tggaggcggt    1920
tcaggcggag gtggatccgg cggtggcgga tcgggtggcg gcggatctga catccagatg    1980
acccagtctc cttccaccct gtctgcatct gtaggagaca gagtcaccat cacttgcagt    2040
gccagctcaa gtgtaagtta catgaactgg tatcagcaga aaccagggaa agcccctaag    2100
agatggattt atgactcatc caaactggct tctggggtcc catcaaggtt cagcggcagt    2160
ggatctggga cagagttcac tctcaccatc agcagcctgc agcctgatga ttttgcaact    2220
tattactgcc aacagtggag tcgtaaccca cccactttcg gcggagggac caaggtggag    2280
atcaaacggt cctccagcta a                                             2301
```

<210> SEQ ID NO 62
<211> LENGTH: 746
<212> TYPE: PRT
<213> ORGANISM: Artificial Sequence
<220> FEATURE:
<223> OTHER INFORMATION: TSC408 Anti-PSMA X anti-CD3 bispecific molecule

<400> SEQUENCE: 62

```
Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Ser Gln Val Gln Leu Val
        115                 120                 125

Gln Ser Gly Ala Glu Val Lys Lys Pro Gly Ala Ser Val Lys Val Ser
    130                 135                 140

Cys Lys Ala Ser Gly Tyr Thr Phe Thr Asp Tyr Tyr Met His Trp Val
145                 150                 155                 160

Arg Gln Ala Pro Gly Gln Gly Leu Glu Trp Met Gly Tyr Phe Asn Pro
```

-continued

```
                165                 170                 175
Tyr Asn Asp Tyr Thr Arg Tyr Ala Gln Lys Phe Gln Gly Arg Val Thr
            180                 185                 190

Met Thr Arg Asp Thr Ser Ile Ser Thr Ala Tyr Met Glu Leu Ser Ser
        195                 200                 205

Leu Arg Ser Asp Asp Thr Ala Val Tyr Tyr Cys Ala Arg Ser Asp Gly
    210                 215                 220

Tyr Tyr Asp Ala Met Asp Tyr Trp Gly Gln Gly Thr Thr Val Thr Val
225                 230                 235                 240

Ser Ser Ser Glu Pro Lys Ser Ser Asp Lys Thr His Thr Cys Pro Pro
            245                 250                 255

Cys Pro Ala Pro Glu Ala Ala Gly Ala Pro Ser Val Phe Leu Phe Pro
        260                 265                 270

Pro Lys Pro Lys Asp Thr Leu Met Ile Ser Arg Thr Pro Glu Val Thr
    275                 280                 285

Cys Val Val Val Asp Val Ser His Glu Asp Pro Glu Val Lys Phe Asn
290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
            325                 330                 335

Leu His Gln Asp Trp Leu Asn Gly Lys Ala Tyr Ala Cys Ala Val Ser
        340                 345                 350

Asn Lys Ala Leu Pro Ala Pro Ile Glu Lys Thr Ile Ser Lys Ala Lys
    355                 360                 365

Gly Gln Pro Arg Glu Pro Gln Val Tyr Thr Leu Pro Pro Ser Arg Asp
370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
            405                 410                 415

Asn Asn Tyr Lys Thr Thr Pro Pro Val Leu Asp Ser Asp Gly Ser Phe
        420                 425                 430

Phe Leu Tyr Ser Lys Leu Thr Val Asp Lys Ser Arg Trp Gln Gln Gly
    435                 440                 445

Asn Val Phe Ser Cys Ser Val Met His Glu Ala Leu His Asn His Tyr
450                 455                 460

Thr Gln Lys Ser Leu Ser Leu Ser Pro Gly Gln Arg His Asn Asn Ser
465                 470                 475                 480

Ser Leu Asn Thr Gly Thr Gln Met Ala Gly His Ser Pro Asn Ser Gln
            485                 490                 495

Val Gln Leu Val Gln Ser Gly Pro Glu Val Lys Lys Pro Gly Ser Ser
        500                 505                 510

Val Lys Val Ser Cys Lys Ala Ser Gly Tyr Thr Phe Ser Arg Ser Thr
    515                 520                 525

Met His Trp Val Arg Gln Ala Pro Gly Gln Gly Leu Glu Trp Ile Gly
530                 535                 540

Tyr Ile Asn Pro Ser Ser Ala Tyr Thr Asn Tyr Asn Gln Lys Phe Lys
545                 550                 555                 560

Asp Arg Val Thr Ile Thr Ala Asp Lys Ser Thr Ser Thr Ala Tyr Met
            565                 570                 575

Glu Leu Ser Ser Leu Arg Ser Glu Asp Thr Ala Val Tyr Tyr Cys Ala
        580                 585                 590
```

```
Arg Pro Gln Val His Tyr Asp Tyr Asn Gly Phe Pro Tyr Trp Gly Gln
        595                 600                 605

Gly Thr Leu Val Thr Val Ser Ser Gly Gly Gly Ser Gly Gly Gly
        610                 615                 620

Gly Ser Gly Gly Gly Gly Ser Gly Gly Gly Ser Asp Ile Gln Met
625                 630                 635                 640

Thr Gln Ser Pro Ser Thr Leu Ser Ala Ser Val Gly Asp Arg Val Thr
                645                 650                 655

Ile Thr Cys Ser Ala Ser Ser Val Ser Tyr Met Asn Trp Tyr Gln
        660                 665                 670

Gln Lys Pro Gly Lys Ala Pro Lys Arg Trp Ile Tyr Asp Ser Ser Lys
                675                 680                 685

Leu Ala Ser Gly Val Pro Ser Arg Phe Ser Gly Ser Gly Ser Gly Thr
        690                 695                 700

Glu Phe Thr Leu Thr Ile Ser Ser Leu Gln Pro Asp Asp Phe Ala Thr
705                 710                 715                 720

Tyr Tyr Cys Gln Gln Trp Ser Arg Asn Pro Pro Thr Phe Gly Gly Gly
                725                 730                 735

Thr Lys Val Glu Ile Lys Arg Ser Ser Ser
        740                 745
```

<210> SEQ ID NO 63
<211> LENGTH: 2301
<212> TYPE: DNA
<213> ORGANISM: Artificial Sequence
<220> FEATURE:
<223> OTHER INFORMATION: TSC409 Anti-PSMA X anti-CD3 bispecific molecule

<400> SEQUENCE: 63

| | |
|---|---|
| atggaagcac cagcgcagct tctcttcctc ctgctactct ggctcccaga taccaccggt | 60 |
| gatatccaga tgacccagtc tccatccgcc atgtctgcat ctgtaggaga cagagtcacc | 120 |
| atcacttgcc gggcgagtaa gagcattagc aaatatttag cctggtttca gcagaaacca | 180 |
| gggaaagttc ctaagctccg catccattct ggatctactt tgcaatcagg ggtcccatct | 240 |
| cggttcagtg gcagtggatc tgggacagaa tttactctca ccatcagcag cctgcagcct | 300 |
| gaagattttg caacttatta ctgtcaacag catattgaat accgtggac gttcggccaa | 360 |
| gggaccaagg tggaaatcaa acgaggtggc ggagggtctg ggggtggcgg atccggaggt | 420 |
| ggtggctctc aggtccagct ggtacagtct ggggctgagg tgaagaagcc tggggcttca | 480 |
| gtgaaggtct cctgcaaggc ttctggatac acattcactg actactacat gcactgggtg | 540 |
| cgacaggccc ctggacaagg gcttgagtgg atgggatatt ttaatcctta taatgattat | 600 |
| actagatacg cacagaagtt ccagggcaga gtcaccatga ccaggacac gtctatcagc | 660 |
| acagcctaca tggagctgag cagcctgaga tctgacgaca cggccgtgta ttactgtgca | 720 |
| agatcggatg ttactacga tgctatggac tactggggtc aaggaaccac agtcaccgtc | 780 |
| tcctcgagtg agcccaaatc ttctgacaaa actcacacat gcccaccgtg cccagcacct | 840 |
| gaagccgcgg gtgcaccgtc agtcttcctc ttccccccaa aacccaagga caccctcatg | 900 |
| atctccccgga cccctgaggt cacatgcgtg gtggtggacg tgagccacga agaccctgag | 960 |
| gtcaagttca actggtacgt ggacggcgtg gaggtgcata atgccaagac aaagccgcgg | 1020 |
| gaggagcagt acaacagcac gtaccgtgtg gtcagcgtcc tcaccgtcct gcaccaggac | 1080 |
| tggctgaatg gcaaggcgta cgcgtgcgcg gtctccaaca aagccctccc agcccccatc | 1140 |

```
gagaaaacca tctccaaagc caaagggcag ccccgagaac cacaggtgta caccctgccc   1200
ccatcccggg atgagctgac caagaaccag gtcagcctga cctgcctggt caaaggcttc   1260
tatccaagcg acatcgccgt ggagtgggag agcaatgggc agccggagaa caactacaag   1320
accacgcctc ccgtgctgga ctccgacggc tccttcttcc tctacagcaa gctcaccgtg   1380
gacaagagca ggtggcagca ggggaacgtc ttctcatgct ccgtgatgca tgaggctctg   1440
cacaaccact acacgcagaa gagcctctcc ctgtctccgg gtcagaggca aacaattct    1500 tccctgaata caggaactca gatggcaggt cattctccga attctcaggt ccagctggtg   1560
caatctgggc ctgaggtgaa gaagcctggg tcctcggtga aggtctcctg caaggcttct   1620
ggatatacct tcagcagatc tacgatgcac tgggtgcgac aggcccctgg acaagggctt   1680
gagtggatgg gatacattaa tcctagcagt gcttatacta attacaatca gaaattcaag   1740
gacagagtca cgattaccgc ggacaaatcc acgagcacag cctacatgga gctgagcagc   1800
ctgagatctg aggacacggc cgtgtattac tgtgcgagac cccaagtcca ctatgattac   1860
aacgggtttc cttactgggg ccaaggaacc ctggtcaccg tctcctcagg tggaggcggt   1920
tcaggcggag gtggatccgg cggtggcgga tcgggtggcg gcggatctga catccagatg   1980
acccagtctc cttccaccct gtctgcatct gtaggagaca gagtcaccat gacttgcagt   2040
gccagctcaa gtgtaagtta catgaactgg tatcagcaga aaccagggaa agcccctaag   2100
agatggattt atgactcatc caaactggct tctggggtcc catcaaggtt cagcggcagt   2160
ggatctggga cagagttcac tctcaccatc agcagcctgc agcctgatga ttttgcaact   2220
tattactgcc aacagtggag tcgtaaccca cccactttcg gcggagggac caaggtggag   2280
atcaaacggt cctccagcta a                                             2301
```

<210> SEQ ID NO 64
<211> LENGTH: 746
<212> TYPE: PRT
<213> ORGANISM: Artificial Sequence
<220> FEATURE:
<223> OTHER INFORMATION: TSC409 Anti-PSMA X anti-CD3 bispecific molecule

<400> SEQUENCE: 64

```
Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Ser Gln Val Gln Leu Val
        115                 120                 125

Gln Ser Gly Ala Glu Val Lys Lys Pro Gly Ala Ser Val Lys Val Ser
    130                 135                 140

Cys Lys Ala Ser Gly Tyr Thr Phe Thr Asp Tyr Tyr Met His Trp Val
145                 150                 155                 160
```

```
Arg Gln Ala Pro Gly Gln Gly Leu Glu Trp Met Gly Tyr Phe Asn Pro
                165                 170                 175
Tyr Asn Asp Tyr Thr Arg Tyr Ala Gln Lys Phe Gln Gly Arg Val Thr
            180                 185                 190
Met Thr Arg Asp Thr Ser Ile Ser Thr Ala Tyr Met Glu Leu Ser Ser
        195                 200                 205
Leu Arg Ser Asp Asp Thr Ala Val Tyr Tyr Cys Ala Arg Ser Asp Gly
    210                 215                 220
Tyr Tyr Asp Ala Met Asp Tyr Trp Gly Gln Gly Thr Thr Val Thr Val
225                 230                 235                 240
Ser Ser Ser Glu Pro Lys Ser Ser Asp Lys Thr His Thr Cys Pro Pro
                245                 250                 255
Cys Pro Ala Pro Glu Ala Ala Gly Ala Pro Ser Val Phe Leu Phe Pro
            260                 265                 270
Pro Lys Pro Lys Asp Thr Leu Met Ile Ser Arg Thr Pro Glu Val Thr
        275                 280                 285
Cys Val Val Val Asp Val Ser His Glu Asp Pro Glu Val Lys Phe Asn
    290                 295                 300
Trp Tyr Val Asp Gly Val Glu Val His Asn Ala Lys Thr Lys Pro Arg
305                 310                 315                 320
Glu Glu Gln Tyr Asn Ser Thr Tyr Arg Val Val Ser Val Leu Thr Val
                325                 330                 335
Leu His Gln Asp Trp Leu Asn Gly Lys Ala Tyr Ala Cys Ala Val Ser
            340                 345                 350
Asn Lys Ala Leu Pro Ala Pro Ile Glu Lys Thr Ile Ser Lys Ala Lys
        355                 360                 365
Gly Gln Pro Arg Glu Pro Gln Val Tyr Thr Leu Pro Pro Ser Arg Asp
    370                 375                 380
Glu Leu Thr Lys Asn Gln Val Ser Leu Thr Cys Leu Val Lys Gly Phe
385                 390                 395                 400
Tyr Pro Ser Asp Ile Ala Val Glu Trp Glu Ser Asn Gly Gln Pro Glu
                405                 410                 415
Asn Asn Tyr Lys Thr Thr Pro Pro Val Leu Asp Ser Asp Gly Ser Phe
            420                 425                 430
Phe Leu Tyr Ser Lys Leu Thr Val Asp Lys Ser Arg Trp Gln Gln Gly
        435                 440                 445
Asn Val Phe Ser Cys Ser Val Met His Glu Ala Leu His Asn His Tyr
    450                 455                 460
Thr Gln Lys Ser Leu Ser Leu Ser Pro Gly Gln Arg His Asn Asn Ser
465                 470                 475                 480
Ser Leu Asn Thr Gly Thr Gln Met Ala Gly His Ser Pro Asn Ser Gln
                485                 490                 495
Val Gln Leu Val Gln Ser Gly Pro Glu Val Lys Lys Pro Gly Ser Ser
            500                 505                 510
Val Lys Val Ser Cys Lys Ala Ser Gly Tyr Thr Phe Ser Arg Ser Thr
        515                 520                 525
Met His Trp Val Arg Gln Ala Pro Gly Gln Gly Leu Glu Trp Met Gly
    530                 535                 540
Tyr Ile Asn Pro Ser Ser Ala Tyr Thr Asn Tyr Asn Gln Lys Phe Lys
545                 550                 555                 560
Asp Arg Val Thr Ile Thr Ala Asp Lys Ser Thr Ser Thr Ala Tyr Met
                565                 570                 575
```

Glu Leu Ser Ser Leu Arg Ser Glu Asp Thr Ala Val Tyr Tyr Cys Ala
            580                 585                 590

Arg Pro Gln Val His Tyr Asp Tyr Asn Gly Phe Pro Tyr Trp Gly Gln
        595                 600                 605

Gly Thr Leu Val Thr Val Ser Ser Gly Gly Gly Ser Gly Gly Gly
        610                 615                 620

Gly Ser Gly Gly Gly Ser Gly Gly Gly Ser Asp Ile Gln Met
625                 630                 635                 640

Thr Gln Ser Pro Ser Thr Leu Ser Ala Ser Val Gly Asp Arg Val Thr
                645                 650                 655

Met Thr Cys Ser Ala Ser Ser Val Ser Tyr Met Asn Trp Tyr Gln
        660                 665                 670

Gln Lys Pro Gly Lys Ala Pro Lys Arg Trp Ile Tyr Asp Ser Ser Lys
            675                 680                 685

Leu Ala Ser Gly Val Pro Ser Arg Phe Ser Gly Ser Gly Ser Gly Thr
        690                 695                 700

Glu Phe Thr Leu Thr Ile Ser Ser Leu Gln Pro Asp Asp Phe Ala Thr
705                 710                 715                 720

Tyr Tyr Cys Gln Gln Trp Ser Arg Asn Pro Pro Thr Phe Gly Gly Gly
                725                 730                 735

Thr Lys Val Glu Ile Lys Arg Ser Ser Ser
            740                 745

<210> SEQ ID NO 65
<211> LENGTH: 2301
<212> TYPE: DNA
<213> ORGANISM: Artificial Sequence
<220> FEATURE:
<223> OTHER INFORMATION: TSC410 Anti-PSMA X anti-CD3 bispecific molecule

<400> SEQUENCE: 65

```
atggaagcac cagcgcagct tctcttcctc ctgctactct ggctcccaga taccaccggt     60
gatatccaga tgacccagtc tccatccgcc atgtctgcat ctgtaggaga cagagtcacc    120
atcacttgcc gggcgagtaa gagcattagc aaatatttag cctggtttca gcagaaacca    180
gggaaagttc ctaagctccg catccattct ggatctactt tgcaatcagg ggtcccatct    240
cggttcagtg gcagtggatc tgggacagaa tttactctca ccatcagcag cctgcagcct    300
gaagattttg caacttatta ctgtcaacag catattgaat acccgtggac gttcggccaa    360
gggaccaagg tggaaatcaa acgaggtggc ggagggtctg gggtggcgg atccggaggt    420 ggtggctctc aggtccagct ggtacagtct ggggctgagg tgaagaagcc tggggcttca    480
gtgaaggtct cctgcaaggc ttctggatac acattcactg actactacat gcactgggtg    540
cgacaggccc ctggacaagg gcttgagtgg atgggatatt taatcctta taatgattat    600 actagatacg cacagaagtt ccagggcaga gtcaccatga ccagggacac gtctatcagc    660
acagcctaca tggagctgag cagcctgaga tctgacgaca cggccgtgta ttactgtgca    720
agatcggatg gttactacga tgctatggac tactggggtc aaggaaccac agtcaccgtc    780
tcctcgagtg agcccaaatc ttctgacaaa actcacacat gcccaccgtg cccagcacct    840
gaagccgcgg gtgcaccgtc agtcttcctc ttccccccaa aacccaagga caccctcatg    900
atctcccgga cccctgaggt cacatgcgtg gtggtggacg tgagccacga agaccctgag    960
gtcaagttca actggtacgt ggacggcgtg gaggtgcata atgccaagac aaagccgcgg   1020
gaggagcagt acaacagcac gtaccgtgtg gtcagcgtcc tcaccgtcct gcaccaggac   1080
```

```
tggctgaatg gcaaggcgta cgcgtgcgcg gtctccaaca aagccctccc agccccatc    1140 gagaaaacca tctccaaagc caaagggcag ccccgagaac acaggtgta caccctgccc     1200 ccatcccggg atgagctgac caagaaccag gtcagcctga cctgcctggt caaaggcttc    1260
tatccaagcg acatcgccgt ggagtgggag agcaatgggc agccggagaa caactacaag    1320
accacgcctc ccgtgctgga ctccgacggc tccttcttcc tctacagcaa gctcaccgtg    1380
gacaagagca ggtggcagca ggggaacgtc ttctcatgct ccgtgatgca tgaggctctg    1440
cacaaccact acacgcagaa gagcctctcc ctgtctccgg gtcagaggca caacaattct    1500
tccctgaata caggaactca gatggcaggt cattctccga attctcaggt ccagctggtg    1560
caatctgggg ctgaggtgaa gaagcctggg tcctcggtga aggtctcctg caaggcttct    1620
ggatatacct tcagcagatc tacgatgcac tgggtgcgac aggcccctgg acaagggctt    1680
gagtggatag gatacattaa tcctagcagt gcttatacta attacaatca gaaattcaag    1740
gacagagtca cgattaccgc ggacaaatcc acgagcacag cctacatgga gctgagcagc    1800
ctgagatctg aggacacggc cgtgtattac tgtgcgagac cccaagtcca ctatgattac    1860
aacgggtttc cttactgggg ccaaggaacc ctggtcaccg tctcctcagg tggaggcggt    1920
tcaggcggag gtggatccgg cggtggcgga tcgggtggcg gcggatctga catccagatg    1980
acccagtctc cttccaccct gtctgcatct gtaggagaca gagtcaccat gacttgcagt    2040
gccagctcaa gtgtaagtta catgaactgg tatcagcaga aaccagggaa agcccctaag    2100
agatggattt atgactcatc caaactggct tctggggtcc catcaaggtt cagcggcagt    2160
ggatctggga cagagttcac tctcaccatc agcagcctgc agcctgatga ttttgcaact    2220
tattactgcc aacagtggag tcgtaaccca cccactttcg gcggagggac caaggtggag    2280
atcaaacggt cctccagcta a                                              2301

<210> SEQ ID NO 66
<211> LENGTH: 746
<212> TYPE: PRT
<213> ORGANISM: Artificial Sequence
<220> FEATURE:
<223> OTHER INFORMATION: TSC410 Anti-PSMA X anti-CD3 bispecific molecule

<400> SEQUENCE: 66
```

Asp Ile Gln Met Thr Gln Ser Pro Ser Ala Met Ser Ala Ser Val Gly
1               5                  10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Ser Gln Val Gln Leu Val
        115                 120                 125

Gln Ser Gly Ala Glu Val Lys Lys Pro Gly Ala Ser Val Lys Val Ser
    130                 135                 140

-continued

```
Cys Lys Ala Ser Gly Tyr Thr Phe Thr Asp Tyr Tyr Met His Trp Val
145                 150                 155                 160

Arg Gln Ala Pro Gly Gln Gly Leu Glu Trp Met Gly Tyr Phe Asn Pro
                165                 170                 175

Tyr Asn Asp Tyr Thr Arg Tyr Ala Gln Lys Phe Gln Gly Arg Val Thr
            180                 185                 190

Met Thr Arg Asp Thr Ser Ile Ser Thr Ala Tyr Met Glu Leu Ser Ser
        195                 200                 205

Leu Arg Ser Asp Asp Thr Ala Val Tyr Tyr Cys Ala Arg Ser Asp Gly
    210                 215                 220

Tyr Tyr Asp Ala Met Asp Tyr Trp Gly Gln Gly Thr Thr Val Thr Val
225                 230                 235                 240

Ser Ser Ser Glu Pro Lys Ser Ser Asp Lys Thr His Thr Cys Pro Pro
                245                 250                 255

Cys Pro Ala Pro Glu Ala Ala Gly Ala Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Ala Tyr Ala Cys Ala Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Gln Arg His Asn Asn Ser
465                 470                 475                 480

Ser Leu Asn Thr Gly Thr Gln Met Ala Gly His Ser Pro Asn Ser Gln
                485                 490                 495

Val Gln Leu Val Gln Ser Gly Ala Glu Val Lys Lys Pro Gly Ser Ser
            500                 505                 510

Val Lys Val Ser Cys Lys Ala Ser Gly Tyr Thr Phe Ser Arg Ser Thr
        515                 520                 525

Met His Trp Val Arg Gln Ala Pro Gly Gln Gly Leu Glu Trp Ile Gly
    530                 535                 540

Tyr Ile Asn Pro Ser Ser Ala Tyr Thr Asn Tyr Asn Gln Lys Phe Lys
545                 550                 555                 560

Asp Arg Val Thr Ile Thr Ala Asp Lys Ser Thr Ser Thr Ala Tyr Met
```

```
                    565                 570                 575
Glu Leu Ser Ser Leu Arg Ser Glu Asp Thr Ala Val Tyr Tyr Cys Ala
                580                 585                 590

Arg Pro Gln Val His Tyr Asp Tyr Asn Gly Phe Pro Tyr Trp Gly Gln
            595                 600                 605

Gly Thr Leu Val Thr Val Ser Ser Gly Gly Gly Ser Gly Gly Gly
        610                 615                 620

Gly Ser Gly Gly Gly Ser Gly Gly Gly Ser Asp Ile Gln Met
625                 630                 635                 640

Thr Gln Ser Pro Ser Thr Leu Ser Ala Ser Val Gly Asp Arg Val Thr
                645                 650                 655

Met Thr Cys Ser Ala Ser Ser Val Ser Tyr Met Asn Trp Tyr Gln
            660                 665                 670

Gln Lys Pro Gly Lys Ala Pro Lys Arg Trp Ile Tyr Asp Ser Ser Lys
                675                 680                 685

Leu Ala Ser Gly Val Pro Ser Arg Phe Ser Gly Ser Gly Ser Gly Thr
            690                 695                 700

Glu Phe Thr Leu Thr Ile Ser Ser Leu Gln Pro Asp Asp Phe Ala Thr
705                 710                 715                 720

Tyr Tyr Cys Gln Gln Trp Ser Arg Asn Pro Pro Thr Phe Gly Gly Gly
                725                 730                 735

Thr Lys Val Glu Ile Lys Arg Ser Ser Ser
            740                 745
```

<210> SEQ ID NO 67
<211> LENGTH: 2301
<212> TYPE: DNA
<213> ORGANISM: Artificial Sequence
<220> FEATURE:
<223> OTHER INFORMATION: TSC411 Anti-PSMA X anti-CD3 bispecific molecule

<400> SEQUENCE: 67

| | |
|---|---|
| atggaagcac cagcgcagct tctcttcctc ctgctactct ggctcccaga taccaccggt | 60 |
| gatatccaga tgacccagtc tccatccgcc atgtctgcat ctgtaggaga cagagtcacc | 120 |
| atcacttgcc gggcgagtaa gagcattagc aaatatttag cctggtttca gcagaaacca | 180 |
| gggaaagttc ctaagctccg catccattct ggatctactt tgcaatcagg ggtcccatct | 240 |
| cggttcagtg gcagtggatc tgggacagaa tttactctca ccatcagcag cctgcagcct | 300 |
| gaagattttg caacttatta ctgtcaacag catattgaat accgtggac gttcggccaa | 360 |
| gggaccaagg tggaaatcaa cgaggtggc ggagggtctg ggggtggcgg atccggaggt | 420 |
| ggtggctctc aggtccagct ggtacagtct ggggctgagg tgaagaagcc tggggcttca | 480 |
| gtgaaggtct cctgcaaggc ttctggatac acattcactg actactacat gcactgggtg | 540 |
| cgacaggccc ctggacaagg gcttgagtgg atgggatatt ttaatcctta taatgattat | 600 |
| actagatacg cacagaagtt ccagggcaga gtcaccatga ccagggacac gtctatcagc | 660 |
| acagcctaca tggagctgag cagcctgaga tctgacgaca cggccgtgta ttactgtgca | 720 |
| agatcggatg ttactacga tgctatggac tactggggtc aaggaaccac agtcaccgtc | 780 |
| tcctcgagtg agcccaaatc ttctgacaaa actcacacat gcccaccgtg cccagcacct | 840 |
| gaagccgcgg gtgcaccgtc agtcttcctc ttccccccaa aacccaagga caccctcatg | 900 |
| atctcccgga cccctgaggt cacatgcgtg gtggtggacg tgagccacga agaccctgag | 960 |
| gtcaagttca actggtacgt ggacggcgtg gaggtgcata atgccaagac aaagccgcgg | 1020 |

```
gaggagcagt acaacagcac gtaccgtgtg gtcagcgtcc tcaccgtcct gcaccaggac    1080
tggctgaatg gcaaggcgta cgcgtgcgcg gtctccaaca aagccctccc agccccatc    1140 gagaaaacca tctccaaagc caagggcag ccccgagaac acaggtgta caccctgccc    1200 ccatcccggg atgagctgac caagaaccag gtcagcctga cctgcctggt caaaggcttc    1260
tatccaagcg acatcgccgt ggagtgggag agcaatgggc agccggagaa caactacaag    1320
accacgcctc ccgtgctgga ctccgacggc tccttcttcc tctacagcaa gctcaccgtg    1380
gacaagagca ggtggcagca ggggaacgtc ttctcatgct ccgtgatgca tgaggctctg    1440
cacaaccact acacgcagaa gagcctctcc ctgtctccgg gtcagaggca acaattct    1500 tccctgaata caggaactca gatggcaggt cattctccga attctcaggt ccagctggtg    1560
caatctgggc ctgaggtgaa gaagcctggg tcctcggtga aggtctcctg caaggcttct    1620
ggatatacct tcagcagatc tacgatgcac tgggtgcgac aggcccctgg acaagggctt    1680
gagtggatag gatacattaa tcctagcagt gcttatacta attacaatca gaaattcaag    1740
gacagagtca cgattaccgc ggacaaatcc acgagcacag cctacatgga gctgagcagc    1800
ctgagatctg aggacacggc cgtgtattac tgtgcgagac cccaagtcca ctatgattac    1860
aacgggtttc cttactgggg ccaaggaacc ctggtcaccg tctcctcagg tggaggcggt    1920
tcaggcggag gtggatccgg cggtggcgga tcgggtggcg gcggatctga catccagatg    1980
acccagtctc cttccaccct gtctgcatct gtaggagaca gagtcaccat gacttgcagt    2040
gccagctcaa gtgtaagtta catgaactgg tatcagcaga aaccaggaa agcccctaag    2100 agatggattt atgactcatc caaactggct tctggggtcc catcaaggtt cagcggcagt    2160
ggatctggga cagagttcac tctcaccatc agcagcctgc agcctgatga ttttgcaact    2220
tattactgcc aacagtggag tcgtaaccca cccactttcg gcggagggac caaggtggag    2280
atcaaacggt cctccagcta a                                             2301

<210> SEQ ID NO 68
<211> LENGTH: 746
<212> TYPE: PRT
<213> ORGANISM: Artificial Sequence
<220> FEATURE:
<223> OTHER INFORMATION: TSC411 Anti-PSMA X anti-CD3 bispecific molecule

<400> SEQUENCE: 68

Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Gly Ser Gln Val Gln Leu Val
        115                 120                 125

Gln Ser Gly Ala Glu Val Lys Lys Pro Gly Ala Ser Val Lys Val Ser
```

```
            130                 135                 140
Cys Lys Ala Ser Gly Tyr Thr Phe Thr Asp Tyr Tyr Met His Trp Val
145                 150                 155                 160

Arg Gln Ala Pro Gly Gln Gly Leu Glu Trp Met Gly Tyr Phe Asn Pro
                165                 170                 175

Tyr Asn Asp Tyr Thr Arg Tyr Ala Gln Lys Phe Gln Gly Arg Val Thr
            180                 185                 190

Met Thr Arg Asp Thr Ser Ile Ser Thr Ala Tyr Met Glu Leu Ser Ser
        195                 200                 205

Leu Arg Ser Asp Asp Thr Ala Val Tyr Tyr Cys Ala Arg Ser Asp Gly
    210                 215                 220

Tyr Tyr Asp Ala Met Asp Tyr Trp Gly Gln Gly Thr Thr Val Thr Val
225                 230                 235                 240

Ser Ser Ser Glu Pro Lys Ser Ser Asp Lys Thr His Thr Cys Pro Pro
                245                 250                 255

Cys Pro Ala Pro Glu Ala Ala Gly Ala Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Ala Tyr Ala Cys Ala Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Gln Arg His Asn Asn Ser
465                 470                 475                 480

Ser Leu Asn Thr Gly Thr Gln Met Ala Gly His Ser Pro Asn Ser Gln
                485                 490                 495

Val Gln Leu Val Gln Ser Gly Pro Glu Val Lys Lys Pro Gly Ser Ser
            500                 505                 510

Val Lys Val Ser Cys Lys Ala Ser Gly Tyr Thr Phe Ser Arg Ser Thr
        515                 520                 525

Met His Trp Val Arg Gln Ala Pro Gly Gln Gly Leu Glu Trp Ile Gly
    530                 535                 540

Tyr Ile Asn Pro Ser Ser Ala Tyr Thr Asn Tyr Asn Gln Lys Phe Lys
545                 550                 555                 560
```

Asp Arg Val Thr Ile Thr Ala Asp Lys Ser Thr Ser Thr Ala Tyr Met
                565                 570                 575

Glu Leu Ser Ser Leu Arg Ser Glu Asp Thr Ala Val Tyr Tyr Cys Ala
            580                 585                 590

Arg Pro Gln Val His Tyr Asp Tyr Asn Gly Phe Pro Tyr Trp Gly Gln
        595                 600                 605

Gly Thr Leu Val Thr Val Ser Ser Gly Gly Gly Gly Ser Gly Gly Gly
    610                 615                 620

Gly Ser Gly Gly Gly Ser Gly Gly Gly Gly Ser Asp Ile Gln Met
625             630                 635                 640

Thr Gln Ser Pro Ser Thr Leu Ser Ala Ser Val Gly Asp Arg Val Thr
                645                 650                 655

Met Thr Cys Ser Ala Ser Ser Ser Val Ser Tyr Met Asn Trp Tyr Gln
            660                 665                 670

Gln Lys Pro Gly Lys Ala Pro Lys Arg Trp Ile Tyr Asp Ser Ser Lys
        675                 680                 685

Leu Ala Ser Gly Val Pro Ser Arg Phe Ser Gly Ser Gly Ser Gly Thr
    690                 695                 700

Glu Phe Thr Leu Thr Ile Ser Ser Leu Gln Pro Asp Asp Phe Ala Thr
705             710                 715                 720

Tyr Tyr Cys Gln Gln Trp Ser Arg Asn Pro Pro Thr Phe Gly Gly Gly
                725                 730                 735

Thr Lys Val Glu Ile Lys Arg Ser Ser Ser
            740                 745

```
<210> SEQ ID NO 69
<211> LENGTH: 2313
<212> TYPE: DNA
<213> ORGANISM: Artificial Sequence
<220> FEATURE:
<223> OTHER INFORMATION: CAS105 Anti-CD37 X anti-CD3 bispecific molecule

<400> SEQUENCE: 69
atggaagcac cagcgcagct tctcttcctc ctgctactct ggctcccaga taccaccggt    60
gaggtgcagc tggtgcagtc tggagcagag gtgaaaaagc ccggagagtc tctgaagatt   120
tcctgtaagg gctccggtta ctcattcact ggctacaata tgaactgggt gcgccagatg   180
cccgggaaag gcctggagtg gatgggcaat attgatcctt attatggtgg tactacctac   240
aaccggaagt tcaagggcca ggtcactatc tccgccgaca gtccatcagc accgcctac   300 ctgcaatgga gcagcctgaa ggcctcggac accgccatgt attactgtgc acgctcagtc   360 ggcccttcg actcctgggg ccagggcacc ctggtcactg tctcctctgg ggtggaggc    420 tctggtggcg gtggctctgg cggaggtgga tccggtggcg gcggatctgg cggggtggc   480 tctgaaattg tgttgacaca gtctccagcc accctgtctt tgtctccagg cgaaagagcc   540 acctctcct gccgagcaag tgaaaatgtt tacagctact tagcctggta ccaacagaaa   600
cctggccagg ctcctaggct cctcatctat tttgcaaaaa ccttagcaga aggtattcca   660
gccaggttca gtggcagtgg ctccgggaca gacttcactc tcaccatcag cagcctagag   720
cctgaagatt ttgcagttta ttactgtcaa catcattccg ataatccgtg acattcggc   780 caagggacca aggtggaaat caaatcctcg agtgagccca atcttctga caaaactcac   840 acatgcccac cgtgcccagc acctgaagcc gcgggtgcac cgtcagtctt cctcttcccc   900
ccaaaaccca aggacaccct catgatctcc cggacccctg aggtcacatg cgtggtggtg   960
```

```
gacgtgagcc acgaagaccc tgaggtcaag ttcaactggt acgtggacgg cgtggaggtg    1020
cataatgcca agacaaagcc gcgggaggag cagtacaaca gcacgtaccg tgtggtcagc    1080
gtcctcaccg tcctgcacca ggactggctg aatggcaagg catacgcgtg cgcggtctcc    1140
aacaaagccc tcccagcccc catcgagaaa accatctcca aagccaaagg gcagccccga    1200
gaaccacagg tgtacaccct gcccccatcc cgggatgagc tgaccaagaa ccaggtcagc    1260
ctgacctgcc tggtcaaagg cttctatcca agcgacatcg ccgtggagtg ggagagcaat    1320
gggcagccgg agaacaacta caagaccacg cctcccgtgc tggactccga cggctccttc    1380
ttcctctaca gcaagctcac cgtggacaag agcaggtggc agcaggggaa cgtcttctca    1440
tgctccgtga tgcatgaggc tctgcacaac cactacacgc agaagagcct ctccctgtct    1500
ccgggtcaga ggcacaacaa ttcttccctg aatacaggaa ctcagatggc aggtcattct    1560
ccgaattctc aggtccagct ggtggagtct ggggcgag tggtgcagcc tgggcggtca    1620
ctgaggctgt cctgcaaggc ttctggctac acctttacta gatctacgat gcactgggta    1680
aggcaggccc ctggacaagg tctggaatgg attggataca ttaatcctag cagtgcttat    1740
actaattaca atcagaaatt caaggacagg ttcacaatca gcgcagacaa atccaagagc    1800
acagccttcc tgcagatgga cagcctgagg cccgaggaca ccggcgtcta tttctgtgca    1860 cggcccaag tccactatga ttacaacggg tttccttact ggggccaagg gactcccgtc    1920
actgtctcta gcggtggcgg agggtctggg ggtggcggat ccgagggtgg tggctctgca    1980
caagacatcc agatgaccca gtctccaagc agcctgtctg caagcgtggg ggacagggtc    2040
accatgacct gcagtgccag ctcaagtgta agttacatga actggtacca gcagaagccg    2100
ggcaaggccc ccaaaagatg gatttatgac tcatccaaac tggcttctgg agtccctgct    2160
cgcttcagtg gcagtgggtc tgggaccgac tataccctca caatcagcag cctgcagccc    2220
gaagatttcg ccacttatta ctgccagcag tggagtcgta acccacccac gttcggaggg    2280
gggaccaagc tacaaattac atcctccagc taa                                2313

<210> SEQ ID NO 70
<211> LENGTH: 750
<212> TYPE: PRT
<213> ORGANISM: Artificial Sequence
<220> FEATURE:
<223> OTHER INFORMATION: CAS105 Anti-CD37 X anti-CD3 bispecific molecule

<400> SEQUENCE: 70

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Gly Tyr
            20                  25                  30

Asn Met Asn Trp Val Arg Gln Met Pro Gly Lys Gly Leu Glu Trp Met
        35                  40                  45

Gly Asn Ile Asp Pro Tyr Tyr Gly Gly Thr Thr Tyr Asn Arg Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Val Gly Pro Phe Asp Ser Trp Gly Gln Gly Thr Leu Val
            100                 105                 110

Thr Val Ser Ser Gly Gly Gly Gly Ser Gly Gly Gly Gly Ser Gly Gly
        115                 120                 125
```

```
Gly Gly Ser Gly Gly Gly Ser Gly Gly Gly Ser Glu Ile Val
130                 135                 140

Leu Thr Gln Ser Pro Ala Thr Leu Ser Leu Ser Pro Gly Glu Arg Ala
145                 150                 155                 160

Thr Leu Ser Cys Arg Ala Ser Glu Asn Val Tyr Ser Tyr Leu Ala Trp
                165                 170                 175

Tyr Gln Gln Lys Pro Gly Gln Ala Pro Arg Leu Leu Ile Tyr Phe Ala
                180                 185                 190

Lys Thr Leu Ala Glu Gly Ile Pro Ala Arg Phe Ser Gly Ser Gly Ser
        195                 200                 205

Gly Thr Asp Phe Thr Leu Thr Ile Ser Ser Leu Glu Pro Glu Asp Phe
210                 215                 220

Ala Val Tyr Tyr Cys Gln His Ser Asp Asn Pro Trp Thr Phe Gly
225                 230                 235                 240

Gln Gly Thr Lys Val Glu Ile Lys Ser Ser Glu Pro Lys Ser Ser
                245                 250                 255

Asp Lys Thr His Thr Cys Pro Pro Cys Pro Ala Pro Glu Ala Ala Gly
                260                 265                 270

Ala Pro Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Ala Tyr Ala Cys Ala Val Ser Asn Lys Ala Leu Pro Ala Pro Ile
        355                 360                 365

Glu Lys Thr Ile Ser Lys Ala Lys Gly Gln Pro Arg Glu Pro Gln Val
        370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
            405                 410                 415

Trp Glu Ser Asn Gly Gln Pro Glu Asn Asn Tyr Lys Thr Thr Pro Pro
            420                 425                 430

Val Leu Asp Ser Asp Gly Ser Phe Phe Leu Tyr Ser Lys Leu Thr Val
            435                 440                 445

Asp Lys Ser Arg Trp Gln Gln Gly Asn Val Phe Ser Cys Ser Val Met
450                 455                 460

His Glu Ala Leu His Asn His Tyr Thr Gln Lys Ser Leu Ser Leu Ser
465                 470                 475                 480

Pro Gly Gln Arg His Asn Asn Ser Ser Leu Asn Thr Gly Thr Gln Met
                485                 490                 495

Ala Gly His Ser Pro Asn Ser Gln Val Gln Leu Val Glu Ser Gly Gly
            500                 505                 510

Gly Val Val Gln Pro Gly Arg Ser Leu Arg Leu Ser Cys Lys Ala Ser
            515                 520                 525

Gly Tyr Thr Phe Thr Arg Ser Thr Met His Trp Val Arg Gln Ala Pro
530                 535                 540
```

| | | | | | | | | | | | | |
|---|---|---|---|---|---|---|---|---|---|---|---|---|
|Gly|Gln|Gly|Leu|Glu|Trp|Ile|Gly|Tyr|Ile|Asn|Pro|Ser Ser Ala Tyr|
|545| | | |550| | | |555| | | |560|
|Thr|Asn|Tyr|Asn|Gln|Lys|Phe|Lys|Asp|Arg|Phe|Thr|Ile Ser Ala Asp|
| | | | |565| | | |570| | | |575|
|Lys|Ser|Lys|Ser|Thr|Ala|Phe|Leu|Gln|Met|Asp|Ser|Leu Arg Pro Glu|
| | | | |580| | | |585| | | |590|
|Asp|Thr|Gly|Val|Tyr|Phe|Cys|Ala|Arg|Pro|Gln|Val|His Tyr Asp Tyr|
| | | |595| | | |600| | | |605| |
|Asn|Gly|Phe|Pro|Tyr|Trp|Gly|Gln|Gly|Thr|Pro|Val|Thr Val Ser Ser|
|610| | | | |615| | | |620| | | |
|Gly|Gly|Gly|Gly|Ser|Gly|Gly|Gly|Ser|Gly|Gly|Gly|Ser Ala|
|625| | | |630| | | |635| | | |640|
|Gln|Asp|Ile|Gln|Met|Thr|Gln|Ser|Pro|Ser|Ser|Leu|Ser Ala Ser Val|
| | | |645| | | |650| | | |655| |
|Gly|Asp|Arg|Val|Thr|Met|Thr|Cys|Ser|Ala|Ser|Ser|Val Ser Tyr|
| | |660| | | |665| | | |670| | |
|Met|Asn|Trp|Tyr|Gln|Gln|Lys|Pro|Gly|Lys|Ala|Pro|Lys Arg Trp Ile|
| | |675| | | |680| | | |685| | |
|Tyr|Asp|Ser|Ser|Lys|Leu|Ala|Ser|Gly|Val|Pro|Ala|Arg Phe Ser Gly|
|690| | | | |695| | | |700| | | |
|Ser|Gly|Ser|Gly|Thr|Asp|Tyr|Thr|Leu|Thr|Ile|Ser|Ser Leu Gln Pro|
|705| | | |710| | | |715| | | |720|
|Glu|Asp|Phe|Ala|Thr|Tyr|Tyr|Cys|Gln|Gln|Trp|Ser|Arg Asn Pro Pro|
| | | |725| | | |730| | | |735| |
|Thr|Phe|Gly|Gly|Gly|Thr|Lys|Leu|Gln|Ile|Thr|Ser|Ser Ser|
| | |740| | | |745| | | |750| | |

<210> SEQ ID NO 71
<211> LENGTH: 2325
<212> TYPE: DNA
<213> ORGANISM: Artificial Sequence
<220> FEATURE:
<223> OTHER INFORMATION: Anti-CD37 X TSC445 anti-CD3 bispecific molecule

<400> SEQUENCE: 71

```
atggaagcac cagcgcagct tctcttcctc ctgctactct ggctcccaga taccaccggt      60
gaggtgcagc tggtgcagtc tggagcagag gtgaaaaagc ccggagagtc tctgaagatt     120
tcctgtaagg gctccggtta ctcattcact ggctacaata tgaactgggt cgcgcagatg     180
cccgggaaag gcctggagtg gatgggcaat attgatcctt attatggtgg tactacctac     240
aaccggaagt tcaagggcca ggtcactatc tccgccgaca gtccatcagc accgcctac      300
ctgcaatgga gcagcctgaa ggcctcggac accgccatgt attactgtgc acgctcagtc     360
ggccctttcg actcctgggg ccagggcacc ctggtcactg tctcctctgg ggtggaggc      420
tctggtggcg gtggctctgg cggaggtgga tccggtggcg gcggatctgg cggggtggc      480
tctgaaattg tgttgacaca gtctccagcc acctgtcctt gtctccagg cgaaagagcc     540
accctctcct gccgagcaag tgaaaatgtt tacagctact agcctggta ccaacagaaa     600
cctggccagg ctcctaggct cctcatctat tttgcaaaaa ccttagcaga aggtattcca     660
gccaggttca gtggcagtgg ctccgggaca gacttcactc tcaccatcag cagcctagag     720
cctgaagatt ttgcagtttta ttactgtcaa catcattccg ataatccgtg gacattcggc     780
caagggacca aggtggaaat caaatcctcg agtgagccca atcttctga caaaactcac     840
acatgcccac cgtgcccagc acctgaagcc gcgggtgcac cgtcagtctt cctcttcccc     900
```

| | |
|---|---|
| ccaaaaccca aggacaccct catgatctcc cggaccsctg aggtcacatg cgtggtggtg | 960 |
| gacgtgagcc acgaagaccc tgaggtcaag ttcaactggt acgtggacgg cgtggaggtg | 1020 |
| cataatgcca agacaaagcc gcgggaggag cagtacaaca gcacgtaccg tgtggtcagc | 1080 |
| gtcctcaccg tcctgcacca ggactggctg aatggcaagg catacgcgtg cgcggtctcc | 1140 |
| aacaaagccc tcccagcccc catcgagaaa accatctcca agccaaagg gcagccccga | 1200 |
| gaaccacagg tgtacaccct gcccccatcc cgggatgagc tgaccaagaa ccaggtcagc | 1260 |
| ctgacctgcc tggtcaaagg cttctatcca agcgacatcg ccgtggagtg ggagagcaat | 1320 |
| gggcagccgg agaacaacta caagaccacg cctcccgtgc tggactccga cggctccttc | 1380 |
| ttcctctaca gcaagctcac cgtggacaag agcaggtggc agcaggggaa cgtcttctca | 1440 |
| tgctccgtga tgcatgaggc tctgcacaac cactacacgc agaagagcct ctccctgtct | 1500 |
| ccgggtcaga ggcacaacaa ttcttccctg aatacaggaa ctcagatggc aggtcattct | 1560 |
| ccgaattctc aggtccagct ggtgcaatct gggcctgagg tgaagaagcc tgggtcctcg | 1620 |
| gtgaaggtct cctgcaaggc ttctggatat accttcagca gatctacgat gcactgggtg | 1680 |
| cgacaggccc ctggacaagg gcttgagtgg ataggataca ttaatcctag cagtgcttat | 1740 |
| actaattaca atcagaaatt caaggacaga gtcacgatta ccgcggacaa atccacgagc | 1800 |
| acagcctaca tggagctgag cagcctgaga tctgaggaca cggccgtgta ttactgtgcg | 1860 |
| agaccccaag tccactatga ttacaacggg tttccttact ggggccaagg aaccctggtc | 1920 |
| accgtctcct caggtggagg cggttcaggc ggaggtggat ccggcggtgg cggatcgggt | 1980 |
| ggcggcggat ctgacatcca gatgacccag tctccttcca ccctgtctgc atctgtagga | 2040 |
| gacagagtca ccatgacttg cagtgccagc tcaagtgtaa gttacatgaa ctggtatcag | 2100 |
| cagaaaccag ggaaagcccc taagagatgg atttatgact catccaaact ggcttctggg | 2160 |
| gtcccatcaa ggttcagcgg cagtggatct gggacagagt tcactctcac catcagcagc | 2220 |
| ctgcagcctg atgattttgc aacttattac tgccaacagt ggagtcgtaa cccacccact | 2280 |
| ttcggcggag ggaccaaggt ggagatcaaa cggtcctcca gctaa | 2325 |

<210> SEQ ID NO 72
<211> LENGTH: 754
<212> TYPE: PRT
<213> ORGANISM: Artificial Sequence
<220> FEATURE:
<223> OTHER INFORMATION: Anti-CD37 X TSC445 anti-CD3 bispecific molecule

<400> SEQUENCE: 72

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Gly Tyr
            20                  25                  30

Asn Met Asn Trp Val Arg Gln Met Pro Gly Lys Gly Leu Glu Trp Met
        35                  40                  45

Gly Asn Ile Asp Pro Tyr Tyr Gly Gly Thr Thr Tyr Asn Arg Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Val Gly Pro Phe Asp Ser Trp Gly Gln Gly Thr Leu Val
            100                 105                 110

```
Thr Val Ser Ser Gly Gly Gly Ser Gly Gly Gly Ser Gly Gly
        115                 120                 125
Gly Gly Ser Gly Gly Gly Ser Gly Gly Gly Ser Glu Ile Val
    130                 135                 140
Leu Thr Gln Ser Pro Ala Thr Leu Ser Leu Ser Pro Gly Glu Arg Ala
145                 150                 155                 160
Thr Leu Ser Cys Arg Ala Ser Glu Asn Val Tyr Ser Tyr Leu Ala Trp
                165                 170                 175
Tyr Gln Gln Lys Pro Gly Gln Ala Pro Arg Leu Leu Ile Tyr Phe Ala
            180                 185                 190
Lys Thr Leu Ala Glu Gly Ile Pro Ala Arg Phe Ser Gly Ser Gly Ser
        195                 200                 205
Gly Thr Asp Phe Thr Leu Thr Ile Ser Ser Leu Glu Pro Glu Asp Phe
    210                 215                 220
Ala Val Tyr Tyr Cys Gln His His Ser Asp Asn Pro Trp Thr Phe Gly
225                 230                 235                 240
Gln Gly Thr Lys Val Glu Ile Lys Ser Ser Glu Pro Lys Ser Ser
                245                 250                 255
Asp Lys Thr His Thr Cys Pro Pro Cys Pro Ala Pro Glu Ala Ala Gly
            260                 265                 270
Ala Pro Ser Val Phe Leu Phe Pro Pro Lys Pro Lys Asp Thr Leu Met
        275                 280                 285
Ile Ser Arg Thr Pro Glu Val Thr Cys Val Val Val Asp Val Ser His
    290                 295                 300
Glu Asp Pro Glu Val Lys Phe Asn Trp Tyr Val Asp Gly Val Glu Val
305                 310                 315                 320
His Asn Ala Lys Thr Lys Pro Arg Glu Glu Gln Tyr Asn Ser Thr Tyr
                325                 330                 335
Arg Val Val Ser Val Leu Thr Val Leu His Gln Asp Trp Leu Asn Gly
            340                 345                 350
Lys Ala Tyr Ala Cys Ala Val Ser Asn Lys Ala Leu Pro Ala Pro Ile
        355                 360                 365
Glu Lys Thr Ile Ser Lys Ala Lys Gly Gln Pro Arg Glu Pro Gln Val
    370                 375                 380
Tyr Thr Leu Pro Pro Ser Arg Asp Glu Leu Thr Lys Asn Gln Val Ser
385                 390                 395                 400
Leu Thr Cys Leu Val Lys Gly Phe Tyr Pro Ser Asp Ile Ala Val Glu
                405                 410                 415
Trp Glu Ser Asn Gly Gln Pro Glu Asn Asn Tyr Lys Thr Thr Pro Pro
            420                 425                 430
Val Leu Asp Ser Asp Gly Ser Phe Phe Leu Tyr Ser Lys Leu Thr Val
        435                 440                 445
Asp Lys Ser Arg Trp Gln Gln Gly Asn Val Phe Ser Cys Ser Val Met
    450                 455                 460
His Glu Ala Leu His Asn His Tyr Thr Gln Lys Ser Leu Ser Leu Ser
465                 470                 475                 480
Pro Gly Gln Arg His Asn Asn Ser Ser Leu Asn Thr Gly Thr Gln Met
                485                 490                 495
Ala Gly His Ser Pro Asn Ser Gln Gln Leu Val Gln Ser Gly Pro
            500                 505                 510
Glu Val Lys Lys Pro Gly Ser Ser Val Lys Val Ser Cys Lys Ala Ser
        515                 520                 525
Gly Tyr Thr Phe Ser Arg Ser Thr Met His Trp Val Arg Gln Ala Pro
```

Gly Gln Gly Leu Glu Trp Ile Gly Tyr Ile Asn Pro Ser Ser Ala Tyr
545                 550                 555                 560

Thr Asn Tyr Asn Gln Lys Phe Lys Asp Arg Val Thr Ile Thr Ala Asp
                565                 570                 575

Lys Ser Thr Ser Thr Ala Tyr Met Glu Leu Ser Ser Leu Arg Ser Glu
            580                 585                 590

Asp Thr Ala Val Tyr Tyr Cys Ala Arg Pro Gln Val His Tyr Asp Tyr
        595                 600                 605

Asn Gly Phe Pro Tyr Trp Gly Gln Gly Thr Leu Val Thr Val Ser Ser
    610                 615                 620

Gly Gly Gly Gly Ser Gly Gly Gly Ser Gly Gly Gly Ser Gly
625                 630                 635                 640

Gly Gly Gly Ser Asp Ile Gln Met Thr Gln Ser Pro Ser Thr Leu Ser
            645                 650                 655

Ala Ser Val Gly Asp Arg Val Thr Met Thr Cys Ser Ala Ser Ser Ser
        660                 665                 670

Val Ser Tyr Met Asn Trp Tyr Gln Gln Lys Pro Gly Lys Ala Pro Lys
    675                 680                 685

Arg Trp Ile Tyr Asp Ser Ser Lys Leu Ala Ser Gly Val Pro Ser Arg
690                 695                 700

Phe Ser Gly Ser Gly Ser Gly Thr Glu Phe Thr Leu Thr Ile Ser Ser
705                 710                 715                 720

Leu Gln Pro Asp Asp Phe Ala Thr Tyr Tyr Cys Gln Gln Trp Ser Arg
            725                 730                 735

Asn Pro Pro Thr Phe Gly Gly Gly Thr Lys Val Glu Ile Lys Arg Ser
        740                 745                 750

Ser Ser

<210> SEQ ID NO 73
<211> LENGTH: 2325
<212> TYPE: DNA
<213> ORGANISM: Artificial Sequence
<220> FEATURE:
<223> OTHER INFORMATION: Anti-CD37 X TSC452 anti-CD3 bispecific molecule

<400> SEQUENCE: 73

| | | |
|---|---|---|
| atggaagcac cagcgcagct tctcttcctc ctgctactct ggctcccaga taccaccggt | 60 |
| gaggtgcagc tggtgcagtc tggagcagag gtgaaaaagc ccggagagtc tctgaagatt | 120 |
| tcctgtaagg gctccggtta ctcattcact ggctacaata tgaactgggt gcgccagatg | 180 |
| cccgggaaag gcctggagtg gatgggcaat attgatcctt attatggtgg tactacctac | 240 |
| aaccggaagt tcaagggcca ggtcactatc tccgccgaca gtccatcag caccgcctac | 300 |
| ctgcaatgga gcagcctgaa ggcctcggac accgccatgt attactgtgc acgctcagtc | 360 |
| ggccctttcg actcctgggg ccagggcacc ctggtcactg tctcctctgg gggtggaggc | 420 |
| tctggtggcg gtggctctgg cggaggtgga tccggtggcg gcggatctgg cggggtggc | 480 |
| tctgaaattg tgttgacaca gtctccagcc accctgtctt tgtctccagg cgaaagagcc | 540 |
| accctctcct gccgagcaag tgaaaatgtt tacagctact tagcctggta ccaacagaaa | 600 |
| cctggccagg ctcctaggct cctcatctat tttgcaaaaa ccttagcaga aggtattcca | 660 |
| gccaggttca gtggcagtgg ctccgggaca gacttcactc tcaccatcag cagcctagag | 720 |
| cctgaagatt ttgcagttta ttactgtcaa catcattccg ataatccgtg gacattcggc | 780 |

```
caagggacca aggtggaaat caaatcctcg agtgagccca atcttctga caaaactcac    840
acatgcccac cgtgcccagc acctgaagcc gcgggtgcac cgtcagtctt cctcttcccc    900
ccaaaaccca aggacaccct catgatctcc cggacccctg aggtcacatg cgtggtggtg    960
gacgtgagcc acgaagaccc tgaggtcaag ttcaactggt acgtggacgg cgtggaggtg   1020
cataatgcca agacaaagcc gcgggaggag cagtacaaca gcacgtaccg tgtggtcagc   1080
gtcctcaccg tcctgcacca ggactggctg aatggcaagg catacgcgtg cgcggtctcc   1140
aacaaagccc tcccagcccc catcgagaaa accatctcca aagccaaagg cagccccga    1200
gaaccacagg tgtacaccct gcccccatcc cgggatgagc tgaccaagaa ccaggtcagc   1260
ctgacctgcc tggtcaaagg cttctatcca agcgacatcg ccgtggagtg ggagagcaat   1320
gggcagccgg agaacaacta caagaccacg cctcccgtgc tggactccga cggctccttc   1380
ttcctctaca gcaagctcac cgtggacaag agcaggtggc agcaggggaa cgtcttctca   1440
tgctccgtga tgcatgaggc tctgcacaac cactacacgc agaagagcct ctccctgtct   1500
ccgggtcaga ggcacaacaa ttcttccctg aatacaggaa ctcagatggc aggtcattct   1560
ccgaattctc aggtccagct ggtggagtct gggggcggag tggtgcagcc tgggcggtca   1620
ctgaggctgt cctgcaaggc ttctggctac acctttacta gatctacgat gcactgggta   1680
aggcaggccc ctggacaagg tctggaatgg attggataca ttaatcctag cagtgcttat   1740
actaattaca atcagaaatt caaggacagg ttcacaatca gcgcagacaa atccaagagc   1800
acagccttcc tgcagatgga cagcctgagg cccgaggaca ccggcgtcta tttctgtgca   1860
cggccccaag tccactatga ttacaacggg tttccttact ggggccaagg gactcccgtc   1920
actgtctcta gcggtggcgg agggtctggg ggtggcggat ccggcggtgg cggatcgggt   1980
ggcggcggat ctgacatcca gatgacccag tctccttcca ccctgtctgc atctgtagga   2040
gacagagtca ccatgacttg cagtgccagc tcaagtgtaa gttacatgaa ctggtatcag   2100
cagaaaccag ggaaagcccc taagagatgg atttatgact catccaaact ggcttctggg   2160
gtcccatcaa ggttcagcgg cagtggatct gggacagagt tcactctcac catcagcagc   2220
ctgcagcctg atgattttgc aacttattac tgccaacagt ggagtcgtaa cccacccact   2280
ttcggcggag ggaccaaggt ggagatcaaa cggtcctcca gctaa               2325
```

<210> SEQ ID NO 74
<211> LENGTH: 754
<212> TYPE: PRT
<213> ORGANISM: Artificial Sequence
<220> FEATURE:
<223> OTHER INFORMATION: Anti-CD37 X TSC452 anti-CD3 bispecific molecule

<400> SEQUENCE: 74

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Gly Tyr
            20                  25                  30

Asn Met Asn Trp Val Arg Gln Met Pro Gly Lys Gly Leu Glu Trp Met
        35                  40                  45

Gly Asn Ile Asp Pro Tyr Tyr Gly Gly Thr Thr Tyr Asn Arg Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

```
Ala Arg Ser Val Gly Pro Phe Asp Ser Trp Gly Gln Gly Thr Leu Val
            100                 105                 110
Thr Val Ser Ser Gly Gly Gly Gly Ser Gly Gly Gly Ser Gly Gly
        115                 120                 125
Gly Gly Ser Gly Gly Gly Ser Gly Gly Gly Ser Glu Ile Val
    130                 135                 140
Leu Thr Gln Ser Pro Ala Thr Leu Ser Leu Ser Pro Gly Glu Arg Ala
145                 150                 155                 160
Thr Leu Ser Cys Arg Ala Ser Glu Asn Val Tyr Ser Tyr Leu Ala Trp
                165                 170                 175
Tyr Gln Gln Lys Pro Gly Gln Ala Pro Arg Leu Leu Ile Tyr Phe Ala
            180                 185                 190
Lys Thr Leu Ala Glu Gly Ile Pro Ala Arg Phe Ser Gly Ser Gly Ser
        195                 200                 205
Gly Thr Asp Phe Thr Leu Thr Ile Ser Ser Leu Glu Pro Glu Asp Phe
    210                 215                 220
Ala Val Tyr Tyr Cys Gln His His Ser Asp Asn Pro Trp Thr Phe Gly
225                 230                 235                 240
Gln Gly Thr Lys Val Glu Ile Lys Ser Ser Glu Pro Lys Ser Ser
                245                 250                 255
Asp Lys Thr His Thr Cys Pro Pro Cys Pro Ala Pro Glu Ala Ala Gly
            260                 265                 270
Ala Pro Ser Val Phe Leu Phe Pro Pro Lys Pro Lys Asp Thr Leu Met
        275                 280                 285
Ile Ser Arg Thr Pro Glu Val Thr Cys Val Val Val Asp Val Ser His
    290                 295                 300
Glu Asp Pro Glu Val Lys Phe Asn Trp Tyr Val Asp Gly Val Glu Val
305                 310                 315                 320
His Asn Ala Lys Thr Lys Pro Arg Glu Glu Gln Tyr Asn Ser Thr Tyr
                325                 330                 335
Arg Val Val Ser Val Leu Thr Val Leu His Gln Asp Trp Leu Asn Gly
            340                 345                 350
Lys Ala Tyr Ala Cys Ala Val Ser Asn Lys Ala Leu Pro Ala Pro Ile
        355                 360                 365
Glu Lys Thr Ile Ser Lys Ala Lys Gly Gln Pro Arg Glu Pro Gln Val
    370                 375                 380
Tyr Thr Leu Pro Pro Ser Arg Asp Glu Leu Thr Lys Asn Gln Val Ser
385                 390                 395                 400
Leu Thr Cys Leu Val Lys Gly Phe Tyr Pro Ser Asp Ile Ala Val Glu
                405                 410                 415
Trp Glu Ser Asn Gly Gln Pro Glu Asn Asn Tyr Lys Thr Thr Pro Pro
            420                 425                 430
Val Leu Asp Ser Asp Gly Ser Phe Phe Leu Tyr Ser Lys Leu Thr Val
        435                 440                 445
Asp Lys Ser Arg Trp Gln Gln Gly Asn Val Phe Ser Cys Ser Val Met
    450                 455                 460
His Glu Ala Leu His Asn His Tyr Thr Gln Lys Ser Leu Ser Leu Ser
465                 470                 475                 480
Pro Gly Gln Arg His Asn Asn Ser Ser Leu Asn Thr Gly Thr Gln Met
                485                 490                 495
Ala Gly His Ser Pro Asn Ser Gln Val Gln Leu Val Glu Ser Gly Gly
            500                 505                 510
```

```
Gly Val Val Gln Pro Gly Arg Ser Leu Arg Leu Ser Cys Lys Ala Ser
            515                 520                 525

Gly Tyr Thr Phe Thr Arg Ser Thr Met His Trp Val Arg Gln Ala Pro
530                 535                 540

Gly Gln Gly Leu Glu Trp Ile Gly Tyr Ile Asn Pro Ser Ser Ala Tyr
545                 550                 555                 560

Thr Asn Tyr Asn Gln Lys Phe Lys Asp Arg Phe Thr Ile Ser Ala Asp
                565                 570                 575

Lys Ser Lys Ser Thr Ala Phe Leu Gln Met Asp Ser Leu Arg Pro Glu
            580                 585                 590

Asp Thr Gly Val Tyr Phe Cys Ala Arg Pro Gln Val His Tyr Asp Tyr
        595                 600                 605

Asn Gly Phe Pro Tyr Trp Gly Gln Gly Thr Pro Val Thr Val Ser Ser
    610                 615                 620

Gly Gly Gly Gly Ser Gly Gly Gly Ser Gly Gly Gly Ser Gly
625                 630                 635                 640

Gly Gly Gly Ser Asp Ile Gln Met Thr Gln Ser Pro Ser Thr Leu Ser
                645                 650                 655

Ala Ser Val Gly Asp Arg Val Thr Met Thr Cys Ser Ala Ser Ser Ser
            660                 665                 670

Val Ser Tyr Met Asn Trp Tyr Gln Gln Lys Pro Gly Lys Ala Pro Lys
        675                 680                 685

Arg Trp Ile Tyr Asp Ser Ser Lys Leu Ala Ser Gly Val Pro Ser Arg
    690                 695                 700

Phe Ser Gly Ser Gly Ser Gly Thr Glu Phe Thr Leu Thr Ile Ser Ser
705                 710                 715                 720

Leu Gln Pro Asp Asp Phe Ala Thr Tyr Tyr Cys Gln Gln Trp Ser Arg
                725                 730                 735

Asn Pro Pro Thr Phe Gly Gly Gly Thr Lys Val Glu Ile Lys Arg Ser
            740                 745                 750

Ser Ser

<210> SEQ ID NO 75
<211> LENGTH: 2322
<212> TYPE: DNA
<213> ORGANISM: Artificial Sequence
<220> FEATURE:
<223> OTHER INFORMATION: Anti-CD37 X TSC453 anti-CD3 bispecific molecule

<400> SEQUENCE: 75
atggaagcac cagcgcagct tctcttcctc ctgctactct ggctcccaga taccaccggt      60
gaggtgcagc tggtgcagtc tggagcagag gtgaaaaagc ccggagagtc tctgaagatt     120
tcctgtaagg gctccggtta ctcattcact ggctacaata tgaactgggt gcgccagatg     180
cccgggaaag gcctggagtg gatgggcaat attgatcctt attatggtgg tactacctac     240
aaccggaagt tcaagggcca ggtcactatc tccgccgaca gtccatcag caccgcctac     300 ctgcaatgga gcagcctgaa ggcctcggac accgccatgt attactgtgc acgctcagtc     360 ggcccttttcg actcctgggg ccagggcacc ctggtcactg tctcctctgg gggtggaggc     420
tctggtggcg gtggctctgg cggaggtgga tccggtggcg gcggatctgg cggggggtggc     480 tctgaaattg tgttgacaca gtctccagcc accctgtctt gtctccagg cgaaagagcc     540 accctctcct gccgagcaag tgaaaatgtt tacagctact tagcctggta ccaacagaaa     600
cctggccagg ctcctaggct cctcatctat tttgcaaaaa ccttagcaga aggtattcca     660
```

```
gccaggttca gtggcagtgg ctccgggaca gacttcactc tcaccatcag cagcctagag    720
cctgaagatt ttgcagttta ttactgtcaa catcattccg ataatccgtg gacattcggc    780
caagggacca aggtggaaat caaatcctcg agtgagccca atcttctga caaaactcac     840
acatgcccac cgtgcccagc acctgaagcc gcgggtgcac cgtcagtctt cctcttcccc    900
ccaaaaccca aggacaccct catgatctcc cggacccctg aggtcacatg cgtggtggtg    960
gacgtgagcc acgaagaccc tgaggtcaag ttcaactggt acgtggacgg cgtggaggtg   1020
cataatgcca agacaaagcc gcgggaggag cagtacaaca gcacgtaccg tgtggtcagc   1080
gtcctcaccg tcctgcacca ggactggctg aatggcaagg catacgcgtg cgcggtctcc   1140
aacaaagccc tcccagcccc catcgagaaa accatctcca aagccaaagg gcagccccga   1200
gaaccacagg tgtacaccct gcccccatcc cgggatgagc tgaccaagaa ccaggtcagc   1260
ctgacctgcc tggtcaaagg cttctatcca agcgacatcg ccgtggagtg ggagagcaat   1320
gggcagccgg agaacaacta caagaccacg cctcccgtgc tggactccga cggctccttc   1380
ttcctctaca gcaagctcac cgtggacaag agcaggtggc agcaggggaa cgtcttctca   1440
tgctccgtga tgcatgaggc tctgcacaac cactacacgc agaagagcct ctccctgtct   1500
ccgggtcaga ggcacaacaa ttcttccctg aatacaggaa ctcagatggc aggtcattct   1560
ccgaattctc aggtccagct ggtgcaatct gggcctgagg tgaagaagcc tgggtcctcg   1620
gtgaaggtct cctgcaaggc ttctggatat accttcagca gatctacgat gcactgggtg   1680
cgacaggccc ctggacaagg gcttgagtgg ataggataca ttaatcctag cagtgcttat   1740
actaattaca atcagaaatt caaggacaga gtcacgatta ccgcggacaa atccacgagc   1800
acagcctaca tggagctgag cagcctgaga tctgaggaca cggccgtgta ttactgtgcg   1860
agaccccaag tccactatga ttacaacggg tttccttact ggggccaagg aaccctggtc   1920
accgtctcct caggtggagg cggttcaggc ggaggtggat ccggaggtgg tggctctggt   1980
ggcggcggat ctgacatcca gatgacccag tctccaagca gcctgtctgc aagcgtgggg   2040
gacagggtca ccatgacctg cagtgccagc tcaagtgtaa gttacatgaa ctggtaccag   2100
cagaagccgg gcaaggcccc caaaagatgg atttatgact catccaaact ggcttctgga   2160
gtccctgctc gcttcagtgg cagtgggtct gggaccgact atccctcac aatcagcagc    2220
ctgcagcccg aagatttcgc cacttattac tgccagcagt ggagtcgtaa cccacccacg   2280
ttcggagggg ggaccaagct acaaattaca tcctccagct aa                       2322
```

<210> SEQ ID NO 76
<211> LENGTH: 753
<212> TYPE: PRT
<213> ORGANISM: Artificial Sequence
<220> FEATURE:
<223> OTHER INFORMATION: Anti-CD37 X TSC453 anti-CD3 bispecific molecule

<400> SEQUENCE: 76

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Gly Tyr
                20                  25                  30

Asn Met Asn Trp Val Arg Gln Met Pro Gly Lys Gly Leu Glu Trp Met
            35                  40                  45

Gly Asn Ile Asp Pro Tyr Tyr Gly Gly Thr Thr Tyr Asn Arg Lys Phe
        50                  55                  60

Lys Gly Gln Val Thr Ile Ser Ala Asp Lys Ser Ile Ser Thr Ala Tyr

-continued

```
                65                  70                  75                  80
Leu Gln Trp Ser Ser Leu Lys Ala Ser Asp Thr Ala Met Tyr Tyr Cys
                    85                  90                  95

Ala Arg Ser Val Gly Pro Phe Asp Ser Trp Gly Gln Gly Thr Leu Val
                100                 105                 110

Thr Val Ser Ser Gly Gly Gly Gly Ser Gly Gly Gly Gly Ser Gly Gly
                115                 120                 125

Gly Gly Ser Gly Gly Gly Ser Gly Gly Gly Ser Glu Ile Val
130                 135                 140

Leu Thr Gln Ser Pro Ala Thr Leu Ser Leu Ser Pro Gly Glu Arg Ala
145                 150                 155                 160

Thr Leu Ser Cys Arg Ala Ser Glu Asn Val Tyr Ser Tyr Leu Ala Trp
                165                 170                 175

Tyr Gln Gln Lys Pro Gly Gln Ala Pro Arg Leu Leu Ile Tyr Phe Ala
                180                 185                 190

Lys Thr Leu Ala Glu Gly Ile Pro Ala Arg Phe Ser Gly Ser Gly Ser
                195                 200                 205

Gly Thr Asp Phe Thr Leu Thr Ile Ser Ser Leu Glu Pro Glu Asp Phe
210                 215                 220

Ala Val Tyr Tyr Cys Gln His Ser Asp Asn Pro Trp Thr Phe Gly
225                 230                 235                 240

Gln Gly Thr Lys Val Glu Ile Lys Ser Ser Glu Pro Lys Ser Ser
                245                 250                 255

Asp Lys Thr His Thr Cys Pro Pro Cys Pro Ala Pro Glu Ala Ala Gly
                260                 265                 270

Ala Pro Ser Val Phe Leu Phe Pro Pro Lys Pro Lys Asp Thr Leu Met
                275                 280                 285

Ile Ser Arg Thr Pro Glu Val Thr Cys Val Val Val Asp Val Ser His
                290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
                340                 345                 350

Lys Ala Tyr Ala Cys Ala Val Ser Asn Lys Ala Leu Pro Ala Pro Ile
                355                 360                 365

Glu Lys Thr Ile Ser Lys Ala Lys Gly Gln Pro Arg Glu Pro Gln Val
                370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
                420                 425                 430

Val Leu Asp Ser Asp Gly Ser Phe Phe Leu Tyr Ser Lys Leu Thr Val
                435                 440                 445

Asp Lys Ser Arg Trp Gln Gln Gly Asn Val Phe Ser Cys Ser Val Met
                450                 455                 460

His Glu Ala Leu His Asn His Tyr Thr Gln Lys Ser Leu Ser Leu Ser
465                 470                 475                 480

Pro Gly Gln Arg His Asn Ser Ser Leu Asn Thr Gly Thr Gln Met
                485                 490                 495
```

Ala Gly His Ser Pro Asn Ser Gln Val Gln Leu Val Gln Ser Gly Pro
                500                 505                 510

Glu Val Lys Lys Pro Gly Ser Ser Val Lys Val Ser Cys Lys Ala Ser
            515                 520                 525

Gly Tyr Thr Phe Ser Arg Ser Thr Met His Trp Val Arg Gln Ala Pro
        530                 535                 540

Gly Gln Gly Leu Glu Trp Ile Gly Tyr Ile Asn Pro Ser Ser Ala Tyr
545                 550                 555                 560

Thr Asn Tyr Asn Gln Lys Phe Lys Asp Arg Val Thr Ile Thr Ala Asp
                565                 570                 575

Lys Ser Thr Ser Thr Ala Tyr Met Glu Leu Ser Ser Leu Arg Ser Glu
            580                 585                 590

Asp Thr Ala Val Tyr Tyr Cys Ala Arg Pro Gln Val His Tyr Asp Tyr
        595                 600                 605

Asn Gly Phe Pro Tyr Trp Gly Gln Gly Thr Leu Val Thr Val Ser Ser
610                 615                 620

Gly Gly Gly Gly Ser Gly Gly Gly Ser Gly Gly Gly Gly Ser Gly
625                 630                 635                 640

Gly Gly Gly Ser Asp Ile Gln Met Thr Gln Ser Pro Ser Ser Leu Ser
                645                 650                 655

Ala Ser Val Gly Asp Arg Val Thr Met Thr Cys Ser Ala Ser Ser Ser
            660                 665                 670

Val Ser Tyr Met Asn Trp Tyr Gln Gln Lys Pro Gly Lys Ala Pro Lys
        675                 680                 685

Arg Trp Ile Tyr Asp Ser Ser Lys Leu Ala Ser Gly Val Pro Ala Arg
        690                 695                 700

Phe Ser Gly Ser Gly Ser Gly Thr Asp Tyr Thr Leu Thr Ile Ser Ser
705                 710                 715                 720

Leu Gln Pro Glu Asp Phe Ala Thr Tyr Tyr Cys Gln Gln Trp Ser Arg
                725                 730                 735

Asn Pro Pro Thr Phe Gly Gly Gly Thr Lys Leu Gln Ile Thr Ser Ser
            740                 745                 750

Ser

<210> SEQ ID NO 77
<211> LENGTH: 2325
<212> TYPE: DNA
<213> ORGANISM: Artificial Sequence
<220> FEATURE:
<223> OTHER INFORMATION: Anti-CD37 X TSC454 anti-CD3 bispecific molecule

<400> SEQUENCE: 77
atggaagcac cagcgcagct tctcttcctc ctgctactct ggctcccaga taccaccggt      60
gaggtgcagc tggtgcagtc tggagcagag gtgaaaaagc ccggagagtc tctgaagatt     120
tcctgtaagg gctccggtta ctcattcact ggctacaata tgaactgggt cgcccagatg     180
cccgggaaag gcctggagtg gatgggcaat attgatcctt attatggtgg tactacctac     240
aaccggaagt tcaagggcca ggtcactatc tccgccgaca gtccatcag caccgcctac      300 ctgcaatgga gcagcctgaa ggcctcggac accgccatgt attactgtgc acgctcagtc     360 ggcccttttcg actcctgggg ccagggcacc ctggtcactg tctcctctgg ggtggaggc     420 tctggtggcg gtggctctgg cggaggtgga tccggtggcg gcggatctgg cggggggtggc    480 tctgaaattg tgttgacaca gtctccagcc accctgtctt gtctccagg cgaaagagcc    540

```
accctctcct gccgagcaag tgaaaatgtt tacagctact tagcctggta ccaacagaaa    600
cctggccagg ctcctaggct cctcatctat tttgcaaaaa ccttagcaga aggtattcca    660
gccaggttca gtggcagtgg ctccgggaca gacttcactc tcaccatcag cagcctagag    720
cctgaagatt ttgcagttta ttactgtcaa catcattccg ataatccgtg acattcggc     780 caagggacca aggtggaaat caaatcctcg agtgagccca atcttctga caaaactcac     840 acatgcccac cgtgcccagc acctgaagcc gcgggtgcac cgtcagtctt cctcttcccc    900
ccaaaaccca aggacaccct catgatctcc cggacccctg aggtcacatg cgtggtggtg    960
gacgtgagcc acgaagaccc tgaggtcaag ttcaactggt acgtggacgg cgtggaggtg   1020
cataatgcca agacaaagcc gcgggaggag cagtacaaca gcacgtaccg tgtggtcagc   1080
gtcctcaccg tcctgcacca ggactggctg aatggcaagg catacgcgtg cgcggtctcc   1140
aacaaagccc tcccagcccc catcgagaaa accatctcca agccaaagg gcagccccga    1200 gaaccacagg tgtacaccct gcccccatcc cgggatgagc tgaccaagaa ccaggtcagc   1260
ctgacctgcc tggtcaaagg cttctatcca agcgacatcg ccgtggagtg ggagagcaat   1320
gggcagccgg agaacaacta caagaccacg cctcccgtgc tggactccga cggctccttc   1380
ttcctctaca gcaagctcac cgtggacaag agcaggtggc agcaggggaa cgtcttctca   1440
tgctccgtga tgcatgaggc tctgcacaac cactacacgc agaagagcct ctccctgtct   1500
ccgggtcaga ggcacaacaa ttcttccctg aatacaggaa ctcagatggc aggtcattct   1560
ccgaattctc aggtccagct ggtgcaatct gggcctgagg tgaagaagcc tgggtcctcg   1620
gtgaaggtct cctgcaaggc ttctggatat accttcagca gatctacgat gcactgggtg   1680
cgacaggccc ctggacaagg gcttgagtgg ataggataca ttaatcctag cagtgcttat   1740
actaattaca atcagaaatt caaggacaga gtcacgatta ccgcggacaa atccacgagc   1800
acagcctaca tggagctgag cagcctgaga tctgaggaca cggccgtgta ttactgtgcg   1860
agaccccaag tccactatga ttacaacggg tttccttact ggggccaagg aaccctggtc   1920
accgtctcct caggtggagg cggttcaggc ggaggtggat ccggcggtgg cggatcgggt   1980
ggcggcggat ctgacatcca gatgacccag tctccttcca ccctgtctgc atctgtagga   2040
gacagagtca ccatgacttg cagtgccagc tcaagtgtaa gttacatgaa ctggtatcag   2100
cagaaaccag ggaaagcccc taagagatgg atttatgact catccaaact ggcttctggg   2160
gtcccatcaa ggttcagcgg cagtggatct gggacagatt tcactctcac catcagcagc   2220
ctgcagcctg atgattttgc aacttattac tgccaacagt ggagtcgtaa cccacccact   2280
ttcggcggag ggaccaaggt ggagatcaaa cggtcctcca gctaa             2325
```

<210> SEQ ID NO 78
<211> LENGTH: 754
<212> TYPE: PRT
<213> ORGANISM: Artificial Sequence
<220> FEATURE:
<223> OTHER INFORMATION: Anti-CD37 X TSC454 anti-CD3 bispecific molecule

<400> SEQUENCE: 78

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Gly Tyr
            20                  25                  30

Asn Met Asn Trp Val Arg Gln Met Pro Gly Lys Gly Leu Glu Trp Met
        35                  40                  45

```
Gly Asn Ile Asp Pro Tyr Tyr Gly Gly Thr Thr Tyr Asn Arg Lys Phe
 50                  55                  60

Lys Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Ser Val Gly Pro Phe Asp Ser Trp Gly Gln Gly Thr Leu Val
                100                 105                 110

Thr Val Ser Ser Gly Gly Gly Gly Ser Gly Gly Gly Gly Ser Gly Gly
            115                 120                 125

Gly Gly Ser Gly Gly Gly Gly Ser Gly Gly Gly Gly Ser Glu Ile Val
130                 135                 140

Leu Thr Gln Ser Pro Ala Thr Leu Ser Leu Ser Pro Gly Glu Arg Ala
145                 150                 155                 160

Thr Leu Ser Cys Arg Ala Ser Glu Asn Val Tyr Ser Tyr Leu Ala Trp
                165                 170                 175

Tyr Gln Gln Lys Pro Gly Gln Ala Pro Arg Leu Leu Ile Tyr Phe Ala
                180                 185                 190

Lys Thr Leu Ala Glu Gly Ile Pro Ala Arg Phe Ser Gly Ser Gly Ser
                195                 200                 205

Gly Thr Asp Phe Thr Leu Thr Ile Ser Ser Leu Glu Pro Glu Asp Phe
210                 215                 220

Ala Val Tyr Tyr Cys Gln His Ser Asp Asn Pro Trp Thr Phe Gly
225                 230                 235                 240

Gln Gly Thr Lys Val Glu Ile Lys Ser Ser Glu Pro Lys Ser Ser
                245                 250                 255

Asp Lys Thr His Thr Cys Pro Pro Cys Pro Ala Pro Glu Ala Ala Gly
                260                 265                 270

Ala Pro Ser Val Phe Leu Phe Pro Pro Lys Pro Lys Asp Thr Leu Met
            275                 280                 285

Ile Ser Arg Thr Pro Glu Val Thr Cys Val Val Val Asp Val Ser His
            290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
                340                 345                 350

Lys Ala Tyr Ala Cys Ala Val Ser Asn Lys Ala Leu Pro Ala Pro Ile
                355                 360                 365

Glu Lys Thr Ile Ser Lys Ala Lys Gly Gln Pro Arg Glu Pro Gln Val
            370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
                420                 425                 430

Val Leu Asp Ser Asp Gly Ser Phe Phe Leu Tyr Ser Lys Leu Thr Val
            435                 440                 445

Asp Lys Ser Arg Trp Gln Gln Gly Asn Val Phe Ser Cys Ser Val Met
450                 455                 460

His Glu Ala Leu His Asn His Tyr Thr Gln Lys Ser Leu Ser Leu Ser
```

Pro Gly Gln Arg His Asn Asn Ser Ser Leu Asn Thr Gly Thr Gln Met
465                 470                 475                 480
            485                     490                 495

Ala Gly His Ser Pro Asn Ser Gln Val Gln Leu Val Gln Ser Gly Pro
                500                 505                 510

Glu Val Lys Lys Pro Gly Ser Ser Val Lys Val Ser Cys Lys Ala Ser
        515                 520                 525

Gly Tyr Thr Phe Ser Arg Ser Thr Met His Trp Val Arg Gln Ala Pro
    530                 535                 540

Gly Gln Gly Leu Glu Trp Ile Gly Tyr Ile Asn Pro Ser Ser Ala Tyr
545                 550                 555                 560

Thr Asn Tyr Asn Gln Lys Phe Lys Asp Arg Val Thr Ile Thr Ala Asp
                565                 570                 575

Lys Ser Thr Ser Thr Ala Tyr Met Glu Leu Ser Ser Leu Arg Ser Glu
            580                 585                 590

Asp Thr Ala Val Tyr Tyr Cys Ala Arg Pro Gln Val His Tyr Asp Tyr
        595                 600                 605

Asn Gly Phe Pro Tyr Trp Gly Gln Gly Thr Leu Val Thr Val Ser Ser
    610                 615                 620

Gly Gly Gly Gly Ser Gly Gly Gly Ser Gly Gly Gly Ser Gly
625                 630                 635                 640

Gly Gly Gly Ser Asp Ile Gln Met Thr Gln Ser Pro Ser Thr Leu Ser
                645                 650                 655

Ala Ser Val Gly Asp Arg Val Thr Met Thr Cys Ser Ala Ser Ser Ser
            660                 665                 670

Val Ser Tyr Met Asn Trp Tyr Gln Gln Lys Pro Gly Lys Ala Pro Lys
        675                 680                 685

Arg Trp Ile Tyr Asp Ser Ser Lys Leu Ala Ser Gly Val Pro Ser Arg
    690                 695                 700

Phe Ser Gly Ser Gly Ser Gly Thr Asp Phe Thr Leu Thr Ile Ser Ser
705                 710                 715                 720

Leu Gln Pro Asp Asp Phe Ala Thr Tyr Tyr Cys Gln Gln Trp Ser Arg
                725                 730                 735

Asn Pro Pro Thr Phe Gly Gly Gly Thr Lys Val Glu Ile Lys Arg Ser
            740                 745                 750

Ser Ser

<210> SEQ ID NO 79
<211> LENGTH: 2325
<212> TYPE: DNA
<213> ORGANISM: Artificial Sequence
<220> FEATURE:
<223> OTHER INFORMATION: Anti-CD37 X TSC455 anti-CD3 bispecific molecule

<400> SEQUENCE: 79
atggaagcac cagcgcagct tctcttcctc ctgctactct ggctcccaga taccaccggt        60
gaggtgcagc tggtgcagtc tggagcagag gtgaaaaagc ccggagagtc tctgaagatt       120
tcctgtaagg gctccggtta ctcattcact ggctacaata tgaactgggt gcgccagatg       180
cccgggaaag gcctggagtg gatgggcaat attgatcctt attatggtgg tactacctac       240
aaccggaagt tcaagggcca ggtcactatc tccgccgaca gtccatcagc accgcctac        300 ctgcaatgga gcagcctgaa ggcctcggac accgccatgt attactgtgc acgtcagtc        360 ggccctttcg actcctgggg ccagggcacc ctggtcactg tctcctctgg gggtggaggc       420

| | |
|---|---|
| tctggtggcg gtggctctgg cggaggtgga tccggtggcg gcggatctgg cggggggtggc | 480 |
| tctgaaattg tgttgacaca gtctccagcc accctgtctt tgtctccagg cgaaagagcc | 540 |
| accctctcct gccgagcaag tgaaaatgtt tacagctact tagcctggta ccaacagaaa | 600 |
| cctggccagg ctcctaggct cctcatctat tttgcaaaaa ccttagcaga aggtattcca | 660 |
| gccaggttca gtggcagtgg ctccgggaca gacttcactc tcaccatcag cagcctagag | 720 |
| cctgaagatt ttgcagttta ttactgtcaa catcattccg ataatccgtg acattcggc | 780 |
| caagggacca aggtggaaat caaatcctcg agtgagccca atcttctga caaaactcac | 840 |
| acatgcccac cgtgcccagc acctgaagcc gcgggtgcac cgtcagtctt cctcttcccc | 900 |
| ccaaaaccca aggacaccct catgatctcc cggacccctg aggtcacatg cgtggtggtg | 960 |
| gacgtgagcc acgaagaccc tgaggtcaag ttcaactggt acgtggacgg cgtggaggtg | 1020 |
| cataatgcca agacaaagcc gcgggaggag cagtacaaca gcacgtaccg tgtggtcagc | 1080 |
| gtcctcaccg tcctgcacca ggactggctg aatggcaagg catacgcgtg cgcggtctcc | 1140 |
| aacaaagccc tcccagcccc catcgagaaa accatctcca aagccaaagg gcagccccga | 1200 |
| gaaccacagg tgtacaccct gcccccatcc cgggatgagc tgaccaagaa ccaggtcagc | 1260 |
| ctgacctgcc tggtcaaagg cttctatcca agcgacatcg ccgtggagtg ggagagcaat | 1320 |
| gggcagccgg agaacaacta caagaccacg cctcccgtgc tggactccga cggctccttc | 1380 |
| ttcctctaca gcaagctcac cgtggacaag agcaggtggc agcaggggaa cgtcttctca | 1440 |
| tgctccgtga tgcatgaggc tctgcacaac cactacacgc agaagagcct ctccctgtct | 1500 |
| ccgggtcaga ggcacaacaa ttcttccctg aatacaggaa ctcagatggc aggtcattct | 1560 |
| ccgaattctc aggtccagct ggtgcaatct gggcctgagg tgaagaagcc tgggtcctcg | 1620 |
| gtgaaggtct cctgcaaggc ttctggatat accttcagca gatctacgat gcactgggtg | 1680 |
| cgacaggccc ctggacaagg gcttgagtgg ataggataca ttaatcctag cagtgcttat | 1740 |
| actaattaca atcagaaatt caaggacaga gtcacgatta ccgcggacaa atccacgagc | 1800 |
| acagcctaca tggagctgag cagcctgaga tctgaggaca cggccgtgta ttactgtgcg | 1860 |
| agaccccaag tccactatga ttacaacggg tttccttact ggggccaagg aaccctggtc | 1920 |
| accgtctcct caggtggagg cggttcaggc ggaggtggat ccggcggtgg cggatcgggt | 1980 |
| ggcggcggat ctgacatcca gatgacccag tctccttcca ccctgtctgc atctgtagga | 2040 |
| gacagagtca ccatgacttg cagtgccagc tcaagtgtaa gttacatgaa ctggtatcag | 2100 |
| cagaaaccag ggaaagcccc taagagatgg atttatgact catccaaact ggcttctggg | 2160 |
| gtcccatcaa ggttcagcgg cagtggatct gggacagagt atactctcac catcagcagc | 2220 |
| ctgcagcctg atgattttgc aacttattac tgccaacagt ggagtcgtaa cccacccact | 2280 |
| ttcggcggag ggaccaaggt ggagatcaaa cggtcctcca gctaa | 2325 |

<210> SEQ ID NO 80
<211> LENGTH: 754
<212> TYPE: PRT
<213> ORGANISM: Artificial Sequence
<220> FEATURE:
<223> OTHER INFORMATION: Anti-CD37 X TSC455 anti-CD3 bispecific molecule

<400> SEQUENCE: 80

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Gly Tyr
            20                  25                  30

```
Asn Met Asn Trp Val Arg Gln Met Pro Gly Lys Gly Leu Glu Trp Met
        35                  40                  45

Gly Asn Ile Asp Pro Tyr Tyr Gly Gly Thr Thr Tyr Asn Arg Lys Phe
 50                  55                  60

Lys Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Ser Val Gly Pro Phe Asp Ser Trp Gly Gln Gly Thr Leu Val
                100                 105                 110

Thr Val Ser Ser Gly Gly Gly Gly Ser Gly Gly Gly Gly Ser Gly Gly
            115                 120                 125

Gly Gly Ser Gly Gly Gly Gly Ser Gly Gly Gly Gly Ser Glu Ile Val
        130                 135                 140

Leu Thr Gln Ser Pro Ala Thr Leu Ser Leu Ser Pro Gly Glu Arg Ala
145                 150                 155                 160

Thr Leu Ser Cys Arg Ala Ser Glu Asn Val Tyr Ser Tyr Leu Ala Trp
                165                 170                 175

Tyr Gln Gln Lys Pro Gly Gln Ala Pro Arg Leu Leu Ile Tyr Phe Ala
            180                 185                 190

Lys Thr Leu Ala Glu Gly Ile Pro Ala Arg Phe Ser Gly Ser Gly Ser
        195                 200                 205

Gly Thr Asp Phe Thr Leu Thr Ile Ser Ser Leu Glu Pro Glu Asp Phe
    210                 215                 220

Ala Val Tyr Tyr Cys Gln His His Ser Asp Asn Pro Trp Thr Phe Gly
225                 230                 235                 240

Gln Gly Thr Lys Val Glu Ile Lys Ser Ser Glu Pro Lys Ser Ser
                245                 250                 255

Asp Lys Thr His Thr Cys Pro Pro Cys Pro Ala Pro Glu Ala Ala Gly
            260                 265                 270

Ala Pro Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
    290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Ala Tyr Ala Cys Ala Val Ser Asn Lys Ala Leu Pro Ala Pro Ile
        355                 360                 365

Glu Lys Thr Ile Ser Lys Ala Lys Gly Gln Pro Arg Glu Pro Gln Val
    370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
            420                 425                 430

Val Leu Asp Ser Asp Gly Ser Phe Phe Leu Tyr Ser Lys Leu Thr Val
        435                 440                 445
```

Asp Lys Ser Arg Trp Gln Gln Gly Asn Val Phe Ser Cys Ser Val Met
    450                 455                 460

His Glu Ala Leu His Asn His Tyr Thr Gln Lys Ser Leu Ser Leu Ser
465                 470                 475                 480

Pro Gly Gln Arg His Asn Asn Ser Ser Leu Asn Thr Gly Thr Gln Met
                485                 490                 495

Ala Gly His Ser Pro Asn Ser Gln Val Gln Leu Val Gln Ser Gly Pro
            500                 505                 510

Glu Val Lys Lys Pro Gly Ser Ser Val Lys Val Ser Cys Lys Ala Ser
        515                 520                 525

Gly Tyr Thr Phe Ser Arg Ser Thr Met His Trp Val Arg Gln Ala Pro
530                 535                 540

Gly Gln Gly Leu Glu Trp Ile Gly Tyr Ile Asn Pro Ser Ser Ala Tyr
545                 550                 555                 560

Thr Asn Tyr Asn Gln Lys Phe Lys Asp Arg Val Thr Ile Thr Ala Asp
                565                 570                 575

Lys Ser Thr Ser Thr Ala Tyr Met Glu Leu Ser Ser Leu Arg Ser Glu
            580                 585                 590

Asp Thr Ala Val Tyr Tyr Cys Ala Arg Pro Gln Val His Tyr Asp Tyr
        595                 600                 605

Asn Gly Phe Pro Tyr Trp Gly Gln Gly Thr Leu Val Thr Val Ser Ser
610                 615                 620

Gly Gly Gly Gly Ser Gly Gly Gly Ser Gly Gly Gly Gly Ser Gly Gly
625                 630                 635                 640

Gly Gly Gly Ser Asp Ile Gln Met Thr Gln Ser Pro Ser Thr Leu Ser
                645                 650                 655

Ala Ser Val Gly Asp Arg Val Thr Met Thr Cys Ser Ala Ser Ser Ser
            660                 665                 670

Val Ser Tyr Met Asn Trp Tyr Gln Gln Lys Pro Gly Lys Ala Pro Lys
        675                 680                 685

Arg Trp Ile Tyr Asp Ser Ser Lys Leu Ala Ser Gly Val Pro Ser Arg
690                 695                 700

Phe Ser Gly Ser Gly Ser Gly Thr Glu Tyr Thr Leu Thr Ile Ser Ser
705                 710                 715                 720

Leu Gln Pro Asp Asp Phe Ala Thr Tyr Tyr Cys Gln Gln Trp Ser Arg
                725                 730                 735

Asn Pro Pro Thr Phe Gly Gly Gly Thr Lys Val Glu Ile Lys Arg Ser
            740                 745                 750

Ser Ser

<210> SEQ ID NO 81
<211> LENGTH: 2325
<212> TYPE: DNA
<213> ORGANISM: Artificial Sequence
<220> FEATURE:
<223> OTHER INFORMATION: Anti-CD37 X TSC456 anti-CD3 bispecific molecule

<400> SEQUENCE: 81
atggaagcac cagcgcagct tctcttcctc ctgctactct ggctcccaga taccaccggt      60
gaggtgcagc tggtgcagtc tggagcagag gtgaaaaagc ccggagagtc tctgaagatt     120
tcctgtaagg gctccggtta ctcattcact ggctacaata tgaactgggt gcgccagatg     180
cccgggaaag gcctggagtg gatgggcaat attgatcctt attatggtgg tactacctac     240
aaccggaagt tcaagggcca ggtcactatc tccgccgaca gtccatcag caccgcctac     300

```
ctgcaatgga gcagcctgaa ggcctcggac accgccatgt attactgtgc acgctcagtc    360
ggcccttttcg actcctgggg ccagggcacc ctggtcactg tctcctctgg ggtggaggc    420
tctggtggcg gtggctctgg cggaggtgga tccggtggcg gcggatctgg cggggtggc    480
tctgaaattg tgttgacaca gtctccagcc accctgtctt tgtctccagg cgaaagagcc    540
accctctcct gccgagcaag tgaaaatgtt tacagctact tagcctggta ccaacagaaa    600
cctggccagg ctcctaggct cctcatctat tttgcaaaaa ccttagcaga aggtattcca    660
gccaggttca gtggcagtgg ctccgggaca gacttcactc tcaccatcag cagcctagag    720
cctgaagatt ttgcagttta ttactgtcaa catcattccg ataatccgtg acattcggc    780
caagggacca aggtggaaat caaatcctcg agtgagccca atcttctga caaaactcac    840
acatgcccac cgtgcccagc acctgaagcc gcgggtgcac cgtcagtctt cctcttcccc    900
ccaaaaccca aggacaccct catgatctcc cggacccctg aggtcacatg cgtggtggtg    960
gacgtgagcc acgaagaccc tgaggtcaag ttcaactggt acgtggacgg cgtggaggtg    1020
cataatgcca agacaaagcc gcgggaggag cagtacaaca gcacgtaccg tgtggtcagc    1080
gtcctcaccg tcctgcacca ggactggctg aatggcaagg catacgcgtg cgcggtctcc    1140
aacaaagccc tcccagcccc catcgagaaa accatctcca agccaaagg gcagccccga    1200
gaaccacagg tgtacaccct gcccccatcc cgggatgagc tgaccaagaa ccaggtcagc    1260
ctgacctgcc tggtcaaagg cttctatcca agcgacatcg ccgtggagtg ggagagcaat    1320
gggcagccgg agaacaacta caagaccacg cctcccgtgc tggactccga cggctccttc    1380
ttcctctaca gcaagctcac cgtggacaag agcaggtggc agcaggggaa cgtcttctca    1440
tgctccgtga tgcatgaggc tctgcacaac cactacacgc agaagagcct ctccctgtct    1500
ccgggtcaga ggcacaacaa ttcttccctg aatacaggaa ctcagatggc aggtcattct    1560
ccgaattctc aggtccagct ggtgcaatct gggcctgagg tgaagaagcc tgggtcctcg    1620
gtgaaggtct cctgcaaggc ttctggatat accttcagca gatctacgat gcactgggtg    1680
cgacaggccc ctggacaagg gcttgagtgg ataggataca ttaatcctag cagtgcttat    1740
actaattaca atcagaaatt caaggacaga gtcacgatta ccgcggacaa atccacgagc    1800
acagcctaca tggagctgag cagcctgaga tctgaggaca cggccgtgta ttactgtgcg    1860
agaccccaag tccactatga ttacaacggg tttccttact ggggccaagg aaccctggtc    1920
accgtctcct caggtggagg cggttcaggc ggaggtggat ccggcggtgg cggatcgggt    1980
ggcggcggat ctgacatcca gatgacccag tctccttcca ccctgtctgc atctgtagga    2040
gacagagtca ccatgacttg cagtgccagc tcaagtgtaa gttacatgaa ctggtatcag    2100
cagaaaccag ggaaagcccc taagagatgg atttatgact catccaaact ggcttctggg    2160
gtcccatcaa ggttcagcgg cagtggatct gggacagatt atactctcac catcagcagc    2220
ctgcagcctg atgattttgc aacttattac tgccaacagt ggagtcgtaa cccacccact    2280
ttcggcggag ggaccaaggt ggagatcaaa cggtcctcca gctaa    2325
```

<210> SEQ ID NO 82
<211> LENGTH: 754
<212> TYPE: PRT
<213> ORGANISM: Artificial Sequence
<220> FEATURE:
<223> OTHER INFORMATION: Anti-CD37 X TSC456 anti-CD3 bispecific molecule

<400> SEQUENCE: 82

Glu Val Gln Leu Val Gln Ser Gly Ala Glu Val Lys Lys Pro Gly Glu

-continued

```
1               5                   10                  15
Ser Leu Lys Ile Ser Cys Lys Gly Ser Gly Tyr Ser Phe Thr Gly Tyr
                20                  25                  30
Asn Met Asn Trp Val Arg Gln Met Pro Gly Lys Gly Leu Glu Trp Met
            35                  40                  45
Gly Asn Ile Asp Pro Tyr Tyr Gly Gly Thr Thr Tyr Asn Arg Lys Phe
        50                  55                  60
Lys Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg Ser Val Gly Pro Phe Asp Ser Trp Gly Gln Gly Thr Leu Val
            100                 105                 110
Thr Val Ser Ser Gly Gly Gly Gly Ser Gly Gly Gly Gly Ser Gly Gly
            115                 120                 125
Gly Gly Ser Gly Gly Gly Gly Ser Gly Gly Gly Gly Ser Glu Ile Val
        130                 135                 140
Leu Thr Gln Ser Pro Ala Thr Leu Ser Leu Ser Pro Gly Glu Arg Ala
145                 150                 155                 160
Thr Leu Ser Cys Arg Ala Ser Glu Asn Val Tyr Ser Tyr Leu Ala Trp
                165                 170                 175
Tyr Gln Gln Lys Pro Gly Gln Ala Pro Arg Leu Leu Ile Tyr Phe Ala
            180                 185                 190
Lys Thr Leu Ala Glu Gly Ile Pro Ala Arg Phe Ser Gly Ser Gly Ser
            195                 200                 205
Gly Thr Asp Phe Thr Leu Thr Ile Ser Ser Leu Glu Pro Glu Asp Phe
        210                 215                 220
Ala Val Tyr Tyr Cys Gln His His Ser Asp Asn Pro Trp Thr Phe Gly
225                 230                 235                 240
Gln Gly Thr Lys Val Glu Ile Lys Ser Ser Glu Pro Lys Ser Ser
                245                 250                 255
Asp Lys Thr His Thr Cys Pro Pro Cys Pro Ala Pro Glu Ala Ala Gly
            260                 265                 270
Ala Pro Ser Val Phe Leu Phe Pro Pro Lys Pro Lys Asp Thr Leu Met
            275                 280                 285
Ile Ser Arg Thr Pro Glu Val Thr Cys Val Val Val Asp Val Ser His
        290                 295                 300
Glu Asp Pro Glu Val Lys Phe Asn Trp Tyr Val Asp Gly Val Glu Val
305                 310                 315                 320
His Asn Ala Lys Thr Lys Pro Arg Glu Glu Gln Tyr Asn Ser Thr Tyr
                325                 330                 335
Arg Val Val Ser Val Leu Thr Val Leu His Gln Asp Trp Leu Asn Gly
            340                 345                 350
Lys Ala Tyr Ala Cys Ala Val Ser Asn Lys Ala Leu Pro Ala Pro Ile
            355                 360                 365
Glu Lys Thr Ile Ser Lys Ala Lys Gly Gln Pro Arg Glu Pro Gln Val
        370                 375                 380
Tyr Thr Leu Pro Pro Ser Arg Asp Glu Leu Thr Lys Asn Gln Val Ser
385                 390                 395                 400
Leu Thr Cys Leu Val Lys Gly Phe Tyr Pro Ser Asp Ile Ala Val Glu
                405                 410                 415
Trp Glu Ser Asn Gly Gln Pro Glu Asn Asn Tyr Lys Thr Thr Pro Pro
            420                 425                 430
```

Val Leu Asp Ser Asp Gly Ser Phe Phe Leu Tyr Ser Lys Leu Thr Val
            435                 440                 445

Asp Lys Ser Arg Trp Gln Gln Gly Asn Val Phe Ser Cys Ser Val Met
        450                 455                 460

His Glu Ala Leu His Asn His Tyr Thr Gln Lys Ser Leu Ser Leu Ser
465                 470                 475                 480

Pro Gly Gln Arg His Asn Asn Ser Ser Leu Asn Thr Gly Thr Gln Met
                485                 490                 495

Ala Gly His Ser Pro Asn Ser Gln Val Gln Leu Val Gln Ser Gly Pro
            500                 505                 510

Glu Val Lys Lys Pro Gly Ser Ser Val Lys Val Ser Cys Lys Ala Ser
        515                 520                 525

Gly Tyr Thr Phe Ser Arg Ser Thr Met His Trp Val Arg Gln Ala Pro
    530                 535                 540

Gly Gln Gly Leu Glu Trp Ile Gly Tyr Ile Asn Pro Ser Ser Ala Tyr
545                 550                 555                 560

Thr Asn Tyr Asn Gln Lys Phe Lys Asp Arg Val Thr Ile Thr Ala Asp
                565                 570                 575

Lys Ser Thr Ser Thr Ala Tyr Met Glu Leu Ser Ser Leu Arg Ser Glu
            580                 585                 590

Asp Thr Ala Val Tyr Tyr Cys Ala Arg Pro Gln Val His Tyr Asp Tyr
        595                 600                 605

Asn Gly Phe Pro Tyr Trp Gly Gln Gly Thr Leu Val Thr Val Ser Ser
    610                 615                 620

Gly Gly Gly Gly Ser Gly Gly Gly Ser Gly Gly Gly Gly Ser Gly
625                 630                 635                 640

Gly Gly Gly Ser Asp Ile Gln Met Thr Gln Ser Pro Ser Thr Leu Ser
                645                 650                 655

Ala Ser Val Gly Asp Arg Val Thr Met Thr Cys Ser Ala Ser Ser Ser
            660                 665                 670

Val Ser Tyr Met Asn Trp Tyr Gln Gln Lys Pro Gly Lys Ala Pro Lys
        675                 680                 685

Arg Trp Ile Tyr Asp Ser Ser Lys Leu Ala Ser Gly Val Pro Ser Arg
    690                 695                 700

Phe Ser Gly Ser Gly Ser Gly Thr Asp Tyr Thr Leu Thr Ile Ser Ser
705                 710                 715                 720

Leu Gln Pro Asp Asp Phe Ala Thr Tyr Tyr Cys Gln Gln Trp Ser Arg
                725                 730                 735

Asn Pro Pro Thr Phe Gly Gly Gly Thr Lys Val Glu Ile Lys Arg Ser
            740                 745                 750

Ser Ser

<210> SEQ ID NO 83
<211> LENGTH: 251
<212> TYPE: PRT
<213> ORGANISM: Artificial Sequence
<220> FEATURE:
<223> OTHER INFORMATION: TSC455 CD3 scFv CD3-binding domain

<400> SEQUENCE: 83

Gln Val Gln Leu Val Gln Ser Gly Pro Glu Val Lys Lys Pro Gly Ser
1               5                   10                  15

Ser Val Lys Val Ser Cys Lys Ala Ser Gly Tyr Thr Phe Ser Arg Ser
            20                  25                  30

```
Thr Met His Trp Val Arg Gln Ala Pro Gly Gln Gly Leu Glu Trp Ile
         35                  40                  45

Gly Tyr Ile Asn Pro Ser Ser Ala Tyr Thr Asn Tyr Asn Gln Lys Phe
 50                      55                  60

Lys Asp Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Pro Gln Val His Tyr Asp Tyr Asn Gly Phe Pro Tyr Trp Gly
             100                 105                 110

Gln Gly Thr Leu Val Thr Val Ser Ser Gly Gly Gly Ser Gly Gly
             115                 120                 125

Gly Gly Ser Gly Gly Gly Ser Gly Gly Gly Ser Asp Ile Gln
     130                 135                 140

Met Thr Gln Ser Pro Ser Thr Leu Ser Ala Ser Val Gly Asp Arg Val
145                 150                 155                 160

Thr Met Thr Cys Ser Ala Ser Ser Val Ser Tyr Met Asn Trp Tyr
                 165                 170                 175

Gln Gln Lys Pro Gly Lys Ala Pro Lys Arg Trp Ile Tyr Asp Ser Ser
             180                 185                 190

Lys Leu Ala Ser Gly Val Pro Ser Arg Phe Ser Gly Ser Gly Ser Gly
         195                 200                 205

Thr Glu Tyr Thr Leu Thr Ile Ser Ser Leu Gln Pro Asp Asp Phe Ala
     210                 215                 220

Thr Tyr Tyr Cys Gln Gln Trp Ser Arg Asn Pro Pro Thr Phe Gly Gly
225                 230                 235                 240

Gly Thr Lys Val Glu Ile Lys Arg Ser Ser
                 245                 250

<210> SEQ ID NO 84
<211> LENGTH: 251
<212> TYPE: PRT
<213> ORGANISM: Artificial Sequence
<220> FEATURE:
<223> OTHER INFORMATION: TSC456 CD3 scFv CD3-binding domain

<400> SEQUENCE: 84

Gln Val Gln Leu Val Gln Ser Gly Pro Glu Val Lys Lys Pro Gly Ser
1               5                  10                  15

Ser Val Lys Val Ser Cys Lys Ala Ser Gly Tyr Thr Phe Ser Arg Ser
             20                  25                  30

Thr Met His Trp Val Arg Gln Ala Pro Gly Gln Gly Leu Glu Trp Ile
         35                  40                  45

Gly Tyr Ile Asn Pro Ser Ser Ala Tyr Thr Asn Tyr Asn Gln Lys Phe
 50                      55                  60

Lys Asp Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Pro Gln Val His Tyr Asp Tyr Asn Gly Phe Pro Tyr Trp Gly
             100                 105                 110

Gln Gly Thr Leu Val Thr Val Ser Ser Gly Gly Gly Ser Gly Gly
             115                 120                 125

Gly Gly Ser Gly Gly Gly Gly Ser Gly Gly Gly Ser Asp Ile Gln
     130                 135                 140
```

```
Met Thr Gln Ser Pro Ser Thr Leu Ser Ala Ser Val Gly Asp Arg Val
145                 150                 155                 160

Thr Met Thr Cys Ser Ala Ser Ser Val Ser Tyr Met Asn Trp Tyr
            165                 170                 175

Gln Gln Lys Pro Gly Lys Ala Pro Lys Arg Trp Ile Tyr Asp Ser Ser
                180                 185                 190

Lys Leu Ala Ser Gly Val Pro Ser Arg Phe Ser Gly Ser Gly Ser Gly
            195                 200                 205

Thr Asp Tyr Thr Leu Thr Ile Ser Ser Leu Gln Pro Asp Phe Ala
    210                 215                 220

Thr Tyr Tyr Cys Gln Gln Trp Ser Arg Asn Pro Pro Thr Phe Gly Gly
225                 230                 235                 240

Gly Thr Lys Val Glu Ile Lys Arg Ser Ser Ser
                245                 250

<210> SEQ ID NO 85
<211> LENGTH: 247
<212> TYPE: PRT
<213> ORGANISM: Artificial Sequence
<220> FEATURE:
<223> OTHER INFORMATION: DRA222 CD3 scFv CD3-binding domain

<400> SEQUENCE: 85

Gln Val Gln Leu Val Glu Ser Gly Gly Gly Val Val Gln Pro Gly Arg
1               5                   10                  15

Ser Leu Arg Leu Ser Cys Lys Ala Ser Gly Tyr Thr Phe Thr Arg Ser
            20                  25                  30

Thr Met His Trp Val Arg Gln Ala Pro Gly Gln Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Arg Phe Thr Ile Ser Ala Asp Lys Ser Lys Ser Thr Ala Phe
65                  70                  75                  80

Leu Gln Met Asp Ser Leu Arg Pro Glu Asp Thr Gly Val Tyr Phe Cys
                85                  90                  95

Ala Arg Pro Gln Val His Tyr Asp Tyr Asn Gly Phe Pro Tyr Trp Gly
                100                 105                 110

Gln Gly Thr Pro Val Thr Val Ser Ser Gly Gly Gly Ser Gly Gly
            115                 120                 125

Gly Gly Ser Gly Gly Gly Ser Ala Gln Asp Ile Gln Met Thr Gln
    130                 135                 140

Ser Pro Ser Ser Leu Ser Ala Ser Val Gly Asp Arg Val Thr Met Thr
145                 150                 155                 160

Cys Ser Ala Ser Ser Val Ser Tyr Met Asn Trp Tyr Gln Gln Lys
            165                 170                 175

Pro Gly Lys Ala Pro Lys Arg Trp Ile Tyr Asp Ser Ser Lys Leu Ala
                180                 185                 190

Ser Gly Val Pro Ala Arg Phe Ser Gly Ser Gly Ser Gly Thr Asp Tyr
            195                 200                 205

Thr Leu Thr Ile Ser Ser Leu Gln Pro Glu Asp Phe Ala Thr Tyr Tyr
        210                 215                 220

Cys Gln Gln Trp Ser Arg Asn Pro Pro Thr Phe Gly Gly Gly Thr Lys
225                 230                 235                 240

Leu Gln Ile Thr Ser Ser Ser
            245
```

<210> SEQ ID NO 86
<211> LENGTH: 121
<212> TYPE: PRT
<213> ORGANISM: Artificial Sequence
<220> FEATURE:
<223> OTHER INFORMATION: TSC455 and TSC456 variable heavy domain
      CD3-binding domain

<400> SEQUENCE: 86

Gln Val Gln Leu Val Gln Ser Gly Pro Glu Val Lys Lys Pro Gly Ser
1               5                   10                  15

Ser Val Lys Val Ser Cys Lys Ala Ser Gly Tyr Thr Phe Ser Arg Ser
                20                  25                  30

Thr Met His Trp Val Arg Gln Ala Pro Gly Gln Gly Leu Glu Trp Ile
            35                  40                  45

Gly Tyr Ile Asn Pro Ser Ser Ala Tyr Thr Asn Tyr Asn Gln Lys Phe
        50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gln Val His Tyr Asp Tyr Asn Gly Phe Pro Tyr Trp Gly
                100                 105                 110

Gln Gly Thr Leu Val Thr Val Ser Ser
            115                 120

<210> SEQ ID NO 87
<211> LENGTH: 121
<212> TYPE: PRT
<213> ORGANISM: Artificial Sequence
<220> FEATURE:
<223> OTHER INFORMATION: DRA222 variable heavy domain CD3-binding domain

<400> SEQUENCE: 87

Gln Val Gln Leu Val Glu Ser Gly Gly Val Val Gln Pro Gly Arg
1               5                   10                  15

Ser Leu Arg Leu Ser Cys Lys Ala Ser Gly Tyr Thr Phe Thr Arg Ser
                20                  25                  30

Thr Met His Trp Val Arg Gln Ala Pro Gly Gln Gly Leu Glu Trp Ile
            35                  40                  45

Gly Tyr Ile Asn Pro Ser Ser Ala Tyr Thr Asn Tyr Asn Gln Lys Phe
        50                  55                  60

Lys Asp Arg Phe Thr Ile Ser Ala Asp Lys Ser Lys Ser Thr Ala Phe
65                  70                  75                  80

Leu Gln Met Asp Ser Leu Arg Pro Glu Asp Thr Gly Val Tyr Phe Cys
                85                  90                  95

Ala Arg Pro Gln Val His Tyr Asp Tyr Asn Gly Phe Pro Tyr Trp Gly
                100                 105                 110

Gln Gly Thr Pro Val Thr Val Ser Ser
            115                 120

<210> SEQ ID NO 88
<211> LENGTH: 108
<212> TYPE: PRT
<213> ORGANISM: Artificial Sequence
<220> FEATURE:
<223> OTHER INFORMATION: TSC455 variable light domain CD3-binding domain

<400> SEQUENCE: 88

```
Asp Ile Gln Met Thr Gln Ser Pro Ser Thr Leu Ser Ala Ser Val Gly
1               5                   10                  15

Asp Arg Val Thr Met Thr Cys Ser Ala Ser Ser Val Ser Tyr Met
            20                  25                  30

Asn Trp Tyr Gln Gln Lys Pro Gly Lys Ala Pro Lys Arg Trp Ile Tyr
            35                  40                  45

Asp Ser Ser Lys Leu Ala Ser Gly Val Pro Ser Arg Phe Ser Gly Ser
        50                  55                  60

Gly Ser Gly Thr Glu Tyr Thr Leu Thr Ile Ser Ser Leu Gln Pro Asp
65                  70                  75                  80

Asp Phe Ala Thr Tyr Tyr Cys Gln Gln Trp Ser Arg Asn Pro Pro Thr
                85                  90                  95

Phe Gly Gly Gly Thr Lys Val Glu Ile Lys Arg Ser
            100                 105
```

<210> SEQ ID NO 89
<211> LENGTH: 108
<212> TYPE: PRT
<213> ORGANISM: Artificial Sequence
<220> FEATURE:
<223> OTHER INFORMATION: TSC456 variable light domain CD3-binding domain

<400> SEQUENCE: 89

```
Asp Ile Gln Met Thr Gln Ser Pro Ser Thr Leu Ser Ala Ser Val Gly
1               5                   10                  15

Asp Arg Val Thr Met Thr Cys Ser Ala Ser Ser Val Ser Tyr Met
            20                  25                  30

Asn Trp Tyr Gln Gln Lys Pro Gly Lys Ala Pro Lys Arg Trp Ile Tyr
            35                  40                  45

Asp Ser Ser Lys Leu Ala Ser Gly Val Pro Ser Arg Phe Ser Gly Ser
        50                  55                  60

Gly Ser Gly Thr Asp Tyr Thr Leu Thr Ile Ser Ser Leu Gln Pro Asp
65                  70                  75                  80

Asp Phe Ala Thr Tyr Tyr Cys Gln Gln Trp Ser Arg Asn Pro Pro Thr
                85                  90                  95

Phe Gly Gly Gly Thr Lys Val Glu Ile Lys Arg Ser
            100                 105
```

<210> SEQ ID NO 90
<211> LENGTH: 107
<212> TYPE: PRT
<213> ORGANISM: Artificial Sequence
<220> FEATURE:
<223> OTHER INFORMATION: DRA222 variable light domain CD3-binding domain

<400> SEQUENCE: 90

```
Asp Ile Gln Met Thr Gln Ser Pro Ser Ser Leu Ser Ala Ser Val Gly
1               5                   10                  15

Asp Arg Val Thr Met Thr Cys Ser Ala Ser Ser Val Ser Tyr Met
            20                  25                  30

Asn Trp Tyr Gln Gln Lys Pro Gly Lys Ala Pro Lys Arg Trp Ile Tyr
            35                  40                  45

Asp Ser Ser Lys Leu Ala Ser Gly Val Pro Ala Arg Phe Ser Gly Ser
        50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Arg Asn Pro Pro Thr
                85                  90                  95
```

Phe Gly Gly Gly Thr Lys Leu Gln Ile Thr Ser
            100                 105

<210> SEQ ID NO 91
<211> LENGTH: 5
<212> TYPE: PRT
<213> ORGANISM: Artificial Sequence
<220> FEATURE:
<223> OTHER INFORMATION: Cris7 and DRA222 VH CDR1 (Kabat) CD3-binding
      domain

<400> SEQUENCE: 91

Arg Ser Thr Met His
1               5

<210> SEQ ID NO 92
<211> LENGTH: 16
<212> TYPE: PRT
<213> ORGANISM: Artificial Sequence
<220> FEATURE:
<223> OTHER INFORMATION: Cris7 and DRA222 VH CDR2 (Kabat) CD3-binding
      domain

<400> SEQUENCE: 92

Tyr Ile Asn Pro Ser Ser Ala Tyr Thr Asn Tyr Asn Gln Lys Phe Lys
1               5                   10                  15

<210> SEQ ID NO 93
<211> LENGTH: 11
<212> TYPE: PRT
<213> ORGANISM: Artificial Sequence
<220> FEATURE:
<223> OTHER INFORMATION: Cris7 and DRA222 VH CDR3 (Kabat) CD3-binding
      domain

<400> SEQUENCE: 93

Gln Val His Tyr Asp Tyr Asn Gly Phe Pro Tyr
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Cris7 and DRA222 VL CDR1 (Kabat) CD3-binding
      domain

<400> SEQUENCE: 94

Ser Ala Ser Ser Ser Val Ser Tyr Met Asn
1               5                   10

<210> SEQ ID NO 95
<211> LENGTH: 7
<212> TYPE: PRT
<213> ORGANISM: Artificial Sequence
<220> FEATURE:
<223> OTHER INFORMATION: Cris7 and DRA222 VL CDR2 (Kabat) CD3-binding
      domain

<400> SEQUENCE: 95

Asp Ser Ser Lys Leu Ala Ser
1               5

<210> SEQ ID NO 96
<211> LENGTH: 9
<212> TYPE: PRT
<213> ORGANISM: Artificial Sequence

```
<220> FEATURE:
<223> OTHER INFORMATION: Cris7 and DRA222 VL CDR3 (Kabat) CD3-binding
      domain

<400> SEQUENCE: 96

Gln Gln Trp Ser Arg Asn Pro Pro Thr
1               5

<210> SEQ ID NO 97
<211> LENGTH: 2304
<212> TYPE: DNA
<213> ORGANISM: Artificial Sequence
<220> FEATURE:
<223> OTHER INFORMATION: ROR133 Anti-ROR1 X anti-CD3 bispecific molecule

<400> SEQUENCE: 97
atggaagcac cagcgcagct tctcttcctc ctgctactct ggctcccaga taccaccggt      60
gacatccaga tgacccagtc cccctcctcc ctgtccgcct ccgtgggcga ccgggtgacc     120
atcaactgcc aggcctccca gtccatcgac tccaacctgg cctggttcca gcagaagccc     180
ggcaagcccc ccaagctgct gatctaccgg gcctccaacc tggctccgg cgtgccctcc      240 cggttctccg gctccggctc cggcaccgac ttcaccctga ccatctcctc cctgcagccc     300
gaggacgtgg ccacctacta ctgcctgggc ggcgtgggcg ccgtgtccta ccggacctcc     360
ttcggcggcg gcaccaaggt ggagatcaag ggtggaggcg gttcaggcgg aggtggatcc     420
ggcggtggcg gctccggtgg cggcggatct gaggtgcagc tggtggagtc ggcggcggc     480 ctggtgcagc ccggcggtc cctgcggctg tcctgcaccg cctccggctc cgacatcaac     540
gactacccca tctcctgggt gcggcaggcc cccggcaagg cctggagtg gatcggcttc     600 atcaactccg gcggctccac ctggtacgcc tcctgggtga agggccggtt caccatctcc     660
cgggacgact ccaagtccat cgcctacctg cagatgaact ccctgaagac cgaggacacc     720
gccgtgtact attgcgcccg gggctactcc acctactacg cgacttcaa catctggggc     780 cagggcaccc tggtgaccgt gtcctcgagt gagcccaaat cttctgacaa aactcacaca     840
tgcccaccgt gcccagcacc tgaagccgcg gtgcaccgt cagtcttcct cttcccccca     900
aaacccaagg acaccctcat gatctcccgg acccctgagg tcacatgcgt ggtggtggac     960
gtgagccacg aagaccctga ggtcaagttc aactggtacg tggacggcgt ggaggtgcat    1020
aatgccaaga caaagccgcg ggaggagcag tacaacagca cgtaccgtgt ggtcagcgtc    1080
ctcaccgtcc tgcaccagga ctggctgaat ggcaaggaat acaagtgcgc ggtctccaac    1140
aaagccctcc cagcccccat cgagaaaacc atctccaaag ccaagggca gccccgagaa    1200 ccacaggtgt acaccctgcc cccatcccgg gatgagctga ccaagaacca ggtcagcctg    1260
acctgcctgg tcaaaggctt ctatccaagc gacatcgccg tggagtggga gagcaatggg    1320
cagccggaga caactacaa gaccacgcct cccgtgctgg actccgacgg ctccttcttc    1380
ctctacagca agctcaccgt ggacaagagc aggtggcagc aggggaacgt cttctcatgc    1440
tccgtgatgc atgaggctct gcacaaccac tacacgcaga agagcctctc cctgtctccg    1500
ggttctggtg gaggcggttc aggcggaggt ggctccggcg gtggcggatc gccgggctct    1560
caggtccagc tggtggagtc tggggcgga gtggtgcagc tgggcggtc actgaggctg    1620 tcctgcaagg cttctggcta cacctttact agatctacga tgcactgggt aaggcaggcc    1680
cctggacaag gtctggaatg gattggatac attaatccta gcagtgctta ctactaattac    1740 aatcagaaat tcaaggacag gttcacaatc agcgcagaca atccaagag cacagccttc    1800
```

```
ctgcagatgg acagcctgag gcccgaggac accggcgtct atttctgtgc acggccccaa    1860
gtccactatg attacaacgg gtttccttac tggggccaag ggactcccgt cactgtctct    1920
agcggtggcg gagggtctgg gggtggcgga tccggaggtg gtggctctgc acaagacatc    1980
cagatgaccc agtctccaag cagcctgtct gcaagcgtgg gggacagggt caccatgacc    2040
tgcagtgcca gctcaagtgt aagttacatg aactggtacc agcagaagcc gggcaaggcc    2100
cccaaaagat ggatttatga ctcatccaaa ctggcttctg gagtccctgc tcgcttcagt    2160
ggcagtgggt ctgggaccga ctatacctc acaatcagca gcctgcagcc cgaagatttc    2220
gccacttatt actgccagca gtggagtcgt aacccaccca cgttcggagg ggggaccaag    2280
ctacaaatta catcctccag ctaa                                           2304
```

<210> SEQ ID NO 98
<211> LENGTH: 747
<212> TYPE: PRT
<213> ORGANISM: Artificial Sequence
<220> FEATURE:
<223> OTHER INFORMATION: ROR133 Anti-ROR1 X anti-CD3 bispecific molecule

<400> SEQUENCE: 98

```
Asp Ile Gln Met Thr Gln Ser Pro Ser Ser Leu Ser Ala Ser Val Gly
1               5                   10                  15

Asp Arg Val Thr Ile Asn Cys Gln Ala Ser Gln Ser Ile Asp Ser Asn
            20                  25                  30

Leu Ala Trp Phe Gln Gln Lys Pro Gly Lys Pro Pro Lys Leu Leu Ile
        35                  40                  45

Tyr Arg Ala Ser Asn Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gly Val Gly Ala Val Ser
                85                  90                  95

Tyr Arg Thr Ser Phe Gly Gly Gly Thr Lys Val Glu Ile Lys Gly Gly
            100                 105                 110

Gly Gly Ser Gly Gly Gly Gly Ser Gly Gly Gly Ser Gly Gly Gly
        115                 120                 125

Gly Ser Glu Val Gln Leu Val Glu Ser Gly Gly Gly Leu Val Gln Pro
    130                 135                 140

Gly Arg Ser Leu Arg Leu Ser Cys Thr Ala Ser Gly Ser Asp Ile Asn
145                 150                 155                 160

Asp Tyr Pro Ile Ser Trp Val Arg Gln Ala Pro Gly Lys Gly Leu Glu
                165                 170                 175

Trp Ile Gly Phe Ile Asn Ser Gly Gly Ser Thr Trp Tyr Ala Ser Trp
            180                 185                 190

Val Lys Gly Arg Phe Thr Ile Ser Arg Asp Asp Ser Lys Ser Ile Ala
        195                 200                 205

Tyr Leu Gln Met Asn Ser Leu Lys Thr Glu Asp Thr Ala Val Tyr Tyr
    210                 215                 220

Cys Ala Arg Gly Tyr Ser Thr Tyr Tyr Gly Asp Phe Asn Ile Trp Gly
225                 230                 235                 240

Gln Gly Thr Leu Val Thr Val Ser Ser Glu Pro Lys Ser Ser Asp
                245                 250                 255

Lys Thr His Thr Cys Pro Pro Cys Pro Ala Pro Glu Ala Ala Gly Ala
            260                 265                 270
```

```
Pro Ser Val Phe Leu Phe Pro Pro Lys Pro Lys Asp Thr Leu Met Ile
            275                 280                 285

Ser Arg Thr Pro Glu Val Thr Cys Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Ala Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Asp Glu Leu Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Ser Gly Gly Gly Gly Ser Gly Gly Gly Ser Gly Gly Gly Gly
                485                 490                 495

Ser Pro Gly Ser Gln Val Gln Leu Val Glu Ser Gly Gly Val Val
            500                 505                 510

Gln Pro Gly Arg Ser Leu Arg Leu Ser Cys Lys Ala Ser Gly Tyr Thr
        515                 520                 525

Phe Thr Arg Ser Thr Met His Trp Val Arg Gln Ala Pro Gly Gln Gly
    530                 535                 540

Leu Glu Trp Ile Gly Tyr Ile Asn Pro Ser Ser Ala Tyr Thr Asn Tyr
545                 550                 555                 560

Asn Gln Lys Phe Lys Asp Arg Phe Thr Ile Ser Ala Asp Lys Ser Lys
                565                 570                 575

Ser Thr Ala Phe Leu Gln Met Asp Ser Leu Arg Pro Glu Asp Thr Gly
            580                 585                 590

Val Tyr Phe Cys Ala Arg Pro Gln Val His Tyr Asp Tyr Asn Gly Phe
        595                 600                 605

Pro Tyr Trp Gly Gln Gly Thr Pro Val Thr Val Ser Ser Gly Gly Gly
    610                 615                 620

Gly Ser Gly Gly Gly Gly Ser Gly Gly Gly Gly Ser Ala Gln Asp Ile
625                 630                 635                 640

Gln Met Thr Gln Ser Pro Ser Ser Leu Ser Ala Ser Val Gly Asp Arg
                645                 650                 655

Val Thr Met Thr Cys Ser Ala Ser Ser Val Ser Tyr Met Asn Trp
            660                 665                 670

Tyr Gln Gln Lys Pro Gly Lys Ala Pro Lys Arg Trp Ile Tyr Asp Ser
        675                 680                 685

Ser Lys Leu Ala Ser Gly Val Pro Ala Arg Phe Ser Gly Ser Gly Ser
```

```
                690            695             700
Gly Thr Asp Tyr Thr Leu Thr Ile Ser Ser Leu Gln Pro Glu Asp Phe
705                 710                 715                 720

Ala Thr Tyr Tyr Cys Gln Gln Trp Ser Arg Asn Pro Pro Thr Phe Gly
                725                 730                 735

Gly Gly Thr Lys Leu Gln Ile Thr Ser Ser Ser
            740                 745

<210> SEQ ID NO 99
<211> LENGTH: 2316
<212> TYPE: DNA
<213> ORGANISM: Artificial Sequence
<220> FEATURE:
<223> OTHER INFORMATION: ROR193 Anti-ROR1 X anti-CD3 bispecific molecule

<400> SEQUENCE: 99
atggaagcac cagcgcagct tctcttcctc ctgctactct ggctcccaga taccaccggt      60
gacatccaga tgacccagtc cccctcctcc ctgtccgcct ccgtgggcga ccgggtgacc     120
atcaactgcc aggcctccca gtccatcgac tccaacctgg cctggttcca gcagaagccc     180
ggcaagcccc ccaagctgct gatctaccgg gcctccaacc tggcctccgg cgtgccctcc     240
cggttctccg gctccggctc cggcaccgac ttcaccctga ccatctcctc cctgcagccc     300
gaggacgtgg ccacctacta ctgcctgggc ggcgtgggcg ccgtgcccta ccggacctcc     360
ttcggcggcg gcaccaaggt ggagatcaag ggtggaggcg gttcaggcgg aggtggatcc     420
ggcggtggcg gctccggtgg cggcggatct gaggtgcagc tggtggagtc cggcggcggc     480
ctggtgcagc ccggccggtc cctgcggctg tcctgcaccg cctccggctc cgacatcaac     540
gactaccccg tctcctgggt gcggcaggcc cccggcaagg gcctggagtg gatcggcttc     600
atcaactccg gcggctccac ctggtacgcc tctgggtga agggccggtt caccatctcc     660
cgggacgact ccaagtccat cgcctacctg cagatgaact ccctgaagac cgaggacacc     720
gccgtgtact attgcgcccg ggctactcc acctactacg gcgacttcaa catctggggc     780
cagggcaccc tggtgaccgt gtcctcgagt gagcccaaat cttctgacaa aactcacaca     840
tgcccaccgt gcccagcacc tgaagccgcg gtgcaccgt cagtcttcct cttcccccca     900
aaacccaagg acaccctcat gatctcccgg acccctgagg tcacatgcgt ggtggtggac     960
gtgagccacg aagaccctga ggtcaagttc aactggtacg tggacggcgt ggaggtgcat    1020
aatgccaaga caaagccgcg ggaggagcag tacaacagca cgtaccgtgt ggtcagcgtc    1080
ctcaccgtcc tgcaccagga ctggctgaat ggcaaggaat acaagtgcgc ggtctccaac    1140
aaagccctcc cagccccat cgagaaaacc atctccaaag ccaagggca ccccgagaa      1200 ccacaggtgt acaccctgcc cccatcccgg gatgagctga ccaagaacca ggtcagcctg    1260
acctgcctgg tcaaaggctt ctatccaagc gacatcgccg tggagtggga gagcaatggg    1320
cagccggaga caactacaa gaccacgcct cccgtgctgg actccgacgg ctccttcttc    1380
ctctacagca agctcaccgt ggacaagagc aggtggcagc aggggaacgt cttctcatgc    1440
tccgtgatgc atgaggctct gcacaaccac tacacgcaga gagcctctc cctgtctccg    1500 ggttctggtg gaggcggttc aggcggaggt ggctccggcg tggcggatc gccgggctct    1560 caggtccagc tggtgcaatc tgggcctgag gtgaagaagc ctgggtcctc ggtgaaggtc    1620
tcctgcaagg cttctggata ccttcagc agatctacga tgcactgggt gcgacaggcc    1680
cctggacaag gcttgagtg gataggatac attaatccta gcagtgctta tactaattac    1740
```

-continued

```
aatcagaaat tcaaggacag agtcacgatt accgcggaca atccacgag cacagcctac    1800 atggagctga gcagcctgag atctgaggac acggccgtgt attactgtgc gagaccccaa    1860
gtccactatg attacaacgg gtttccttac tggggccaag aaccctggt caccgtctcc     1920 tcaggtggag gcggttcagg cggaggtgga tccggcggtg gcggatcggg tggcggcgga    1980
tctgacatcc agatgaccca gtctccttcc accctgtctg catctgtagg agacagagtc    2040
accatgactt gcagtgccag ctcaagtgta agttacatga actggtatca gcagaaacca    2100
gggaaagccc ctaagagatg gatttatgac tcatccaaac tggcttctgg ggtcccatca    2160
aggttcagcg gcagtggatc tgggacagag tatactctca ccatcagcag cctgcagcct    2220
gatgattttg caacttatta ctgccaacag tggagtcgta acccacccac tttcggcgga    2280
gggaccaagg tggagatcaa acggtcctcc agctaa                              2316
```

<210> SEQ ID NO 100
<211> LENGTH: 751
<212> TYPE: PRT
<213> ORGANISM: Artificial Sequence
<220> FEATURE:
<223> OTHER INFORMATION: ROR193 Anti-ROR1 X anti-CD3 bispecific molecule

<400> SEQUENCE: 100

```
Asp Ile Gln Met Thr Gln Ser Pro Ser Ser Leu Ser Ala Ser Val Gly
1               5                   10                  15

Asp Arg Val Thr Ile Asn Cys Gln Ala Ser Gln Ser Ile Asp Ser Asn
            20                  25                  30

Leu Ala Trp Phe Gln Gln Lys Pro Gly Lys Pro Pro Lys Leu Leu Ile
        35                  40                  45

Tyr Arg Ala Ser Asn Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gly Gly Val Gly Ala Val Ser
                85                  90                  95

Tyr Arg Thr Ser Phe Gly Gly Gly Thr Lys Val Glu Ile Lys Gly Gly
            100                 105                 110

Gly Gly Ser Gly Gly Gly Gly Ser Gly Gly Gly Gly Ser Gly Gly Gly
        115                 120                 125

Gly Ser Glu Val Gln Leu Val Glu Ser Gly Gly Gly Leu Val Gln Pro
    130                 135                 140

Gly Arg Ser Leu Arg Leu Ser Cys Thr Ala Ser Gly Ser Asp Ile Asn
145                 150                 155                 160

Asp Tyr Pro Ile Ser Trp Val Arg Gln Ala Pro Gly Lys Gly Leu Glu
                165                 170                 175

Trp Ile Gly Phe Ile Asn Ser Gly Gly Ser Thr Trp Tyr Ala Ser Trp
            180                 185                 190

Val Lys Gly Arg Phe Thr Ile Ser Arg Asp Asp Ser Lys Ser Ile Ala
        195                 200                 205

Tyr Leu Gln Met Asn Ser Leu Lys Thr Glu Asp Thr Ala Val Tyr Tyr
    210                 215                 220

Cys Ala Arg Gly Tyr Ser Thr Tyr Tyr Gly Asp Phe Asn Ile Trp Gly
225                 230                 235                 240

Gln Gly Thr Leu Val Thr Val Ser Ser Glu Pro Lys Ser Ser Asp
                245                 250                 255

Lys Thr His Thr Cys Pro Pro Cys Pro Ala Pro Glu Ala Ala Gly Ala
```

-continued

```
                260                 265                 270
Pro Ser Val Phe Leu Phe Pro Pro Lys Pro Lys Asp Thr Leu Met Ile
        275                 280                 285
Ser Arg Thr Pro Glu Val Thr Cys Val Val Val Asp Val Ser His Glu
        290                 295                 300
Asp Pro Glu Val Lys Phe Asn Trp Tyr Val Asp Gly Val Glu Val His
305                 310                 315                 320
Asn Ala Lys Thr Lys Pro Arg Glu Glu Gln Tyr Asn Ser Thr Tyr Arg
                325                 330                 335
Val Val Ser Val Leu Thr Val Leu His Gln Asp Trp Leu Asn Gly Lys
        340                 345                 350
Glu Tyr Lys Cys Ala Val Ser Asn Lys Ala Leu Pro Ala Pro Ile Glu
        355                 360                 365
Lys Thr Ile Ser Lys Ala Lys Gly Gln Pro Arg Glu Pro Gln Val Tyr
        370                 375                 380
Thr Leu Pro Pro Ser Arg Asp Glu Leu Thr Lys Asn Gln Val Ser Leu
385                 390                 395                 400
Thr Cys Leu Val Lys Gly Phe Tyr Pro Ser Asp Ile Ala Val Glu Trp
                405                 410                 415
Glu Ser Asn Gly Gln Pro Glu Asn Asn Tyr Lys Thr Thr Pro Pro Val
                420                 425                 430
Leu Asp Ser Asp Gly Ser Phe Phe Leu Tyr Ser Lys Leu Thr Val Asp
        435                 440                 445
Lys Ser Arg Trp Gln Gln Gly Asn Val Phe Ser Cys Ser Val Met His
        450                 455                 460
Glu Ala Leu His Asn His Tyr Thr Gln Lys Ser Leu Ser Leu Ser Pro
465                 470                 475                 480
Gly Ser Gly Gly Gly Gly Ser Gly Gly Gly Gly Ser Gly Gly Gly Gly
                485                 490                 495
Ser Pro Gly Ser Gln Val Gln Leu Val Gln Ser Gly Pro Glu Val Lys
                500                 505                 510
Lys Pro Gly Ser Ser Val Lys Val Ser Cys Lys Ala Ser Gly Tyr Thr
        515                 520                 525
Phe Ser Arg Ser Thr Met His Trp Val Arg Gln Ala Pro Gly Gln Gly
        530                 535                 540
Leu Glu Trp Ile Gly Tyr Ile Asn Pro Ser Ser Ala Tyr Thr Asn Tyr
545                 550                 555                 560
Asn Gln Lys Phe Lys Asp Arg Val Thr Ile Thr Ala Asp Lys Ser Thr
                565                 570                 575
Ser Thr Ala Tyr Met Glu Leu Ser Ser Leu Arg Ser Glu Asp Thr Ala
                580                 585                 590
Val Tyr Tyr Cys Ala Arg Pro Gln Val His Tyr Asp Tyr Asn Gly Phe
        595                 600                 605
Pro Tyr Trp Gly Gln Gly Thr Leu Val Thr Val Ser Ser Gly Gly Gly
        610                 615                 620
Gly Ser Gly Gly Gly Gly Ser Gly Gly Gly Gly Ser Gly Gly Gly Gly
625                 630                 635                 640
Ser Asp Ile Gln Met Thr Gln Ser Pro Ser Thr Leu Ser Ala Ser Val
                645                 650                 655
Gly Asp Arg Val Thr Met Thr Cys Ser Ala Ser Ser Ser Val Ser Tyr
                660                 665                 670
Met Asn Trp Tyr Gln Gln Lys Pro Gly Lys Ala Pro Lys Arg Trp Ile
                675                 680                 685
```

```
Tyr Asp Ser Ser Lys Leu Ala Ser Gly Val Pro Ser Arg Phe Ser Gly
            690                 695                 700

Ser Gly Ser Gly Thr Glu Tyr Thr Leu Thr Ile Ser Ser Leu Gln Pro
705                 710                 715                 720

Asp Asp Phe Ala Thr Tyr Tyr Cys Gln Gln Trp Ser Arg Asn Pro Pro
                725                 730                 735

Thr Phe Gly Gly Gly Thr Lys Val Glu Ile Lys Arg Ser Ser Ser
            740                 745                 750
```

<210> SEQ ID NO 101
<211> LENGTH: 2304
<212> TYPE: DNA
<213> ORGANISM: Artificial Sequence
<220> FEATURE:
<223> OTHER INFORMATION: ROR134 Anti-ROR1 X anti-CD3 bispecific molecule

<400> SEQUENCE: 101

| | | | | | |
|---|---|---|---|---|---|
| atggaagcac | cagcgcagct | tctcttcctc | ctgctactct | ggctcccaga | taccaccggt | 60 |
| gacatccaga | tgacccagtc | ccctcctcc | ctgtccgcct | ccgtgggcga | ccgggtgacc | 120 |
| atcaactgcc | aggcctccca | gtccatcgac | tccaacctgg | cctggttcca | gcagaagccc | 180 |
| ggcaagcccc | ccaagctgct | gatctaccgg | gcctccaacc | tggcctccgg | cgtgccctcc | 240 |
| cggttctccg | gctccggctc | cggcaccgac | ttcaccctga | ccatctcctc | cctgcagccc | 300 |
| gaggacgtgg | ccacctacta | ctgcctgggc | ggcgtgggcg | ccgtgtccta | ccggacctcc | 360 |
| ttcggcggcg | gcaccaaggt | ggagatcaag | ggtggaggcg | gttcaggcgg | aggtggatcc | 420 |
| ggcggtggcg | gctccggtgg | cggcggatct | gaggtgcagc | tggtggagtc | cggcggcggc | 480 |
| ctggtgcagc | ccggcggctc | cctgcggctg | tcctgcaccg | cctccggctc | cgacatcaac | 540 |
| gactacccca | tctcctgggt | gcggcaggcc | cccggcaagg | cctggagtg | gatcggcttc | 600 |
| atcaactccg | gcggctccac | ctggtacgcc | gactcggtga | agggccggtt | caccatctcc | 660 |
| cggcactcct | ccaagaacac | cctgtacctg | cagatgaact | ccctgcgggc | cgaggacacc | 720 |
| gccgtgtact | tctgcgcccg | gggctactcc | acctactacg | gcgacttcaa | catctggggc | 780 |
| cagggcaccc | tggtgaccgt | gtcctcgagt | gagcccaaat | cttctgacaa | aactcacaca | 840 |
| tgcccaccgt | gcccagcacc | tgaagccgcg | ggtgcaccgt | cagtcttcct | cttccccca | 900 |
| aaacccaagg | acaccctcat | gatctcccgg | acccctgagg | tcacatgcgt | ggtggtggac | 960 |
| gtgagccacg | aagaccctga | ggtcaagttc | aactggtacg | tggacggcgt | ggaggtgcat | 1020 |
| aatgccaaga | caaagccgcg | ggaggagcag | tacaacagca | cgtaccgtgt | ggtcagcgtc | 1080 |
| ctcaccgtcc | tgcaccagga | ctggctgaat | ggcaaggaat | acaagtgcgc | ggtctccaac | 1140 |
| aaagccctcc | cagcccccat | cgagaaaacc | atctccaaag | ccaagggca | gccccgagaa | 1200 |
| ccacaggtgt | acaccctgcc | cccatcccgg | gatgagctga | ccaagaacca | ggtcagcctg | 1260 |
| acctgcctgg | tcaaaggctt | ctatccaagc | gacatcgccg | tggagtggga | gagcaatggg | 1320 |
| cagccggaga | caaactacaa | gaccacgcct | cccgtgctgg | actccgacgg | ctccttcttc | 1380 |
| ctctacagca | agctcaccgt | ggacaagagc | aggtggcagc | aggggaacgt | cttctcatgc | 1440 |
| tccgtgatgc | atgaggctct | gcacaaccac | tacacgcaga | agagcctctc | cctgtctccg | 1500 |
| ggttctggtg | gaggcggttc | aggcggaggt | ggctccggcg | gtggcggatc | gccgggctct | 1560 |
| caggtccagc | tggtggagtc | tgggggcgga | gtggtgcagc | ctgggcggtc | actgaggctg | 1620 |
| tcctgcaagg | cttctggcta | caccttcact | agatctacga | tgcactgggt | aaggcaggcc | 1680 |

```
cctggacaag gtctggaatg gattggatac attaatccta gcagtgctta tactaattac    1740
aatcagaaat tcaaggacag gttcacaatc agcgcagaca atccaagag  cacagccttc    1800 ctgcagatgg acagcctgag gcccgaggac accggcgtct atttctgtgc acggccccaa    1860
gtccactatg attacaacgg gtttccttac tggggccaag ggactcccgt cactgtctct    1920
agcggtggcg gagggtctgg gggtggcgga tccggaggtg gtggctctgc acaagacatc    1980
cagatgaccc agtctccaag cagcctgtct gcaagcgtgg gggacagggt caccatgacc    2040
tgcagtgcca gctcaagtgt aagttacatg aactggtacc agcagaagcc gggcaaggcc    2100
cccaaaagat ggatttatga ctcatccaaa ctggcttctg gagtccctgc tcgcttcagt    2160
ggcagtgggt ctgggaccga ctatacccct acaatcagca gcctgcagcc cgaagatttc    2220
gccacttatt actgccagca gtggagtcgt aacccaccca cgttcggagg ggggaccaag    2280
ctacaaatta catcctccag ctaa                                          2304
```

<210> SEQ ID NO 102
<211> LENGTH: 747
<212> TYPE: PRT
<213> ORGANISM: Artificial Sequence
<220> FEATURE:
<223> OTHER INFORMATION: ROR134 Anti-ROR1 X anti-CD3 bispecific molecule

<400> SEQUENCE: 102

```
Asp Ile Gln Met Thr Gln Ser Pro Ser Ser Leu Ser Ala Ser Val Gly
1               5                   10                  15

Asp Arg Val Thr Ile Asn Cys Gln Ala Ser Gln Ser Ile Asp Ser Asn
            20                  25                  30

Leu Ala Trp Phe Gln Gln Lys Pro Gly Lys Pro Pro Lys Leu Leu Ile
        35                  40                  45

Tyr Arg Ala Ser Asn Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gly Gly Val Gly Ala Val Ser
                85                  90                  95

Tyr Arg Thr Ser Phe Gly Gly Gly Thr Lys Val Glu Ile Lys Gly Gly
            100                 105                 110

Gly Gly Ser Gly Gly Gly Gly Ser Gly Gly Gly Ser Gly Gly Gly
        115                 120                 125

Gly Ser Glu Val Gln Leu Val Glu Ser Gly Gly Leu Val Gln Pro
    130                 135                 140

Gly Gly Ser Leu Arg Leu Ser Cys Thr Ala Ser Gly Ser Asp Ile Asn
145                 150                 155                 160

Asp Tyr Pro Ile Ser Trp Val Arg Gln Ala Pro Gly Lys Gly Leu Glu
                165                 170                 175

Trp Ile Gly Phe Ile Asn Ser Gly Gly Ser Thr Trp Tyr Ala Asp Ser
            180                 185                 190

Val Lys Gly Arg Phe Thr Ile Ser Arg His Ser Ser Lys Asn Thr Leu
        195                 200                 205

Tyr Leu Gln Met Asn Ser Leu Arg Ala Glu Asp Thr Ala Val Tyr Phe
    210                 215                 220

Cys Ala Arg Gly Tyr Ser Thr Tyr Tyr Gly Asp Phe Asn Ile Trp Gly
225                 230                 235                 240

Gln Gly Thr Leu Val Thr Val Ser Ser Ser Glu Pro Lys Ser Ser Asp
                245                 250                 255
```

```
Lys Thr His Thr Cys Pro Pro Cys Pro Ala Pro Glu Ala Ala Gly Ala
            260                 265                 270

Pro Ser Val Phe Leu Phe Pro Lys Pro Lys Asp Thr Leu Met Ile
        275                 280                 285

Ser Arg Thr Pro Glu Val Thr Cys Val Val Val Asp Val Ser His Glu
290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Ala Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Asp Glu Leu Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Ser Gly Gly Gly Gly Ser Gly Gly Gly Gly Ser Gly Gly Gly Gly
                485                 490                 495

Ser Pro Gly Ser Gln Val Gln Leu Val Glu Ser Gly Gly Gly Val Val
            500                 505                 510

Gln Pro Gly Arg Ser Leu Arg Leu Ser Cys Lys Ala Ser Gly Tyr Thr
        515                 520                 525

Phe Thr Arg Ser Thr Met His Trp Val Arg Gln Ala Pro Gly Gln Gly
    530                 535                 540

Leu Glu Trp Ile Gly Tyr Ile Asn Pro Ser Ser Ala Tyr Thr Asn Tyr
545                 550                 555                 560

Asn Gln Lys Phe Lys Asp Arg Phe Thr Ile Ser Ala Asp Lys Ser Lys
                565                 570                 575

Ser Thr Ala Phe Leu Gln Met Asp Ser Leu Arg Pro Glu Asp Thr Gly
            580                 585                 590

Val Tyr Phe Cys Ala Arg Pro Gln Val His Tyr Asp Tyr Asn Gly Phe
        595                 600                 605

Pro Tyr Trp Gly Gln Gly Thr Pro Val Thr Val Ser Ser Gly Gly Gly
    610                 615                 620

Gly Ser Gly Gly Gly Gly Ser Gly Gly Gly Gly Ser Ala Gln Asp Ile
625                 630                 635                 640

Gln Met Thr Gln Ser Pro Ser Ser Leu Ser Ala Ser Val Gly Asp Arg
                645                 650                 655

Val Thr Met Thr Cys Ser Ala Ser Ser Ser Val Ser Tyr Met Asn Trp
            660                 665                 670
```

```
Tyr Gln Gln Lys Pro Gly Lys Ala Pro Lys Arg Trp Ile Tyr Asp Ser
            675                 680                 685

Ser Lys Leu Ala Ser Gly Val Pro Ala Arg Phe Ser Gly Ser Gly Ser
        690                 695                 700

Gly Thr Asp Tyr Thr Leu Thr Ile Ser Ser Leu Gln Pro Glu Asp Phe
705                 710                 715                 720

Ala Thr Tyr Tyr Cys Gln Gln Trp Ser Arg Asn Pro Pro Thr Phe Gly
            725                 730                 735

Gly Gly Thr Lys Leu Gln Ile Thr Ser Ser Ser
            740                 745

<210> SEQ ID NO 103
<211> LENGTH: 2316
<212> TYPE: DNA
<213> ORGANISM: Artificial Sequence
<220> FEATURE:
<223> OTHER INFORMATION: ROR189 Anti-ROR1 X anti-CD3 bispecific molecule

<400> SEQUENCE: 103
atggaagcac cagcgcagct tctcttcctc ctgctactct ggctcccaga taccaccggt     60
gacatccaga tgacccagtc cccctcctcc ctgtccgcct ccgtgggcga ccgggtgacc    120
atcaactgcc aggcctccca gtccatcgac tccaacctgg cctggttcca gcagaagccc    180
ggcaagcccc ccaagctgct gatctaccgg gcctccaacc tggcctccgg cgtgccctcc    240
cggttctccg gctccggctc cggcaccgac ttcaccctga ccatctcctc cctgcagccc    300
gaggacgtgg ccacctacta ctgcctgggc ggcgtgggcg ccgtgtccta ccggacctcc    360
ttcggcggcg gcaccaaggt ggagatcaag ggtggaggcg gttcaggcgg aggtggatcc    420
ggcggtggcg gctccggtgg cggcggatct gaggtgcagc tggtggagtc cggcggcggc    480
ctggtgcagc ccggcggctc cctgcggctg tcctgcaccg cctccggctc cgacatcaac    540
gactacccca tctcctgggt gcggcaggcc cccggcaagg gcctggagtg gatcggcttc    600
atcaactccg gcggctccac ctggtacgcc gactccgtga agggccggtt caccatctcc    660
cggcactcct ccaagaacac cctgtacctg cagatgaact ccctgcgggc cgaggacacc    720
gccgtgtact tctgcgcccg gggctactcc acctactacg cgacttcaa catctggggc     780 cagggcaccc tggtgaccgt gtcctcgagt gagcccaaat cttctgacaa aactcacaca    840
tgcccaccgt gcccagcacc tgaagccgcg gtgcaccgt cagtcttcct cttcccccca    900
aaacccaagg acaccctcat gatctcccgg acccctgagg tcacatgcgt ggtggtggac    960
gtgagccacg aagaccctga ggtcaagttc aactggtacg tggacggcgt ggaggtgcat   1020
aatgccaaga caaagccgcg ggaggagcag tacaacagca cgtaccgtgt ggtcagcgtc   1080
ctcaccgtcc tgcaccagga ctggctgaat ggcaaggaat acaagtgcgc ggtctccaac   1140
aaagccctcc cagcccccat cgagaaaacc atctccaaag ccaagggcag ccccgagaa   1200 ccacaggtgt acaccctgcc cccatcccgg gatgagctga ccaagaacca ggtcagcctg   1260
acctgcctgg tcaaaggctt ctatccaagc gacatcgccg tggagtggga gagcaatggg   1320
cagccggaga acaactacaa gaccacgcct cccgtgctgg actccgacgg ctccttcttc   1380
ctctacagca agctcaccgt ggacaagagc aggtggcagc aggggaacgt cttctcatgc   1440
tccgtgatgc atgaggctct gcacaaccac tacacgcaga agagcctctc cctgtctccg   1500
ggttctggtg gaggcggttc aggcggaggt ggctccggcg gtggcggatc gccgggctct   1560
caggtccagc tggtgcaatc tggggctgag gtgaagaagc ctggggcctc ggtgaaggtc   1620
```

```
tcctgcaagg cttctggata taccttcagc agatctacga tgcactgggt gcgacaggcc    1680
cctggacaag ggcttgagtg gataggatac attaatccta gcagtgctta tactaattac    1740
aatcagaaat tcaaggacag agtcacgatt accgcggaca atccacgag cacagcctac     1800 atggagctga gcagcctgag atctgaggac acggccgtgt attactgtgc agaccccaa     1860 gtccactatg attacaacgg gtttccttac tggggccaag aaccctggt caccgtctcc     1920 tcaggtggag gcggttcagg cggaggtgga tccggcggtg gcggatcggg tggcggcgga    1980
tctgacatcc agatgaccca gtctccttcc accctgtctg catctgtagg agacagagtc    2040
accatgactt gcagtgccag ctcaagtgta agttacatga actggtatca gcagaaacca    2100
gggaaagccc ctaagagatg gatttatgac tcatccaaac tggcttctgg ggtcccatca    2160
aggttcagcg gcagtggatc tgggacagat tatactctca ccatcagcag cctgcagcct    2220
gatgattttg caacttatta ctgccaacag tggagtcgta acccacccac tttcggcgga    2280
gggaccaagg tggagatcaa acggtcctcc agctaa                              2316
```

<210> SEQ ID NO 104
<211> LENGTH: 751
<212> TYPE: PRT
<213> ORGANISM: Artificial Sequence
<220> FEATURE:
<223> OTHER INFORMATION: ROR189 Anti-ROR1 X anti-CD3 bispecific molecule

<400> SEQUENCE: 104

```
Asp Ile Gln Met Thr Gln Ser Pro Ser Ser Leu Ser Ala Ser Val Gly
1               5                   10                  15

Asp Arg Val Thr Ile Asn Cys Gln Ala Ser Gln Ser Ile Asp Ser Asn
            20                  25                  30

Leu Ala Trp Phe Gln Gln Lys Pro Gly Lys Pro Pro Lys Leu Leu Ile
        35                  40                  45

Tyr Arg Ala Ser Asn Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gly Gly Val Gly Ala Val Ser
                85                  90                  95

Tyr Arg Thr Ser Phe Gly Gly Gly Thr Lys Val Glu Ile Lys Gly Gly
            100                 105                 110

Gly Gly Ser Gly Gly Gly Gly Ser Gly Gly Gly Gly Ser Gly Gly Gly
        115                 120                 125

Gly Ser Glu Val Gln Leu Val Glu Ser Gly Gly Gly Leu Val Gln Pro
    130                 135                 140

Gly Gly Ser Leu Arg Leu Ser Cys Thr Ala Ser Gly Ser Asp Ile Asn
145                 150                 155                 160

Asp Tyr Pro Ile Ser Trp Val Arg Gln Ala Pro Gly Lys Gly Leu Glu
                165                 170                 175

Trp Ile Gly Phe Ile Asn Ser Gly Gly Ser Thr Trp Tyr Ala Asp Ser
            180                 185                 190

Val Lys Gly Arg Phe Thr Ile Ser Arg His Ser Ser Lys Asn Thr Leu
        195                 200                 205

Tyr Leu Gln Met Asn Ser Leu Arg Ala Glu Asp Thr Ala Val Tyr Phe
    210                 215                 220

Cys Ala Arg Gly Tyr Ser Thr Tyr Tyr Gly Asp Phe Asn Ile Trp Gly
225                 230                 235                 240
```

```
Gln Gly Thr Leu Val Thr Val Ser Ser Ser Glu Pro Lys Ser Ser Asp
                    245                 250                 255

Lys Thr His Thr Cys Pro Pro Cys Pro Ala Pro Glu Ala Ala Gly Ala
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Ala Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Asp Glu Leu Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Ser Gly Gly Gly Gly Ser Gly Gly Gly Gly Ser Gly Gly Gly Gly
                485                 490                 495

Ser Pro Gly Ser Gln Val Gln Leu Val Gln Ser Gly Pro Glu Val Lys
            500                 505                 510

Lys Pro Gly Ser Ser Val Lys Val Ser Cys Lys Ala Ser Gly Tyr Thr
        515                 520                 525

Phe Ser Arg Ser Thr Met His Trp Val Arg Gln Ala Pro Gly Gln Gly
    530                 535                 540

Leu Glu Trp Ile Gly Tyr Ile Asn Pro Ser Ser Ala Tyr Thr Asn Tyr
545                 550                 555                 560

Asn Gln Lys Phe Lys Asp Arg Val Thr Ile Thr Ala Asp Lys Ser Thr
                565                 570                 575

Ser Thr Ala Tyr Met Glu Leu Ser Ser Leu Arg Ser Glu Asp Thr Ala
            580                 585                 590

Val Tyr Tyr Cys Ala Arg Pro Gln Val His Tyr Asp Tyr Asn Gly Phe
        595                 600                 605

Pro Tyr Trp Gly Gln Gly Thr Leu Val Thr Val Ser Ser Gly Gly Gly
    610                 615                 620

Gly Ser Gly Gly Gly Gly Ser Gly Gly Gly Gly Ser Gly Gly Gly Gly
625                 630                 635                 640

Ser Asp Ile Gln Met Thr Gln Ser Pro Ser Thr Leu Ser Ala Ser Val
                645                 650                 655

Gly Asp Arg Val Thr Met Thr Cys Ser Ala Ser Ser Ser Val Ser Tyr
```

```
                      660               665                670
Met Asn Trp Tyr Gln Gln Lys Pro Gly Lys Ala Pro Lys Arg Trp Ile
                675                680                685

Tyr Asp Ser Ser Lys Leu Ala Ser Gly Val Pro Ser Arg Phe Ser Gly
            690                695                700

Ser Gly Ser Gly Thr Asp Tyr Thr Leu Thr Ile Ser Ser Leu Gln Pro
705                710                715                720

Asp Asp Phe Ala Thr Tyr Tyr Cys Gln Gln Trp Ser Arg Asn Pro Pro
                725                730                735

Thr Phe Gly Gly Gly Thr Lys Val Glu Ile Lys Arg Ser Ser Ser
                740                745                750

<210> SEQ ID NO 105
<211> LENGTH: 2304
<212> TYPE: DNA
<213> ORGANISM: Artificial Sequence
<220> FEATURE:
<223> OTHER INFORMATION: ROR154 Anti-ROR1 X anti-CD3 bispecific molecule

<400> SEQUENCE: 105
atggaagcac cagcgcagct tctcttcctc ctgctactct ggctcccaga taccaccggt      60
gacatccaga tgacccagtc ccctcctcc ctgtccgcct ccgtgggcga ccgggtgacc      120
atcaactgcc aggcctccca gtccatcgac tccaacctgg cctggttcca gcagaagccc     180
ggcaagcccc ccaagctgct gatctaccgg gcctccaacc tggcctccgg cgtgccctcc     240
cggttctccg gctccggctc cggcaccgac ttcaccctga ccatctcctc cctgcagccc     300
gaggacgtgg ccacctacta ctgcctgggc ggcgtgggcg ccgtgtccta ccggacctcc     360
ttcggcggcg gcaccaaggt ggagatcaag ggtggaggcg gttcaggcgg aggtggatcc     420
ggcggtggcg gctccggtgg cggcggatct gaggtgcagc tggtggagtc cggcggcggc     480
ctggtgcagc ccggccggtc cctgcggctg tcctgcaccg cctccggctc cgacatcaac     540
gactacccca tcacctgggt gcggcaggcc cccggcaagg gcctggagtg gatcggcttc     600
atcaactccg cggctccac ctggtacgcc tcctgggtga agggccggtt caccatctcc      660
cgggacgact ccagtccat cgcctacctg cagatgaact ccctgaagac cgaggacacc      720
gccgtgtact attgcgcccg gggctactcc acctactacc gggacttcaa catctggggc     780
cagggcaccc tggtgaccgt gtcctcgagt gagcccaaat cttctgacaa aactcacaca     840
tgcccaccgt gcccagcacc tgaagccgcg gtgcaccgt cagtcttcct cttcccccca     900
aaacccaagg acaccctcat gatctcccgg acccctgagg tcacatgcgt ggtggtggac     960
gtgagccacg aagaccctga ggtcaagttc aactggtacg tggacggcgt ggaggtgcat    1020
aatgccaaga caaagccgcg ggaggagcag tacaacagca cgtaccgtgt ggtcagcgtc    1080
ctcaccgtcc tgcaccagga ctggctgaat ggcaaggaat acaagtgcgc ggtctccaac    1140
aaagccctcc cagcccccat cgagaaaacc atctccaaag ccaagggca gccccgagaa     1200 ccacaggtgt acaccctgcc cccatcccgg gatgagctga ccaagaacca ggtcagcctg    1260
acctgcctgg tcaaaggctt ctatccaagc gacatcgccg tggagtggga gagcaatggg    1320
cagccggaga caactacaa gaccacgcct cccgtgctgg actccgacgg ctccttcttc      1380
ctctacagca agctcaccgt ggacaagagc aggtggcagc aggggaacgt cttctcatgc    1440
tccgtgatgc atgaggctct gcacaaccac tacacgcaga gagcctctc cctgtctccg     1500 ggttctggtg gaggcggttc aggcggaggt ggctccggcg gtggcggatc gccgggctct    1560
```

```
caggtccagc tggtggagtc tgggggcgga gtggtgcagc tgggcggtc actgaggctg    1620 tcctgcaagg cttctggcta cacctttact agatctacga tgcactgggt aaggcaggcc    1680
cctggacaag gtctggaatg gattggatac attaatccta gcagtgctta tactaattac    1740
aatcagaaat tcaaggacag gttcacaatc agcgcagaca atccaagag cacagccttc     1800 ctgcagatgg acagcctgag gcccgaggac accggcgtct atttctgtgc acggccccaa    1860
gtccactatg attacaacgg gtttccttac tggggccaag ggactcccgt cactgtctct    1920
agcggtggcg gagggtctgg gggtggcgga tccgaggtg gtggctctgc acaagacatc      1980
cagatgaccc agtctccaag cagcctgtct gcaagcgtgg gggacagggt caccatgacc    2040
tgcagtgcca gctcaagtgt aagttacatg aactggtacc agcagaagcc gggcaaggcc    2100
cccaaaagat ggatttatga ctcatccaaa ctggcttctg gagtccctgc tcgcttcagt    2160
ggcagtgggt ctgggaccga ctatacctc acaatcagca gcctgcagcc cgaagatttc     2220
gccacttatt actgccagca gtggagtcgt aacccaccca cgttcggagg ggggaccaag    2280
ctacaaatta catcctccag ctaa                                           2304

<210> SEQ ID NO 106
<211> LENGTH: 747
<212> TYPE: PRT
<213> ORGANISM: Artificial Sequence
<220> FEATURE:
<223> OTHER INFORMATION: ROR154 Anti-ROR1 X anti-CD3 bispecific molecule

<400> SEQUENCE: 106

Asp Ile Gln Met Thr Gln Ser Pro Ser Ser Leu Ser Ala Ser Val Gly
1               5                   10                  15

Asp Arg Val Thr Ile Asn Cys Gln Ala Ser Gln Ser Ile Asp Ser Asn
            20                  25                  30

Leu Ala Trp Phe Gln Gln Lys Pro Gly Lys Pro Pro Lys Leu Leu Ile
        35                  40                  45

Tyr Arg Ala Ser Asn Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gly Val Gly Ala Val Ser
                85                  90                  95

Tyr Arg Thr Ser Phe Gly Gly Gly Thr Lys Val Glu Ile Lys Gly Gly
            100                 105                 110

Gly Gly Ser Gly Gly Gly Gly Ser Gly Gly Gly Gly Ser Gly Gly Gly
        115                 120                 125

Gly Ser Glu Val Gln Leu Val Glu Ser Gly Gly Leu Val Gln Pro
    130                 135                 140

Gly Arg Ser Leu Arg Leu Ser Cys Thr Ala Ser Gly Ser Asp Ile Asn
145                 150                 155                 160

Asp Tyr Pro Ile Thr Trp Val Arg Gln Ala Pro Gly Lys Gly Leu Glu
                165                 170                 175

Trp Ile Gly Phe Ile Asn Ser Gly Gly Ser Thr Trp Tyr Ala Ser Trp
            180                 185                 190

Val Lys Gly Arg Phe Thr Ile Ser Arg Asp Asp Ser Lys Ser Ile Ala
        195                 200                 205

Tyr Leu Gln Met Asn Ser Leu Lys Thr Glu Asp Thr Ala Val Tyr Tyr
    210                 215                 220

Cys Ala Arg Gly Tyr Ser Thr Tyr Tyr Arg Asp Phe Asn Ile Trp Gly
```

```
                225                 230                 235                 240
Gln Gly Thr Leu Val Thr Val Ser Ser Ser Glu Pro Lys Ser Ser Asp
                    245                 250                 255

Lys Thr His Thr Cys Pro Pro Cys Pro Ala Pro Glu Ala Ala Gly Ala
                    260                 265                 270

Pro Ser Val Phe Leu Phe Pro Pro Lys Pro Lys Asp Thr Leu Met Ile
                    275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
                    340                 345                 350

Glu Tyr Lys Cys Ala Val Ser Asn Lys Ala Leu Pro Ala Pro Ile Glu
                355                 360                 365

Lys Thr Ile Ser Lys Ala Lys Gly Gln Pro Arg Glu Pro Gln Val Tyr
    370                 375                 380

Thr Leu Pro Pro Ser Arg Asp Glu Leu Thr Lys Asn Gln Val Ser Leu
385                 390                 395                 400

Thr Cys Leu Val Lys Gly Phe Tyr Pro Ser Asp Ile Ala Val Glu Trp
                    405                 410                 415

Glu Ser Asn Gly Gln Pro Glu Asn Asn Tyr Lys Thr Thr Pro Pro Val
                420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Ser Gly Gly Gly Gly Ser Gly Gly Gly Ser Gly Gly Gly Gly
                    485                 490                 495

Ser Pro Gly Ser Gln Val Gln Leu Val Glu Ser Gly Gly Val Val
                500                 505                 510

Gln Pro Gly Arg Ser Leu Arg Leu Ser Cys Lys Ala Ser Gly Tyr Thr
    515                 520                 525

Phe Thr Arg Ser Thr Met His Trp Val Arg Gln Ala Pro Gly Gln Gly
    530                 535                 540

Leu Glu Trp Ile Gly Tyr Ile Asn Pro Ser Ser Ala Tyr Thr Asn Tyr
545                 550                 555                 560

Asn Gln Lys Phe Lys Asp Arg Phe Thr Ile Ser Ala Asp Lys Ser Lys
                565                 570                 575

Ser Thr Ala Phe Leu Gln Met Asp Ser Leu Arg Pro Glu Asp Thr Gly
                580                 585                 590

Val Tyr Phe Cys Ala Arg Pro Gln Val His Tyr Asp Tyr Asn Gly Phe
                595                 600                 605

Pro Tyr Trp Gly Gln Gly Thr Pro Val Thr Val Ser Ser Gly Gly Gly
    610                 615                 620

Gly Ser Gly Gly Gly Gly Ser Gly Gly Gly Gly Ser Ala Gln Asp Ile
625                 630                 635                 640

Gln Met Thr Gln Ser Pro Ser Ser Leu Ser Ala Ser Val Gly Asp Arg
                645                 650                 655
```

```
Val Thr Met Thr Cys Ser Ala Ser Ser Val Ser Tyr Met Asn Trp
            660                 665                 670

Tyr Gln Gln Lys Pro Gly Lys Ala Pro Lys Arg Trp Ile Tyr Asp Ser
        675                 680                 685

Ser Lys Leu Ala Ser Gly Val Pro Ala Arg Phe Ser Gly Ser Gly Ser
690                 695                 700

Gly Thr Asp Tyr Thr Leu Thr Ile Ser Ser Leu Gln Pro Glu Asp Phe
705                 710                 715                 720

Ala Thr Tyr Tyr Cys Gln Gln Trp Ser Arg Asn Pro Pro Thr Phe Gly
                725                 730                 735

Gly Gly Thr Lys Leu Gln Ile Thr Ser Ser Ser
            740                 745

<210> SEQ ID NO 107
<211> LENGTH: 2316
<212> TYPE: DNA
<213> ORGANISM: Artificial Sequence
<220> FEATURE:
<223> OTHER INFORMATION: ROR185 Anti-ROR1 X anti-CD3 bispecific molecule

<400> SEQUENCE: 107
atggaagcac cagcgcagct tctcttcctc ctgctactct ggctcccaga taccaccggt      60
gacatccaga tgacccagtc ccctcctcc ctgtccgcct ccgtgggcga ccgggtgacc     120
atcaactgcc aggcctccca gtccatcgac tccaacctgg cctggttcca gcagaagccc     180
ggcaagcccc ccaagctgct gatctaccgg gcctccaacc tggcctccgg cgtgccctcc     240
cggttctccg gctccggctc cggcaccgac ttcaccctga ccatctcctc cctgcagccc     300
gaggacgtgg ccacctacta ctgcctgggc ggcgtgggcg ccgtgtccta ccggacctcc     360
ttcggcggcg gcaccaaggt ggagatcaag ggtggaggcg gttcaggcgg aggtggatcc     420
ggcggtggcg gctccggtgg cggcggatct gaggtgcagc tggtggagtc cggcggcggc     480
ctggtgcagc ccggccggtc cctgcggctg tcctgcaccg cctccggctc cgacatcaac     540
gactacccca tcacctgggt gcggcaggcc cccggcaagg gcctggagtg gatcggcttc     600
atcaactccg gcggctccac ctggtacgcc tcctgggtga agggccggtt caccatctcc     660
cgggacgact ccaagtccat cgcctacctg cagatgaact ccctgaagac cgaggacacc     720
gccgtgtact attgcgcccg ggctactcc acctactacc gggacttcaa catctggggc     780
cagggcaccc tggtgaccgt gtcctcgagt gagcccaaat cttctgacaa aactcacaca     840
tgcccaccgt gcccagcacc tgaagccgcg ggtgcaccgt cagtcttcct cttcccccca     900
aaacccaagg acaccctcat gatctcccgg acccctgagg tcacatgcgt ggtggtggac     960
gtgagccacg aagaccctga ggtcaagttc aactggtacg tggacggcgt ggaggtgcat    1020
aatgccaaga caaagccgcg ggaggagcag tacaacagca cgtaccgtgt ggtcagcgtc    1080
ctcaccgtcc tgcaccagga ctggctgaat ggcaaggaat acaagtgcgc ggtctccaac    1140
aaagccctcc cagcccccat cgagaaaacc atctccaaag ccaaagggca gccccgagaa    1200
ccacaggtgt acaccctgcc cccatcccgg gatgagctga ccaagaacca ggtcagcctg    1260
acctgcctgg tcaaaggctt ctatccaagc gacatcgccg tggagtggga gagcaatggg    1320
cagccggaga acaactacaa gaccacgcct cccgtgctgg actccgacgg ctccttcttc    1380
ctctacagca agctcaccgt ggacaagagc aggtggcagc aggggaacgt cttctcatgc    1440
tccgtgatgc atgaggctct gcacaaccac tacacgcaga agagcctctc cctgtctccg    1500
```

```
ggttctggtg gaggcggttc aggcggaggt ggctccggcg gtggcggatc gccgggctct      1560
caggtccagc tggtgcaatc tgggcctgag gtgaagaagc ctgggtcctc ggtgaaggtc      1620
tcctgcaagg cttctggata taccttcagc agatctacga tgcactgggt gcgacaggcc      1680
cctggacaag gcttgagtg gataggatac attaatccta gcagtgctta tactaattac       1740
aatcagaaat tcaaggacag agtcacgatt accgcggaca atccacgag cacagcctac       1800 atggagctga gcagcctgag atctgaggac acggccgtgt attactgtgc gagaccccaa      1860
gtccactatg attacaacgg gtttccttac tggggccaag aaccctggt caccgtctcc       1920 tcaggtggag gcggttcagg cggaggtgga tccggcggtg gcggatcggg tggcggcgga      1980
tctgacatcc agatgaccca gtctccttcc accctgtctg catctgtagg agacagagtc      2040
accatgactt gcagtgccag ctcaagtgta agttacatga actggtatca gcagaaacca      2100
gggaaagccc ctaagagatg gatttatgac tcatccaaac tggcttctgg ggtcccatca      2160
aggttcagcg gcagtggatc tgggacagat tatactctca ccatcagcag cctgcagcct      2220
gatgattttg caacttatta ctgccaacag tggagtcgta acccacccac tttcggcgga      2280
gggaccaagg tggagatcaa acggtcctcc agctaa                               2316
```

<210> SEQ ID NO 108
<211> LENGTH: 751
<212> TYPE: PRT
<213> ORGANISM: Artificial Sequence
<220> FEATURE:
<223> OTHER INFORMATION: ROR185 Anti-ROR1 X anti-CD3 bispecific molecule

<400> SEQUENCE: 108

```
Asp Ile Gln Met Thr Gln Ser Pro Ser Ser Leu Ser Ala Ser Val Gly
1               5                   10                  15

Asp Arg Val Thr Ile Asn Cys Gln Ala Ser Gln Ser Ile Asp Ser Asn
            20                  25                  30

Leu Ala Trp Phe Gln Gln Lys Pro Gly Lys Pro Pro Lys Leu Leu Ile
        35                  40                  45

Tyr Arg Ala Ser Asn Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gly Gly Val Gly Ala Val Ser
                85                  90                  95

Tyr Arg Thr Ser Phe Gly Gly Gly Thr Lys Val Glu Ile Lys Gly Gly
            100                 105                 110

Gly Gly Ser Gly Gly Gly Gly Ser Gly Gly Gly Gly Ser Gly Gly Gly
        115                 120                 125

Gly Ser Glu Val Gln Leu Val Glu Ser Gly Gly Gly Leu Val Gln Pro
    130                 135                 140

Gly Arg Ser Leu Arg Leu Ser Cys Thr Ala Ser Gly Ser Asp Ile Asn
145                 150                 155                 160

Asp Tyr Pro Ile Thr Trp Val Arg Gln Ala Pro Gly Lys Gly Leu Glu
                165                 170                 175

Trp Ile Gly Phe Ile Asn Ser Gly Gly Ser Thr Trp Tyr Ala Ser Trp
            180                 185                 190

Val Lys Gly Arg Phe Thr Ile Ser Arg Asp Asp Ser Lys Ser Ile Ala
        195                 200                 205

Tyr Leu Gln Met Asn Ser Leu Lys Thr Glu Asp Thr Ala Val Tyr Tyr
    210                 215                 220
```

-continued

```
Cys Ala Arg Gly Tyr Ser Thr Tyr Tyr Arg Asp Phe Asn Ile Trp Gly
225                 230                 235                 240

Gln Gly Thr Leu Val Thr Val Ser Ser Ser Glu Pro Lys Ser Ser Asp
            245                 250                 255

Lys Thr His Thr Cys Pro Pro Cys Pro Ala Pro Glu Ala Ala Gly Ala
        260                 265                 270

Pro Ser Val Phe Leu Phe Pro Pro Lys Pro Lys Asp Thr Leu Met Ile
    275                 280                 285

Ser Arg Thr Pro Glu Val Thr Cys Val Val Val Asp Val Ser His Glu
290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Ala Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Asp Glu Leu Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Ser Gly Gly Gly Ser Gly Gly Gly Ser Gly Gly Gly Gly
                485                 490                 495

Ser Pro Gly Ser Gln Val Gln Leu Val Gln Ser Gly Pro Glu Val Lys
        500                 505                 510

Lys Pro Gly Ser Ser Val Lys Val Ser Cys Lys Ala Ser Gly Tyr Thr
    515                 520                 525

Phe Ser Arg Ser Thr Met His Trp Val Arg Gln Ala Pro Gly Gln Gly
530                 535                 540

Leu Glu Trp Ile Gly Tyr Ile Asn Pro Ser Ser Ala Tyr Thr Asn Tyr
545                 550                 555                 560

Asn Gln Lys Phe Lys Asp Arg Val Thr Ile Thr Ala Asp Lys Ser Thr
                565                 570                 575

Ser Thr Ala Tyr Met Glu Leu Ser Ser Leu Arg Ser Glu Asp Thr Ala
            580                 585                 590

Val Tyr Tyr Cys Ala Arg Pro Gln Val His Tyr Asp Tyr Asn Gly Phe
        595                 600                 605

Pro Tyr Trp Gly Gln Gly Thr Leu Val Thr Val Ser Ser Gly Gly Gly
    610                 615                 620

Gly Ser Gly Gly Gly Gly Ser Gly Gly Gly Gly Ser Gly Gly Gly Gly
625                 630                 635                 640
```

```
Ser Asp Ile Gln Met Thr Gln Ser Pro Ser Thr Leu Ser Ala Ser Val
            645                 650                 655

Gly Asp Arg Val Thr Met Thr Cys Ser Ala Ser Ser Val Ser Tyr
        660                 665                 670

Met Asn Trp Tyr Gln Gln Lys Pro Gly Lys Ala Pro Lys Arg Trp Ile
            675                 680                 685

Tyr Asp Ser Ser Lys Leu Ala Ser Gly Val Pro Ser Arg Phe Ser Gly
        690                 695                 700

Ser Gly Ser Gly Thr Asp Tyr Thr Leu Thr Ile Ser Ser Leu Gln Pro
705                 710                 715                 720

Asp Asp Phe Ala Thr Tyr Tyr Cys Gln Gln Trp Ser Arg Asn Pro Pro
                725                 730                 735

Thr Phe Gly Gly Gly Thr Lys Val Glu Ile Lys Arg Ser Ser Ser
            740                 745                 750

<210> SEQ ID NO 109
<211> LENGTH: 2304
<212> TYPE: DNA
<213> ORGANISM: Artificial Sequence
<220> FEATURE:
<223> OTHER INFORMATION: ROR179 Anti-ROR1 X anti-CD3 bispecific molecule

<400> SEQUENCE: 109
atggaagcac cagcgcagct tctcttcctc ctgctactct ggctcccaga taccaccggt      60
gacatccaga tgacccagtc ccctcctcc ctgtccgcct ccgtgggcga ccgggtgacc     120
atcaactgcc aggcctccca gtccatcgac tccaacctgg cctggttcca gcagaagccc     180
ggcaagcccc ccaagctgct gatctaccgg gcctccaacc tggcctccgg cgtgccctcc     240
cggttctccg gctccggctc cggcaccgac ttcaccctga ccatctcctc cctgcagccc     300
gaggacgtgg ccacctacta ctgcctgggc ggcgtgggcg ccgtgtccta ctggacctcc     360
ttcggcggcg gcaccaaggt ggagatcaag ggtggaggcg gttcaggcgg aggtggatcc     420
ggcggtggcg gctccggtgg cggcggatct gaggtgcagc tggtggagtc cggcggcggc     480
ctggtgcagc ccggcggtc cctgcggctg tcctgcaccg cctccggctc cgacatcaac     540
gactacccca tcacctgggt gcggcaggcc cccggcaagg gcctggagtg gatcggcttc     600
atcaactccg gcggctccac ctggtacgcc tcctgggtga agggccggtt caccatctcc     660
cgggacgact ccagtccat cgcctacctg cagatgaact ccctgaagac cgaggacacc     720
gccgtgtact attgcgcccg gggctactcc acctactacc gggacttcaa catctggggc     780
cagggcaccc tggtgaccgt gtcctcgagt gagcccaaat cttctgacaa aactcacaca     840
tgcccaccgt gcccagcacc tgaagccgcg ggtgcaccgt cagtcttcct cttccccca      900 aaacccaagg acaccctcat gatctcccgg acccctgagg tcacatgcgt ggtggtggac     960
gtgagccacg aagaccctga ggtcaagttc aactggtacg tggacggcgt ggaggtgcat    1020
aatgccaaga caaagccgcg ggaggagcag tacaacagca cgtaccgtgt ggtcagcgtc    1080
ctcaccgtcc tgcaccagga ctggctgaat ggcaaggaat acaagtgcgc ggtctccaac    1140
aaagccctcc cagccccat cgagaaaacc atctccaaag ccaaagggca gccccgagaa    1200
ccacaggtgt acaccctgcc cccatcccgg gatgagctga ccaagaacca ggtcagcctg    1260
acctgcctgg tcaaaggctt ctatccaagc gacatcgccg tggagtggga gagcaatggg    1320
cagccggaga acaactacaa gaccacgcct cccgtgctgg actccgacgg ctccttcttc    1380
ctctacagca agctcaccgt ggacaagagc aggtggcagc aggggaacgt cttctcatgc    1440
```

```
tccgtgatgc atgaggctct gcacaaccac tacacgcaga agagcctctc cctgtctccg   1500
ggttctggtg gaggcggttc aggcggaggt ggctccggcg gtggcggatc gccgggctct   1560
caggtccagc tggtggagtc tgggggcgga gtggtgcagc ctgggcggtc actgaggctg   1620
tcctgcaagg cttctggcta cacctttact agatctacga tgcactgggt aaggcaggcc   1680
cctggacaag gtctggaatg gattggatac attaatccta gcagtgctta tactaattac   1740
aatcagaaat tcaaggacag gttcacaatc agcgcagaca atccaagag cacagccttc   1800 ctgcagatgg acagcctgag gcccgaggac accggcgtct atttctgtgc acggccccaa   1860
gtccactatg attacaacgg gtttccttac tggggccaag ggactcccgt cactgtctct   1920
agcggtggcg gagggtctgg gggtggcgga tccggaggtg gtggctctgc acaagacatc   1980
cagatgaccc agtctccaag cagcctgtct gcaagcgtgg gggacagggt caccatgacc   2040
tgcagtgcca gctcaagtgt aagttacatg aactggtacc agcagaagcc gggcaaggcc   2100
cccaaaagat ggatttatga ctcatccaaa ctggcttctg gagtccctgc tcgcttcagt   2160
ggcagtgggt ctgggaccga ctataccctc acaatcagca gcctgcagcc cgaagatttc   2220
gccacttatt actgccagca gtggagtcgt aacccaccca cgttcggagg ggggaccaag   2280
ctacaaatta catcctccag ctaa                                          2304
```

<210> SEQ ID NO 110
<211> LENGTH: 747
<212> TYPE: PRT
<213> ORGANISM: Artificial Sequence
<220> FEATURE:
<223> OTHER INFORMATION: ROR179 Anti-ROR1 X anti-CD3 bispecific molecule

<400> SEQUENCE: 110

```
Asp Ile Gln Met Thr Gln Ser Pro Ser Ser Leu Ser Ala Ser Val Gly
1               5                   10                  15

Asp Arg Val Thr Ile Asn Cys Gln Ala Ser Gln Ser Ile Asp Ser Asn
            20                  25                  30

Leu Ala Trp Phe Gln Gln Lys Pro Gly Lys Pro Pro Lys Leu Leu Ile
        35                  40                  45

Tyr Arg Ala Ser Asn Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gly Val Gly Ala Val Ser
                85                  90                  95

Tyr Trp Thr Ser Phe Gly Gly Gly Thr Lys Val Glu Ile Lys Gly Gly
                100                 105                 110

Gly Gly Ser Gly Gly Gly Gly Ser Gly Gly Gly Gly Ser Gly Gly Gly
            115                 120                 125

Gly Ser Glu Val Gln Leu Val Glu Ser Gly Gly Leu Val Gln Pro
        130                 135                 140

Gly Arg Ser Leu Arg Leu Ser Cys Thr Ala Ser Gly Ser Asp Ile Asn
145                 150                 155                 160

Asp Tyr Pro Ile Thr Trp Val Arg Gln Ala Pro Gly Lys Gly Leu Glu
                165                 170                 175

Trp Ile Gly Phe Ile Asn Ser Gly Gly Ser Thr Trp Tyr Ala Ser Trp
                180                 185                 190

Val Lys Gly Arg Phe Thr Ile Ser Arg Asp Asp Ser Lys Ser Ile Ala
            195                 200                 205
```

```
Tyr Leu Gln Met Asn Ser Leu Lys Thr Glu Asp Thr Ala Val Tyr Tyr
    210                 215                 220
Cys Ala Arg Gly Tyr Ser Thr Tyr Tyr Arg Asp Phe Asn Ile Trp Gly
225                 230                 235                 240
Gln Gly Thr Leu Val Thr Val Ser Ser Glu Pro Lys Ser Ser Asp
                245                 250                 255
Lys Thr His Thr Cys Pro Pro Cys Pro Ala Pro Glu Ala Ala Gly Ala
                260                 265                 270
Pro Ser Val Phe Leu Phe Pro Lys Pro Lys Asp Thr Leu Met Ile
                275                 280                 285
Ser Arg Thr Pro Glu Val Thr Cys Val Val Asp Val Ser His Glu
    290                 295                 300
Asp Pro Glu Val Lys Phe Asn Trp Tyr Val Asp Gly Val Glu Val His
305                 310                 315                 320
Asn Ala Lys Thr Lys Pro Arg Glu Glu Gln Tyr Asn Ser Thr Tyr Arg
                325                 330                 335
Val Val Ser Val Leu Thr Val Leu His Gln Asp Trp Leu Asn Gly Lys
                340                 345                 350
Glu Tyr Lys Cys Ala Val Ser Asn Lys Ala Leu Pro Ala Pro Ile Glu
        355                 360                 365
Lys Thr Ile Ser Lys Ala Lys Gly Gln Pro Arg Glu Pro Gln Val Tyr
    370                 375                 380
Thr Leu Pro Pro Ser Arg Asp Glu Leu Thr Lys Asn Gln Val Ser Leu
385                 390                 395                 400
Thr Cys Leu Val Lys Gly Phe Tyr Pro Ser Asp Ile Ala Val Glu Trp
                405                 410                 415
Glu Ser Asn Gly Gln Pro Glu Asn Asn Tyr Lys Thr Thr Pro Pro Val
                420                 425                 430
Leu Asp Ser Asp Gly Ser Phe Phe Leu Tyr Ser Lys Leu Thr Val Asp
        435                 440                 445
Lys Ser Arg Trp Gln Gln Gly Asn Val Phe Ser Cys Ser Val Met His
    450                 455                 460
Glu Ala Leu His Asn His Tyr Thr Gln Lys Ser Leu Ser Leu Ser Pro
465                 470                 475                 480
Gly Ser Gly Gly Gly Gly Ser Gly Gly Gly Gly Ser Gly Gly Gly Gly
                485                 490                 495
Ser Pro Gly Ser Gln Val Gln Leu Val Glu Ser Gly Gly Gly Val Val
                500                 505                 510
Gln Pro Gly Arg Ser Leu Arg Leu Ser Cys Lys Ala Ser Gly Tyr Thr
        515                 520                 525
Phe Thr Arg Ser Thr Met His Trp Val Arg Gln Ala Pro Gly Gln Gly
    530                 535                 540
Leu Glu Trp Ile Gly Tyr Ile Asn Pro Ser Ser Ala Tyr Thr Asn Tyr
545                 550                 555                 560
Asn Gln Lys Phe Lys Asp Arg Phe Thr Ile Ser Ala Asp Lys Ser Lys
                565                 570                 575
Ser Thr Ala Phe Leu Gln Met Asp Ser Leu Arg Pro Glu Asp Thr Gly
                580                 585                 590
Val Tyr Phe Cys Ala Arg Pro Gln Val His Tyr Asp Tyr Asn Gly Phe
        595                 600                 605
Pro Tyr Trp Gly Gln Gly Thr Pro Val Thr Val Ser Ser Gly Gly Gly
    610                 615                 620
Gly Ser Gly Gly Gly Gly Ser Gly Gly Gly Gly Ser Ala Gln Asp Ile
```

| | | | | | | | | | | | |
|---|---|---|---|---|---|---|---|---|---|---|---|
| | | 625 | | | 630 | | | 635 | | | 640 |
| Gln | Met | Thr | Gln | Ser | Pro | Ser | Ser | Leu | Ser | Ala | Ser |
| | | | | 645 | | | | 650 | | | |
| Val | Gly | Asp | Arg | | | | | | | | |
| | | 655 | | | | | | | | | |

Val Thr Met Thr Cys Ser Ala Ser Ser Val Ser Tyr Met Asn Trp
    660                 665                 670

Tyr Gln Gln Lys Pro Gly Lys Ala Pro Lys Arg Trp Ile Tyr Asp Ser
        675                 680                 685

Ser Lys Leu Ala Ser Gly Val Pro Ala Arg Phe Ser Gly Ser Gly Ser
    690                 695                 700

Gly Thr Asp Tyr Thr Leu Thr Ile Ser Ser Leu Gln Pro Glu Asp Phe
705                 710                 715                 720

Ala Thr Tyr Tyr Cys Gln Gln Trp Ser Arg Asn Pro Pro Thr Phe Gly
                725                 730                 735

Gly Gly Thr Lys Leu Gln Ile Thr Ser Ser Ser
            740                 745

<210> SEQ ID NO 111
<211> LENGTH: 2316
<212> TYPE: DNA
<213> ORGANISM: Artificial Sequence
<220> FEATURE:
<223> OTHER INFORMATION: ROR186 Anti-ROR1 X anti-CD3 bispecific molecule

<400> SEQUENCE: 111

```
atggaagcac cagcgcagct tctcttcctc ctgctactct ggctcccaga taccaccggt      60
gacatccaga tgacccagtc ccctcctcc ctgtccgcct ccgtgggcga ccgggtgacc      120
atcaactgcc aggcctccca gtccatcgac tccaacctgg cctggttcca gcagaagccc     180
ggcaagcccc ccaagctgct gatctaccgg gcctccaacc tggcctccgg cgtgccctcc     240
cggttctccg gctccggctc cggcaccgac ttcaccctga ccatctcctc cctgcagccc     300
gaggacgtgg ccacctacta ctgcctgggc ggcgtgggcg ccgtgtccta ctggacctcc     360
ttcggcggcg gcaccaaggt ggagatcaag ggtggaggcg gttcaggcgg aggtggatcc     420
ggcggtggcg gctccggtgg cggcggatct gaggtgcagc tggtggagtc cggcggcggc     480
ctggtgcagc ccggccggtc cctgcggctg tcctgcaccg cctccggctc cgacatcaac     540
gactacccca tcacctgggt gcggcaggcc cccggcaagg gcctggagtg gatcggcttc     600
atcaactccg gcgcctccac ctggtacgcc tcctgggtga agggccggtt caccatctcc     660
cgggacgact ccaagtccat cgcctacctg cagatgaact ccctgaagac cgaggacacc     720
gccgtgtact attgcgcccg gggctactcc acctactacc gggacttcaa catctggggc     780
cagggcaccc tggtgaccgt gtcctcgagt gagcccaaat cttctgacaa aactcacaca     840
tgcccaccgt gcccagcacc tgaagccgcg gtgcaccgt cagtcttcct cttccccca      900
aaacccaagg acaccctcat gatctcccgg acccctgagg tcacatgcgt ggtggtggac     960
gtgagccacg aagaccctga ggtcaagttc aactggtacg tggacggcgt ggaggtgcat    1020
aatgccaaga caaagccgcg ggaggagcag tacaacagca cgtaccgtgt ggtcagcgtc    1080
ctcaccgtcc tgcaccagga ctggctgaat ggcaaggaat acaagtgcgc ggtctccaac    1140
aaagccctcc cagccccat cgagaaaacc atctccaaag ccaagggca gccccgagaa     1200
ccacaggtgt acaccctgcc cccatcccgg gatgagctga ccaagaacca ggtcagcctg    1260
acctgcctgg tcaaaggctt ctatccaagc gacatcgccg tggagtggga gagcaatggg    1320
cagccggaga acaactacaa gaccacgcct cccgtgctgg actccgacgg ctccttcttc    1380
```

```
ctctacagca agctcaccgt ggacaagagc aggtggcagc aggggaacgt cttctcatgc    1440
tccgtgatgc atgaggctct gcacaaccac tacacgcaga agagcctctc cctgtctccg    1500
ggttctggtg gaggcggttc aggcggaggt ggctccggcg gtggcggatc gccgggctct    1560
caggtccagc tggtgcaatc tgggcctgag gtgaagaagc ctgggtcctc ggtgaaggtc    1620
tcctgcaagg cttctggata taccttcagc agatctacga tgcactgggt gcgacaggcc    1680
cctggacaag gcttgagtg gataggatac attaatccta gcagtgctta tactaattac    1740
aatcagaaat tcaaggacag agtcacgatt accgcggaca atccacgag cacagcctac    1800 atggagctga gcagcctgag atctgaggac acggccgtgt attactgtgc gagaccccaa    1860
gtccactatg attacaacgg gtttccttac tggggccaag gaaccctggt caccgtctcc    1920
tcaggtggag gcggttcagg cggaggtgga tccggcggtg gcggatcggg tggcggcgga    1980
tctgacatcc agatgaccca gtctccttcc accctgtctg catctgtagg agacagagtc    2040
accatgactt gcagtgccag ctcaagtgta agttacatga actggtatca gcagaaacca    2100
gggaaagccc ctaagagatg gatttatgac tcatccaaac tggcttctgg ggtcccatca    2160
aggttcagcg gcagtggatc tgggacagat tatactctca ccatcagcag cctgcagcct    2220
gatgattttg caacttatta ctgccaacag tggagtcgta acccacccac tttcggcgga    2280
gggaccaagg tggagatcaa acggtcctcc agctaa                              2316
```

<210> SEQ ID NO 112
<211> LENGTH: 751
<212> TYPE: PRT
<213> ORGANISM: Artificial Sequence
<220> FEATURE:
<223> OTHER INFORMATION: ROR186 Anti-ROR1 X anti-CD3 bispecific molecule

<400> SEQUENCE: 112

```
Asp Ile Gln Met Thr Gln Ser Pro Ser Ser Leu Ser Ala Ser Val Gly
1               5                   10                  15

Asp Arg Val Thr Ile Asn Cys Gln Ala Ser Gln Ser Ile Asp Ser Asn
            20                  25                  30

Leu Ala Trp Phe Gln Gln Lys Pro Gly Lys Pro Pro Lys Leu Leu Ile
        35                  40                  45

Tyr Arg Ala Ser Asn Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gly Gly Val Gly Ala Val Ser
                85                  90                  95

Tyr Trp Thr Ser Phe Gly Gly Gly Thr Lys Val Glu Ile Lys Gly Gly
            100                 105                 110

Gly Gly Ser Gly Gly Gly Gly Ser Gly Gly Gly Gly Ser Gly Gly Gly
        115                 120                 125

Gly Ser Glu Val Gln Leu Val Glu Ser Gly Gly Gly Leu Val Gln Pro
    130                 135                 140

Gly Arg Ser Leu Arg Leu Ser Cys Thr Ala Ser Gly Ser Asp Ile Asn
145                 150                 155                 160

Asp Tyr Pro Ile Thr Trp Val Arg Gln Ala Pro Gly Lys Gly Leu Glu
                165                 170                 175

Trp Ile Gly Phe Ile Asn Ser Gly Gly Ser Thr Trp Tyr Ala Ser Trp
            180                 185                 190

Val Lys Gly Arg Phe Thr Ile Ser Arg Asp Asp Ser Lys Ser Ile Ala
```

```
            195                 200                 205
Tyr Leu Gln Met Asn Ser Leu Lys Thr Glu Asp Thr Ala Val Tyr Tyr
    210                 215                 220

Cys Ala Arg Gly Tyr Ser Thr Tyr Tyr Arg Asp Phe Asn Ile Trp Gly
225                 230                 235                 240

Gln Gly Thr Leu Val Thr Val Ser Ser Ser Glu Pro Lys Ser Ser Asp
                245                 250                 255

Lys Thr His Thr Cys Pro Pro Cys Pro Ala Pro Glu Ala Ala Gly Ala
                    260                 265                 270

Pro Ser Val Phe Leu Phe Pro Pro Lys Pro Lys Asp Thr Leu Met Ile
                275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
                340                 345                 350

Glu Tyr Lys Cys Ala Val Ser Asn Lys Ala Leu Pro Ala Pro Ile Glu
            355                 360                 365

Lys Thr Ile Ser Lys Ala Lys Gly Gln Pro Arg Glu Pro Gln Val Tyr
    370                 375                 380

Thr Leu Pro Pro Ser Arg Asp Glu Leu Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
                420                 425                 430

Leu Asp Ser Asp Gly Ser Phe Phe Leu Tyr Ser Lys Leu Thr Val Asp
            435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Ser Gly Gly Gly Gly Ser Gly Gly Gly Gly Ser Gly Gly Gly Gly
                485                 490                 495

Ser Pro Gly Ser Gln Val Gln Leu Val Gln Ser Gly Pro Glu Val Lys
            500                 505                 510

Lys Pro Gly Ser Ser Val Lys Val Ser Cys Lys Ala Ser Gly Tyr Thr
    515                 520                 525

Phe Ser Arg Ser Thr Met His Trp Val Arg Gln Ala Pro Gly Gln Gly
530                 535                 540

Leu Glu Trp Ile Gly Tyr Ile Asn Pro Ser Ser Ala Tyr Thr Asn Tyr
545                 550                 555                 560

Asn Gln Lys Phe Lys Asp Arg Val Thr Ile Thr Ala Asp Lys Ser Thr
                565                 570                 575

Ser Thr Ala Tyr Met Glu Leu Ser Ser Leu Arg Ser Glu Asp Thr Ala
            580                 585                 590

Val Tyr Tyr Cys Ala Arg Pro Gln Val His Tyr Asp Tyr Asn Gly Phe
    595                 600                 605

Pro Tyr Trp Gly Gln Gly Thr Leu Val Thr Val Ser Ser Gly Gly Gly
610                 615                 620
```

| Gly | Ser | Gly | Gly | Gly | Ser | Gly | Gly | Gly | Ser | Gly | Gly | Gly |
| | | | | | | | | | | | | |
| 625 | | | | 630 | | | | 635 | | | | 640 |

Ser Asp Ile Gln Met Thr Gln Ser Pro Ser Thr Leu Ser Ala Ser Val
            645                 650                 655

Gly Asp Arg Val Thr Met Thr Cys Ser Ala Ser Ser Val Ser Tyr
        660                 665                 670

Met Asn Trp Tyr Gln Gln Lys Pro Gly Lys Ala Pro Lys Arg Trp Ile
        675                 680                 685

Tyr Asp Ser Ser Lys Leu Ala Ser Gly Val Pro Ser Arg Phe Ser Gly
        690                 695                 700

Ser Gly Ser Gly Thr Asp Tyr Thr Leu Thr Ile Ser Ser Leu Gln Pro
705                 710                 715                 720

Asp Asp Phe Ala Thr Tyr Tyr Cys Gln Gln Trp Ser Arg Asn Pro Pro
                725                 730                 735

Thr Phe Gly Gly Gly Thr Lys Val Glu Ile Lys Arg Ser Ser Ser
            740                 745                 750

<210> SEQ ID NO 113
<211> LENGTH: 2304
<212> TYPE: DNA
<213> ORGANISM: Artificial Sequence
<220> FEATURE:
<223> OTHER INFORMATION: ROR181 Anti-ROR1 X anti-CD3 bispecific molecule

<400> SEQUENCE: 113

| atggaagcac | cagcgcagct | tctcttcctc | ctgctactct | ggctcccaga | taccaccggt | 60 |
| gacatccaga | tgacccagtc | ccctcctcc | ctgtccgcct | ccgtgggcga | ccgggtgacc | 120 |
| atcaactgcc | aggcctccca | gtccatcgac | tccaacctgg | cctggttcca | gcagaagccc | 180 |
| ggcaagcccc | ccaagctgct | gatctaccgg | gcctccaacc | tggcctccgg | cgtgccctcc | 240 |
| cggttctccg | gctccggctc | cggcaccgac | ttcaccctga | ccatctcctc | cctgcagccc | 300 |
| gaggacgtgg | ccacctacta | ctgcctgggc | ggcgtgggcg | ccgtgtccta | ccggacctcc | 360 |
| ttcggcggcg | gcaccaaggt | ggagatcaag | ggtggaggcg | gttcaggcgg | aggtggatcc | 420 |
| ggcggtggcg | gctccggtgg | cggcggatct | gaggtgcagc | tggtggagtc | cggcggcggc | 480 |
| ctggtgcagc | ccggcggctc | cctgcggctg | tcctgcaccg | tgtccggcac | cgacatcaac | 540 |
| gactacccca | tctcctgggt | gcggcaggcc | cccggcaagg | cctggagtg | gatcggcttc | 600 |
| atcaactccg | gcggctccac | ctggtacgcc | gactcggtga | agggccggtt | caccatctcc | 660 |
| cggcactcct | ccaagaacac | cctgtacctg | cagatgaact | ccctgcgggc | cgaggacacc | 720 |
| gccgtgtact | tctgcgcccg | gggctactcc | acctactacc | gggacttcaa | catctggggc | 780 |
| cagggcaccc | tggtgaccgt | gtcctcgagt | gagcccaaat | cttctgacaa | aactcacaca | 840 |
| tgcccaccgt | gcccagcacc | tgaagccgcg | ggtgcaccgt | cagtcttcct | cttcccccca | 900 |
| aaacccaagg | acaccctcat | gatctcccgg | acccctgagg | tcacatgcgt | ggtggtggac | 960 |
| gtgagccacg | aagaccctga | ggtcaagttc | aactggtacg | tggacggcgt | ggaggtgcat | 1020 |
| aatgccaaga | caaagccgcg | ggaggagcag | tacaacagca | cgtaccgtgt | ggtcagcgtc | 1080 |
| ctcaccgtcc | tgcaccagga | ctggctgaat | ggcaaggaat | acaagtgcgc | ggtctccaac | 1140 |
| aaagccctcc | cagcccccat | cgagaaaacc | atctccaaag | ccaaagggca | gccccgagaa | 1200 |
| ccacaggtgt | acaccctgcc | cccatcccgg | gatgagctga | ccaagaacca | ggtcagcctg | 1260 |
| acctgcctgg | tcaaaggctt | ctatccaagc | gacatcgccg | tggagtggga | gagcaatggg | 1320 |

```
cagccggaga caactacaa gaccacgcct cccgtgctgg actccgacgg ctccttcttc    1380
ctctacagca agctcaccgt ggacaagagc aggtggcagc aggggaacgt cttctcatgc    1440
tccgtgatgc atgaggctct gcacaaccac tacacgcaga agagcctctc cctgtctccg    1500
ggttctggtg gaggcggttc aggcggaggt ggctccggcg gtggcggatc cgggctct     1560 caggtccagc tggtggagtc tgggggcgga gtggtgcagc ctgggcggtc actgaggctg    1620
tcctgcaagg cttctggcta cacctttact agatctacga tgcactgggt aaggcaggcc    1680
cctggacaag gtctggaatg gattggatac attaatccta gcagtgctta tactaattac    1740
aatcagaaat tcaaggacag gttcacaatc agcgcagaca atccaagag cacagccttc    1800 ctgcagatgg acagcctgag gcccgaggac accggcgtct atttctgtgc acggccccaa    1860
gtccactatg attacaacgg gtttccttac tggggccaag gactcccgt cactgtctct    1920 agcggtggcg gagggtctgg gggtggcgga tccgaggtg gtggctctgc acaagacatc    1980
cagatgaccc agtctccaag cagcctgtct gcaagcgtgg gggacagggt caccatgacc    2040
tgcagtgcca gctcaagtgt aagttacatg aactggtacc agcagaagcc gggcaaggcc    2100
cccaaaagat ggatttatga ctcatccaaa ctggcttctg gagtccctgc tcgcttcagt    2160
ggcagtgggt ctgggaccga ctataccctc acaatcagca gcctgcagcc cgaagatttc    2220
gccacttatt actgccagca gtggagtcgt aacccaccca cgttcggagg ggggaccaag    2280
ctacaaatta catcctccag ctaa                                          2304
```

<210> SEQ ID NO 114
<211> LENGTH: 747
<212> TYPE: PRT
<213> ORGANISM: Artificial Sequence
<220> FEATURE:
<223> OTHER INFORMATION: ROR181 Anti-ROR1 X anti-CD3 bispecific molecule

<400> SEQUENCE: 114

```
Asp Ile Gln Met Thr Gln Ser Pro Ser Ser Leu Ser Ala Ser Val Gly
1               5                  10                  15

Asp Arg Val Thr Ile Asn Cys Gln Ala Ser Gln Ser Ile Asp Ser Asn
            20                  25                  30

Leu Ala Trp Phe Gln Gln Lys Pro Gly Lys Pro Pro Lys Leu Leu Ile
        35                  40                  45

Tyr Arg Ala Ser Asn Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gly Gly Val Gly Ala Val Ser
                85                  90                  95

Tyr Arg Thr Ser Phe Gly Gly Gly Thr Lys Val Glu Ile Lys Gly Gly
            100                 105                 110

Gly Gly Ser Gly Gly Gly Gly Ser Gly Gly Gly Gly Ser Gly Gly Gly
        115                 120                 125

Gly Ser Glu Val Gln Leu Val Glu Ser Gly Gly Gly Leu Val Gln Pro
    130                 135                 140

Gly Gly Ser Leu Arg Leu Ser Cys Thr Val Ser Gly Thr Asp Ile Asn
145                 150                 155                 160

Asp Tyr Pro Ile Ser Trp Val Arg Gln Ala Pro Gly Lys Gly Leu Glu
                165                 170                 175

Trp Ile Gly Phe Ile Asn Ser Gly Gly Ser Thr Trp Tyr Ala Asp Ser
            180                 185                 190
```

```
Val Lys Gly Arg Phe Thr Ile Ser Arg His Ser Lys Asn Thr Leu
    195                 200                 205

Tyr Leu Gln Met Asn Ser Leu Arg Ala Glu Asp Thr Ala Val Tyr Phe
    210                 215                 220

Cys Ala Arg Gly Tyr Ser Thr Tyr Tyr Arg Asp Phe Asn Ile Trp Gly
225                 230                 235                 240

Gln Gly Thr Leu Val Thr Val Ser Ser Glu Pro Lys Ser Ser Asp
                245                 250                 255

Lys Thr His Thr Cys Pro Pro Cys Pro Ala Pro Glu Ala Ala Gly Ala
                260                 265                 270

Pro Ser Val Phe Leu Phe Pro Pro Lys Pro Lys Asp Thr Leu Met Ile
            275                 280                 285

Ser Arg Thr Pro Glu Val Thr Cys Val Val Val Asp Val Ser His Glu
        290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
                340                 345                 350

Glu Tyr Lys Cys Ala Val Ser Asn Lys Ala Leu Pro Ala Pro Ile Glu
            355                 360                 365

Lys Thr Ile Ser Lys Ala Lys Gly Gln Pro Arg Glu Pro Gln Val Tyr
        370                 375                 380

Thr Leu Pro Pro Ser Arg Asp Glu Leu Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
                420                 425                 430

Leu Asp Ser Asp Gly Ser Phe Phe Leu Tyr Ser Lys Leu Thr Val Asp
            435                 440                 445

Lys Ser Arg Trp Gln Gln Gly Asn Val Phe Ser Cys Ser Val Met His
        450                 455                 460

Glu Ala Leu His Asn His Tyr Thr Gln Lys Ser Leu Ser Leu Ser Pro
465                 470                 475                 480

Gly Ser Gly Gly Gly Ser Gly Gly Gly Ser Gly Gly Gly
                485                 490                 495

Ser Pro Gly Ser Gln Val Gln Leu Val Glu Ser Gly Gly Val Val
                500                 505                 510

Gln Pro Gly Arg Ser Leu Arg Leu Ser Cys Lys Ala Ser Gly Tyr Thr
            515                 520                 525

Phe Thr Arg Ser Thr Met His Trp Val Arg Gln Ala Pro Gly Gln Gly
        530                 535                 540

Leu Glu Trp Ile Gly Tyr Ile Asn Pro Ser Ser Ala Tyr Thr Asn Tyr
545                 550                 555                 560

Asn Gln Lys Phe Lys Asp Arg Phe Thr Ile Ser Ala Asp Lys Ser Lys
                565                 570                 575

Ser Thr Ala Phe Leu Gln Met Asp Ser Leu Arg Pro Glu Asp Thr Gly
            580                 585                 590

Val Tyr Phe Cys Ala Arg Pro Gln Val His Tyr Asp Tyr Asn Gly Phe
        595                 600                 605
```

```
Pro Tyr Trp Gly Gln Gly Thr Pro Val Thr Val Ser Gly Gly Gly
        610                 615                 620
Gly Ser Gly Gly Gly Ser Gly Gly Gly Ser Ala Gln Asp Ile
625                 630                 635                 640
Gln Met Thr Gln Ser Pro Ser Ser Leu Ser Ala Ser Val Gly Asp Arg
                645                 650                 655
Val Thr Met Thr Cys Ser Ala Ser Ser Val Ser Tyr Met Asn Trp
            660                 665                 670
Tyr Gln Gln Lys Pro Gly Lys Ala Pro Lys Arg Trp Ile Tyr Asp Ser
                675                 680                 685
Ser Lys Leu Ala Ser Gly Val Pro Ala Arg Phe Ser Gly Ser Gly Ser
            690                 695                 700
Gly Thr Asp Tyr Thr Leu Thr Ile Ser Ser Leu Gln Pro Glu Asp Phe
705                 710                 715                 720
Ala Thr Tyr Tyr Cys Gln Gln Trp Ser Arg Asn Pro Pro Thr Phe Gly
                725                 730                 735
Gly Gly Thr Lys Leu Gln Ile Thr Ser Ser Ser
                740                 745
```

<210> SEQ ID NO 115
<211> LENGTH: 2316
<212> TYPE: DNA
<213> ORGANISM: Artificial Sequence
<220> FEATURE:
<223> OTHER INFORMATION: ROR191 Anti-ROR1 X anti-CD3 bispecific molecule

<400> SEQUENCE: 115

| | | |
|---|---|---|
| atggaagcac cagcgcagct tctcttcctc ctgctactct ggctcccaga taccaccggt | 60 |
| gacatccaga tgacccagtc ccctcctcc ctgtccgcct ccgtgggcga ccgggtgacc | 120 |
| atcaactgcc aggcctccca gtccatcgac tccaacctgg cctggttcca gcagaagccc | 180 |
| ggcaagcccc ccaagctgct gatctaccgg gcctccaacc tggcctccgg cgtgccctcc | 240 |
| cggttctccg gctccggctc cggcaccgac ttcaccctga ccatctcctc cctgcagccc | 300 |
| gaggacgtgg ccacctacta ctgcctgggc ggcgtgggcg ccgtgtccta ccggacctcc | 360 |
| ttcggcggcg caccaaggt ggagatcaag ggtgaggcg ttcaggcgg aggtggatcc | 420 |
| ggcggtggcg gctccggtgg cggcggatct gaggtgcagc tggtggagtc cggcggcggc | 480 |
| ctggtgcagc ccggcggctc cctgcggctg tcctgcaccg tgtccggcac cgacatcaac | 540 |
| gactacccca tctcctgggt gcggcaggcc ccggcaagg cctggagtg atcggcttc | 600 |
| atcaactccg gcggctccac ctggtacgcc gactcggtga agggccggtt caccatctcc | 660 |
| cggcactcct ccaagaacac cctgtacctg cagatgaact ccctgcgggc cgaggacacc | 720 |
| gccgtgtact tctgcgcccg gggctactcc acctactacc gggacttcaa catctggggc | 780 |
| cagggcaccc tggtgaccgt gtcctcgagt gagcccaaat cttctgacaa aactcacaca | 840 |
| tgcccaccgt gcccagcacc tgaagccgcg gtgcaccgt cagtcttcct cttcccccca | 900 |
| aaacccaagg acaccctcat gatctcccgg acccctgagg tcacatgcgt ggtggtggac | 960 |
| gtgagccacg aagaccctga ggtcaagttc aactggtacg tggacggcgt ggaggtgcat | 1020 |
| aatgccaaga caaagccgcg ggaggagcag tacaacagca cgtaccgtgt ggtcagcgtc | 1080 |
| ctcaccgtcc tgcaccagga ctggctgaat ggcaaggaat acaagtgcgc ggtctccaac | 1140 |
| aaagccctcc cagcccccat cgagaaaacc atctccaaag ccaagggca gccccgagaa | 1200 |
| ccacaggtgt acaccctgcc cccatcccgg gatgagctga ccaagaacca ggtcagcctg | 1260 |

```
acctgcctgg tcaaaggctt ctatccaagc gacatcgccg tggagtggga gagcaatggg    1320
cagccggaga caactacaa gaccacgcct cccgtgctgg actccgacgg ctccttcttc    1380
ctctacagca agctcaccgt ggacaagagc aggtggcagc aggggaacgt cttctcatgc    1440
tccgtgatgc atgaggctct gcacaaccac tacacgcaga agagcctctc cctgtctccg    1500
ggttctggtg gaggcggttc aggcggaggt ggctccggcg gtggcggatc gccgggctct    1560
caggtccagc tggtgcaatc tgggcctgag gtgaagaagc ctgggtcctc ggtgaaggtc    1620
tcctgcaagg cttctggata taccttcagc agatctacga tgcactgggt gcgacaggcc    1680
cctggacaag gcttgagtg gataggatac attaatccta gcagtgctta tactaattac    1740
aatcagaaat tcaaggacag agtcacgatt accgcggaca atccacgag cacagcctac    1800 atggagctga gcagcctgag atctgaggac acggccgtgt attactgtgc gagaccccaa    1860
gtccactatg attacaacgg gtttccttac tggggccaag gaaccctggt caccgtctcc    1920
tcaggtggag gcggttcagg cggaggtgga tccggcggtg gcggatcggg tggcggcgga    1980
tctgacatcc agatgaccca gtctccttcc accctgtctg catctgtagg agacagagtc    2040
accatgactt gcagtgccag ctcaagtgta agttacatga actggtatca gcagaaacca    2100
gggaaagccc ctaagagatg gatttatgac tcatccaaac tggcttctgg ggtcccatca    2160
aggttcagcg gcagtggatc tgggacagat tatactctca ccatcagcag cctgcagcct    2220
gatgattttg caacttatta ctgccaacag tggagtcgta acccacccac tttcggcgga    2280
gggaccaagg tggagatcaa acggtcctcc agctaa                              2316
```

<210> SEQ ID NO 116
<211> LENGTH: 751
<212> TYPE: PRT
<213> ORGANISM: Artificial Sequence
<220> FEATURE:
<223> OTHER INFORMATION: ROR191 Anti-ROR1 X anti-CD3 bispecific molecule

<400> SEQUENCE: 116

```
Asp Ile Gln Met Thr Gln Ser Pro Ser Ser Leu Ser Ala Ser Val Gly
1               5                   10                  15

Asp Arg Val Thr Ile Asn Cys Gln Ala Ser Gln Ser Ile Asp Ser Asn
            20                  25                  30

Leu Ala Trp Phe Gln Gln Lys Pro Gly Lys Pro Pro Lys Leu Leu Ile
        35                  40                  45

Tyr Arg Ala Ser Asn Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gly Gly Val Gly Ala Val Ser
                85                  90                  95

Tyr Arg Thr Ser Phe Gly Gly Gly Thr Lys Val Glu Ile Lys Gly Gly
            100                 105                 110

Gly Gly Ser Gly Gly Gly Gly Ser Gly Gly Gly Gly Ser Gly Gly Gly
        115                 120                 125

Gly Ser Glu Val Gln Leu Val Glu Ser Gly Gly Gly Leu Val Gln Pro
    130                 135                 140

Gly Gly Ser Leu Arg Leu Ser Cys Thr Val Ser Gly Thr Asp Ile Asn
145                 150                 155                 160

Asp Tyr Pro Ile Ser Trp Val Arg Gln Ala Pro Gly Lys Gly Leu Glu
                165                 170                 175
```

```
Trp Ile Gly Phe Ile Asn Ser Gly Gly Ser Thr Trp Tyr Ala Asp Ser
            180                 185                 190

Val Lys Gly Arg Phe Thr Ile Ser Arg His Ser Ser Lys Asn Thr Leu
        195                 200                 205

Tyr Leu Gln Met Asn Ser Leu Arg Ala Glu Asp Thr Ala Val Tyr Phe
    210                 215                 220

Cys Ala Arg Gly Tyr Ser Thr Tyr Tyr Arg Asp Phe Asn Ile Trp Gly
225                 230                 235                 240

Gln Gly Thr Leu Val Thr Val Ser Ser Glu Pro Lys Ser Ser Asp
                245                 250                 255

Lys Thr His Thr Cys Pro Pro Cys Pro Ala Pro Glu Ala Ala Gly Ala
                260                 265                 270

Pro Ser Val Phe Leu Phe Pro Pro Lys Pro Lys Asp Thr Leu Met Ile
            275                 280                 285

Ser Arg Thr Pro Glu Val Thr Cys Val Val Val Asp Val Ser His Glu
        290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Ala Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Asp Glu Leu Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
450                 455                 460

Glu Ala Leu His Asn His Tyr Thr Gln Lys Ser Leu Ser Leu Ser Pro
465                 470                 475                 480

Gly Ser Gly Gly Gly Gly Ser Gly Gly Gly Gly Ser Gly Gly Gly Gly
                485                 490                 495

Ser Pro Gly Ser Gln Val Gln Leu Val Gln Ser Gly Pro Glu Val Lys
        500                 505                 510

Lys Pro Gly Ser Ser Val Lys Val Ser Cys Lys Ala Ser Gly Tyr Thr
    515                 520                 525

Phe Ser Arg Ser Thr Met His Trp Val Arg Gln Ala Pro Gly Gln Gly
530                 535                 540

Leu Glu Trp Ile Gly Tyr Ile Asn Pro Ser Ser Ala Tyr Thr Asn Tyr
545                 550                 555                 560

Asn Gln Lys Phe Lys Asp Arg Val Thr Ile Thr Ala Asp Lys Ser Thr
                565                 570                 575

Ser Thr Ala Tyr Met Glu Leu Ser Ser Leu Arg Ser Glu Asp Thr Ala
            580                 585                 590

Val Tyr Tyr Cys Ala Arg Pro Gln Val His Tyr Asp Tyr Asn Gly Phe
```

```
              595                 600                 605
Pro Tyr Trp Gly Gln Gly Thr Leu Val Thr Val Ser Ser Gly Gly Gly
    610                 615                 620
Gly Ser Gly Gly Gly Ser Gly Gly Gly Gly Ser Gly Gly Gly Gly
625                 630                 635                 640
Ser Asp Ile Gln Met Thr Gln Ser Pro Ser Thr Leu Ser Ala Ser Val
                645                 650                 655
Gly Asp Arg Val Thr Met Thr Cys Ser Ala Ser Ser Val Ser Tyr
            660                 665                 670
Met Asn Trp Tyr Gln Gln Lys Pro Gly Lys Ala Pro Lys Arg Trp Ile
        675                 680                 685
Tyr Asp Ser Ser Lys Leu Ala Ser Gly Val Pro Ser Arg Phe Ser Gly
    690                 695                 700
Ser Gly Ser Gly Thr Asp Tyr Thr Leu Thr Ile Ser Ser Leu Gln Pro
705                 710                 715                 720
Asp Asp Phe Ala Thr Tyr Tyr Cys Gln Gln Trp Ser Arg Asn Pro Pro
                725                 730                 735
Thr Phe Gly Gly Gly Thr Lys Val Glu Ile Lys Arg Ser Ser Ser
            740                 745                 750

<210> SEQ ID NO 117
<211> LENGTH: 2304
<212> TYPE: DNA
<213> ORGANISM: Artificial Sequence
<220> FEATURE:
<223> OTHER INFORMATION: ROR182 Anti-ROR1 X anti-CD3 bispecific molecule

<400> SEQUENCE: 117
atggaagcac cagcgcagct tctcttcctc ctgctactct ggctcccaga taccaccggt      60
gacatccaga tgacccagtc ccctcctcc ctgtccgcct ccgtgggcga ccgggtgacc     120
atcaactgcc aggcctccca gtccatcgac tccaacctgg cctggttcca gcagaagccc     180
ggccagcccc ccaagctgct gatctaccgg gcctccaacc tggcctccgg cgtgcccgac     240
cggttctccg gctccggctc cggcaccgac ttcaccctga ccatctcctc cctggaggcc     300
gaggacgtgg ccacctacta ctgcctgggc ggcgtgggcg ccgtgtccta ccggacctcc     360
ttcggcggcg gcaccaaggt ggagatcaag gtggaggcg gttcaggcgg aggtggatcc     420
ggcggtggcg gctccggtgg cggcggatct gaggtgcagc tggtggagtc cggcggcggc     480
ctggtgcagc ccggccggtc cctgcggctg tcctgcaccg cctccggctc cgacatcaac     540
gactacccca tcacctgggt gcggcaggcc cccggccagg gcctggagtg gatcggcttc     600
atcaactccg gcggctccac ctggtacgcc tcctgggtga agggccggtt caccatctcc     660
cgggacgact ccaagtccat cgcctacctg cagatgaact ccctgaagac cgaggacacc     720
gccgtgtact attgcgcccg ggctactcc acctactacc gggacttcaa catctgggc      780 cagggcaccc tggtgaccgt gtcctcgagt gagcccaaat cttctgacaa aactcacaca     840
tgcccaccgt gcccagcacc tgaagccgcg ggtgcaccgt cagtcttcct cttccccca      900 aaacccaagg acaccctcat gatctcccgg acccctgagg tcacatgcgt ggtggtggac     960
gtgagccacg aagaccctga ggtcaagttc aactggtacg tggacggcgt ggaggtgcat    1020
aatgccaaga caaagccgcg ggaggagcag tacaacagca cgtaccgtgt ggtcagcgtc    1080
ctcaccgtcc tgcaccagga ctggctgaat ggcaaggaat acaagtgcgc ggtctccaac    1140
aaagccctcc cagcccccat cgagaaaacc atctccaaag ccaaagggca gccccgagaa    1200
```

-continued

```
ccacaggtgt acaccctgcc cccatcccgg gatgagctga ccaagaacca ggtcagcctg    1260
acctgcctgg tcaaaggctt ctatccaagc gacatcgccg tggagtggga gagcaatggg    1320
cagccggaga caaactacaa gaccacgcct cccgtgctgg actccgacgg ctccttcttc    1380
ctctacagca agctcaccgt ggacaagagc aggtggcagc aggggaacgt cttctcatgc    1440
tccgtgatgc atgaggctct gcacaaccac tacacgcaga agagcctctc cctgtctccg    1500
ggttctggtg gaggcggttc aggcggaggt ggctccggcg gtggcggatc gccgggctct    1560
caggtccagc tggtggagtc tgggggcgga gtggtgcagc ctgggcggtc actgaggctg    1620
tcctgcaagg cttctggcta cacctttact agatctacga tgcactgggt aaggcaggcc    1680
cctggacaag gtctggaatg gattggatac attaatccta gcagtgctta tactaattac    1740
aatcagaaat tcaaggacag gttcacaatc agcgcagaca atccaagag cacagccttc     1800 ctgcagatgg acagcctgag gcccgaggac accggcgtct atttctgtgc acggccccaa    1860
gtccactatg attacaacgg gtttccttac tggggccaag ggactcccgt cactgtctct    1920
agcggtggcg gagggtctgg gggtggcgga tccgaggtg gtggctctgc acaagacatc     1980
cagatgaccc agtctccaag cagcctgtct gcaagcgtgg gggacagggt caccatgacc    2040
tgcagtgcca gctcaagtgt aagttacatg aactggtacc agcagaagcc gggcaaggcc    2100
cccaaaagat ggatttatga ctcatccaaa ctggcttctg gagtccctgc tcgcttcagt    2160
ggcagtgggt ctgggaccga ctatacctc acaatcagca gcctgcagcc cgaagatttc     2220
gccacttatt actgccagca gtggagtcgt aacccaccca cgttcggagg ggggaccaag    2280
ctacaaatta catcctccag ctaa                                           2304
```

<210> SEQ ID NO 118
<211> LENGTH: 747
<212> TYPE: PRT
<213> ORGANISM: Artificial Sequence
<220> FEATURE:
<223> OTHER INFORMATION: ROR182 Anti-ROR1 X anti-CD3 bispecific molecule

<400> SEQUENCE: 118

```
Asp Ile Gln Met Thr Gln Ser Pro Ser Ser Leu Ser Ala Ser Val Gly
1               5                   10                  15

Asp Arg Val Thr Ile Asn Cys Gln Ala Ser Gln Ser Ile Asp Ser Asn
            20                  25                  30

Leu Ala Trp Phe Gln Gln Lys Pro Gly Gln Pro Pro Lys Leu Leu Ile
        35                  40                  45

Tyr Arg Ala Ser Asn Leu Ala Ser Gly Val Pro Asp Arg Phe Ser Gly
    50                  55                  60

Ser Gly Ser Gly Thr Asp Phe Thr Leu Thr Ile Ser Ser Leu Glu Ala
65                  70                  75                  80

Glu Asp Val Ala Thr Tyr Tyr Cys Leu Gly Gly Val Gly Ala Val Ser
                85                  90                  95

Tyr Arg Thr Ser Phe Gly Gly Gly Thr Lys Val Glu Ile Lys Gly Gly
            100                 105                 110

Gly Gly Ser Gly Gly Gly Gly Ser Gly Gly Gly Gly Ser Gly Gly Gly
        115                 120                 125

Gly Ser Glu Val Gln Leu Val Glu Ser Gly Gly Gly Leu Val Gln Pro
    130                 135                 140

Gly Arg Ser Leu Arg Leu Ser Cys Thr Ala Ser Gly Ser Asp Ile Asn
145                 150                 155                 160

Asp Tyr Pro Ile Thr Trp Val Arg Gln Ala Pro Gly Gln Gly Leu Glu
```

-continued

```
                165                 170                 175
Trp Ile Gly Phe Ile Asn Ser Gly Ser Thr Trp Tyr Ala Ser Trp
                180                 185                 190

Val Lys Gly Arg Phe Thr Ile Ser Arg Asp Asp Ser Lys Ser Ile Ala
                195                 200                 205

Tyr Leu Gln Met Asn Ser Leu Lys Thr Glu Asp Thr Ala Val Tyr Tyr
                210                 215                 220

Cys Ala Arg Gly Tyr Ser Thr Tyr Tyr Arg Asp Phe Asn Ile Trp Gly
225                 230                 235                 240

Gln Gly Thr Leu Val Thr Val Ser Ser Glu Pro Lys Ser Ser Asp
                245                 250                 255

Lys Thr His Thr Cys Pro Pro Cys Pro Ala Pro Glu Ala Ala Gly Ala
                260                 265                 270

Pro Ser Val Phe Leu Phe Pro Pro Lys Pro Lys Asp Thr Leu Met Ile
                275                 280                 285

Ser Arg Thr Pro Glu Val Thr Cys Val Val Val Asp Val Ser His Glu
                290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
                340                 345                 350

Glu Tyr Lys Cys Ala Val Ser Asn Lys Ala Leu Pro Ala Pro Ile Glu
                355                 360                 365

Lys Thr Ile Ser Lys Ala Lys Gly Gln Pro Arg Glu Pro Gln Val Tyr
                370                 375                 380

Thr Leu Pro Pro Ser Arg Asp Glu Leu Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
                420                 425                 430

Leu Asp Ser Asp Gly Ser Phe Phe Leu Tyr Ser Lys Leu Thr Val Asp
                435                 440                 445

Lys Ser Arg Trp Gln Gln Gly Asn Val Phe Ser Cys Ser Val Met His
                450                 455                 460

Glu Ala Leu His Asn His Tyr Thr Gln Lys Ser Leu Ser Leu Ser Pro
465                 470                 475                 480

Gly Ser Gly Gly Gly Gly Ser Gly Gly Gly Ser Gly Gly Gly Gly
                485                 490                 495

Ser Pro Gly Ser Gln Val Gln Leu Val Glu Ser Gly Gly Gly Val Val
                500                 505                 510

Gln Pro Gly Arg Ser Leu Arg Leu Ser Cys Lys Ala Ser Gly Tyr Thr
                515                 520                 525

Phe Thr Arg Ser Thr Met His Trp Val Arg Gln Ala Pro Gly Gln Gly
                530                 535                 540

Leu Glu Trp Ile Gly Tyr Ile Asn Pro Ser Ser Ala Tyr Thr Asn Tyr
545                 550                 555                 560

Asn Gln Lys Phe Lys Asp Arg Phe Thr Ile Ser Ala Asp Lys Ser Lys
                565                 570                 575

Ser Thr Ala Phe Leu Gln Met Asp Ser Leu Arg Pro Glu Asp Thr Gly
                580                 585                 590
```

```
Val Tyr Phe Cys Ala Arg Pro Gln Val His Tyr Asp Tyr Asn Gly Phe
            595                 600                 605

Pro Tyr Trp Gly Gln Gly Thr Pro Val Thr Val Ser Ser Gly Gly Gly
610                 615                 620

Gly Ser Gly Gly Gly Ser Gly Gly Gly Ser Ala Gln Asp Ile
625                 630                 635                 640

Gln Met Thr Gln Ser Pro Ser Ser Leu Ser Ala Ser Val Gly Asp Arg
                645                 650                 655

Val Thr Met Thr Cys Ser Ala Ser Ser Ser Val Ser Tyr Met Asn Trp
                660                 665                 670

Tyr Gln Gln Lys Pro Gly Lys Ala Pro Lys Arg Trp Ile Tyr Asp Ser
            675                 680                 685

Ser Lys Leu Ala Ser Gly Val Pro Ala Arg Phe Ser Gly Ser Gly Ser
            690                 695                 700

Gly Thr Asp Tyr Thr Leu Thr Ile Ser Ser Leu Gln Pro Glu Asp Phe
705                 710                 715                 720

Ala Thr Tyr Tyr Cys Gln Gln Trp Ser Arg Asn Pro Pro Thr Phe Gly
                725                 730                 735

Gly Gly Thr Lys Leu Gln Ile Thr Ser Ser Ser
            740                 745
```

<210> SEQ ID NO 119
<211> LENGTH: 2316
<212> TYPE: DNA
<213> ORGANISM: Artificial Sequence
<220> FEATURE:
<223> OTHER INFORMATION: ROR192 Anti-ROR1 X anti-CD3 bispecific molecule

<400> SEQUENCE: 119

```
atggaagcac cagcgcagct tctcttcctc ctgctactct ggctcccaga taccaccggt     60
gacatccaga tgacccagtc cccctcctcc ctgtccgcct ccgtgggcga ccgggtgacc    120
atcaactgcc aggcctccca gtccatcgac tccaacctgg cctggttcca gcagaagccc    180
ggccagcccc ccaagctgct gatctaccgg gcctccaacc tggcctccgg cgtgcccgac    240
cggttctccg gctccggctc cggcaccgac ttcaccctga ccatctcctc cctggaggcc    300
gaggacgtgg ccacctacta ctgcctgggg ggcgtgggcg ccgtgtccta ccggacctcc    360
ttcggcggcg gcaccaaggt ggagatcaag ggtggaggcg ttcaggcgg aggtggatcc    420
ggcggtggcg gctccggtgg cggcggatct gaggtgcagc tggtggagtc cggcggcggc    480
ctggtgcagc ccggccggtc cctgcggctg tcctgcaccg cctccggctc cgacatcaac    540
gactacccca tcacctgggt gcggcaggcc cccggccagg gcctggagtg gatcggcttc    600
atcaactccg gcggctccac ctggtacgcc tcctgggtga agggccggtt caccatctcc    660
cgggacgact ccaagtccat cgcctacctg cagatgaact ccctgaagac cgaggacacc    720
gccgtgtact attgcgcccg gggctactcc acctactacc gggacttcaa catctggggc    780
cagggcaccc tggtgaccgt gtcctcgagt gagcccaaat cttctgacaa aactcacaca    840
tgcccaccgt gcccagcacc tgaagccgcg ggtgcaccgt cagtcttcct cttccccca    900
aaacccaagg acaccctcat gatctcccgg acccctgagg tcacatgcgt ggtggtggac    960
gtgagccacg aagaccctga ggtcaagttc aactggtacg tggacggcgt ggaggtgcat   1020
aatgccaaga caaagccgcg ggaggagcag tacaacagca cgtaccgtgt ggtcagcgtc   1080
ctcaccgtcc tgcaccagga ctggctgaat ggcaaggaat acaagtgcgc ggtctccaac   1140
```

-continued

```
aaagccctcc cagcccccat cgagaaaacc atctccaaag ccaaagggca gccccgagaa    1200
ccacaggtgt acaccctgcc cccatcccgg gatgagctga ccaagaacca ggtcagcctg    1260
acctgcctgg tcaaaggctt ctatccaagc gacatcgccg tggagtggga gagcaatggg    1320
cagccggaga acaactacaa gaccacgcct cccgtgctgg actccgacgg ctccttcttc    1380
ctctacagca agctcaccgt ggacaagagc aggtggcagc aggggaacgt cttctcatgc    1440
tccgtgatgc atgaggctct gcacaaccac tacacgcaga agagcctctc cctgtctccg    1500
ggttctggtg gaggcggttc aggcggaggt ggctccggcg gtggcggatc gccgggctct    1560
caggtccagc tggtgcaatc tgggcctgag gtgaagaagc ctgggtcctc ggtgaaggtc    1620
tcctgcaagg cttctggata taccttcagc agatctacga tgcactgggt gcgacaggcc    1680
cctggacaag gcttgagtg gataggatac attaatccta gcagtgctta tactaattac    1740
aatcagaaat tcaaggacag agtcacgatt accgcggaca atccacgag cacagcctac    1800 atggagctga gcagcctgag atctgaggac acggccgtgt attactgtgc gagaccccaa    1860
gtccactatg attacaacgg gtttccttac tggggccaag gaaccctggt caccgtctcc    1920
tcaggtggag gcggttcagg cggaggtgga tccggcggtg gcggatcggg tggcggcgga    1980
tctgacatcc agatgaccca gtctccttcc accctgtctg catctgtagg agacagagtc    2040
accatgactt gcagtgccag ctcaagtgta agttacatga actggtatca gcagaaacca    2100
gggaaagccc ctaagagatg gatttatgac tcatccaaac tggcttctgg ggtcccatca    2160
aggttcagcg gcagtggatc tgggacagat tatactctca ccatcagcag cctgcagcct    2220
gatgattttg caacttatta ctgccaacag tggagtcgta acccacccac tttcggcgga    2280
gggaccaagg tggagatcaa acggtcctcc agctaa                              2316
```

<210> SEQ ID NO 120
<211> LENGTH: 751
<212> TYPE: PRT
<213> ORGANISM: Artificial Sequence
<220> FEATURE:
<223> OTHER INFORMATION: ROR192 Anti-ROR1 X anti-CD3 bispecific molecule

<400> SEQUENCE: 120

```
Asp Ile Gln Met Thr Gln Ser Pro Ser Ser Leu Ser Ala Ser Val Gly
1               5                   10                  15

Asp Arg Val Thr Ile Asn Cys Gln Ala Ser Gln Ser Ile Asp Ser Asn
            20                  25                  30

Leu Ala Trp Phe Gln Gln Lys Pro Gly Gln Pro Pro Lys Leu Leu Ile
        35                  40                  45

Tyr Arg Ala Ser Asn Leu Ala Ser Gly Val Pro Asp Arg Phe Ser Gly
    50                  55                  60

Ser Gly Ser Gly Thr Asp Phe Thr Leu Thr Ile Ser Ser Leu Glu Ala
65                  70                  75                  80

Glu Asp Val Ala Thr Tyr Tyr Cys Leu Gly Gly Val Gly Ala Val Ser
                85                  90                  95

Tyr Arg Thr Ser Phe Gly Gly Gly Thr Lys Val Glu Ile Lys Gly Gly
            100                 105                 110

Gly Gly Ser Gly Gly Gly Ser Gly Gly Gly Ser Gly Gly Gly
        115                 120                 125

Gly Ser Glu Val Gln Leu Val Glu Ser Gly Gly Gly Leu Val Gln Pro
    130                 135                 140

Gly Arg Ser Leu Arg Leu Ser Cys Thr Ala Ser Gly Ser Asp Ile Asn
145                 150                 155                 160
```

-continued

Asp Tyr Pro Ile Thr Trp Val Arg Gln Ala Pro Gly Gln Gly Leu Glu
            165                 170                 175
Trp Ile Gly Phe Ile Asn Ser Gly Gly Ser Thr Trp Tyr Ala Ser Trp
        180                 185                 190
Val Lys Gly Arg Phe Thr Ile Ser Arg Asp Asp Ser Lys Ser Ile Ala
    195                 200                 205
Tyr Leu Gln Met Asn Ser Leu Lys Thr Glu Asp Thr Ala Val Tyr Tyr
210                 215                 220
Cys Ala Arg Gly Tyr Ser Thr Tyr Tyr Arg Asp Phe Asn Ile Trp Gly
225                 230                 235                 240
Gln Gly Thr Leu Val Thr Val Ser Ser Glu Pro Lys Ser Ser Asp
            245                 250                 255
Lys Thr His Thr Cys Pro Pro Cys Pro Ala Pro Glu Ala Ala Gly Ala
        260                 265                 270
Pro Ser Val Phe Leu Phe Pro Pro Lys Pro Lys Asp Thr Leu Met Ile
    275                 280                 285
Ser Arg Thr Pro Glu Val Thr Cys Val Val Val Asp Val Ser His Glu
290                 295                 300
Asp Pro Glu Val Lys Phe Asn Trp Tyr Val Asp Gly Val Glu Val His
305                 310                 315                 320
Asn Ala Lys Thr Lys Pro Arg Glu Glu Gln Tyr Asn Ser Thr Tyr Arg
            325                 330                 335
Val Val Ser Val Leu Thr Val Leu His Gln Asp Trp Leu Asn Gly Lys
        340                 345                 350
Glu Tyr Lys Cys Ala Val Ser Asn Lys Ala Leu Pro Ala Pro Ile Glu
    355                 360                 365
Lys Thr Ile Ser Lys Ala Lys Gly Gln Pro Arg Glu Pro Gln Val Tyr
370                 375                 380
Thr Leu Pro Pro Ser Arg Asp Glu Leu Thr Lys Asn Gln Val Ser Leu
385                 390                 395                 400
Thr Cys Leu Val Lys Gly Phe Tyr Pro Ser Asp Ile Ala Val Glu Trp
            405                 410                 415
Glu Ser Asn Gly Gln Pro Glu Asn Asn Tyr Lys Thr Thr Pro Pro Val
        420                 425                 430
Leu Asp Ser Asp Gly Ser Phe Phe Leu Tyr Ser Lys Leu Thr Val Asp
    435                 440                 445
Lys Ser Arg Trp Gln Gln Gly Asn Val Phe Ser Cys Ser Val Met His
450                 455                 460
Glu Ala Leu His Asn His Tyr Thr Gln Lys Ser Leu Ser Leu Ser Pro
465                 470                 475                 480
Gly Ser Gly Gly Gly Gly Ser Gly Gly Gly Gly Ser Gly Gly Gly Gly
            485                 490                 495
Ser Pro Gly Ser Gln Val Gln Leu Val Gln Ser Gly Pro Glu Val Lys
        500                 505                 510
Lys Pro Gly Ser Ser Val Lys Val Ser Cys Lys Ala Ser Gly Tyr Thr
    515                 520                 525
Phe Ser Arg Ser Thr Met His Trp Val Arg Gln Ala Pro Gly Gln Gly
530                 535                 540
Leu Glu Trp Ile Gly Tyr Ile Asn Pro Ser Ser Ala Tyr Thr Asn Tyr
545                 550                 555                 560
Asn Gln Lys Phe Lys Asp Arg Val Thr Ile Thr Ala Asp Lys Ser Thr
            565                 570                 575

-continued

```
Ser Thr Ala Tyr Met Glu Leu Ser Ser Leu Arg Ser Glu Asp Thr Ala
            580                 585                 590

Val Tyr Tyr Cys Ala Arg Pro Gln Val His Tyr Asp Tyr Asn Gly Phe
        595                 600                 605

Pro Tyr Trp Gly Gln Gly Thr Leu Val Thr Val Ser Ser Gly Gly Gly
    610                 615                 620

Gly Ser Gly Gly Gly Gly Ser Gly Gly Gly Gly Ser Gly Gly Gly Gly
625                 630                 635                 640

Ser Asp Ile Gln Met Thr Gln Ser Pro Ser Thr Leu Ser Ala Ser Val
                645                 650                 655

Gly Asp Arg Val Thr Met Thr Cys Ser Ala Ser Ser Ser Val Ser Tyr
            660                 665                 670

Met Asn Trp Tyr Gln Gln Lys Pro Gly Lys Ala Pro Lys Arg Trp Ile
        675                 680                 685

Tyr Asp Ser Ser Lys Leu Ala Ser Gly Val Pro Ser Arg Phe Ser Gly
    690                 695                 700

Ser Gly Ser Gly Thr Asp Tyr Thr Leu Thr Ile Ser Ser Leu Gln Pro
705                 710                 715                 720

Asp Asp Phe Ala Thr Tyr Tyr Cys Gln Gln Trp Ser Arg Asn Pro Pro
                725                 730                 735

Thr Phe Gly Gly Gly Thr Lys Val Glu Ile Lys Arg Ser Ser Ser
            740                 745                 750
```

<210> SEQ ID NO 121
<211> LENGTH: 15
<212> TYPE: PRT
<213> ORGANISM: Artificial Sequence
<220> FEATURE:
<223> OTHER INFORMATION: sss(s)-hIgG1 hinge

<400> SEQUENCE: 121

```
Glu Pro Lys Ser Ser Asp Lys Thr His Thr Ser Pro Pro Ser Ser
1               5                   10                  15
```

<210> SEQ ID NO 122
<211> LENGTH: 15
<212> TYPE: PRT
<213> ORGANISM: Artificial Sequence
<220> FEATURE:
<223> OTHER INFORMATION: csc(s)-hIgG1 hinge

<400> SEQUENCE: 122

```
Glu Pro Lys Ser Cys Asp Lys Thr His Thr Ser Pro Pro Cys Ser
1               5                   10                  15
```

<210> SEQ ID NO 123
<211> LENGTH: 15
<212> TYPE: PRT
<213> ORGANISM: Artificial Sequence
<220> FEATURE:
<223> OTHER INFORMATION: ssc(s)-hIgG1 hinge

<400> SEQUENCE: 123

```
Glu Pro Lys Ser Ser Asp Lys Thr His Thr Ser Pro Pro Cys Ser
1               5                   10                  15
```

<210> SEQ ID NO 124
<211> LENGTH: 15
<212> TYPE: PRT
<213> ORGANISM: Artificial Sequence
<220> FEATURE:
<223> OTHER INFORMATION: scc(s)-hIgG1 hinge

```
<400> SEQUENCE: 124

Glu Pro Lys Ser Ser Asp Lys Thr His Thr Cys Pro Pro Cys Ser
1               5                   10                  15

<210> SEQ ID NO 125
<211> LENGTH: 15
<212> TYPE: PRT
<213> ORGANISM: Artificial Sequence
<220> FEATURE:
<223> OTHER INFORMATION: css(s)-hIgG1 hinge

<400> SEQUENCE: 125

Glu Pro Lys Ser Cys Asp Lys Thr His Thr Ser Pro Pro Ser Ser
1               5                   10                  15

<210> SEQ ID NO 126
<211> LENGTH: 15
<212> TYPE: PRT
<213> ORGANISM: Artificial Sequence
<220> FEATURE:
<223> OTHER INFORMATION: scs(s)-hIgG1 hinge

<400> SEQUENCE: 126

Glu Pro Lys Ser Ser Asp Lys Thr His Thr Cys Pro Pro Ser Ser
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: ccc(s)-hIgG1 hinge

<400> SEQUENCE: 127

Glu Pro Lys Ser Cys Asp Lys Thr His Thr Ser Pro Pro Cys Ser
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: ccc(p)-hIgG1 hinge

<400> SEQUENCE: 128

Glu Pro Lys Ser Cys Asp Lys Thr His Thr Ser Pro Pro Cys Pro
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: sss(p)-hIgG1 hinge

<400> SEQUENCE: 129

Glu Pro Lys Ser Ser Asp Lys Thr His Thr Ser Pro Pro Ser Pro
1               5                   10                  15

<210> SEQ ID NO 130
<211> LENGTH: 15
<212> TYPE: PRT
<213> ORGANISM: Artificial Sequence
<220> FEATURE:
<223> OTHER INFORMATION: csc(p)-hIgG1 hinge
```

<400> SEQUENCE: 130

Glu Pro Lys Ser Cys Asp Lys Thr His Thr Ser Pro Pro Cys Pro
1               5                   10                  15

<210> SEQ ID NO 131
<211> LENGTH: 15
<212> TYPE: PRT
<213> ORGANISM: Artificial Sequence
<220> FEATURE:
<223> OTHER INFORMATION: ssc(p)-hIgG1 hinge

<400> SEQUENCE: 131

Glu Pro Lys Ser Ser Asp Lys Thr His Thr Ser Pro Pro Cys Pro
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: scc(p)-hIgG1 hinge

<400> SEQUENCE: 132

Glu Pro Lys Ser Ser Asp Lys Thr His Thr Cys Pro Pro Cys Pro
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: css(p)-hIgG1 hinge

<400> SEQUENCE: 133

Glu Pro Lys Ser Cys Asp Lys Thr His Thr Ser Pro Pro Ser Pro
1               5                   10                  15

<210> SEQ ID NO 134
<211> LENGTH: 15
<212> TYPE: PRT
<213> ORGANISM: Artificial Sequence
<220> FEATURE:
<223> OTHER INFORMATION: scs(p)-hIgG1 hinge

<400> SEQUENCE: 134

Glu Pro Lys Ser Ser Asp Lys Thr His Thr Cys Pro Pro Ser Pro
1               5                   10                  15

<210> SEQ ID NO 135
<211> LENGTH: 6
<212> TYPE: PRT
<213> ORGANISM: Artificial Sequence
<220> FEATURE:
<223> OTHER INFORMATION: Scppcp linker

<400> SEQUENCE: 135

Ser Cys Pro Pro Cys Pro
1               5

<210> SEQ ID NO 136
<211> LENGTH: 20
<212> TYPE: PRT
<213> ORGANISM: Artificial Sequence
<220> FEATURE:
<223> OTHER INFORMATION: STD1 linker

<400> SEQUENCE: 136

Asn Tyr Gly Gly Gly Gly Ser Gly Gly Gly Ser Gly Gly Gly
1               5                   10                  15

Ser Gly Asn Ser
            20

<210> SEQ ID NO 137
<211> LENGTH: 38
<212> TYPE: PRT
<213> ORGANISM: Artificial Sequence
<220> FEATURE:
<223> OTHER INFORMATION: STD2 linker

<400> SEQUENCE: 137

Asn Tyr Gly Gly Gly Gly Ser Gly Gly Gly Ser Gly Gly Gly
1               5                   10                  15

Ser Gly Asn Tyr Gly Gly Gly Ser Gly Gly Gly Ser Gly Gly
            20                  25                  30

Gly Gly Ser Gly Asn Ser
            35

<210> SEQ ID NO 138
<211> LENGTH: 2
<212> TYPE: PRT
<213> ORGANISM: Artificial Sequence
<220> FEATURE:
<223> OTHER INFORMATION: H1 linker

<400> SEQUENCE: 138

Asn Ser
1

<210> SEQ ID NO 139
<211> LENGTH: 8
<212> TYPE: PRT
<213> ORGANISM: Artificial Sequence
<220> FEATURE:
<223> OTHER INFORMATION: H2 linker

<400> SEQUENCE: 139

Gly Gly Gly Gly Ser Gly Asn Ser
1               5

<210> SEQ ID NO 140
<211> LENGTH: 10
<212> TYPE: PRT
<213> ORGANISM: Artificial Sequence
<220> FEATURE:
<223> OTHER INFORMATION: H3 linker

<400> SEQUENCE: 140

Asn Tyr Gly Gly Gly Gly Ser Gly Asn Ser
1               5                   10

<210> SEQ ID NO 141
<211> LENGTH: 13
<212> TYPE: PRT
<213> ORGANISM: Artificial Sequence
<220> FEATURE:
<223> OTHER INFORMATION: H4 linker

<400> SEQUENCE: 141

Gly Gly Gly Gly Ser Gly Gly Gly Gly Ser Gly Asn Ser
1               5                   10

-continued

```
<210> SEQ ID NO 142
<211> LENGTH: 15
<212> TYPE: PRT
<213> ORGANISM: Artificial Sequence
<220> FEATURE:
<223> OTHER INFORMATION: H5 linker

<400> SEQUENCE: 142

Asn Tyr Gly Gly Gly Gly Ser Gly Gly Gly Ser Gly Asn Ser
1               5                   10                  15

<210> SEQ ID NO 143
<211> LENGTH: 18
<212> TYPE: PRT
<213> ORGANISM: Artificial Sequence
<220> FEATURE:
<223> OTHER INFORMATION: H6 linker

<400> SEQUENCE: 143

Gly Gly Gly Gly Ser Gly Gly Gly Gly Ser Gly Gly Gly Gly Ser Gly
1               5                   10                  15

Asn Ser

<210> SEQ ID NO 144
<211> LENGTH: 8
<212> TYPE: PRT
<213> ORGANISM: Artificial Sequence
<220> FEATURE:
<223> OTHER INFORMATION: H7 linker

<400> SEQUENCE: 144

Gly Cys Pro Pro Cys Pro Asn Ser
1               5

<210> SEQ ID NO 145
<211> LENGTH: 15
<212> TYPE: PRT
<213> ORGANISM: Artificial Sequence
<220> FEATURE:
<223> OTHER INFORMATION: (G4S)3 linker

<400> SEQUENCE: 145

Gly Gly Gly Gly Ser Gly Gly Gly Gly Ser Gly Gly Gly Gly Ser
1               5                   10                  15

<210> SEQ ID NO 146
<211> LENGTH: 16
<212> TYPE: PRT
<213> ORGANISM: Artificial Sequence
<220> FEATURE:
<223> OTHER INFORMATION: H105 linker

<400> SEQUENCE: 146

Ser Gly Gly Gly Gly Ser Gly Gly Gly Gly Ser Gly Gly Gly Gly Ser
1               5                   10                  15

<210> SEQ ID NO 147
<211> LENGTH: 20
<212> TYPE: PRT
<213> ORGANISM: Artificial Sequence
<220> FEATURE:
<223> OTHER INFORMATION: (G4S)4 linker

<400> SEQUENCE: 147

Gly Gly Gly Gly Ser Gly Gly Gly Gly Ser Gly Gly Gly Gly Ser Gly
1               5                   10                  15
```

Gly Gly Gly Ser
         20

<210> SEQ ID NO 148
<211> LENGTH: 21
<212> TYPE: PRT
<213> ORGANISM: Artificial Sequence
<220> FEATURE:
<223> OTHER INFORMATION: H75 (NKG2A quadruple mutant) linker

<400> SEQUENCE: 148

Gln Arg His Asn Asn Ser Ser Leu Asn Thr Gly Thr Gln Met Ala Gly
1               5                   10                  15

His Ser Pro Asn Ser
         20

<210> SEQ ID NO 149
<211> LENGTH: 16
<212> TYPE: PRT
<213> ORGANISM: Artificial Sequence
<220> FEATURE:
<223> OTHER INFORMATION: H83 (NKG2A derived) linker

<400> SEQUENCE: 149

Ser Ser Leu Asn Thr Gly Thr Gln Met Ala Gly His Ser Pro Asn Ser
1               5                   10                  15

<210> SEQ ID NO 150
<211> LENGTH: 18
<212> TYPE: PRT
<213> ORGANISM: Artificial Sequence
<220> FEATURE:
<223> OTHER INFORMATION: H106 (NKG2A derived) linker

<400> SEQUENCE: 150

Gln Arg His Asn Asn Ser Ser Leu Asn Thr Gly Thr Gln Met Ala Gly
1               5                   10                  15

His Ser

<210> SEQ ID NO 151
<211> LENGTH: 14
<212> TYPE: PRT
<213> ORGANISM: Artificial Sequence
<220> FEATURE:
<223> OTHER INFORMATION: H81 (NKG2D derived) linker

<400> SEQUENCE: 151

Glu Val Gln Ile Pro Leu Thr Glu Ser Tyr Ser Pro Asn Ser
1               5                   10

<210> SEQ ID NO 152
<211> LENGTH: 20
<212> TYPE: PRT
<213> ORGANISM: Artificial Sequence
<220> FEATURE:
<223> OTHER INFORMATION: H91 (NKG2D derived) linker

<400> SEQUENCE: 152

Asn Ser Leu Ala Asn Gln Glu Val Gln Ile Pro Leu Thr Glu Ser Tyr
1               5                   10                  15

Ser Pro Asn Ser
         20

<210> SEQ ID NO 153
<211> LENGTH: 19

```
<212> TYPE: PRT
<213> ORGANISM: Artificial Sequence
<220> FEATURE:
<223> OTHER INFORMATION: H94 linker

<400> SEQUENCE: 153

Ser Gly Gly Gly Gly Ser Gly Gly Gly Gly Ser Gly Gly Gly Gly Ser
1               5                   10                  15

Pro Asn Ser

<210> SEQ ID NO 154
<211> LENGTH: 15
<212> TYPE: PRT
<213> ORGANISM: Artificial Sequence
<220> FEATURE:
<223> OTHER INFORMATION: H16 hinge

<400> SEQUENCE: 154

Leu Ser Val Lys Ala Asp Phe Leu Thr Pro Ser Ile Gly Asn Ser
1               5                   10                  15

<210> SEQ ID NO 155
<211> LENGTH: 20
<212> TYPE: PRT
<213> ORGANISM: Artificial Sequence
<220> FEATURE:
<223> OTHER INFORMATION: H17 hinge

<400> SEQUENCE: 155

Leu Ser Val Lys Ala Asp Phe Leu Thr Pro Ser Ile Ser Cys Pro Pro
1               5                   10                  15

Cys Pro Asn Ser
            20

<210> SEQ ID NO 156
<211> LENGTH: 15
<212> TYPE: PRT
<213> ORGANISM: Artificial Sequence
<220> FEATURE:
<223> OTHER INFORMATION: H18 hinge

<400> SEQUENCE: 156

Leu Ser Val Leu Ala Asn Phe Ser Gln Pro Glu Ile Gly Asn Ser
1               5                   10                  15

<210> SEQ ID NO 157
<211> LENGTH: 20
<212> TYPE: PRT
<213> ORGANISM: Artificial Sequence
<220> FEATURE:
<223> OTHER INFORMATION: H19 hinge

<400> SEQUENCE: 157

Leu Ser Val Leu Ala Asn Phe Ser Gln Pro Glu Ile Ser Cys Pro Pro
1               5                   10                  15

Cys Pro Asn Ser
            20

<210> SEQ ID NO 158
<211> LENGTH: 15
<212> TYPE: PRT
<213> ORGANISM: Artificial Sequence
<220> FEATURE:
<223> OTHER INFORMATION: H20 hinge

<400> SEQUENCE: 158
```

Leu Lys Ile Gln Glu Arg Val Ser Lys Pro Lys Ile Ser Asn Ser
1               5                   10                  15

<210> SEQ ID NO 159
<211> LENGTH: 20
<212> TYPE: PRT
<213> ORGANISM: Artificial Sequence
<220> FEATURE:
<223> OTHER INFORMATION: H21 hinge

<400> SEQUENCE: 159

Leu Lys Ile Gln Glu Arg Val Ser Lys Pro Lys Ile Ser Cys Pro Pro
1               5                   10                  15

Cys Pro Asn Ser
            20

<210> SEQ ID NO 160
<211> LENGTH: 15
<212> TYPE: PRT
<213> ORGANISM: Artificial Sequence
<220> FEATURE:
<223> OTHER INFORMATION: H22 hinge

<400> SEQUENCE: 160

Leu Asn Val Ser Glu Arg Pro Phe Pro Pro His Ile Gln Asn Ser
1               5                   10                  15

<210> SEQ ID NO 161
<211> LENGTH: 21
<212> TYPE: PRT
<213> ORGANISM: Artificial Sequence
<220> FEATURE:
<223> OTHER INFORMATION: H23 hinge

<400> SEQUENCE: 161

Leu Asp Val Ser Glu Arg Pro Phe Pro Pro His Ile Gln Ser Cys Pro
1               5                   10                  15

Pro Cys Pro Asn Ser
            20

<210> SEQ ID NO 162
<211> LENGTH: 15
<212> TYPE: PRT
<213> ORGANISM: Artificial Sequence
<220> FEATURE:
<223> OTHER INFORMATION: H24 hinge

<400> SEQUENCE: 162

Arg Glu Gln Leu Ala Glu Val Thr Leu Ser Leu Lys Ala Asn Ser
1               5                   10                  15

<210> SEQ ID NO 163
<211> LENGTH: 20
<212> TYPE: PRT
<213> ORGANISM: Artificial Sequence
<220> FEATURE:
<223> OTHER INFORMATION: H25 hinge

<400> SEQUENCE: 163

Arg Glu Gln Leu Ala Glu Val Thr Leu Ser Leu Lys Ala Cys Pro Pro
1               5                   10                  15

Cys Pro Asn Ser
            20

-continued

```
<210> SEQ ID NO 164
<211> LENGTH: 15
<212> TYPE: PRT
<213> ORGANISM: Artificial Sequence
<220> FEATURE:
<223> OTHER INFORMATION: H26 hinge

<400> SEQUENCE: 164

Arg Ile His Gln Met Asn Ser Glu Leu Ser Val Leu Ala Asn Ser
1               5                   10                  15

<210> SEQ ID NO 165
<211> LENGTH: 20
<212> TYPE: PRT
<213> ORGANISM: Artificial Sequence
<220> FEATURE:
<223> OTHER INFORMATION: H27 hinge

<400> SEQUENCE: 165

Arg Ile His Gln Met Asn Ser Glu Leu Ser Val Leu Ala Cys Pro Pro
1               5                   10                  15

Cys Pro Asn Ser
            20

<210> SEQ ID NO 166
<211> LENGTH: 15
<212> TYPE: PRT
<213> ORGANISM: Artificial Sequence
<220> FEATURE:
<223> OTHER INFORMATION: H28 hinge

<400> SEQUENCE: 166

Asp Thr Lys Gly Lys Asn Val Leu Glu Lys Ile Phe Ser Asn Ser
1               5                   10                  15

<210> SEQ ID NO 167
<211> LENGTH: 15
<212> TYPE: PRT
<213> ORGANISM: Artificial Sequence
<220> FEATURE:
<223> OTHER INFORMATION: H30 hinge

<400> SEQUENCE: 167

Leu Pro Pro Glu Thr Gln Glu Ser Gln Glu Val Thr Leu Asn Ser
1               5                   10                  15

<210> SEQ ID NO 168
<211> LENGTH: 15
<212> TYPE: PRT
<213> ORGANISM: Artificial Sequence
<220> FEATURE:
<223> OTHER INFORMATION: H32 hinge

<400> SEQUENCE: 168

Arg Ile His Leu Asn Val Ser Glu Arg Pro Phe Pro Pro Asn Ser
1               5                   10                  15

<210> SEQ ID NO 169
<211> LENGTH: 20
<212> TYPE: PRT
<213> ORGANISM: Artificial Sequence
<220> FEATURE:
<223> OTHER INFORMATION: H33 hinge

<400> SEQUENCE: 169

Arg Ile His Leu Asn Val Ser Glu Arg Pro Phe Pro Pro Cys Pro Pro
1               5                   10                  15
```

Cys Pro Asn Ser
            20

<210> SEQ ID NO 170
<211> LENGTH: 13
<212> TYPE: PRT
<213> ORGANISM: Artificial Sequence
<220> FEATURE:
<223> OTHER INFORMATION: H36 hinge

<400> SEQUENCE: 170

Gly Cys Pro Pro Cys Pro Gly Gly Gly Ser Asn Ser
1               5                   10

<210> SEQ ID NO 171
<211> LENGTH: 9
<212> TYPE: PRT
<213> ORGANISM: Artificial Sequence
<220> FEATURE:
<223> OTHER INFORMATION: H40 hinge

<400> SEQUENCE: 171

Gly Cys Pro Pro Cys Pro Ala Asn Ser
1               5

<210> SEQ ID NO 172
<211> LENGTH: 9
<212> TYPE: PRT
<213> ORGANISM: Artificial Sequence
<220> FEATURE:
<223> OTHER INFORMATION: H41 hinge

<400> SEQUENCE: 172

Gly Cys Pro Pro Cys Pro Ala Asn Ser
1               5

<210> SEQ ID NO 173
<211> LENGTH: 8
<212> TYPE: PRT
<213> ORGANISM: Artificial Sequence
<220> FEATURE:
<223> OTHER INFORMATION: H42 hinge

<400> SEQUENCE: 173

Gly Cys Pro Pro Cys Pro Asn Ser
1               5

<210> SEQ ID NO 174
<211> LENGTH: 13
<212> TYPE: PRT
<213> ORGANISM: Artificial Sequence
<220> FEATURE:
<223> OTHER INFORMATION: H44 hinge

<400> SEQUENCE: 174

Gly Gly Gly Ala Ser Cys Pro Pro Cys Pro Gly Asn Ser
1               5                   10

<210> SEQ ID NO 175
<211> LENGTH: 13
<212> TYPE: PRT
<213> ORGANISM: Artificial Sequence
<220> FEATURE:
<223> OTHER INFORMATION: H45 hinge

<400> SEQUENCE: 175

```
Gly Gly Gly Ala Ser Cys Pro Pro Cys Ala Gly Asn Ser
1               5                   10
```

<210> SEQ ID NO 176
<211> LENGTH: 12
<212> TYPE: PRT
<213> ORGANISM: Artificial Sequence
<220> FEATURE:
<223> OTHER INFORMATION: H46 hinge

<400> SEQUENCE: 176

```
Gly Gly Gly Ala Ser Cys Pro Pro Cys Ala Asn Ser
1               5                   10
```

<210> SEQ ID NO 177
<211> LENGTH: 15
<212> TYPE: PRT
<213> ORGANISM: Artificial Sequence
<220> FEATURE:
<223> OTHER INFORMATION: H47 hinge

<400> SEQUENCE: 177

```
Leu Ser Val Lys Ala Asp Phe Leu Thr Pro Ser Ile Gly Asn Ser
1               5                   10                  15
```

<210> SEQ ID NO 178
<211> LENGTH: 11
<212> TYPE: PRT
<213> ORGANISM: Artificial Sequence
<220> FEATURE:
<223> OTHER INFORMATION: H48 hinge

<400> SEQUENCE: 178

```
Ala Asp Phe Leu Thr Pro Ser Ile Gly Asn Ser
1               5                   10
```

<210> SEQ ID NO 179
<211> LENGTH: 15
<212> TYPE: PRT
<213> ORGANISM: Artificial Sequence
<220> FEATURE:
<223> OTHER INFORMATION: H50 hinge

<400> SEQUENCE: 179

```
Leu Ser Val Leu Ala Asn Phe Ser Gln Pro Glu Ile Gly Asn Ser
1               5                   10                  15
```

<210> SEQ ID NO 180
<211> LENGTH: 15
<212> TYPE: PRT
<213> ORGANISM: Artificial Sequence
<220> FEATURE:
<223> OTHER INFORMATION: H51 hinge

<400> SEQUENCE: 180

```
Leu Ser Val Leu Ala Asn Phe Ser Gln Pro Glu Ile Gly Asn Ser
1               5                   10                  15
```

<210> SEQ ID NO 181
<211> LENGTH: 11
<212> TYPE: PRT
<213> ORGANISM: Artificial Sequence
<220> FEATURE:
<223> OTHER INFORMATION: H52 hinge

<400> SEQUENCE: 181

Ser Gln Pro Glu Ile Val Pro Ile Ser Asn Ser

<210> SEQ ID NO 182
<211> LENGTH: 16
<212> TYPE: PRT
<213> ORGANISM: Artificial Sequence
<220> FEATURE:
<223> OTHER INFORMATION: H53 hinge

<400> SEQUENCE: 182

Ser Gln Pro Glu Ile Val Pro Ile Ser Cys Pro Pro Cys Pro Asn Ser
1               5                   10                  15

<210> SEQ ID NO 183
<211> LENGTH: 19
<212> TYPE: PRT
<213> ORGANISM: Artificial Sequence
<220> FEATURE:
<223> OTHER INFORMATION: H54 hinge

<400> SEQUENCE: 183

Ser Val Leu Ala Asn Phe Ser Gln Pro Glu Ile Ser Cys Pro Pro Cys
1               5                   10                  15

Pro Asn Ser

<210> SEQ ID NO 184
<211> LENGTH: 15
<212> TYPE: PRT
<213> ORGANISM: Artificial Sequence
<220> FEATURE:
<223> OTHER INFORMATION: H55 hinge

<400> SEQUENCE: 184

Arg Ile His Gln Met Asn Ser Glu Leu Ser Val Leu Ala Asn Ser
1               5                   10                  15

<210> SEQ ID NO 185
<211> LENGTH: 12
<212> TYPE: PRT
<213> ORGANISM: Artificial Sequence
<220> FEATURE:
<223> OTHER INFORMATION: H56 hinge

<400> SEQUENCE: 185

Gln Met Asn Ser Glu Leu Ser Val Leu Ala Asn Ser
1               5                   10

<210> SEQ ID NO 186
<211> LENGTH: 10
<212> TYPE: PRT
<213> ORGANISM: Artificial Sequence
<220> FEATURE:
<223> OTHER INFORMATION: H57 hinge

<400> SEQUENCE: 186

Val Ser Glu Arg Pro Phe Pro Pro Asn Ser
1               5                   10

<210> SEQ ID NO 187
<211> LENGTH: 15
<212> TYPE: PRT
<213> ORGANISM: Artificial Sequence
<220> FEATURE:
<223> OTHER INFORMATION: H58 hinge

<400> SEQUENCE: 187

```
Lys Pro Phe Phe Thr Cys Gly Ser Ala Asp Thr Cys Pro Asn Ser
1               5                   10                  15

<210> SEQ ID NO 188
<211> LENGTH: 15
<212> TYPE: PRT
<213> ORGANISM: Artificial Sequence
<220> FEATURE:
<223> OTHER INFORMATION: H59 hinge

<400> SEQUENCE: 188

Lys Pro Phe Phe Thr Cys Gly Ser Ala Asp Thr Cys Pro Asn Ser
1               5                   10                  15

<210> SEQ ID NO 189
<211> LENGTH: 15
<212> TYPE: PRT
<213> ORGANISM: Artificial Sequence
<220> FEATURE:
<223> OTHER INFORMATION: H60 hinge

<400> SEQUENCE: 189

Gln Tyr Asn Cys Pro Gly Gln Tyr Thr Phe Ser Met Pro Asn Ser
1               5                   10                  15

<210> SEQ ID NO 190
<211> LENGTH: 21
<212> TYPE: PRT
<213> ORGANISM: Artificial Sequence
<220> FEATURE:
<223> OTHER INFORMATION: H61 hinge

<400> SEQUENCE: 190

Glu Pro Ala Phe Thr Pro Gly Pro Asn Ile Glu Leu Gln Lys Asp Ser
1               5                   10                  15

Asp Cys Pro Asn Ser
            20

<210> SEQ ID NO 191
<211> LENGTH: 21
<212> TYPE: PRT
<213> ORGANISM: Artificial Sequence
<220> FEATURE:
<223> OTHER INFORMATION: H62 hinge

<400> SEQUENCE: 191

Gln Arg His Asn Asn Ser Ser Leu Asn Thr Arg Thr Gln Lys Ala Arg
1               5                   10                  15

His Cys Pro Asn Ser
            20

<210> SEQ ID NO 192
<211> LENGTH: 20
<212> TYPE: PRT
<213> ORGANISM: Artificial Sequence
<220> FEATURE:
<223> OTHER INFORMATION: H63 hinge

<400> SEQUENCE: 192

Asn Ser Leu Phe Asn Gln Glu Val Gln Ile Pro Leu Thr Glu Ser Tyr
1               5                   10                  15

Cys Pro Asn Ser
            20

<210> SEQ ID NO 193
```

-continued

```
<211> LENGTH: 15
<212> TYPE: PRT
<213> ORGANISM: Artificial Sequence
<220> FEATURE:
<223> OTHER INFORMATION: ((Gly4Ser)3) linker

<400> SEQUENCE: 193

Gly Gly Gly Gly Ser Gly Gly Gly Gly Ser Gly Gly Gly Gly Ser
1               5                   10                  15

<210> SEQ ID NO 194
<211> LENGTH: 25
<212> TYPE: PRT
<213> ORGANISM: Artificial Sequence
<220> FEATURE:
<223> OTHER INFORMATION: (Gly4Ser)n linker
<220> FEATURE:
<221> NAME/KEY: MISC_FEATURE
<222> LOCATION: (6)..(25)
<223> OTHER INFORMATION: amino acid residues may be absent

<400> SEQUENCE: 194

Gly Gly Gly Gly Ser Gly Gly Gly Ser Gly Gly Gly Gly Ser Gly
1               5                   10                  15

Gly Gly Gly Ser Gly Gly Gly Gly Ser
            20                  25

<210> SEQ ID NO 195
<211> LENGTH: 20
<212> TYPE: PRT
<213> ORGANISM: Artificial Sequence
<220> FEATURE:
<223> OTHER INFORMATION: secretory signal sequence

<400> SEQUENCE: 195

Met Glu Ala Pro Ala Gln Leu Leu Phe Leu Leu Leu Leu Trp Leu Pro
1               5                   10                  15

Asp Thr Thr Gly
            20

<210> SEQ ID NO 196
<211> LENGTH: 19
<212> TYPE: PRT
<213> ORGANISM: Artificial Sequence
<220> FEATURE:
<223> OTHER INFORMATION: H1l1 linker

<400> SEQUENCE: 196

Ser Gly Gly Gly Gly Ser Gly Gly Gly Gly Ser Gly Gly Gly Gly Ser
1               5                   10                  15

Pro Gly Ser

<210> SEQ ID NO 197
<211> LENGTH: 751
<212> TYPE: PRT
<213> ORGANISM: Artificial Sequence
<220> FEATURE:
<223> OTHER INFORMATION: Chimeric bispecific anti-CD123 (VLVH) x
      anti-CD3 (TSC456) scFv-Fc-scFv CD3-binding domain

<400> SEQUENCE: 197

Asp Ile Met Met Ser Gln Ser Pro Ser Ser Leu Ala Val Ser Val Gly
1               5                   10                  15

Glu Lys Phe Thr Met Thr Cys Lys Ser Ser Gln Ser Leu Phe Phe Gly
            20                  25                  30
```

```
Ser Thr Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Ala
 65                  70                  75                  80

Ile Ser Ser Val Met Pro Glu Asp Leu Ala Val Tyr Cys Gln Gln
                 85                  90                  95

Tyr Tyr Asn Tyr Pro Trp Thr Phe Gly Gly Gly Thr Lys Leu Glu Ile
            100                 105                 110

Lys Gly Gly Gly Gly Ser Gly Gly Gly Gly Ser Gly Gly Gly Gly Ser
            115                 120                 125

Gly Gly Gly Gly Ser Val Gln Leu Gln Glu Ser Gly Pro Gly Leu Val
 130                 135                 140

Lys Pro Ser Gln Ser Leu Ser Leu Thr Cys Ser Val Thr Asp Tyr Ser
145                 150                 155                 160

Ile Thr Ser Gly Tyr Tyr Trp Asn Trp Ile Arg Gln Phe Pro Gly Asn
            165                 170                 175

Lys Leu Glu Trp Met Gly Tyr Ile Ser Tyr Asp Gly Ser Asn Asn Tyr
            180                 185                 190

Asn Pro Ser Leu Lys Asn Arg Ile Ser Ile Thr Arg Asp Thr Ser Lys
            195                 200                 205

Asn Gln Phe Phe Leu Lys Leu Ser Ser Val Thr Thr Glu Asp Thr Ala
            210                 215                 220

Thr Tyr Tyr Cys Ser Arg Gly Glu Gly Phe Tyr Phe Asp Ser Trp Gly
225                 230                 235                 240

Gln Gly Thr Thr Leu Thr Val Ser Ser Glu Pro Lys Ser Ser Asp
                245                 250                 255

Lys Thr His Thr Cys Pro Pro Cys Pro Ala Pro Glu Ala Ala Gly Ala
            260                 265                 270

Pro Ser Val Phe Leu Phe Pro Pro Lys Pro Lys Asp Thr Leu Met Ile
            275                 280                 285

Ser Arg Thr Pro Glu Val Thr Cys Val Val Val Asp Val Ser His Glu
            290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
            325                 330                 335

Val Val Ser Val Leu Thr Val Leu His Gln Asp Trp Leu Asn Gly Lys
            340                 345                 350

Glu Tyr Lys Cys Ala Val Ser Asn Lys Ala Leu Pro Ala Pro Ile Glu
            355                 360                 365

Lys Thr Ile Ser Lys Ala Lys Gly Gln Pro Arg Glu Pro Gln Val Tyr
            370                 375                 380

Thr Leu Pro Pro Ser Arg Asp Glu Leu Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
            435                 440                 445

Lys Ser Arg Trp Gln Gln Gly Asn Val Phe Ser Cys Ser Val Met His
```

```
                450             455             460
Glu Ala Leu His Asn His Tyr Thr Gln Lys Ser Leu Ser Leu Ser Pro
465                 470                 475                 480

Gly Ser Gly Gly Gly Ser Gly Gly Gly Ser Gly Gly Gly Gly
                485                 490                 495

Ser Pro Gly Ser Gln Val Gln Leu Val Gln Ser Gly Pro Glu Val Lys
                500                 505                 510

Lys Pro Gly Ser Val Lys Val Ser Cys Lys Ala Ser Gly Tyr Thr
                515                 520                 525

Phe Ser Arg Ser Thr Met His Trp Val Arg Gln Ala Pro Gly Gln Gly
                530                 535                 540

Leu Glu Trp Ile Gly Tyr Ile Asn Pro Ser Ser Ala Tyr Thr Asn Tyr
545                 550                 555                 560

Asn Gln Lys Phe Lys Asp Arg Val Thr Ile Thr Ala Asp Lys Ser Thr
                565                 570                 575

Ser Thr Ala Tyr Met Glu Leu Ser Ser Leu Arg Ser Glu Asp Thr Ala
                580                 585                 590

Val Tyr Tyr Cys Ala Arg Pro Gln Val His Tyr Asp Tyr Asn Gly Phe
                595                 600                 605

Pro Tyr Trp Gly Gln Gly Thr Leu Val Thr Val Ser Ser Gly Gly Gly
                610                 615                 620

Gly Ser Gly Gly Gly Gly Ser Gly Gly Gly Ser Gly Gly Gly Gly
625                 630                 635                 640

Ser Asp Ile Gln Met Thr Gln Ser Pro Ser Thr Leu Ser Ala Ser Val
                645                 650                 655

Gly Asp Arg Val Thr Met Thr Cys Ser Ala Ser Ser Val Ser Tyr
                660                 665                 670

Met Asn Trp Tyr Gln Gln Lys Pro Gly Lys Ala Pro Lys Arg Trp Ile
                675                 680                 685

Tyr Asp Ser Ser Lys Leu Ala Ser Gly Val Pro Ser Arg Phe Ser Gly
                690                 695                 700

Ser Gly Ser Gly Thr Asp Tyr Thr Leu Thr Ile Ser Ser Leu Gln Pro
705                 710                 715                 720

Asp Asp Phe Ala Thr Tyr Tyr Cys Gln Gln Trp Ser Arg Asn Pro Pro
                725                 730                 735

Thr Phe Gly Gly Gly Thr Lys Val Glu Ile Lys Arg Ser Ser Ser
                740                 745                 750

<210> SEQ ID NO 198
<211> LENGTH: 753
<212> TYPE: PRT
<213> ORGANISM: Artificial Sequence
<220> FEATURE:
<223> OTHER INFORMATION: Chimeric bispecific anti-CD123 (VHVL) x
      anti-CD3 (TSC456) scFv-Fc-scFv CD3-binding domain

<400> SEQUENCE: 198

Val Gln Leu Gln Glu Ser Gly Pro Gly Leu Val Lys Pro Ser Gln Ser
1               5                   10                  15

Leu Ser Leu Thr Cys Ser Val Thr Asp Tyr Ser Ile Thr Ser Gly Tyr
                20                  25                  30

Tyr Trp Asn Trp Ile Arg Gln Phe Pro Gly Asn Lys Leu Glu Trp Met
                35                  40                  45

Gly Tyr Ile Ser Tyr Asp Gly Ser Asn Asn Tyr Asn Pro Ser Leu Lys
                50                  55                  60
```

```
Asn Arg Ile Ser Ile Thr Arg Asp Thr Ser Lys Asn Gln Phe Phe Leu
 65                  70                  75                  80

Lys Leu Ser Ser Val Thr Thr Glu Asp Thr Ala Thr Tyr Tyr Cys Ser
                 85                  90                  95

Arg Gly Glu Gly Phe Tyr Phe Asp Ser Trp Gly Gln Gly Thr Thr Leu
            100                 105                 110

Thr Val Ser Ser Gly Gly Gly Ser Gly Gly Gly Ser Gly Gly
        115                 120                 125

Gly Gly Ser Gly Gly Gly Ser Asp Ile Met Met Ser Gln Ser Pro
130                 135                 140

Ser Ser Leu Ala Val Ser Val Gly Glu Lys Phe Thr Met Thr Cys Lys
145             150                 155                     160

Ser Ser Gln Ser Leu Phe Phe Gly Ser Thr Gln Lys Asn Tyr Leu Ala
                165                 170                 175

Trp Tyr Gln Gln Lys Pro Gly Gln Ser Pro Lys Leu Leu Ile Tyr Trp
                180                 185                 190

Ala Ser Thr Arg Glu Ser Gly Val Pro Asp Arg Phe Thr Gly Ser Gly
            195                 200                 205

Ser Gly Thr Asp Phe Thr Leu Ala Ile Ser Ser Val Met Pro Glu Asp
        210                 215                 220

Leu Ala Val Tyr Tyr Cys Gln Gln Tyr Tyr Asn Tyr Pro Trp Thr Phe
225                 230                 235                 240

Gly Gly Gly Thr Lys Leu Glu Ile Lys Ser Ser Glu Pro Lys Ser
                245                 250                 255

Ser Asp Lys Thr His Thr Cys Pro Pro Cys Pro Ala Pro Glu Ala Ala
            260                 265                 270

Gly Ala Pro Ser Val Phe Leu Phe Pro Pro Lys Pro Lys Asp Thr Leu
            275                 280                 285

Met Ile Ser Arg Thr Pro Glu Val Thr Cys Val Val Val Asp Val Ser
        290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
                325                 330                 335

Tyr Arg Val Val Ser Val Leu Thr Val Leu His Gln Asp Trp Leu Asn
            340                 345                 350

Gly Lys Glu Tyr Lys Cys Ala Val Ser Asn Lys Ala Leu Pro Ala Pro
        355                 360                 365

Ile Glu Lys Thr Ile Ser Lys Ala Lys Gly Gln Pro Arg Glu Pro Gln
370                 375                 380

Val Tyr Thr Leu Pro Pro Ser Arg Asp Glu Leu Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
                420                 425                 430

Pro Val Leu Asp Ser Asp Gly Ser Phe Phe Leu Tyr Ser Lys Leu Thr
            435                 440                 445

Val Asp Lys Ser Arg Trp Gln Gln Gly Asn Val Phe Ser Cys Ser Val
            450                 455                 460

Met His Glu Ala Leu His Asn His Tyr Thr Gln Lys Ser Leu Ser Leu
465                 470                 475                 480

Ser Pro Gly Ser Gly Gly Gly Gly Ser Gly Gly Gly Gly Ser Gly Gly
```

```
                    485                 490                 495
Gly Gly Ser Pro Gly Ser Gln Val Gln Leu Val Gln Ser Gly Pro Glu
                500                 505                 510
Val Lys Lys Pro Gly Ser Ser Val Lys Val Ser Cys Lys Ala Ser Gly
            515                 520                 525
Tyr Thr Phe Ser Arg Ser Thr Met His Trp Val Arg Gln Ala Pro Gly
        530                 535                 540
Gln Gly Leu Glu Trp Ile Gly Tyr Ile Asn Pro Ser Ser Ala Tyr Thr
545                 550                 555                 560
Asn Tyr Asn Gln Lys Phe Lys Asp Arg Val Thr Ile Thr Ala Asp Lys
                565                 570                 575
Ser Thr Ser Thr Ala Tyr Met Glu Leu Ser Ser Leu Arg Ser Glu Asp
            580                 585                 590
Thr Ala Val Tyr Tyr Cys Ala Arg Pro Gln Val His Tyr Asp Tyr Asn
        595                 600                 605
Gly Phe Pro Tyr Trp Gly Gln Gly Thr Leu Val Thr Val Ser Ser Gly
610                 615                 620
Gly Gly Ser Gly Gly Gly Gly Ser Gly Gly Gly Ser Gly Gly
625                 630                 635                 640
Gly Gly Ser Asp Ile Gln Met Thr Gln Ser Pro Ser Thr Leu Ser Ala
                645                 650                 655
Ser Val Gly Asp Arg Val Thr Met Thr Cys Ser Ala Ser Ser Ser Val
            660                 665                 670
Ser Tyr Met Asn Trp Tyr Gln Gln Lys Pro Gly Lys Ala Pro Lys Arg
        675                 680                 685
Trp Ile Tyr Asp Ser Ser Lys Leu Ala Ser Gly Val Pro Ser Arg Phe
    690                 695                 700
Ser Gly Ser Gly Ser Gly Thr Asp Tyr Thr Leu Thr Ile Ser Ser Leu
705                 710                 715                 720
Gln Pro Asp Asp Phe Ala Thr Tyr Tyr Cys Gln Gln Trp Ser Arg Asn
                725                 730                 735
Pro Pro Thr Phe Gly Gly Gly Thr Lys Val Glu Ile Lys Arg Ser Ser
            740                 745                 750
Ser

<210> SEQ ID NO 199
<211> LENGTH: 8
<212> TYPE: PRT
<213> ORGANISM: Artificial Sequence
<220> FEATURE:
<223> OTHER INFORMATION: Cris7 and DRA222 VH CDR1 (IMGT) CD3-binding
      domain

<400> SEQUENCE: 199

Gly Tyr Thr Phe Thr Arg Ser Thr
1               5

<210> SEQ ID NO 200
<211> LENGTH: 8
<212> TYPE: PRT
<213> ORGANISM: Artificial Sequence
<220> FEATURE:
<223> OTHER INFORMATION: Cris7 and DRA222 VH CDR2 (IMGT) CD3-binding
      domain

<400> SEQUENCE: 200

Ile Asn Pro Ser Ser Ala Tyr Thr
1               5
```

<210> SEQ ID NO 201
<211> LENGTH: 14
<212> TYPE: PRT
<213> ORGANISM: Artificial Sequence
<220> FEATURE:
<223> OTHER INFORMATION: Cris7 and DRA222 VH CDR3 (IMGT) CD3-binding
domain

<400> SEQUENCE: 201

Ala Arg Pro Gln Val His Tyr Asp Tyr Asn Gly Phe Pro Tyr
1               5                   10

<210> SEQ ID NO 202
<211> LENGTH: 7
<212> TYPE: PRT
<213> ORGANISM: Artificial Sequence
<220> FEATURE:
<223> OTHER INFORMATION: Cris7 and DRA222 VL CDR1 (IMGT) CD3-binding
domain

<400> SEQUENCE: 202

Ala Ser Ser Ser Val Ser Tyr
1               5

<210> SEQ ID NO 203
<211> LENGTH: 3
<212> TYPE: PRT
<213> ORGANISM: Artificial Sequence
<220> FEATURE:
<223> OTHER INFORMATION: Cris7 and DRA222 VL CDR2 (IMGT) CD3-binding
domain

<400> SEQUENCE: 203

Asp Ser Ser
1

<210> SEQ ID NO 204
<211> LENGTH: 9
<212> TYPE: PRT
<213> ORGANISM: Artificial Sequence
<220> FEATURE:
<223> OTHER INFORMATION: Cris7 and DRA222 VL CDR3 (IMGT) CD3-binding
domain

<400> SEQUENCE: 204

Gln Gln Trp Ser Arg Asn Pro Pro Thr
1               5

<210> SEQ ID NO 205
<211> LENGTH: 2286
<212> TYPE: DNA
<213> ORGANISM: Artificial Sequence
<220> FEATURE:
<223> OTHER INFORMATION: TSC471 Anti-PSMA X anti-CD3 bispecific molecule

<400> SEQUENCE: 205
atggaagcac cagcgcagct tctcttcctc ctgctactct ggctcccaga taccaccggt      60
gatatccaga tgacccagtc tccatccgcc atgtctgcat ctgtaggaga cagagtcacc     120
atcacttgcc gggcgagtaa gagcattagc aaatatttag cctggtttca gcagaaacca     180
gggaaagttc ctaagctccg catccattct ggatctactt tgcaatcagg ggtcccatct     240
cggttcagtg gcagtggatc tgggacagaa tttactctca ccatcagcag cctgcagcct     300
gaagattttg caacttatta ctgtcaacag catattgatc acccgtggac gttcggccaa     360

| | | |
|---|---|---|
| gggaccaagg tggaaatcaa acgaggtggc ggagggtctg ggggtggcgg atccggaggt | 420 | |
| ggtggctctc aggtccagct ggtacagtct ggggctgagg tgaagaagcc tggggcttca | 480 | |
| gtgaaggtct cctgcaaggc ttctggatac acattcactg actactacat gcactgggtg | 540 | |
| cgacaggccc ctggacaagg gcttgagtgg atgggatatt ttaatcctta taatgattat | 600 | |
| actagatacg cacagaagtt ccagggcaga gtcaccatga ccagggacac gtctatcagc | 660 | |
| acagcctaca tggagctgag cagcctgaga tctgacgaca cggccgtgta ttactgtgca | 720 | |
| agatcggatg gttactacga tgctatggac tactggggtc aaggaaccac agtcaccgtc | 780 | |
| tcctcgagtg agcccaaatc ttctgacaaa actcacacat gcccaccgtg cccagcacct | 840 | |
| gaagccgcgg gtgcaccgtc agtcttcctc ttccccccaa acccaagga caccctcatg | 900 | |
| atctcccgga cccctgaggt cacatgcgtg gtggtggacg tgagccacga agaccctgag | 960 | |
| gtcaagttca actggtacgt ggacggcgtg gaggtgcata atgccaagac aaagccgcgg | 1020 | |
| gaggagcagt acaacagcac gtaccgtgtg gtcagcgtcc tcaccgtcct gcaccaggac | 1080 | |
| tggctgaatg gcaaggaata caagtgcgcg gtctccaaca aagcccctcc cagcccccatc | 1140 | |
| gagaaaacca tctccaaagc caaagggcag ccccgagaac acaggtgta cacctgcccc | 1200 | |
| ccatcccggg atgagctgac caagaaccag gtcagcctga cctgcctggt caaaggcttc | 1260 | |
| tatccaagcg acatcgccgt ggagtgggag agcaatgggc agccggagaa caactacaag | 1320 | |
| accacgcctc ccgtgctgga ctccgacggc tccttcttcc tctacagcaa gctcaccgtg | 1380 | |
| gacaagagca ggtggcagca ggggaacgtc ttctcatgct ccgtgatgca tgaggctctg | 1440 | |
| cacaaccact acacgcagaa gagcctctcc ctgtctccgg gttccggagg tggcggttcg | 1500 | |
| ggaggtggcg ggtcaggagg tggggctct ccttcacagg tgcagctggt gcagtctggt | 1560 | |
| cctgaggtga aaaagcctgg ctccagcgtg aaggtgtcct gcaaggccag cggatacacc | 1620 | |
| tttagccggt ccaccatgca ttgggtgagg caggctcctg gacagggcct ggagtggatc | 1680 | |
| ggctacatca accccagcag cgcttatacc aactacaatc agaagtttaa ggaccgggtg | 1740 | |
| accatcaccg ccgataagtc caccagcacc gcctacatgg agctgtccag cctgaggagc | 1800 | |
| gaggataccg ccgtgtacta ttgcgcccgg ccccaggtcc attacgacta caacggcttc | 1860 | |
| ccctattggg gccagggaac cctggtgacc gtgtccagcg gtggcggtgg cagcggcggc | 1920 | |
| ggcggctctg gcggaggtgg cagcggcgga ggggctccg acattcagat gacccagtcc | 1980 | |
| ccctccaccc tgtccgctag cgtgggcgat cgggtgacca tgacctgcag cgccagcagc | 2040 | |
| tccgtgtcct acatgaactg gtaccagcag aagcccggca aggctcccaa gaggtggatt | 2100 | |
| tacgactcca gcaagctggc ctctggtgtc cccagcaggt tctctggtag cggcagcggc | 2160 | |
| acagactaca ccctgaccat ctcctccctg cagcccgacg atttcgccac ctactattgc | 2220 | |
| cagcagtggt cccggaatcc ccctacctt ggcggcggca ccaaggtgga gatcaagagg | 2280 | |
| agctaa | 2286 | |

<210> SEQ ID NO 206
<211> LENGTH: 741
<212> TYPE: PRT
<213> ORGANISM: Artificial Sequence
<220> FEATURE:
<223> OTHER INFORMATION: TSC471 Anti-PSMA X anti-CD3 bispecific molecule

<400> SEQUENCE: 206

Asp Ile Gln Met Thr Gln Ser Pro Ser Ala Met Ser Ala Ser Val Gly
1               5                   10                  15

-continued

Asp Arg Val Thr Ile Thr Cys Arg Ala Ser Lys Ser Ile Ser Lys Tyr
                20                  25                  30

Leu Ala Trp Phe Gln Gln Lys Pro Gly Lys Val Pro Lys Leu Arg Ile
            35                  40                  45

His Ser Gly Ser Thr Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Gly Ser Gln Val Gln Leu Val
        115                 120                 125

Gln Ser Gly Ala Glu Val Lys Lys Pro Gly Ala Ser Val Lys Val Ser
    130                 135                 140

Cys Lys Ala Ser Gly Tyr Thr Phe Thr Asp Tyr Tyr Met His Trp Val
145                 150                 155                 160

Arg Gln Ala Pro Gly Gln Gly Leu Glu Trp Met Gly Tyr Phe Asn Pro
                165                 170                 175

Tyr Asn Asp Tyr Thr Arg Tyr Ala Gln Lys Phe Gln Gly Arg Val Thr
            180                 185                 190

Met Thr Arg Asp Thr Ser Ile Ser Thr Ala Tyr Met Glu Leu Ser Ser
        195                 200                 205

Leu Arg Ser Asp Asp Thr Ala Val Tyr Tyr Cys Ala Arg Ser Asp Gly
    210                 215                 220

Tyr Tyr Asp Ala Met Asp Tyr Trp Gly Gln Gly Thr Thr Val Thr Val
225                 230                 235                 240

Ser Ser Ser Glu Pro Lys Ser Ser Asp Lys Thr His Thr Cys Pro Pro
                245                 250                 255

Cys Pro Ala Pro Glu Ala Ala Gly Ala Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Ala Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly

```
            435                 440                 445
Asn Val Phe Ser Cys Ser Val Met His Glu Ala Leu His Asn His Tyr
        450                 455                 460

Thr Gln Lys Ser Leu Ser Leu Ser Pro Gly Ser Gly Gly Gly Gly Ser
465                 470                 475                 480

Gly Gly Gly Gly Ser Gly Gly Gly Ser Pro Ser Gln Val Gln Leu
                        485                 490                 495

Val Gln Ser Gly Pro Glu Val Lys Lys Pro Gly Ser Ser Val Lys Val
            500                 505                 510

Ser Cys Lys Ala Ser Gly Tyr Thr Phe Ser Arg Ser Thr Met His Trp
        515                 520                 525

Val Arg Gln Ala Pro Gly Gln Gly Leu Glu Trp Ile Gly Tyr Ile Asn
    530                 535                 540

Pro Ser Ser Ala Tyr Thr Asn Tyr Asn Gln Lys Phe Lys Asp Arg Val
545                 550                 555                 560

Thr Ile Thr Ala Asp Lys Ser Thr Ser Thr Ala Tyr Met Glu Leu Ser
                565                 570                 575

Ser Leu Arg Ser Glu Asp Thr Ala Val Tyr Tyr Cys Ala Arg Pro Gln
            580                 585                 590

Val His Tyr Asp Tyr Asn Gly Phe Pro Tyr Trp Gly Gln Gly Thr Leu
        595                 600                 605

Val Thr Val Ser Ser Gly Gly Gly Gly Ser Gly Gly Gly Ser Gly
    610                 615                 620

Gly Gly Ser Gly Gly Gly Gly Ser Asp Ile Gln Met Thr Gln Ser
625                 630                 635                 640

Pro Ser Thr Leu Ser Ala Ser Val Gly Asp Arg Val Thr Met Thr Cys
                645                 650                 655

Ser Ala Ser Ser Ser Val Ser Tyr Met Asn Trp Tyr Gln Gln Lys Pro
            660                 665                 670

Gly Lys Ala Pro Lys Arg Trp Ile Tyr Asp Ser Ser Lys Leu Ala Ser
        675                 680                 685

Gly Val Pro Ser Arg Phe Ser Gly Ser Gly Ser Gly Thr Asp Tyr Thr
    690                 695                 700

Leu Thr Ile Ser Ser Leu Gln Pro Asp Asp Phe Ala Thr Tyr Tyr Cys
705                 710                 715                 720

Gln Gln Trp Ser Arg Asn Pro Pro Thr Phe Gly Gly Gly Thr Lys Val
                725                 730                 735

Glu Ile Lys Arg Ser
            740

<210> SEQ ID NO 207
<211> LENGTH: 2307
<212> TYPE: DNA
<213> ORGANISM: Artificial Sequence
<220> FEATURE:
<223> OTHER INFORMATION: ROR243 Anti-ROR1 X anti-CD3 bispecific molecule

<400> SEQUENCE: 207
atggaggctc cgctcagct gctgttcctc ctgctgctct ggctgcccga caccacaggc      60
gacatccaga tgacccagtc ccttcctcc ctgtccgcta gcgtgggcga tagggtgacc    120
atcaactgcc aggcctccca gtccattgac tccaatctgg cctggttcca gcagaagccc    180
ggacagcccc ccaagctgct gatttacagg gcctccaacc tggcttccgg cgtgcctgac    240
aggttctccg gatccggcag cggcaccgac ttcaccctga ccatctcctc cctggaggcc    300
```

```
gaggatgtcg ccacctacta ctgtctgggc ggcgtgggcg ctgtgagcta tcggacctcc    360
ttcggcggcg gcaccaaggt ggagatcaag ggcggcggcg gcagcggcgg cggcggcagc    420
ggcggcggag gctccggcgg cggcggcagc gaggtgcagc tggtggaaag cggaggaggc    480
ctggtgcagc ctggaaggtc cctgaggctg tcctgcacag ccagcggctc cgacatcaac    540
gactacccca tcacctgggt gaggcaggct cctggccagg gcctggaatg gatcggcttt    600
atcaacagcg gcggcagcac ctggtatgct tcctgggtga agggccggtt caccattagc    660
agggacgact ccaagtccat tgcctacctg cagatgaact ccctgaagac cgaggacacc    720
gccgtgtact actgcgccag ggctacagc acctattacc gggactttaa catctggggc    780
cagggcacac tggtcaccgt gtcctcgagt gagcccaaat cttctgacaa aactcacaca    840
tgcccaccgt gcccagcacc tgaagccgcg ggtgcaccgt cagtcttcct cttcccccca    900
aaacccaagg acaccctcat gatctcccgg acccctgagg tcacatgcgt ggtggtggac    960
gtgagccacg aagaccctga ggtcaagttc aactggtacg tggacggcgt ggaggtgcat   1020
aatgccaaga caaagccgcg ggaggagcag tacaacagca cgtaccgtgt ggtcagcgtc   1080
ctcaccgtcc tgcaccagga ctggctgaat ggcaaggaat acaagtgcgc ggtctccaac   1140
aaagccctcc cagcccccat cgagaaaacc atctccaaag ccaaagggca gccccgagaa   1200
ccacaggtgt acaccctgcc cccatcccgg gatgagctga ccaagaacca ggtcagcctg   1260
acctgcctgg tcaaaggctt ctatccaagc gacatcgccg tggagtggga gagcaatggg   1320
cagccggaga caactacaa gaccacgcct cccgtgctgg actccgacgg ctccttcttc   1380
ctctacagca agctcaccgt ggacaagagc aggtggcagc aggggaacgt cttctcatgc   1440
tccgtgatgc atgaggctct gcacaaccac tacacgcaga agagcctctc cctgtctccg   1500
ggttccggag gaggggttc aggtgggga ggttctggcg gcggggggaag cccttcacag   1560 gtgcaactgg tgcagagtgg acccgaggtt aaaaaaccag ggtcctccgt taaggttagc   1620
tgcaaagcct ctggctacac attttccagg agtacaatgc actgggtgag gcaggctcct   1680
ggacagggac tcgagtggat cgggtatatc aacccatcta gcgcctatac caattacaac   1740
caaaagttta aggaccgagt taccattacc gctgacaaat ccaccagtac agcttatatg   1800
gagctgtcat ctcttaggtc cgaggacact gctgtttatt actgcgctcg tcctcaggtt   1860
cactatgact ataatggttt tccctactgg ggtcagggaa ccctggtgac tgtctcttct   1920
ggcggtggag gcagcggtgg gggtgggtct ggaggcggtg gcagtggcgg cggaggctct   1980
gatattcaga tgactcagtc tcctagcact ctcagcgcca gcgtggggga tcgtgtgaca   2040
atgacttgct ccgctagcag tagtgtgtct tacatgaatt ggtatcagca gaagcccggg   2100
aaagcaccta gcgctggat ctatgactct tccaagctgg caagtggtgt ccctcacgg   2160 ttctctggct caggttctgg tactgactat actttgacta tctcctccct ccagcccgat   2220
gatttcgcta cctattattg tcagcagtgg agccgtaacc cacccacttt cggaggcggt   2280
accaaagtgg agatcaagag gtcatga                                      2307
```

<210> SEQ ID NO 208
<211> LENGTH: 748
<212> TYPE: PRT
<213> ORGANISM: Artificial Sequence
<220> FEATURE:
<223> OTHER INFORMATION: ROR243 Anti-ROR1 X anti-CD3 bispecific molecule

<400> SEQUENCE: 208

Asp Ile Gln Met Thr Gln Ser Pro Ser Ser Leu Ser Ala Ser Val Gly

-continued

```
1               5               10              15
Asp Arg Val Thr Ile Asn Cys Gln Ala Ser Gln Ser Ile Asp Ser Asn
                20              25              30

Leu Ala Trp Phe Gln Gln Lys Pro Gly Gln Pro Pro Lys Leu Leu Ile
            35              40              45

Tyr Arg Ala Ser Asn Leu Ala Ser Gly Val Pro Asp Arg Phe Ser Gly
            50              55              60

Ser Gly Ser Gly Thr Asp Phe Thr Leu Thr Ile Ser Ser Leu Glu Ala
65              70              75              80

Glu Asp Val Ala Thr Tyr Tyr Cys Leu Gly Val Gly Ala Val Ser
                85              90              95

Tyr Arg Thr Ser Phe Gly Gly Thr Lys Val Glu Ile Lys Gly Gly
                100             105             110

Gly Gly Ser Gly Gly Gly Ser Gly Gly Gly Ser Gly Gly Gly
            115             120             125

Gly Ser Glu Val Gln Leu Val Glu Ser Gly Gly Leu Val Gln Pro
            130             135             140

Gly Arg Ser Leu Arg Leu Ser Cys Thr Ala Ser Gly Ser Asp Ile Asn
145             150             155             160

Asp Tyr Pro Ile Thr Trp Val Arg Gln Ala Pro Gly Gln Gly Leu Glu
                165             170             175

Trp Ile Gly Phe Ile Asn Ser Gly Gly Ser Thr Trp Tyr Ala Ser Trp
            180             185             190

Val Lys Gly Arg Phe Thr Ile Ser Arg Asp Asp Ser Lys Ser Ile Ala
            195             200             205

Tyr Leu Gln Met Asn Ser Leu Lys Thr Glu Asp Thr Ala Val Tyr Tyr
        210             215             220

Cys Ala Arg Gly Tyr Ser Thr Tyr Tyr Arg Asp Phe Asn Ile Trp Gly
225             230             235             240

Gln Gly Thr Leu Val Thr Val Ser Ser Ser Glu Pro Lys Ser Ser Asp
            245             250             255

Lys Thr His Thr Cys Pro Pro Cys Pro Ala Pro Glu Ala Ala Gly Ala
            260             265             270

Pro Ser Val Phe Leu Phe Pro Pro Lys Pro Lys Asp Thr Leu Met Ile
        275             280             285

Ser Arg Thr Pro Glu Val Thr Cys Val Val Val Asp Val Ser His Glu
            290             295             300

Asp Pro Glu Val Lys Phe Asn Trp Tyr Val Asp Gly Val Glu Val His
305             310             315             320

Asn Ala Lys Thr Lys Pro Arg Glu Glu Gln Tyr Asn Ser Thr Tyr Arg
                325             330             335

Val Val Ser Val Leu Thr Val Leu His Gln Asp Trp Leu Asn Gly Lys
            340             345             350

Glu Tyr Lys Cys Ala Val Ser Asn Lys Ala Leu Pro Ala Pro Ile Glu
            355             360             365

Lys Thr Ile Ser Lys Ala Lys Gly Gln Pro Arg Glu Pro Gln Val Tyr
        370             375             380

Thr Leu Pro Pro Ser Arg Asp Glu Leu Thr Lys Asn Gln Val Ser Leu
385             390             395             400

Thr Cys Leu Val Lys Gly Phe Tyr Pro Ser Asp Ile Ala Val Glu Trp
            405             410             415

Glu Ser Asn Gly Gln Pro Glu Asn Asn Tyr Lys Thr Thr Pro Pro Val
            420             425             430
```

Leu Asp Ser Asp Gly Ser Phe Phe Leu Tyr Ser Lys Leu Thr Val Asp
            435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Ser Gly Gly Gly Ser Gly Gly Gly Ser Gly Gly Gly Gly
                485                 490                 495

Ser Pro Ser Gln Val Gln Leu Val Gln Ser Gly Pro Glu Val Lys Lys
                500                 505                 510

Pro Gly Ser Ser Val Lys Val Ser Cys Lys Ala Ser Gly Tyr Thr Phe
            515                 520                 525

Ser Arg Ser Thr Met His Trp Val Arg Gln Ala Pro Gly Gln Gly Leu
    530                 535                 540

Glu Trp Ile Gly Tyr Ile Asn Pro Ser Ser Ala Tyr Thr Asn Tyr Asn
545                 550                 555                 560

Gln Lys Phe Lys Asp Arg Val Thr Ile Thr Ala Asp Lys Ser Thr Ser
                565                 570                 575

Thr Ala Tyr Met Glu Leu Ser Ser Leu Arg Ser Glu Asp Thr Ala Val
            580                 585                 590

Tyr Tyr Cys Ala Arg Pro Gln Val His Tyr Asp Tyr Asn Gly Phe Pro
    595                 600                 605

Tyr Trp Gly Gln Gly Thr Leu Val Thr Val Ser Ser Gly Gly Gly Gly
610                 615                 620

Ser Gly Gly Gly Gly Ser Gly Gly Gly Gly Ser Gly Gly Gly Gly Ser
625                 630                 635                 640

Asp Ile Gln Met Thr Gln Ser Pro Ser Thr Leu Ser Ala Ser Val Gly
                645                 650                 655

Asp Arg Val Thr Met Thr Cys Ser Ala Ser Ser Ser Val Ser Tyr Met
            660                 665                 670

Asn Trp Tyr Gln Gln Lys Pro Gly Lys Ala Pro Lys Arg Trp Ile Tyr
    675                 680                 685

Asp Ser Ser Lys Leu Ala Ser Gly Val Pro Ser Arg Phe Ser Gly Ser
690                 695                 700

Gly Ser Gly Thr Asp Tyr Thr Leu Thr Ile Ser Ser Leu Gln Pro Asp
705                 710                 715                 720

Asp Phe Ala Thr Tyr Tyr Cys Gln Gln Trp Ser Arg Asn Pro Pro Thr
                725                 730                 735

Phe Gly Gly Gly Thr Lys Val Glu Ile Lys Arg Ser
            740                 745

<210> SEQ ID NO 209
<211> LENGTH: 2289
<212> TYPE: DNA
<213> ORGANISM: Artificial Sequence
<220> FEATURE:
<223> OTHER INFORMATION: TSC266 Anti-PSMA X anti-CD3 bispecific molecule

<400> SEQUENCE: 209
atggaagcac cagcgcagct tctcttcctc ctgctactct ggctcccaga taccaccggt    60
gatatccaga tgacccagtc tccatccgcc atgtctgcat ctgtaggaga cagagtcacc   120
atcacttgcc gggcgagtaa gagcattagc aaatatttag cctggtttca gcagaaacca   180
gggaaagttc ctaagctccg catccattct ggatctactt tgcaatcagg ggtcccatct   240

```
cggttcagtg gcagtggatc tgggacagaa tttactctca ccatcagcag cctgcagcct    300
gaagattttg caacttatta ctgtcaacag catattgaat acccgtggac gttcggccaa    360
gggaccaagg tggaaatcaa acgaggtggc ggagggtctg ggggtggcgg atccggaggt    420
ggtggctctc aggtccagct ggtacagtct ggggctgagg tgaagaagcc tggggcttca    480
gtgaaggtct cctgcaaggc ttctggatac acattcactg actactacat gcactgggtg    540
cgacaggccc ctggacaagg gcttgagtgg atgggatatt ttaatcctta taatgattat    600
actagatacg cacagaagtt ccagggcaga gtcaccatga ccagggacac gtctatcagc    660
acagcctaca tggagctgag cagcctgaga tctgacgaca cggccgtgta ttactgtgca    720
agatcggatg gttactacga tgctatggac tactggggtc aaggaaccac agtcaccgtc    780
tcctcgagtg agcccaaatc ttctgacaaa actcacacat gcccaccgtg cccagcacct    840
gaagccgcgg gtgcaccgtc agtcttcctc ttccccccaa acccaaggac acccctcatg    900
atctcccgga cccctgaggt cacatgcgtg gtggtggacg tgagccacga agaccctgag    960
gtcaagttca actggtacgt ggacggcgtg gaggtgcata atgccaagac aaagccgcgg   1020
gaggagcagt acaacagcac gtaccgtgtg gtcagcgtcc tcaccgtcct gcaccaggac   1080
tggctgaatg gcaaggcgta cgcgtgcgcg gtctccaaca agccctccc agcccccatc   1140
gagaaaacca tctccaaagc caaagggcag ccccgagaac acaggtgta caccctgccc   1200
ccatcccggg atgagctgac caagaaccag gtcagcctga cctgcctggt caaaggcttc   1260
tatccaagcg acatcgccgt ggagtgggag agcaatgggc agccggagaa caactacaag   1320
accacgcctc ccgtgctgga ctccgacggc tccttcttcc tctacagcaa gctcaccgtg   1380
gacaagagca ggtggcagca ggggaacgtc ttctcatgct ccgtgatgca tgaggctctg   1440
cacaaccact acacgcagaa gagcctctcc ctgtctccgg gtcagaggca acaattct   1500
tccctgaata caggaactca gatggcaggt cattctccga attctcaggt ccagctggtg   1560
gagtctgggg gcggagtggt gcagcctggg cggtcactga ggctgtcctg caaggcttct   1620
ggctacacct ttactagatc tacgatgcac tgggtaaggc aggccctgg acaaggtctg   1680
gaatggattg gatacattaa tcctagcagt gcttatacta attacaatca gaaattcaag   1740
gacaggttca caatcagcgc agacaaatcc aagagcacag ccttcctgca gatggacagc   1800
ctgaggcccg aggacaccgg cgtctatttc tgtgcacggc cccaagtcca ctatgattac   1860
aacgggtttc cttactgggg ccaagggact cccgtcactg tctctagcgg tggcggaggg   1920
tctggggggtg gcggatccgg aggtggtggc tctgcacaag acatccagat gacccagtct   1980
ccaagcagcc tgtctgcaag cgtggggggac agggtcacca tgacctgcag tgccagctca   2040
agtgtaagtt acatgaactg gtaccagcag aagccgggca aggcccccaa agatgggatt   2100
tatgactcat ccaaactggc ttctggagtc cctgctcgct tcagtggcag tgggtctggg   2160
accgactata ccctcacaat cagcagcctg cagccgaag atttcgccac ttattactgc   2220
cagcagtgga gtcgtaaccc acccacgttc ggagggggga ccaagctaca aattacatcc   2280
tccagctaa                                                           2289
```

<210> SEQ ID NO 210
<211> LENGTH: 742
<212> TYPE: PRT
<213> ORGANISM: Artificial Sequence
<220> FEATURE:
<223> OTHER INFORMATION: TSC266 Anti-PSMA X anti-CD3 bispecific molecule

<400> SEQUENCE: 210

```
Asp Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Lys Pro Gly Lys Val Pro Lys Leu Arg Ile
        35                  40                  45

His Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Ile Glu Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Ser Gln Val Gln Leu Val
        115                 120                 125

Gln Ser Gly Ala Glu Val Lys Lys Pro Gly Ala Ser Val Lys Val Ser
    130                 135                 140

Cys Lys Ala Ser Gly Tyr Thr Phe Thr Asp Tyr Tyr Met His Trp Val
145                 150                 155                 160

Arg Gln Ala Pro Gly Gln Gly Leu Glu Trp Met Gly Tyr Phe Asn Pro
                165                 170                 175

Tyr Asn Asp Tyr Thr Arg Tyr Ala Gln Lys Phe Gln Gly Arg Val Thr
            180                 185                 190

Met Thr Arg Asp Thr Ser Ile Ser Thr Ala Tyr Met Glu Leu Ser Ser
        195                 200                 205

Leu Arg Ser Asp Asp Thr Ala Val Tyr Tyr Cys Ala Arg Ser Asp Gly
210                 215                 220

Tyr Tyr Asp Ala Met Asp Tyr Trp Gly Gln Gly Thr Thr Val Thr Val
225                 230                 235                 240

Ser Ser Ser Glu Pro Lys Ser Ser Asp Lys Thr His Thr Cys Pro Pro
                245                 250                 255

Cys Pro Ala Pro Glu Ala Ala Gly Ala Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Ala Tyr Ala Cys Ala Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415
```

```
Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Gln Arg His Asn Asn Ser
465                 470                 475                 480

Ser Leu Asn Thr Gly Thr Gln Met Ala Gly His Ser Pro Asn Ser Gln
            485                 490                 495

Val Gln Leu Val Glu Ser Gly Gly Val Val Gln Pro Gly Arg Ser
        500                 505                 510

Leu Arg Leu Ser Cys Lys Ala Ser Gly Tyr Thr Phe Thr Arg Ser Thr
        515                 520                 525

Met His Trp Val Arg Gln Ala Pro Gly Gln Gly Leu Glu Trp Ile Gly
    530                 535                 540

Tyr Ile Asn Pro Ser Ser Ala Tyr Thr Asn Tyr Asn Gln Lys Phe Lys
545                 550                 555                 560

Asp Arg Phe Thr Ile Ser Ala Asp Lys Ser Lys Ser Thr Ala Phe Leu
                565                 570                 575

Gln Met Asp Ser Leu Arg Pro Glu Asp Thr Gly Val Tyr Phe Cys Ala
            580                 585                 590

Arg Pro Gln Val His Tyr Asp Tyr Asn Gly Phe Pro Tyr Trp Gly Gln
        595                 600                 605

Gly Thr Pro Val Thr Val Ser Ser Gly Gly Gly Ser Gly Gly Gly
        610                 615                 620

Gly Ser Gly Gly Gly Gly Ser Ala Gln Asp Ile Gln Met Thr Gln Ser
625                 630                 635                 640

Pro Ser Ser Leu Ser Ala Ser Val Gly Asp Arg Val Thr Met Thr Cys
                645                 650                 655

Ser Ala Ser Ser Ser Val Ser Tyr Met Asn Trp Tyr Gln Gln Lys Pro
            660                 665                 670

Gly Lys Ala Pro Lys Arg Trp Ile Tyr Asp Ser Ser Lys Leu Ala Ser
        675                 680                 685

Gly Val Pro Ala Arg Phe Ser Gly Ser Gly Ser Gly Thr Asp Tyr Thr
    690                 695                 700

Leu Thr Ile Ser Ser Leu Gln Pro Glu Asp Phe Ala Thr Tyr Tyr Cys
705                 710                 715                 720

Gln Gln Trp Ser Arg Asn Pro Pro Thr Phe Gly Gly Gly Thr Lys Leu
                725                 730                 735

Gln Ile Thr Ser Ser Ser
            740

<210> SEQ ID NO 211
<211> LENGTH: 2301
<212> TYPE: DNA
<213> ORGANISM: Artificial Sequence
<220> FEATURE:
<223> OTHER INFORMATION: ROR206 Anti-ROR1 X anti-CD3 bispecific molecule

<400> SEQUENCE: 211
atggaagcac cagcgcagct tctcttcctc ctgctactct ggctcccaga taccaccggt      60
gacatccaga tgacccagtc ccctcctcc ctgtccgcct ccgtgggcga ccgggtgacc      120
atcaactgcc aggcctccca gtccatcgac tccaacctgg cctggttcca gcagaagccc      180
```

| | |
|---|---|
| ggcaagcccc ccaagctgct gatctaccgg gcctccaacc tggcctccgg cgtgccctcc | 240 |
| cggttctccg gctccggctc cggcaccgac ttcaccctga ccatctcctc cctgcagccc | 300 |
| gaggacgtgg ccacctacta ctgcctgggc ggcgtgggcg ccgtgtccta ccggacctcc | 360 |
| ttcggcggcg gcaccaaggt ggagatcaag ggtggaggcg gttcaggcgg aggtggatcc | 420 |
| ggcggtggcg gctccggtgg cggcggatct gaggtgcagc tggtggagtc cggcggcggc | 480 |
| ctggtgcagc ccggccggtc cctgcggctg tcctgcaccg cctccggctc cgacatcaac | 540 |
| gactacccca tcacctgggt gcggcaggcc cccggcaagg gcctggagtg gatcggcttc | 600 |
| atcaactccg cgggctccac ctggtacgcc tcctgggtga agggccggtt caccatctcc | 660 |
| cgggacgact ccaagtccat cgcctacctg cagatgaact ccctgaagac cgaggacacc | 720 |
| gccgtgtact attgcgcccg gggctactcc acctactacc gggacttcaa catctggggc | 780 |
| cagggcaccc tggtgaccgt gtcctcgagt gagcccaaat cttctgacaa aactcacaca | 840 |
| tgcccaccgt gcccagcacc tgaagccgcg ggtgcaccgt cagtcttcct cttcccccca | 900 |
| aaacccaagg acaccctcat gatctcccgg acccctgagg tcacatgcgt ggtggtggac | 960 |
| gtgagccacg aagaccctga ggtcaagttc aactggtacg tggacggcgt ggaggtgcat | 1020 |
| aatgccaaga caaagccgcg ggaggagcag tacaacagca cgtaccgtgt ggtcagcgtc | 1080 |
| ctcaccgtcc tgcaccagga ctggctgaat ggcaaggaat acaagtgcgc ggtctccaac | 1140 |
| aaagccctcc cagcccccat cgagaaaacc atctccaaag ccaaagggca gccccgagaa | 1200 |
| ccacaggtgt acaccctgcc cccatcccgg gatgagctga ccaagaacca ggtcagcctg | 1260 |
| acctgcctgg tcaaaggctt ctatccaagc gacatcgccg tggagtggga gagcaatggg | 1320 |
| cagccggaga caactacaa gaccacgcct cccgtgctgg actccgacgg ctccttcttc | 1380 |
| ctctacagca agctcaccgt ggacaagagc aggtggcagc aggggaacgt cttctcatgc | 1440 |
| tccgtgatgc atgaggctct gcacaaccac tacacgcaga agagcctctc cctgtctccg | 1500 |
| ggttctggtg gaggcggttc aggcggaggt ggctccggcg gtggcggatc gccgggctct | 1560 |
| caggtccagc tggtggagtc tgggggcgga gtggtgcagc ctgggcggtc actgaggctg | 1620 |
| tcctgcaagg cttctggcta cacctttact agatctacga tgcactgggt aaggcaggcc | 1680 |
| cctggacaag gtctggaatg gattggatac attaatccta gcagtgctta tactaattac | 1740 |
| aatcagaaat tcaaggacag gttcacaatc agcgcagaca atccaagag cacagccttc | 1800 |
| ctgcagatgg acagcctgag gccggaggac accggcgtct atttctgtgc acggccccaa | 1860 |
| gtccactatg attacaacgg gtttccttac tggggccaag gactcccgt cactgtctct | 1920 |
| agcggtggcg gagggtctgg gggtggcgga tccggaggtg gtggctctgc acaagacatc | 1980 |
| cagatgaccc agtctccaag cagcctgtct gcaagcgtgg gggacagggt caccatgacc | 2040 |
| tgcagtgcca gctcaagtgt aagttacatg aactggtacc agcagaagcc gggcaaggcc | 2100 |
| cccaaaagat ggatttatga ctcatccaaa ctggcttctg gagtccctgc tcgcttcagt | 2160 |
| ggcagtgggt ctgggaccga ctataccctc acaatcagca gcctgcagcc cgaagatttt | 2220 |
| gccacttatt actgccagca gtggagtcgt aacccaccca cgttcggagg ggggaccaag | 2280 |
| ctacaaatta tcctccag c | 2301 |

<210> SEQ ID NO 212
<211> LENGTH: 767
<212> TYPE: PRT
<213> ORGANISM: Artificial Sequence
<220> FEATURE:
<223> OTHER INFORMATION: ROR206 Anti-ROR1 X anti-CD3 bispecific molecule

<400> SEQUENCE: 212

```
Met Glu Ala Pro Ala Gln Leu Leu Phe Leu Leu Leu Leu Trp Leu Pro
 1               5                  10                  15

Asp Thr Thr Gly Asp Ile Gln Met Thr Gln Ser Pro Ser Ser Leu Ser
            20                  25                  30

Ala Ser Val Gly Asp Arg Val Thr Ile Asn Cys Gln Ala Ser Gln Ser
        35                  40                  45

Ile Asp Ser Asn Leu Ala Trp Phe Gln Gln Lys Pro Gly Lys Pro Pro
 50                  55                  60

Lys Leu Leu Ile Tyr Arg Ala Ser Asn Leu Ala Ser Gly Val Pro Ser
 65                  70                  75                  80

Arg Phe Ser Gly Ser Gly Ser Gly Thr Asp Phe Thr Leu Thr Ile Ser
                85                  90                  95

Ser Leu Gln Pro Glu Asp Val Ala Thr Tyr Tyr Cys Leu Gly Gly Val
            100                 105                 110

Gly Ala Val Ser Tyr Arg Thr Ser Phe Gly Gly Gly Thr Lys Val Glu
        115                 120                 125

Ile Lys Gly Gly Gly Gly Ser Gly Gly Gly Gly Ser Gly Gly Gly Gly
130                 135                 140

Ser Gly Gly Gly Gly Ser Glu Val Gln Leu Val Glu Ser Gly Gly Gly
145                 150                 155                 160

Leu Val Gln Pro Gly Arg Ser Leu Arg Leu Ser Cys Thr Ala Ser Gly
                165                 170                 175

Ser Asp Ile Asn Asp Tyr Pro Ile Thr Trp Val Arg Gln Ala Pro Gly
            180                 185                 190

Lys Gly Leu Glu Trp Ile Gly Phe Ile Asn Ser Gly Gly Ser Thr Trp
        195                 200                 205

Tyr Ala Ser Trp Val Lys Gly Arg Phe Thr Ile Ser Arg Asp Asp Ser
210                 215                 220

Lys Ser Ile Ala Tyr Leu Gln Met Asn Ser Leu Lys Thr Glu Asp Thr
225                 230                 235                 240

Ala Val Tyr Tyr Cys Ala Arg Gly Tyr Ser Thr Tyr Tyr Arg Asp Phe
                245                 250                 255

Asn Ile Trp Gly Gln Gly Thr Leu Val Thr Val Ser Ser Glu Pro
            260                 265                 270

Lys Ser Ser Asp Lys Thr His Thr Cys Pro Pro Cys Pro Ala Pro Glu
        275                 280                 285

Ala Ala Gly Ala Pro Ser Val Phe Leu Phe Pro Pro Lys Pro Lys Asp
290                 295                 300

Thr Leu Met Ile Ser Arg Thr Pro Glu Val Thr Cys Val Val Val Asp
305                 310                 315                 320

Val Ser His Glu Asp Pro Glu Val Lys Phe Asn Trp Tyr Val Asp Gly
                325                 330                 335

Val Glu Val His Asn Ala Lys Thr Lys Pro Arg Glu Glu Gln Tyr Asn
            340                 345                 350

Ser Thr Tyr Arg Val Val Ser Val Leu Thr Val Leu His Gln Asp Trp
        355                 360                 365

Leu Asn Gly Lys Glu Tyr Lys Cys Ala Val Ser Asn Lys Ala Leu Pro
370                 375                 380

Ala Pro Ile Glu Lys Thr Ile Ser Lys Ala Lys Gly Gln Pro Arg Glu
385                 390                 395                 400

Pro Gln Val Tyr Thr Leu Pro Pro Ser Arg Asp Glu Leu Thr Lys Asn
```

```
                405                 410                 415
Gln Val Ser Leu Thr Cys Leu Val Lys Gly Phe Tyr Pro Ser Asp Ile
            420                 425                 430
Ala Val Glu Trp Glu Ser Asn Gly Gln Pro Glu Asn Asn Tyr Lys Thr
            435                 440                 445
Thr Pro Pro Val Leu Asp Ser Asp Gly Ser Phe Phe Leu Tyr Ser Lys
            450                 455                 460
Leu Thr Val Asp Lys Ser Arg Trp Gln Gln Gly Asn Val Phe Ser Cys
465                 470                 475                 480
Ser Val Met His Glu Ala Leu His Asn His Tyr Thr Gln Lys Ser Leu
            485                 490                 495
Ser Leu Ser Pro Gly Ser Gly Gly Gly Ser Gly Gly Gly Gly Ser
            500                 505                 510
Gly Gly Gly Gly Ser Pro Gly Ser Gln Val Gln Leu Val Glu Ser Gly
            515                 520                 525
Gly Gly Val Val Gln Pro Gly Arg Ser Leu Arg Leu Ser Cys Lys Ala
            530                 535                 540
Ser Gly Tyr Thr Phe Thr Arg Ser Thr Met His Trp Val Arg Gln Ala
545                 550                 555                 560
Pro Gly Gln Gly Leu Glu Trp Ile Gly Tyr Ile Asn Pro Ser Ser Ala
            565                 570                 575
Tyr Thr Asn Tyr Asn Gln Lys Phe Lys Asp Arg Phe Thr Ile Ser Ala
            580                 585                 590
Asp Lys Ser Lys Ser Thr Ala Phe Leu Gln Met Asp Ser Leu Arg Pro
            595                 600                 605
Glu Asp Thr Gly Val Tyr Phe Cys Ala Arg Pro Gln Val His Tyr Asp
            610                 615                 620
Tyr Asn Gly Phe Pro Tyr Trp Gly Gln Gly Thr Pro Val Thr Val Ser
625                 630                 635                 640
Ser Gly Gly Gly Gly Ser Gly Gly Gly Gly Ser Gly Gly Gly Gly Ser
            645                 650                 655
Ala Gln Asp Ile Gln Met Thr Gln Ser Pro Ser Ser Leu Ser Ala Ser
            660                 665                 670
Val Gly Asp Arg Val Thr Met Thr Cys Ser Ala Ser Ser Ser Val Ser
            675                 680                 685
Tyr Met Asn Trp Tyr Gln Gln Lys Pro Gly Lys Ala Pro Lys Arg Trp
            690                 695                 700
Ile Tyr Asp Ser Ser Lys Leu Ala Ser Gly Val Pro Ala Arg Phe Ser
705                 710                 715                 720
Gly Ser Gly Ser Gly Thr Asp Tyr Thr Leu Thr Ile Ser Ser Leu Gln
            725                 730                 735
Pro Glu Asp Phe Ala Thr Tyr Tyr Cys Gln Gln Trp Ser Arg Asn Pro
            740                 745                 750
Pro Thr Phe Gly Gly Gly Thr Lys Leu Gln Ile Thr Ser Ser Ser
            755                 760                 765

<210> SEQ ID NO 213
<211> LENGTH: 2313
<212> TYPE: DNA
<213> ORGANISM: Artificial Sequence
<220> FEATURE:
<223> OTHER INFORMATION: ROR207 Anti-ROR1 X anti-CD3 bispecific molecule

<400> SEQUENCE: 213
atggaagcac cagcgcagct tctcttcctc ctgctactct ggctcccaga taccaccggt    60
```

```
gacatccaga tgacccagtc cccctcctcc ctgtccgcct ccgtgggcga ccgggtgacc    120
atcaactgcc aggcctccca gtccatcgac tccaacctgg cctggttcca gcagaagccc    180
ggcaagcccc ccaagctgct gatctaccgg gcctccaacc tggcctccgg cgtgccctcc    240
cggttctccg gctccggctc cggcaccgac ttcaccctga ccatctcctc cctgcagccc    300
gaggacgtgg ccacctacta ctgcctgggc ggcgtgggcg ccgtgtccta ccggacctcc    360
ttcggcggcg gcaccaaggt ggagatcaag ggtggaggcg gttcaggcgg aggtggatcc    420
ggcggtggcg gctccggtgg cggcggatct gaggtgcagc tggtggagtc cggcggcggc    480
ctggtgcagc ccggccggtc cctgcggctg tcctgcaccg cctccggctc cgacatcaac    540
gactacccca tcacctgggt gcggcaggcc cccggcaagg gcctggagtg gatcggcttc    600
atcaactccg gcggctccac ctggtacgcc tcctgggtga agggccggtt caccatctcc    660
cgggacgact ccaagtccat cgcctacctg cagatgaact ccctgaagac cgaggacacc    720
gccgtgtact attgcgcccg ggctactccc acctactacc gggacttcaa catctggggc    780
cagggcaccc tggtgaccgt gtcctcgagt gagcccaaat cttctgacaa aactcacaca    840
tgcccaccgt gcccagcacc tgaagccgcg ggtgcaccgt cagtcttcct cttcccccca    900
aaacccaagg acaccctcat gatctcccgg acccctgagg tcacatgcgt ggtggtggac    960
gtgagccacg aagaccctga ggtcaagttc aactggtacg tggacggcgt ggaggtgcat   1020
aatgccaaga caaagccgcg ggaggagcag tacaacagca cgtaccgtgt ggtcagcgtc   1080
ctcaccgtcc tgcaccagga ctggctgaat ggcaaggaat acaagtgcgc ggtctccaac   1140
aaagccctcc cagcccccat cgagaaaacc atctccaaag ccaaagggca gccccgagaa   1200
ccacaggtgt acaccctgcc cccatcccgg gatgagctga ccaagaacca ggtcagcctg   1260
acctgcctgg tcaaaggctt ctatccaagc gacatcgccg tggagtggga gagcaatggg   1320
cagccggaga acaactacaa gaccacgcct cccgtgctgg actccgacgg ctccttcttc   1380
ctctacagca agctcaccgt ggacaagagc aggtggcagc aggggaacgt cttctcatgc   1440
tccgtgatgc atgaggctct gcacaaccac tacacgcaga agagcctctc cctgtctccg   1500
ggttctggtg gaggcggttc aggcggaggt ggctccggcg gtggcggatc gccgggctct   1560
caggtccagc tggtgcaatc tgggcctgag gtgaagaagc ctgggtcctc ggtgaaggtc   1620
tcctgcaagg cttctggata taccttcagc agatctacga tgcactgggt gcgacaggcc   1680
cctggacaag gcttgagtg gataggatac attaatccta gcagtgctta tactaattac   1740
aatcagaaat tcaaggacag agtcacgatt accgcggaca atccacgag cacagcctac   1800 atggagctga gcagcctgag atctgaggac acggccgtgt attactgtgc gagacccaa    1860 gtccactatg attacaacgg gtttccttac tggggccaag aaccctggt caccgtctcc    1920 tcaggtggag gcggttcagg cggaggtgga tccggcggtg gcggatcggg tggcggcgga   1980
tctgacatcc agatgaccca gtctccttcc accctgtctg catctgtagg agacagagtc   2040
accatgactt gcagtgccag ctcaagtgta agttacatga actggtatca gcagaaacca   2100
gggaaagccc ctaagagatg gatttatgac tcatccaaac tggcttctgg ggtcccatca   2160
aggttcagcg gcagtggatc tgggacagat tatactctca ccatcagcag cctgcagcct   2220
gatgattttg caacttatta ctgccaacag tggagtcgta acccacccac tttcggcgga   2280
gggaccaagg tggagatcaa acggtcctcc agc                                2313
```

<210> SEQ ID NO 214

<211> LENGTH: 771
<212> TYPE: PRT
<213> ORGANISM: Artificial Sequence
<220> FEATURE:
<223> OTHER INFORMATION: ROR207 Anti-ROR1 X anti-CD3 bispecific molecule

<400> SEQUENCE: 214

```
Met Glu Ala Pro Ala Gln Leu Leu Phe Leu Leu Leu Leu Trp Leu Pro
1               5                   10                  15

Asp Thr Thr Gly Asp Ile Gln Met Thr Gln Ser Pro Ser Ser Leu Ser
            20                  25                  30

Ala Ser Val Gly Asp Arg Val Thr Ile Asn Cys Gln Ala Ser Gln Ser
        35                  40                  45

Ile Asp Ser Asn Leu Ala Trp Phe Gln Gln Lys Pro Gly Lys Pro Pro
    50                  55                  60

Lys Leu Leu Ile Tyr Arg Ala Ser Asn Leu Ala Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Val Ala Thr Tyr Tyr Cys Leu Gly Gly Val
            100                 105                 110

Gly Ala Val Ser Tyr Arg Thr Ser Phe Gly Gly Gly Thr Lys Val Glu
        115                 120                 125

Ile Lys Gly Gly Gly Gly Ser Gly Gly Gly Ser Gly Gly Gly Gly
    130                 135                 140

Ser Gly Gly Gly Gly Ser Glu Val Gln Leu Val Glu Ser Gly Gly Gly
145                 150                 155                 160

Leu Val Gln Pro Gly Arg Ser Leu Arg Leu Ser Cys Thr Ala Ser Gly
                165                 170                 175

Ser Asp Ile Asn Asp Tyr Pro Ile Thr Trp Val Arg Gln Ala Pro Gly
            180                 185                 190

Lys Gly Leu Glu Trp Ile Gly Phe Ile Asn Ser Gly Gly Ser Thr Trp
        195                 200                 205

Tyr Ala Ser Trp Val Lys Gly Arg Phe Thr Ile Ser Arg Asp Asp Ser
    210                 215                 220

Lys Ser Ile Ala Tyr Leu Gln Met Asn Ser Leu Lys Thr Glu Asp Thr
225                 230                 235                 240

Ala Val Tyr Tyr Cys Ala Arg Gly Tyr Ser Thr Tyr Tyr Arg Asp Phe
                245                 250                 255

Asn Ile Trp Gly Gln Gly Thr Leu Val Thr Val Ser Ser Glu Pro
            260                 265                 270

Lys Ser Ser Asp Lys Thr His Thr Cys Pro Pro Cys Pro Ala Pro Glu
        275                 280                 285

Ala Ala Gly Ala Pro Ser Val Phe Leu Phe Pro Pro Lys Pro Lys Asp
    290                 295                 300

Thr Leu Met Ile Ser Arg Thr Pro Glu Val Thr Cys Val Val Val Asp
305                 310                 315                 320

Val Ser His Glu Asp Pro Glu Val Lys Phe Asn Trp Tyr Val Asp Gly
                325                 330                 335

Val Glu Val His Asn Ala Lys Thr Lys Pro Arg Glu Glu Gln Tyr Asn
            340                 345                 350

Ser Thr Tyr Arg Val Val Ser Val Leu Thr Val Leu His Gln Asp Trp
        355                 360                 365

Leu Asn Gly Lys Glu Tyr Lys Cys Ala Val Ser Asn Lys Ala Leu Pro
    370                 375                 380
```

```
Ala Pro Ile Glu Lys Thr Ile Ser Lys Ala Lys Gly Gln Pro Arg Glu
385                 390                 395                 400

Pro Gln Val Tyr Thr Leu Pro Pro Ser Arg Asp Glu Leu Thr Lys Asn
            405                 410                 415

Gln Val Ser Leu Thr Cys Leu Val Lys Gly Phe Tyr Pro Ser Asp Ile
        420                 425                 430

Ala Val Glu Trp Glu Ser Asn Gly Gln Pro Glu Asn Asn Tyr Lys Thr
            435                 440                 445

Thr Pro Pro Val Leu Asp Ser Asp Gly Ser Phe Phe Leu Tyr Ser Lys
    450                 455                 460

Leu Thr Val Asp Lys Ser Arg Trp Gln Gln Gly Asn Val Phe Ser Cys
465                 470                 475                 480

Ser Val Met His Glu Ala Leu His Asn His Tyr Thr Gln Lys Ser Leu
                485                 490                 495

Ser Leu Ser Pro Gly Ser Gly Gly Gly Ser Gly Gly Gly Gly Ser
            500                 505                 510

Gly Gly Gly Gly Ser Pro Gly Ser Gln Val Gln Leu Val Gln Ser Gly
        515                 520                 525

Pro Glu Val Lys Lys Pro Gly Ser Ser Val Lys Val Ser Cys Lys Ala
    530                 535                 540

Ser Gly Tyr Thr Phe Ser Arg Ser Thr Met His Trp Val Arg Gln Ala
545                 550                 555                 560

Pro Gly Gln Gly Leu Glu Trp Ile Gly Tyr Ile Asn Pro Ser Ser Ala
            565                 570                 575

Tyr Thr Asn Tyr Asn Gln Lys Phe Lys Asp Arg Val Thr Ile Thr Ala
        580                 585                 590

Asp Lys Ser Thr Ser Thr Ala Tyr Met Glu Leu Ser Ser Leu Arg Ser
            595                 600                 605

Glu Asp Thr Ala Val Tyr Tyr Cys Ala Arg Pro Gln Val His Tyr Asp
    610                 615                 620

Tyr Asn Gly Phe Pro Tyr Trp Gly Gln Gly Thr Leu Val Thr Val Ser
625                 630                 635                 640

Ser Gly Gly Gly Gly Ser Gly Gly Gly Gly Ser Gly Gly Gly Gly Ser
            645                 650                 655

Gly Gly Gly Gly Ser Asp Ile Gln Met Thr Gln Ser Pro Ser Thr Leu
        660                 665                 670

Ser Ala Ser Val Gly Asp Arg Val Thr Met Thr Cys Ser Ala Ser Ser
            675                 680                 685

Ser Val Ser Tyr Met Asn Trp Tyr Gln Gln Lys Pro Gly Lys Ala Pro
        690                 695                 700

Lys Arg Trp Ile Tyr Asp Ser Ser Lys Leu Ala Ser Gly Val Pro Ser
705                 710                 715                 720

Arg Phe Ser Gly Ser Gly Ser Gly Thr Asp Tyr Thr Leu Thr Ile Ser
            725                 730                 735

Ser Leu Gln Pro Asp Asp Phe Ala Thr Tyr Tyr Cys Gln Gln Trp Ser
        740                 745                 750

Arg Asn Pro Pro Thr Phe Gly Gly Gly Thr Lys Val Glu Ile Lys Arg
    755                 760                 765

Ser Ser Ser
    770

<210> SEQ ID NO 215
<211> LENGTH: 2301
```

<212> TYPE: DNA
<213> ORGANISM: Artificial Sequence
<220> FEATURE:
<223> OTHER INFORMATION: ROR208 Anti-ROR1 X anti-CD3 bispecific molecule

<400> SEQUENCE: 215

| | |
|---|---|
| atggaagcac cagcgcagct tctcttcctc ctgctactct ggctcccaga taccaccggt | 60 |
| gacatccaga tgacccagtc cccctcctcc ctgtccgcct ccgtgggcga ccgggtgacc | 120 |
| atcaactgcc aggcctccca gtccatcgac tccaacctgg cctggttcca gcagaagccc | 180 |
| ggccagcccc ccaagctgct gatctaccgg gcctccaacc tggcctccgg cgtgcccgac | 240 |
| cggttctccg gctccggctc cggcaccgac ttcaccctga ccatctcctc cctggaggcc | 300 |
| gaggacgtgg ccacctacta ctgcctgggc ggcgtgggcg ccgtgtccta ccggacctcc | 360 |
| ttcggcggcg gcaccaaggt ggagatcaag ggtggaggcg gttcaggcgg aggtggatcc | 420 |
| ggcggtggcg gctccggtgg cggcggatct gaggtgcagc tggtggagtc cggcggcggc | 480 |
| ctggtgcagc ccggccggtc cctgcggctg tcctgcaccg cctccggctc cgacatcaac | 540 |
| gactacccca tcacctgggt gcggcaggcc cccggccagg gcctggagtg gatcggcttc | 600 |
| atcaactccg cggctccac ctggtacgcc tcctgggtga agggccggtt caccatctcc | 660 |
| cgggacgact ccaagtccat cgcctacctg cagatgaact ccctgaagac cgaggacacc | 720 |
| gccgtgtact attgcgcccg gggctactcc acctactacc gggacttcaa catctggggc | 780 |
| cagggcaccc tggtgaccgt gtcctcgagt gagcccaaat cttctgacaa aactcacaca | 840 |
| tgcccaccgt gcccagcacc tgaagccgcg ggtgcaccgt cagtcttcct cttcccccca | 900 |
| aaacccaagg acaccctcat gatctcccgg acccctgagg tcacatgcgt ggtggtggac | 960 |
| gtgagccacg aagaccctga ggtcaagttc aactggtacg tggacggcgt ggaggtgcat | 1020 |
| aatgccaaga caaagccgcg ggaggagcag tacaacagca cgtaccgtgt ggtcagcgtc | 1080 |
| ctcaccgtcc tgcaccagga ctggctgaat ggcaaggaat acaagtgcgc ggtctccaac | 1140 |
| aaagccctcc cagcccccat cgagaaaacc atctccaaag ccaaagggca gccccgagaa | 1200 |
| ccacaggtgt acaccctgcc cccatcccgg gatgagctga ccaagaacca ggtcagcctg | 1260 |
| acctgcctgg tcaaaggctt ctatccaagc gacatcgccg tggagtggga gagcaatggg | 1320 |
| cagccggaga acaactacaa gaccacgcct cccgtgctgg actccgacgg ctccttcttc | 1380 |
| ctctacagca agctcaccgt ggacaagagc aggtggcagc aggggaacgt cttctcatgc | 1440 |
| tccgtgatgc atgaggctct gcacaaccac tacacgcaga agagcctctc cctgtctccg | 1500 |
| ggttctggtg gaggcggttc aggcggaggt ggctccggcg gtggcggatc gccgggctct | 1560 |
| caggtccagc tggtggagtc tggggcgga gtggtgcagc ctgggcggtc actgagctg | 1620 |
| tcctgcaagg cttctggcta cacctttact agatctacga tgcactgggt aaggcaggcc | 1680 |
| cctggacaag gtctggaatg gattggatac attaatccta gcagtgctta ctactaattac | 1740 |
| aatcagaaat tcaaggacag gttcacaatc agcgcagaca atccaagag cacagccttc | 1800 |
| ctgcagatgg acagcctgag gcccgaggac accggcgtct atttctgtgc acggcccaa | 1860 |
| gtccactatg attacaacgg gtttccttac tggggccaag gactcccgt cactgtctct | 1920 |
| agcggtggcg gagggtctgg gggtggcgga tccgaggtg gtgcctctgc acaagacatc | 1980 |
| cagatgaccc agtctccaag cagcctgtct gcaagcgtgg gggacagggt caccatgacc | 2040 |
| tgcagtgcca gctcaagtgt aagttacatg aactggtacc agcagaagcc gggcaaggcc | 2100 |
| cccaaaagat ggatttatga ctcatccaaa ctggcttctg gagtccctgc tcgcttcagt | 2160 |

```
ggcagtgggt ctgggaccga ctataccctc acaatcagca gcctgcagcc cgaagatttc    2220
gccacttatt actgccagca gtggagtcgt aacccaccca cgttcggagg ggggaccaag    2280
ctacaaatta catcctccag c                                              2301
```

<210> SEQ ID NO 216
<211> LENGTH: 767
<212> TYPE: PRT
<213> ORGANISM: Artificial Sequence
<220> FEATURE:
<223> OTHER INFORMATION: ROR208 Anti-ROR1 X anti-CD3 bispecific molecule

<400> SEQUENCE: 216

```
Met Glu Ala Pro Ala Gln Leu Leu Phe Leu Leu Leu Leu Trp Leu Pro
1               5                   10                  15

Asp Thr Thr Gly Asp Ile Gln Met Thr Gln Ser Pro Ser Ser Leu Ser
            20                  25                  30

Ala Ser Val Gly Asp Arg Val Thr Ile Asn Cys Gln Ala Ser Gln Ser
        35                  40                  45

Ile Asp Ser Asn Leu Ala Trp Phe Gln Gln Lys Pro Gly Gln Pro Pro
    50                  55                  60

Lys Leu Leu Ile Tyr Arg Ala Ser Asn Leu Ala Ser Gly Val Pro Asp
65                  70                  75                  80

Arg Phe Ser Gly Ser Gly Ser Gly Thr Asp Phe Thr Leu Thr Ile Ser
                85                  90                  95

Ser Leu Glu Ala Glu Asp Val Ala Thr Tyr Tyr Cys Leu Gly Gly Val
            100                 105                 110

Gly Ala Val Ser Tyr Arg Thr Ser Phe Gly Gly Gly Thr Lys Val Glu
        115                 120                 125

Ile Lys Gly Gly Gly Gly Ser Gly Gly Gly Gly Ser Gly Gly Gly Gly
    130                 135                 140

Ser Gly Gly Gly Gly Ser Glu Val Gln Leu Val Glu Ser Gly Gly Gly
145                 150                 155                 160

Leu Val Gln Pro Gly Arg Ser Leu Arg Leu Ser Cys Thr Ala Ser Gly
                165                 170                 175

Ser Asp Ile Asn Asp Tyr Pro Ile Thr Trp Val Arg Gln Ala Pro Gly
            180                 185                 190

Gln Gly Leu Glu Trp Ile Gly Phe Ile Asn Ser Gly Gly Ser Thr Trp
        195                 200                 205

Tyr Ala Ser Trp Val Lys Gly Arg Phe Thr Ile Ser Arg Asp Asp Ser
    210                 215                 220

Lys Ser Ile Ala Tyr Leu Gln Met Asn Ser Leu Lys Thr Glu Asp Thr
225                 230                 235                 240

Ala Val Tyr Tyr Cys Ala Arg Gly Tyr Ser Thr Tyr Tyr Arg Asp Phe
                245                 250                 255

Asn Ile Trp Gly Gln Gly Thr Leu Val Thr Val Ser Ser Glu Pro
            260                 265                 270

Lys Ser Ser Asp Lys Thr His Thr Cys Pro Pro Cys Pro Ala Pro Glu
        275                 280                 285

Ala Ala Gly Ala Pro Ser Val Phe Leu Phe Pro Pro Lys Pro Lys Asp
    290                 295                 300

Thr Leu Met Ile Ser Arg Thr Pro Glu Val Thr Cys Val Val Val Asp
305                 310                 315                 320

Val Ser His Glu Asp Pro Glu Val Lys Phe Asn Trp Tyr Val Asp Gly
                325                 330                 335
```

-continued

```
Val Glu Val His Asn Ala Lys Thr Lys Pro Arg Glu Glu Gln Tyr Asn
                340                 345                 350
Ser Thr Tyr Arg Val Val Ser Val Leu Thr Val Leu His Gln Asp Trp
            355                 360                 365
Leu Asn Gly Lys Glu Tyr Lys Cys Ala Val Ser Asn Lys Ala Leu Pro
        370                 375                 380
Ala Pro Ile Glu Lys Thr Ile Ser Lys Ala Lys Gly Gln Pro Arg Glu
385                 390                 395                 400
Pro Gln Val Tyr Thr Leu Pro Pro Ser Arg Asp Glu Leu Thr Lys Asn
                405                 410                 415
Gln Val Ser Leu Thr Cys Leu Val Lys Gly Phe Tyr Pro Ser Asp Ile
            420                 425                 430
Ala Val Glu Trp Glu Ser Asn Gly Gln Pro Glu Asn Asn Tyr Lys Thr
        435                 440                 445
Thr Pro Pro Val Leu Asp Ser Asp Gly Ser Phe Phe Leu Tyr Ser Lys
        450                 455                 460
Leu Thr Val Asp Lys Ser Arg Trp Gln Gln Gly Asn Val Phe Ser Cys
465                 470                 475                 480
Ser Val Met His Glu Ala Leu His Asn His Tyr Thr Gln Lys Ser Leu
                485                 490                 495
Ser Leu Ser Pro Gly Ser Gly Gly Gly Ser Gly Gly Gly Gly Ser
            500                 505                 510
Gly Gly Gly Gly Ser Pro Gly Ser Gln Val Gln Leu Val Glu Ser Gly
        515                 520                 525
Gly Gly Val Val Gln Pro Gly Arg Ser Leu Arg Leu Ser Cys Lys Ala
        530                 535                 540
Ser Gly Tyr Thr Phe Thr Arg Ser Thr Met His Trp Val Arg Gln Ala
545                 550                 555                 560
Pro Gly Gln Gly Leu Glu Trp Ile Gly Tyr Ile Asn Pro Ser Ser Ala
                565                 570                 575
Tyr Thr Asn Tyr Asn Gln Lys Phe Lys Asp Arg Phe Thr Ile Ser Ala
            580                 585                 590
Asp Lys Ser Lys Ser Thr Ala Phe Leu Gln Met Asp Ser Leu Arg Pro
        595                 600                 605
Glu Asp Thr Gly Val Tyr Phe Cys Ala Arg Pro Gln Val His Tyr Asp
610                 615                 620
Tyr Asn Gly Phe Pro Tyr Trp Gly Gln Gly Thr Pro Val Thr Val Ser
625                 630                 635                 640
Ser Gly Gly Gly Gly Ser Gly Gly Gly Gly Ser Gly Gly Gly Gly Ser
                645                 650                 655
Ala Gln Asp Ile Gln Met Thr Gln Ser Pro Ser Ser Leu Ser Ala Ser
            660                 665                 670
Val Gly Asp Arg Val Thr Met Thr Cys Ser Ala Ser Ser Ser Val Ser
        675                 680                 685
Tyr Met Asn Trp Tyr Gln Gln Lys Pro Gly Lys Ala Pro Lys Arg Trp
        690                 695                 700
Ile Tyr Asp Ser Ser Lys Leu Ala Ser Gly Val Pro Ala Arg Phe Ser
705                 710                 715                 720
Gly Ser Gly Ser Gly Thr Asp Tyr Thr Leu Thr Ile Ser Ser Leu Gln
                725                 730                 735
Pro Glu Asp Phe Ala Thr Tyr Tyr Cys Gln Gln Trp Ser Arg Asn Pro
            740                 745                 750
Pro Thr Phe Gly Gly Gly Thr Lys Leu Gln Ile Thr Ser Ser Ser
```

<210> SEQ ID NO 217
<211> LENGTH: 2313
<212> TYPE: DNA
<213> ORGANISM: Artificial Sequence
<220> FEATURE:
<223> OTHER INFORMATION: ROR209 Anti-ROR1 X anti-CD3 bispecific molecule

<400> SEQUENCE: 217

| | | | | | |
|---|---|---|---|---|---|
| atggaagcac | cagcgcagct | tctcttcctc | ctgctactct | ggctcccaga | taccaccggt | 60 |
| gacatccaga | tgacccagtc | cccctcctcc | ctgtccgcct | ccgtgggcga | ccgggtgacc | 120 |
| atcaactgcc | aggcctccca | gtccatcgac | tccaacctgg | cctggttcca | gcagaagccc | 180 |
| ggccagcccc | ccaagctgct | gatctaccgg | gcctccaacc | tggcctccgg | cgtgcccgac | 240 |
| cggttctccg | gctccggctc | cggcaccgac | ttcaccctga | ccatctcctc | cctggaggcc | 300 |
| gaggacgtgg | ccacctacta | ctgcctgggc | ggcgtgggcg | ccgtgtccta | ccggacctcc | 360 |
| ttcggcggcg | gcaccaaggt | ggagatcaag | ggtggaggcg | gttcaggcgg | aggtggatcc | 420 |
| ggcggtggcg | gctccgtggg | cggcggatct | gaggtgcagc | tggtggagtc | cggcggcggc | 480 |
| ctggtgcagc | ccggccggtc | cctgcggctg | tcctgcaccg | cctccggctc | cgacatcaac | 540 |
| gactacccca | tcacctgggt | gcggcaggcc | cccggccagg | gcctggagtg | gatcggcttc | 600 |
| atcaactccg | gcggctccac | ctggtacgcc | tctgggtga | agggccggtt | caccatctcc | 660 |
| cgggacgact | ccaagtccat | cgcctacctg | cagatgaact | ccctgaagac | cgaggacacc | 720 |
| gccgtgtact | attgcgcccg | gggctactcc | acctactacc | gggacttcaa | catctggggc | 780 |
| cagggcaccc | tggtgaccgt | gtcctcgagt | gagcccaaat | cttctgacaa | aactcacaca | 840 |
| tgcccaccgt | gcccagcacc | tgaagccgcg | gtgcaccgt | cagtcttcct | cttccccca | 900 |
| aaacccaagg | acaccctcat | gatctcccgg | acccctgagg | tcacatgcgt | ggtggtggac | 960 |
| gtgagccacg | aagaccctga | ggtcaagttc | aactggtacg | tggacggcgt | ggaggtgcat | 1020 |
| aatgccaaga | caaagccgcg | ggaggagcag | tacaacagca | cgtaccgtgt | ggtcagcgtc | 1080 |
| ctcaccgtcc | tgcaccagga | ctggctgaat | ggcaaggaat | acaagtgcgc | ggtctccaac | 1140 |
| aaagccctcc | cagcccccat | cgagaaaacc | atctccaaag | ccaagggca | gccccgagaa | 1200 |
| ccacaggtgt | acaccctgcc | cccatcccgg | gatgagctga | ccaagaacca | ggtcagcctg | 1260 |
| acctgcctgg | tcaaaggctt | ctatccaagc | gacatcgccg | tggagtggga | gagcaatggg | 1320 |
| cagccggaga | acaactacaa | gaccacgcct | cccgtgctgg | actccgacgg | ctccttcttc | 1380 |
| ctctacagca | agctcaccgt | ggacaagagc | aggtggcagc | aggggaacgt | cttctcatgc | 1440 |
| tccgtgatgc | atgaggctct | gcacaaccac | tacacgcaga | agagcctctc | cctgtctccg | 1500 |
| ggttctggtg | gaggcggttc | aggcggaggt | ggctccggcg | gtggcggatc | gccgggctct | 1560 |
| caggtccagc | tggtgcaatc | tgggcctgag | gtgaagaagc | ctgggtcctc | ggtgaaggtc | 1620 |
| tcctgcaagg | cttctggata | taccttcagc | agatctacga | tgcactgggt | gcgacaggcc | 1680 |
| cctggacaag | ggcttgagtg | gataggatac | attaatccta | gcagtgctta | tactaattac | 1740 |
| aatcagaaat | tcaaggacag | agtcacgatt | accgcggaca | aatccacgag | cacagcctac | 1800 |
| atggagctga | gcagcctgag | atctgaggac | acggccgtgt | attactgtgc | gagacccaa | 1860 |
| gtccactatg | attacaacgg | gtttccttac | tggggccaag | gaaccctggt | caccgtctcc | 1920 |
| tcaggtggag | gcggttcagg | cggaggtgga | tccggcggtg | gcggatcggg | tggcggcgga | 1980 |
| tctgacatcc | agatgaccca | gtctccttcc | accctgtctg | catctgtagg | agacagagtc | 2040 |

```
accatgactt gcagtgccag ctcaagtgta agttacatga actggtatca gcagaaacca  2100
gggaaagccc ctaagagatg gatttatgac tcatccaaac tggcttctgg ggtcccatca  2160
aggttcagcg gcagtggatc tgggacagat tatactctca ccatcagcag cctgcagcct  2220
gatgattttg caacttatta ctgccaacag tggagtcgta acccacccac tttcggcgga  2280
gggaccaagg tggagatcaa acggtcctcc agc                                2313
```

<210> SEQ ID NO 218
<211> LENGTH: 771
<212> TYPE: PRT
<213> ORGANISM: Artificial Sequence
<220> FEATURE:
<223> OTHER INFORMATION: ROR209 Anti-ROR1 X anti-CD3 bispecific molecule

<400> SEQUENCE: 218

```
Met Glu Ala Pro Ala Gln Leu Leu Phe Leu Leu Leu Leu Trp Leu Pro
1               5                   10                  15

Asp Thr Thr Gly Asp Ile Gln Met Thr Gln Ser Pro Ser Ser Leu Ser
            20                  25                  30

Ala Ser Val Gly Asp Arg Val Thr Ile Asn Cys Gln Ala Ser Gln Ser
        35                  40                  45

Ile Asp Ser Asn Leu Ala Trp Phe Gln Gln Lys Pro Gly Gln Pro Pro
    50                  55                  60

Lys Leu Leu Ile Tyr Arg Ala Ser Asn Leu Ala Ser Gly Val Pro Asp
65                  70                  75                  80

Arg Phe Ser Gly Ser Gly Ser Gly Thr Asp Phe Thr Leu Thr Ile Ser
                85                  90                  95

Ser Leu Glu Ala Glu Asp Val Ala Thr Tyr Tyr Cys Leu Gly Gly Val
            100                 105                 110

Gly Ala Val Ser Tyr Arg Thr Ser Phe Gly Gly Gly Thr Lys Val Glu
        115                 120                 125

Ile Lys Gly Gly Gly Gly Ser Gly Gly Gly Gly Ser Gly Gly Gly Gly
    130                 135                 140

Ser Gly Gly Gly Gly Ser Glu Val Gln Leu Val Glu Ser Gly Gly Gly
145                 150                 155                 160

Leu Val Gln Pro Gly Arg Ser Leu Arg Leu Ser Cys Thr Ala Ser Gly
                165                 170                 175

Ser Asp Ile Asn Asp Tyr Pro Ile Thr Trp Val Arg Gln Ala Pro Gly
            180                 185                 190

Gln Gly Leu Glu Trp Ile Gly Phe Ile Asn Ser Gly Gly Ser Thr Trp
        195                 200                 205

Tyr Ala Ser Trp Val Lys Gly Arg Phe Thr Ile Ser Arg Asp Asp Ser
    210                 215                 220

Lys Ser Ile Ala Tyr Leu Gln Met Asn Ser Leu Lys Thr Glu Asp Thr
225                 230                 235                 240

Ala Val Tyr Tyr Cys Ala Arg Gly Tyr Ser Thr Tyr Tyr Arg Asp Phe
                245                 250                 255

Asn Ile Trp Gly Gln Gly Thr Leu Val Thr Val Ser Ser Glu Pro
            260                 265                 270

Lys Ser Ser Asp Lys Thr His Thr Cys Pro Pro Cys Pro Ala Pro Glu
        275                 280                 285

Ala Ala Gly Ala Pro Ser Val Phe Leu Phe Pro Pro Lys Pro Lys Asp
    290                 295                 300

Thr Leu Met Ile Ser Arg Thr Pro Glu Val Thr Cys Val Val Val Asp
```

```
                305                 310                 315                 320
            Val Ser His Glu Asp Pro Glu Val Lys Phe Asn Trp Tyr Val Asp Gly
                        325                 330                 335

Val Glu Val His Asn Ala Lys Thr Lys Pro Arg Glu Glu Gln Tyr Asn
                        340                 345                 350

Ser Thr Tyr Arg Val Val Ser Val Leu Thr Val Leu His Gln Asp Trp
                        355                 360                 365

Leu Asn Gly Lys Glu Tyr Lys Cys Ala Val Ser Asn Lys Ala Leu Pro
                370                 375                 380

Ala Pro Ile Glu Lys Thr Ile Ser Lys Ala Lys Gly Gln Pro Arg Glu
            385                 390                 395                 400

Pro Gln Val Tyr Thr Leu Pro Pro Ser Arg Asp Glu Leu Thr Lys Asn
                        405                 410                 415

Gln Val Ser Leu Thr Cys Leu Val Lys Gly Phe Tyr Pro Ser Asp Ile
                        420                 425                 430

Ala Val Glu Trp Glu Ser Asn Gly Gln Pro Glu Asn Asn Tyr Lys Thr
                        435                 440                 445

Thr Pro Pro Val Leu Asp Ser Asp Gly Ser Phe Phe Leu Tyr Ser Lys
                450                 455                 460

Leu Thr Val Asp Lys Ser Arg Trp Gln Gln Gly Asn Val Phe Ser Cys
            465                 470                 475                 480

Ser Val Met His Glu Ala Leu His Asn His Tyr Thr Gln Lys Ser Leu
                        485                 490                 495

Ser Leu Ser Pro Gly Ser Gly Gly Gly Ser Gly Gly Gly Gly Ser
                        500                 505                 510

Gly Gly Gly Gly Ser Pro Gly Ser Gln Val Gln Leu Val Gln Ser Gly
                        515                 520                 525

Pro Glu Val Lys Lys Pro Gly Ser Ser Val Lys Val Ser Cys Lys Ala
                        530                 535                 540

Ser Gly Tyr Thr Phe Ser Arg Ser Thr Met His Trp Val Arg Gln Ala
            545                 550                 555                 560

Pro Gly Gln Gly Leu Glu Trp Ile Gly Tyr Ile Asn Pro Ser Ser Ala
                        565                 570                 575

Tyr Thr Asn Tyr Asn Gln Lys Phe Lys Asp Arg Val Thr Ile Thr Ala
                        580                 585                 590

Asp Lys Ser Thr Ser Thr Ala Tyr Met Glu Leu Ser Ser Leu Arg Ser
                        595                 600                 605

Glu Asp Thr Ala Val Tyr Tyr Cys Ala Arg Pro Gln Val His Tyr Asp
                        610                 615                 620

Tyr Asn Gly Phe Pro Tyr Trp Gly Gln Gly Thr Leu Val Thr Val Ser
            625                 630                 635                 640

Ser Gly Gly Gly Gly Ser Gly Gly Gly Ser Gly Gly Gly Gly Ser
                        645                 650                 655

Gly Gly Gly Gly Ser Asp Ile Gln Met Thr Gln Ser Pro Ser Thr Leu
                        660                 665                 670

Ser Ala Ser Val Gly Asp Arg Val Thr Met Thr Cys Ser Ala Ser Ser
                        675                 680                 685

Ser Val Ser Tyr Met Asn Trp Tyr Gln Gln Lys Pro Gly Lys Ala Pro
                        690                 695                 700

Lys Arg Trp Ile Tyr Asp Ser Ser Lys Leu Ala Ser Gly Val Pro Ser
            705                 710                 715                 720

Arg Phe Ser Gly Ser Gly Ser Gly Thr Asp Tyr Thr Leu Thr Ile Ser
                        725                 730                 735
```

```
Ser Leu Gln Pro Asp Asp Phe Ala Thr Tyr Tyr Cys Gln Gln Trp Ser
            740                 745                 750

Arg Asn Pro Pro Thr Phe Gly Gly Gly Thr Lys Val Glu Ile Lys Arg
        755                 760                 765

Ser Ser Ser
    770

<210> SEQ ID NO 219
<211> LENGTH: 2313
<212> TYPE: DNA
<213> ORGANISM: Artificial Sequence
<220> FEATURE:
<223> OTHER INFORMATION: ROR231 Anti-ROR1 X anti-CD3 bispecific molecule

<400> SEQUENCE: 219
atggaggcac ccgcccagct gctgttcttg ttgctgctgt ggctccctga taccaccgga      60
gacatccaga tgacccaatc cccttctagt ctctccgcta gcgtcggaga ccgcgtgacc     120
atcaattgtc aagcatctca gagtattgac agcaatctcg cctggtttca gcagaagcca     180
ggaaagccac ccaagctcct gatttatagg gctagcaacc tggcttctgg tgtccctagt     240
aggttcagcg gctctgggag tggcacagac ttcaccctga ccattagtag tctgcagccc     300
gaagatgtcg ctacctatta ctgcctcgga ggagtgggtg ccgtttctta tcgcacctca     360 tttgaggtg gcaccaaagt ggagatcaaa ggtggtggcg ctccggggg tggcgggtca     420 ggggggggag ggtctggagg cggcggatca gaagttcagc tggtggaatc tggaggaggt     480
ctggtgcagc caggcaggtc cctccggctg agctgcactg catccggctc tgacattaat     540
gactacccta tcacctgggt gaggcaggcc ccggtaaag gcctggagtg gatcgggttc     600
atcaattctg gtggatctac ttggtacgca agctgggtga aggacgctt cacaattagt     660 agagacgact ctaagtctat cgcatatctg cagatgaata gcttgaagac agaggacacc     720
gccgtgtact attgtgcaag aggatactcc acttactacc gcgatttcaa tatctggggc     780
cagggaaccc tggtgacagt gtcctcgagt gagcccaaat cttctgacaa aactcacaca     840
tgcccaccgt gcccagcacc tgaagccgcg gtgcaccgt cagtcttcct cttccccca      900 aaacccaagg acaccctcat gatctcccgg acccctgagg tcacatgcgt ggtggtggac     960
gtgagccacg aagaccctga ggtcaagttc aactggtacg tggacggcgt ggaggtgcat    1020
aatgccaaga caaagccgcg ggaggagcag tacaacagca cgtaccgtgt ggtcagcgtc    1080
ctcaccgtcc tgcaccagga ctggctgaat ggcaaggaat acaagtgcgc ggtctccaac    1140
aaagccctcc cagcccccat cgagaaaacc atctccaaag ccaaagggca gccccgagaa    1200
ccacaggtgt acaccctgcc cccatcccgg gatgagctga ccaagaacca ggtcagcctg    1260
acctgcctgg tcaaaggctt ctatccaagc gacatcgccg tggagtggga gagcaatggg    1320
cagccggaga acaactacaa gaccacgcct cccgtgctgg actccgacgg ctccttcttc    1380
ctctacagca agctcaccgt ggacaagagc aggtggcagc aggggaacgt cttctcatgc    1440
tccgtgatgc atgaggctct gcacaaccac tacacgcaga agagcctctc cctgtctccg    1500
ggttccggag cgcggctc cggcggcgg ggcagcggcg cggcggcag ccccggatcc    1560 caggtgcagc tggtgcagtc tggtcctgag gtgaaaaagc ctggctccag cgtgaaggtg    1620
tcctgcaagg ccagcggata cacctttagc cggtccacca tgcattggt gaggcaggct    1680 cctggacagg gcctggagtg gatcggctac atcaacccca gcagcgctta taccaactac    1740
aatcagaagt ttaaggaccg ggtgaccatc accgccgata agtccaccag caccgcctac    1800
```

```
atggagctgt ccagcctgag gagcgaggat accgccgtgt actattgcgc ccggccccag    1860
gtccattacg actacaacgg cttcccctat tggggccagg gaaccctggt gaccgtgtcc    1920
agcggaggcg gcggcagcgg cggcggcggc agcggcggag gaggcagcgg cggaggaggc    1980
tccgacattc agatgaccca gtccccctcc accctgtccg ctagcgtggg cgatcgggtg    2040
accatgacct gcagcgccag cagctccgtg tcctacatga actggtacca gcagaagccc    2100
ggcaaggctc ccaagaggtg gatttacgac tccagcaagc tggcctctgg tgtccccagc    2160
aggttctctg gtagcggcag cggcacagac tacaccctga ccatctcctc cctgcagccc    2220
gacgatttcg ccacctacta ttgccagcag tggtcccgga tcccccctac ctttggcggc    2280
ggcaccaagg tggagatcaa gaggagctcc agc                                 2313
```

<210> SEQ ID NO 220
<211> LENGTH: 771
<212> TYPE: PRT
<213> ORGANISM: Artificial Sequence
<220> FEATURE:
<223> OTHER INFORMATION: ROR231 Anti-ROR1 X anti-CD3 bispecific molecule

<400> SEQUENCE: 220

```
Met Glu Ala Pro Ala Gln Leu Leu Phe Leu Leu Leu Leu Trp Leu Pro
1               5                   10                  15

Asp Thr Thr Gly Asp Ile Gln Met Thr Gln Ser Pro Ser Ser Leu Ser
            20                  25                  30

Ala Ser Val Gly Asp Arg Val Thr Ile Asn Cys Gln Ala Ser Gln Ser
        35                  40                  45

Ile Asp Ser Asn Leu Ala Trp Phe Gln Gln Lys Pro Gly Lys Pro Pro
    50                  55                  60

Lys Leu Leu Ile Tyr Arg Ala Ser Asn Leu Ala Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Val Ala Thr Tyr Tyr Cys Leu Gly Gly Val
            100                 105                 110

Gly Ala Val Ser Tyr Arg Thr Ser Phe Gly Gly Gly Thr Lys Val Glu
        115                 120                 125

Ile Lys Gly Gly Gly Gly Ser Gly Gly Gly Gly Ser Gly Gly Gly Gly
    130                 135                 140

Ser Gly Gly Gly Gly Ser Glu Val Gln Leu Val Glu Ser Gly Gly Gly
145                 150                 155                 160

Leu Val Gln Pro Gly Arg Ser Leu Arg Leu Ser Cys Thr Ala Ser Gly
                165                 170                 175

Ser Asp Ile Asn Asp Tyr Pro Ile Thr Trp Val Arg Gln Ala Pro Gly
            180                 185                 190

Lys Gly Leu Glu Trp Ile Gly Phe Ile Asn Ser Gly Gly Ser Thr Trp
        195                 200                 205

Tyr Ala Ser Trp Val Lys Gly Arg Phe Thr Ile Ser Arg Asp Asp Ser
    210                 215                 220

Lys Ser Ile Ala Tyr Leu Gln Met Asn Ser Leu Lys Thr Glu Asp Thr
225                 230                 235                 240

Ala Val Tyr Tyr Cys Ala Arg Gly Tyr Ser Thr Tyr Tyr Arg Asp Phe
                245                 250                 255

Asn Ile Trp Gly Gln Gly Thr Leu Val Thr Val Ser Ser Ser Glu Pro
            260                 265                 270
```

```
Lys Ser Ser Asp Lys Thr His Thr Cys Pro Cys Pro Ala Pro Glu
    275                 280                 285

Ala Ala Gly Ala Pro Ser Val Phe Leu Phe Pro Pro Lys Pro Lys Asp
    290                 295                 300

Thr Leu Met Ile Ser Arg Thr Pro Glu Val Thr Cys Val Val Val Asp
305                 310                 315                 320

Val Ser His Glu Asp Pro Glu Val Lys Phe Asn Trp Tyr Val Asp Gly
                325                 330                 335

Val Glu Val His Asn Ala Lys Thr Lys Pro Arg Glu Glu Gln Tyr Asn
            340                 345                 350

Ser Thr Tyr Arg Val Val Ser Val Leu Thr Val Leu His Gln Asp Trp
        355                 360                 365

Leu Asn Gly Lys Glu Tyr Lys Cys Ala Val Ser Asn Lys Ala Leu Pro
    370                 375                 380

Ala Pro Ile Glu Lys Thr Ile Ser Lys Ala Lys Gly Gln Pro Arg Glu
385                 390                 395                 400

Pro Gln Val Tyr Thr Leu Pro Pro Ser Arg Asp Glu Leu Thr Lys Asn
                405                 410                 415

Gln Val Ser Leu Thr Cys Leu Val Lys Gly Phe Tyr Pro Ser Asp Ile
            420                 425                 430

Ala Val Glu Trp Glu Ser Asn Gly Gln Pro Glu Asn Asn Tyr Lys Thr
        435                 440                 445

Thr Pro Pro Val Leu Asp Ser Asp Gly Ser Phe Phe Leu Tyr Ser Lys
    450                 455                 460

Leu Thr Val Asp Lys Ser Arg Trp Gln Gln Gly Asn Val Phe Ser Cys
465                 470                 475                 480

Ser Val Met His Glu Ala Leu His Asn His Tyr Thr Gln Lys Ser Leu
                485                 490                 495

Ser Leu Ser Pro Gly Ser Gly Gly Gly Ser Gly Gly Gly Gly Ser
            500                 505                 510

Gly Gly Gly Gly Ser Pro Gly Ser Gln Val Gln Leu Val Gln Ser Gly
        515                 520                 525

Pro Glu Val Lys Lys Pro Gly Ser Ser Val Lys Val Ser Cys Lys Ala
    530                 535                 540

Ser Gly Tyr Thr Phe Ser Arg Ser Thr Met His Trp Val Arg Gln Ala
545                 550                 555                 560

Pro Gly Gln Gly Leu Glu Trp Ile Gly Tyr Ile Asn Pro Ser Ser Ala
                565                 570                 575

Tyr Thr Asn Tyr Asn Gln Lys Phe Lys Asp Arg Val Thr Ile Thr Ala
            580                 585                 590

Asp Lys Ser Thr Ser Thr Ala Tyr Met Glu Leu Ser Ser Leu Arg Ser
        595                 600                 605

Glu Asp Thr Ala Val Tyr Tyr Cys Ala Arg Pro Gln Val His Tyr Asp
    610                 615                 620

Tyr Asn Gly Phe Pro Tyr Trp Gly Gln Gly Thr Leu Val Thr Val Ser
625                 630                 635                 640

Ser Gly Gly Gly Gly Ser Gly Gly Gly Gly Ser Gly Gly Gly Gly Ser
                645                 650                 655

Gly Gly Gly Gly Ser Asp Ile Gln Met Thr Gln Ser Pro Ser Thr Leu
            660                 665                 670

Ser Ala Ser Val Gly Asp Arg Val Thr Met Thr Cys Ser Ala Ser Ser
        675                 680                 685
```

```
Ser Val Ser Tyr Met Asn Trp Tyr Gln Gln Lys Pro Gly Lys Ala Pro
    690             695                 700

Lys Arg Trp Ile Tyr Asp Ser Ser Lys Leu Ala Ser Gly Val Pro Ser
705             710                 715                 720

Arg Phe Ser Gly Ser Gly Ser Gly Thr Asp Tyr Thr Leu Thr Ile Ser
                725                 730                 735

Ser Leu Gln Pro Asp Asp Phe Ala Thr Tyr Tyr Cys Gln Gln Trp Ser
            740                 745                 750

Arg Asn Pro Pro Thr Phe Gly Gly Gly Thr Lys Val Glu Ile Lys Arg
            755                 760                 765

Ser Ser Ser
    770

<210> SEQ ID NO 221
<211> LENGTH: 2313
<212> TYPE: DNA
<213> ORGANISM: Artificial Sequence
<220> FEATURE:
<223> OTHER INFORMATION: ROR233 Anti-ROR1 X anti-CD3 bispecific molecule

<400> SEQUENCE: 221
atggaggctc cgctcagct gctgttcctc ctgctgctct ggctgcccga caccacaggc      60
gacatccaga tgacccagtc cccttcctcc ctgtccgcta gcgtgggcga tagggtgacc     120
atcaactgcc aggcctccca gtccattgac tccaatctgg cctggttcca gcagaagccc     180
ggacagcccc ccaagctgct gatttacagg gcctccaacc tggcttccgg cgtgcctgac     240
aggttctccg gatccggcag cggcaccgac ttcaccctga ccatctcctc cctggaggcc     300
gaggatgtcg ccacctacta ctgtctgggc ggcgtgggcg ctgtgagcta tcggacctcc     360
ttcggcggcg gcaccaaggt ggagatcaag ggcggcggcg gcagcggcgg cggcggcagc     420
ggcggcggag gctccggcgg cggcggcagc gaggtgcagc tggtggaaag cggaggaggc     480
ctggtgcagc ctggaaggtc cctgaggctg tcctgcacag ccagcggctc cgacatcaac     540
gactacccca tcacctgggt gaggcaggct cctggccagg gcctggaatg gatcggcttt     600
atcaacagcg gcggcagcac ctggtatgct tcctgggtga agggccggtt caccattagc     660
agggacgact ccaagtccat tgcctacctg cagatgaact ccctgaagac cgaggacacc     720
gccgtgtact actgcgccag ggctacagc acctattacc gggactttaa catctggggc     780
cagggcacac tggtcaccgt gtcctcgagt gagcccaaat cttctgacaa aactcacaca     840
tgcccaccgt gcccagcacc tgaagccgcg gtgcaccgt cagtcttcct cttcccccca     900
aaacccaagg acaccctcat gatctcccgg accccctgagg tcacatgcgt ggtggtggac     960
gtgagccacg aagaccctga ggtcaagttc aactggtacg tggacggcgt ggaggtgcat    1020
aatgccaaga caaagccgcg ggaggagcag tacaacagca cgtaccgtgt ggtcagcgtc    1080
ctcaccgtcc tgcaccagga ctggctgaat ggcaaggaat acaagtgcgc ggtctccaac    1140
aaagccctcc cagccccat cgagaaaacc atctccaaag ccaagggca gccccgagaa      1200 ccacaggtgt acaccctgcc cccatcccgg gatgagctga ccaagaacca ggtcagcctg    1260
acctgcctgg tcaaaggctt ctatccaagc gacatcgccg tggagtggga gagcaatggg    1320
cagccggaga acaactacaa gaccacgcct cccgtgctgg actccgacgg ctccttcttc    1380
ctctacagca agctcaccgt ggacaagagc aggtggcagc aggggaacgt cttctcatgc    1440
tccgtgatgc atgaggctct gcacaaccac tacacgcaga gagcctctc cctgtctccg    1500 ggttccggag gcggcggctc cggcggcggc ggcagcggcg gcggcggcag ccccggatcc    1560
```

```
caggtgcagc tggtgcagtc tggtcctgag gtgaaaaagc ctggctccag cgtgaaggtg    1620
tcctgcaagg ccagcggata cacctttagc cggtccacca tgcattgggt gaggcaggct    1680
cctggacagg gcctggagtg gatcggctac atcaacccca gcagcgctta taccaactac    1740
aatcagaagt ttaaggaccg ggtgaccatc accgccgata gtccaccag caccgcctac    1800 atggagctgt ccagcctgag gagcgaggat accgccgtgt actattgcgc cggccccag    1860 gtccattacg actacaacgg cttcccctat tggggccagg gaaccctggt gaccgtgtcc    1920
agcggaggcg gcggcagcgg cggcggcggc agcggcggag gaggcagcgg cggaggaggc    1980
tccgacattc agatgaccca gtccccctcc accctgtccg ctagcgtggg cgatcgggtg    2040
accatgacct gcagcgccag cagctccgtg tcctacatga actggtacca gcagaagccc    2100
ggcaaggctc ccaagaggtg gatttacgac tccagcaagc tggcctctgg tgtccccagc    2160
aggttctctg gtagcggcag cggcacagac tacaccctga ccatctcctc cctgcagccc    2220
gacgatttcg ccacctacta ttgccagcag tggtcccgga atccccctac ctttggcggc    2280
ggcaccaagg tggagatcaa gaggagctcc agc                                 2313
```

<210> SEQ ID NO 222
<211> LENGTH: 771
<212> TYPE: PRT
<213> ORGANISM: Artificial Sequence
<220> FEATURE:
<223> OTHER INFORMATION: ROR233 Anti-ROR1 X anti-CD3 bispecific molecule

<400> SEQUENCE: 222

```
Met Glu Ala Pro Ala Gln Leu Leu Phe Leu Leu Leu Leu Trp Leu Pro
1               5                   10                  15

Asp Thr Thr Gly Asp Ile Gln Met Thr Gln Ser Pro Ser Ser Leu Ser
            20                  25                  30

Ala Ser Val Gly Asp Arg Val Thr Ile Asn Cys Gln Ala Ser Gln Ser
        35                  40                  45

Ile Asp Ser Asn Leu Ala Trp Phe Gln Gln Lys Pro Gly Gln Pro Pro
    50                  55                  60

Lys Leu Leu Ile Tyr Arg Ala Ser Asn Leu Ala Ser Gly Val Pro Asp
65                  70                  75                  80

Arg Phe Ser Gly Ser Gly Ser Gly Thr Asp Phe Thr Leu Thr Ile Ser
                85                  90                  95

Ser Leu Glu Ala Glu Asp Val Ala Thr Tyr Tyr Cys Leu Gly Gly Val
            100                 105                 110

Gly Ala Val Ser Tyr Arg Thr Ser Phe Gly Gly Gly Thr Lys Val Glu
        115                 120                 125

Ile Lys Gly Gly Gly Gly Ser Gly Gly Gly Ser Gly Gly Gly Gly
    130                 135                 140

Ser Gly Gly Gly Gly Ser Glu Val Gln Leu Val Glu Ser Gly Gly Gly
145                 150                 155                 160

Leu Val Gln Pro Gly Arg Ser Leu Arg Leu Ser Cys Thr Ala Ser Gly
                165                 170                 175

Ser Asp Ile Asn Asp Tyr Pro Ile Thr Trp Val Arg Gln Ala Pro Gly
            180                 185                 190

Gln Gly Leu Glu Trp Ile Gly Phe Ile Asn Ser Gly Gly Ser Thr Trp
        195                 200                 205

Tyr Ala Ser Trp Val Lys Gly Arg Phe Thr Ile Ser Arg Asp Asp Ser
    210                 215                 220
```

```
Lys Ser Ile Ala Tyr Leu Gln Met Asn Ser Leu Lys Thr Glu Asp Thr
225                 230                 235                 240

Ala Val Tyr Tyr Cys Ala Arg Gly Tyr Ser Thr Tyr Tyr Arg Asp Phe
            245                 250                 255

Asn Ile Trp Gly Gln Gly Thr Leu Val Thr Val Ser Ser Glu Pro
        260                 265                 270

Lys Ser Ser Asp Lys Thr His Thr Cys Pro Pro Cys Pro Ala Pro Glu
    275                 280                 285

Ala Ala Gly Ala Pro Ser Val Phe Leu Phe Pro Pro Lys Pro Lys Asp
    290                 295                 300

Thr Leu Met Ile Ser Arg Thr Pro Glu Val Thr Cys Val Val Val Asp
305                 310                 315                 320

Val Ser His Glu Asp Pro Glu Val Lys Phe Asn Trp Tyr Val Asp Gly
            325                 330                 335

Val Glu Val His Asn Ala Lys Thr Lys Pro Arg Glu Glu Gln Tyr Asn
            340                 345                 350

Ser Thr Tyr Arg Val Val Ser Val Leu Thr Val Leu His Gln Asp Trp
        355                 360                 365

Leu Asn Gly Lys Glu Tyr Lys Cys Ala Val Ser Asn Lys Ala Leu Pro
    370                 375                 380

Ala Pro Ile Glu Lys Thr Ile Ser Lys Ala Lys Gly Gln Pro Arg Glu
385                 390                 395                 400

Pro Gln Val Tyr Thr Leu Pro Pro Ser Arg Asp Glu Leu Thr Lys Asn
            405                 410                 415

Gln Val Ser Leu Thr Cys Leu Val Lys Gly Phe Tyr Pro Ser Asp Ile
        420                 425                 430

Ala Val Glu Trp Glu Ser Asn Gly Gln Pro Glu Asn Asn Tyr Lys Thr
    435                 440                 445

Thr Pro Pro Val Leu Asp Ser Asp Gly Ser Phe Phe Leu Tyr Ser Lys
    450                 455                 460

Leu Thr Val Asp Lys Ser Arg Trp Gln Gln Gly Asn Val Phe Ser Cys
465                 470                 475                 480

Ser Val Met His Glu Ala Leu His Asn His Tyr Thr Gln Lys Ser Leu
            485                 490                 495

Ser Leu Ser Pro Gly Ser Gly Gly Gly Ser Gly Gly Gly Gly Ser
        500                 505                 510

Gly Gly Gly Ser Pro Gly Ser Gln Val Gln Leu Val Gln Ser Gly
    515                 520                 525

Pro Glu Val Lys Lys Pro Gly Ser Ser Val Lys Val Ser Cys Lys Ala
530                 535                 540

Ser Gly Tyr Thr Phe Ser Arg Ser Thr Met His Trp Val Arg Gln Ala
545                 550                 555                 560

Pro Gly Gln Gly Leu Glu Trp Ile Gly Tyr Ile Asn Pro Ser Ser Ala
            565                 570                 575

Tyr Thr Asn Tyr Asn Gln Lys Phe Lys Asp Arg Val Thr Ile Thr Ala
            580                 585                 590

Asp Lys Ser Thr Ser Thr Ala Tyr Met Glu Leu Ser Ser Leu Arg Ser
            595                 600                 605

Glu Asp Thr Ala Val Tyr Tyr Cys Ala Arg Pro Gln Val His Tyr Asp
            610                 615                 620

Tyr Asn Gly Phe Pro Tyr Trp Gly Gln Gly Thr Leu Val Thr Val Ser
625                 630                 635                 640

Ser Gly Gly Gly Gly Ser Gly Gly Gly Gly Ser Gly Gly Gly Gly Ser
```

-continued

```
                645                 650                 655
Gly Gly Gly Gly Ser Asp Ile Gln Met Thr Gln Ser Pro Ser Thr Leu
            660                 665                 670

Ser Ala Ser Val Gly Asp Arg Val Thr Met Thr Cys Ser Ala Ser Ser
        675                 680                 685

Ser Val Ser Tyr Met Asn Trp Tyr Gln Gln Lys Pro Gly Lys Ala Pro
    690                 695                 700

Lys Arg Trp Ile Tyr Asp Ser Ser Lys Leu Ala Ser Gly Val Pro Ser
705                 710                 715                 720

Arg Phe Ser Gly Ser Gly Ser Gly Thr Asp Tyr Thr Leu Thr Ile Ser
                725                 730                 735

Ser Leu Gln Pro Asp Asp Phe Ala Thr Tyr Tyr Cys Gln Gln Trp Ser
            740                 745                 750

Arg Asn Pro Pro Thr Phe Gly Gly Gly Thr Lys Val Glu Ile Lys Arg
        755                 760                 765

Ser Ser Ser
    770
```

CD3 BINDING POLYPEPTIDES

This application is a 35 U.S.C. § 371 National Phase Entry of International Patent Application No. PCT/US2016/052942, filed on Sep. 21, 2016, which claims priority to and benefit of U.S. Provisional Patent Application No. 62/221,190, filed on Sep. 21, 2015. The contents of each of these applications are herein incorporated by reference in their entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: APVO-052_01US_SubSeqList_ST25.txt, date recorded: Jul. 31, 2020, file size ~557,928 bytes).

FIELD OF THE DISCLOSURE

The present disclosure relates to molecules that specifically bind to CD3, which may have at least one humanized CD3-binding domain. A protein therapeutic binding to CD3 may be a monospecific protein therapeutic or a multispecific protein therapeutic. A multspecific protein therapeutic may bind both a tumor antigen and CD3 subunits of the T-cell receptor complex on T-cells to induce target-dependent T-cell cytotoxicity, activation and proliferation.

BACKGROUND OF THE DISCLOSURE

Targeting the T-cell receptor complex (TCR) on human T-cells with anti-CD3 antibodies has been proposed for treatment of autoimmune disease and related disorders, such as for treatment of organ allograft rejection. In addition to monospecific therapeutics that target CD3, multispecific polypeptides that bind selectively to both T-cells and tumor cells could offer a mechanism to redirect T-cell cytotoxicity towards the tumor cells. Such multispecific polypeptides may be useful for treatment of cancer.

Clinical use of some anti-CD3 antibodies has been hampered by serious side effects. For example, OKT3, a mouse monoclonal antibody specific for human CD3, induced T-cell proliferation and cytokine production in vitro and led to a large scale release of cytokine in vivo (Hirsch et al. (1989) J. Immunol 142: 737-43). The cytokine release (also referred to as "cytokine storm") in turn led to a "flu-like" syndrome, characterized by fever, chills, headaches, nausea, vomiting, diarrhea, respiratory distress, septic meningitis and hypotension (Chatenoud (2003) Nature Reviews 3:123-132).

There is a need for CD3-binding molecules that have improved thermal stability with a favorable manufacturability profile and reduced adverse effects.

SUMMARY OF THE DISCLOSURE

The disclosure encompasses CD3-binding domains and polypeptides that have an advantageous manufacturability profile. Polypeptides comprising CD3-binding domains disclosed herein may be thermally stable. In some cases, a polypeptide has an improved thermal stability compared to another CD3-binding polypeptide. CD3-binding domains and polypeptides disclosed herein may have reduced side effects (for example, may lead to release of low levels of cytokines when administered to a subject).

In certain embodiments, the disclosure relates to a CD3-binding domain that binds specifically to human CD3 and that comprises an immunoglobulin light chain variable region and an immunoglobulin heavy chain variable region; wherein the immunoglobulin light chain variable region comprises an amino acid sequence that is (a) at least about 93% identical, at least about 95% identical, at least about 97% identical, at least about 98% identical or at least about 99% identical to the amino acid sequence in SEQ ID NO:88; or (b) at least about 94% identical, at least about 95% identical, at least about 97% identical, at least about 98% identical or at least about 99% identical to the amino acid sequence in SEQ ID NO:89; and wherein the immunoglobulin heavy chain variable region comprises an amino acid sequence that is at least about 82% identical, at least about 85% identical, at least about 87% identical, at least about 90% identical, at least about 92% identical, at least about 95% identical, at least about 97% identical, at least about 98% identical or at least about 99% identical to the amino acid sequence in SEQ ID NO:86. A CD3-binding domain may comprise an amino acid sequence that is at least about 87% identical, at least about 90% identical, at least about 92% identical, at least about 95% identical, at least about 97% identical, at least about 98% identical or at least about 99% identical to the amino acid sequence in SEQ ID NO:83 or SEQ ID NO:84. A CD3-binding domain may comprise SEQ ID NO:83 or SEQ ID NO:84.

In one embodiment, a CD3-binding domain comprises an immunoglobulin light chain variable region that comprises an LCDR1 amino acid sequence of SEQ ID NO:94, an LCDR2 amino acid sequence of SEQ ID NO:95, and an LCDR3 amino acid sequence of SEQ ID NO:96 and an immunoglobulin heavy chain variable region that comprises an HCDR1 amino acid sequence of SEQ ID NO:91, an HCDR2 amino acid sequence of SEQ ID NO:92, and an HCDR3 amino acid sequence of SEQ ID NO:93. In another embodiment, a CD3-binding domain comprises an immunoglobulin light chain variable region that comprises an LCDR1 amino acid sequence of SEQ ID NO:202, an LCDR2 amino acid sequence of SEQ ID NO:203, and an LCDR3 amino acid sequence of SEQ ID NO:204 and an immunoglobulin heavy chain variable region that comprises an HCDR1 amino acid sequence of SEQ ID NO:199, an HCDR2 amino acid sequence of SEQ ID NO:200, and an HCDR3 amino acid sequence of SEQ ID NO:201.

In certain aspects, a CD3-binding domain may comprise an immunoglobulin light chain variable region and an immunoglobulin heavy chain variable region that comprise framework regions and at least one of the immunoglobulin light chain variable region and the immunoglobulin heavy chain variable region may be humanized. In one embodiment, an immunoglobulin light chain variable region comprises framework regions based on the human IGKV3D-20*1 germline amino acid sequence. In another embodiment, an immunoglobulin heavy chain variable region comprises framework regions based on the human IGHV1-69*02 germline amino acid sequence.

In some embodiments, the amino acid residue at position 52 according to the IMGT numbering system of the immunoglobulin light chain variable region of a CD3-binding domain is arginine and/or the amino acid residue at position 53 according to the IMGT numbering system of the immunoglobulin light chain variable region of a CD3-binding domain is tryptophan. The amino acid residue at position 27 according to the IMGT numbering system of the immunoglobulin heavy chain variable region of a CD3-binding domain may be tyrosine. In some embodiments, a CD3- binding domain comprises one or more of the following: (a) the amino acid residue at position 9 according to the IMGT numbering system of the immunoglobulin heavy chain variable region is proline; (b) the amino acid residue at position 53 according to the IMGT numbering system of the immunoglobulin heavy chain variable region is isoleucine; and (c) the amino acid residue at position 21 according to the IMGT numbering system of the immunoglobulin light chain variable region is methionine. The amino acid residue at position 87 according to the IMGT numbering system of the immunoglobulin light chain variable region of a CD3-binding domain may be tyrosine. The amino acid residue at position 86 according to the IMGT numbering system of the immunoglobulin light chain variable region of a CD3-binding domain may be aspartic acid. In one embodiment, the amino acid residue at position 86 according to the IMGT numbering system of the immunoglobulin light chain variable region of a CD3-binding domain is aspartic acid and the amino acid residue at position 87 according to the IMGT numbering system of the immunoglobulin light chain variable region of a CD3-binding domain is tyrosine.

The disclosure encompasses a CD3-binding domain that is a single chain variable fragment (scFv). In some aspects, an scFv may comprise a linker between the heavy chain variable region and the light chain variable region. In one embodiment, a linker between the heavy chain variable region and the light chain variable region comprises the amino acid sequence QRHNNSSLNTGTQMAGHSPNS (SEQ ID NO:148). In some embodiments, the heavy chain variable region of an scFv is amino-terminal to the light chain variable region of the scFv. In other embodiments, the light chain variable region of an scFv is amino-terminal to the heavy chain variable region of the scFv.

The disclosure encompasses a CD3-binding domain that has a thermal stability that is increased at least about 10% when compared to the thermal stability of a CD3-binding domain comprising a light chain variable region comprising SEQ ID NO:90 and a heavy chain variable region comprising SEQ ID NO:87. The thermal transition midpoint (Tm) of a CD3-binding domain may be increased at least about 3° C., at least about 4° C., at least about 5° C., or at least about 6° C. increased and up to about 20° C. when compared to the Tm of a CD3-binding domain comprising a light chain variable region comprising SEQ ID NO:90 and a heavy chain variable region comprising SEQ ID NO:87. The thermal transition midpoint of a CD3-binding domain may be at least about 54° C., at least about 55° C., at least about 56° C., or at least about 57° C. and up to about 72° C. The thermal stability or the thermal transition midpoint of a CD3-binding domain may be measured by differential scanning calorimetry or differential scanning fluorimetry.

A CD3-binding domain as disclosed herein may have storage stability that is increased at least about 5%, at least about 10%, at least about 20%, at least about 30%, at least about 40%, at least about 50%, at least about 60%, at least about 70%, at least about 80%, at least about 90% and up to about 100% when compared to the storage stability of a CD3-binding domain comprising a light chain variable region comprising SEQ ID NO:90 and a heavy chain variable region comprising SEQ ID NO:87. Storage stability may be measured after a CD3-binding domain is stored in PBS at about 25° C. In one embodiment, a CD3-binding domain is stable in storage in PBS at about 25° C. for at least about 6 days, at least about 10 days, or at least about 13 days and up to about 90 days.

In some aspects, a CD3-binding domain as disclosed herein has a level of high molecular weight aggregates produced during recombinant expression that is at least about 5%, at least about 10%, at least about 20% decreased, at least about 30% decreased and up to about 50% decreased when compared to the level of high molecular weight aggregates produced during recombinant expression of a CD3-binding domain comprising a light chain variable region comprising SEQ ID NO:90 and a heavy chain variable region comprising SEQ ID NO:87.

The disclosure also relates to a CD3-binding domain that binds to human CD3 with an EC50 of about 10 nM or lower. In some embodiments, a CD3-binding domain of the disclosure may also bind specifically to cynomolgus CD3. For example, a CD3-binding domain may bind to cynomolgus CD3 with an EC50 of about 30 nM or lower.

The disclosure encompasses a CD3-binding domain that binds specifically to human CD3 and that comprises an immunoglobulin light chain variable region and an immunoglobulin heavy chain variable region, wherein (a) the immunoglobulin light chain variable region comprises an LCDR1 amino acid sequence of SEQ ID NO:94, an LCDR2 amino acid sequence of SEQ ID NO:95, and an LCDR3 amino acid sequence of SEQ ID NO:96 and wherein the immunoglobulin heavy chain variable region comprises an HCDR1 amino acid sequence of SEQ ID NO:91, an HCDR2 amino acid sequence of SEQ ID NO:92, and an HCDR3 amino acid sequence of SEQ ID NO:93; or (b) the immunoglobulin light chain variable region comprises an LCDR1 amino acid sequence of SEQ ID NO:202, an LCDR2 amino acid sequence of SEQ ID NO:203, and an LCDR3 amino acid sequence of SEQ ID NO:204 and wherein the immunoglobulin heavy chain variable region comprises an HCDR1 amino acid sequence of SEQ ID NO:199, an HCDR2 amino acid sequence of SEQ ID NO:200, and an HCDR3 amino acid sequence of SEQ ID NO:201; and wherein the CD3-binding domain has any one or more of the properties described herein. For example, (i) the thermal transition midpoint of the CD3-binding domain (or a protein comprising the CD3-binding domain) is at least about 54° C., at least about 55° C., at least about 56° C., or at least about 57° C. and up to about 72° C.; (ii) the CD3-binding domain (or a protein comprising the CD3-binding domain) is stable in storage in PBS at about 25° C. for at least about 6 days, at least about 10 days, or at least about 13 days and up to about 90 days; (iii) the CD3-binding domain (or a protein comprising the CD3-binding domain) binds to human CD3 with an EC50 of about 10 nM or lower; and (iv) the CD3-binding domain (or a protein comprising the CD3-binding domain) binds to cynomolgus CD3 with an EC50 of about 30 nM or lower.

The disclosure also relates to a CD3-binding polypeptide comprising any of the CD3-binding domains described herein. In some variations, a CD3-binding polypeptide may comprise an immunoglobulin constant region. This immunoglobulin constant region may comprise immunoglobulin CH2 and CH3 domains of IgG1, IgG2, IgG3, IgG4, IgA1, IgA2 or IgD. In some embodiments, an immunoglobulin constant region comprises a human IgG1 CH2 domain comprising the substitutions L234A, L235A, G237A, and K322A, according to the EU numbering system. In certain embodiments, an immunoglobulin constant region comprises a human IgG1 CH2 domain comprising one or more of the substitutions L234A, L235A, G237A, and K322A, according to the EU numbering system. In some embodiments, a CD3-binding polypeptide when bound to a CD3 protein on a T cell does not induce or induces a minimally detectable cytokine release from said T cell. In certain aspects, a CD3-binding protein or polypeptide exhibits reduced cytokine release in a patient as compared to the cytokine released when anti-CD3 antibody OKT3 is administered to a patient. In some cases, a CD3-binding polypeptide may induce T-cell activation or T-cell proliferation.

In certain aspects, a CD3-binding polypeptide further comprises a second binding domain. The second binding domain may be a single chain variable fragment (scFv). In some embodiments, the second binding domain binds or interacts with a tumor associated antigen (e.g., PSMA, CD19, CD20, CD37, CD38, CD123, Her2, ROR1, RON, glycoprotein A33 antigen (gpA33) or CEA).

The disclosure further encompasses a CD3-binding polypeptide comprising: (i) a CD3-binding domain and (ii) a second binding domain. In some embodiments, a CD3-binding polypeptide comprises, in order from amino-terminus to carboxyl-terminus or in order from carboxyl-terminus to amino-terminus, (i) a CD3-binding domain, (ii) a hinge region and (iii) an immunoglobulin constant region. In some embodiments, a CD3-binding polypeptide comprises, in order from amino-terminus to carboxyl-terminus, (i) a second binding domain, (ii) a hinge region, (iii) an immunoglobulin constant region, (iv) a carboxyl-terminus linker, and (v) a CD3-binding domain. In other embodiments, a CD3-binding polypeptide comprises, in order from carboxyl-terminus to amino-terminus, (i) a second binding domain, (ii) a hinge region, (iii) an immunoglobulin constant region, (iv) an amino-terminus linker, and (v) a CD3-binding domain. In certain variations, the first and/or the second binding domain is an scFv. Non-limiting examples of carboxyl-terminus and amino-terminus linkers include flexible linkers comprising glycine-serine (e.g., (Gly$_4$Ser)) repeats and linkers derived from (i) a stalk region of a type II C lectin or (ii) an immunoglobulin hinge region. In certain aspects, a carboxyl-terminus linker (or an amino-terminus linker) comprises or consists of SEQ ID NO:196. In some aspects, the disclosure relates to a CD3-binding polypeptide (e.g., multispecific), wherein (i) the CD3-binding domain comprises (a) an immunoglobulin light chain variable region comprising LCDR1, LCDR2, and LCDR3, and (b) an immunoglobulin heavy chain variable region comprising HCDR1, HCDR2, and HCDR3; and (ii) the second binding domain comprises (a) an immunoglobulin light chain variable region comprising LCDR1, LCDR2, and LCDR3, and (b) an immunoglobulin heavy chain variable region comprising HCDR1, HCDR2, and HCDR3.

The disclosure encompasses a CD3-binding polypeptide that induces redirected T-cell cytotoxicity (RTCC). For example, a CD3-binding polypeptide may induce RTCC with an EC50 of about 30 pM or lower. In some embodiments, a CD3-binding polypeptide does not exhibit or exhibits minimal antibody-dependent cell-mediated cytotoxicity (ADCC) activity and/or complement-dependent cytotoxicity (CDC) activity. In certain aspects, null ADCC and/or CDC activity is accomplished through mutations in the hinge region and Ig constant region (e.g, Fc).

A CD3-binding polypeptide may further comprise an immunoglobulin heterodimerization domain. In some embodiments, an immunoglobulin heterodimerization domain comprises an immunoglobulin CH1 domain or an immunoglobulin CL domain. In some aspects, a CD3-binding polypeptide is a heterodimeric CD3-binding protein comprising (i) a first polypeptide chain comprising, in order from amino-terminus to carboxyl-terminus or from carboxyl-terminus to amino-terminus, (a) a CD3-binding domain that specifically binds human CD3, (b) a first hinge region, (c) a first immunoglobulin constant region, and (d) a first immunoglobulin heterodimerization domain; and (ii) a second polypeptide chain comprising, in order from amino-terminus to carboxyl-terminus or from carboxyl-terminus to amino-terminus, (a') a second hinge region, (b') a second immunoglobulin constant region, and (c') a second immunoglobulin heterodimerization domain that is different from the first immunoglobulin heterodimerization domain of the first single chain polypeptide, wherein the first and second immunoglobulin heterodimerization domains associate with each other to form a heterodimer. In one embodiment, the first immunoglobulin heterodimerization domain comprises an immunoglobulin CH1 domain and the second immunoglobulin heterodimerization domain comprises an immunoglobulin CL domain, or wherein the first immunoglobulin heterodimerization domain comprises an immunoglobulin CL domain and the second immunoglobulin heterodimerization domain comprises an immunoglobulin CH1 domain. At least one of the first and second immunoglobulin constant regions may comprise immunoglobulin CH2 and CH3 domains of IgG1, IgG2, IgG3, IgG4, IgA1, IgA2, IgD or any combination thereof; an immunoglobulin CH3 domain of IgG1, IgG2, IgG3, IgG4, IgA1, IgA2, IgD, IgE, IgM or any combination thereof; or immunoglobulin CH3 and CH4 domains of IgE, IgM or a combination thereof. In some aspects, the second polypeptide chain of a heterodimeric CD3-binding protein may further comprise a second binding domain. In certain embodiments, the second binding domain may be amino-terminal or carboxy-terminal to the second hinge region.

In some variations, a CD3-binding polypeptide may be a bispecific single chain antibody molecule comprising a CD3-binding domain and a second binding domain, wherein the binding domains are arranged in the order VH CD3-VL CD3-VH second binding domain-VL second binding domain or VL CD3-VH CD3-VH second binding domain-VL second binding domain or VH second binding domain-VL second binding domain-VH CD3-VL CD3 or VH second binding domain-VL second binding domain-VL CD3-VH CD3.

The disclosure also relates to an isolated nucleic acid molecule encoding a CD3-binding domain or a CD3-binding polypeptide described herein or a portion of said CD3-binding domain or polypeptide. In some aspects, the disclosure encompasses an expression vector comprising a nucleic acid segment encoding a CD3-binding domain or a CD3-binding polypeptide described herein, wherein the nucleic acid segment is operatively linked to regulatory sequences suitable for expression of the nucleic acid segment in a host cell. A recombinant host cell comprising an expression vector is included in the disclosure.

The disclosure encompasses an expression vector comprising first and second expression units, wherein the first and second expression units respectively comprise first and second nucleic acid segments encoding the first and second polypeptide chains of a heterodimeric CD3-binding polypeptide, and wherein the first and second nucleic acid segments are operably linked to regulatory sequences suitable for expression of the nucleic acid segments in a host cell. A recombinant host cell comprising an expression vector comprising first and second expression units is part of the disclosure.

The disclosure further relates to a method for producing a CD3-binding polypeptide, the method comprising: culturing a recombinant host cell comprising an expression vector described herein under conditions whereby the nucleic acid segment is expressed, thereby producing the CD3-binding polypeptide. In some embodiments, a method for producing a heterodimeric CD3-binding protein comprises: culturing a recombinant host cell comprising first and second expression units, wherein the first and second expression units respectively comprise first and second nucleic acid segments encoding the first and second polypeptide chains of a heterodimeric CD3-binding protein, wherein the first and second nucleic acid segments are operably linked to regulatory sequences suitable for expression of the nucleic acid segments in a host cell, and wherein said culturing is under conditions whereby the first and second nucleic acid segments are expressed and the encoded polypeptide chains are produced as the heterodimeric CD3-binding protein. These methods may further comprise recovering the CD3-binding polypeptide or the heterodimeric CD3-binding protein.

The disclosure encompasses a pharmaceutical composition comprising a CD3-binding polypeptide disclosed herein and a pharmaceutically acceptable carrier, diluent, or excipient. The disclosure also relates to a method for inducing redirected T-cell cytotoxicity (RTCC) against a cell expressing a tumor associated antigen, the method comprising: contacting said tumor associated antigen-expressing cell with a CD3-binding polypeptide, wherein said contacting is under conditions whereby RTCC against the tumor associated antigen-expressing cell is induced. One aspect of the disclosure includes a method for inhibiting tumor growth in a subject in need thereof, comprising administering a therapeutically effective amount of a CD3-binding polypeptide or a pharmaceutical composition described herein to the subject. The disclosure encompasses a method for treating cancer or an autoimmune disorder in a subject in need thereof, comprising administering a therapeutically effective amount of a CD3-binding polypeptide or a pharmaceutical composition described herein to the subject. Non-limiting examples of cancer that may be treated by methods and CD3-binding polypeptides described herein include prostate cancer, colorectal cancer, renal cell carcinoma, bladder cancer, salivary gland cancer, pancreatic cancer, ovarian cancer, non-small cell lung cancer, breast cancer (e.g., triple negative breast cancer), melanoma, adrenal cancer, mantle cell lymphoma, acute lymphoblastic leukemia, chronic lymphocytic leukemia, Non-Hodgkin's lymphoma, acute myeloid leukemia (AML), B-lymphoid leukemia, blastic plasmocytoid dendritic neoplasm (BPDCN), and hairy cell leukemia.

The disclosure encompasses a CD3-binding domain that binds specifically to human CD3 and that comprises SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, or 60.

The disclosure also relates to a CD3-binding protein that is a dimer of two identical polypeptides, wherein each polypeptide is any of the CD3-binding polypeptides disclosed herein.

These and other embodiments and/or other aspects of the disclosure will become evident upon reference to the following detailed description of the disclosure and the attached drawings.

BRIEF DESCRIPTION OF THE DRAWINGS

FIG. 13 shows an alignment of the amino acid sequences of the DRA222 scFv (SEQ ID NO:85), TSC455 scFv (SEQ ID NO:83), and TSC456 scFv (SEQ ID NO:84). The sequences of these constructs are also shown in Table 14.

FIG. 15 is a table showing a comparison of pharmacokinetic parameters of anti-PSMA×anti-CD3 bispecific binding molecules in BALB/c mice.

FIG. 17A and FIG. 17B are tables showing a comparison of pharmacokinetic parameters of anti-ROR1×anti-CD3 bispecific binding molecules in NSG mice. FIG. 17A shows pharmacokinetic parameter estimates calculated using NCA for IV dosing with sparse sampling and uniform weighting for each treatment group. FIG. 17B shows pharmacokinetic parameter estimates determined using a 2 Compartment IV model with 1/Y weighting for each treatment group.

DETAILED DESCRIPTION OF THE DISCLOSURE

Figure 1:
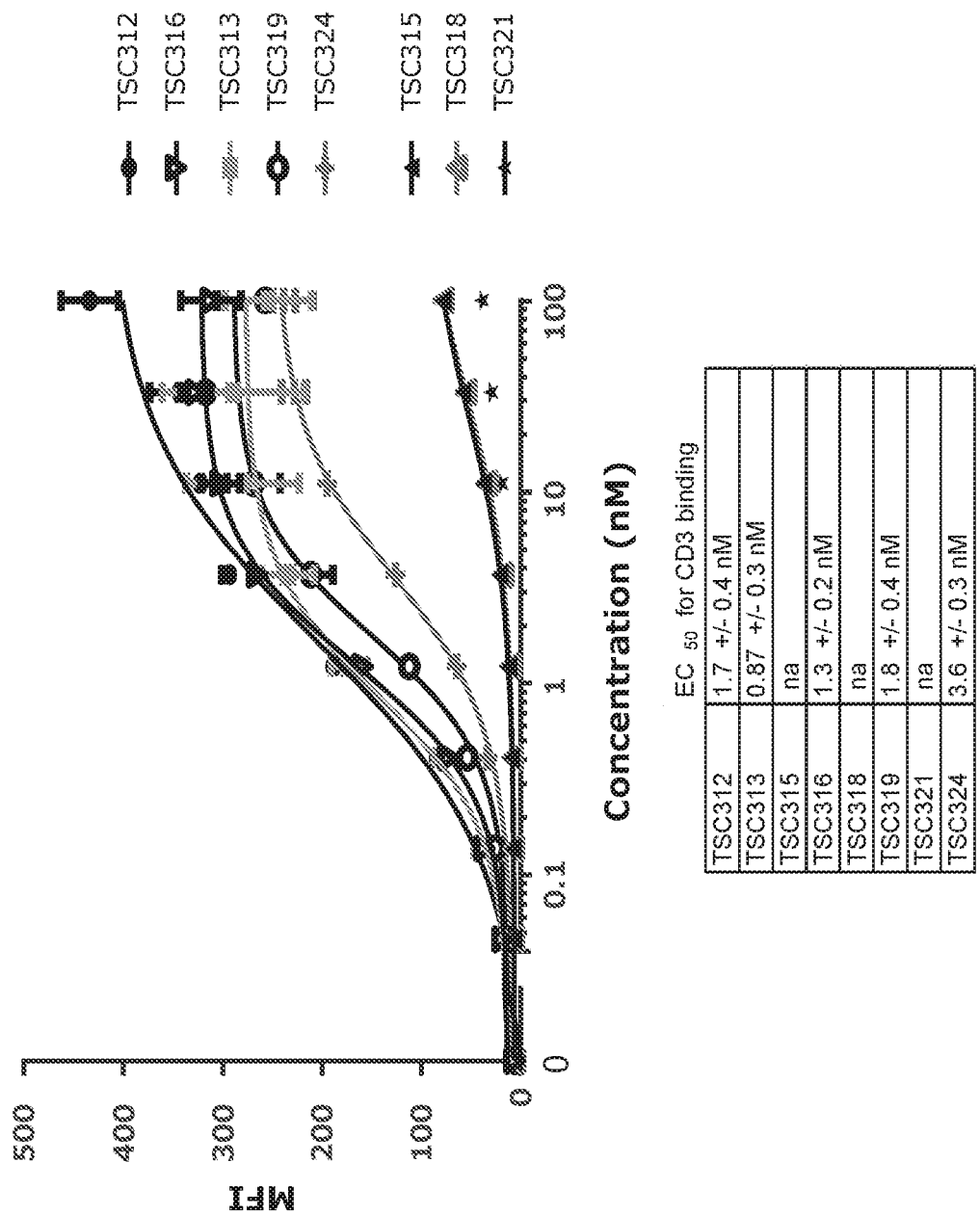
FIG. 1 (top panel) is a graph showing the results of a flow cytometry study measuring the binding of CD3-binding domain constructs to Jurkat T-cells. Mean fluorescence intensity (MFI) of bound molecules on live cells is shown on the y-axis. Concentration (nM) of the CD3-binding domain constructs is shown on the x-axis. The table (bottom panel) shows the $EC_{50}$ values obtained from the data in the graph.

The disclosure provides binding domains that specifically bind to CD3 (cluster of differentiation 3) and binding molecules (e.g. polypeptides and proteins) that specifically bind to CD3. These binding molecules may bind specifically to CD3 and to at least one other target. In some embodiments, a CD3-binding molecule described herein has a favorable manufacturability profile, having one or more of the properties described below. In certain embodiments, CDRs from the Cris7 anti-CD3 antibody have been used to engineer CD3-binding molecules with improved and novel properties. Accordingly, the disclosure relates to humanized anti-CD3 binding domains and proteins that have improved properties (e.g., thermal stability, storage stability, serum half-life, reduced formation of high molecular weight aggregates) compared to other anti-CD3 binding domains and proteins. In some aspects of the disclosure, a CD3-binding molecule is thermally stable. For example, the molecule may have improved thermal stability compared to another CD3-binding molecule (e.g., DRA222). CD3-binding molecules may have a high production yield and a long serum half-life and long storage half-life. Further, CD3-binding molecules described herein may have a low risk of adverse side effects when administered to a subject. For example, CD3-binding molecules may lead to release of low levels of cytokines.

In the present description, any concentration range, percentage range, ratio range, or integer range is to be understood to include the value of any integer within the recited range and, when appropriate, fractions thereof (such as one tenth and one hundredth of an integer), unless otherwise indicated. It should be understood that the terms "a" and "an" as used herein refer to "one or more" of the enumerated components unless otherwise indicated. The use of the alternative (e.g., "or") should be understood to mean either one, both, or any combination thereof of the alternatives. As used herein, the terms "include" and "comprise" are used synonymously. In addition, it should be understood that the polypeptides comprising the various combinations of the components (e.g., domains or regions) and substituents described herein, are disclosed by the present application to the same extent as if each polypeptide was set forth individually. Thus, selection of particular components of individual polypeptides is within the scope of the present disclosure.

All documents, or portions of documents, cited herein, including but not limited to patents, patent applications, articles, books, and treatises, are hereby expressly incorporated by reference in their entirety for any purpose. In the event that one or more of the incorporated documents or portions of documents define a term that contradicts that term's definition in the application, the definition that appears in this application controls. However, mention of any reference, article, publication, patent, patent publication, and patent application cited herein is not, and should not be taken as an acknowledgment, or any form of suggestion, that they constitute valid prior art or form part of the common general knowledge in any country in the world.

As used herein, the term "binding domain" or "binding region" refers to the domain, region, portion, or site of a protein, polypeptide, oligopeptide, or peptide or antibody or binding domain derived from an antibody that possesses the ability to specifically recognize and bind to a target molecule, such as an antigen, ligand, receptor, substrate, or inhibitor (e.g., CD3). Exemplary binding domains include single-chain antibody variable regions (e.g., domain antibodies, sFv, scFv, scFab), receptor ectodomains, and ligands (e.g., cytokines, chemokines). In certain embodiments, the binding domain comprises or consists of an antigen binding site (e.g., comprising a variable heavy chain sequence and variable light chain sequence or three light chain complementary determining regions (CDRs) and three heavy chain CDRs from an antibody placed into alternative framework regions (FRs) (e.g., human FRs optionally comprising one or more amino acid substitutions). A variety of assays are known for identifying binding domains of the present disclosure that specifically bind a particular target, including Western blot, ELISA, phage display library screening, and BIACORE® interaction analysis. As used herein, a CD3-binding polypeptide can have a "first binding domain" and, optionally, a "second binding domain." In certain embodiments, the "first binding domain" is a CD3-binding domain and the format is an antibody or antibody-like protein or domain. In certain embodiments comprising both the first and second binding domains, the second binding domain is a tumor antigen-binding domain. In other embodiments, the second binding domain is a second CD3-binding domain. In yet other embodiments, the second binding domain is a binding domain other than a tumor antigen-binding domain.

A binding domain or protein "specifically binds" a target if it binds the target with an affinity or $K_a$ (i.e., an equilibrium association constant of a particular binding interaction with units of 1/M) equal to or greater than $10^5$ $M^{-1}$, while not significantly binding other components present in a test sample. Binding domains can be classified as "high affinity" binding domains and "low affinity" binding domains. "High affinity" binding domains refer to those binding domains with a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, or at least $10^{13}$ $M^{-1}$. "Low affinity" binding domains refer to those binding domains with a $K_a$ of up to $10^7$ $M^{-1}$, up to $10^6$ $M^{-1}$, up to $10^5$ $M^{-1}$. Alternatively, affinity can be defined as an equilibrium dissociation constant ($K_d$) of a particular binding interaction with units of M (e.g., $10^{-5}$ M to $10^{-13}$ M). Affinities of binding domain polypeptides and single chain polypeptides according to the present disclosure can be readily determined using conventional techniques (see, e.g., Scatchard et al. (1949) Ann. N.Y. Acad. Sci. 51:660; and U.S. Pat. Nos. 5,283,173, 5,468,614, or the equivalent).

"CD3" is known in the art as a multi-protein complex of six chains (see, e.g., Abbas and Lichtman, 2003; Janeway et al., p. 172 and 178, 1999), which are subunits of the T-cell receptor complex. In mammals, the CD3 subunits of the T-cell receptor complex are a CD3γ chain, a CD3δ chain, two CD3ε chains, and a homodimer of CD3ζ chains. The CD3γ, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged T-cell receptor chains. The intracellular tails of the CD3γ, CD3δ, and CD3ε chains each contain a single conserved motif known as an immunoreceptor tyrosine-based activation motif or ITAM, whereas each CD3ζ chain has three. It is believed the ITAMs are important for the signaling capacity of a TCR complex. CD3 as used in the present disclosure can be from various animal species, including human, monkey, mouse, rat, or other mammals.

As used herein, a "conservative substitution" is recognized in the art as a substitution of one amino acid for another amino acid that has similar properties. Exemplary conservative substitutions are well-known in the art (see, e.g., WO 97/09433, page 10, published Mar. 13, 1997; Lehninger, Biochemistry, Second Edition; Worth Publishers, Inc. NY:NY (1975), pp. 71-77; Lewin, Genes IV, Oxford University Press, NY and Cell Press, Cambridge, Mass. (1990), p. 8). In certain embodiments, a conservative substitution includes a leucine to serine substitution.

As used herein, the term "derivative" refers to a modification of one or more amino acid residues of a peptide by chemical or biological means, either with or without an enzyme, e.g., by glycosylation, alkylation, acylation, ester formation, or amide formation.

As used herein, a polypeptide or amino acid sequence "derived from" a designated polypeptide or protein refers to the origin of the polypeptide. In certain embodiments, the polypeptide or amino acid sequence which is derived from a particular sequence (sometimes referred to as the "starting" or "parent" or "parental" sequence) has an amino acid sequence that is essentially identical to the starting sequence or a portion thereof, wherein the portion consists of at least 10-20 amino acids, at least 20-30 amino acids, or at least 30-50 amino acids, or at least 50-150 amino acids, or which is otherwise identifiable to one of ordinary skill in the art as having its origin in the starting sequence. For example, a binding domain can be derived from an antibody, e.g., a Fab, F(ab')2, Fab', scFv, single domain antibody (sdAb), etc.

Polypeptides derived from another polypeptide can have one or more mutations relative to the starting polypeptide, e.g., one or more amino acid residues which have been substituted with another amino acid residue or which has one or more amino acid residue insertions or deletions. The polypeptide can comprise an amino acid sequence which is not naturally occurring. Such variations necessarily have less than 100% sequence identity or similarity with the starting polypeptide. In one embodiment, the variant will have an amino acid sequence from about 60% to less than 100% amino acid sequence identity or similarity with the amino acid sequence of the starting polypeptide. In another embodiment, the variant will have an amino acid sequence from about 75% to less than 100%, from about 80% to less than 100%, from about 85% to less than 100%, from about 90% to less than 100%, from about 95% to less than 100% amino acid sequence identity or similarity with the amino acid sequence of the starting polypeptide.

As used herein, unless otherwise provided, a position of an amino acid residue in a variable region of an immunoglobulin molecule is numbered using the IMGT criteria (Brochet, X, et al, Nucl. Acids Res. (2008) 36, W503-508), and a position of an amino acid residue in a constant region of an immunoglobulin molecule is numbered according to EU nomenclature (Ward et al., 1995 *Therap. Immunol.* 2:77-94). The Kabat numbering convention (Kabat, Sequences of Proteins of Immunological Interest, 5th ed. Bethesda, Md.: Public Health Service, National Institutes of Health (1991)) is an alternative system used to refer to a position of an amino acid residue in a variable region of an immunoglobulin molecule.

As used herein, the term "dimer" refers to a biological entity that consists of two subunits associated with each other via one or more forms of intramolecular forces, including covalent bonds (e.g., disulfide bonds) and other interactions (e.g., electrostatic interactions, salt bridges, hydrogen bonding, and hydrophobic interactions), and is stable under appropriate conditions (e.g., under physiological conditions, in an aqueous solution suitable for expressing, purifying, and/or storing recombinant proteins, or under conditions for non-denaturing and/or non-reducing electrophoresis). A "heterodimer" or "heterodimeric protein," as used herein, refers to a dimer formed from two different polypeptides. A heterodimer does not include an antibody formed from four polypeptides (i.e., two light chains and two heavy chains). A "homodimer" or "homodimeric protein," as used herein, refers to a dimer formed from two identical polypeptides.

In some embodiments, a CD3-binding polypeptide comprises, in order from amino-terminus to carboxyl-terminus or in order from carboxyl-terminus to amino-terminus, (i) a second binding domain, (ii) a hinge region, (iii) an immunoglobulin constant region, (iv) a carboxyl-terminus linker (or an amino-terminus linker), and (v) a CD3-binding domain. As used herein and depending on context, a "hinge region" or a "hinge" refers to a polypeptide region between a binding domain (e.g., a CD3-binding domain or a second binding domain) and an immunoglobulin constant region. As used herein and depending on context, a "linker" may refer to (1) a polypeptide region between $V_H$ and $V_L$ regions in a single-chain Fv (scFv) or (2) a polypeptide region between an immunoglobulin constant region and a second binding domain in a CD3-binding polypeptide comprising two binding domains. A polypeptide region between an immunoglobulin constant region and a CD3-binding domain in a CD3-binding polypeptide comprising two binding domains may also be referred to as a "carboxyl-terminus linker" or an "amino-terminus linker." Non-limiting examples of carboxyl-terminus and amino-terminus linkers include flexible linkers comprising glycine-serine repeats, and linkers derived from (a) an interdomain region of a transmembrane protein (e.g., a type I transmembrane protein); (b) a stalk region of a type II C-lectin; or (c) an immunoglobulin hinge. Non-limiting examples of hinges and linkers are provided in Tables 1 and 2. In some embodiments, a "linker" provides a spacer function compatible with interaction of the two sub-binding domains so that the resulting polypeptide retains a specific binding affinity to the same target molecule as an antibody that comprises the same light and heavy chain variable regions. In certain embodiments, a linker is comprised of five to about 35 amino acids, for instance, about 15 to about 25 amino acids.

A "wild-type immunoglobulin hinge region" refers to a naturally occurring upper and middle hinge amino acid sequences interposed between and connecting the CH1 and CH2 domains (for IgG, IgA, and IgD) or interposed between and connecting the CH1 and CH3 domains (for IgE and IgM) found in the heavy chain of an antibody. In certain embodiments, a wild type immunoglobulin hinge region sequence is human, and can comprise a human IgG hinge region.

An "altered wild-type immunoglobulin hinge region" or "altered immunoglobulin hinge region" refers to (a) a wild type immunoglobulin hinge region with up to 30% amino acid changes (e.g., up to 25%, 20%, 15%, 10%, or 5% amino acid substitutions or deletions), or (b) a portion of a wild type immunoglobulin hinge region that has a length of about 5 amino acids (e.g., about 5, 6, 7, 8, 9, 10, 11, 12, 13, 14, 15, 16, 17, 18, 19, or 20 amino acids) up to about 120 amino acids (for instance, having a length of about 10 to about 40 amino acids or about 15 to about 30 amino acids or about 15 to about 20 amino acids or about 20 to about 25 amino acids), has up to about 30% amino acid changes (e.g., up to about 25%, 20%, 15%, 10%, 5%, 4%, 3%, 2%, or 1% amino acid substitutions or deletions or a combination thereof), and has an IgG core hinge region as disclosed in US 2013/0129723 and US 2013/0095097.

As used herein, the term "humanized" refers to a process of making an antibody or immunoglobulin binding proteins and polypeptides derived from a non-human species (e.g., mouse or rat) less immunogenic to humans, while still retaining antigen-binding properties of the original antibody, using genetic engineering techniques. In some embodiments, the binding domain(s) of an antibody or immunoglobulin binding proteins and polypeptides (e.g., light and heavy chain variable regions, Fab, scFv) are humanized. Non-human binding domains can be humanized using techniques known as CDR grafting (Jones et al., Nature 321:522 (1986)) and variants thereof, including "reshaping" (Verhoeyen, et al., 1988 Science 239:1534-1536; Riechmann, et al., 1988 Nature 332:323-337; Tempest, et al., Bio/Technol 1991 9:266-271), "hyperchimerization" (Queen, et al., 1989 Proc Natl Acad Sci USA 86:10029-10033; Co, et al., 1991 Proc Natl Acad Sci USA 88:2869-2873; Co, et al., 1992 J Immunol 148:1149-1154), and "veneering" (Mark, et al., "Derivation of therapeutically active humanized and veneered anti-CD18 antibodies." In: Metcalf B W, Dalton B J, eds. Cellular adhesion: molecular definition to therapeutic potential. New York: Plenum Press, 1994: 291-312). If derived from a non-human source, other regions of the antibody or immunoglobulin binding proteins and polypeptides, such as the hinge region and constant region domains, can also be humanized.

An "immunoglobulin dimerization domain" or "immunoglobulin heterodimerization domain", as used herein, refers to an immunoglobulin domain of a polypeptide chain that preferentially interacts or associates with a different immunoglobulin domain of a second polypeptide chain, wherein the interaction of the different immunoglobulin heterodimerization domains substantially contributes to or efficiently promotes heterodimerization of the first and second polypeptide chains (i.e., the formation of a dimer between two different polypeptide chains, which is also referred to as a "heterodimer"). The interactions between immunoglobulin heterodimerization domains "substantially contributes to or efficiently promotes" the heterodimerization of first and second polypeptide chains if there is a statistically significant reduction in the dimerization between the first and second polypeptide chains in the absence of the immunoglobulin heterodimerization domain of the first polypeptide chain and/or the immunoglobulin heterodimerization domain of the second polypeptide chain. In certain embodiments, when the first and second polypeptide chains are co-expressed, at least 60%, at least about 60% to about 70%, at least about 70% to about 80%, at least 80% to about 90%, 91%, 92%, 93%, 94%, 95%, 96%, 97%, 98%, or 99% of the first and second polypeptide chains form heterodimers with each other. Representative immunoglobulin heterodimerization domains include an immunoglobulin CH1 domain, an immunoglobulin CL domain (e.g., Cκ or Cλ isotypes), or derivatives thereof, including wild type immunoglobulin CH1 and CL domains and altered (or mutated) immunoglobulin CH1 and CL domains, as provided therein.

An "immunoglobulin constant region" or "constant region" is a term defined herein to refer to a peptide or polypeptide sequence that corresponds to or is derived from part or all of one or more constant region domains. In certain embodiments, the immunoglobulin constant region corresponds to or is derived from part or all of one or more constant region domains, but not all constant region domains of a source antibody. In certain embodiments, the constant region comprises IgG CH2 and CH3 domains, e.g., IgG1 CH2 and CH3 domains. In certain embodiments, the constant region does not comprise a CH1 domain. In certain embodiments, the constant region domains making up the constant region are human. In some embodiments (for example, in certain variations of a CD3-binding polypeptide or protein), the constant region domains of a fusion protein of this disclosure lack or have minimal effector functions of antibody-dependent cell-mediated cytotoxicity (ADCC) and complement activation and complement-dependent cytotoxicity (CDC), while retaining the ability to bind some Fc receptors (such as $F_cRn$, the neonatal Fc receptor) and retaining a relatively long half life in vivo. In other variations, a fusion protein of this disclosure includes constant domains that retain such effector function of one or both of ADCC and CDC. In certain embodiments, a binding domain of this disclosure is fused to a human IgG1 constant region, wherein the IgG1 constant region has one or more of the following amino acids mutated: leucine at position 234 (L234), leucine at position 235 (L235), glycine at position 237 (G237), glutamate at position 318 (E318), lysine at position 320 (K320), lysine at position 322 (K322), or any combination thereof (numbering according to EU). For example, any one or more of these amino acids can be changed to alanine. In a further embodiment, an IgG1 Fc domain has each of L234, L235, G237, E318, K320, and K322 (according to EU numbering) mutated to an alanine (i.e., L234A, L235A, G237A, E318A, K320A, and K322A, respectively), and optionally an N297A mutation as well (i.e., essentially eliminating glycosylation of the CH2 domain).

"Fc region" or "Fc domain" refers to a polypeptide sequence corresponding to or derived from the portion of a source antibody that is responsible for binding to antibody receptors on cells and the C1q component of complement. Fc stands for "fragment crystalline," the fragment of an antibody that will readily form a protein crystal. Distinct protein fragments, which were originally described by proteolytic digestion, can define the overall general structure of an immunoglobulin protein. As originally defined in the literature, the Fc fragment consists of the disulfide-linked heavy chain hinge regions, CH2, and CH3 domains. However, more recently the term has been applied to a single chain consisting of CH3, CH2, and at least a portion of the hinge sufficient to form a disulfide-linked dimer with a second such chain. For a review of immunoglobulin structure and function, see Putnam, *The Plasma Proteins*, Vol. V (Academic Press, Inc., 1987), pp. 49-140; and Padlan, *Mol. Immunol.* 31:169-217, 1994. As used herein, the term Fc includes variants of naturally occurring sequences.

In some embodiments, a CD3-binding protein comprises a protein scaffold as generally disclosed in, for example, in US Patent Application Publication Nos. 2003/0133939, 2003/0118592, and 2005/0136049. A CD3-binding protein may comprise, in order from amino-terminus to carboxyl-terminus, a first binding domain, a hinge region, and an immunoglobulin constant region. In other embodiments, a CD3-binding protein comprises a protein scaffold as generally disclosed in, for example, in US Patent Application Publication No. 2009/0148447. A CD3-binding protein may comprise, in order from carboxyl-terminus to amino-terminus, an immunoglobulin constant region, a hinge region and a first binding domain.

CD3-binding polypeptides and proteins disclosed herein may incorporate a multi-specific binding protein scaffold. Multi-specific binding proteins and polypeptides using scaffolds are disclosed, for instance, in PCT Application Publication No. WO 2007/146968, U.S. Patent Application Publication No. 2006/0051844, PCT Application Publication No. WO 2010/040105, PCT Application Publication No. WO 2010/003108, U.S. Pat. Nos. 7,166,707 and 8,409,577, which are each incorporated herein by reference in their entirety. A CD3-binding protein may comprise two binding domains (the domains can be designed to specifically bind the same or different targets), two hinge regions, and an immunoglobulin constant region. A CD3-binding protein may be a homodimeric protein comprising two identical, disulfide-bonded polypeptides.

As used herein, the "stalk region" of a type II C-lectin refers to the portion of the extracellular domain of the type II C-lectin that is located between the C-type lectin-like domain (CTLD; e.g., similar to CTLD of natural killer cell receptors) and the transmembrane domain. For example, in the human CD94 molecule (GenBank Accession No. AAC50291.1, PRI Nov. 30, 1995), the extracellular domain corresponds to amino acid residues 34-179, whereas the CTLD corresponds to amino acid residues 61-176. Accordingly, the stalk region of the human CD94 molecule includes amino acid residues 34-60, which is found between the membrane and the CTLD (see Boyington et al., *Immunity* 10:75, 1999; for descriptions of other stalk regions, see also Beavil et al., *Proc. Nat'l. Acad. Sci. USA* 89:753, 1992; and Figdor et al., *Nature Rev. Immunol.* 2:77, 2002). These type II C-lectins can also have from six to 10 junction amino acids between the stalk region and the transmembrane region or the CTLD. In another example, the 233 amino acid human NKG2A protein (GenBank Accession No. P26715.1, PRI Jun. 15, 2010) has a transmembrane domain ranging from amino acids 71-93 and an extracellular domain ranging from amino acids 94-233. The CTLD is comprised of amino acids 119-231, and the stalk region comprises amino acids 99-116, which is flanked by junctions of five and two amino acids. Other type II C-lectins, as well as their extracellular ligand-bind domains, interdomain or stalk regions, and CTLDs are known in the art (see, e.g., GenBank Accession Nos. NP_001993.2; AAH07037.1, PRI Jul. 15, 2006; NP_001773.1, PRI Jun. 20, 1010; AAL65234.1, PRI Jan. 17, 2002, and CAA04925.1, PRI Nov. 14, 2006, for the sequences of human CD23, CD69, CD72, NKG2A and NKG2D and their descriptions, respectively).

As used herein, the "interdomain region" of a transmembrane protein (e.g., a type I transmembrane protein) refers to a portion of the extracellular domain of the transmembrane protein that is located between two adjacent domains. Examples of interdomain regions include regions linking adjacent Ig domains of immunoglobulin superfamily members (e.g., an immunoglobulin hinge region from IgG, IgA, IgD, or IgE; the region linking the IgV and IgC2 domains of CD2; or the region linking the IgV and IgC domains of CD80 or CD86). Another example of an interdomain region is the region linking the non-Ig and IgC2 domain of CD22, a type I sialic acid-binding Ig-like lectin.

A polypeptide region "derived from" a stalk region of a type II C-lectin, or "derived from" a transmembrane protein interdomain region (e.g., an immunoglobulin hinge region), refers to an about five to about 150 amino acid sequence, an about 5 to about 100 amino acid sequence, an about 5 to about 50 amino acid sequence, an about 5 to about 40 amino acid sequence, an about 5 to about 30 amino acid sequence, an about 5 to about 25 amino acid sequence, an about 5 to about 20 amino acid sequence, an about 10 to about 25 amino acid sequence, an about 10 to about 20 amino acid sequence, about 8 to about 20 amino acid sequence, about 9 to about 20 amino acid sequence, about 10 to about 20 amino acid sequence, about 11 to about 20 amino acid sequence, about 12 to about 20 amino acid sequence, about 13 to about 20 amino acid sequence, about 14 to about 20 amino acid sequence, about 15 to about 20 amino acid sequence, or an about 5, 6, 7, 8, 9, 10, 11, 12, 13, 14, 15, 16, 17, 18, 19, or 20 amino acid sequence, wherein all or at least a portion of which includes (i) a wild-type stalk region or interdomain region sequence; (ii) a fragment of the wild-type stalk region or interdomain region sequence; (iii) a polypeptide having at least 80%, 85%, 90%, or 95% amino acid sequence identity with either (i) or (ii); or (iv) either (i) or (ii) in which one, two, three, four, or five amino acids have a deletion, insertion, substitution, or any combination thereof, for instance, the one or more changes are substitutions or the one or more mutations include only one deletion. In some embodiments, a derivative of a stalk region is more resistant to proteolytic cleavage as compared to the wild-type stalk region sequence, such as those derived from about eight to about 20 amino acids of NKG2A, NKG2D, CD23, CD64, CD72, or CD94.

As used herein, the term "junction amino acids" or "junction amino acid residues" refers to one or more (e.g., about 2-10) amino acid residues between two adjacent regions or domains of a polypeptide, such as between a hinge and an adjacent immunoglobulin constant region or between a hinge and an adjacent binding domain or between a peptide linker and an adjacent immunoglobulin variable domain or an adjacent immunoglobulin constant region. Junction amino acids can result from the construct design of a polypeptide (e.g., amino acid residues resulting from the use of a restriction enzyme site during the construction of a nucleic acid molecule encoding a polypeptide).

As used herein, the phrase a "linker between CH3 and CH1 or CL" refers to one or more (e.g., about 2-12, about 2-10, about 4-10, about 5-10, about 6-10, about 7-10, about 8-10, about 9-10, about 8-12, about 9-12, or about 10-12) amino acid residues between the C-terminus of a CH3 domain (e.g., a wild type CH3 or a mutated CH3) and the N-terminus of a CH1 domain or CL domain (e.g., Ck).

As used herein, the term "patient in need" or "subject in need" refers to a patient or a subject at risk of, or suffering from, a disease, disorder or condition that is amenable to treatment or amelioration with a CD3-binding protein or polypeptide or a composition thereof provided herein.

As used herein, the term "pharmaceutically acceptable" refers to molecular entities and compositions that do not generally produce allergic or other serious adverse reactions when administered using routes well known in the art. Molecular entities and compositions approved by a regulatory agency of the Federal or a state government or listed in the U.S. Pharmacopeia or other generally recognized pharmacopeia for use in animals, and more particularly in humans are considered to be "pharmaceutically acceptable."

As used herein, the term "promoter" refers to a region of DNA involved in binding RNA polymerase to initiate transcription.

As used herein, the terms "nucleic acid," "nucleic acid molecule," or "polynucleotide" refer to deoxyribonucleotides or ribonucleotides and polymers thereof in either single- or double-stranded form. Unless specifically limited, the terms encompass nucleic acids containing analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions can be achieved by generating sequences in which the third position of one or more selected (or all) codons is substituted with mixed-base and/or deoxyinosine residues (Batzer et al. (1991) *Nucleic Acid Res.* 19:5081; Ohtsuka et al. (1985) *J. Biol. Chem.* 260:2605-2608; Cassol et al. (1992); Rossolini et al. (1994) *Mol. Cell. Probes* 8:91-98). The term nucleic acid is used interchangeably with gene, cDNA, and mRNA encoded by a gene. As used herein, the terms "nucleic acid," "nucleic acid molecule," or "polynucleotide" are intended to include DNA molecules (e.g., cDNA or genomic DNA), RNA molecules (e.g., mRNA), analogs of the DNA or RNA generated using nucleotide analogs, and derivatives, fragments and homologs thereof.

The term "expression" refers to the biosynthesis of a product encoded by a nucleic acid. For example, in the case of nucleic acid segment encoding a polypeptide of interest, expression involves transcription of the nucleic acid segment into mRNA and the translation of mRNA into one or more polypeptides.

The terms "expression unit" and "expression cassette" are used interchangeably herein and denote a nucleic acid segment encoding a polypeptide of interest and capable of providing expression of the nucleic acid segment in a host cell. An expression unit typically comprises a transcription promoter, an open reading frame encoding the polypeptide of interest, and a transcription terminator, all in operable configuration. In addition to a transcriptional promoter and terminator, an expression unit can further include other nucleic acid segments such as, e.g., an enhancer or a polyadenylation signal.

The term "expression vector," as used herein, refers to a nucleic acid molecule, linear or circular, comprising one or more expression units. In addition to one or more expression units, an expression vector can also include additional nucleic acid segments such as, for example, one or more origins of replication or one or more selectable markers. Expression vectors are generally derived from plasmid or viral DNA, or can contain elements of both.

As used herein, the term "sequence identity" refers to a relationship between two or more polynucleotide sequences or between two or more polypeptide sequences. When a position in one sequence is occupied by the same nucleic acid base or amino acid residue in the corresponding position of the comparator sequence, the sequences are said to be "identical" at that position. The percentage "sequence identity" is calculated by determining the number of positions at which the identical nucleic acid base or amino acid residue occurs in both sequences to yield the number of "identical" positions. The number of "identical" positions is then divided by the total number of positions in the comparison window and multiplied by 100 to yield the percentage of "sequence identity." Percentage of "sequence identity" is determined by comparing two optimally aligned sequences over a comparison window. The comparison window for nucleic acid sequences can be, for instance, at least 20, 30, 40, 50, 60, 70, 80, 90, 100, 110, 120, 130, 140, 150, 160, 170, 180, 190, 200, 300, 400, 500, 600, 700, 800, 900 or 1000 or more nucleic acids in length. The comparison window for polypeptide sequences can be, for instance, at least 20, 30, 40, 50, 60, 70, 80, 90, 100, 110, 120, 130, 140, 150, 160, 170, 180, 190, 200, 300 or more amino acids in length. In order to optimally align sequences for comparison, the portion of a polynucleotide or polypeptide sequence in the comparison window can comprise additions or deletions termed gaps while the reference sequence is kept constant. An optimal alignment is that alignment which, even with gaps, produces the greatest possible number of "identical" positions between the reference and comparator sequences. Percentage "sequence identity" between two sequences can be determined using the version of the program "BLAST 2 Sequences" which was available from the National Center for Biotechnology Information as of Sep. 1, 2004, which program incorporates the programs BLASTN (for nucleotide sequence comparison) and BLASTP (for polypeptide sequence comparison), which programs are based on the algorithm of Karlin and Altschul (Proc. Natl. Acad. Sci. USA 90(12):5873-5877, 1993). When utilizing "BLAST 2 Sequences," parameters that were default parameters as of Sep. 1, 2004, can be used for word size (3), open gap penalty (11), extension gap penalty (1), gap dropoff (50), expect value (10) and any other required parameter including but not limited to matrix option. Two nucleotide or amino acid sequences are considered to have "substantially similar sequence identity" or "substantial sequence identity" if the two sequences have at least 80%, at least 85%, at least 90%, at least 95%, at least 96%, at least 97%, at least 98%, or at least 99% sequence identity relative to each other.

As used herein, a "polypeptide" or "polypeptide chain" is a single, linear and contiguous arrangement of covalently linked amino acids. It does not include two polypeptide chains that link together in a non-linear fashion, such as via an interchain disulfide bond (e.g., a half immunoglobulin molecule in which a light chain links with a heavy chain via a disulfide bond). Polypeptides can have or form one or more intrachain disulfide bonds. With regard to polypeptides as described herein, reference to amino acid residues corresponding to those specified by SEQ ID NO includes post-translational modifications of such residues.

As used herein, "CD3-binding protein" may be used interchangeably with "CD3-binding polypeptide." Such molecules specifically bind to cluster of differentiation 3 protein (CD3) (e.g., human CD3).

A "protein" is a macromolecule comprising one or more polypeptide chains. A protein can also comprise non-peptidic components, such as carbohydrate groups. Carbohydrates and other non-peptidic substituents can be added to a protein by the cell in which the protein is produced, and will vary with the type of cell. Proteins are defined herein in terms of their amino acid backbone structures; substituents such as carbohydrate groups are generally not specified, but may be present nonetheless. A protein may be an antibody or an antigen-binding fragment of an antibody. In some embodiments, a protein may also be an scFv-Fc-scFv molecule, scFv-scFv dimer, or a diabody.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl-terminus of the reference sequence, but is not necessarily at the carboxyl-terminus of the complete polypeptide.

"T-cell receptor" (TCR) is a molecule found on the surface of T-cells that, along with CD3, is generally responsible for recognizing antigens bound to major histocompatibility complex (MHC) molecules. It consists of a disulfide-linked heterodimer of the highly variable α and β chains in most T-cells. In other T-cells, an alternative receptor made up of variable γ and δ chains is expressed. Each chain of the TCR is a member of the immunoglobulin superfamily and possesses one N-terminal immunoglobulin variable domain, one immunoglobulin constant domain, a transmembrane region, and a short cytoplasmic tail at the C-terminal end (see Abbas and Lichtman, *Cellular and Molecular Immunology* (5th Ed.), Editor Saunders, Philadelphia, 2003; Janeway et al., *Immunobiology: The Immune System in Health and Disease*, 4th Ed., Current Biology Publications, p 148, 149, and 172, 1999). TCR as used in the present disclosure can be from various animal species, including human, mouse, rat, or other mammals.

"TCR complex," as used herein, refers to a complex formed by the association of CD3 chains with other TCR chains. For example, a TCR complex can be composed of a CD3γ chain, a CD3δ chain, two CD3ε chains, a homodimer of CD3ζ chains, a TCRα chain, and a TCRβ chain. Alternatively, a TCR complex can be composed of a CD3γ chain, a CD3δ chain, two CD3ε chains, a homodimer of CD3ζ chains, a TCRγ chain, and a TCRδ chain.

"A component of a TCR complex," as used herein, refers to a TCR chain (i.e., TCRα, TCRβ, TCRγ or TCRδ), a CD3 chain (i.e., CD3γ, CD3δ, CD3ε or CD3ζ), or a complex formed by two or more TCR chains or CD3 chains (e.g., a complex of TCRα and TCRβ, a complex of TCRγ and TCRδ, a complex of CD3ε and CD3δ, a complex of CD3γ and CD3ε, or a sub-TCR complex of TCRα, TCRβ, CD3γ, CD3δ, and two CD3ε chains).

"Antibody-dependent cell-mediated cytotoxicity" and "ADCC," as used herein, refer to a cell-mediated process in which nonspecific cytotoxic cells that express FcγRs (e.g., monocytic cells such as Natural Killer (NK) cells and macrophages) recognize bound antibody (or other protein capable of binding FcγRs) on a target cell and subsequently cause lysis of the target cell. In principle, any effector cell with an activating FcγR can be triggered to mediate ADCC. The primary cells for mediating ADCC are NK cells, which express only FcγRIII, whereas monocytes, depending on their state of activation, localization, or differentiation, can express FcγRI, FcγRII, and FcγRIII. For a review of FcγR expression on hematopoietic cells, see, e.g., Ravetch et al., 1991, Annu. Rev. Immunol., 9:457-92.

The term "having ADCC activity," as used herein in reference to a polypeptide or protein, means that the polypeptide or protein (for example, one comprising an immunoglobulin hinge region and an immunoglobulin constant region having CH2 and CH3 domains, such as derived from IgG (e.g., IgG1)), is capable of mediating antibody-dependent cell-mediated cytotoxicity (ADCC) through binding of a cytolytic Fc receptor (e.g., FcγRIII) on a cytolytic immune effector cell expressing the Fc receptor (e.g., an NK cell).

"Complement-dependent cytotoxicity" and "CDC," as used herein, refer to a process in which components in normal serum ("complement"), together with an antibody or other C1 q-complement-binding protein bound to a target antigen, exhibit lysis of a target cell expressing the target antigen. Complement consists of a group of serum proteins that act in concert and in an orderly sequence to exert their effect.

The terms "classical complement pathway" and "classical complement system," as used herein, are synonymous and refer to a particular pathway for the activation of complement. The classical pathway requires antigen-antibody complexes for initiation and involves the activation, in an orderly fashion, of nine major protein components designated C1 through C9. For several steps in the activation process, the product is an enzyme that catalyzes the subsequent step. This cascade provides amplification and activation of large amounts of complement by a relatively small initial signal.

The term "having CDC activity," as used herein in reference to a polypeptide or protein, means that the polypeptide or protein (for example, one comprising an immunoglobulin hinge region and an immunoglobulin constant region having CH2 and CH3 domains, such as derived from IgG (e.g., IgG1)) is capable of mediating complement-dependent cytotoxicity (CDC) through binding of C1q complement protein and activation of the classical complement system.

"Redirected T-cell cytotoxicity" and "RTCC," as used herein, refer to a T-cell-mediated process in which a cytotoxic T-cell is recruited to a target cell using a multi-specific protein that is capable of specifically binding both the cytotoxic T-cell and the target cell, and whereby a target-dependent cytotoxic T-cell response is elicited against the target cell. Polypeptides and proteins comprising CD3-binding domains, as disclosed herein, and tumor antigen-binding domains are capable of RTCC.

As used herein, the term "treatment," "treating," or "ameliorating" refers to either a therapeutic treatment or prophylactic/preventative treatment. A treatment is therapeutic if at least one symptom of disease in an individual receiving treatment improves or a treatment can delay worsening of a progressive disease in an individual, or prevent onset of additional associated diseases.

As used herein, the term "therapeutically effective amount (or dose)" or "effective amount (or dose)" of a specific binding molecule or compound refers to that amount of the compound sufficient to result in amelioration of one or more symptoms of the disease being treated in a statistically significant manner or a statistically significant improvement in organ function. When referring to an individual active ingredient, administered alone, a therapeutically effective dose refers to that ingredient alone. When referring to a combination, a therapeutically effective dose refers to combined amounts of the active ingredients that result in the therapeutic effect, whether administered serially or simultaneously (in the same formulation or concurrently in separate formulations).

As used herein, the term "transformation," "transfection," and "transduction" refer to the transfer of nucleic acid (i.e., a nucleotide polymer) into a cell. As used herein, the term "genetic transformation" refers to the transfer and incorporation of DNA, especially recombinant DNA, into a cell. The transferred nucleic acid can be introduced into a cell via an expression vector.

As used herein, the term "variant" or "variants" refers to a nucleic acid or polypeptide differing from a reference nucleic acid or polypeptide, but retaining essential properties thereof. Generally, variants are overall closely similar, and, in many regions, identical to the reference nucleic acid or polypeptide. For instance, a variant may exhibit at least about 70%, at least about 80%, at least about 90%, at least about 95%, at least about 96%, at least about 97%, at least about 98% or at least about 99% sequence identity compared to the active portion or full length reference nucleic acid or polypeptide.

The terms "light chain variable region" (also referred to as "light chain variable domain" or "VL" or $V_L$) and "heavy chain variable region" (also referred to as "heavy chain variable domain" or "VH" or $V_H$) refer to the variable binding region from an antibody light and heavy chain, respectively. The variable binding regions are made up of discrete, well-defined sub-regions known as "complementarity determining regions" (CDRs) and "framework regions" (FRs), generally comprising in order FR1-CDR1-FR2-CDR2-FR3-CDR3-FR4 from amino-terminus to carboxyl-terminus. In one embodiment, the FRs are humanized. The term "CL" refers to an "immunoglobulin light chain constant region" or a "light chain constant region," i.e., a constant region from an antibody light chain. The term "CH" refers to an "immunoglobulin heavy chain constant region" or a "heavy chain constant region," which is further divisible, depending on the antibody isotype into CH1, CH2, and CH3 (IgA, IgD, IgG), or CH1, CH2, CH3, and CH4 domains (IgE, IgM). A "Fab" (fragment antigen binding) is the part of an antibody that binds to antigens and includes the variable region and CH1 domain of the heavy chain linked to the light chain via an inter-chain disulfide bond.

The present disclosure describes binding domains that specifically bind CD3 (e.g., human CD3), as well as polypeptides and proteins comprising these binding domains. In some embodiments, the CD3-binding proteins and polypeptides comprise a second binding domain, which may bind to a tumor antigen (e.g., PSMA, CD19, CD20, CD37, CD38, CD123, Her2, ROR1, RON, glycoprotein A33 antigen (gpA33) or CEA). The polypeptides and proteins comprising binding domains of this disclosure can further comprise immunoglobulin constant regions, linker peptides, hinge regions, immunoglobulin dimerization/heterodimerization domains, junctional amino acids, tags, etc. These components of the disclosed polypeptides and proteins are described in further detail below.

Additionally, the CD3-binding polypeptides and proteins disclosed herein can be in the form of an antibody or a fusion protein of any of a variety of different formats (e.g., the fusion protein can be in the form of a CD3-binding bispecific or multispecific molecule). Non-limiting examples of bispecific molecules include a scFv-Fc-scFv molecule. Some bispecific molecules typically comprise or consist of an anti-tumor antigen scFv linked to an anti-CD3 scFv and typically do not include other sequences such as an immunoglobulin constant region. In other embodiments, a CD3-binding protein is a diabody.

A CD3-binding protein in accordance with the present disclosure generally includes at least one CD3-binding polypeptide chain comprising (a) a CD3-binding domain as set forth herein. In certain variations, the CD3-binding polypeptide further includes (b) a hinge region carboxyl-terminal to the CD3-binding domain, and (c) an immunoglobulin constant region. In further variations, the ROR1-binding polypeptide further includes (d) a carboxyl-terminus linker carboxyl-terminal to the immunoglobulin constant region, and (e) a second binding domain carboxyl-terminal to the carboxyl-terminus linker.

In yet other variations, the CD3-binding polypeptide comprises (b) a hinge region amino-terminal to the CD3-binding domain, and (c) an immunoglobulin sub-region amino-terminal to the hinge region. In some variations, the CD3-binding polypeptide comprises (b) a hinge region carboxyl-terminal to the CD3-binding domain, and (c) an immunoglobulin sub-region carboxyl-terminal to the hinge region In some embodiments, CD3-binding polypeptides are capable of homodimerization, typically through disulfide bonding, via the immunoglobulin constant region and/or hinge region (e.g., via an immunoglobulin constant region comprising IgG CH2 and CH3 domains and an IgG hinge region). Thus, in certain embodiments of the present disclosure, two identical single chain CD3-binding polypeptides homodimerize to form a dimeric CD3-binding protein.

In other embodiments, a CD3-binding polypeptide includes a heterodimerization domain that is capable of heterodimerization with a different heterodimerization domain in a second, non-identical polypeptide chain. In certain variations, the second polypeptide chain for heterodimerization includes a second binding domain. Accordingly, in certain embodiments of the present disclosure, two non-identical polypeptide chains, one comprising the CD3-binding domain and the second optionally comprising a second binding domain, dimerize to form a heterodimeric CD3-binding protein. Examples of types of heterodimers include those described in US 2013/0095097 and US 2013/0129723.

In some embodiments, a CD3-binding domain, protein or polypeptide is conjugated to a drug or a toxic moiety.

CD3-binding polypeptides, proteins, and their various components used in the present disclosure are further described below.

As indicated above, the disclosure relates to binding domains that specifically bind CD3 (e.g., human CD3). A CD3-binding domain may comprise amino acid sequences shown in Table 14. In some embodiments, a CD3-binding polypeptide or protein comprises a signal sequence. The disclosure also encompasses CD3-binding domains and proteins comprising or encoded by any of the sequences shown in Table 14, excluding the signal sequences that are part of these sequences. CD3-binding domains and polypeptides, their internal designations, and their sequences are summarized in Table 15. In some cases, CD3-binding domains of the disclosure contain amino acid substitutions. For example, TSC370 has the amino acid sequence of TSC342 with the glycine residue at position 27 according to the IMGT numbering system substituted with tyrosine.

In certain embodiments, the disclosure relates to a CD3-binding domain that binds specifically to human CD3 and that comprises an immunoglobulin light chain variable region and an immunoglobulin heavy chain variable region; wherein the immunoglobulin light chain variable region comprises an amino acid sequence that is (a) at least about 93% identical, at least about 95% identical, at least about 97% identical, at least about 98% identical or at least about 99% identical to the amino acid sequence in SEQ ID NO:88; or (b) at least about 94% identical, at least about 95% identical, at least about 97% identical, at least about 98% identical or at least about 99% identical to the amino acid sequence in SEQ ID NO:89; and wherein the immunoglobulin heavy chain variable region comprises an amino acid sequence that is at least about 82% identical, at least about 85% identical, at least about 87% identical, at least about 90% identical, at least about 92% identical, at least about 95% identical, at least about 97% identical, at least about 98% identical or at least about 99% identical to the amino acid sequence in SEQ ID NO:86. A CD3-binding domain may comprise an amino acid sequence that is at least about 87% identical, at least about 90% identical, at least about 92% identical, at least about 95% identical, at least about 97% identical, at least about 98% identical or at least about 99% identical to the amino acid sequence in SEQ ID NO:83 or SEQ ID NO:84. A CD3-binding domain may comprise or consist of SEQ ID NO:83 or SEQ ID NO:84. In some embodiments, a CD3-binding domain comprises an amino acid sequence that is at least about 87% identical, at least about 90% identical, at least about 92% identical, at least about 95% identical, at least about 97% identical, at least about 98% identical, at least about 99% identical, or 100% identical to the amino acid sequence in SEQ ID NO:4, 6, 8, 10, 12, 14, 16, 18, 20, 22, 24, 26, 28, 30, 32, 34, 36, 38, 40, 42, 44, 46, 48, 50, 52, 54, 56, 58, or 60.

In some embodiments, a CD3-binding domain may comprise an immunoglobulin light chain variable region that comprises an LCDR1 amino acid sequence that differs from SEQ ID NO:94 by at least one amino acid substitution, an LCDR2 amino acid sequence that differs from SEQ ID NO:95 by at least one amino acid substitution, and an LCDR3 amino acid sequence that differs from SEQ ID NO:96 by at least one amino acid substitution, and an immunoglobulin heavy chain variable region that comprises an HCDR1 amino acid sequence that differs from SEQ ID NO:91 by at least one amino acid substitution, an HCDR2 amino acid sequence that differs from SEQ ID NO:92 by at least one amino acid substitution, and an HCDR3 amino acid sequence that differs from SEQ ID NO:93 by at least one amino acid substitution. In other embodiments, a CD3-binding domain may comprise an immunoglobulin light chain variable region that comprises an LCDR1 amino acid sequence that differs from SEQ ID NO:202 by at least one amino acid substitution, an LCDR2 amino acid sequence that differs from SEQ ID NO:203 by at least one amino acid substitution, and an LCDR3 amino acid sequence that differs from SEQ ID NO:204 by at least one amino acid substitution, and an immunoglobulin heavy chain variable region that comprises an HCDR1 amino acid sequence that differs from SEQ ID NO:199 by at least one amino acid substitution, an HCDR2 amino acid sequence that differs from SEQ ID NO:200 by at least one amino acid substitution, and an HCDR3 amino acid sequence that differs from SEQ ID NO:201 by at least one amino acid substitution. The CDR amino acid sequence of a CD3-binding domain may differ from the recited sequence by at least one amino acid substitution. The at least one amino acid substitution may be a conservative or a non-conservative amino acid substitution. In some embodiments, a LCDR1, LCDR2, LCDR3, HCDR1, HCDR2, and/or HCDR3 differs from an above-listed CDR sequence by 1, 2, 3, 4, 5, 6, 7, 8, 9, or 10 amino acids. In certain embodiments, a CDR of the present disclosure contains about one or more (e.g., about 2, 3, 4, 5, 6, 7, 8, 9, 10) insertions, about one or more (e.g., about 2, 3, 4, 5, 6, 7, 8, 9, 10) deletions, about one or more (e.g., about 2, 3, 4, 5, 6, 7, 8, 9, 10) amino acid substitutions (e.g., conservative amino acid substitutions or non-conservative amino acid substitutions), or a combination of the above-noted changes, when compared to the CDR sequence of a known monoclonal antibody.

When describing the amino acid substitutions in this disclosure, a position of an amino acid residue in a variable region of an immunoglobulin molecule is usually numbered using the IMGT criteria (Brochet, X, et al, Nucl. Acids Res. (2008) 36, W503-508). In some embodiments, the amino acid residue at position 52 of the immunoglobulin light chain variable region of a CD3-binding domain is arginine and/or the amino acid residue at position 53 of the immunoglobulin light chain variable region of a CD3-binding domain is tryptophan. The amino acid residue at position 27 of the immunoglobulin heavy chain variable region of a CD3-binding domain may be tyrosine. In some embodiments, a CD3-binding domain comprises one or more of the following: (a) the amino acid residue at position 9 of the immunoglobulin heavy chain variable region is proline; (b) the amino acid residue at position 53 of the immunoglobulin heavy chain variable region is isoleucine; and (c) the amino acid residue at position 21 of the immunoglobulin light chain variable region is methionine. The amino acid residue at position 87 of the immunoglobulin light chain variable region of a CD3-binding domain may be tyrosine. The amino acid residue at position 86 of the immunoglobulin light chain variable region of a CD3-binding domain may be aspartic acid. In one embodiment, the amino acid residue at position 86 of the immunoglobulin light chain variable region of a CD3-binding domain is aspartic acid and the amino acid residue at position 87 of the immunoglobulin light chain variable region of a CD3-binding domain is tyrosine.

In certain embodiments, a CD3-binding domain comprises humanized immunoglobulin VL and/or VH regions. Techniques for humanizing immunoglobulin VL and VH regions are known in the art and are discussed, for example, in U.S. Patent Application Publication No. 2006/0153837. In certain aspects, a CD3-binding domain may comprise an immunoglobulin light chain variable region and an immunoglobulin heavy chain variable region that comprise framework regions and at least one of the immunoglobulin light chain variable region and the immunoglobulin heavy chain variable region may be humanized. In one embodiment, an immunoglobulin light chain variable region comprises framework regions based on the human IGKV3D-20*1 germline amino acid sequence. In another embodiment, an immunoglobulin heavy chain variable region comprises framework regions based on the human IGHV1-69*02 germline amino acid sequence. In some aspects, an immunoglobulin heavy chain variable region comprises framework regions based on the human IGHV1-2*02 (H7), IGHV1-

46*02 (H8), IGHV1-3*01(H9), or IGHV1-69*02 (H10) germline amino acid sequence. An immunoglobulin light chain variable region may comprise framework regions based on the human IGKV3-11*01 (L4), IGKV1-33*01 (L5), IGKV1-39*01 (L7), or IGKV3D-20*1 (L8) germline amino acid sequence.

The disclosure relates to CD3-binding domains that have improved properties compared to the DRA222 CD3-binding domain. DRA222 has a light chain variable region comprising SEQ ID NO:90 and a heavy chain variable region comprising SEQ ID NO:87. DRA222 is described in WO 2013/158856. DRA222 is sometimes referred to as TSC311 or TSC312 in this disclosure. Fc DRA222 has the amino acid sequence of SEQ ID NO:2. The disclosure encompasses a CD3-binding domain (or a protein comprising said domain) that has a thermal stability that is increased at least about 10% when compared to the thermal stability of a CD3-binding domain comprising a light chain variable region comprising SEQ ID NO:90 and a heavy chain variable region comprising SEQ ID NO:87. The thermal transition midpoint (Tm) of a CD3-binding domain (or a protein comprising said domain) may be at least about 3° C., at least about 4° C., at least about 5° C., or at least about 6° C. increased and up to about 20° C. increased when compared to the Tm of a CD3-binding domain comprising a light chain variable region comprising SEQ ID NO:90 and a heavy chain variable region comprising SEQ ID NO:87. The thermal transition midpoint of a CD3-binding domain (or a protein comprising said domain) may be at least about 54° C., at least about 55° C., at least about 56° C., or at least about 57° C. and up to about 72° C. The thermal stability or the thermal transition midpoint of a CD3-binding domain (or a protein comprising said domain) may be measured by differential scanning calorimetry or differential scanning fluorimetry.

A CD3-binding domain as disclosed herein (or a protein comprising said domain) may have storage stability that is increased at least about 5%, at least about 10%, at least about 20%, at least about 30%, at least about 40%, at least about 50%, at least about 60%, at least about 70%, at least about 80%, at least about 90% and up to about 100% when compared to the storage stability of a CD3-binding domain comprising a light chain variable region comprising SEQ ID NO:90 and a heavy chain variable region comprising SEQ ID NO:87. Storage stability may be measured after a CD3-binding domain (or a protein comprising said domain) is stored in PBS at about 25° C. In one embodiment, a CD3-binding domain (or a protein comprising said domain) is stable in storage in PBS at about 25° C. for at least about 6 days, at least about 10 days, or at least about 13 days and up to about 90 days.

In some aspects, a CD3-binding domain as disclosed herein (or a protein comprising said domain) has a level of high molecular weight aggregates produced during recombinant expression that are at least about 5%, at least about 10%, at least about 20% decreased, at least about 30% decreased and up to about 50% decreased when compared to the level of high molecular weight aggregates produced during recombinant expression of a CD3-binding domain comprising a light chain variable region comprising SEQ ID NO:90 and a heavy chain variable region comprising SEQ ID NO:87.

The disclosure also relates to a CD3-binding domain that binds to human CD3 with an EC50 of about 10 nM or lower. A CD3-binding domain of the disclosure may bind specifically to both human CD3 and cynomolgus CD3. For example, a CD3-binding domain may bind to cynomolgus CD3 with an EC50 of about 30 nM or lower. Binding to cynomolgus CD3 allows the anti-CD3 therapeutic to be tested in non-human primates.

The disclosure encompasses a CD3-binding domain that binds specifically to human CD3 and that comprises an immunoglobulin light chain variable region and an immunoglobulin heavy chain variable region, wherein the immunoglobulin light chain variable region comprises an LCDR1 amino acid sequence of SEQ ID NO:94, an LCDR2 amino acid sequence of SEQ ID NO:95, and an LCDR3 amino acid sequence of SEQ ID NO:96 and wherein the immunoglobulin heavy chain variable region comprises an HCDR1 amino acid sequence of SEQ ID NO:91, an HCDR2 amino acid sequence of SEQ ID NO:92, and an HCDR3 amino acid sequence of SEQ ID NO:93, and wherein the CD3-binding domain has any one or more of the properties described herein. For example, (i) the thermal transition midpoint of the CD3-binding domain (or a protein comprising the CD3-binding domain) is at least about 54° C., at least about 55° C., at least about 56° C., or at least about 57° C. and up to about 72° C.; (ii) the CD3-binding domain (or a protein comprising the CD3-binding domain) is stable in storage in PBS at about 25° C. for at least about 6 days, at least about 10 days, or at least about 13 days and up to about 90 days; (iii) the CD3-binding domain (or a protein comprising the CD3-binding domain) binds to human CD3 with an EC50 of about 10 nM or lower; and (iv) the CD3-binding domain (or a protein comprising the CD3-binding domain) binds to cynomolgus CD3 with an EC50 of about 30 nM or lower.

In some embodiments, a CD3-binding polypeptide when bound to a CD3 protein on a T cell does not induce or induces a minimally detectable cytokine release from said T cell. In certain aspects, a CD3-binding protein or polypeptide exhibits reduced cytokine release in a patient as compared to the cytokine released when anti-CD3 antibody OKT3 is administered to a patient. A CD3-binding polypeptide may induce T-cell activation or T-cell proliferation.

In certain embodiments, a CD3-binding protein can comprise one or more additional binding domains (e.g., second binding domain) that bind a target other than CD3. These other binding domains can comprise, for example, a particular cytokine or a molecule that targets the binding domain polypeptide to a particular cell type, a toxin, an additional cell receptor, an antibody, etc.

In certain embodiments, a CD3-binding polypeptide used in the methods and compositions described herein is a bispecific single chain molecule comprising a CD3-binding domain and a second binding domain. In some embodiments, a CD3- and/or a second binding domain is derived from an antibody and comprises a variable heavy chain (VH) and a variable light chain (VL). These binding domains and variable chains may be arranged in any order that still retains some binding to the target(s). For example, the variable domains may be arranged in the order such as VH SBD-VL SBD-VH CD3-VL CD3; VL SBD-VH SBD-VH CD3-VL CD3; VH SBD-VL SBD-VL CD3-VH CD3; VL SBD-VH SBD-VL CD3-VH CD3; VH CD3-VL CD3-VH SBD-VL SBD; VL CD3-VH CD3-VL SBD-VH SBD; VH CD3-VL CD3-VL SBD-VH SBD; or VL CD3-VH CD3-VH SBD-VL SBD (where SBD refers to "second binding domain"). In certain aspects, the pairs of VH regions and VL regions in the binding domain binding to CD3 are in the format of a single chain antibody (scFv). The VH and VL regions may be arranged in the order VH-VL or VL-VH. In certain embodiments, the scFv may bind more effectively to CD3 in the VL-VH orientation than in the VH-VL orientation, or vice versa. The VH-region may be positioned N-terminally to a linker sequence. The VL region may be positioned C-terminally to the linker sequence. The domain arrangement in the CD3 binding domain of the bispecific single chain molecule may be VH-VL, with said CD3 binding domain located C-terminally to the second binding domain. In some cases, a bispecific molecule may comprise an scFv binding to a second binding domain linked to an scFv binding to CD3. These scFvs may be linked with a short peptide. In some embodiments, bispecific single chain molecules do not comprise a hinge region or a constant region (see, for example, US 2013/0295121, US 2013/0129730, US 2011/0293619, U.S. Pat. No. 7,635,472, WO 2010/037836, WO 2004/106381 and WO 2011/121110; each incorporated herein by reference in its entirety).

In some embodiments, a binding domain is a single-chain Fv fragment (scFv) that comprises $V_H$ and $V_L$ regions specific for a target of interest. In certain embodiments, the $V_H$ and $V_L$ regions are human or humanized. In some variations, a binding domain is a single-chain Fv (scFv) comprising immunoglobulin $V_L$ and $V_H$ regions joined by a peptide linker. The use of peptide linkers for joining $V_L$ and $V_H$ regions is well-known in the art, and a large number of publications exist within this particular field. A linker may comprise the amino acid sequence QRHNNSSLNTGTQMAGHSPNS (SEQ ID NO:148). In some embodiments, a peptide linker is a 15 mer consisting of three repeats of a Gly-Gly-Gly-Gly-Ser amino acid sequence ((Gly$_4$Ser)$_3$) (SEQ ID NO:193). Other linkers have been used, and phage display technology, as well as selective infective phage technology, has been used to diversify and select appropriate linker sequences (Tang et al., *J. Biol. Chem.* 271, 15682-15686, 1996; Hennecke et al., *Protein Eng.* 11, 405-410, 1998). In certain embodiments, the $V_L$ and $V_H$ regions are joined by a peptide linker having an amino acid sequence comprising the formula (Gly$_4$Ser)$_n$, wherein n=1-5 (SEQ ID NO:194). In some embodiments, a Gly$_4$Ser sequence may be repeated between 6 and 10 times. Other suitable linkers can be obtained by optimizing a simple linker (e.g., (Gly$_4$Ser), (SEQ ID NO:194)) through random mutagenesis. In some embodiments, the heavy chain variable region of an scFv is amino-terminal to the light chain variable region of the scFv. In other embodiments, the light chain variable region of an scFv is amino-terminal to the heavy chain variable region of the scFv.

In some embodiments, a CD3-binding polypeptide comprises, in order from amino-terminus to carboxyl-terminus (or in order from carboxyl-terminus to amino-terminus), (i) a second binding domain, (ii) a hinge region, (iii) an immunoglobulin constant region, (iv) a carboxyl-terminus linker (or an amino-terminus linker), and (v) a CD3-binding domain. As used herein in the context of a polypeptide construct comprising a first binding domain and a second binding domain, a "hinge region" or a "hinge" refers to a polypeptide region between the first binding domain and the Fc region. A "carboxyl-terminus linker" or "an amino-terminus linker" refers to a polypeptide region between the Fc region and the second binding domain. In some embodiments, a carboxyl-terminus (or an amino-terminus linker) linker comprises or consists of SEQ ID NO:196. In certain embodiments, a hinge is a wild-type human immunoglobulin hinge region. In certain other embodiments, one or more amino acid residues can be added at the amino- or carboxyl-terminus of a wild type immunoglobulin hinge region as part of a fusion protein construct design. For example, additional junction amino acid residues at the hinge amino-terminus can be "RT," "RSS," "TG," or "T," or at the hinge carboxyl-terminus can be "SG", or a hinge deletion can be combined with an addition, such as ΔP with "SG" added at the carboxyl-terminus.

In certain embodiments, a hinge, a carboxyl-terminus linker, or an amino-terminus linker is an altered immunoglobulin hinge in which one or more cysteine residues in a wild type immunoglobulin hinge region is substituted with one or more other amino acid residues (e.g., serine or alanine).

Exemplary altered immunoglobulin hinges, carboxyl-terminus linkers, and amino-terminus linkers include an immunoglobulin human IgG1 hinge region having one, two or three cysteine residues found in a wild type human IgG1 hinge substituted by one, two or three different amino acid residues (e.g., serine or alanine). An altered immunoglobulin hinge can additionally have a proline substituted with another amino acid (e.g., serine or alanine). For example, the above-described altered human IgG1 hinge can additionally have a proline located carboxyl-terminal to the three cysteines of wild type human IgG1 hinge region substituted by another amino acid residue (e.g., serine, alanine). In one embodiment, the prolines of the core hinge region are not substituted.

In certain embodiments, a hinge, a carboxyl-terminus linker, or an amino-terminus linker polypeptide comprises or is a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a wild type immunoglobulin hinge region, such as a wild type human IgG1 hinge, a wild type human IgG2 hinge, or a wild type human IgG4 hinge.

In further embodiments, a hinge, a carboxyl-terminus linker, or an amino-terminus linker present in a CD3-binding polypeptide can be a hinge that is not based on or derived from an immunoglobulin hinge (i.e., not a wild-type immunoglobulin hinge or an altered immunoglobulin hinge). Examples for such hinges and carboxyl-terminus linkers include peptides of about five to about 150 amino acids derived from an interdomain region of a transmembrane protein or stalk region of a type II C-lectin, for instance, peptides of about eight to 25 amino acids and peptides of about seven to 18 amino acids.

In certain embodiments, interdomain or stalk region hinges, carboxyl-terminus linkers, and amino-terminus linkers have seven to 18 amino acids and can form an α-helical coiled coil structure. In certain embodiments, interdomain or stalk region hinges, carboxyl-terminus linkers, or amino-terminus linkers contain 0, 1, 2, 3, or 4 cysteines. Exemplary interdomain or stalk region hinges, carboxyl-terminus linkers, and amino-terminus linkers are peptide fragments of the interdomain or stalk regions, such as ten to 150 amino acid fragments from the stalk regions of CD69, CD72, CD94, NKG2A and NKG2D. A hinge, a carboxyl-terminus linker, or an amino-terminus linker may also be a flexible linker sequence comprising (Gly$_4$Ser) repeats. In some embodiments, a hinge is a 15 mer consisting of three repeats of a Gly-Gly-Gly-Gly-Ser amino acid sequence ((Gly$_4$Ser)$_3$) (SEQ ID NO:193). In certain embodiments, a hinge has an amino acid sequence comprising the formula (Gly$_4$Ser)$_n$, wherein n=1-5 (SEQ ID NO:194). In some embodiments, a Gly$_4$Ser sequence may be repeated between 6 and 10 times. Other suitable hinges can be obtained by optimizing a simple linker (e.g., (Gly$_4$Ser), (SEQ ID NO:194)) through random mutagenesis.

In certain embodiments, hinge, carboxyl-terminus linker, and amino-terminal linker sequences have about 5 to 150 amino acids, 5 to 10 amino acids, 10 to 20 amino acids, 20 to 30 amino acids, 30 to 40 amino acids, 40 to 50 amino acids, 50 to 60 amino acids, 5 to 60 amino acids, 5 to 40 amino acids, 8 to 20 amino acids, or 10 to 15 amino acids. The hinge or linker can be primarily flexible, but can also provide more rigid characteristics or can contain primarily α-helical structure with minimal β-sheet structure. The lengths or the sequences of the hinges and linkers can affect the binding affinities of the binding domains to which the hinges are directly or indirectly (via another region or domain, such as an heterodimerization domain) connected as well as one or more activities of the Fc region portions to which the hinges or linkers are directly or indirectly connected.

In certain embodiments, hinge, carboxyl-terminus linker, and amino-terminal linker sequences are stable in plasma and serum and are resistant to proteolytic cleavage. The first lysine in the IgG1 upper hinge region can be mutated to minimize proteolytic cleavage, for instance, the lysine can be substituted with methionine, threonine, alanine or glycine, or is deleted.

In some embodiments of the disclosure, the CD3-binding polypeptide is capable of forming a heterodimer with a second polypeptide chain and comprises a hinge region (a) immediately amino-terminal to an immunoglobulin constant region (e.g., amino-terminal to a CH2 domain wherein the immungbloubolin constant region includes CH2 and CH3 domains, or amino-terminal to a CH3 domain wherein the immunoglobulin sub-regions includes CH3 and CH4 domains), (b) interposed between and connecting a binding domain (e.g., scFv) and a immunoglobulin heterodimerization domain, (c) interposed between and connecting a immunoglobulin heterodimerization domain and an immunoglobulin constant region (e.g., wherein the immunoglobulin constant region includes CH2 and CH3 domains or CH3 and CH4 domains), (d) interposed between and connecting an immunoglobulin constant region and a binding domain, (e) at the amino-terminus of a polypeptide chain, or (f) at the carboxyl-terminus of a polypeptide chain. A polypeptide chain comprising a hinge region as described herein will be capable of associating with a different polypeptide chain to form a heterodimeric protein provided herein, and the heterodimer formed will contain a binding domain that retains its target specificity or its specific target binding affinity.

In certain embodiments, a hinge present in a polypeptide that forms a heterodimer with another polypeptide chain can be an immunoglobulin hinge, such as a wild-type immunoglobulin hinge region or an altered immunoglobulin hinge region thereof. In certain embodiments, a hinge of one polypeptide chain of a heterodimeric protein is identical to a corresponding hinge of the other polypeptide chain of the heterodimer. In certain other embodiments, a hinge of one chain is different from that of the other chain (in their length or sequence). The different hinges in the different chains allow different manipulation of the binding affinities of the binding domains to which the hinges are connected, so that the heterodimer is able to preferentially bind to the target of one binding domain over the target of the other binding domain. For example, in certain embodiments, a heterodimeric protein has a CD3-binding domain in one chain and a second binding domain in another chain. Having two different hinges in the two chains may allow the heterodimer to bind to the second target first, and then to a CD3 component second. Thus, the heterodimer may recruit CD3+ T-cells to the second target-expressing cells (e.g., tumor or cancer cells), which in turn may damage or destroy the second target-expressing cells.

Some exemplary hinge, carboxyl-terminus linker, and amino-terminus linker sequences suitable for use in accordance with the present disclosure are shown in the Tables 1 and 2 below. Additional exemplary hinge and linker regions are set forth in SEQ ID NOs: 241-244, 601, 78, 763-791, 228, 379-434, 618-749 of US 2013/0129723 (said sequences incorporated by reference herein).

TABLE 1

Exemplary hinges and linkers

| Hinge Region | Amino Acid Sequence | SEQ ID NO |
|---|---|---|
| sss(s)-hIgG1 hinge | EPKSSDKTHTSPPSS | SEQ ID NO: 121 |
| csc(s)-hIgG1 hinge | EPKSCDKTHTSPPCS | SEQ ID NO: 122 |
| ssc(s)-hIgG1 hinge | EPKSSDKTHTSPPCS | SEQ ID NO: 123 |
| scc(s)-hIgG1 hinge | EPKSSDKTHTCPPCS | SEQ ID NO: 124 |
| css(s)-hIgG1 hinge | EPKSCDKTHTSPPSS | SEQ ID NO: 125 |
| scs(s)-hIgG1 hinge | EPKSSDKTHTCPPSS | SEQ ID NO: 126 |
| ccc(s)-hIgG1 hinge | EPKSCDKTHTSPPCS | SEQ ID NO: 127 |
| ccc(p)-hIgG1 hinge | EPKSCDKTHTSPPCP | SEQ ID NO: 128 |
| sss(p)-hIgG1 hinge | EPKSSDKTHTSPPSP | SEQ ID NO: 129 |
| csc(p)-hIgG1 hinge | EPKSCDKTHTSPPCP | SEQ ID NO: 130 |
| ssc(p)-hIgG1 hinge | EPKSSDKTHTSPPCP | SEQ ID NO: 131 |
| scc(p)-hIgG1 hinge | EPKSSDKTHTCPPCP | SEQ ID NO: 132 |
| css(p)-hIgG1 hinge | EPKSCDKTHTSPPSP | SEQ ID NO: 133 |
| scs(p)-hIgG1 hinge | EPKSSDKTHTCPPSP | SEQ ID NO: 134 |
| Scppcp | SCPPCP | SEQ ID NO: 135 |
| STD1 | NYGGGGSGGGGSGGGGSGNS | SEQ ID NO: 136 |
| STD2 | NYGGGGSGGGGSGGGGSGNYGGGGSGGGGSGGGGSGNS | SEQ ID NO: 137 |
| H1 | NS | SEQ ID NO: 138 |
| H2 | GGGGSGNS | SEQ ID NO: 139 |
| H3 | NYGGGGSGNS | SEQ ID NO: 140 |
| H4 | GGGGSGGGGSGNS | SEQ ID NO: 141 |
| H5 | NYGGGGSGGGGSGNS | SEQ ID NO: 142 |
| H6 | GGGGSGGGGSGGGGSGNS | SEQ ID NO: 143 |
| H7 | GCPPCPNS | SEQ ID NO: 144 |

TABLE 1-continued

Exemplary hinges and linkers

| Hinge Region | Amino Acid Sequence | SEQ ID NO |
|---|---|---|
| (G4S)3 | GGGGSGGGGSGGGGS | SEQ ID NO: 145 |
| H105 | SGGGGSGGGGSGGGGS | SEQ ID NO: 146 |
| (G4S)4 | GGGGSGGGGSGGGGSGGGGS | SEQ ID NO: 147 |
| H75 (NKG2A quadruple mutant) | QRHNNSSLNTGTQMAGHSPNS | SEQ ID NO: 148 |
| H83 (NKG2A derived) | SSLNTGTQMAGHSPNS | SEQ ID NO: 149 |
| H106 (NKG2A derived) | QRHNNSSLNTGTQMAGHS | SEQ ID NO: 150 |
| H81 (NKG2D derived) | EVQIPLTESYSPNS | SEQ ID NO: 151 |
| H91 (NKG2D derived) | NSLANQEVQIPLTESYSPNS | SEQ ID NO: 152 |
| H94 | SGGGGSGGGGSGGGGSPNS | SEQ ID NO: 153 |
| H111 | SGGGGSGGGGSGGGGSPGS | SEQ ID NO: 196 |

TABLE 2

Exemplary hinges and linkers (derived from H7 hinge, stalk region of a type II C-lectin, or interdomain region of a type I transmembrane protein)

| Hinge Region | Amino Acid Sequence | Molecule and/or hinge from which derived | SEQ ID NO: |
|---|---|---|---|
| H16 | LSVKADFLTPSIGNS | CD80 | SEQ ID NO: 154 |
| H17 | LSVKADFLTPSISCPPCPNS | CD80 + H7 | SEQ ID NO: 155 |
| H18 | LSVLANFSQPEIGNS | CD86 | SEQ ID NO: 156 |
| H19 | LSVLANFSQPEISCPPCPNS | CD86 + H7 | SEQ ID NO: 157 |
| H20 | LKIQERVSKPKISNS | CD2 | SEQ ID NO: 158 |
| H21 | LKIQERVSKPKISCPPCPNS | CD2 + H7 | SEQ ID NO: 159 |
| H22 | LNVSERPFPPHIQNS | CD22 | SEQ ID NO: 160 |
| H23 | LDVSERPFPPHIQSCPPCPNS | CD22 + H7 | SEQ ID NO: 161 |
| H24 | REQLAEVTLSLKANS | CD80 | SEQ ID NO: 162 |
| H25 | REQLAEVTLSLKACPPCPNS | CD80 + H7 | SEQ ID NO: 163 |
| H26 | RIHQMNSELSVLANS | CD86 | SEQ ID NO: 164 |
| H27 | RIHQMNSELSVLACPPCPNS | CD86 + H7 | SEQ ID NO: 165 |
| H28 | DTKGKNVLEKIFSNS | CD2 | SEQ ID NO: 166 |
| H30 | LPPETQESQEVTLNS | CD22 | SEQ ID NO: 167 |
| H32 | RIHLNVSERPFPPNS | CD22 | SEQ ID NO: 168 |
| H33 | RIHLNVSERPFPPCPPCPNS | CD22 + H7 | SEQ ID NO: 169 |
| H36 | GCPPCPGGGGSNS | H7 | SEQ ID NO: 170 |
| H40 | GCPPCPANS | H7 | SEQ ID NO: 171 |
| H41 | GCPPCPANS | H7 | SEQ ID NO: 172 |
| H42 | GCPPCPNS | H7 | SEQ ID NO: 173 |
| H44 | GGGASCPPCPGNS | H7 | SEQ ID NO: 174 |
| H45 | GGGASCPPCAGNS | H7 | SEQ ID NO: 175 |
| H46 | GGGASCPPCANS | H7 | SEQ ID NO: 176 |
| H47 | LSVKADFLTPSIGNS | CD80 | SEQ ID NO: 177 |
| H48 | ADFLTPSIGNS | CD80 | SEQ ID NO: 178 |
| H50 | LSVLANFSQPEIGNS | CD86 | SEQ ID NO: 179 |
| H51 | LSVLANFSQPEIGNS | CD86 | SEQ ID NO: 180 |
| H52 | SQPEIVPISNS | CD86 | SEQ ID NO: 181 |
| H53 | SQPEIVPISCPPCPNS | CD86 + H7 | SEQ ID NO: 182 |
| H54 | SVLANFSQPEISCPPCPNS | CD86 + H7 | SEQ ID NO: 183 |
| H55 | RIHQMNSELSVLANS | CD86 | SEQ ID NO: 184 |
| H56 | QMNSELSVLANS | CD86 | SEQ ID NO: 185 |

TABLE 2-continued

Exemplary hinges and linkers (derived from H7 hinge, stalk region of a type II C-lectin, or interdomain region of a type I transmembrane protein)

| Hinge Region | Amino Acid Sequence | Molecule and/or hinge from which derived | SEQ ID NO: |
|---|---|---|---|
| H57 | VSERPFPPNS | CD22 | SEQ ID NO: 186 |
| H58 | KPFFTCGSADTCPNS | CD72 | SEQ ID NO: 187 |
| H59 | KPFFTCGSADTCPNS | CD72 | SEQ ID NO: 188 |
| H60 | QYNCPGQYIFSMPNS | CD69 | SEQ ID NO: 189 |
| H61 | EPAFTPGPNIELQKDSDCPNS | CD94 | SEQ ID NO: 190 |
| H62 | QRHNNSSLNTRTQKARHCPNS | NKG2A | SEQ ID NO: 191 |
| H63 | NSLFNQEVQIPLTESYCPNS | NKG2D | SEQ ID NO: 192 |

In certain embodiments, a CD3-binding polypeptide or protein of the disclosure can comprise an "immunoglobulin dimerization domain" or "immunoglobulin heterodimerization domain."

An "immunoglobulin dimerization domain" or "immunoglobulin heterodimerization domain," as used herein, refers to an immunoglobulin domain of a polypeptide chain that preferentially interacts or associates with a different immunoglobulin domain of another polypeptide chain, wherein the interaction of the different immunoglobulin heterodimerization domains substantially contributes to or efficiently promotes heterodimerization of the first and second polypeptide chains (i.e., the formation of a dimer between two different polypeptide chains, which is also referred to as a "heterodimer" or "heterodimeric protein"). The interactions between immunoglobulin heterodimerization domains "substantially contributes to or efficiently promotes" the heterodimerization of first and second polypeptide chains if there is a statistically significant reduction in the dimerization between the first and second polypeptide chains in the absence of the immunoglobulin heterodimerization domain of the first polypeptide chain and/or the immunoglobulin heterodimerization domain of the second polypeptide chain. In certain embodiments, when the first and second polypeptide chains are co-expressed, at least 60%, at least about 60% to about 70%, at least about 70% to about 80%, at least 80% to about 90%, 91%, 92%, 93%, 94%, 95%, 96%, 97%, 98%, or 99% of the first and second polypeptide chains form heterodimers with each other. Representative immunoglobulin heterodimerization domains include an immunoglobulin CH1 domain, an immunoglobulin CL1 domain (e.g., Cκ or Cλ isotypes), or derivatives thereof, including wild-type immunoglobulin CH1 and CL domains and altered (or mutated) immunoglobulin CH1 and CL domains, such as provided herein.

Dimerization/heterodimerization domains can be used where it is desired to form heterodimers from two non-identical polypeptide chains, where one or both polypeptide chains comprise a binding domain. In certain embodiments, one polypeptide chain member of certain heterodimers described herein does not contain a binding domain. As indicated above, a heterodimeric protein of the present disclosure comprises an immunoglobulin heterodimerization domain in each polypeptide chain. The immunoglobulin heterodimerization domains in the polypeptide chains of a heterodimer are different from each other and thus can be differentially modified to facilitate heterodimerization of both chains and to minimize homodimerization of either chain. Immunoglobulin heterodimerization domains provided herein allow for efficient heterodimerization between different polypeptides and facilitate purification of the resulting heterodimeric protein.

As provided herein, immunoglobulin heterodimerization domains useful for promoting heterodimerization of two different single chain polypeptides (e.g., one short and one long) according to the present disclosure include immunoglobulin CH1 and CL domains, for instance, human CH1 and CL domains. In certain embodiments, an immunoglobulin heterodimerization domain is a wild-type CH1 domain, such as a wild type IgG1, IgG2, IgG3, IgG4, IgA1, IgA2, IgD, IgE, or IgM CH1 domain. In further embodiments, an immunoglobulin heterodimerization domain is a wild-type human IgG1, IgG2, IgG3, IgG4, IgA1, IgA2, IgD, IgE, or IgM CH1 domain as set forth in SEQ ID NOS:114, 186-192 and 194, respectively, of US 2013/0129723 (said sequences incorporated by reference herein). In certain embodiments, an immunoglobulin heterodimerization domain is a wild-type human IgG1 CH1 domain as set forth in SEQ ID NO:114 of US 2013/0129723 (said sequence incorporated by reference herein).

In further embodiments, an immunoglobulin heterodimerization domain is an altered immunoglobulin CH1 domain, such as an altered IgG1, IgG2, IgG3, IgG4, IgA1, IgA2 IgD, IgE, or IgM CH1 domain. In certain embodiments, an immunoglobulin heterodimerization domain is an altered human IgG1, IgG2, IgG3, IgG4, IgA1, IgA2, IgD, IgE, or IgM CH1 domain. In still further embodiments, a cysteine residue of a wild-type CH1 domain (e.g., a human CH1) involved in forming a disulfide bond with a wild type immunoglobulin CL domain (e.g., a human CL) is deleted or substituted in the altered immunoglobulin CH1 domain such that a disulfide bond is not formed between the altered CH1 domain and the wild-type CL domain.

In certain embodiments, an immunoglobulin heterodimerization domain is a wild-type CL domain, such as a wild type Cκ domain or a wild type Cλ domain. In certain embodiments, an immunoglobulin heterodimerization domain is a wild type human Cκ or human Cλ domain as set forth in SEQ ID NOS:112 and 113, respectively, of US 2013/0129723 (said sequences incorporated by reference herein). In further embodiments, an immunoglobulin heterodimerization domain is an altered immunoglobulin CL domain, such as an altered Cκ or Cλ domain, for instance, an altered human Cκ or human Cλ domain.

In certain embodiments, a cysteine residue of a wild-type CL domain (e.g., a human CL) involved in forming a disulfide bond with a wild type immunoglobulin CH1 domain (e.g., a human CH1) is deleted or substituted in the altered immunoglobulin CL domain. Such altered CL domains can further comprise an amino acid deletion at their amino-termini. An exemplary Cκ domain is set forth in SEQ ID NO:141 of US 2013/0129723 (said sequence incorporated by reference herein), in which the first arginine and the last cysteine of the wild type human Ck domain are both deleted. In certain embodiments, only the last cysteine of the wild type human Ck domain is deleted in the altered Ck domain because the first arginine deleted from the wild type human Ck domain can be provided by a linker that has an arginine at its carboxyl-terminus and links the amino-terminus of the altered Ck domain with another domain (e.g., an immunoglobulin sub-region, such as a sub-region comprising immunoglobulin CH2 and CH3 domains). An exemplary Cλ domain is set forth in SEQ ID NO:140 of US 2013/0129723 (said sequence incorporated by reference herein), in which the first arginine of a wild type human Cλ domain is deleted and the cysteine involved in forming a disulfide bond with a cysteine in a CH1 domain is substituted by a serine.

In further embodiments, an immunoglobulin heterodimerization domain is an altered Cκ domain that contains one or more amino acid substitutions, as compared to a wild type Cκ domain, at positions that may be involved in forming the interchain-hydrogen bond network at a Cκ-Cκ interface. For example, in certain embodiments, an immunoglobulin heterodimerization domain is an altered human Cκ domain having one or more amino acids at positions N29, N30, Q52, V55, T56, S68 or T70 that are substituted with a different amino acid. The numbering of the amino acids is based on their positions in the altered human Cκ sequence as set forth in SEQ ID NO:141 of US 2013/0129723 (said sequence incorporated by reference herein). In certain embodiments, an immunoglobulin heterodimerization domain is an altered human Cκ domain having one, two, three or four amino acid substitutions at positions N29, N30, V55, or T70. The amino acid used as a substitute at the above-noted positions can be an alanine, or an amino acid residue with a bulk side chain moiety such as arginine, tryptophan, tyrosine, glutamate, glutamine, or lysine. Additional amino acid residues that can be used to substitute amino acid residues of the wild type human Ck sequence at the above noted positions (e.g., N30) include aspartate, methionine, serine and phenylalanine. Exemplary altered human Cκ domains are set forth in SEQ ID NOS:142-178 of US 2013/0129723 (said sequences incorporated by reference herein). Altered human Cκ domains are those that facilitate heterodimerization with a CH1 domain, but minimize homodimerization with another Cκ domain. Representative altered human Cκ domains are set forth in SEQ ID NOS:160 (N29W V55A T70A), 161 (N29Y V55A T70A), 202 (T70E N29A N30A V55A), 167 (N30R V55A T70A), 168 (N30K V55A T70A), 170 (N30E V55A T70A), 172 (V55R N29A N30A), 175 (N29W N30Y V55A T70E), 176 (N29Y N30Y V55A T70E), 177 (N30E V55A T70E), 178 (N30Y V55A T70E), 838 (N30D V55A T70E), 839 (N30M V55A T70E), 840 (N30S V55A T70E), and 841 (N30F V55A T70E) of US 2013/0129723 (said sequences incorporated by reference herein).

In certain embodiments, in addition to or alternative to the mutations in Ck domains described herein, both the immunoglobulin heterodimerization domains (i.e., immunoglobulin CH1 and CL domains) of a polypeptide heterodimer have mutations so that the resulting immunoglobulin heterodimerization domains form salt bridges (i.e., ionic interactions) between the amino acid residues at the mutated sites. For example, the immunoglobulin heterodimerization domains of a polypeptide heterodimer can be a mutated CH1 domain in combination with a mutated Ck domain. In the mutated CH1 domain, valine at position 68 (V68) of the wild type human CH1 domain is substituted by an amino acid residue having a negative charge (e.g., aspartate or glutamate), whereas leucine at position 29 (L29) of a mutated human Ck domain in which the first arginine and the last cysteine have been deleted is substituted by an amino acid residue having a positive charge (e.g., lysine, arginine or histidine). The charge-charge interaction between the amino acid residue having a negative charge of the resulting mutated CH1 domain and the amino acid residue having a positive charge of the resulting mutated Ck domain forms a salt bridge, which stabilizes the heterodimeric interface between the mutated CH1 and Ck domains. Alternatively, V68 of the wild type CH1 can be substituted by an amino acid residue having a positive charge, whereas L29 of a mutated human Ck domain in which the first arginine and the last cysteine have been deleted can be substituted by an amino acid residue having a negative charge. Exemplary mutated CH1 sequences in which V68 is substituted by an amino acid with either a negative or positive charge are set forth in SEQ ID NOS:844 and 845 of US 2013/0129723 (said sequences incorporated by reference herein). Exemplary mutated Ck sequences in which L29 is substituted by an amino acid with either a negative or positive charge are set forth in SEQ ID NOS:842 and 843 of US 2013/0129723 (said sequences incorporated by reference herein).

Positions other than V68 of human CH1 domain and L29 of human Ck domain can be substituted with amino acids having opposite charges to produce ionic interactions between the amino acids in addition or alternative to the mutations in V68 of CH1 domain and L29 of Ck domain. Such positions can be identified by any suitable method, including random mutagenesis, analysis of the crystal structure of the CH1-Ck pair to identify amino acid residues at the CH1-Ck interface, and further identifying suitable positions among the amino acid residues at the CH1-Ck interface using a set of criteria (e.g., propensity to engage in ionic interactions, proximity to a potential partner residue, etc.).

In certain embodiments, polypeptide heterodimers of the present disclosure contain only one pair of immunoglobulin heterodimerization domains. For example, a first chain of a polypeptide heterodimer can comprise a CH1 domain as an immunoglobulin heterodimerization domain, while a second chain can comprise a CL domain (e.g., a Cκ or Cλ) as an immunoglobulin heterodimerization domain. Alternatively, a first chain can comprise a CL domain (e.g., a Cκ or Cλ) as an immunoglobulin heterodimerization domain, while a second chain can comprise a CH1 domain as an immunoglobulin heterodimerization domain. As set forth herein, the immunoglobulin heterodimerization domains of the first and second chains are capable of associating to form a heterodimeric protein of this disclosure.

In certain other embodiments, heterodimeric proteins of the present disclosure can have two pairs of immunoglobulin heterodimerization domains. For example, a first chain of a heterodimer can comprise two CH1 domains, while a second chain can have two CL domains that associate with the two CH1 domains in the first chain. Alternatively, a first chain can comprise two CL domains, while a second chain can have two CH1 domains that associate with the two CL domains in the first chain. In certain embodiments, a first polypeptide chain comprises a CH1 domain and a CL domain, while a second polypeptide chain comprises a CL domain and a CH1 domain that associate with the CH1 domain and the CL domain, respectively, of the first polypeptide chain.

In the embodiments where a heterodimeric protein comprises only one heterodimerization pair (i.e., one immunoglobulin heterodimerization domain in each chain), the immunoglobulin heterodimerization domain of each chain can be located amino-terminal to the immunoglobulin constant region of that chain. Alternatively, the immunoglobulin heterodimerization domain in each chain can be located carboxyl-terminal to the immunoglobulin constant region of that chain.

In the embodiments where a heterodimeric protein comprises two heterodimerization pairs (i.e., two immunoglobulin heterodimerization domains in each chain), both immunoglobulin heterodimerization domains in each chain can be located amino-terminal to the immunoglobulin constant region of that chain. Alternatively, both immunoglobulin heterodimerization domains in each chain can be located carboxyl-terminal to the immunoglobulin constant region of that chain. In further embodiments, one immunoglobulin heterodimerization domain in each chain can be located amino-terminal to the immunoglobulin constant region of that chain, while the other immunoglobulin heterodimerization domain of each chain can be located carboxyl-terminal to the immunoglobulin constant region of that chain. In other words, in those embodiments, the immunoglobulin constant region is interposed between the two immunoglobulin heterodimerization domains of each chain.

As indicated herein, in certain embodiments, CD3-binding polypeptides of the present disclosure comprise an immunoglobulin constant region (also referred to as a constant region) in a polypeptide chain. The inclusion of an immunoglobulin constant region slows clearance of the homodimeric and heterodimeric proteins formed from two CD3-binding polypeptide chains from circulation after administration to a subject. By mutations or other alterations, an immunoglobulin constant region further enables relatively easy modulation of dimeric polypeptide effector functions (e.g., ADCC, ADCP, CDC, complement fixation, and binding to Fc receptors), which can either be increased or decreased depending on the disease being treated, as known in the art and described herein. In certain embodiments, an immunoglobulin constant region of one or both of the polypeptide chains of the polypeptide homodimers and heterodimers of the present disclosure will be capable of mediating one or more of these effector functions In other embodiments, one or more of these effector functions are reduced or absent in an immunoglobulin constant region of one or both of the polypeptide chains of the polypeptide homodimers and heterodimers of the present disclosure, as compared to a corresponding wild-type immunoglobulin constant region. For example, for dimeric CD3-binding polypeptides designed to elicit RTCC, such as, e.g., via the inclusion of a second binding domain, an immunoglobulin constant region may have reduced or no effector function relative to a corresponding wild-type immunoglobulin constant region.

An immunoglobulin constant region present in CD3-binding polypeptides of the present disclosure can comprise or is derived from part or all of: a CH2 domain, a CH3 domain, a CH4 domain, or any combination thereof. For example, an immunoglobulin constant region can comprise a CH2 domain, a CH3 domain, both CH2 and CH3 domains, both CH3 and CH4 domains, two CH3 domains, a CH4 domain, two CH4 domains, and a CH2 domain and part of a CH3 domain.

A CH2 domain that can form an immunoglobulin constant region of a CD3-binding polypeptide of the present disclosure can be a wild type immunoglobulin CH2 domain or an altered immunoglobulin CH2 domain thereof from certain immunoglobulin classes or subclasses (e.g., IgG1, IgG2, IgG3, IgG4, IgA1, IgA2, or IgD) and from various species (including human, mouse, rat, and other mammals).

In certain embodiments, a CH2 domain is a wild type human immunoglobulin CH2 domain, such as wild type CH2 domains of human IgG1, IgG2, IgG3, IgG4, IgA1, IgA2, or IgD, as set forth in SEQ ID NOS:115, 199-201 and 195-197, respectively, of US 2013/0129723 (said sequences incorporated by reference herein). In certain embodiments, the CH2 domain is a wild type human IgG1 CH2 domain as set forth in SEQ ID NO:115 of US 2013/0129723 (said sequence incorporated by reference herein).

In certain embodiments, a CH2 domain is an altered immunoglobulin CH2 region (e.g., an altered human IgG1 CH2 domain) that comprises an amino acid substitution at the asparagine of position 297 (e.g., asparagine to alanine). Such an amino acid substitution reduces or eliminates glycosylation at this site and abrogates efficient Fc binding to FcγR and C1q. The sequence of an altered human IgG1 CH2 domain with an Asn to Ala substitution at position 297 is set forth in SEQ ID NO:324 of US 2013/0129723 (said sequence incorporated by reference herein).

In certain embodiments, a CH2 domain is an altered immunoglobulin CH2 region (e.g., an altered human IgG1 CH2 domain) that comprises at least one substitution or deletion at positions 234 to 238. For example, an immunoglobulin CH2 region can comprise a substitution at position 234, 235, 236, 237 or 238, positions 234 and 235, positions 234 and 236, positions 234 and 237, positions 234 and 238, positions 234-236, positions 234, 235 and 237, positions 234, 236 and 238, positions 234, 235, 237, and 238, positions 236-238, or any other combination of two, three, four, or five amino acids at positions 234-238. In addition or alternatively, an altered CH2 region can comprise one or more (e.g., two, three, four or five) amino acid deletions at positions 234-238, for instance, at one of position 236 or position 237 while the other position is substituted. The above-noted mutation(s) decrease or eliminate the antibody-dependent cell-mediated cytotoxicity (ADCC) activity or Fc receptor-binding capability of a polypeptide heterodimer that comprises the altered CH2 domain. In certain embodiments, the amino acid residues at one or more of positions 234-238 has been replaced with one or more alanine residues. In further embodiments, only one of the amino acid residues at positions 234-238 have been deleted while one or more of the remaining amino acids at positions 234-238 can be substituted with another amino acid (e.g., alanine or serine).

In certain other embodiments, a CH2 domain is an altered immunoglobulin CH2 region (e.g., an altered human IgG1 CH2 domain) that comprises one or more amino acid substitutions at positions 253, 310, 318, 320, 322, and 331. For example, an immunoglobulin CH2 region can comprise a substitution at position 253, 310, 318, 320, 322, or 331, positions 318 and 320, positions 318 and 322, positions 318, 320 and 322, or any other combination of two, three, four, five or six amino acids at positions 253, 310, 318, 320, 322, and 331. The above-noted mutation(s) decrease or eliminate the complement-dependent cytotoxicity (CDC) of a polypeptide heterodimer that comprises the altered CH2 domain.

In certain other embodiments, in addition to the amino acid substitution at position 297, an altered CH2 region (e.g., an altered human IgG1 CH2 domain) can further comprise one or more (e.g., two, three, four, or five) additional substitutions at positions 234-238. For example, an immunoglobulin CH2 region can comprise a substitution at positions 234 and 297, positions 234, 235, and 297, positions 234, 236 and 297, positions 234-236 and 297, positions 234, 235, 237 and 297, positions 234, 236, 238 and 297, positions 234, 235, 237, 238 and 297, positions 236-238 and 297, or any combination of two, three, four, or five amino acids at positions 234-238 in addition to position 297. In addition or alternatively, an altered CH2 region can comprise one or more (e.g., two, three, four or five) amino acid deletions at positions 234-238, such as at position 236 or position 237. The additional mutation(s) decreases or eliminates the antibody-dependent cell-mediated cytotoxicity (ADCC) activity or Fc receptor-binding capability of a polypeptide heterodimer that comprises the altered CH2 domain. In certain embodiments, the amino acid residues at one or more of positions 234-238 have been replaced with one or more alanine residues. In further embodiments, only one of the amino acid residues at positions 234-238 has been deleted while one or more of the remaining amino acids at positions 234-238 can be substituted with another amino acid (e.g., alanine or serine).

In certain embodiments, in addition to one or more (e.g., 2, 3, 4, or 5) amino acid substitutions at positions 234-238, a mutated CH2 region (e.g., an altered human IgG1 CH2 domain) in a fusion protein of the present disclosure can contain one or more (e.g., 2, 3, 4, 5, or 6) additional amino acid substitutions (e.g., substituted with alanine) at one or more positions involved in complement fixation (e.g., at positions I253, H310, E318, K320, K322, or P331). Examples of mutated immunoglobulin CH2 regions include human IgG1, IgG2, IgG4 and mouse IgG2a CH2 regions with alanine substitutions at positions 234, 235, 237 (if present), 318, 320 and 322. An exemplary mutated immunoglobulin CH2 region is mouse IGHG2c CH2 region with alanine substitutions at L234, L235, G237, E318, K320, and K322.

In still further embodiments, in addition to the amino acid substitution at position 297 and the additional deletion(s) or substitution(s) at positions 234-238, an altered CH2 region (e.g., an altered human IgG1 CH2 domain) can further comprise one or more (e.g., two, three, four, five, or six) additional substitutions at positions 253, 310, 318, 320, 322, and 331. For example, an immunoglobulin CH2 region can comprise a (1) substitution at position 297, (2) one or more substitutions or deletions or a combination thereof at positions 234-238, and one or more (e.g., 2, 3, 4, 5, or 6) amino acid substitutions at positions I253, H310, E318, K320, K322, and P331, such as one, two, three substitutions at positions E318, K320 and K322. The amino acids at the above-noted positions can be substituted by alanine or serine.

In certain embodiments, an immunoglobulin CH2 region polypeptide comprises: (i) an amino acid substitution at the asparagines of position 297 and one amino acid substitution at position 234, 235, 236 or 237; (ii) an amino acid substitution at the asparagine of position 297 and amino acid substitutions at two of positions 234-237; (iii) an amino acid substitution at the asparagine of position 297 and amino acid substitutions at three of positions 234-237; (iv) an amino acid substitution at the asparagine of position 297, amino acid substitutions at positions 234, 235 and 237, and an amino acid deletion at position 236; (v) amino acid substitutions at three of positions 234-237 and amino acid substitutions at positions 318, 320 and 322; or (vi) amino acid substitutions at three of positions 234-237, an amino acid deletion at position 236, and amino acid substitutions at positions 318, 320 and 322.

Exemplary altered immunoglobulin CH2 regions with amino acid substitutions at the asparagine of position 297 include: human IgG1 CH2 region with alanine substitutions at L234, L235, G237 and N297 and a deletion at G236 (SEQ ID NO:325 of US 2013/0129723, said sequence incorporated by reference herein), human IgG2 CH2 region with alanine substitutions at V234, G236, and N297 (SEQ ID NO:326 of US 2013/0129723, said sequence incorporated by reference herein), human IgG4 CH2 region with alanine substitutions at F234, L235, G237 and N297 and a deletion of G236 (SEQ ID NO:322 of US 2013/0129723, said sequence incorporated by reference herein), human IgG4 CH2 region with alanine substitutions at F234 and N297 (SEQ ID NO:343 of US 2013/0129723, said sequence incorporated by reference herein), human IgG4 CH2 region with alanine substitutions at L235 and N297 (SEQ ID NO:344 of US 2013/0129723, said sequence incorporated by reference herein), human IgG4 CH2 region with alanine substitutions at G236 and N297 (SEQ ID NO:345 of US 2013/0129723, said sequence incorporated by reference herein), and human IgG4 CH2 region with alanine substitutions at G237 and N297 (SEQ ID NO:346 of US 2013/0129723, said sequence incorporated by reference herein).

In certain embodiments, in addition to the amino acid substitutions described above, an altered CH2 region (e.g., an altered human IgG1 CH2 domain) can contain one or more additional amino acid substitutions at one or more positions other than the above-noted positions. Such amino acid substitutions can be conservative or non-conservative amino acid substitutions. For example, in certain embodiments, P233 can be changed to E233 in an altered IgG2 CH2 region (see, e.g., SEQ ID NO:326 of US 2013/0129723, said sequence incorporated by reference herein). In addition or alternatively, in certain embodiments, the altered CH2 region can contain one or more amino acid insertions, deletions, or both. The insertion(s), deletion(s) or substitution(s) can be anywhere in an immunoglobulin CH2 region, such as at the N- or C-terminus of a wild type immunoglobulin CH2 region resulting from linking the CH2 region with another region (e.g., a binding domain or an immunoglobulin heterodimerization domain) via a hinge.

In certain embodiments, an altered CH2 region in a polypeptide of the present disclosure comprises or is a sequence that is at least 90%, at least 91%, at least 92%, at least 93%, at least 94%, at least 95%, at least 96%, at least 97%, at least 98%, at least 99% identical to a wild type immunoglobulin CH2 region, such as the CH2 region of wild type human IgG1, IgG2, or IgG4, or mouse IgG2a (e.g., IGHG2c).

An altered immunoglobulin CH2 region in a CD3-binding polypeptide of the present disclosure can be derived from a CH2 region of various immunoglobulin isotypes, such as IgG1, IgG2, IgG3, IgG4, IgA1, IgA2, and IgD, from various species (including human, mouse, rat, and other mammals). In certain embodiments, an altered immunoglobulin CH2 region in a fusion protein of the present disclosure can be derived from a CH2 region of human IgG1, IgG2 or IgG4, or mouse IgG2a (e.g., IGHG2c), whose sequences are set forth in SEQ ID NOS:115, 199, 201, and 320 of US 2013/0129723 (said sequences incorporated by reference herein).

In certain embodiments, an altered CH2 domain is a human IgG1 CH2 domain with alanine substitutions at positions 235, 318, 320, and 322 (i.e., a human IgG1 CH2 domain with L235A, E318A, K320A and K322A substitutions) (SEQ ID NO:595 of US 2013/0129723, said sequence incorporated by reference herein), and optionally an N297 mutation (e.g., to alanine). In certain other embodiments, an altered CH2 domain is a human IgG1 CH2 domain with alanine substitutions at positions 234, 235, 237, 318, 320 and 322 (i.e., a human IgG1 CH2 domain with L234A, L235A, G237A, E318A, K320A and K322A substitutions)

(SEQ ID NO:596 of US 2013/0129723, said sequence incorporated by reference herein), and optionally an N297 mutation (e.g., to alanine).

In certain embodiments, an altered CH2 domain is an altered human IgG1 CH2 domain with mutations known in the art that enhance immunological activities such as ADCC, ADCP, CDC, complement fixation, Fc receptor binding, or any combination thereof.

The CH3 domain that can form an immunoglobulin constant region of a CD3-binding polypeptide of the present disclosure can be a wild type immunoglobulin CH3 domain or an altered immunoglobulin CH3 domain thereof from certain immunoglobulin classes or subclasses (e.g., IgG1, IgG2, IgG3, IgG4, IgA1, IgA2, IgD, IgE, IgM) of various species (including human, mouse, rat, and other mammals). In certain embodiments, a CH3 domain is a wild type human immunoglobulin CH3 domain, such as wild type CH3 domains of human IgG1, IgG2, IgG3, IgG4, IgA1, IgA2, IgD, IgE, or IgM as set forth in SEQ ID NOS:116, 208-210, 204-207, and 212, respectively of US 2013/0129723 (said sequences incorporated by reference herein). In certain embodiments, the CH3 domain is a wild type human IgG1 CH3 domain as set forth in SEQ ID NO:116 of US 2013/0129723 (said sequence incorporated by reference herein). In certain embodiments, a CH3 domain is an altered human immunoglobulin CH3 domain, such as an altered CH3 domain based on or derived from a wild-type CH3 domain of human IgG1, IgG2, IgG3, IgG4, IgA1, IgA2, IgD, IgE, or IgM antibodies. For example, an altered CH3 domain can be a human IgG1 CH3 domain with one or two mutations at positions H433 and N434 (positions are numbered according to EU numbering). The mutations in such positions can be involved in complement fixation. In certain other embodiments, an altered CH3 domain can be a human IgG1 CH3 domain but with one or two amino acid substitutions at position F405 or Y407. The amino acids at such positions are involved in interacting with another CH3 domain. In certain embodiments, an altered CH3 domain can be an altered human IgG1 CH3 domain with its last lysine deleted. The sequence of this altered CH3 domain is set forth in SEQ ID NO:761 of US 2013/0129723 (said sequence incorporated by reference herein).

In certain embodiments, CD3-binding polypeptides forming a polypeptide heterodimer comprise a CH3 pair that comprises so called "knobs-into-holes" mutations (see, Marvin and Zhu, Acta Pharmacologica Sinica 26:649-58, 2005; Ridgway et al., Protein Engineering 9:617-21, 1966). More specifically, mutations can be introduced into each of the two CH3 domains of each polypeptide chain so that the steric complementarity required for CH3/CH3 association obligates these two CH3 domains to pair with each other. For example, a CH3 domain in one single chain polypeptide of a polypeptide heterodimer can contain a T366W mutation (a "knob" mutation, which substitutes a small amino acid with a larger one), and a CH3 domain in the other single chain polypeptide of the polypeptide heterodimer can contain a Y407A mutation (a "hole" mutation, which substitutes a large amino acid with a smaller one). Other exemplary knobs-into-holes mutations include (1) a T366Y mutation in one CH3 domain and a Y407T in the other CH3 domain, and (2) a T366W mutation in one CH3 domain and T366S, L368A and Y407V mutations in the other CH3 domain.

The CH4 domain that can form an immunoglobulin constant region of CD3-binding polypeptides of the present disclosure can be a wild type immunoglobulin CH4 domain or an altered immunoglobulin CH4 domain thereof from IgE or IgM molecules. In certain embodiments, the CH4 domain is a wild type human immunoglobulin CH4 domain, such as wild type CH4 domains of human IgE and IgM molecules as set forth in SEQ ID NOS:213 and 214, respectively, of US 2013/0129723 (said sequences incorporated by reference herein). In certain embodiments, a CH4 domain is an altered human immunoglobulin CH4 domain, such as an altered CH4 domain based on or derived from a CH4 domain of human IgE or IgM molecules, which have mutations that increase or decrease an immunological activity known to be associated with an IgE or IgM Fc region.

In certain embodiments, an immunoglobulin constant region of CD3-binding polypeptides of the present disclosure comprises a combination of CH2, CH3 or CH4 domains (i.e., more than one constant region domain selected from CH2, CH3 and CH4). For example, the immunoglobulin constant region can comprise CH2 and CH3 domains or CH3 and CH4 domains. In certain other embodiments, the immunoglobulin constant region can comprise two CH3 domains and no CH2 or CH4 domains (i.e., only two or more CH3). The multiple constant region domains that form an immunoglobulin constant region can be based on or derived from the same immunoglobulin molecule, or the same class or subclass immunoglobulin molecules. In certain embodiments, the immunoglobulin constant region is an IgG CH2CH3 (e.g., IgG1 CH2CH3, IgG2 CH2CH3, and IgG4 CH2CH3) and can be a human (e.g., human IgG1, IgG2, and IgG4) CH2CH3. For example, in certain embodiments, the immunoglobulin constant region comprises (1) wild type human IgG1 CH2 and CH3 domains, (2) human IgG1 CH2 with N297A substitution (i.e., CH2(N297A)) and wild type human IgG1 CH3, or (3) human IgG1 CH2(N297A) and an altered human IgG1 CH3 with the last lysine deleted.

Alternatively, the multiple constant region domains can be based on or derived from different immunoglobulin molecules, or different classes or subclasses immunoglobulin molecules. For example, in certain embodiments, an immunoglobulin constant region comprises both human IgM CH3 domain and human IgG1 CH3 domain. The multiple constant region domains that form an immunoglobulin constant region can be directly linked together or can be linked to each other via one or more (e.g., about 2-10) amino acids.

Exemplary immunoglobulin constant regions are set forth in SEQ ID NOS:305-309, 321, 323, 341, 342, and 762 of US 2013/0129723 (said sequences incorporated by reference herein).

In certain embodiments, the immunoglobulin constant regions of both CD3-binding polypeptides of a polypeptide homodimer or heterodimer are identical to each other. In certain other embodiments, the immunoglobulin constant region of one polypeptide chain of a heterodimeric protein is different from the immunoglobulin constant region of the other polypeptide chain of the heterodimer. For example, one immunoglobulin constant region of a heterodimeric protein can contain a CH3 domain with a "knob" mutation, whereas the other immunoglobulin constant region of the heterodimeric protein can contain a CH3 domain with a "hole" mutation.

The disclosure relates to CD3-binding proteins and polypeptides that may comprise any of the sequences shown in Table 14. Amino acid sequences for polypeptide constructs may or may not include signal sequences. CD3-binding proteins may comprise any of the CD3-binding domains described above. In some aspects, CD3-binding proteins comprise humanized $V_H$ or $V_L$ amino acid sequences, or both.

Examples of bispecific CD3-binding polypeptides are provided in Tables 12 and 13. Such examples include anti-PSMA×anti-CD3 binding molecules (SEQ ID NOs:62, 64, 66, and 68), anti-CD37×anti-CD3 binding molecules (SEQ ID NOs:72, 74, 76, 78, 80, and 82), anti-ROR1×anti-CD3 binding molecules (SEQ ID NOs:100, 104, 108, 112, 116, and 120), and anti-CD123×anti-CD3 binding molecules (SEQ ID NOs:197 and 198).

CD3-binding molecules may be made using scaffolding as generally disclosed in US 2013/0129723 and US 2013/0095097, which are each incorporated herein by reference in their entirety. The CD3-binding proteins may comprise two non-identical polypeptide chains, each polypeptide chain comprising an immunoglobulin heterodimerization domain. The interfacing immunoglobulin heterodimerization domains are different. In one embodiment, the immunoglobulin heterodimerization domain comprises a CH1 domain or a derivative thereof. In another embodiment, the immunoglobulin heterodimerization domain comprises a CL domain or a derivative thereof. In one embodiment, the CL domain is a Cκ or Cλ isotype or a derivative thereof.

The disclosure also includes nucleic acids (e.g., DNA or RNA) encoding CD3-binding domains, proteins and polypeptides described herein, or one or more polypeptide chains of a homodimeric or heterodimeric CD3-binding protein as described herein. Nucleic acids of the disclosure include nucleic acids having a region that is substantially identical to a polynucleotide as listed in Table 14, infra. In certain embodiments, a nucleic acid in accordance with the present disclosure has at least 80%, typically at least about 90%, and more typically at least about 95% or at least about 98% identity to a polypeptide-encoding polynucleotide as listed in Table 14. Nucleic acids of the disclosure also include complementary nucleic acids. In some instances, the sequences will be fully complementary (no mismatches) when aligned. In other instances, there can be up to about a 20% mismatch in the sequences. In some embodiments of the disclosure are provided nucleic acids encoding both first and second polypeptide chains of a heterodimeric CD3-binding protein of the disclosure. The nucleic acid sequences provided herein can be exploited using codon optimization, degenerate sequence, silent mutations, and other DNA techniques to optimize expression in a particular host, and the present disclosure encompasses such sequence modifications.

The disclosure relates to an isolated nucleic acid molecule encoding CD3-binding domains, proteins and polypeptides (or portions thereof) described herein, wherein said nucleic acid molecule comprises a nucleotide sequence set forth in SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, or 59.

Polynucleotide molecules comprising a desired polynucleotide sequence are propagated by placing the molecule in a vector. Viral and non-viral vectors are used, including plasmids. The choice of plasmid will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. The partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

For expression, an expression cassette or system may be employed. To express a nucleic acid encoding a polypeptide disclosed herein, a nucleic acid molecule encoding the polypeptide, operably linked to regulatory sequences that control transcriptional expression in an expression vector, is introduced into a host cell. In addition to transcriptional regulatory sequences, such as promoters and enhancers, expression vectors can include translational regulatory sequences and a marker gene which is suitable for selection of cells that carry the expression vector. The gene product encoded by a polynucleotide of the disclosure is expressed in any convenient expression system, including, for example, bacterial, yeast, insect, amphibian and mammalian systems. In the expression vector, the polypeptide-encoding polynucleotide is linked to a regulatory sequence as appropriate to obtain the desired expression properties. These can include promoters, enhancers, terminators, operators, repressors, and inducers. The promoters can be regulated (e.g., the promoter from the steroid inducible pIND vector (Invitrogen)) or constitutive (e.g., promoters from CMV, SV40, Elongation Factor, or LTR sequences). These are linked to the desired nucleotide sequence using the techniques described above for linkage to vectors. Any techniques known in the art can be used. Accordingly, the expression vector will generally provide a transcriptional and translational initiation region, which can be inducible or constitutive, where the coding region is operably linked under the transcriptional control of the transcriptional initiation region, and a transcriptional and translational termination region.

An expression cassette ("expression unit") can be introduced into a variety of vectors, e.g., plasmid, BAC, YAC, bacteriophage such as lambda, P1, M13, etc., plant or animal viral vectors (e.g., retroviral-based vectors, adenovirus vectors), and the like, where the vectors are normally characterized by the ability to provide selection of cells comprising the expression vectors. The vectors can provide for extrachromosomal maintenance, particularly as plasmids or viruses, or for integration into the host chromosome. Where extrachromosomal maintenance is desired, an origin sequence is provided for the replication of the plasmid, which can be low- or high copy-number. A wide variety of markers are available for selection, particularly those which protect against toxins, more particularly against antibiotics. The particular marker that is chosen is selected in accordance with the nature of the host, where, in some cases, complementation can be employed with auxotrophic hosts. Introduction of the DNA construct can use any convenient method, including, e.g., conjugation, bacterial transformation, calcium-precipitated DNA, electroporation, fusion, transfection, infection with viral vectors, biolistics, and the like. The disclosure relates to an expression vector comprising a nucleic acid segment, wherein said nucleic acid segment may comprise a nucleotide sequence set forth in SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, or 59.

Accordingly, proteins for use within the present disclosure can be produced in genetically engineered host cells according to conventional techniques. Suitable host cells are those cell types that can be transformed or transfected with exogenous DNA and grown in culture, and include bacteria, fungal cells, and cultured higher eukaryotic cells (including cultured cells of multicellular organisms), particularly cultured mammalian cells. Techniques for manipulating cloned DNA molecules and introducing exogenous DNA into a variety of host cells are disclosed by Sambrook and Russell, *Molecular Cloning: A Laboratory Manual* (3rd ed., Cold Spring Harbor Laboratory Press, Cold Spring Harbor, N.Y., 2001), and Ausubel et al., *Short Protocols in Molecular Biology* (4th ed., John Wiley & Sons, 1999).

For example, for recombinant expression of a homodimeric CD3-binding protein comprising two identical CD3-binding polypeptides as described herein, an expression vector will generally include a nucleic acid segment encoding the CD3-binding polypeptide, operably linked to a promoter. For recombinant expression of a heterodimeric CD3-binding protein, comprising different first and second polypeptide chains, the first and second polypeptide chains can be co-expressed from separate vectors in the host cell for expression of the entire heterodimeric protein. Alternatively, for the expression of heterodimeric CD3-binding proteins, the first and second polypeptide chains are co-expressed from separate expression units in the same vector in the host cell for expression of the entire heterodimeric protein. The expression vector(s) are transferred to a host cell by conventional techniques, and the transfected cells are then cultured by conventional techniques to produce the encoded polypeptide(s) to produce the corresponding CD3-binding protein.

To direct a recombinant protein into the secretory pathway of a host cell, a secretory signal sequence (also known as a leader sequence) is provided in the expression vector. The secretory signal sequence can be that of the native form of the recombinant protein, or can be derived from another secreted protein or synthesized de novo. The secretory signal sequence is operably linked to the polypeptide-encoding DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain signal sequences can be positioned elsewhere in the DNA sequence of interest (see, e.g., Welch et al., U.S. Pat. No. 5,037,743; Holland et al., U.S. Pat. No. 5,143,830). In certain variations, a secretory signal sequence for use in accordance with the present disclosure has the amino acid sequence MEAPAQLLFLLLLWLPDTTG (SEQ ID NO:195).

Cultured mammalian cells are suitable hosts for production of recombinant proteins for use within the present disclosure. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841-845, 1982), DEAE-dextran mediated transfection (Ausubel et al., supra), and liposome-mediated transfection (Hawley-Nelson et al., *Focus* 15:73, 1993; Ciccarone et al., *Focus* 15:80, 1993). The production of recombinant polypeptides in cultured mammalian cells is disclosed by, for example, Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44; CHO DXB11 (Hyclone, Logan, Utah); see also, e.g., Chasin et al., *Som. Cell. Molec. Genet.* 12:555, 1986)), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658). Additional suitable cell lines are known in the art and available from public depositories such as the American Type Culture Collection, Manassas, Va. Strong transcription promoters can be used, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants." Cells that have been cultured in the presence of the selective agent and are able to pass the gene of interest to their progeny are referred to as "stable transfectants." Exemplary selectable markers include a gene encoding resistance to the antibiotic neomycin, which allows selection to be carried out in the presence of a neomycin-type drug, such as G-418 or the like; the gpt gene for xanthine-guanine phosphoribosyl transferase, which permits host cell growth in the presence of mycophenolic acid/xanthine; and markers that provide resistance to zeocin, bleomycin, blastocidin, and hygromycin (see, e.g., Gatignol et al., *Mol. Gen. Genet.* 207:342, 1987; Drocourt et al., *Nucl. Acids Res.* 18:4009, 1990). Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. An exemplary amplifiable selectable marker is dihydrofolate reductase, which confers resistance to methotrexate. Other drug resistance genes (e.g., hygromycin resistance, multi-drug resistance, puromycin acetyltransferase) can also be used.

Other higher eukaryotic cells can also be used as hosts, including insect cells, plant cells and avian cells. The use of *Agrobacterium rhizogenes* as a vector for expressing genes in plant cells has been reviewed by Sinkar et al., *J. Biosci. (Bangalore)* 11:47-58, 1987. Transformation of insect cells and production of foreign polypeptides therein is disclosed by Guarino et al., U.S. Pat. No. 5,162,222 and WO 94/06463.

Insect cells can be infected with recombinant baculovirus, commonly derived from *Autographa californica* nuclear polyhedrosis virus (AcNPV). See King and Possee, *The Baculovirus Expression System: A Laboratory Guide* (Chapman & Hall, London); O'Reilly et al., *Baculovirus Expression Vectors: A Laboratory Manual* (Oxford University Press., New York 1994); and *Baculovirus Expression Protocols. Methods in Molecular Biology* (Richardson ed., Humana Press, Totowa, N.J., 1995). Recombinant baculovirus can also be produced through the use of a transposon-based system described by Luckow et al. (*J. Virol.* 67:4566-4579, 1993). This system, which utilizes transfer vectors, is commercially available in kit form (BAC-TO-BAC kit; Life Technologies, Gaithersburg, Md.). The transfer vector (e.g., PFASTBAC1; Life Technologies) contains a Tn7 transposon to move the DNA encoding the protein of interest into a baculovirus genome maintained in *E. coli* as a large plasmid called a "bacmid." See Hill-Perkins and Possee, *J. Gen. Virol.* 71:971-976, 1990; Bonning et al., *J. Gen. Virol.* 75:1551-1556, 1994; and Chazenbalk and Rapoport, *J. Biol. Chem.* 270:1543-1549, 1995. In addition, transfer vectors can include an in-frame fusion with DNA encoding a polypeptide extension or affinity tag as disclosed above. Using techniques known in the art, a transfer vector containing a protein-encoding DNA sequence is transformed into *E. coli* host cells, and the cells are screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, such as Sf9 cells. Recombinant virus that expresses the protein or interest is subsequently produced. Recombinant viral stocks are made by methods commonly used in the art.

For protein production, the recombinant virus is used to infect host cells, typically a cell line derived from the fall armyworm, *Spodoptera frugiperda* (e.g., Sf9 or Sf21 cells) or *Trichoplusia ni* (e.g., HIGH FIVE cells; Invitrogen, Carlsbad, Calif.). See generally Glick and Pastemak, *Molecular Biotechnology, Principles & Applications of Recombinant DNA* (ASM Press, Washington, D.C., 1994). See also U.S. Pat. No. 5,300,435. Serum-free media are used to grow and maintain the cells. Suitable media formulations are known in the art and can be obtained from commercial suppliers. The cells are grown up from an inoculation density of approximately $2-5\times10^5$ cells to a density of $1-2\times10^6$ cells, at which time a recombinant viral stock is added at a multiplicity of infection (MOI) of 0.1 to 10, more typically near 3. Procedures used are generally described in available laboratory manuals (see, e.g., King and Possee, supra; O'Reilly et al., supra; Richardson, supra).

Fungal cells, including yeast cells, can also be used within the present disclosure. Yeast species of in this regard include, e.g., *Saccharomyces cerevisiae*, *Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). An exemplary vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936; and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii*, and *Candida maltosa* are known in the art. See, e.g., Gleeson et al., *J. Gen. Microbiol.* 132:3459-3465, 1986; Cregg, U.S. Pat. No. 4,882,279; and Raymond et al., *Yeast* 14:11-23, 1998. *Aspergillus* cells can be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533. Production of recombinant proteins in *Pichia methanolica* is disclosed in U.S. Pat. Nos. 5,716,808; 5,736,383; 5,854,039; and 5,888,768.

Prokaryotic host cells, including strains of the bacteria *Escherichia coli, Bacillus*, and other genera are also useful host cells within the present disclosure. Techniques for transforming these hosts and expressing foreign DNA sequences cloned therein are well-known in the art (see, e.g., Sambrook and Russell, supra). When expressing a recombinant protein in bacteria such as *E. coli*, the protein can be retained in the cytoplasm, typically as insoluble granules, or can be directed to the periplasmic space by a bacterial secretion sequence. In the former case, the cells are lysed, and the granules are recovered and denatured using, for example, guanidine isothiocyanate or urea. The denatured protein can then be refolded and dimerized by diluting the denaturant, such as by dialysis against a solution of urea and a combination of reduced and oxidized glutathione, followed by dialysis against a buffered saline solution. In the alternative, the protein can be recovered from the cytoplasm in soluble form and isolated without the use of denaturants. The protein is recovered from the cell as an aqueous extract in, for example, phosphate buffered saline. To capture the protein of interest, the extract is applied directly to a chromatographic medium, such as an immobilized antibody or heparin-Sepharose column. Secreted proteins can be recovered from the periplasmic space in a soluble and functional form by disrupting the cells (by, for example, sonication or osmotic shock) to release the contents of the periplasmic space and recovering the protein, thereby obviating the need for denaturation and refolding. Antibodies, including single-chain antibodies, can be produced in bacterial host cells according to known methods. See, e.g., Bird et al., *Science* 242:423-426, 1988; Huston et al., *Proc. Natl. Acad. Sci. USA* 85:5879-5883, 1988; and Pantoliano et al., *Biochem.* 30:10117-10125, 1991.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media can also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

CD3-binding proteins may be purified by conventional protein purification methods, typically by a combination of chromatographic techniques. See generally *Affinity Chromatography: Principles & Methods* (Pharmacia LKB Biotechnology, Uppsala, Sweden, 1988); Scopes, *Protein Purification: Principles and Practice* (Springer-Verlag, New York 1994). Proteins comprising an immunoglobulin Fc region can be purified by affinity chromatography on immobilized protein A or protein G. Additional purification steps, such as gel filtration, can be used to obtain the desired level of purity or to provide for desalting, buffer exchange, and the like.

CD3-binding molecules disclosed herein may be used in a method for treating a subject (for example, a human or a non-human primate) or for manufacture of a medicament for treating a subject. Generally, such methods include administering to a subject in need of such treatment a CD3-binding protein as described herein.

CD3-binding molecules disclosed herein may be used in a method for treating a subject (for example, a human or a non-human primate) or for manufacture of a medicament for treating a subject. Generally, such methods include administering to a subject in need of such treatment a CD3-binding protein as described herein. In some embodiments, a CD3-binding protein comprises at least one effector function selected from antibody-dependent cell-mediated cytotoxicity (ADCC) and complement-dependent cytotoxicity (CDC), such that the CD3-binding protein induces ADCC and/or CDC against CD3-expressing cells in the subject.

In some aspects, the present disclosure provides methods for treating a subject with a disorder characterized by over-expression of CD3. In one case, a monospecific CD3 binding polypeptide is administered to a patient suffering from an autoimmune disease (e.g., rheumatoid arthritis). In certain variations, a CD3-binding protein provided herein could be used for the modulation of T-cell function and fate, thereby providing therapeutic treatment of T cell mediated disease, including autoimmune or inflammatory diseases in which T-cells are significant contributors. Because some CD3-binding proteins of the present disclosure do not activate T-cells and/or do not induce cytokine release, they are advantageous over other molecules directed against the TCR complex (e.g., anti-CD3 antibodies) for having no or reduced side effects such as cytokine release syndrome and acute toxicity. In another case, a CD3-binding polypeptide is administered to a subject about to undergo an organ transplant.

In another aspect, the present disclosure provides a method for treating a disorder characterized by overexpression of a tumor antigen, such as cancer. Examples of tumor antigens that may be recognized by bispecific CD3-binding proteins include PSMA, CD19, CD20, CD37, CD38, CD123, Her2, ROR1, RON, glycoprotein A33 antigen (gpA33) and CEA. Generally, such methods include administering to a subject in need of such treatment a therapeutically effective amount of a CD3-binding protein comprising a second binding domain that binds a tumor antigen as described herein. In some embodiments, the CD3 binding protein induces redirected T-cell cytotoxicity (RTCC) against tumor antigen-expressing cells in the subject. Exemplary cancers amenable to treatment in accordance with the present disclosure include, for example, prostate cancer, colorectal cancer, renal cell carcinoma, bladder cancer, salivary gland cancer, pancreatic cancer, ovarian cancer, non-small cell lung cancer, melanoma, breast cancer (e.g., triple negative breast cancer), adrenal cancer, mantle cell lymphoma, acute lymphoblastic leukemia, chronic lymphocytic leukemia, Non-Hodgkin's lymphoma, acute myeloid leukemia (AML), B-lymphoid leukemia, blastic plasmocytoid dendritic neoplasm (BPDCN), and hairy cell leukemia.

The disclosure also provides methods for treating cancer or an autoimmune disorder comprising administering a therapeutically effective amount of the compositions or CD3-binding polypeptides described herein to a patient in need thereof.

In some embodiments, the disclosure provides a method of treating a patient with a cancer, comprising administering to the patient a CD3-binding polypeptide comprising a CD3-binding domain that binds specifically to human CD3 and that comprises an immunoglobulin light chain variable region and an immunoglobulin heavy chain variable region; wherein the immunoglobulin light chain variable region comprises an amino acid sequence that is (a) at least about 93% identical, at least about 95% identical, at least about 97% identical, at least about 98% identical or at least about 99% identical to the amino acid sequence in SEQ ID NO:88; or (b) at least about 94% identical, at least about 95% identical, at least about 97% identical, at least about 98% identical or at least about 99% identical to the amino acid sequence in SEQ ID NO:89; and wherein the immunoglobulin heavy chain variable region comprises an amino acid sequence that is at least about 82% identical, at least about 85% identical, at least about 87% identical, at least about 90% identical, at least about 92% identical, at least about 95% identical, at least about 97% identical, at least about 98% identical or at least about 99% identical to the amino acid sequence in SEQ ID NO:86.

In some embodiments, for treatment methods and uses described herein, a CD3-binding protein is delivered in a manner consistent with conventional methodologies associated with management of the disease or disorder for which treatment is sought. In accordance with the disclosure herein, a therapeutically effective amount of the CD3-binding protein is administered to a subject in need of such treatment for a time and under conditions sufficient to prevent or treat the disease or disorder.

Subjects for administration of CD3-binding proteins as described herein include patients at high risk for developing a particular disorder as well as patients presenting with an existing such disorder. Typically, the subject has been diagnosed as having the disorder for which treatment is sought. Further, subjects can be monitored during the course of treatment for any change in the disorder (e.g., for an increase or decrease in clinical symptoms of the disorder). Also, in some variations, the subject does not suffer from another disorder requiring treatment that involves targeting CD3-expressing cells.

In prophylactic applications, pharmaceutical compositions or medicants are administered to a patient susceptible to, or otherwise at risk of, a particular disorder in an amount sufficient to eliminate or reduce the risk or delay the onset of the disorder. In therapeutic applications, compositions or medicants are administered to a patient suspected of, or already suffering from such a disorder in an amount sufficient to cure, or at least partially arrest, the symptoms of the disorder and its complications. An amount adequate to accomplish this is referred to as a therapeutically effective dose or amount. In both prophylactic and therapeutic regimes, agents are usually administered in several dosages until a sufficient response has been achieved. Typically, the response is monitored and repeated dosages are given if the desired response starts to fade.

To identify subject patients for treatment according to the methods of the disclosure, accepted screening methods can be employed to determine risk factors associated with specific disorders or to determine the status of an existing disorder identified in a subject. Such methods can include, for example, determining whether an individual has relatives who have been diagnosed with a particular disorder. Screening methods can also include, for example, conventional work-ups to determine familial status for a particular disorder known to have a heritable component. For example, various cancers are also known to have certain inheritable components. Inheritable components of cancers include, for example, mutations in multiple genes that are transforming (e.g., Ras, Raf, EGFR, cMet, and others), the presence or absence of certain HLA and killer inhibitory receptor (KIR) molecules, or mechanisms by which cancer cells are able to modulate immune suppression of cells like NK cells and T-cells, either directly or indirectly (see, e.g., Ljunggren and Malmberg, *Nature Rev. Immunol.* 7:329-339, 2007; Boyton and Altmann, *Clin. Exp. Immunol.* 149:1-8, 2007). Toward this end, nucleotide probes can be routinely employed to identify individuals carrying genetic markers associated with a particular disorder of interest. In addition, a wide variety of immunological methods are known in the art that are useful to identify markers for specific disorder. For example, various ELISA immunoassay methods are available and well-known in the art that employ monoclonal antibody probes to detect antigens associated with specific tumors. Screening can be implemented as indicated by known patient symptomology, age factors, related risk factors, etc. These methods allow the clinician to routinely select patients in need of the methods described herein for treatment. In accordance with these methods, targeting pathological, tumor antigen-expressing cells can be implemented as an independent treatment program or as a follow-up, adjunct, or coordinate treatment regimen to other treatments.

For administration, a CD3-binding protein may be formulated as a pharmaceutical composition. A pharmaceutical composition may comprise: (i) a CD3-binding polypeptide; and (ii) a pharmaceutically acceptable carrier, diluent or excipient. A pharmaceutical composition comprising a CD3-binding protein can be formulated according to known methods to prepare pharmaceutically useful compositions, whereby the therapeutic molecule is combined in a mixture with a pharmaceutically acceptable carrier, diluent or excipient. A carrier is said to be a "pharmaceutically acceptable carrier" if its administration can be tolerated by a recipient patient. Sterile phosphate-buffered saline is one example of a pharmaceutically acceptable carrier. Other suitable carriers, diluents or excipients are well-known to those in the art. (See, e.g., Gennaro (ed.), *Remington's Pharmaceutical Sciences* (Mack Publishing Company, 19th ed. 1995).) Formulations can further include one or more excipients, preservatives, solubilizers, buffering agents, albumin to prevent protein loss on vial surfaces, etc.

A pharmaceutical composition may be formulated in a dosage form selected from the group consisting of: an oral unit dosage form, an intravenous unit dosage form, an intranasal unit dosage form, a suppository unit dosage form, an intradermal unit dosage form, an intramuscular unit dosage form, an intraperitoneal unit dosage form, a subcutaneous unit dosage form, an epidural unit dosage form, a sublingual unit dosage form, and an intracerebral unit dosage form. The oral unit dosage form may be selected from the group consisting of: tablets, pills, pellets, capsules, powders, lozenges, granules, solutions, suspensions, emulsions, syrups, elixirs, sustained-release formulations, aerosols, and sprays.

A pharmaceutical composition comprising a CD3-binding protein therapeutic may be administered to a subject in a therapeutically effective amount. According to the methods of the present disclosure, a CD3-binding protein can be administered to subjects by a variety of administration modes, including, for example, by intramuscular, subcutaneous, intravenous, intra-atrial, intra-articular, parenteral, intranasal, intrapulmonary, transdermal, intrapleural, intrathecal, and oral routes of administration. For prevention and treatment purposes, an antagonist can be administered to a subject in a single bolus delivery, via continuous delivery (e.g., continuous transdermal delivery) over an extended time period, or in a repeated administration protocol (e.g., on an hourly, daily, weekly, or monthly basis).

Determination of effective dosages in this context is typically based on animal model studies followed up by human clinical trials and is guided by determining effective dosages and administration protocols that significantly reduce the occurrence or severity of the subject disorder in model subjects. Effective doses of the compositions of the present disclosure vary depending upon many different factors, including means of administration, target site, physiological state of the patient, whether the patient is human or an animal, other medications administered, whether treatment is prophylactic or therapeutic, as well as the specific activity of the composition itself and its ability to elicit the desired response in the individual. Usually, the patient is a human, but in some diseases, the patient can be a nonhuman mammal. Typically, dosage regimens are adjusted to provide an optimum therapeutic response, i.e., to optimize safety and efficacy. Accordingly, a therapeutically effective amount is also one in which any undesired collateral effects are outweighed by the beneficial effects of administering a CD3-binding protein as described herein. For administration of a CD3-binding protein, a dosage may range from about 0.1 µg to 100 mg/kg or 1 µg/kg to about 50 mg/kg, and more usually 10 µg to 5 mg/kg of the subject's body weight. In more specific embodiments, an effective amount of the agent is between about 1 µg/kg and about 20 mg/kg, between about 10 µg/kg and about 10 mg/kg, or between about 0.1 mg/kg and about 5 mg/kg. Dosages within this range can be achieved by single or multiple administrations, including, e.g., multiple administrations per day or daily, weekly, bi-weekly, or monthly administrations. For example, in certain variations, a regimen consists of an initial administration followed by multiple, subsequent administrations at weekly or bi-weekly intervals. Another regimen consists of an initial administration followed by multiple, subsequent administrations at monthly or bi-monthly intervals. Alternatively, administrations can be on an irregular basis as indicated by monitoring clinical symptoms of the disorder.

Dosage of the pharmaceutical composition can be varied by the attending clinician to maintain a desired concentration at a target site. For example, if an intravenous mode of delivery is selected, local concentration of the agent in the bloodstream at the target tissue can be between about 0.01-50 nanomoles of the composition per liter, sometimes between about 1.0 nanomole per liter and 10, 15, or 25 nanomoles per liter depending on the subject's status and projected measured response. Higher or lower concentrations can be selected based on the mode of delivery, e.g., trans-epidermal delivery versus delivery to a mucosal surface. Dosage should also be adjusted based on the release rate of the administered formulation, e.g., nasal spray versus powder, sustained release oral or injected particles, transdermal formulations, etc. To achieve the same serum concentration level, for example, slow-release particles with a release rate of 5 nanomolar (under standard conditions) would be administered at about twice the dosage of particles with a release rate of 10 nanomolar.

The anti-CD3 therapeutic (e.g., CD3-binding protein) may also be administered at a daily dosage of from about 0.001 to about 10 milligrams (mg) per kilogram (mpk) of body weight, preferably given as a single daily dose or in divided doses about two to six times a day. For administration to a human adult patient, the therapeutically effective amount may be administered in doses in the range of 0.2 mg to 800 mg per dose, including but not limited to 0.2 mg per dose, 0.5 mg per dose, 1 mg per dose, 5 mg per dose, 10 mg per dose, 25 mg per dose, 100 mg per dose, 200 mg per dose, and 400 mg per dose, and multiple, usually consecutive daily doses may be administered in a course of treatment. The anti-CD3 therapeutic can be administered at different times of the day. In one embodiment the optimal therapeutic dose can be administered in the evening. In another embodiment the optimal therapeutic dose can be administered in the morning. The total daily dosage of the anti-CD3 therapeutic thus can in one embodiment range from about 1 mg to about 2 g, and often ranges from about 100 mg to about 1.5 g, and most often ranges from about 200 mg to about 1200 mg. In the case of a typical 70 kg adult human, the total daily dose of the anti-CD3 therapeutic can range from about 2 mg to about 1200 mg and will often range, as noted above, from about 0.2 mg to about 800 mg.

With particular regard to treatment of solid tumors, protocols for assessing endpoints and anti-tumor activity are well-known in the art. While each protocol may define tumor response assessments differently, the RECIST (Response evaluation Criteria in solid tumors) criteria is currently considered to be the recommended guidelines for assessment of tumor response by the National Cancer Institute (see Therasse et al., *J. Natl. Cancer Inst.* 92:205-216, 2000). According to the RECIST criteria tumor response means a reduction or elimination of all measurable lesions or metastases. Disease is generally considered measurable if it comprises lesions that can be accurately measured in at least one dimension as ≥20 mm with conventional techniques or ≥10 mm with spiral CT scan with clearly defined margins by medical photograph or X-ray, computerized axial tomography (CT), magnetic resonance imaging (MRI), or clinical examination (if lesions are superficial). Non-measurable disease means the disease comprises of lesions <20 mm with conventional techniques or <10 mm with spiral CT scan, and truly non-measurable lesions (too small to accurately measure). Non-measurable disease includes pleural effusions, ascites, and disease documented by indirect evidence.

The criteria for objective status are required for protocols to assess solid tumor response. Representative criteria include the following: (1) Complete Response (CR), defined as complete disappearance of all measurable disease; no new lesions; no disease related symptoms; no evidence of non-measurable disease; (2) Partial Response (PR) defined as 30% decrease in the sum of the longest diameter of target lesions (3) Progressive Disease (PD), defined as 20% increase in the sum of the longest diameter of target lesions or appearance of any new lesion; (4) Stable or No Response, defined as not qualifying for CR, PR, or Progressive Disease. (See Therasse et al., supra.)

Additional endpoints that are accepted within the oncology art include overall survival (OS), disease-free survival (DFS), objective response rate (ORR), time to progression (TTP), and progression-free survival (PFS) (see *Guidance for Industry: Clinical Trial Endpoints for the Approval of Cancer Drugs and Biologics*, April 2005, Center for Drug Evaluation and Research, FDA, Rockville, Md.)

Pharmaceutical compositions can be supplied as a kit comprising a container that comprises the pharmaceutical composition as described herein. A pharmaceutical composition can be provided, for example, in the form of an injectable solution for single or multiple doses, or as a sterile powder that will be reconstituted before injection. Alternatively, such a kit can include a dry-powder disperser, liquid aerosol generator, or nebulizer for administration of a pharmaceutical composition. Such a kit can further comprise written information on indications and usage of the pharmaceutical composition.

The disclosure will be further clarified by the following examples, which are intended to be purely exemplary of the disclosure and in no way limiting.

EXAMPLES

Example 1. Generation of Stabilized CD3-Binding Molecules

To improve thermal stability of the CD3-binding molecule DRA222, an engineered variant of the humanized Cris7 antibody, the Cris7 variable domains were re-humanized using alternate human germline framework sequences. The DRA222 variable heavy chain domain is SEQ ID NO:87, and the DRA222 variable light chain domain is SEQ ID NO:90. Fc DRA222 is sometimes referred to as TSC311 or TSC312 (amino acid sequence is SEQ ID NO:2; nucleic acid sequence is SEQ ID NO:1). See, Reinherz, E. L. et al. (eds.), Leukocyte typing II., Springer Verlag, New York, (1986) for description of parent Cris7 antibody. Additional changes were also made to improve affinity and thermal stability.

Methods

The following methods were used to obtain results shown in this example:

Differential Scanning Calorimetry (DSC).

Thermograms for recombinant proteins purified by standard purification techniques were obtained on a GE VP-Capillary DSC instrument equipped with an autosampler. Approximately 550 µL of each sample (typically 0.5 mg/mL) in PBS was injected into the sample capillary, using PBS as a control in the second capillary. Analysis was conducted at temperatures from 25° C. to 130° C., with a heating rate of 1° C. per min. Feedback was set to low, and a sampling time of 8 ms was used. Data analysis was conducted using Origin. Sample thermogram was corrected for heat capacity of the buffer by subtracting a previous buffer/buffer scan using formulation vehicle, and normalized based on sample concentration and baseline corrected.

Differential Scanning Fluorimetry (DSF).

In a high throughput format, thermograms for recombinant proteins purified by standard purification techniques were also obtained by DSF assay run on a Real Time PCR machine (Bio-Rad iCycler iQ5). Approximately 40 µL of each sample in a concentration of 0.8 mg/mL in PBS was mixed with 5 µL of pre-diluted SYPRO Orange Dye (Catalogue #S-6650, Life Technologies). A melting curve protocol was set up as ramping the temperature up from 25° C. to 90° C., 0.2° C. per step. Fluorescent signals were collected through the TexasRed Fluorescent Dye filter set, which is 575/30X Excitation Filter and 620/30M Emission Filter. The collected fluorescent intensity data was exported to data analysis software Prism 6 (GraphPad Software, Inc.). Protein thermal Tm value was calculated as the temperature when second derivatives of fluorescent intensity against temperature−d(RUF)/dT2=0.

Flow Cytometry on Human Jurkat T-Cells.

Binding studies were performed by standard flow cytometry-based staining procedures using the CD3+ Jurkat T-cell line. All labeling and washes were performed in U-bottom 96-well plates in saline buffer with 3% BSA and 2 mM EDTA. Jurkat cells were plated at 200,000 cells per well and incubated with a range of 0.1 nM to 200 nM concentrations of test molecules in 50 µL volume/well, for 30 minutes on ice. Cells were washed three times then incubated for another 30 minutes on ice with fluorescently-labeled minimum cross reactive secondary polyclonal antibody, F(ab')$_2$ goat anti-human IgG, (Jackson ImmunoResearch Laboratories) and the viability dye 7-AAD. The cells were then washed twice, and the samples acquired in a BD LSRII flow cytometer. The sample files were analyzed using FlowJo software; the mean fluorescence intensity (MFI) of the live population of Jurkat cells in each well was calculated after gating on live cells (forward vs. side scatter, then 7-AAD cells).

Homology Modeling, Spatial Aggregation Propensity Analysis.

Homology models were constructed within Accelrys Discovery Studio 4.0 for variable domains using the Annotate Antibody Sequence, Identify Framework Templates, Model Antibody Framework, and Model Antibody Loops protocols. Spatial Aggregation Propensity analysis was also conducted within Accelrys Discovery Studio 4.0 using the Calculate Aggregation Scores protocol.

Chromium Release Assays with Human T-Cells.

Target positive tumor cell lines (MDA-MB-231, Kasumi-2, C4-2B and Ramos cell lines) were all cultured according to the provided protocols. Peripheral blood mononuclear cells (PBMC) were isolated from human blood using standard ficoll gradients. The isolated cells were washed in saline buffer. T-cells were additionally isolated using a Pan T-cell Isolation Kit (catalogue #130-096-535, Miltenyi Biotec, Bergisch Gladbach, Germany) using the manufacturers protocol. Isolated T-cells were aliquoted and stored long term in Liquid Nitrogen. The pre-prepared T-cells were thawed one day before the assay into warm RPMI media with 10% human serum. During the assay, concentrations of bispecific molecules with final concentration ranging from 200 pM to 0.01 pM were added to the pre-prepared T-cells (approximately 100,000 per well). A total lysis control was generated by including 0.04% NP-40 as the treatment.

Approximately $2.5 \times 10^8$ target cells were treated with 0.125 mCi of $^{51}$Cr and incubated for 90 minutes in a 37° C., 5% $CO_2$ humidified incubator. After incubation, cells were washed 4 times with diluted assay media (RPMI with 1% human serum) and re-suspended in 12.5 mL of the complete assay media (RPMI with 10% human serum). From this suspension, 50 µL was dispensed per well into 96 well U-bottom plates (approximately 10,000 cells per well) to bring the total volume to 200 mL per well, and the T-cell to target cell ratio to 10:1. A zero lysis control was generated by target cells only, omitting the T-cells.

Plates were incubated for 4 hours (and occasionally also for 24 hours) at 37° C., 5% $CO_2$ in a humidified incubator, after which they were centrifuged at 1000 rpm for 3 minutes, and 25 µL of supernatant was transferred from each well to the corresponding well of a 96-well Luma sample plate. Sample plates were allowed to air dry in a chemical safety hood for 18 hours, and then radioactivity was read on a TopCount microplate scintillation counter (PerkinElmer) using a standard protocol.

Percent specific lysis was calculated using the formula: ((signal in drug treated sample−background signal from samples with Target Cell only)/(signal in total lysis wells−background signal from samples with Target Cell only))×100.

Flow Cytometry on Cynomolgus T-Cells.

Cynomolgus macaque peripheral blood collected in heparin tubes was shipped overnight from a vendor (Charles River laboratories). When received, peripheral blood cells (PBMC) were isolated using density separation tubes (CPT tubes, Beckton Dickinson). Blood was diluted 1 to 1.5 in saline buffer prior to transfer into CPT tubes. CPT tubes were centrifuged and the separated PBMC population was collected and washed with saline buffer containing 0.2% BSA and 5 nM EDTA. Remaining red blood cells in the preparation were lysed using Ammonium-Chloride-Potassium red blood lysis buffer. Cells were washed an additional time to remove remaining platelets.

PBMC labeling and washing steps were performed in U-bottom 96-well plates in saline buffer with 0.2% BSA and 2 mM EDTA. PBMC were plated at 200,000 cells per well and incubated with a range of 0.1 nM to 300 nM concentrations of test molecules in 50 µL volume/well, for 30 minutes on ice. Cells were washed three times, then incubated for another 30 min on ice with fluorescently-labeled antibodies to non-human primate CD2 and CD16 (Biolegend), anti-idiotypic antibodies to either anti-PSMA or anti-CD37 binding domains, and the viability dye 7-AAD. The samples were washed twice, fixed for 20 minutes on ice with 1% formaldehyde solution in saline, washed again, and acquired in a BD LSRII flow cytometer. The sample files were analyzed using FlowJo software; the mean fluorescence intensity (MFI) of test molecule binding on T-cells in each well was calculated after gating on live T-cells (forward vs. side scatter, 7-AAD$^-$, CD2$^+$ CD16$^-$ cells).

Chromium Release Assays with Cynomolgus PBMC.

C4-2B and Ramos cell lines were both cultured according to the provided protocols. Peripheral blood mononuclear cells (PBMC) were isolated from cynomolgus macaque peripheral blood using BD VACUTAINER® CPT™ Cell Preparation Tube with Sodium Heparin (Cat #362753). The isolated cells were washed in saline buffer. Concentrations of bispecific molecules with final concentration ranging from 10000 pM to 0.0128 pM were added to isolated PBMC (approximately 100,000). A total lysis control was generated by including 0.04% NP-40 as the treatment.

Approximately $5 \times 10^6$ target C4-2B or Ramos cells were treated with 0.25 mCi of $^{51}$Cr and incubated for 75 minutes at 37° C. After incubation, cells were washed 4 times with the cell culture media (RPMI with 10% FBS, 1% NEAA, 1% sodium pyruvate, Na Glutamine and 20 mM HEPES) and re-suspended in 25 mL of media. From this suspension, 50 µL was dispensed per well into 96 well U-bottom plates (approximately 10,000 cells/well) to bring the T-cell to target cell ratio to 10:1.

Plates were incubated for 4 hours at 37° C., 5% $CO_2$ in a humidified incubator, after which they were centrifuged at 225×G for 3 minutes, and 25 µL of supernatant was transferred from each well to the corresponding well of a 96-well Luma sample plate. Sample plates were allowed to air dry in a chemical safety hood for 18 hours, and then radioactivity was read on a Topcount scintillation counter using a standard protocol.

Results

Step 1: Generation of Initial Humanized CD3-Binding Constructs

The Cris7 variable domains were re-humanized using four human variable heavy germline sequences (IGHV1-2*02 (H7), IGHV1-46*02 (H8), IGHV1-3*01(H9) and IGHV1-69*02 (H10)) and 2 human variable light chain germline sequences (IGKV3-11*01 (L4) and IGKV1-33*01 (L5)) based on sequence homology. A total of 12 single chain variable fragment (scFv) constructs were generated in the Fc anti-CD3 scFv format using the H75 linker (QRHNNSSLNTGTQMAGHSPNS; SEQ ID NO:148) (Table 3). Sequences of the 12 constructs and the control molecule Fc DRA222 (TSC311 or TSC312) are provided in Table 14.

TABLE 3

Variable Domain Composition of Initial Constructs

| Heavy chain | L1 (original light chain) | Light chain L4 | L5 |
|---|---|---|---|
| H7 | H7L1 (TSC313) | H7L4 (TSC314) | H7L5 (TSC315) |
| H8 | H8L1 (TSC316) | H8L4 (TSC317) | H8L5 (TSC318) |
| H9 | H9L1 (TSC319) | H9L4 (TSC320) | H9L5 (TSC321) |
| H10 | H10L1 (TSC322) | H10L4 (TSC323) | H10L5 (TSC324) |

All 12 constructs were expressed transiently in HEK293 cells, purified and tested for binding to Jurkat T-cells and evaluated for thermal stability. Constructs containing the L4 light chain or H9 heavy chain had lower levels of protein expression (see final yield column in Table 4) and/or higher levels of high molecular weight aggregates (see analytical SEC column in Table 4) and were eliminated in the subsequent optimization step. While most of the other constructs had some improvement in thermal stability of the scFv over the original humanized domains (TSC312) as measured by the midpoint of thermal denaturation (Tm) using Differential Scanning Calorimetry (DSC) (Table 5), the level of binding saturation observed on Jurkat T-cells was reduced by varying levels (FIG. 1). The most stable construct, TSC324, had a nearly 50% reduction in observed median fluorescence intensity at saturation and an two-fold increase in the EC50 of binding (3.6 nM) when compared to the original humanized construct (TSC312, also known as DRA222).

TABLE 4

Expression and Purity of Transiently Expressed Material

| Molecule | Database Name | 1st step titer (µg/ml) | Final yield (mg) | Analytical SEC - Main Peak (%) | Analytical SEC - Recovery % |
|---|---|---|---|---|---|
| Fc DRA222 | TSC312 | 43.8 | 4.12 | 92.6 | 100.3 |
| Fc H7L1 | TSC313 | 35.2 | 2.66 | 95.3 | 90.2 |
| Fc H7L4 | TSC314 | 57.8 | 5.78 | 58.8 | 96.0 |
| Fc H7L5 | TSC315 | 52.6 | 6.99 | 90.6 | 93.3 |
| Fc H8L1 | TSC316 | 39.9 | 3.73 | 93.4 | 99.5 |
| Fc H8L4 | TSC317 | 52.9 | 4.95 | 66.5 | 97.6 |
| Fc H8L5 | TSC318 | 48.1 | 4.83 | 92.1 | 96.2 |
| Fc DRA222 | TSC312 | 16.1 | 1.41 | 95.4 | 97.8 |
| Fc H9L1 | TSC319 | 8.0 | 0.71 | 80.0 | 85.8 |
| Fc H9L4 | TSC320 | 43.1 | 3.60 | 69.3 | 102.5 |
| Fc H9L5 | TSC321 | 31.1 | 2.66 | 92.6 | 98.6 |
| Fc H10L1 | TSC322 | 45.6 | 3.94 | 73.2 | 56.7 |
| Fc H10L4 | TSC323 | 50.6 | 4.58 | 67.3 | 106.7 |
| Fc H10L5 | TSC324 | 33.1 | 2.85 | 90.7 | 104.0 |

TABLE 5

Thermal Stability as Measured by Differential Scanning Calorimetry

| Molecules | Tm of anti-CD3 scFv (° C.) | Improvement in Tm (over DRA222) |
|---|---|---|
| TSC312 (DRA222) | 53.02 | |
| TSC313 (H7L1) | 54.47 | 1.45 |
| TSC315 (H7L5) | 54.99 | 1.97 |
| TSC316 (H8L1) | 53.70 | 0.68 |
| TSC318 (H8L5) | 55.16 | 2.14 |
| TSC312 (H7L1) | 52.88 | −0.14 |
| TSC321 (H9L5) | 53.10 | 0.08 |
| TSC324 (H10L5) | 55.83 | 2.81 |

Step 2: Initial Optimization to Restore Binding to CD3

The goal of the next step was to improve binding to CD3 while maintaining improved thermal stability over DRA222. Three additional light chain sequences were introduced at this step. The first light chain was based on the L5 sequence containing two amino acid reverted to the parental murine residues at positions 52 and 53 (LL to RW), and this light chain was named L6. Two additional germline light chains were also used (IGKV1-39*01 (L7) and IGKV3D-20*1 (L8) containing the same two amino acids reverted at position 52 and 53. The 3 new light chains (L6, L7 and L8) were combined with 3 heavy chains (H7, H8 and H10) in the Fc anti-CD3 scFv format to give the following scFv combinations (Table 6):

TABLE 6

Variable Domain Composition of Second Round Constructs

| Heavy Chain | L6 | Light chain L7 | L8 |
|---|---|---|---|
| H7 | H7L6 (TSC334) | H7L7 (TSC335) | H7L8 (TSC336) |
| H8 | H8L6 (TSC337) | H8L7 (TSC338) | H8L8 (TSC339) |
| H10 | H10L6 (TSC340) | H10L7 (TSC341) | H10L8 (TSC342) |

Figure 2:
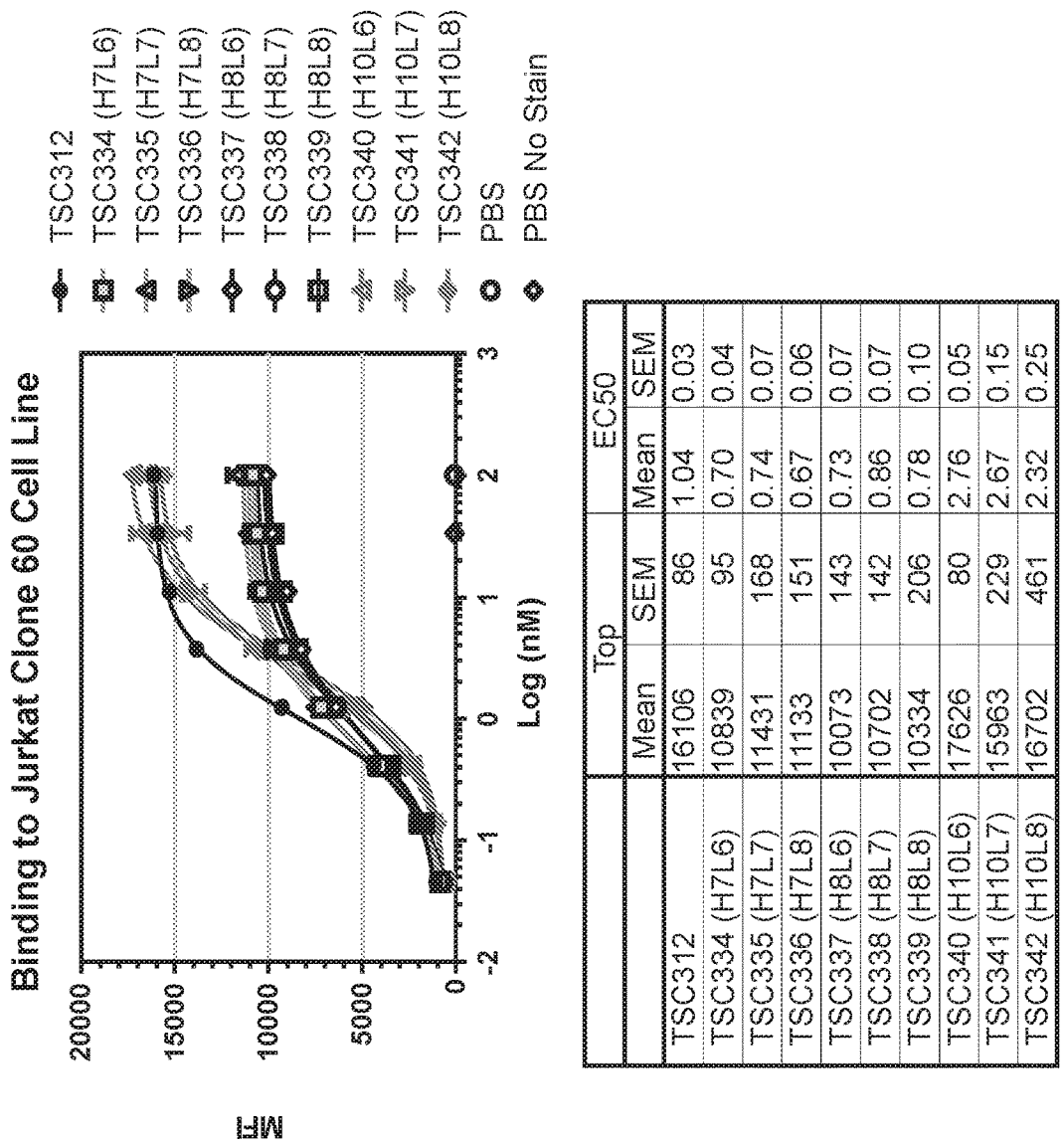
FIG. 2 (top panel) is a graph showing the results of a flow cytometry study measuring the binding of CD3-binding domain constructs to a subclone of the Jurkat T-cell line with higher levels of CD3 expression. Mean fluorescence intensity (MFI) of bound molecules on live cells is shown on the y-axis. Concentration (nM) of the CD3-binding domain constructs is shown on the x-axis. The table (bottom panel) shows the EC50 values obtained from the data in the graph.
Figure 3:
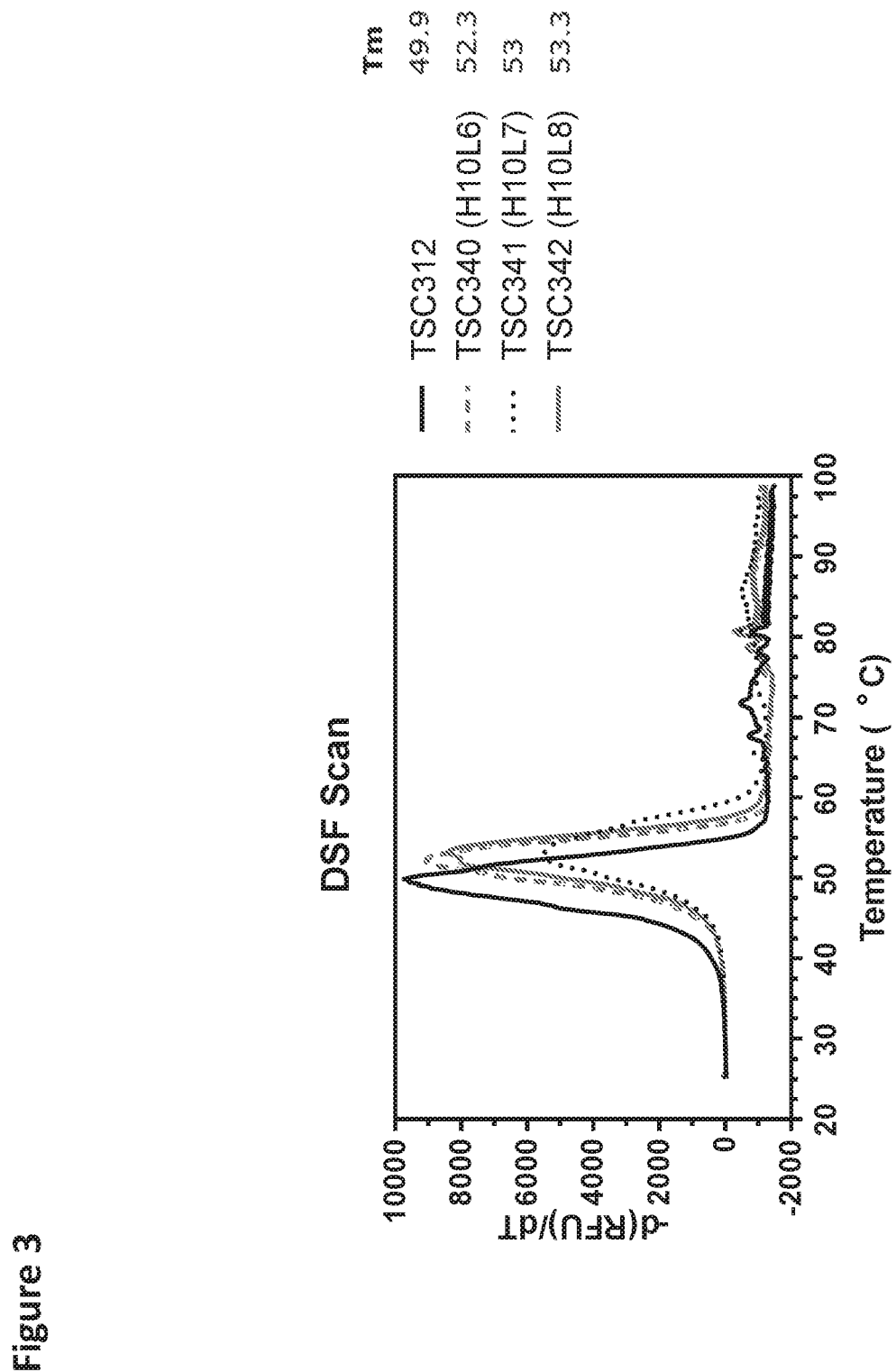
FIG. 3 is a graph showing the results of a differential scanning fluorimetry study performed with CD3-binding domain constructs. The figure also shows the thermal transition midpoint (Tm) values obtained from the data in the graph.

These 9 constructs were expressed transiently in HEK293 cells and examined for protein quality, expression, binding and thermal stability. The sequences of these 9 constructs are found in Table 14. The H10 series of molecules (TSC340, TSC341, TSC342) had the best binding of all the new constructs (FIG. 2), and achieved comparable levels of binding saturation on Jurkat T-cells as TSC312. However, the EC50 measured for binding was still two-fold higher than the original molecule, TSC312. The H10 series of molecules also had significant improvement in thermal stability as measured by increase in Tm over TSC312 using Differential Scanning Fluorimetry (DSF) (FIG. 3). Of these three molecules, TSC342 was picked as the lead molecule for further optimization due to its improvement in thermal stability.

Figure 4:
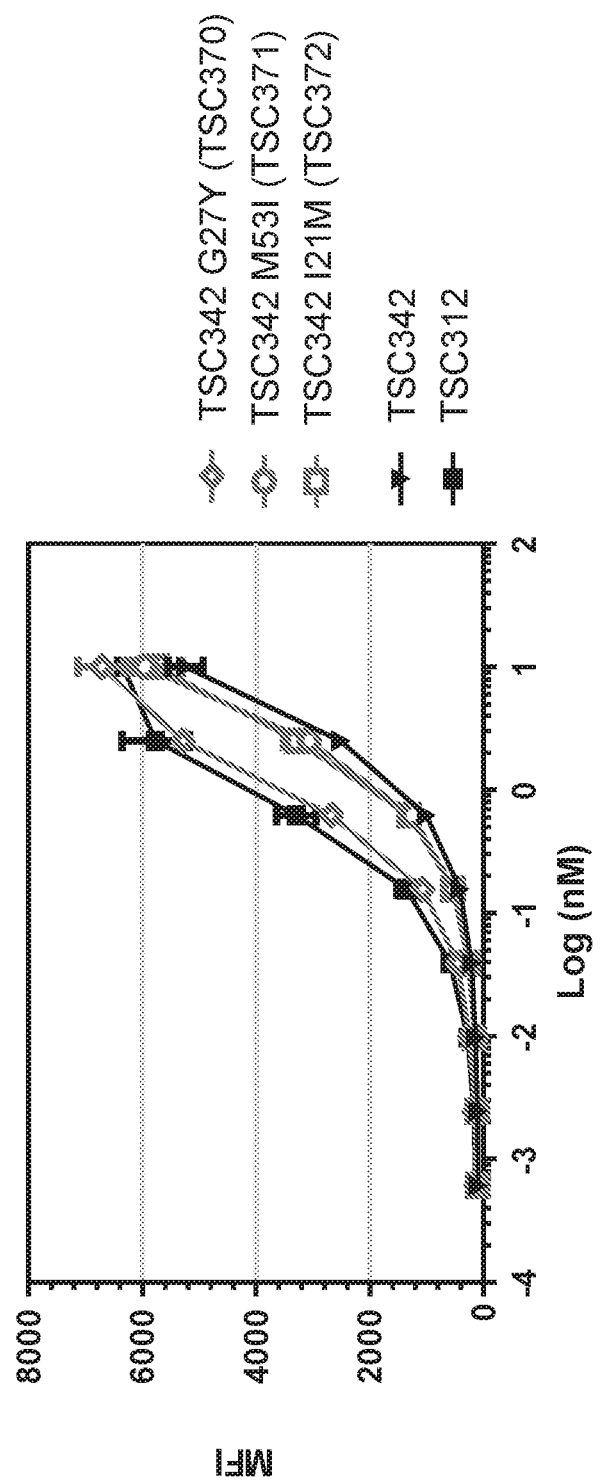
FIG. 4 is a graph showing the results of a flow cytometry study measuring the binding of CD3-binding domain constructs to a subclone of the Jurkat T-cell line with higher levels of CD3 expression. Mean fluorescence intensity (MFI) of bound molecules on live cells is shown on the y-axis. Concentration (nM) of the CD3-binding domain constructs is shown on the x-axis.

The parent murine sequence was then examined for potential hotspots to mutate to improve binding. Three residues were chosen for reversion and back-mutated independently: G27Y(TSC370), M53I(TSC371) and I21M (TSC372). Binding studies of these three constructs on Jurkat T-cells revealed that the G27Y mutation on the heavy chain restored binding to CD3 to comparable levels as the original construct TSC312 (FIG. 4). The stability of these three constructs was also evaluated by DSC. While the G27Y mutation did not improve Tm, surprisingly, both of the remaining mutations, M53I on the heavy chain and I21M on the light chain independently improved Tm by 3-4° C. (Table 7).

TABLE 7

Thermal Stability of Mutants Designed to Improve Binding

| Mutations | Constructs | Tm (° C.) | ΔTm (° C.) |
|---|---|---|---|
| No mutation | TSC312 | 52.8 | — |
| TSC342 G27Y | TSC370 | 53.6 | 0.8 |
| TSC342 M53I | TSC371 | 55.97 | 3.17 |
| TSC342 I21M | TSC372 | 56.55 | 3.75 |

Step 3: Final Optimization Step to Improve Thermal Stability

The homology model of TSC370 was examined using Spatial Aggregation Propensity to identify hotspots for potential aggregation. One mutation, A9P on the heavy chain, was identified to reduce a potential aggregation hotspot in the homology model. This mutation was introduced into the TSC370 backbone to produce TSC390. This mutation alone had a mild effect on improving Tm (0.25° C.). A9P mutation was combined with the M53I and I21M mutations described above to generate the following Fc anti-CD3 constructs (Table 8):

TABLE 8

Rationale behind Mutation Set of Fourth Round Constructs

| Constructs | G27Y (improved affinity) | A9P (improved stability) | M53I (improved stability) | I21M (improved stability) |
|---|---|---|---|---|
| TSC390 | X | X | | |
| TSC391 | X | X | X | |
| TSC392 | X | X | | X |
| TSC393 | X | | X | X |
| TSC394 | X | X | X | X |

TABLE 9

Thermal Stability of Fourth Round Constructs Assessed by DSC

| Mutations | Name | Tm | ΔTm |
|---|---|---|---|
| No mutation | TSC312 | 52.8 | — |
| TSC370_A9P | TSC390 | 53.05 | 0.25 |
| TSC370_A9P_M53I | TSC391 | 56.57 | 3.77 |
| TSC370_A9P_I21M | TSC392 | 59.15 | 6.35 |
| TSC370_M53I_I21M | TSC393 | 58.29 | 5.49 |
| TSC370_A9P_M53I_I21M | TSC394 | 59.3 | 6.5 |

Figure 5:
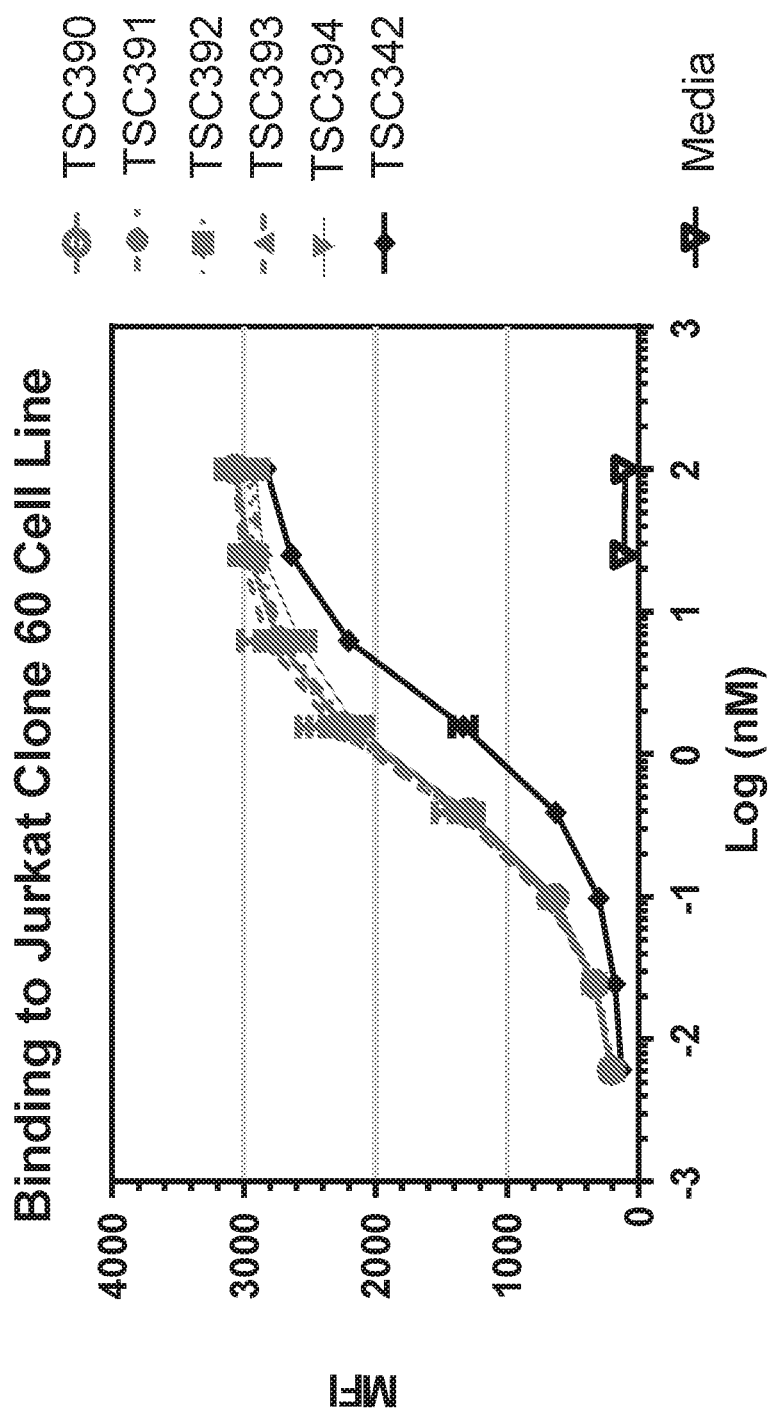
FIG. 5 is a graph showing the results of a flow cytometry study measuring the binding of CD3-binding domain constructs to a subclone of the Jurkat T-cell line with higher levels of CD3 expression. Mean fluorescence intensity (MFI) of bound molecules on live cells is shown on the y-axis. Concentration (nM) of the CD3-binding domain constructs is shown on the x-axis.

Combining two or more of these mutations seemed to have beneficial effect on thermal stability as shown by a substantial increase in Tm from DSC analysis (Table 9). Surprisingly, the A9P mutation was also synergistic with the other mutations, providing anywhere from a 1 to 2.6 C increase in stability compared to the matched constructs not featuring the A9P mutation. More importantly, the stabilizing mutations did not affect the binding to CD3 (FIG. 5).

Figure 6:
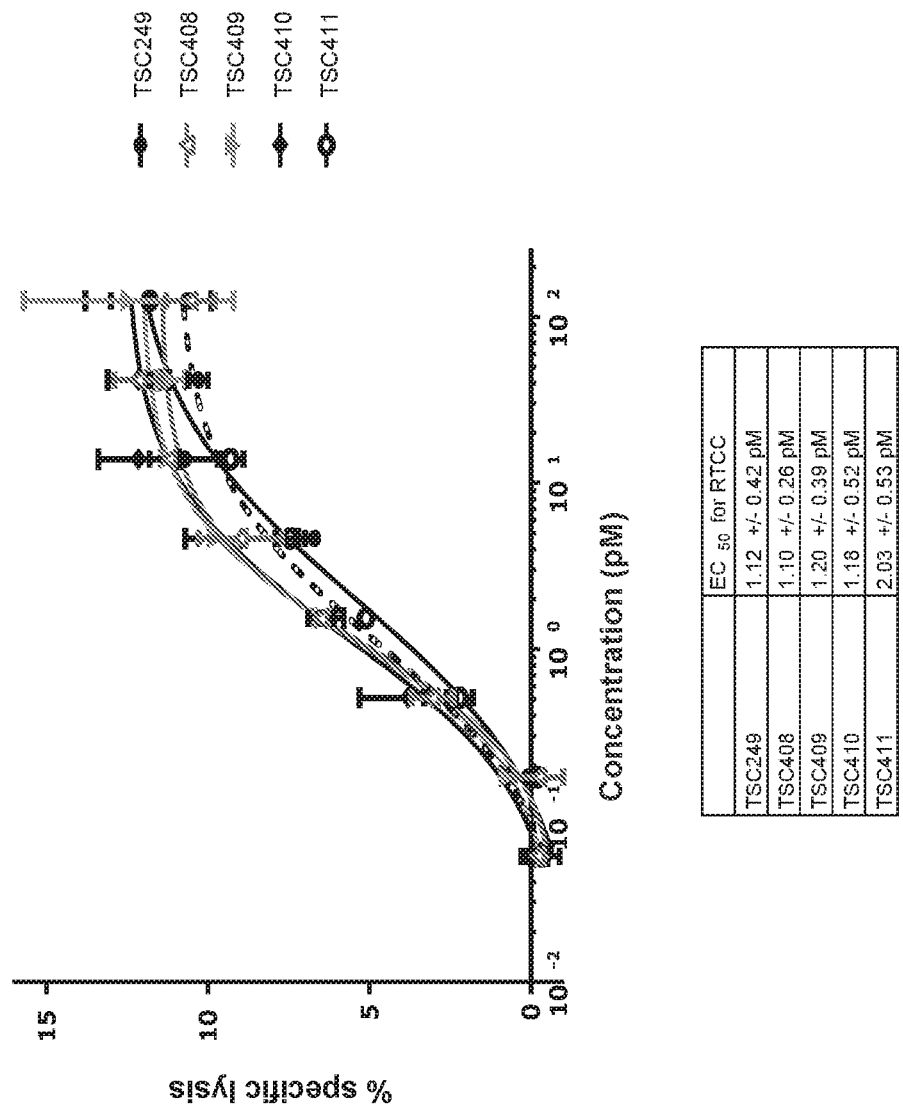
FIG. 6 (top panel) is a graph showing the results of a chromium-51 release assay measuring the effectiveness of bispecific anti-PSMA and anti-CD3 constructs at inducing target-dependent T-cell cytotoxicity with human PBMC in 4 hours against C4-2B cells. Percent specific lysis relative to a total lysis control is shown on the y-axis. Concentration (pM) of the CD3-binding domain constructs is shown on the x-axis. The table (bottom panel) shows the $EC_{50}$ values obtained from the data in the graph.

Bispecific molecules targeting PSMA and CD3 were also built using these new anti-CD3 scFv molecules to study the effect, if any, of the changes to the anti-CD3 scFv on redirected T-cell cytotoxicity (RTCC) activity. The original humanized construct (DRA222) is highly efficient at redirecting T-cell cytotoxicity (see, e.g., US 2014/0161800). The new constructs were tested for their ability to show similar activity. Four different anti-PSMA×anti-CD3 constructs were made using TSC391, TSC392, TSC393 and TSC394 and these were named as TSC408, TSC409, TSC410 and TSC411 respectively. All the four constructs had similar RTCC activity as a molecule built with the parental DRA222 scFv (TSC249) (FIG. 6), verifying that cytotoxic activity as well as binding was comparable with human T-cells.

Step 4: Optimization Step to Restore Cynomolgus Cross-Reactivity and Activity

Figure 7A:
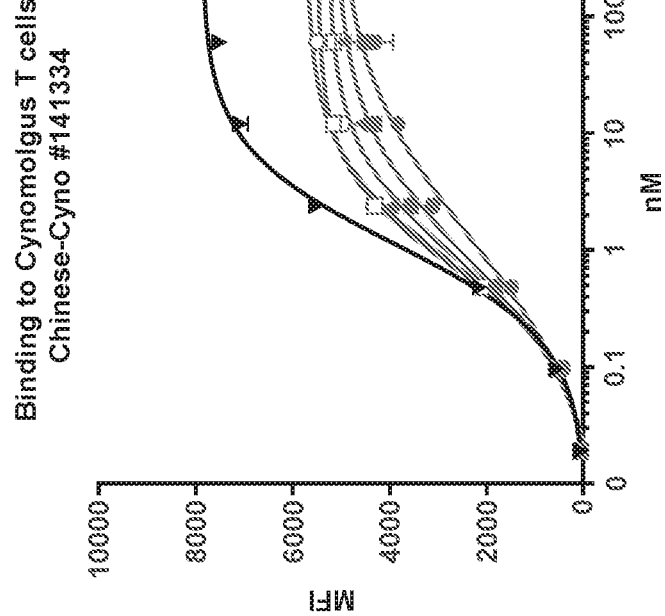
FIG. 7A and FIG. 7B are graphs showing the results of a flow cytometry study measuring the binding of CD3-binding domain constructs to Cynomolgus T-cells. Mean fluorescence intensity (MFI) of bound molecules on live cells is shown on the y-axis of each graph. Concentration (nM) of the CD3-binding domain constructs is shown on the x-axis of each graph.
Figure 7B:
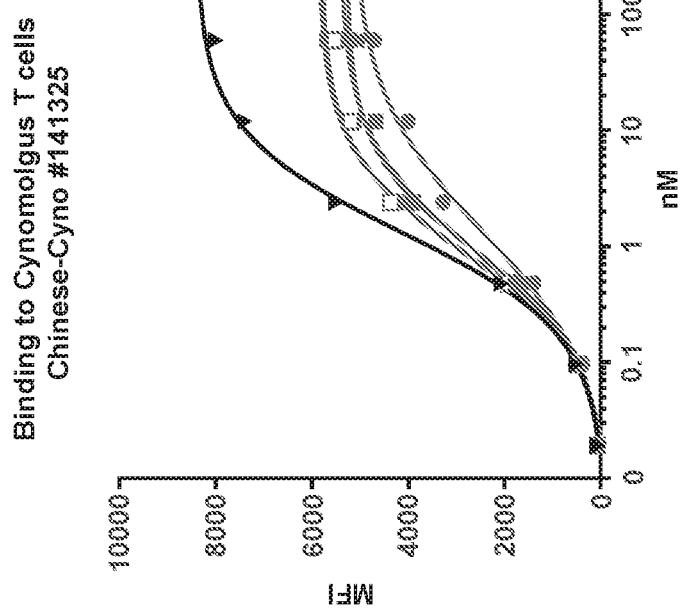
Figure 8A:
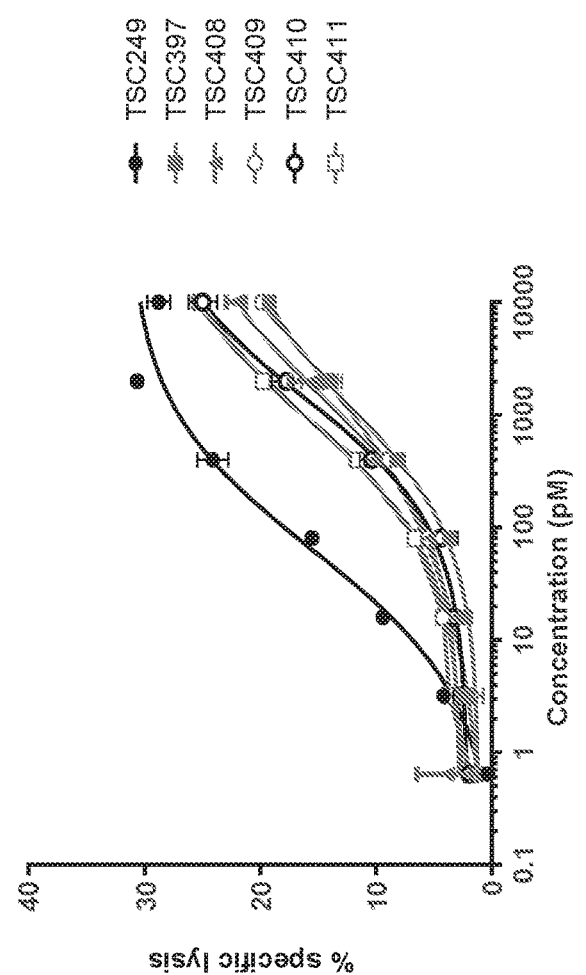
FIG. 8A and FIG. 8B are graphs showing the results of a chromium-51 release assay measuring the effectiveness of CD3-binding domain constructs at inducing target-dependent T-cell cytotoxicity with Cynomolgus PBMC in 4 hours against C4-2B cells. Percent specific lysis relative to a total lysis control is shown on the y-axis of each graph. Concentration (pM) of the CD3-binding domain constructs is shown on the x-axis of each graph.
Figure 8B:
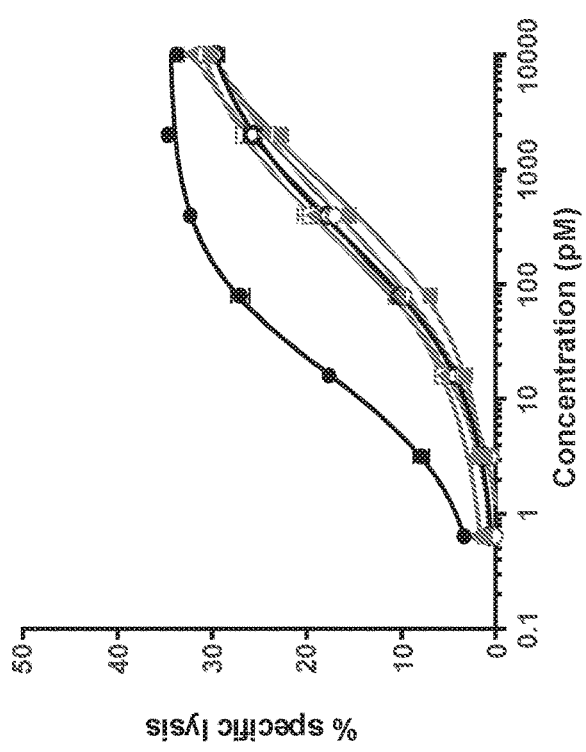

The original humanized construct (DRA222) was previously shown to also bind cynomolgus monkey T-cells and redirect their cytotoxic activity towards target cells when used in a bispecific format. TSC408, TSC409, TSC410 and TSC411 were all evaluated for binding and cytotoxic activity with cynomolgus T-cells. Unexpectedly, TSC408, TSC409, TSC410 and TSC411 all had reduced binding to cynomolgus monkey T-cells (FIGS. 7A and 7B) and significant reduction in RTCC activity using cynomolgus T-cells as effector cells when compared to an anti-PSMA×anti-CD3 bispecific molecule containing DRA222 (FIGS. 8A and 8B). This was not anticipated as the binding and activity with human T-cells was directly comparable to constructs containing DRA222.

Figure 9:
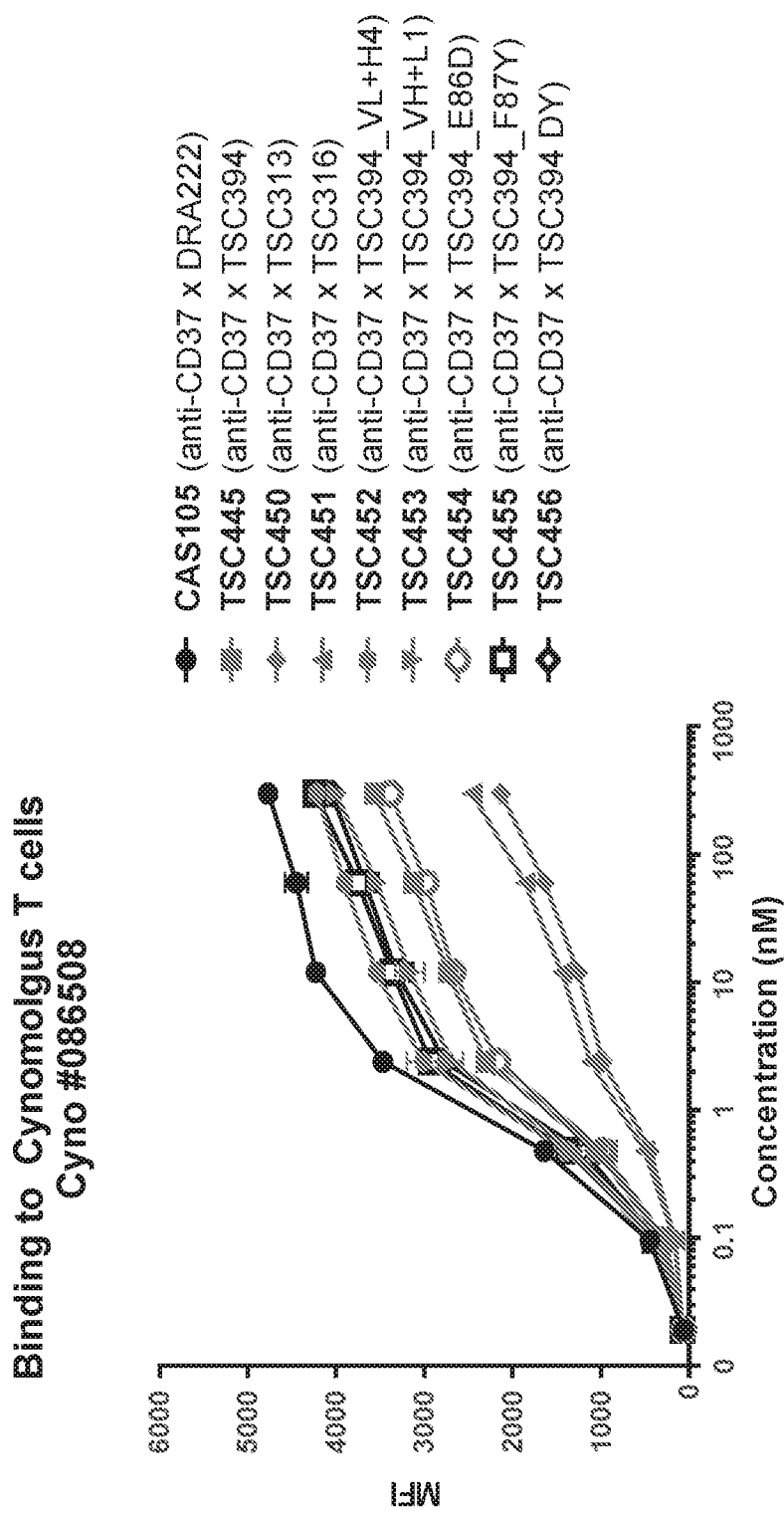
FIG. 9 is a graph showing the results of a flow cytometry study measuring the binding of bispecific anti-CD37 and anti-CD3 constructs to Cynomolgus T-cells. Mean fluorescence intensity (MFI) of bound molecules on live cells is shown on the y-axis. Concentration (nM) of the CD3-binding domain constructs is shown on the x-axis. TSC394 DY refers to the TSC394 construct including the E86D and F87Y substitutions.
Figure 10:
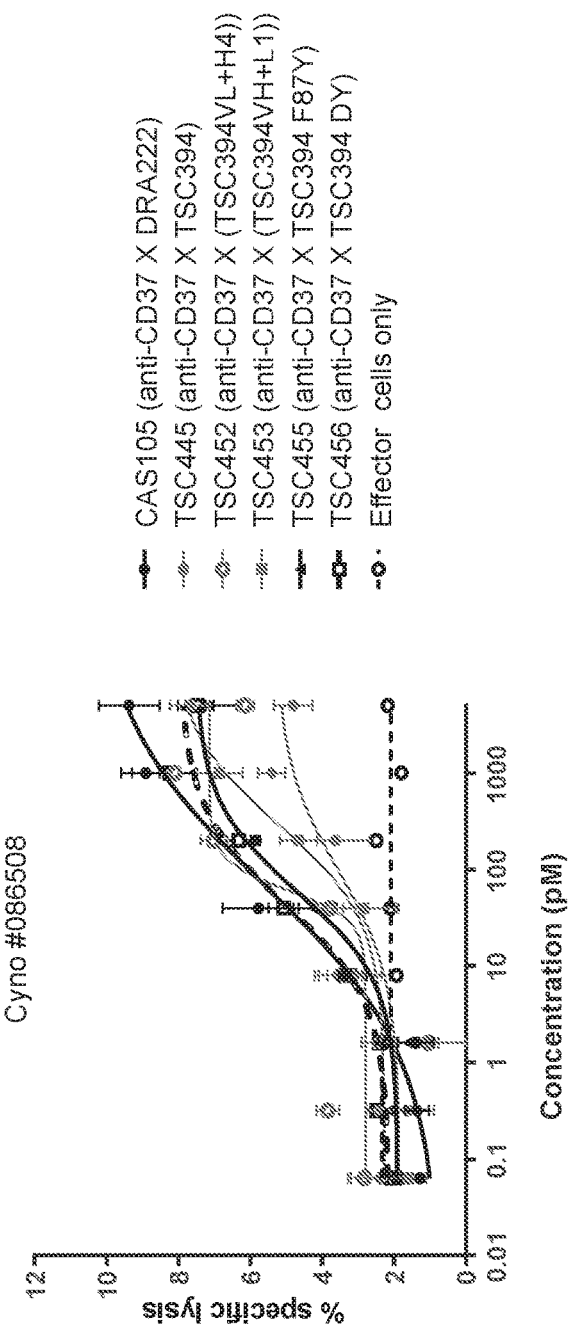
FIG. 10 (top panel) is a graph showing the results of a chromium-51 release assay measuring the effectiveness of bispecific anti-CD37 and anti-CD3 constructs at inducing target-dependent T-cell cytotoxicity with Cynomolgus PBMC in 4 hours against Ramos cells. Percent specific lysis relative to a total lysis control is shown on the y-axis of each graph. Concentration (pM) of the CD3-binding domain constructs is shown on the x-axis of each graph. The table (bottom panel) shows the $EC_{50}$ values obtained from the data in the graph. TSC394 DY refers to the TSC394 construct including the E86D and F87Y substitutions.

Two approaches were used to attempt to restore binding to cynomolgus CD3. One approach was to combine the light chain from TSC394 with the heavy chain from DRA222 or to combine the heavy chain from TSC394 with the light chain from DRA222 to see if framework residues specific to one framework were contributing to binding. The second approach was to back mutate residues at positions 86 and 87 on the light chain of TSC394. Residues at these two positions interact with light chain CDRs that could influence binding to cynomolgus CD3. These variants were incorporated into anti-CD37×anti-CD3 bispecific molecules (Table 10). Some of the variants, especially TSC455, TSC456 and TSC452 displayed improved binding to cynomolgus T-cells when compared to anti-CD37×TSC394 (TSC445), as reflected by higher levels of binding at saturating concentrations (FIG. 9). A cynomolgus RTCC assay was also performed that showed TSC456 and TSC452 had comparable activity to CAS105 (FIG. 10). In addition, these molecules had superior thermal stability compared to CAS105 (Table 11) as shown by a higher Tm1 when analyzed by DSC. Alignments of the DRA222 scFv, TSC455 scFv, and TSC456 scFv are shown in FIG. 13.

TABLE 10

Fifth Round of Optimized Constructs

| Anti-CD3 Constructs | Description of anti-CD37 × anti-CD3 bispecific molecules |
|---|---|
| CAS105 | anti-CD37 × DRA222 |
| TSC445 | anti-CD37 × TSC394 |
| TSC452 | anti-CD37 × (TSC394VL + DRA222 VH) |
| TSC453 | anti-CD37 × (TSC394VH + DRA222 VL) |
| TSC454 | anti CD37 × TSC394 E86D |
| TSC455 | anti-CD37 × TSC394 F87Y |
| TSC456 | anti-CD37 × TSC394 E86D F87Y |

TABLE 11

Stability of Bispecific Constructs

| Anti-CD3 Constructs | Description of anti-CD37 × anti-CD3 bispecific molecules | Tm 1 |
|---|---|---|
| CAS105 | Anti-CD37 × DRA222 | 53.04 |
| TSC445 | anti-CD37 × TSC394 | 55.45 |
| TSC452 | anti-CD37 × (TSC394VL + DRA222 VH) | 55.37 |
| TSC453 | Anti-CD37 × (TSC394VH + DRA222 VL) | 56.54 |
| TSC454 | Anti-CD37 × TSC394 E86D | 57.94 |
| TSC455 | Anti-CD37 × TSC394 F87Y | 56.73 |
| TSC456 | Anti-CD37 × TSC394 E86D F87Y | 55.45 |

Example 2. Impacts of Improved Thermal Stability on Storage Stability

In principle, proteins with improved thermodynamic stability should also be more resistant to aggregation upon storage, and should have enhanced storage stability compared to less stable proteins. To determine whether or not the increases seen in Tm correlated with improved storage stability, the proteins listed in Table 10 were evaluated for storage stability in PBS at 25° C. over two weeks.

Each protein was buffer exchanged into PBS using preparative size exclusion chromatography and the protein concentration was adjusted to 1 mg/mL. For every protein to be assessed, four vials each containing approximately 120 µL were prepared. One vial was used at each stability time point. Purity was determined by analyzing 25 µL (or 25 µg) on an analytical size exclusion HPLC column equilibrated in PBS and measuring the absorbance at 280 nm. Triplicate injections were performed for each construct at each time point. Following completion of the SEC method, the chromatograph was integrated using the Agilent ChemStation software. The percent purity of each protein was calculated by dividing the peak area of the intact molecule by the total peak area, then multiplying by 100.

(peak area of intact molecule)/(total peak area)×100=% Purity

The reported purity was an average of the values obtained from three injections from the same vial. Purity was typically determined at T=0, 3, 7 and 14 days. Purity values were plotted on a graph as a function of time and a linear regression analysis was performed. The slope of the regression line represented the rate at purity was decreasing for each protein. The rate of purity decline was used to estimate the number of days of storage that would cause a 2% decrease in purity. The stability of different variants was compared by ranking them by the highest to lowest number of days estimated to cause a 2% decline. To mitigate inter-assay variability, storage stability values were not compared across different experiments, constructs within the same experimental group were only ranked against each other.

Figure 11:
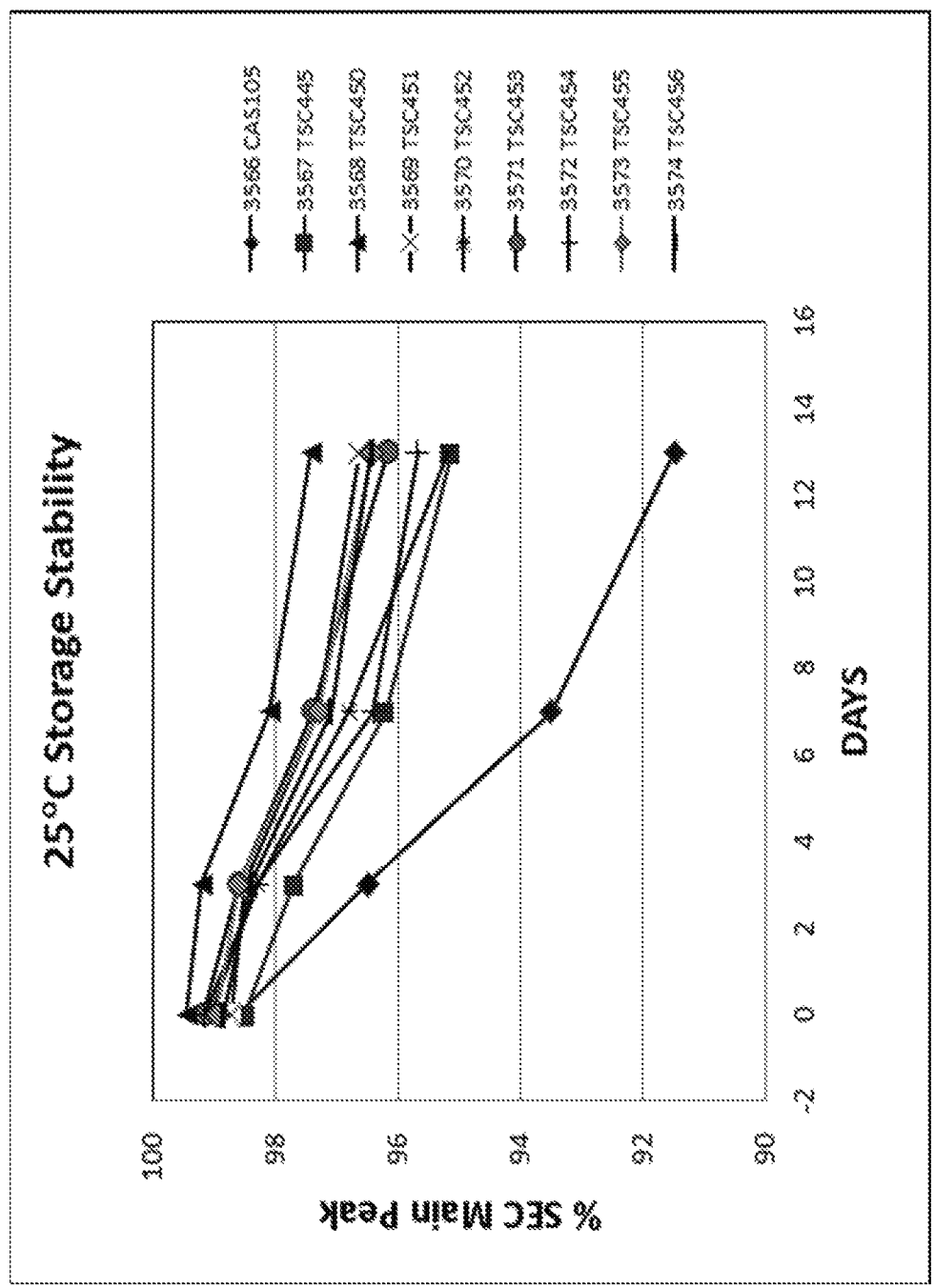
FIG. 11 is a graph showing the results of a study measuring the storage stability of CD3-binding domain constructs at 25° C. over the number of days specified on the x-axis. CAS105 is a control construct comprising the DRA222 CD3-binding domain.

All new molecules displayed superior solution stability in PBS at 25° C. compared to CAS105 (FIG. 11). The time to the formation of aggregate was also calculated for each construct (Table 12).

TABLE 12

Relative Storage Stability at 25° C.

| Anti-CDS Construct | Description of anti-CD37 × anti-CD3 bispecific molecules | # of days to drop 2% |
|---|---|---|
| CAS105 | Anti-CD37 × DRA222 | 4 |
| TSC445 | Anti-CD37 × TSC394 | 8 |
| TSC450 | Anti-CD37 × TSC313 | 12 |
| TSC451 | Anti-CD37 × TSC316 | 12 |
| TSC452 | Anti-CD37 × (TSC394VL + H4) | 7 |
| TSC453 | Anti-CD37 × (TSC394VH + L1) | 8 |
| TSC454 | Anti-CD37 × TSC394 E462D | 7 |
| TSC455 | Anti-CD37 × TSC394 F463Y | 10 |
| TSC456 | Anti-CD37 × TSC394 DY | 10 |

This data showed that almost all constructs had a two-fold or greater increase in storage stability at 25° C. when compared to the construct containing the original anti-CD3 scFv (DRA222).

Example 3. Impacts of Improved Thermal Stability on Serum Stability

Similar to storage stability, molecules with higher thermodynamic stability are also frequently more resistant to proteolysis, which can improve stability in human serum. This can in turn improve overall serum pharmacokinetics and the overall exposure of a therapeutic.

To test if the improvements in thermodynamic stability impacted the overall serum stability, one of the stabilized anti-CD3 scFv molecules (TSC394 F463Y) was evaluated for serum stability in the context of an anti-ROR1×anti-CD3 bispecific molecule (ROR193). A similar bispecific molecule was also evaluated simultaneously which contained the original anti-CD3 scFv, DRA222 (ROR133). The parent rabbit anti-ROR1 antibody R11 used to generate the ROR1-binding domains is described in, for example, U.S. Patent Application Publication No. 2013/0251642 and Yang et al., PLoS ONE 6(6): e21018 (2011).

Human serum donated by a random healthy donor was collected in a Red/Grey Vacutanor (BD #367988), and was prepared according to vendor suggested protocol. Test articles were spiked into 50 µL serum at a concentration of 1 pM in sterile PCR tubes, and were incubated in a humidified 37° C. tissue culture incubator for up to 21 days. Specific time points were 21, 14, 7, 3 and 0 days. Samples were incubated in a reverse chronological order starting as "assay day 21", and all samples were assessed simultaneously using a chromium release RTCC assay at the end of incubation on "experiment day 0" following the protocol listed above in Example 1. EC50 values were fit from titration curves conducted with samples at each time points and were normalized against the EC50 value measured for each construct at day 0.

Figure 12:
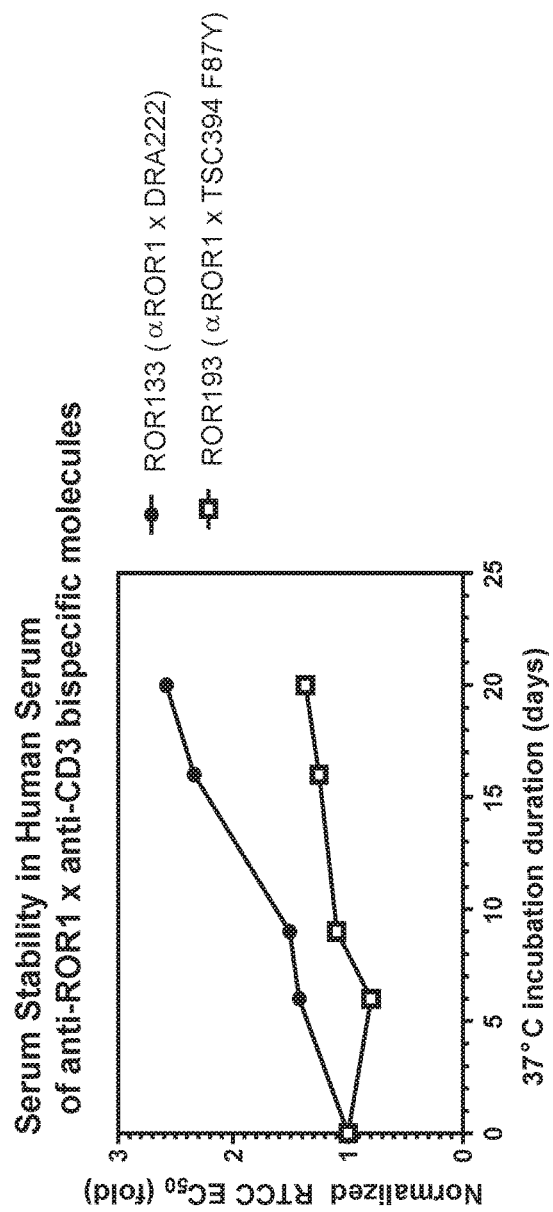
FIG. 12 is a graph showing the results of a study measuring the serum stability in human serum of anti-ROR1×anti-CD3 bispecific molecules over the number of days specified on the x-axis.

Plotting the EC50 values over time showed a dramatic difference for the observed serum stability of ROR133 vs ROR193 (FIG. 12), with a 2.5 fold loss in observed EC50 over 21 days for ROR133 but minimal change in EC50 for ROR193. This demonstrates that a moderate change in thermodynamic stability can have a noticeable impact on serum stability.

Example 4. Impacts of Improved Thermodynamic Stability on Protein Expression and Quality Previously, it has also been shown that improvements in thermodynamic stability can result in improvements in protein expression and overall protein quality, as measured by the production of high molecular weight aggregates during protein production.

To test whether or not the improved thermodynamic stability of the new anti-CD3 scFv regions translated into improved protein expression or protein quality, one of the anti-CD3 domains (TSC394DY) was compared to DRA222 in the context of five different pairs of anti-ROR1×anti-CD3 bispecific molecules, each featuring the same anti-ROR1 scFv (Table 13).

TABLE 13

Relative Expression and Protein Quality

| BD pair | Construct ID | CD3 binding domain | Expression (ug/mL) | % improvement | SEC (post-ProA) | % HMW aggregate | % reduction aggregate |
|---|---|---|---|---|---|---|---|
| A | ROR134 | DRA222 | 26 | | 78 | 22 | |
|   | ROR189 | TSC394DY | 37 | 42% | 89 | 11 | 50% |

TABLE 13-continued

Relative Expression and Protein Quality

| BD pair | Construct ID | CD3 binding domain | Expression (ug/mL) | % improvement | SEC (post-ProA) | % HMW aggregate | % reduction aggregate |
|---|---|---|---|---|---|---|---|
| B | ROR154 | DRA222 | 16 | | 91 | 9 | |
| | ROR185 | TSC394DY | 26 | 63% | 94 | 6 | 33% |
| C | ROR179 | DRA222 | 14 | | 83 | 17 | |
| | ROR186 | TSC394DY | 27 | 93% | 88 | 12 | 29% |
| D | ROR181 | DRA222 | 25 | | 81 | 19 | |
| | ROR191 | TSC394DY | 33 | 32% | 90 | 10 | 47% |
| E | ROR182 | DRA222 | 16 | | 90 | 10 | |
| | ROR192 | TSC394DY | 21 | 31% | 92 | 8 | 20% |

With each molecule pair, a higher titer of overall protein expression was seen—from 31% to 93% higher—with the construct featuring the stabilized anti-CD3 scFv (TSC394DY). Also, within each molecule pair, the construct featuring the stabilized anti-CD3 scFv had a lower level of high molecular weight aggregates after protein A purification (anywhere from a 20% to 50% reduction in aggregate levels). This confirms that inclusion of a stabilized anti-CD3 scFv can result in improved protein expression and improved protein quality when compared to the original anti-CD3 scFv.

Example 5. Effects of Stabilized Anti-CD3 Binding Domains on Stability and Pharmacokinetics of Anti-PSMA×Anti-CD3 Binding Molecules To test the effects of a stabilized anti-CD3 scFv on stability and pharmacokinetics of a bispecific binding molecule, the PSMA-binding domain of TSC266 (an anti-PSMA×anti-CD3 bispecific molecule comprising the DRA222 CD3 binding domain) was transferred into a bispecific molecule utilizing the TSC456 anti-CD3 scFv. This new bispecific molecule is referred to as TSC471. BALB/c mice were dosed intravenously with TSC266 and TSC471 at approximately 10 mg/kg. TSC266 was diluted into PBS, while TSC471 was diluted into formulation buffer, which was used for all dilutions (5 mM succinate, 6.5% sucrose, 0.02% Tween80, pH 4.8). Serum was collected from 3 animals at 10 time points (n=30 total). The time points were 15 min and 2, 6, 24, 48, 72, 96, 168, 336, and 504 hr post-administration of the bispecific molecules. Terminal bleeds were used to collect larger volumes. Serum concentrations were determined using ELISA methods capturing the anti-PSMA binding domain and detecting the anti-CD3 binding domain. Serum concentrations over time were used to determine pharmacokinetic (PK) parameter estimates by non-compartmental analysis (NCA) and compartmental analysis. Serum samples from late time points were also tested for anti-drug antibodies using a standard bridging ELISA with the respective bispecific molecules +/− biotin.

More specifically, the following ELISA methods were used. Concentrations of anti-PSMA×anti-CD3 bispecifics were determined using 96-well plates coated with a mouse monoclonal antibody (mAb 1H5) to capture the anti-PSMA portion of each construct. The other ends of constructs were detected using a biotin conjugated mouse monoclonal antibody targeting the anti-CD3-binding domain (mAb 5H5), so only intact protein would be measured with this ELISA method. To quantify bound immune complexes from serum samples and assay controls, polymerized horseradish peroxidase (poly HRP) and a fluorogenic peroxidase substrate were used, with results measured on a fluorescent plate reader. Standard curves used to calculate serum concentrations consisted of various known concentrations of the appropriate PSMA bispecific construct spiked into ELISA diluent. SOFTMAX® Pro software was used to calculate serum concentrations using a 4-parameter logistic equation, as well as precision and accuracy for standards and test samples.

Figure 14:
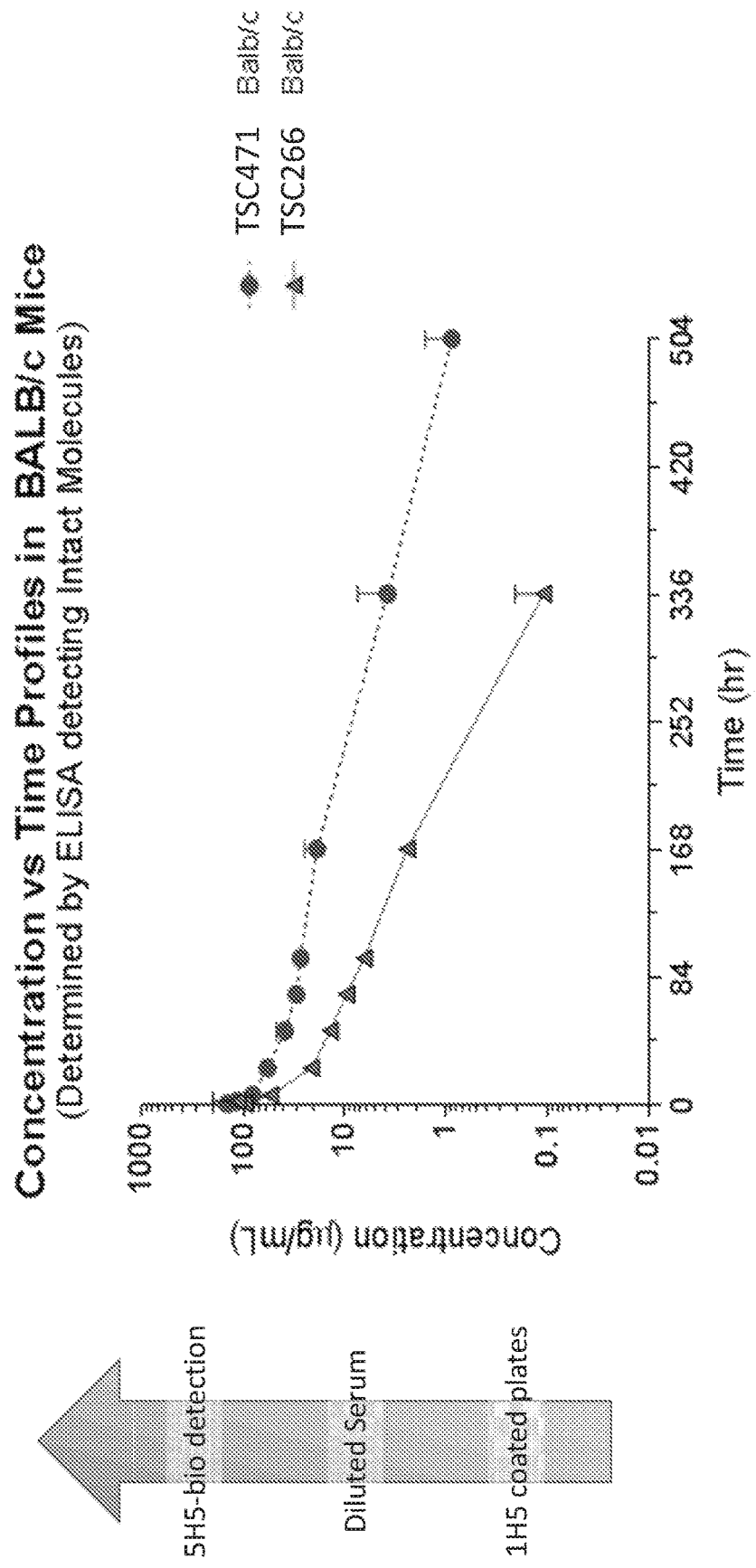
FIG. 14 is a graph showing the results of a study measuring serum concentrations of anti-PSMA×anti-CD3 bispecific binding molecules in BALB/c mice as a function of time. Results are expressed as mean serum concentration (μg/mL) over time for each of the treatment groups. Each point shows the mean (+standard deviation) of individual animals.

Results of these studies are shown in FIGS. 14 and 15. By non compartmental analysis (NCA) using Phoenix-64 WinNonLin Software, TSC471 had about a 2-fold improvement in half-life, with a 3-4 fold reduction in clearance parameter, over TSC266. The Fc of TSC471 maintained functional characteristics of TSC266 (no ADCC or CDC activity, equivalent FcRn binding) with improved stability. The Fc of TSC471 comprises a stability improved version of the CH2 domain. The mutations are the same in the '234-236' region of the molecule as in the TSC266 Fc, but the TSC471 Fc has a reduced number of mutations in the CDC region, maintaining only the K322A mutation, rather than all three found in the null Fc CH2. The anti-CD3 scFv of TSC471 maintained binding and activity on human and cynomolgus T-cells. The linker used in TSC471 had enhanced resistance to CHO proteases and other PTMs and does not contain an N-linked glycosylation site.

Example 6. Effects of Stabilized Anti-CD3 Binding Domains on Pharmacokinetics of Anti-ROR1×Anti-CD3 Binding Molecules The pharmacokinetics of anti-ROR1×anti-CD3 bispecific molecules containing either the less stable DRA222 CD3 binding domain or the more stable TSC456 CD3 binding domain were compared. The following constructs were evaluated. The sequences of the constructs are provided in Table 14.

| Construct | Anti-ROR1 | Anti-CD3 |
|---|---|---|
| ROR206 (CHO line: ROR206a) | Binding domain A | DRA222 |
| ROR207 (CHO line: ROR207a) | Binding domain A | TSC456 |
| ROR208 (CHO line: ROR208a) | Binding domain B | DRA222 |
| ROR209 (CHO line: ROR209a) | Binding domain B | TSC456 |

NSG mice were dosed intravenously with the anti-ROR1×anti-CD3 bispecifics at approximately 10 mg/kg. All bispecifics were diluted into PBS. Serum was collected from 3 animals at 10 time points (n=30 for each construct) post-administration as well as at one time point pre-dose. The time points were 15 min and 2, 6, 24, 48, 72, 96, 168, 336, and 504 hr post-administration of the bispecific molecules. Terminal bleeds were used to collect larger volumes. Serum concentrations were determined using ELISA methods to detect the intact molecule. Serum concentrations over time were used to determine PK parameter estimates by non-compartmental analysis (NCA) and compartmental analysis.

More specifically, the following ELISA methods were used. Concentrations of anti-ROR1×anti-CD3 bispecifics were determined using 96-well plates coated with ROR1 ECD-AFH (ROR177) to capture the anti-ROR1 portion of each construct. The other end of ROR constructs was detected using a biotin conjugated mouse monoclonal antibody targeting the anti-CD3-binding-domain (mAb 5H5), so only intact protein would be measured with this ELISA method. To quantify bound immune complexes from serum samples and assay controls, polymerized horseradish peroxidase (poly HRP) and a fluorogenic peroxidase substrate were used, with results measured on a fluorescent plate reader. Standard curves used to calculate serum concentrations consisted of various known concentrations of the appropriate ROR construct spiked into ELISA diluent. SOFTMAX® Pro software was used to calculate serum concentrations using a 4-parameter logistic equation, as well as precision and accuracy for standards and test samples.

Figure 16:
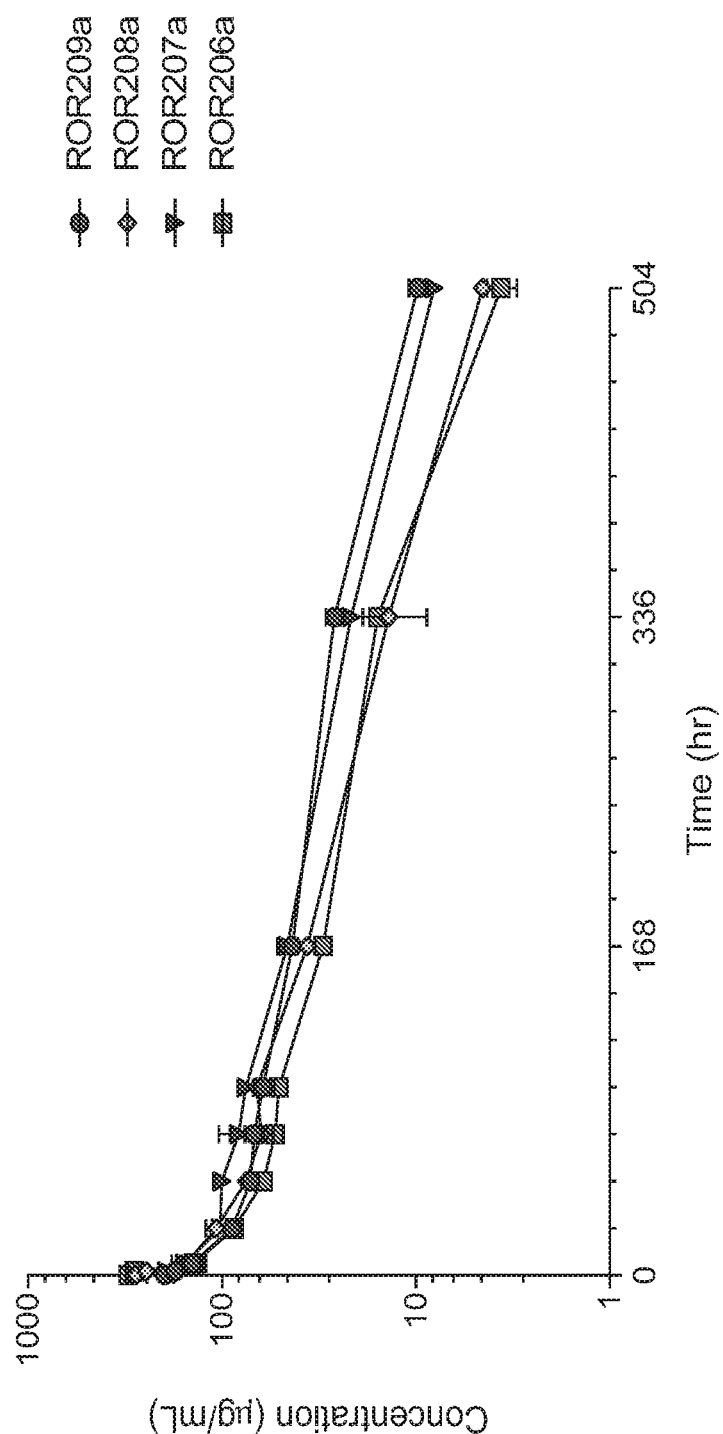
FIG. 16 is a graph showing the results of a study measuring serum concentrations of anti-ROR1×anti-CD3 bispecific binding molecules in NSG mice as a function of time. Results are expressed as mean serum concentration (μg/mL) over time for each of the treatment groups.

Results of these studies are shown in FIGS. 16, 17A and 17B. By NCA and compartmental analysis, ROR209a had the longest half-life. ROR207a had the lowest clearance and volume estimates by both analysis methods. Both anti-ROR1 bispecifics with the DRA222 CD3 binding domain had shorter half-life and faster clearance parameters. Notably, constructs with the improved anti-CD3 binding domain (TSC456) had better pharmacokinetics than those with the less stable anti-CD3 binding domain (DRA222).

Figure 18:
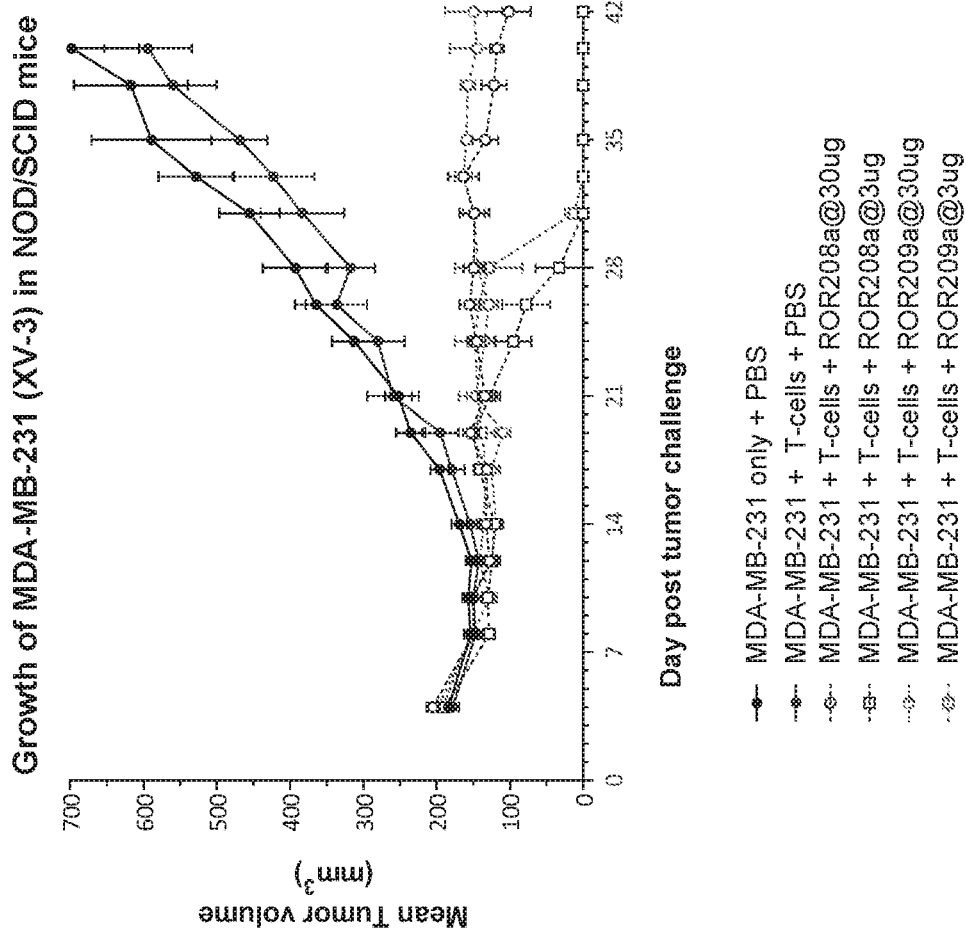
FIG. 18 is a graph showing the results of a study analyzing the effects of anti-ROR1×anti-CD3 bispecific binding molecules on MDA-MB-231 xenograft tumor growth.

Example 7. Effects of Stabilized Anti-CD3 Binding Domains on In Vivo Efficacy of Anti-ROR1×Anti-CD3 Binding Molecules MDA-MB-231 cells were co-mixed with donor T-cells and matrigel and implanted into the flank of NOD/SCID mice on day 0 of the study. Each group contained N=5 animals, with T-cells from one donor. FIG. 18 shows an example graph which shows minimal impact of T-cells on tumor growth by the donor T-cells. Animals were treated with PBS or with 30 μg or 3 μg of ROR208 (DRA222 anti-CD3 binding domain) or ROR209 (TSC456 anti-CD3 binding domain). The dose was administered on day 0, 4, and 8. Tumor growth was measured with calipers over time of study.

Significant inhibition of tumor growth was seen after treatment with both ROR bispecifics. No significant difference of tumor growth was seen with T-cells from the donor (FIG. 18) compared to tumor only. There were no significant differences between animals treated with ROR208 compared to ROR209 at any dose level, indicating the stability improved anti-CD3 binding domain had the same potency as the non-stable anti-CD3 binding domain.

Figure 19:
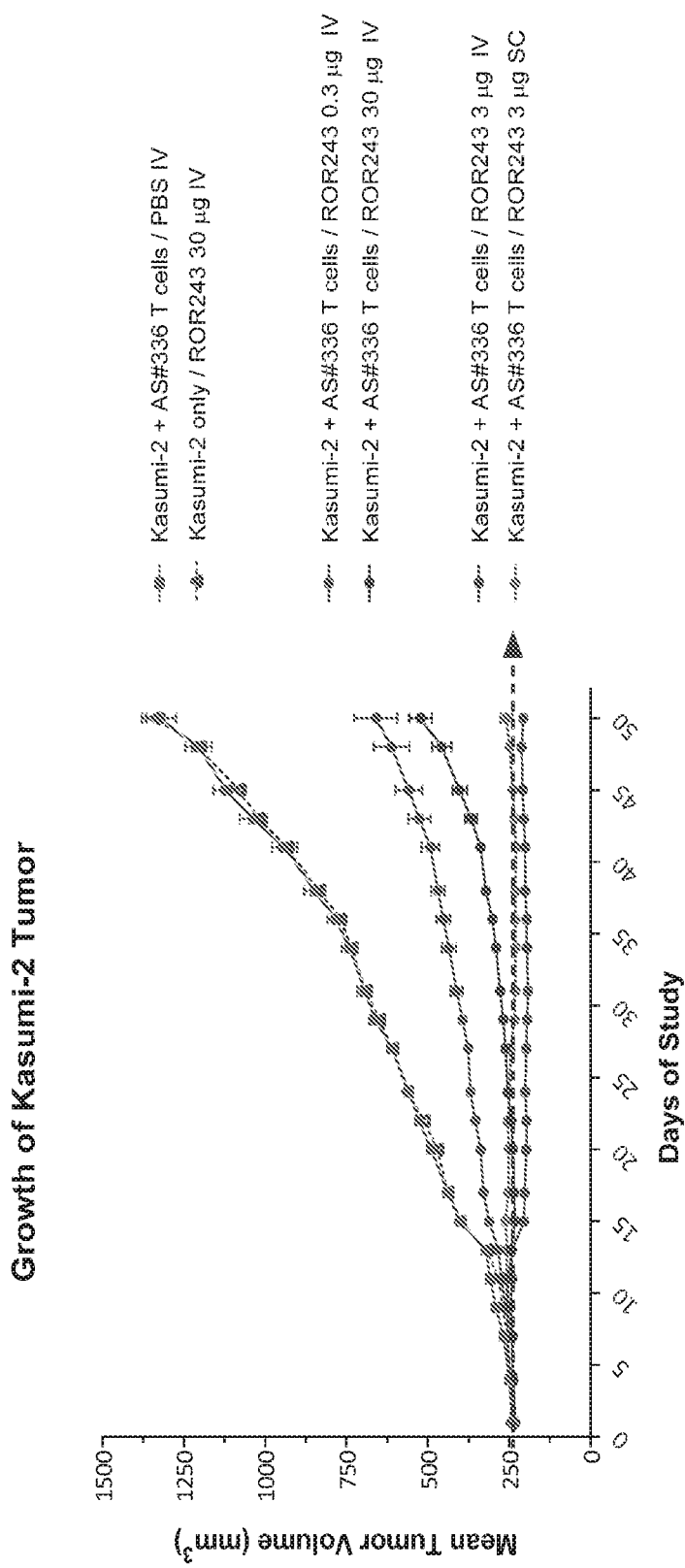
FIG. 19 is a graph showing the results of a study analyzing the effects of anti-ROR1×anti-CD3 bispecific binding molecules on Kasumi-2 xenograft tumor growth. Results are shown for human T-cell donor #336.

Example 8. Effects of Stabilized Anti-CD3 Binding Domains on In Vivo Efficacy of Anti-ROR1×Anti-CD3 Binding Molecules Kasumi-2 cells were co-mixed with donor T-cells and matrigel and implanted into the flank of NOD/SCID mice on day 0 of the study. Each group contained N=10 animals, with T-cells from one donor. Animals were treated with PBS or with 30 μg, 3 μg or 0.3 μg of ROR243 (TSC456 anti-CD3 binding domain) as shown in FIG. 19. The dose was administered on day 0, 4, and 8. The route for administration was intravenous (IV), with exception of one group, where the dose was administered subcutaneously (SC). FIG. 19 shows results of the assay. Tumor growth was measured with calipers over time of study.

No inhibition of tumor growth was seen in the presence of T-cells in the absence of ROR243 or with ROR243 treatment in the absence of T-cells. Significant inhibition of tumor growth was seen at 0.3 μg per dose, with dose dependent titration. No difference in route of administration was seen.

TABLE 14

Binding Domain and Polypeptide Sequences and Components

DNA sequence of Fc DRA222 (TSC311 or TSC312):

```
atggaagcac cagcgcagct tctcttcctc ctgctactct ggctcccaga taccaccggt      60
gagcccaaat cttctgacaa aactcacaca tgcccaccgt gcccagcacc tgaagccgcg     120
ggtgcaccgt cagtcttcct cttccccca  aaacccaagg acaccctcat gatctcccgg     180
acccctgagg tcacatgcgt ggtggtggac gtgagccacg aagaccctga ggtcaagttc     240
aactggtacg tggacggcgt ggaggtgcat aatgccaaga caaagccgcg ggaggagcag     300
tacaacagca cgtaccgtgt ggtcagcgtc ctcaccgtcc tgcaccagga ctggctgaat     360
ggcaaggcat acgcgtgcgc ggtctccaac aaagccctcc cagcccccat cgagaaaacc     420
atctccaaag ccaaagggca gccccgagaa ccacaggtgt acaccctgcc cccatcccgg     480
gatgagctga ccaagaacca ggtcagcctg acctgcctgg tcaaaggctt ctatccaagc     540
gacatcgccg tggagtggga gagcaatggg cagccggaga acaactacaa gaccacgcct     600
cccgtgctgg actccgacgg ctccttcttc ctctacagca agctcaccgt ggacaagagc     660
aggtggcagc aggggaacgt cttctcatgc tccgtgatgc atgaggctct gcacaaccac     720
tacacgcaga agagcctctc cctgtctccg ggtcagaggc acaacaattc ttccctgaat     780
acaggaactc agatggcagg tcattctccg aattctcagg tccagctggt ggagtctggg     840
ggcggagtgg tgcagcctgg gcggtcactg aggctgtcct gcaaggcttc tggctacacc     900
tttactagat ctacgatgca ctgggtaagg caggccctg  gacaaggtct ggaatggatt     960
ggatacatta atcctagcag tgcttatact aattacaatc agaaattcaa ggacaggttc    1020
acaatcagcg cagacaaatc caagagcaca gccttcctgc agatggacag cctgaggccc    1080
gaggacaccg gcgtctattt ctgtgcacgg ccccaagtcc actatgatta caacgggttt    1140
ccttactggg gccaagggac tcccgtcact gtctctagcg gtggcggagg gtctggggt     1200
ggcggatccg gaggtggtgg ctctgcacaa gacatccaga tgacccagtc tccaagcagc    1260
ctgtctgcaa gcgtggggga cagggtcacc atgacctgca gtgccagctc aagtgtaagt    1320
tacatgaact ggtaccagca gaagccgggc aaggccccca aaagatggat ttatgactca    1380
tccaaactgg cttctggagt ccctgctcgc ttcagtggca gtgggtctgg gaccgactat    1440
accctcacaa tcagcagcct gcagcccgaa gatttcgcca cttattactg ccagcagtgg    1500
```

TABLE 14-continued

Binding Domain and Polypeptide Sequences and Components

| | |
|---|---|
| agtcgtaacc cacccacgtt cggaggggg accaagctac aaattacatc ctccagctaa | 1560 |

(SEQ ID NO: 1)
Signal sequence is residue 1 to 60. Fc region is residue 61-753.
Linker is 754 to 816. Anti-CD scFv is 317 to 1560.

Mature protein sequence of Fc DRA222 (TSC311 or TSC312)

| | |
|---|---|
| EPKSSDKTHT CPPCPAPEAA GAPSVFLFPP KPKDTLMISR TPEVTCVVVD VSHEDPEVKF | 60 |
| NWYVDGVEVH NAKTKPREEQ YNSTYRVVSV LTVLHQDWLN GKAYACAVSN KALPAPIEKT | 120 |
| ISKAEGQPRE PQVYTLPPSR DELTKNQVSL TCLVKGFYPS DIAVEWESNG QPENNYKTTP | 180 |
| PVLDSDGSFF LYSKLTVDKS RWQQGNVFSC SVMHEALHNH YTQKSLSLSP GQRHNNSSLN | 240 |
| TGTQMAGHSP NSQVQLVESG GGVVQPGRSL RLSCKASGYT FTRSTMHWVR QAPGQGLEWI | 300 |
| GYINPSSAYT NYNQKFKDRF TISADKSKST AFLQMDSLRP EDTGVYFCAR PQVHYDYNGF | 360 |
| PYWGQGTPVT VSSGGGGSGG GGSGGGGSAQ DIQMTQSPSS LSASVGDRVT MTCSASSSVS | 420 |
| YMNWYQQKPG KAPKRWIYDS SKLASGVPAR FSGSGSGTDY TLTISSLQPE DFATYYCQQW | 480 |
| SRNPRTFGGG TKLQITSSS | 499 |

(SEQ ID NO: 2)

DNA sequence of Fc H7L1 (TSC313):

| | |
|---|---|
| atggaagcac cagcgcagct tctcttcctc ctgctactct ggctcccaga taccaccggt | 60 |
| gagcccaaat cttctgacaa aactcacaca tgcccaccgt gcccagcacc tgaagccgcg | 120 |
| ggtgcaccgt cagtcttcct cttcccccca aaacccaagg acaccctgat gatctcccgg | 180 |
| accctgagg tcacatgcgt ggtggtggac gtgagccacg aagaccctga ggtcaagttc | 240 |
| aactggtacg tggacggcgt ggaggtgcat aatgccaaga caaagccgcg ggaggagcag | 300 |
| tacaacagca cgtaccgtgt ggtcagcgtc ctcaccgtcc tgcaccagga ctggctgaat | 360 |
| ggcaaggcat acgcgtgcgc ggtctccaac aaagccctcc cagccccat cgagaaaacc | 420 |
| atctccaaag ccaaagggca gccccgagaa ccacaggtgt acaccctgcc cccatcccgg | 480 |
| gatgagctga ccaagaacca ggtcagcctg acctgcctgg tcaaaggctt ctatccaagc | 540 |
| gacatcgccg tggagtggga gagcaatggg cagccggaga caactacaa gaccacgcct | 600 |
| cccgtgctgg actccgacgg ctccttcttc ctctacagca agctcaccgt ggacaagagc | 660 |
| aggtggcagc aggggaacgt cttctcatgc tccgtgatgc atgaggctct gcacaaccac | 720 |
| tacacgcaga agagcctctc cctgtctccg ggtcagaggc acaacaattc ttccctgaat | 780 |
| acaggaactc agatggcagg tcattctccg aattctcagg tgcagctggt gcagtctggg | 840 |
| gctgaggtga agaagcctgg ggcctcagtg aaggtctcct gcaaggcttc tggatacacc | 900 |
| ttcaccagat ctacgatgca ctgggtgcga caggccccta gacaagggct tgagtgaata | 960 |
| ggatacatta tcctagcag tgcttatact aattacaatc agaaattcaa ggacagggtc | 1020 |
| accatgacca gggacacgtc catcagcaca gcctacatgg agctgagcag gctgagatct | 1080 |
| gacgacacgg ccgtgtatta ctgtgcgaga ccccaagtcc actatgatta caacgggttt | 1140 |
| ccttactggg gccaaggaac cctggtcacc gtctcctcag gtggaggcgg ttcaggcgga | 1200 |
| ggtggatccg gcggtggcgg atcgggtggc ggcggatctg acatccagat gacccagtct | 1260 |
| ccaagcagcc tgtctgcaag cgtgggggac agggtcacca tgacctgcag tgccagctca | 1320 |
| agtgtaagtt acatgaactg gtaccagcag aagccgggca aggcccccaa agatggatt | 1380 |
| tatgactcat ccaaactggc ttctggagtc cctgctcgct tcagtggcag tgggtctggg | 1440 |
| accgactata cccctcacaat cagcagcctg cagcccgaag atttcgccac ttattactgc | 1500 |
| cagcagtgga gtcgtaaccc acccacgttc ggaggggga ccaagctaca aattacatcc | 1560 |
| tccagctaa | 1569 |

(SEQ ID NO: 3)
Signal sequence is residue 1 to 60. Fc region is residue 61-753.
Linker is 754 to 816. Anti-CD3 scFv is 817 to 1569.

Mature protein sequence of Fc H7L1 (TSC313):

| | |
|---|---|
| EPKSSDKTHT CPPCPAPEAA GAPSVFLFPP KPKDTLMISR TPEVTCVVVD VSHEDPEVKF | 60 |
| NWYVDGVEVH NAKTKPREEQ YNSTYRVVSV LTVLHQDWLN GKAYACAVSN KALPAPIEKT | 120 |
| ISKAKGQPRE PQVYTLPPSR DELTKNQVSL TCLVKGFYPS DIAVEWESNG QPENNYKTTP | 180 |
| PVLDSDGSFF LYSKLTVDKS RWQQGNVFSC SVMHEALHNH YTQKSLSLSP GQRHNNSSLN | 240 |
| TGTQMAGHSP NSQVQLVQSG AEVKKPGASV KVSCKASGYT FTRSTMHWVR QAPGQGLEWM | 300 |
| GYINPSSAYT NYNQKFKDRV TMTRDTSIST AYMELSRLRS DDTAVYYCAR PQVHYDYNGF | 360 |
| PYWGQGTLVT VSSGGGGSGG GGSGGGGSGG GGSDIQMTQS PSSLSASVGD RVTMTCSASS | 420 |
| SVSYMNWYQQ KPGKAPKRWI YDSSKLASGV RARFSGSGSG TDYTLTISSL QPEDFATYYC | 480 |
| QQWSRNPPTF GGGTKLQITS SS | 502 |

(SEQ ID NO: 4)

DNA sequence of Fc H7L4 (TSC314):

| | |
|---|---|
| atggaagcac cagcgcagct tctcttcctc ctgctactct ggctcccaga taccaccggt | 60 |
| gagcccaaat cttctgacaa aactcacaca tgcccaccgt gcccagcacc tgaagccgcg | 120 |
| ggtgcaccgt cagtcttcct cttcccccca aaacccaagg acaccctgat gatctcccgg | 180 |
| accctgagg tcacatgcgt ggtggtggac gtgagccacg aagaccctga ggtcaagttc | 240 |
| aactggtacg tggacggcgt ggaggtgcat aatgccaaga caaagccgcg ggaggagcag | 300 |
| tacaacagca cgtaccgtgt ggtcagcgtc ctcaccgtcc tgcaccagga ctggctgaat | 360 |
| ggcaaggcat acgcgtgcgc ggtctccaac aaagccctcc cagccccat cgagaaaacc | 420 |
| atctccaaag ccaaagggca gccccgagaa ccacaggtgt acaccctgcc cccatcccgg | 480 |
| gatgagctga ccaagaacca ggtcagcctg acctgcctgg tcaaaggctt ctatccaagc | 540 |
| gacatcgccg tggagtggga gagcaatggg cagccggaga caactacaa gaccacgcct | 600 |
| cccgtgctgg actccgacgg ctccttcttc ctctacagca agctcaccgt ggacaagagc | 660 |
| aggtggcagc aggggaacgt cttctcatgc tccgtgatgc atgaggctct gcacaaccac | 720 |

TABLE 14-continued

Binding Domain and Polypeptide Sequences and Components

```
tacacgcaga agagcctctc cctgtctccg ggtcagaggc acaacaattc ttccctgaat     780
acaggaactc agatggcagg tcattctccg aattctcagg tgcagctggt gcagtctggg     840
gctgaggtga agaagcctgg ggcctcagtg aaggtctcct gcaaggcttc tggatacacc     900
ttcaccagat ctacgatgca ctgggtgcga caggccctg  acaagggct tgagtggatg      960
ggatacatta atcctagcag tgcttatact aattacaatc agaaattcaa ggacagggtc    1020
accatgacca gggacacgtc catcagcaca gcctacatgg agctgagcag gctgagatct    1080
gacgacacgg ccgtgtatta ctgtgcgaga ccccaagtcc actatgatta acgggttt     1140
ccttactggg gccaaggaac cctggtcacc gtctcctcag gtggaggcgg ttcaggcgga    1200
ggtggatccg gcggtggcgg atcgggtggc ggcggatctg aaattgtgtt gacacagtct    1260
ccagccaccc tgtctttgtc tccaggggaa agagccaccc tctcctgcag tgccagctca    1320
agtgtaagtt acatgaactg gtaccaacag aaacctccg  aggctcccatc                1380
tatgactcat ccaaactggc ttctggcatc ccagccaggt tcagtggcag tgggtctggg    1440
acagacttca ctctcaccat cagcagccta gagcctgaag attttgcagt ttattactgt    1500
cagcagtgga gtcgtaaccc acccactttc ggcggaggga ccaaggtgga gatcaaacgg    1560
tcctccagct aa                                                        1572
(SEQ ID NO: 5)
Signal sequence is residue 1 to 60
```

Mature protein sequence of Fc H7L4 (TSC314):

```
EPKSSDKTHT CPPCPAPEAA GAPSVFLFPP KPKDTLMISR TPEVTCVVVD VSHEDPEVKF      60
NWYVDGVEVH NAKTKPREEQ YNSTYRVVSV LTVLHQDWLN GKAYACAVSN KALPAPIEKT    120
ISKAKGQPRE PQVYTLPPSR DELTKNQVSL TCLVKGFYPS DIAVEWESNG QPENNYKTTP    180
PVLDSDGSFF LYSKLTVDKS RWQQGNVFSC SVMHEALHNH YTQKSLSLSP GQRHNNSSLN    240
TGTQMAGHSP NSQVQLVQSG AEVKKPGASV KVSCKASGYT FTRSTMHWVR QAPGQGLEWM    300
GYINPSSAYT NYNQKFKDRV TMTRDTSIST AYMELSRLRS DDTAVYYCAR PQVHYDYNGF    360
PYWGQGTLVT VSSGGGGSGG GGSGGGGSGG GGSEIVLTQS PATLSLSPGE RATLSCSASS    420
SVSYMNWYQQ KPGQAPRLLI YDSSKLASGI PARFSGSGSG TDFTLTISSL EPEDFAVYYC    480
QQWSRNPPTF GGGTKVEIKR SSS                                            503
(SEQ ID NO: 6)
```

DNA sequence of Fc H7L5 (TSC315):

```
atggaagcac cagcgcagct tctcttcctc ctgctactct ggctcccaga taccaccggt      60
gagcccaaat cttctgacaa aactcacaca tgcccaccgt gcccagcacc tgaagccgcg    120
ggtgcaccgt cagtcttcct cttccccccca aaacccaagg acaccctcat gatctcccgg    180
acccctgagg tcacatgcgt ggtggtggac gtgagccacg aagaccctga ggtcaagttc    240
aactggtacg tggacggcgt ggaggtgcat aatgccaaga caaagccgcg ggaggagcag    300
tacaacagca cgtaccgtgt ggtcagcgtc ctcaccgtcc tgcaccagga ctggctgaat    360
ggcaaggcat acgcgtgcgc ggtctccaac aaagcccctcc cagcccccat cgagaaaacc    420
atctccaaag ccaaagggca gccccgagaa ccacaggtgt acaccctgcc cccatcccgg    480
gatgagctga ccaagaacca ggtcagcctg acctgcctgg tcaaaggctt ctatccaagc    540
gacatcgccg tggagtggga gagcaatggg cagccggaga acaactacaa gaccacgcct    600
cccgtgctgg actccgacgg ctccttcttc ctctacagca agctcaccgt ggacaagagc    660
aggtggcagc aggggaacgt cttctcatgc tccgtgatgc atgaggctct gcacaaccac    720
tacacgcaga agagcctctc cctgtctccg ggtcagaggc acaacaattc ttccctgaat     780
acaggaactc agatggcagg tcattctccg aattctcagg tgcagctggt gcagtctggg     840
gctgaggtga agaagcctgg ggcctcagtg aaggtctcct gcaaggcttc tggatacacc     900
ttcaccagat ctacgatgca ctgggtgcga caggccctg  acaagggct tgagtggatg      960
ggatacatta atcctagcag tgcttatact aattacaatc agaaattcaa ggacagggtc    1020
accatgacca gggacacgtc catcagcaca gcctacatgg agctgagcag gctgagatct    1080
gacgacacgg ccgtgtatta ctgtgcgaga ccccaagtcc actatgatta acgggttt     1140
ccttactggg gccaaggaac cctggtcacc gtctcctcag gtggaggcgg ttcaggcgga    1200
ggtggatccg gcggtggcgg atcgggtggc ggcggatctg acatccagat gacccagtct    1260
ccatcctccc tgtctgcatc tgtaggagac agagtcacca tcacttgcag tgccagctca    1320
agtgtaagtt acatgaactg gtatcagcag aaaccaggga agcccctaa gctcctgatc    1380
tatgactcat ccaaactggc ttctggggtc ccatcaaggt tcagtggcag tggatctggg    1440
acagatttca ctctcaccat cagcagtctg caacctgaag attttgcaac ttactactgt    1500
caacagtgga gtcgtaaccc acccactttc ggcggaggga ccaaggtgga gatcaaacgg    1560
tcctccagct aa                                                        1572
(SEQ ID NO: 7)
Signal sequence is residue 1 to 60
```

Mature protein sequence of Fc H7L5 (TSC315):

```
EPKSSDKTHT CPPCPAPEAA GAPSVFLFPP KPKDTLMISR TPEVTCVVVD VSHEDPEVKF      60
NWYVDGVEVH NAKTKPREEQ YNSTYRVVSV LTVLHQDWLN GKAYACAVSN KALPAPIEKT    120
ISKAKGQPRE PQVYTLPPSR DELTKNQVSL TCLVKGFYPS DIAVEWESNG QPENNYKTTP    180
PVLDSDGSFF LYSKLTVDKS RWQQGNVFSC SVMEEALHNH YTQKSLSLSP GQRHNNSSLN    240
TGTQMAGHSP NSQVQLVQSG AEVKKPGASV KVSCKASGYT FTRSTMHWVR QAPGQGLEWM    300
GYINPSSAYT NYNQKFKDRV TMTRDTSIST AYMELSRLRS DDTAVYYCAR PQVHYDYNGF    360
PYWGQGTLVT VSSGGGGSGG GGSGGGGSGG GGSDIQMTQS PSSLSASVGD RVTITCSASS    420
SVSYMNWYQQ KPGKAPKLLI YDSSKLASGV PSPFSGSGSG TDFTLTISSL QPEDFATYYC    480
QQWSRNPPTF GGGTKVEIKR SSS                                            503
(SEQ ID NO: 8)
```

TABLE 14-continued

Binding Domain and Polypeptide Sequences and Components

DNA sequence of Fc H8L1 (TSC316):

```
atggaagcac cagcgcagct tctcttcctc ctgatactct ggctcccaga taccaccggt      60
gagcccaaat cttctgacaa aactcacaca tgcccaccgt gcccagcacc tgaagccgcg     120
ggtgcaccgt cagtcttcct cttccccca aacccaagg acaccctcat gatctcccgg      180
accctgagg tcacatgcgt ggtggtggac gtgagccacg aagaccctga ggtcaagttc      240
aactggtacg tggacggcgt ggaggtgcat aatgccaaga caaagccgcg ggaggagcag     300
tacaacagca cgtaccgtgt ggtcagcgtc ctcaccgtcc tgcaccagga ctggctgaat     360
ggcaaggcat acgcgtgcgc ggtctccaac aaagccctcc cagcccccat cgagaaaacc     420
atctccaaag ccaaagggca gccccgagaa ccacaggtgt acaccctgcc cccatcccgg     480
gatgagctga ccaagaacca ggtcagcctg acctgcctgg tcaaaggctt ctatccaagc     540
gacatcgccg tggagtggga gagcaatggg cagccggaga acaactacaa gaccacgcct     600
cccgtgctgg actccgacgg ctccttcttc ctctacagca agctcaccgt ggacaagagc     660
aggtggcagc aggggaacgt cttctcatgc tccgtgatgc atgaggctct gcacaaccac     720
tacacgcaga agagcctctc cctgtctccg ggtcagaggc acaacaattc ttccctgaat     780
acaggaactc agatggcagg tcattctccg aattctcagg tgcagctggt gcagtctggg     840
gctgaggtga agaagcctgg ggcctcagtg aaggtttcct gcaaggcatc tggatacacc     900
ttcaccagat ctacgatgca ctgggtgcga caggcccctg gacaagggct tgagtggatg     960
ggatacatta atcctagcag tgcttatact aattacaatc agaaattcaa ggacagagtc    1020
accatgacca gggacacgtc cacgagcaca gtctacatgg agctgagcag cctgagatct    1080
gaggacacgg ccgtgtatta ctgtgctaga ccccaagtcc actatgatta acgggttt    1140
ccttactggg gccaaggaac cctggtcacc gtctcctcag gtggaggcgg ttcaggcgga    1200
ggtggatccg gcggtggcgg atcgggtggc ggcggatctg acatccagat gacccagtct    1260
ccaagcagcc tgtctgcaag cgtggggac agggtcacca tgacctgcag tgccagctca    1320
agtgtaagtt acatgaactg gtaccagcag aagccgggca aggcccccaa agatggatt    1380
tatgactcat ccaaactggc ttctggagtc cctgctcgct tcagtggcag tgggtctggg    1440
accgactata ccctcacaat cagcagcctg cagcccgaag attttgccac ttattactgc    1500
cagcagtgga gtcgtaaccc acccacgttc ggaggggga caagctaca aattacatcc    1560
tccagctaa                                                              1569
```
(SEQ ID NO: 9)
Signal sequence is residue 1 to 60

Mature protein sequence of Fc H8L1 (TSC316):

```
EPKSSDKTHT CPPCPAPEAA GAPSVFLFPP KPKDTLMISR TPEVTCVVVD VSHEDPEVKF      60
NWYVDGVEVH NAKTKPREEQ YNSTYRVVSV LTVLHQDWLN GKAYACAVSN KALPAPIEKT     120
ISKAKGQPRE PQVYTLPPSR DELTKNQVSL TCLVKGFYPS DIAVEWESNG QPENNYKTTP     180
PVLDSDGSFF LYSKLTVDKS PWQQGNVFSC SVMEEALHNH YTQKSLSLSP GQRHNNSSLN     240
TGTQMAGHSP NSQVQLVQSG AEVKKPGASV KVSCKASGYT FTRSTMHWVR QAPGQGLEWM     300
GYINPSSAYT NYNQKFKDRV TMTRDTSTST VYMELSSLRS EDTAVYYCAR PQVHYDYNGF     360
PYWGQGTLVT VSSGGGGSGG GGSGGGGSGG GGSDIQMTQS PSSLSASVGD RVTMTCSASS     420
SVSYMNWYQQ KPGKAPKRWI YDSSKLASGV PARFSGSGSG TDYTLTISSL QPEDFATYYC     480
QQWSRNPPTF GGGTKLQITS SS                                              502
```
(SEQ ID NO: 10)

DNA sequence of Fc H8L4 (TSC317):

```
atggaagcac cagcgcagct tctcttcctc ctgctactct ggctcccaga taccaccggt      60
gagcccaaat cttctgacaa aactcacaca tgcccaccgt gcccagcacc tgaagccgcg     120
ggtgcaccgt cagtcttcct cttccccca aacccaagg acaccctcat gatctcccgg      180
accctgagg tcacatgcgt ggtggtggac gtgagccacg aagaccctga ggtcaagttc      240
aactggtacg tggacggcgt ggaggtgcat aatgccaaga caaagccgcg ggaggagcag     300
tacaacagca cgtaccgtgt ggtcagcgtc ctcaccgtcc tgcaccagga ctggctgaat     360
ggcaaggcat acgcgtgcgc ggtctccaac aaagccctcc cagcccccat cgagaaaacc     420
atctccaaag ccaaagggca gccccgagaa ccacaggtgt acaccctgcc cccatcccgg     480
gatgagctga ccaagaacca ggtcagcctg acctgcctgg tcaaaggctt ctatccaagc     540
gacatcgccg tggagtggga gagcaatggg cagccggaga acaactacaa gaccacgcct     600
cccgtgctgg actccgacgg ctccttcttc ctctacagca agctcaccgt ggacaagagc     660
aggtggcagc aggggaacgt cttctcatgc tccgtgatgc atgaggctct gcacaaccac     720
tacacgcaga agagcctctc cctgtctccg ggtcagaggc acaacaattc ttccctgaat     780
acaggaactc agatggcagg tcattctccg aattctcagg tgcagctggt gcagtctggg     840
gctgaggtga agaagcctgg ggcctcagtg aaggtttcct gcaaggcatc tggatacacc     900
ttcaccagat ctacgatgca ctgggtgcga caggcccctg gacaagggct tgagtggatg     960
ggatacatta atcctagcag tgcttatact aattacaatc agaaattcaa ggacagagtc    1020
accatgacca gggacacgtc cacgagcaca gtctacatgg agctgagcag cctgagatct    1080
gaggacacgg ccgtgtatta ctgtgctaga ccccaagtcc actatgatta acgggttt    1140
ccttactggg gccaaggaac cctggtcacc gtctcctcag gtggaggcgg ttcaggcgga    1200
ggtggatccg gcggtggcgg atcgggtggc ggcggatctg aaattgtgtt gacagtct    1260
ccagccaccc tgtctttgtc tccaggggaa agagccaccc tctcctgcag tgccagctca    1320
agtgtaagtt acatgaactg gtaccaacag aaacctggcc aggctcccag gctcctcatc    1380
tatgactcat ccaaactggc ttctggcatc cagccaggt tcagtggcag tgggtctggg    1440
acagacttca ctctcaccat cagcagccta gagcctgaag attttgcagt ttattactgt    1500
cagcagtgga gtcgtaaccc acccactttc ggcgaggga ccaaggtgga gatcaaacgg    1560
tcctccagct aa                                                          1572
```
(SEQ ID NO: 11)
Signal sequence is residue 1 to 60

TABLE 14-continued

Binding Domain and Polypeptide Sequences and Components

Mature protein sequence of Fc H8L4 (TSC317):

```
EPKSSDKTHT CPPCPAPEAA GAPSVFLFPP KPKDTLMISR TPEVTCVVVD VSHEDPEVKF    60
NWYVDGVEVH NAKTKPREEQ YNSTYRVVSV LTVLHQDWLN GKAYACAVSN KALPAPIEKT   120
ISKAKGQPRE PQVYTLPPSR DELTKNQVSL TCLVKGFYPS DIAVEWESNG QPENNYKTTP   180
PVLDSDGSFF LYSKLTVDKS RWQQGNVFSC SVMHEALHNH YTQKSLSLSP GQRHNNSSLN   240
TGTQMAGHSP NSQVQLVQSG AEVKKPGASV KVSCKASGYT FTRSTMHWVR QAPGQGLEWM   300
GYINPSSAYT NYNQKFKDRV TMTRDTSTST VYMELSSLRS EDTAVYYCAR PQVHYDYNGF   360
PYWGQGTLVT VSSGGGGSGG GGSGGGGSGG GGSEIVLTQS PATLSLSPGE RATLSCSASS   420
SVSYMNWYQQ KPGQAPRLLI YDSSKLASGI PARFSGSGSG TDFTLTISSL EPEDFAVYYC   480
QQWSRNPPTF GGGTKVEIKR SSS                                         503
(SEQ ID NO: 12)
```

DNA sequence of Fc H8L5 (TSC318):

```
atggaagcac cagcgcagct tctcttcctc ctgctactct ggctcccaga taccaccggt    60
gagcccaaat cttctgacaa aactcacaca tgcccaccgt gcccagcacc tgaagccgcg   120
ggtgcaccgt cagtcttcct cttccccca aaacccaagg acaccctcat gatctcccgg    180
acccctgagg tcacatgcgt ggtggtggac gtgagccacg aagaccctga ggtcaagttc   240
aactggtacg tggacggcgt ggaggtgcat aatgccaaga caaagccgcg ggaggagcag   300
tacaacagca cgtaccgtgt ggtcagcgtc ctcaccgtcc tgcaccagga ctggctgaat   360
ggcaaggcat acgcgtgcgc ggtctccaac aaagcccctcc cagcccccat cgagaaaacc   420
atctccaaag ccaaagggca gccccgagaa ccacaggtgt acaccctgcc cccatcccgg   480
gatgagctga ccaagaacca ggtcagcctg acctgcctgg tcaaaggctt ctatccaagc   540
gacatcgccg tggagtggga gagcaatggg cagccggaga acaactacaa gaccacgcct   600
cccgtgctga actccgacgg ctccttcttc ctctacagca agctcaccgt ggacaagagc   660
aggtggcagc aggggaacgt cttctcatgc tccgtgatgc atgaggctct gcacaaccac   720
tacacgcaga gagcctctc cctgtctccg ggtcagaggc acaacaattc ttccctgaat   780
acaggaactc agatggcagg tcattctccg aattctcagg tgcagctggt gcagtctggg   840
gctgaggtga agaagcctgg gcctcagtg aaggtttcct gcaaggcatc tggatacacc   900
ttcaccgat ctacgatgca ctgggtgcga caggcccctg gacaagggct tgagtggatg    960
ggatacatta atcctagcag tgcttatact aattacaatc agaaattcaa ggacagagtc  1020
accatgacca gggacacgtc cacgagcaca gtctacatgg agctgagcag cctgagatct  1080
gaggacacgg ccgtgtatta ctgtgctaga ccccaagtcc actatgatta caacgggttt  1140
ccttactggg gccaaggaac cctggtcacc gtctcctcag gtggaggcgg ttcaggcgga  1200
ggtggatccg gcggtggcgg atcgggtggc ggcggatctg atatccagat gacccagtct  1260
ccatcctccc tgtctgcatc tgtaggagac agagtcacca tcacttgcag tgccagctca  1320
agtgtaagtt acatgaactg gtatcagcag aaaccaggga agcccctaa gctcctgatc  1380
tatgactcat ccaaactggc ttctggggtc ccatcaaggt tcagtggcag tggatctggg  1440
acagatttca ctctctccacc atcagcagtc tgcaacctgaag attttgcaac ttactactgt  1500
caacagtgga gtcgtaaccc acccactttc ggcggaggga ccaaggtgga gatcaaacgc  1560
tcctccagct aa                                                     1572
(SEQ ID NO: 13)
Signal sequence is residue 1 to 60
```

Mature protein sequence of Fc H8L5 (TSC318):

```
EPKSSDKTHT CPPCPAPEAA GAPSVFLFPP KPKDTLMISR TPEVTCVVVD VSHEDPEVKF    60
NWYVDGVEVH NAKTKPREEQ YNSTYRVVSV LTVLHQDWLN GKAYACAVSN KALPAPIEKT   120
ISKAKGQPRE PQVYTLPPSR DELTKMQVSL TCLVKGFYPS DIAVEWESNG QPENNYKTTP   180
PVLDSDGSFF LYSKLTVDKS RWQQGNVFSC SVMHEALHNH YTQKSLSLSP GQRHNNSSLN   240
TGTQMAGHSP NSQVQLVQSG AEVKKPGASV KVSCKASGYT FTRSTMHWVR QAPGQGLEWM   300
GYINPSSAYT NYNQKFKDRV TMTRDTSTST VYMELSSLRS EDTAVYYCAR PQVHYDYNGF   360
PYWGQGTLVT VSSGGGGSGG GGSGGGGSGG GGSDIQMTQS PSSLSASVGD RVTITCSASS   420
SVSYMNWYQQ KPGKAPKLLI YDSSKLASGV PSRFSGSGSG TDFTLTISSL QPEDFATYYC   480
QQWSRMPPTF GGGTKVEIKR SSS                                         503
(SEQ ID NO: 14)
```

DNA sequence of Fc H9L1 (TSC319):

```
atggaagcac cagcgcagct tctcttcctc ctgctactct ggctcccaga taccaccggt    60
gagcccaaat cttctgacaa aactcacaca tgcccaccgt gcccagcacc tgaagccgcg   120
ggtgcaccgt cagtcttcct cttccccca aaacccaagg acaccctcat gatctcccgg    180
acccctgagg tcacatgcgt ggtggtggac gtgagccacg aagaccctga ggtcaagttc   240
aactggtacg tggacggcgt ggaggtgcat aatgccaaga caaagccgcg ggaggagcag   300
tacaacagca cgtaccgtgt ggtcagcgtc ctcaccgtcc tgcaccagga ctggctgaat   360
ggcaaggcat acgcgtgcgc ggtctccaac aaagcccctcc cagcccccat cgagaaaacc   420
atctccaaag ccaaagggca gccccgagaa ccacaggtgt acaccctgcc cccatcccgg   480
gatgagctga ccaagaacca ggtcagcctg acctgcctgg tcaaaggctt ctatccaagc   540
gacatcgccg tggagtggga gagcaatggg cagccggaga acaactacaa gaccacgcct   600
cccgtgctga actccgacgg ctccttcttc ctctacagca agctcaccgt ggacaagagc   660
aggtggcagc aggggaacgt cttctcatgc tccgtgatgc atgaggctct gcacaaccac   720
tacacgcaga gagcctctc cctgtctccg ggtcagaggc acaacaattc ttccctgaat   780
acaggaactc agatggcagg tcattctccg aattctcagg tccagcttgt gcagtctggg   840
gctgaggtga agaagcctgg gcctcagtg aaggtttcct gcaaggcttc tggctacacc   900
tttactagat ctacgatgca ttgggtgcga caggcccccg acaaaggct tgagtggatg    960
ggatacatta atcctagcag tgcttatact aattacaatc agaaattcaa ggacagggtc  1020
accattacca gggacacatc cgcgagcaca gcctacatgg agctgagcag cctgagatct  1080
```

TABLE 14-continued

Binding Domain and Polypeptide Sequences and Components

```
gaagacacgg ctgtgtatta ctgtgcgaga ccccaagtcc actatgatta caacgggttt      1140
ccttactggg gccaaggaac cctggtcacc gtctcctcag gtggaggcgg ttcaggcgga      1200
ggtggatccg gcggtggcgg atcggggtggc ggcggatctg acatccagat gacccagtct     1260
ccaagcagcc tgtctgcaag cgtggggggac agggtcacca tgacctgcag tgccagctca     1320
agtgtaagtt acatgaactg gtaccagcag aagccgggca aggcccccaa agatggatt      1380
tatgactcat ccaaactggc ttctggagtc cctgctcgct tcagtggcag tgggtctggg     1440
accgactata ccctcacaat cagcagcctg cagcccgaag atttcgccac ttattactgc     1500
cagcagtgga gtcgtaaccc acccacgttc ggaggggga ccaagctaca aattacatcc      1560
tccagctaa                                                             1569
(SEQ ID NO: 15)
Signal sequence is residue 1 to 60
```

Mature protein sequence of Fc H9L1 (TSC319):

```
EPKSSDKTHT CPPCPAPEAA GAPSVFLFPP KPKDTLMISR TPEVTCVVVD VSHEDPEVKF       60
NWYVDGVEVH NAKTKPREEQ YNSTYRVVSV LTVLHQDWLN GKAYACAVSN KALPAPIEKT      120
ISKAKGQPRE PQVYTLPPSR DELTKNQVSL TCLVKGFYPS DIAVEWESNG QPENNYKTTP      180
PVLDSDGSFF LYSKLTVDKS RWQQGNVFSC SVMHEALHNH YTQKSLSLSP GQRHNNSSLN      240
TGTQMAGHSP NSQVQLVQSG AEVKKPGASV KVSCKASGYT FTRSTMHWVR QGQRLEWM       300
GYINPSSAYT NYNQKFKDRV TITRDTSAST AYMELSSLRS EDTAVYYCAR PQVHYDYNGF      360
PYWGQGTLVT VSSGGGGSGG GGSGGGGSGG GGSDIQMTQS PSSLSASVGD RVTMTCSASS      420
SVSYMNWYQQ KPGKAPKRWI YDSSKLASGV RARFSGSGSG TDYTLTISSL QPEFFATYYC      480
QQWSRNPPTF GGGTKLQITS SS                                              502
(SEQ ID NO: 16)
```

DNA sequence of Fc H9L4 (TSC320):

```
atggaagcac cagcgcagct tctcttcctc ctgctactct ggctcccaga taccaccggt       60
gagcccaaat cttctgacaa aactcacaca tgcccaccgt gcccagcacc tgaagccgcg      120
ggtgcaccgt cagtcttcct cttccccca aaacccaagg acaccctcat gatctcccgg      180
acccctgagg tcacatgcgt ggtggtggac gtgagccacg aagaccctga ggtcaagttc      240
aactggtacg tggacggcgt ggaggtgcat aatgccaaga caaagccgcg ggaggagcag      300
tacaacagca cgtaccgtgt ggtcagcgtc ctcaccgtcc tgcaccagga ctggctgaat      360
ggcaaggcat acgcgtgcgc ggtctccaac aaagccctcc cagcccccat cgagaaaacc      420
atctccaaag ccaaagggca gccccgagaa ccacaggtgt acaccctgcc cccatcccgg      480
gatgagctga ccaagaacca ggtcagcctg acctgcctgg tcaaaggctt ctatcccaagc     540
gacatcgccg tggagtggga gagcaatggg cagccggaga acaactacaa gaccacgcct      600
cccgtgctgg actccgacgg ctccttcttc ctctacagca agctcaccgt ggacaagagc      660
aggtggcagc aggggaacgt cttctcatgc tccgtgatgc atgaggctct gcacaaccac      720
tacacgcaga gagcctctc cctgtctccg ggtcagaggc acaacaattc ttccctgaat     780
acaggaactc agatggcagg tcattctccg aattctcagg tccagcttgt gcagtctggg      840
gctgaggtga agaagcctgg ggcctcagtg aaggtttcct gcaaggcttc tggctacacc      900
tttactagat ctacgatgca ttgggtgcgc caggcccccg gacaaaggct tgagtggatg      960
ggatacatta tgcttatact aattacaatc agaaattcaa gacagggtc                 1020
accattacca gggacacatc cgcgagcaca gcctacatgg agctgagcag cctgagatct     1080
gaagacacgg ctgtgtatta ctgtgcgaga ccccaagtcc actatgatta caacgggttt      1140
ccttactggg gccaaggaac cctggtcacc gtctcctcag gtggaggcgg ttcaggcgga      1200
ggtggatccg gcggtggcgg atcggggtggc ggcggatctg aaattgtgtt gacacagtct     1260
ccagccaccc tgtctttgtc tccaggggaa agagccaccc tctcctgcag tgccagctca     1320
agtgtaagtt acatgaactg gtaccaacag aaacctggcc aggctcccag gctcctcatc     1380
tatgactcat ccaaactggc ttctggcatc ccagccaggt tcagtggcag tgggtctggg     1440
acagacttca ctctcaccat cagcagccta gagcctgaag attttgcagt ttattactgt     1500
cagcagtgga gtcgtaaccc acccactttc ggcgaggga ccaaggtgga gatcaaacgg      1560
tcctccagct aa                                                         1572
(SEQ ID NO: 17)
Signal sequence is residue 1 to 60
```

Mature protein sequence of Fc H9L4 (TSC320):

```
EPKSSDKTHT CPPCPAPEAA GAPSVFLFPP KPKDTLMISR TPEVTCVVVD VSHEDPEVKF       60
NWYVDGVEVH NAKTKPREEQ YNSTYRVVSV LTVLHQDWLN GKAYACAVSN KALPAPIEKT      120
ISKAKGQPRE PQVYTLPPSR DELTKNQVSL TCLVKGFYPS DIAVEWESNG QPENNYKTTP      180
PVLDSDGSFF LYSKLTVDKS RWQQGNVFSC SVMHEALHNH YTQKSLSLSP GQRHNNSSLN      240
TGTQMAGHSP NSQVQLVQSG AEVKKPGASV KVSCKASGYT FTRSTMHWVR QAPGQRLEWM      300
GYINPSSAYT NYNQKFKDRV TITRDTSAST AYMELSSLRS EDTAVYYCAR PQVHYDYNGF      360
PYWGQGTLVT VSSGGGGSGG GGSGGGGSGG GGSEIVLTQS PATLSLSPGE RATLSCSASS      420
SVSYMNWYQQ KRGQARRLLI YDSSKLASGI PARFSGSGSG TDFTLTISSL EPEDFAVYYC      480
QQWSRNPPTF GGGTKVEIKR SSS                                             503
(SEQ ID NO: 18)
```

DNA sequence of Fc H9L5 (TSC321):

```
atggaagcac cagcgcagct tctcttcctc ctgctactct ggctcccaga taccaccggt       60
gagcccaaat cttctgacaa aactcacaca tgcccaccgt gcccagcacc tgaagccgcg      120
ggtgcaccgt cagtcttcct cttccccca aaacccaagg acaccctcat gatctcccgg      180
acccctgagg tcacatgcgt ggtggtggac gtgagccacg aagaccctga ggtcaagttc      240
aactggtacg tggacggcgt ggaggtgcat aatgccaaga caaagccgcg ggaggagcag      300
tacaacagca cgtaccgtgt ggtcagcgtc ctcaccgtcc tgcaccagga ctggctgaat      360
```

TABLE 14-continued

Binding Domain and Polypeptide Sequences and Components

```
ggcaaggcat acgcgtgcgc ggtctccaac aaagcccctcc cagcccccat cgagaaaacc      420
atctccaaag ccaaagggca gccccgagaa ccacaggtgt acaccctgcc cccatcccgg      480
gatgagctga ccaagaacca ggtcagcctg acctgcctgg tcaaaggctt ctatccaagc      540
gacatcgccg tggagtggga gagcaatggg cagccggaga acaactacaa gaccacgcct      600
cccgtgctgg actccgacgg ctccttcttc ctctacagca agctcaccgt ggacaagagc      660
aggtggcagc aggggaacgt cttctcatgc tccgtgatgc atgaggctct gcacaaccac      720
tacacgcaga gagcctctc cctgtctccg ggtcagagc acaacaattc ttccctgaat       780
acaggaactc agatggcagg tcattctccg aattctcagg tccagcttgt gcagtctggg      840
gctgaggtga gaagcctggg gcctcagtg aaggtttcct gcaaggcttc tggctacacc       900
tttactagat ctacgatgca ttgggtgcgc caggcccccg acaaaggct tgagtggatg      960
ggatacatta atcctagcag tgcttatact aattacaatc agaaattcaa ggacagggtc     1020
accattacca gggacacatc cgcgagcaca gcctacatgg agctgagcag cctgagatct     1080
gaagacacgc tgtgtatta ctgtgcgaga ccccaagtcc actatgatta acgggtttt    1140
ccttactggg gccaaggaac cctggtcacc gtctcctcag gtgaggcgg ttcaggcgga     1200
ggtggatccg gcggtggcgg atcgggtggc ggcggatctg acatccagat gacccagtct     1260
ccatcctccc tgtctgcatc tgtaggagac agagtcacca tcacttgcag tgccagctca     1320
agtgtaagtt acatgaactg gtatcagcag aaaccaggga aagcccctaa gctcctgatc     1380
tatgactcat ccaaactggc ttctggggtc ccatcaaggt tcagtggcag tggatctggg     1440
acagatttca ctctcaccat cagcagtctg caacctgaag attttgcaac ttactactgt     1500
caacagtgga gtcgtaaccc acccactttc ggcggaggga ccaaggtgga gatcaaacgg     1560
tcctccagct aa                                                         1572
(SEQ ID NO: 19)
Signal sequence is residue 1 to 60
```

Mature protein sequence of Fc H9L5 (TSC321):

```
EPKSSDKTHT CPPCPAPEAA GAPSVFLFPP KPKDTLMISR TPEVTCVVVD VSHEDPEVKF       60
NWYVDGVEVH NAKTKPREEQ YNSTYRVVSV LTVLHQDWLN GKAYACAVSN KALPAPIEKT      120
ISKAKGQPRE PQVYTLPPSR DELTKNQVSL TCLVKGFYPS DIAVEWESNG QPENNYKTTP      180
PVLDSDGSFF LYSKLTVDKS RWQQGNVFSC SVMHEALHNH YTQKSLSLSP GQRHNNSSLN      240
TGTQMAGHSP NSQVQLVQSG AEVKKPGASV KVSCKASGYT FTRSTMHWVR QAPGQRLEWM      300
GYINPSSAYT NYNQKFKDRV TITRDTSAST AYMELSSLRS EDTAVYYCAR PQVHYDYNGF      360
PYWGQGTLVT VSSGGGGSGG GGSGGGGSGG GGSDIQMTQS PSSLSASVGD RVTITCSASS      420
SVSYMNWYQQ KPGKAPKLLI YDSSKLASGV PSRFSGSGSG TDFTLTISSL QPEDFATYYC      480
QQWSRNPPTF GGGTKVEIKR SSS                                              503
(SEQ ID NO: 20)
```

DNA sequence of Fc H10L1 (TSC322):

```
atggaagcac cagcgcagct tctcttcctc ctgctactct ggctcccaga taccaccggt       60
gagcccaaat cttctgacaa aactcacaca tgcccaccgt gcccagcacc tgaagccgcg      120
ggtgcaccgt cagtcttcct cttccccca aaacccaagg acaccctcat gatctcccgg      180
acccctgagg tcacatgcgt ggtggtggac gtgagccacg aagaccctga ggtcaagttc      240
aactggtacg tggacggcgt ggaggtgcat aatgccaaga caaagccgcg ggaggagcag      300
tacaacagca cgtaccgtgt ggtcagcgtc ctcaccgtcc tgcaccagga ctggctgaat      360
ggcaaggcat acgcgtgcgc ggtctccaac aaagcccctcc cagcccccat cgagaaaacc    420
atctccaaag ccaaagggca gccccgagaa ccacaggtgt acaccctgcc cccatcccgg      480
gatgagctga ccaagaacca ggtcagcctg acctgcctgg tcaaaggctt ctatccaagc      540
gacatcgccg tggagtggga gagcaatggg cagccggaga acaactacaa gaccacgcct      600
cccgtgctgg actccgacgg ctccttcttc ctctacagca agctcaccgt ggacaagagc      660
aggtggcagc aggggaacgt cttctcatgc tccgtgatgc atgaggctct gcacaaccac      720
tacacgcaga gagcctctc cctgtctccg ggtcagagc acaacaattc ttccctgaat        780
acaggaactc agatggcagg tcattctccg aattctcagg tccagctggt gcaatctggg      840
gctgaggtga agaagcctgg gtcctcggtg aaggtctcct gcaaggcttc tggaggcacc      900
ttcagcagat ctacgatgca ctgggtgcga caggcccctg gacaagggct tgagtggatg      960
ggatacatta atcctagcag tgcttatact aattacaatc agaaattcaa ggacagagtc     1020
acgattaccg cggacaaatc cacgagcaca gcctacatgg agctgagcag cctgagatct     1080
gaggacacgg ccgtgtatta ctgtgcgaga ccccaagtcc actatgatta acgggtttt    1140
ccttactggg gccaaggaac cctggtcacc gtctcctcag gtgaggcgg ttcaggcgga     1200
ggtggatccg gcggtggcgg atcgggtggc ggcggatctg acatccagat gacccagtct     1260
ccaagcagcc tgtctgcaag cgtgggggac agggtcacca tgacctgcag tgccagctca     1320
agtgtaagtt acatgaactg gtaccagcag aagccgacca aggcccccaa agatggatt    1380
tatgactcat ccaaactggc ttctggagtc cctgctcgct tcagtggcag tgggtctggg     1440
accgactata cacctcacaa cagcagcctg agcccgaag atttcgccac ttattactgc      1500
cagcagtgga gtcgtaaccc acccacgttc ggagggggga ccaagctaca aattacatcc    1560
tccagctaa                                                             1569
(SEQ ID NO: 21)
Signal sequence is residue 1 to 60
```

Mature protein sequence of FC H10L1 (TSC322):

```
EPKSSDKTHT CPPCPAPEAA GAPSVFLFPP KPKDTLMISR TPEVTCVVVD VSHEDPEVKF       60
NWYVDGVEVH NAKTKPREEQ YNSTYRVVSV LTVLHQDWLN GKAYACAVSN KALPAPIEKT      120
ISKAKGQPRE PQVYTLPPSR DELTKNQVSL TCLVKGFYPS DIAVEWESNG QPENNYKTTP      180
PVLDSDGSFF LYSKLTVDKS RWQQGNVFSC SVMHEALHNH YTQKSLSLSP GQRHNNSSLN      240
TGTQMAGHSP NSQVQLVQSG AEVKNPGSSV KVSCKASGGT FSRSTMHWVR QAPGQGLEWM      300
GYINPSSAYT NYNQKFKDRV TITADKSTST AYMELSSLRS EDTAVYYCAR PQVHYDYNGF      360
PYWGQGTLVT VSSGGGGSGG GGSGGGGSGG GGSDIQMTQS PSSLSASVGD RVTMTCSASS      420
```

TABLE 14-continued

Binding Domain and Polypeptide Sequences and Components

```
SVSYMNWYQQ KPGKAPKRWI YDSSKLASGV PAPFSGSGSG TDYTLTISSL QPEDFATYYC     480
QQWSPNPPTF GGGTKLQITS SS                                              502
(SEQ ID NO: 22)
```

DNA sequence of Fc H10L4 (TSC323):

```
atggaagcac cagcgcagct tctcttcctc ctgctactct ggctcccaga taccaccggt      60
gagcccaaat cttctgacaa aactcacaca tgcccaccgt gcccagcacc tgaagccgcg     120
ggtgcaccgt cagtcttcct cttccccca  aaacccaagg acaccctcat gatctcccgg     180
acccctgagg tcacatgcgt ggtggtggac gtgagccacg aagaccctga ggtcaagttc     240
aactggtacg tggacggcgt ggaggtgcat aatgccaaga caaagccgcg ggaggagcag     300
tacaacagca cgtaccgtgt ggtcagcgtc ctcaccgtcc tgcaccagga ctggctgaat     360
ggcaaggcat acgcgtgcgc ggtctccaac aaagcccctcc cagcccccat cgagaaaacc    420
atctccaaag ccaaagggca gccccgagaa ccacaggtgt acaccctgcc cccatcccgg     480
gatgagctga ccaagaacca ggtcagcctg acctgcctgg tcaaaggctt ctatccaagc     540
gacatcgccg tggagtggga gagcaatggg cagccggaga acaactacaa gaccacgcct     600
cccgtgctgg actccgacgg ctccttcttc ctctacagca agctcaccgt ggacaagagc     660
aggtggcagc aggggaacgt cttctcatgc tccgtgatgc atgaggctct gcacaaccac     720
tacacgcaga gagcctctc  cctgtctccg ggtcagaggc acaacaattc ttccctgaat     780
acaggaactc agatggcagg tcattctccg aattctcagg tccagctggt gcaatctggg     840
gctgaggtga agaagcctgg gtcctcggtg aaggtctcct gcaaggcttc tggaggcacc    900
ttcagcagat ctacgatgca ctgggtgcga caggcccctg gacaagggct gagtggatg     960
ggatacatta atcctagcag tgcttatact aattacaatc agaaattcaa ggacagagtc    1020
acgattaccg cggacaaatc cacgagcaca gcctacatgg agctgagcag cctgagatct    1080
gaggacacgg ccgtgtatta ctgtgcgaga ccccaagtcc actatgatta acgggttt     1140
ccttactggg gccaaggaac cctggtcacc gtctcctcag gtggaggcgg ttcaggcgga    1200
ggtggatccg gcggtggcgg atcgggtggc ggcggatctg aaattgtgtt gacacagtct    1260
ccagccaccc tgtctttgtc tccaggggaa agagccaccc tctcctgcag tgccagctca    1320
agtgtaagtt acatgaactg gtaccaacag aaacctggcc aggctcccag gctcctcatc    1380
tatgactcat ccaaactggc ttctggcatc ccagccaggt tcagtggcag tgggtctggg    1440
acagacttca ctctcaccat cagcagccta gagcctgaag attttgcagt ttattactgt    1500
cagcagtgga gtcgtaaccc accactttc  ggcggaggga ccaaggtgga gatcaaacgg    1560
tcctccagct aa                                                         1572
(SEQ ID NO: 23)
Signal sequence is residue 1 to 60
```

Mature protein sequence of Fc H10L4 (TSC323):

```
EPKSSDKTHT CPPCPAPEAA GAPSVFLFPP KPKDTLMISR TPEVTCVVVD VSHEDPEWKF      60
NWYVDGVEVH NAKTKPREEQ YNSTYRVVSV LTVLHQDWLN GKAYACAVSN KALPAPIEKT     120
ISKAKGQPRE PQVYTLPPSR DELTKNQVSL TCLVKGFYPS DIAVEWESNG QPENNYKTTP     180
PVLDSDGSFF LYSKLTVDKS RWQQGNVFSC SVMHEALHNH YTQKSLSLSP GQRHNNSSLN     240
TGTQMAGHSP NSQVQLVQSG AEVKKPGSSV KVSCKASGGT FSRSTMHWVR QAPGQGLEWM     300
GYINPSSAYT NYNQKFKDRV TITADKSTST AYMELSSLRS EDTAVYYCAR PQVHYDYNGF     360
PYWGQGTLVT VSSGGGGSGG GGSGGGGSGG GGSEIVLTQS PATLSLSPGE RATLSCSASS     420
SVSYMNWYQQ KPGQAPRLLI YDSSKLASGI PARFSGSGSG TDFTLTISSL EPEDFAVYYC     480
QQWSRNPPTF GGGTKVEIKR SSS                                             503
(SEQ ID NO: 24)
```

DNA sequence of Fc H10L5 (TSC324):

```
atggaagcac cagcgcagct tctcttcctc ctgctactct ggctcccaga taccaccggt      60
gagcccaaat cttctgacaa aactcacaca tgcccaccgt gcccagcacc tgaagccgcg     120
ggtgcaccgt cagtcttcct cttccccca  aaacccaagg acaccctcat gatctcccgg     180
acccctgagg tcacatgcgt ggtggtggac gtgagccacg aagaccctga ggtcaagttc     240
aactggtacg tggacggcgt ggaggtgcat aatgccaaga caaagccgcg ggaggagcag     300
tacaacagca cgtaccgtgt ggtcagcgtc ctcaccgtcc tgcaccagga ctggctgaat     360
ggcaaggcat acgcgtgcgc ggtctccaac aaagcccctcc cagcccccat cgagaaaacc    420
atctccaaag ccaaagggca gccccgagaa ccacaggtgt acaccctgcc cccatcccgg     480
gatgagctga ccaagaacca ggtcagcctg acctgcctgg tcaaaggctt ctatccaagc     540
gacatcgccg tggagtggga gagcaatggg cagccggaga acaactacaa gaccacgcct     600
cccgtgctgg actccgacgg ctccttcttc ctctacagca agctcaccgt ggacaagagc     660
aggtggcagc aggggaacgt cttctcatgc tccgtgatgc atgaggctct gcacaaccac     720
tacacgcaga gagcctctc  cctgtctccg ggtcagaggc acaacaattc ttccctgaat     780
acaggaactc agatggcagg tcattctccg aattctcagg tccagctggt gcaatctggg     840
gctgaggtga agaagcctgg gtcctcggtg aaggtctcct gcaaggcttc tggaggcacc    900
ttcagcagat ctacgatgca ctgggtgcga caggcccctg gacaagggct gagtggatg     960
ggatacatta atcctagcag tgcttatact aattacaatc agaaattcaa ggacagagtc    1020
acgattaccg cggacaaatc cacgagcaca gcctacatgg agctgagcag cctgagatct    1080
gaggacacgg ccgtgtatta ctgtgcgaga ccccaagtcc actatgatta acgggttt     1140
ccttactggg gccaaggaac cctggtcacc gtctcctcag gtggaggcgg ttcaggcgga    1200
ggtggatccg gcggtggcgg atcgggtggc ggcggatctg acatccagat gacccagtct    1260
ccatcctccc tgtctgcatc tgtaggagac cgagtcacca tcacttgcag tgccagctca    1320
agtgtaagtt acatgaactg gtatcagcag aaaccaggga agagccccaa gctcctgatc    1380
tatgactcat ccaaactggc ttctggggtc ccatcaaggt tcagtggcag tggatctggg    1440
acagatttca ctctcaccat cagcagtctg caacctgaag attttgcaac ttactactgt    1500
caacagtgga gtcgtaaccc accactttc  ggcggaggga ccaaggtgga gatcaaacgg    1560
tcctccagct aa                                                         1572
```

TABLE 14-continued

Binding Domain and Polypeptide Sequences and Components (SEQ ID NO: 25)
Signal sequence is residue 1 to 60

Mature protein sequence of Fc H10L5 (TSC324):

```
EPKSSDKTHT CPPCPAPEAA GAPSVFLFPP KPKDTLMISR TPEVTCVVVD VSHEDPEVKF         60
NWYVDGVEVH NAKTKPREEQ YNSTYRVVSV LTVLHQDWLN GKAYACAVSN KALPAPIEKT        120
ISKAKGQPRE PQVYTLPPSR DELTKNQVSL TCLVKGFYPS DIAVEWESNG QPENNYKTTP        180
PVLDSDGSFF LYSKLTVDKS RWQQGNVFSC SVMHEALHNH YTQKSLSLSP GQRHNNSSLN        240
TGTQMAGHSP NSQVQLVQSG AEVKKPGSSV KVSCKASGGT FSRSTMHWVR QAPGQGLEWM        300
GYINPSSAYT NYNQKFKDRV TITADKSTST AYMELSSLRS EDTAVYYCAR PQVHYDYNGF        360
PYWGQGTLVT VSSGGGGSGG GGSGGGGSGG GGSDIQMTQS PSSLSASVGD RVTITCSASS        420
SVSYMNWYQQ KPGKAPKLLI YDSSKLASGV PSRFSGSGSG TDFTLTISSL QPEDFATYYC        480
QQWSRNPPTF GGGTKVEIKR SSS                                               503
```
(SEQ ID NO: 26)

DNA sequence of Fc H7L6 (TSC334):

```
atggaagcac cagcgcagct tctcttcctc ctgctactct ggctcccaga taccaccggt         60
gagcccaaat cttctgacaa aactcacaca tgcccaccgt gcccagcacc tgaagccgcg        120
ggtgcaccgt cagtcttcct cttcccccca aaacccaagg acaccctcat gatctcccgg        180
acccctgagg tcacatgcgt ggtggtggac gtgagccacg aagaccctga ggtcaagttc        240
aactggtacg tggacggcgt ggaggtgcat aatgccaaga caaagccgcg ggaggagcag        300
tacaacagca cgtaccgtgt ggtcagcgtc ctcaccgtcc tgcaccagga ctggctgaat        360
ggcaaggcat acgcatgcgc ggtctccaac aaagccctcc cagcccccat cgagaaaacc        420
atctccaaag ccaaagggca gccccgagaa ccacaggtgt acaccctgcc cccatcccgg        480
gatgagctga ccaagaacca ggtcagcctg acctgcctgg tcaaaggctt ctatccaagc        540
gacatcgccg tggagtggga gagcaatggg cagccggaga acaactacaa gaccacgcct        600
cccgtgctgg actccgacgg ctccttcttc ctctacagca agctcaccgt ggacaagagc        660
aggtggcagc aggggaacgt cttctcatgc tccgtgatgc atgaggctct gcacaaccac        720
tacacgcaga gagcctctcc cctgtctccg ggtcagaggc acaacaattc ttccctgaat        780
acaggaactc agatggcagg tcattctccg aattctcagg tgcagctggt gcagtctggg        840
gctgaggtga agaagcctgg ggcctcagtg aaggtctcct gcaaggcttc tggatacacc        900
ttcaccagat actacatgca ctgggtgcga caggcccctg gacaagggct tgagtggatg        960
ggatacatta atcctagcag tgcttatact aattacaatc agaaattcaa ggacagggtc       1020
accatgacca gggacacgtc catcagcaca gcctacatgg agctgagcag gctgagatct       1080
gacgacacgg ccgtgtatta ctgtgcgaga ccccaagtcc actatgatta caacgggttt       1140
ccttactggg gccaaggaac cctggtcacc gtctcctcag gtggaggcgg ttcaggcgga       1200
ggtggatccg gcggtggcgg atcgggtggc ggcggatctg acatccagat gacccagtct       1260
ccatcctccc tgtctgcatc tgtaggagac agagtcacca tcacttgcag tgccagtcca       1320
agtgtaagtt acatgaactg gtatcagcag aaaccaggga agcccctaa gagatggatt       1380
tatgactcat ccaaactggc ttctggggtc ccatcaaggt tcagtggcag tggatctggg       1440
acagatttca ctctcaccat cagcagtctg caacctgaag attttgcaac ttactactgt       1500
caacagtgga gtcgtaaccc acccactttc ggcgagggga ccaaggtgga gatcaaacgg       1560
tcctccagct aa                                                           1572
```
(SEQ ID NO: 27)
Signal sequence is residue 1 to 60

Mature protein sequence of Fc H7L6 (TSC334):

```
EPKSSDKTHT CPPCPAPEAA GAPSVFLFPP KPKDTLMISR TPEVTCVVVD VSHEDPEVKF         60
NWYVDGVEVH NAKTKPREEQ YNSTYRVVSV LTVLHQDWLN GKAYACAVSN KALPAPIEKT        120
ISKAKGQPRE PQVYTLPPSR DELTKNQVSL TCLVKGFYPS DIAVEWESNG QPENNYKTTP        180
PVLDSDGSFF LYSKLTVDKS RWQQGNVFSC SVMHEALHNH YTQKSLSLSP GQRHNNSSLN        240
TGTQMAGHSP NSQVQLVQSG AEVKKPGASV KVSCKASGYT FTRSTMHWVR QAPGQGLEWM        300
GYINPSSAYT NYNQKFKDRV TMTRDTSIST AYMELSRLRS DDTAVYYCAR PQVHYDYNGF        360
PYWGQGTLVT VSSGGGGSGG GGSGGGGSGG GGSDIQMTQS PSSLSASVGD RVTITCSASS        420
SVSYMNWYQQ KPGKAPKRWI YDSSKLASGV PSRFSGSGSG TDFTLTISSL QPEDFATYYC        480
QQWSRNPPTF GGGTKVEIKR SSS*                                              504
```
(SEQ ID NO: 28)

DNA sequence of Fc H7L7 (TSC335):

```
atggaagcac cagcgcagct tctcttcctc ctgctactct ggctcccaga taccaccggt         60
gagcccaaat cttctgacaa aactcacaca tgcccaccgt gcccagcacc tgaagccgcg        120
ggtgcaccgt cagtcttcct cttcccccca aaacccaagg acaccctcat gatctcccgg        180
acccctgagg tcacatgcgt ggtggtggac gtgagccacg aagaccctga ggtcaagttc        240
aactggtacg tggacggcgt ggaggtgcat aatgccaaga caaagccgcg ggaggagcag        300
tacaacagca cgtaccgtgt ggtcagcgtc ctcaccgtcc tgcaccagga ctggctgaat        360
ggcaaggcat acgcatgcgc ggtctccaac aaagccctcc cagcccccat cgagaaaacc        420
atctccaaag ccaaagggca gccccgagaa ccacaggtgt acaccctgcc cccatcccgg        480
gatgagctga ccaagaacca ggtcagcctg acctgcctgg tcaaaggctt ctatccaagc        540
gacatcgccg tggagtggga gagcaatggg cagccggaga acaactacaa gaccacgcct        600
cccgtgctgg actccgacgg ctccttcttc ctctacagca agctcaccgt ggacaagagc        660
aggtggcagc aggggaacgt cttctcatgc tccgtgatgc atgaggctct gcacaaccac        720
tacacgcaga gagcctctcc cctgtctccg ggtcagaggc acaacaattc ttccctgaat        780
acaggaactc agatggcagg tcattctccg aattctcagg tgcagctggt gcagtctggg        840
gctgaggtga agaagcctgg ggcctcagtg aaggtctcct gcaaggcttc tggatacacc        900
```

TABLE 14-continued

Binding Domain and Polypeptide Sequences and Components

```
ttcaccagat ctacgatgca ctgggtgcga caggcccctg acaagggct tgagtggatg      960
ggatacatta atcctagcag tgcttatact aattacaatc agaaattcaa ggacagggtc     1020
accatgacca gggacacgtc catcagcaca gcctacatgg agctgagcag gctgagatct     1080
gacgacacgg ccgtgtatta ctgtgcgaga ccccaagtcc actatgatta acgggttt      1140
ccttactggg gccaaggaac cctggtcacc gtctcctcag gtggaggcgg ttcaggcgga     1200
ggtggatccg gcggtggcgg atcgggtggc ggcggatctg aaattgtgtt gacgcagtct     1260
ccagccaccc tgtctttgtc tccaggggaa agagccaccc tctcctgcag tgccagctca     1320
agtgtaagtt acatgaactg gtaccagcag aaacctggcc tggcgcccag gagatggatt     1380
tatgactcat ccaaactggc ttctggcatc ccagacaggt tcagtggcag tgggtctggg     1440
acagacttca ctctcaccat cagcagactg gagcctgaag attttgcagt gtattactgt     1500
cagcagtgga gtcgtaaccc acccactttc ggcggaggga ccaaggtgga gatcaaacgg    1560
tcctccagct aa                                                         1572
(SEQ ID NO: 29)
Signal sequence is residue 1 to 60
```

Mature protein sequence of Fc H7L7 (TSC335):

```
EPKSSDKTHT CPPCPAPEAA GAPSVFLFPP KPKDTLMISR TPEVTCVVVD VSHEDPEVKF       60
NWYVDGVEVH NAKTKPREEQ YNSTYRVVSV LTVLEQDWLN GKAYACAVSN KALPAPIEKT     120
ISKAKGQPRE PQVYTLPPSR DELTKNQVSL TCLVKGFYPS DIAVEWESNG QPENNYKTTP     180
PVLDSDGSFF LYSKLTVDKS RWQQGNVFSC SVMHEALHNH YTQKSLSLSP GQRHNNSSLN     240
TGTQMAGHSP NSQVQLVQSG AEVKKPGASV KVSCKASGYT FTRSTMHWVR QAPGQGLEWM     300
GYINPSSAYT NYNQKFKDRV TMTRDTSIST AYMELSRLRS DDTAVYYCAR PQVHYDYNGF     360
PYWGQGTLVT VSSGGGGSGG GGSGGGGSGG GGSEIVLTQS PATLSLSPGE RATLSCSASS     420
SVSYMNWYQQ KPGLAPRRWI YDSSKLASGI PDRFSGSGSG TDFTLTISRL EPEDFAVYYC     480
QQWSRNPPTF GGGTKVEIKR SSS                                             504
(SEQ ID NO: 30)
```

DNA sequence of Fc H7L8 (TSC336):

```
atggaagcac cagcgcagct tctcttcctc ctgctactct ggctcccaga taccaccggt       60
gagcccaaat cttctgacaa aactcacaca tgcccaccgt gcccagcacc tgaagccgcg     120
ggtgcaccgt cagtcttcct cttccccca aaacccaagg acaccctcat gatctcccgg      180
acccctgagg tcacatgcgt ggtggtggac gtgagccacg aagacccga ggtcaagttc      240
aactggtacg tggacggcgt ggaggtgcat aatgccaaga caaagccgcg ggaggagcag     300
tacaacagca cgtaccgtgt ggtcagcgtc ctcaccgtcc tgcaccagga ctggctgaat     360
ggcaaggcat acgcatgcgc ggtctccaac aaagcctc cagcccccat cgagaaaacc       420
atctccaaag ccaaagggca gccccgagaa ccacaggtgt acaccctgcc cccatcccgg     480
gatgagctga ccaagaacca ggtcagcctg acctgcctgg tcaaaggctt ctatccaagc     540
gacatcgccg tggagtggga gagcaatggg cagccggaga acaactacaa gaccacgcct     600
cccgtgctgg actccgacgg ctccttcttc ctctacagca agctcaccgt ggacaagagc     660
aggtggcagc aggggaacgt cttctcatgc tccgtgatgc atgaggctct gcacaaccac     720
tacacgcaga agagcctctc cctgtctccg ggtcagaggc acaacaattc ttccctgaat     780
acaggaactc agatggcagg tcattctccg aattctcagg tgcagctgt cgagtctggg     840
gctgaggtga agaagcctgg ggcctcagtg aaggtctcct gcaaggcttc tggatacacc     900
ttcaccagat ctacgatgca ctgggtgcga caggcccctg acaagggct tgagtggatg      960
ggatacatta atcctagcag tgcttatact aattacaatc agaaattcaa ggacagggtc     1020
accatgacca gggacacgtc catcagcaca gcctacatgg agctgagcag gctgagatct     1080
gacgacacgg ccgtgtatta ctgtgcgaga ccccaagtcc actatgatta acgggttt      1140
ccttactggg gccaaggaac cctggtcacc gtctcctcag gtggaggcgg ttcaggcgga     1200
ggtggatccg gcggtggcgg atcgggtggc ggcggatctg acatccagat gacccagtct     1260
ccttccaccc tgtctctgcat tgtaggagac agagtcacca tcacttgcag tgccagctca     1320
agtgtaagtt acatgaactg gtatcagcag aaaccaggga aagccccta agctggatt      1380
tatgactcat ccaaactggc ttctggggtc ccatcaaggt tcagcggcag tggatctggg     1440
acagaattca ctctcaccat cagcagcctg cagcctgatg attttgcaac ttattactgc     1500
caacagtgga gtcgtaaccc acccactttc ggcggaggga ccaaggtgga gatcaaacgg    1560
tcctccagct aa                                                         1572
(SEQ ID NO: 31)
Signal sequence is residue 1 to 60
```

Mature protein sequence of Fc H7L8 (TsC336):

```
EPKSSDKTHT CPPCPAPEAA GAPSVFLFPP KPKDTLMISR TPEVTCVVVD VSHEDPEVKF       60
NWYVDGVEVH NAKTKPREEQ YNSTYRVVSV LTVLHQDWLN GKAYACAVSN KALPAPIEKT     120
ISKAKGQPRE PQVYTLPPSR DELTKNQVSL TCLVKGFYPS DIAVEWESNG QPENNYKTTP     180
PVLDSDGSFF LYSKLTVDKS RWQQGNVFSC SVMHEALHNH YTQKSLSLSP GQRHNNSSLN     240
TGTQMAGHSP NSQVQLVQSG AEVKKPGASV KVSCKASGYT FTRSTMHWVR QAPGQGLEWM     300
GYINPSSAYT NYNQKFKDRV TMTRDTSIST AYMELSRLRS DDTAVYYCAR PQVHYDYNGF     360
PYWGQGTLVT VSSGGGGSGG GGSGGGGSGG GGSDIQMTQS PSTLSASVGD RVTITCSASS     420
SVSYMNWYQQ KPGKAPKRWI YDSSKLASGV PSRFSGSGSG TEFTLTISSL QPDDFATYYC     480
QQWSRNPPTF GGGTKVEIKR SSS*                                            504
(SEQ ID NO: 32)
```

DNA sequence of Fc H8L6 (TSC337):

```
atggaagcac cagcgcagct tctcttcctc ctgctactct ggctcccaga taccaccggt       60
gagcccaaat cttctgacaa aactcacaca tgcccaccgt gcccagcacc tgaagccgcg     120
ggtgcaccgt cagtcttcct cttccccca aaacccaagg acaccctcat gatctcccgg      180
```

TABLE 14-continued

Binding Domain and Polypeptide Sequences and Components

```
acccctgagg tcacatgcgt ggtggtggac gtgagccacg aagaccctga ggtcaagttc    240
aactggtacg tggacggcgt ggaggtgcat aatgccaaga caaagccgcg ggaggagcag    300
tacaacagca cgtaccgtgt ggtcagcgtc ctcaccgtcc tgcaccagga ctggctgaat    360
ggcaaggcat acgcatgcgc ggtctccaac aaagcccatc cagcccccat cgagaaaacc    420
atctccaaag ccaaagggca gccccgagaa ccacaggtgt acaccctgcc cccatcccgg    480
gatgagctga ccaagaacca ggtcagcctg acctgcctgg tcaaaggctt ctatccaagc    540
gacatcgccg tggagtggga gagcaatggg cagccggaga acaactacaa gaccacgcct    600
cccgtgctgg actccgacgg ctccttcttc ctctacagca agctcaccgt ggacaagagc    660
aggtggcagc aggggaacgt cttctcatgc tccgtgatgc atgaggctct gcacaaccac    720
tacacgcaga gagcctctc cctgtctccg ggtcagaggc acaacaattc ttccctgaat    780
acaggaactc agatggcagg tcattctccg aattctcagg tgcagctggt gcagtctggg    840
gctgaggtga agaagcctgg ggcctcagtg aaggtttcct gcaaggcatc tggatacacc    900
ttcaccagat ctacgatgca ctgggtgcga caggcccctg gacaagggct gagtggatg     960
ggatacatta atcctagcag tgcttatact aattacaatc agaaattcaa ggacagagtc   1020
accatgacca gggacacgtc cacgagcaca gtctacatgg agctgagcag cctgagatct   1080
gaggacacgg ccgtgtatta ctgtgctaga ccccaagtcc actatgatta caacgggttt   1140
ccttactggg gccaaggaac cctggtcacc gtctcctcag gtggaggcgg ttcaggcgga   1200
ggtggatccg gcggtggcgg atcgggtggc ggcggatctg acatccagat gacccagtct   1260
ccatcctccc tgtctgcatc tgtaggagac agagtcacca tcacttgcag tgccagtcca   1320
agtgtaagtt acatgaactg gtatcagcag aaaccaggga agcccctaa gagatggatt    1380
tatgactcat ccaaactggc ttctggggtc ccatcaaggt tcagtggcag tggatctggg   1440
acagatttca ctctcaccat cagcagtctg caacctgaag attttgcaac ttactactgt   1500
caacagtgga gtcgtaaccc acccactttc ggcggaggga ccaaggtgga gatcaaacgg   1560
tcctccagct aa                                                       1572
(SEQ ID NO: 33)
Signal sequence is residue 1 to 60
```

Mature protein sequence of Fc H8L6 (TSC337):

```
EPKSSDKTHT CPPCPAPEAA GAPSVFLFPP PKPKDTLMISR TPEVTCVVVD VSHEDPEVKF    60
NWYVDGVEVH NAKTKPREEQ YNSTYRVVSV LTVLHQDWLN GKAYACAVSN KALPAPIEKT   120
ISKAKGQPRE PQVYTLPPSR DELTKNQVSL TCLVKGFYPS DIAVEWESNG QPENNYKTTP   180
PVLDSDGSFF LYSKLTVDKS RWQQGNVFSC SVMHEALHNH YTQKSLSLSP GQRHNNSSLN   240
TGTQMAGHSP NSQVQLVQSG AEVKKPGASV KVSCKASGYT FTRSTMHWVR QAPGQGLEWM   300
GYINPSSAYT NYNQKFKDRV TMTRDTSTST VYMELSSLRS EDTAVYYCAR PQVHYDYNGF   360
PYWGQGTLVT VSSGGGGSGG GGSGGGGSGG GGSDIQMTQS PSSLSASVGD RVTITCSASS   420
SVSYMNWYQQ KPGKAPKRWI YDSSKLASGV PSRFSGSGSG TDFTLTISSL QPEDFATYYC   480
QQWSRNPPTF GGGTKVEIKR SSS*                                          504
(SEQ ID NO: 34)
```

DNA sequence of Fc H8L7 (TSC338):

```
atggaagcac cagcgcagct tctcttcctc ctgctactct ggctcccaga taccaccggt     60
gagcccaaat cttctgacaa aactcacaca tgcccaccgt gcccagcacc tgaagccgca   120
ggtgcaccgt cagtcttcct cttcccccca aaacccaagg acaccctcat gatctcccgg   180
acccctgagg tcacatgcgt ggtggtggac gtgagccacg aagaccctga ggtcaagttc   240
aactggtacg tggacggcgt ggaggtgcat aatgccaaga caaagccgcg ggaggagcag   300
tacaacagca cgtaccgtgt ggtcagcgtc ctcaccgtcc tgcaccagga ctggctgaat   360
ggcaaggcat acgcatgcgc ggtctccaac aaagccctcc cagcccccat cgagaaaacc   420
atctccaaag ccaaagggca gccccgagaa ccacaggtgt acaccctgcc cccatcccgg   480
gatgagctga ccaagaacca ggtcagcctg acctgcctgg tcaaaggctt ctatccaagc   540
gacatcgccg tggagtggga gagcaatggg cagccggaga acaactacaa gaccacgcct   600
cccgtgctgg actccgacgg ctccttcttc ctctacagca agctcaccgt ggacaagagc   660
aggtggcagc aggggaacgt cttctcatgc tccgtgatgc atgaggctct gcacaaccac   720
tacacgcaga gagcctctc cctgtctccg ggtcagaggc acaacaattc ttccctgaat    780
acaggaactc agatggcagg tcattctccg aattctcagg tgcagctggt gcagtctggg   840
gctgaggtga agaagcctgg ggcctcagtg aaggtttcct gcaaggcatc tggatacacc   900
ttcaccagat ctacgatgca ctgggtgcga caggcccctg gacaagggct gagtggatg    960
ggatacatta atcctagcag tgcttatact aattacaatc agaaattcaa ggacagagtc  1020
accatgacca gggacacgtc cacgagcaca gtctacatgg agctgagcag cctgagatct  1080
gaggacacgg ccgtgtatta ctgtgctaga ccccaagtcc actatgatta caacgggttt  1140
ccttactggg gccaaggaac cctggtcacc gtctcctcag gtggaggcgg ttcaggcgga  1200
ggtggatccg gcggtggcgg atcgggtggc ggcggatctg aaattgtgtt gacgcagtct  1260
ccagccaccc tgtctttgtc tccaggggaa agagccaccc tctcctgcag tgccagctca  1320
agtgtaagtt acatgaactg gtaccagcag aaacctggcc aggcccgag gagatggatt   1380
tatgactcat ccaaactggc ttctggcatc ccagacaggt tcagtggcag tgggtctggg  1440
acagacttca ctctcaccat cagcagactg gagcctgaag attttgcagt gtattactgt  1500
cagcagtgga gtcgtaaccc acccactttc ggcggaggga ccaaggtgga gatcaaacgg  1560
tcctccagct aa                                                      1572
(SEQ ID NO: 35)
Signal sequence is residue 1 to 60
```

Mature protein sequence of Fc H8L7 (TSC338):

```
EPKSSDKTHT CPPCPAPEAA GAPSVFLFPP PKPKDTLMISR TPEVTCVVVD VSHEDPEVKF    60
NWYVDGVEVH NAKTKPREEQ YNSTYRVVSV LTVLHQDWLN GKAYACAVSN KALPAPIEKT   120
ISKAKGQPRE PQVYTLPPSR DELTKNQVSL TCLVKGFYPS DIAVEWESNG QPENNYKTTP   180
PVLDSDGSFF LYSKLTVDKS RWQQGNVFSC SVMHEALHNH YTQKSLSLSP GQRHNNSSLN   240
```

TABLE 14-continued

Binding Domain and Polypeptide Sequences and Components

```
TGTQMAGHSP NSQVQLVQSG AEVKKPGASV KVSCKASGYT FTRSTMHWVR QAPGQGLEWM    300
GYINPSSAYT NYNQKFKDRV TMTRDTSTST VYMELSSLRS EDTAVYYCAR PQVHYDYNGF    360
PYWGQGTLVT VSSGGGGSGG GGSGGGGSGG GGSEIVLTQS PATLSLSPGE PATLSCSASS    420
SVSYMNWYQQ KPGLAPRRWI YDSSKLASGI PDRFSGSGSG TDFTLTISRL EPEDFAVYYC    480
QQWSRNPPTF GGGTKVEIKR SSS                                           503
(SEQ ID NO: 36)
```

DNA sequence of Fc H8L8 (TSC339):

```
atggaagcac cagcgcagct tctcttcctc ctgctactct ggctcccaga taccaccggt     60
gagcccaaat cttctgacaa aactcacaca tgcccaccgt gcccagccgt tgaagccgcg    120
ggtgcaccgt cagtcttcct cttcccccca aaacccaagg acaccctcat gatctcccgg    180
acccctgagg tcacatgcgt ggtggtggac gtgagccacg aagaccctga ggtcaagttc    240
aactggtacg tggacggcgt ggaggtgcat aatgccaaga caaagccgcg ggaggagcag    300
tacaacagca cgtaccgtgt ggtcagcgtc ctcaccgtcc tgcaccagga ctggctgaat    360
ggcaaggcat acgcatgcgc ggtctccaac aaagccctcc cagcccccat cgagaaaacc    420
atctccaaag ccaaagggca gccccgagaa ccacaggtgt acaccctgcc cccatcccgg    480
gatgagctga ccaagaacca ggtcagcctg acctgcctgg tcaaaggctt ctatccaagc    540
gacatcgccg tggagtggga gagcaatggg cagccggaga acaactacaa gaccacgcct    600
cccgtgctgg actccgacgg ctccttcttc ctctacagca agctcaccgt ggacaagagc    660
aggtggcagc aggggaacgt cttctcatgc tccgtgatgc atgaggctct gcacaaccac    720
tacacgcaga gagcctctc cctgtctccg ggtcagaggc acaacaattc ttccctgaat    780
acaggaactc agatggcagg tcattctccg aattctcagg tgcagctggt gcagtctgga    840
gctgaggtga agaagcctgg ggcctcagtg aaggtttcct gcaaggcatc tggatacacc    900
ttcaccagat ctacgatgca ctgggtgcga caggcccctg gacaagggct tgagtggatg    960
ggatacatta atcctagcag tgcttatact aattacaatc agaaattcaa ggacagagtc   1020
accatgacca gggacacgtc cacgagcaca gtctacatgg agctgagcag cctgagatct   1080
gaggacacgg ccgtgtatta ctgtgctaga ccccaagtcc actatgatta caacgggttt   1140
ccttactggg gccaaggaac cctggtcacc gtctcctcag gtggaggcgg ttcaggcgga   1200
ggtggatccg gcggtggcgg atcgggtggc ggcggatctg acatccagat gacccagtct   1260
ccttccaccc tgtctgcatc tgtaggagac agagtcacca tcacttgcag tgccagctca   1320
agtgtaagtt acatgaactg gtatcagcag aaaccaggga agccccctaa gagatggatt   1380
tatgactcat ccaaactggc ttctggggtc ccatcaaggt tcagcggcag tggatctggg   1440
acagaattca ctctcaccat cagcagcctg cagcctgatg attttgcaac ttattactgc   1500
caacagtgga gtcgtaaccc acccactttc ggcggaggga ccaaggtgga gatcaaacgg   1560
tcctccagct aa                                                      1572
(SEQ ID NO: 37)
Signal sequence is residue 1 to 60
```

Mature protein sequence of Fc H8L8 (TSC339):

```
EPKSSDKTHT CPPCPAPEAA GAPSVFLFPP KPKDTLMISR TPEVTCVVVD VSHEDPEVKF     60
NWYVDGVEVH NAKTKPREEQ YNSTYRVVSV LTVLHQDWLN GKAYACAVSN KALPAPIEKT    120
ISKARGQPRE PQVYTLPPSR DELTKNQVSL TCLVKGFYPS DIAVEWESNG QPENNYKTTP    180
PVLDSDGSFF LYSKLTVDKS RWQQGNVFSC SVMHEALHNH YTQKSLSLSP GQRHNNSSLN    240
TGTQMAGHSP NSQVQLVQSG AEVKKPGASV KVSCKASGYT FTRSTMHWVR QAPGQGLEWM    300
GYINPSSAYT NYNQKFKDRV TMTRDTSTST VYMELSSLRS EDTAVYYCAR PQVHYDYNGF    360
PYWGQGTLVT VSSGGGGSGG GGSGGGGSGG GGSDIQMTQS PSTLSASVGD RVTITCSASS    420
SVSYMNWYQQ KPGKAPKRWI YDSSKLASGV PSRFSGSGSG TEFTLTISSL QPDDFATYYC    480
QQWSRNPPTF GGGTKVEIKR SSS                                           504
(SEQ ID NO: 38)
```

DNA sequence of Fc H10L6 (TSC340):

```
atggaagcac cagcgcagct tctcttcctc ctgctactct ggctcccaga taccaccggt     60
gagcccaaat cttctgacaa aactcacaca tgcccaccgt gcccagcacc tgaagccgcg    120
ggtgcaccgt cagtcttcct cttcccccca aaacccaagg acaccctcat gatctcccgg    180
acccctgagg tcacatgcgt ggtggtggac gtgagccacg aagaccctga ggtcaagttc    240
aactggtacg tggacggcgt ggaggtgcat aatgccaaga caaagccgcg ggaggagcag    300
tacaacagca cgtaccgtgt ggtcagcgtc ctcaccgtcc tgcaccagga ctggctgaat    360
ggcaaggcat acgcatgcgc ggtctccaac aaagccctcc cagcccccat cgagaaaacc    420
atctccaaag ccaaagggca gccccgagaa ccacaggtgt acaccctgcc cccatcccgg    480
gatgagctga ccaagaacca ggtcagcctg acctgcctgg tcaaaggctt ctatccaagc    540
gacatcgccg tggagtggga gagcaatggg cagccggaga acaactacaa gaccacgcct    600
cccgtgctgg actccgacgg ctccttcttc ctctacagca agctcaccgt ggacaagagc    660
aggtggcagc aggggaacgt cttctcatgc tccgtgatgc atgaggctct gcacaaccac    720
tacacgcaga gagcctctc cctgtctccg ggtcagaggc acaacaattc ttccctgaat    780
acaggaactc agatggcagg tcattctccg aattctcagg tccagctggt gcaatctggg    840
gctgaggtga agaagcctgg ggtctcggtg aaggtctcct gcaaggcttc tggaggcacc    900
ttcagcagat ctacgatgca ctgggtgcga caggcccctg gacaagggct tgagtggatg    960
ggatacatta atcctagcag tgcttatact aattacaatc agaaattcaa ggacagagtc   1020
acgattaccc gggacaaatc cacgagcaca gcctacatgg agctgagcag cctgagatct   1080
gaggacacgg ccgtgtatta ctgtgcgaga ccccaagtcc actatgatta caacgggttt   1140
ccttactggg gccaaggaac cctggtcacc gtctcctcag gtggaggcgg ttcaggcgga   1200
ggtggatccg gcggtggcgg atcgggtggc ggcggatctg acatccagat gacccagtct   1260
ccatcctccc tgtctgcatc tgtaggagac agagtcacca tcacttgcag tgccagctca   1320
agtgtaagtt acatgaactg gtatcagcag aaaccaggga agcccctaa gagatggatt   1380
tatgactcat ccaaactggc ttctggggtc ccatcaaggt tcagtggcag tggatctggg   1440
```

TABLE 14-continued

Binding Domain and Polypeptide Sequences and Components

```
acagatttca ctctcaccat cagcagtctg caacctgaag attttgcaac ttactactgt      1500
caacagtgga gtcgtaaccc acccactttc ggcggaggga ccaaggtgga gatcaaacgg      1560
tcctccagct aa                                                          1572
(SEQ ID NO: 39)
Signal sequence is residue 1 to 60
```

Mature protein sequence of Fc H10L6 (TSC340):

```
EPKSSDKTHT CPPCPAPEAA GAPSVFLFPP KPKDTLMISR TPEVTCVVVD VSHEDPEVKF       60
NWYVDGVEVH NAKTKPREEQ YNSTYRVVSV LTVLHQDWLN GKAYACAVSN KALPAPIEKT      120
ISKAKGQPRE PQVYTLPPSR DELTKNQVSL TCLVKGFYPS DIAVEWESNG QPENNYKTTP      180
PVLDSDGSFF LYSKLTVDKS RWQQGNVFSC SVMHEALHNH YTQKSLSLSP GQRHNNSSLN      240
TGTQMAGHSP NSQVQLVQSG AEVKKPGSSV KVSCKASGGT FSRSTMHWVR QAPGQGLEWM      300
GYINPSSAYT NYNQKFKDRV TITADKSTST AYMELSSLRS EDTAVYYCAR PQVHYDYNGF      360
PYWGQGTLVT VSSGGGGSGG GGSGGGGSGG GGSDIQMTQS PSSLSASVGD RVTITCSASS      420
SVSYMNWYQQ KPGKAPKRWI YDSSKLASGV PSRFSGSGSG TDFTLTISSL QPEDFATYYC      480
QQWSRNPPTF GGGTKVEIKR SSS                                             503
(SEQ ID NO: 40)
```

DNA sequence of Fc H10L7 (TSC341):

```
atggaagcac cagcgcagct tctcttcctc ctgctactct ggctcccaga taccaccggt       60
gagcccaaat cttctgacaa aactcacaca tgcccaccgt gcccagcacc tgaagccgcg      120
ggtgcaccgt cagtcttcct cttcccccca aaacccaagg acaccctcat gatctcccgg      180
acccctgagg tcacatgcgt ggtggtggac gtgagccacg aagaccctga ggtcaagttc      240
aactggtacg tggacggcgt ggaggtgcat aatgccaaga caaagccgcg ggaggagcag      300
tacaacagca cgtaccgtgt ggtcagcgtc ctcaccgtcc tgcaccagga ctggctgaat      360
ggcaaggcat acgcatgcgc ggtctccaac aaagccctcc cagccccat cgagaaaacc       420
atctccaaag ccaaagggca gccccgagaa ccacaggtgt acaccctgcc cccatcccgg      480
gatgagctga ccaagaacca ggtcagcctg acctgcctgg tcaaaggctt ctatccaagc      540
gacatcgccg tggagtggga gagcaatggg cagccggaga acaactacaa gaccacgcct      600
cccgtgctgg actccgacgg ctccttcttc ctctacagca agctcaccgt ggacaagagc      660
aggtggcagc aggggaacgt cttctcatgc tccgtgatgc atgaggctct gcacaaccac      720
tacacgcaga gagcctctc cctgtctccg ggtcagaggc acaacaattc ttccctgaat      780
acaggaactc agatggcagg tcattctccg aattctcagg tccagctggt gcaatctggg      840
gctgaggtga agaagcctgg gtcctcggtg aaggtctcct gcaaggcttc tggaggcacc      900
ttcagcagat ctacgatgca ctgggtgcga caggcccctg gacaagggct tgagtggatg      960
ggatacatta atcctagcag tgcttatact aattacaatc agaaattcaa ggacagagtc     1020
acgattaccg cggacaaatc cacgagcaca gcctacatgg agctgagcag cctgagatct     1080
gaggacacgg ccgtgtatta ctgtgcgaga cccaagtcc actatgatta caacgggttt     1140
ccttactggg gccaaggaac cctggtcacc gtctcctcag gtggaggcgg ttcaggcgga    1200
ggtggatccg gcggtggcgg atcgggtggc ggcggatctg aaattgtgtt gacgcagtct    1260
ccagccaccc tgtctttgtc tccaggggaa agagccaccc tctcctgcag tgccagctca     1320
agtaagtt acatgaactg gtaccagcag aaacctggcc aggcgccag tgggtctggg        1380
tatgactcat ccaaactggc ttctggcatc ccagacaggt tcagtggcag tgggtctggg    1440
acagacttca ctctcaccat cagcagactg gagcctgaag attttgcagt gtattactgt    1500
cagcagtgga gtcgtaaccc acccactttc ggcggaggga ccaaggtgga gatcaaacgg    1560
tcctccagct aa                                                       1572
(SEQ ID NO: 41)
Signal sequence is residue 1 to 60
```

Mature protein sequence of Fc H10L7 (TSC341):

```
EPKSSDKTHT CPPCPAPEAA GAPSVFLFPP KPKDTLMISR TPEVTCVVVD VSHEDPEVKF       60
NWYVDGVEVH NAKTKPREEQ YNSTYRVVSV LTVLHQDWLN GKAYACAVSN KALPAPIEKT      120
ISKAKGQPRE PQVYTIPPSR DELTKNQVSL TCLVKGFYPS DIAVEWESNG QPENNYKTTP      180
PVLDSDGSFF LYSKLTVDKS RWQQGNVFSC SVMHEALHNH YTQKSLSLSP GQRHNNSSLN      240
TGTQMAGHSP NSQVQLVQSG AEVKKPGSSV KVSCKASGGT FSRSTMHWVR QAPGQGLEWM      300
GYINPSSAYT NYNQKFKDRV TITADKSTST AYMELSSLRS EDTAVYYCAR PQVHYDYNGF      360
PYWGQGTLVT VSSGGGGSGG GGSGGGGSGG GGSEIVLTQS PATLSLSPGE RATLSCSASS      420
SVSYMNWYQQ KPGLAPRRWI YDSSKLASGI PDRFSGSGSG TDFTLTISRL EPEDFAVYYC      480
QQWSRNPPTF GGGTKVEIKR SSS                                             503
(SEQ ID NO: 42)
```

DNA sequence of Fc H10L8 (TSC342):

```
atggaagcac cagcgcagct tctcttcctc ctgctactct ggctcccaga taccaccggt       60
gagcccaaat cttctgacaa aactcacaca tgcccaccgt gcccagcacc tgaagccgcg      120
ggtgcaccgt cagtcttcct cttcccccca aaacccaagg acaccctcat gatctcccgg      180
acccctgagg tcacatgcgt ggtggtggac gtgagccacg aagaccctga ggtcaagttc      240
aactggtacg tggacggcgt ggaggtgcat aatgccaaga caaagccgcg ggaggagcag      300
tacaacagca cgtaccgtgt ggtcagcgtc ctcaccgtcc tgcaccagga ctggctgaat      360
ggcaaggcat acgcatgcgc ggtctccaac aaagccctcc cagccccat cgagaaaacc       420
atctccaaag ccaaagggca gccccgagaa ccacaggtgt acaccctgcc cccatcccgg      480
gatgagctga ccaagaacca ggtcagcctg acctgcctgg tcaaaggctt ctatccaagc      540
gacatcgccg tggagtggga gagcaatggg cagccggaga acaactacaa gaccacgcct      600
cccgtgctgg actccgacgg ctccttcttc ctctacagca agctcaccgt ggacaagagc      660
aggtggcagc aggggaacgt cttctcatgc tccgtgatgc atgaggctct gcacaaccac      720
```

TABLE 14-continued

Binding Domain and Polypeptide Sequences and Components

```
tacacgcaga agagcctctc cctgtctccg ggtcagaggc acaacaattc ttccctgaat    780
acaggaactc agatggcagg tcattctccg aattctcagg tccagctggt gcaatctggg    840
gctgaggtga agaagcctgg gtcctcggtg aaggtctcct gcaaggcttc tggaggcacc    900
ttcagcagat ctacgatgca ctgggtgcga caggcccctg gacaagggct tgagtggatg    960
ggatacatta atcctagcag tgcttatact aattacaatc agaaattcaa ggacagagtc   1020
acgattaccg cggacaaatc cacgagcaca gcctacatgg agctgagcag cctgagatct   1080
gaggacacgg ccgtgtatta ctgtgcgaga ccccaagtcc actatgatta acgggttt     1140
ccttactggg gccaaggaac cctggtcacc gtctcctcag gtggaggcgg ttcaggcgga   1200
ggtggatccg gcggtggcgg atcgggtggc ggcggatctg acatccagat gacccagtct   1260
ccttccaccc tgtctgcatc tgtaggagac agagtcacca tcacttgcag tgccagctca   1320
agtgtaagtt acatgaactg gtatcagcag aaaccctaa gatgggatt                1380
tatgactcat ccaaactggc ttctggggtc ccatcaaggt tcagcggcag tggatctggg   1440
acagaattca ctctcaccat cagcagcctg cagcctgatg attttgcaac ttattactgc   1500
caacagtgga gtcgtaaccc acccactttc ggcggaggga ccaaggtgga gatcaaacgg   1560
tcctccagct aa                                                       1572
(SEQ ID NO: 45)
Signal sequence is residue 1 to 60
```

Mature protein sequence of Fc H10L8 (TSC342):

```
EPKSSDKTHT CPPCPAPEAA GAPSVFLFPP KPKDTLMISR TPEVTCVVVD VSHEDPEVKF     60
NWYVDGVEVH NAKTKPREEQ YNSTYRVVSV LTVLHQDWLN GKAYACAVSN KALPAPIEKT    120
ISKAKGQPRE PQVYTLPPSR DELTKNQVSL TCLVKGFYPS DIAVEWESNG QPENNYKTTP    180
PVLDSDGSFF LYSKLTVDKS RWQQGNVFSC SVMHEALHNH YTQKSLSLSP GQRHNNSSLN    240
TGTQMAGHSP NSQVQLVQSG AEVKKPGSSV KVSCKASGGT FSRSTMHWVR QAPGQGLEWM    300
GYINPSSAYT NYNQKFKDRV TITADKSTST AYMELSSLRS EDTAVYYCAR PQVHYDYNGF    360
PYWGQGTLVT VSSGGGGSGG GGSGGGGSGG GGSDIQMTQS PSTLSASVGD RVTITCSASS    420
SVSYMNWYQQ KPGKAPKRWI YDSSKLASGV PSRFSGSGSG TEFTLTISSL QPDDFATYYC    480
QQWSRNPPTF GGGTKVEIKR SSS                                           503
(SEQ ID NO: 44)
```

DNA sequence of TSC370:

```
atggaagcac cagcgcagct tctcttcctc ctgctactct ggctcccaga taccaccggt     60
gagcccaaat cttctgacaa aactcacaca tgcccaccgt gcccagcacc tgaagccgcg    120
ggtgcaccgt cagtcttcct cttccccca aaacccaagg acaccctcat gatctcccgg    180
acccctgagg tcacatgcgt ggtggtggac gtgagccacg aagaccctga ggtcaagttc    240
aactggtacg tggacggcgt ggaggtgcat aatgccaaga caaagccgcg ggaggagcag    300
tacaacagca cgtaccgtgt ggtcagcgtc ctcaccgtcc tgcaccagga ctggctgaat    360
ggcaaggcat acgcatgcgc ggtctccaac aaagccctcc cagcccccat cgagaaaacc    420
atctccaaag ccaaagggca gccccgagaa ccacaggtgt acaccctgcc cccatcccgg    480
gatgagctga ccaagaacca ggtcagcctg acctgcctgg tcaaaggctt ctatccaagc    540
gacatcgccg tggagtggga gagcaatggg cagccggaga acaactacaa gaccacgcct    600
cccgtgctgg actccgacgg ctccttcttc ctctacagca agctcaccgt ggacaagagc    660
aggtggcagc aggggaacgt cttctcatgc tccgtgatgc atgaggctct gcacaaccac    720
tacacgcaga agagcctctc cctgtctccg ggtcagaggc acaacaattc ttccctgaat    780
acaggaactc agatggcagg tcattctccg aattctcagg tccagctggt gcaatctggg    840
gctgaggtga agaagcctgg gtcctcggtg aaggtctcct gcaaggcttc tggatatacc    900
ttcagcagat ctacgatgca ctgggtgcga caggcccctg gacaagggct tgagtggatg    960
ggatacatta atcctagcag tgcttatact aattacaatc agaaattcaa ggacagagtc   1020
acgattaccg cggacaaatc cacgagcaca gcctacatgg agctgagcag cctgagatct   1080
gaggacacgg ccgtgtatta ctgtgcgaga ccccaagtcc actatgatta acgggttt     1140
ccttactggg gccaaggaac cctggtcacc gtctcctcag gtggaggcgg ttcaggcgga   1200
ggtggatccg gcggtggcgg atcgggtggc ggcggatctg acatccagat gacccagtct   1260
ccttccaccc tgtctgcatc tgtaggagac agagtcacca tcacttgcag tgccagctca   1320
agtgtaagtt acatgaactg gtatcagcag aaaccaggga agcccctaa gatgggatt     1380
tatgactcat ccaaactggc ttctggggtc ccatcaaggt tcagcggcag tggatctggg   1440
acagaattca ctctcaccat cagcagcctg cagcctgatg attttgcaac ttattactgc   1500
caacagtgga gtcgtaaccc acccactttc ggcggaggga ccaaggtgga gatcaaacgg   1560
tcctccagct aa                                                       1572
(SEQ ID NO: 45)
Signal sequence is residue 1 to 60
```

Mature protein sequence of TSC370:

```
EPKSSDKTHT CPPCPAPEAA GAPSVFLFPP KPKDTLMISR TPEVTCVVVD VSHEDPEVKF     60
NWYVDGVEVH NANTKPREEQ YNSTYPVVSV LTVLHQDWLN GKAYACAVSN KALPAPIEKT    120
ISKAKGQPRE PQVYTLPPSR DELTKNQVSL TCLVKGFYPS DIAVEWESNG QPENNYKTTP    180
PVLDSDGSFF LYSKLTVDKS RWQQGNVFSC SVMHEALHNH YTQKSLSLSP GQRHNNSSLN    240
TGTQMAGHSP NSQVQLVQSG AEVKKPGSSV KVSCKASGYT FSRSTMHWVR QAPGQGLEWM    300
GYINPSSAYT NYNQKFKDRV TITADKSTST AYMELSSLRS EDTAVYYCAR PQVHYDYNGF    360
PYWGQGTLVT VSSGGGGSGG GGSGGGGSGG GGSDIQMTQS PSTLSASVGD RVTITCSASS    420
SVSYMNWYQQ KPGKAPKRWI YDSSKLASGV PSRFSGSGSG TEFTLTISSL QPDDFATYYC    480
QQWSPNPPTF GGGTKVEIKR SSS                                           503
(SEQ ID NO: 46)
```

TABLE 14-continued

Binding Domain and Polypeptide Sequences and Components

DNA sequence of TSC371:

```
atggaagcac cagcgcagct tctcttcctc ctgctactct ggctcccaga taccaccggt      60
gagcccaaat cttctgacaa aactcacaca tgcccaccgt gcccagcacc tgaagccgcg     120
ggtgcaccgt cagtcttcct cttcccccca aacccaagg acaccctcat gatctcccgg      180
accccctgagg tcacatgcgt ggtggtggac gtgagccacg aagaccctga ggtcaagttc    240
aactggtacg tggacggcgt ggaggtgcat aatgccaaga caaagccgcg ggaggagcag     300
tacaacagca cgtaccgtgt ggtcagcgtc ctcaccgtcc tgcaccagga ctggctgaat     360
ggcaaggcat acgcatgcgc ggtctccaac aaagcccctcc cagcccccat cgagaaaacc   420
atctccaaag ccaaagggca gccccgagaa ccacaggtat acaccctgcc cccatcccgg    480
gatgagctga ccaagaacca ggtcagcctg acctgcctgg tcaaaggctt ctatccaagc    540
gacatcgccg tggagtggga gagcaatggg cagccggaga acaactacaa gaccacgcct    600
cccgtgctgg actccgacgg ctccttcttc ctctacagca agctcaccgt ggacaagagc    660
aggtggcagc aggggaacgt cttctcatgc tccgtgatgc atgaggctct gcacaaccac    720
tacacgcaga agagcctctc cctgtctccg ggtcagaggc acaacaattc ttccctgaat    780
acaggaactc agatggcagg tcattctccg aattctcagg tccagctggt gcaatctggg    840
gctgaggtga agaagcctgg gtcctcggtg aaggtctcct gcaaggcttc tggaggcacc    900
ttcagcagat ctacgatgca ctgggtgcga caggcccctg gacaagggct tgagtggata    960
ggatacatta atcctagcag tgcttatact aattacaatc agaaattcaa ggacagagtc    1020
acgattaccg cggacaaatc cacgagcaca gcctacatgg agctgagcag cctgagatct    1080
gaggacacgg ccgtgtatta ctgtgcgaga ccccaagtcc actatgatta caacgggttt    1140
ccttactggg gccaaggaac cctggtcacc gtctcctcag gtggaggcgg ttcaggcgga    1200
ggtggatccg gcggtggcgg atcgggtggc ggcggatctg acatccagat gacccagtct    1260
ccttccaccc tgtctgcatc tgtaggagac agagtcacca tcacttgcag tgccagctca    1320
agtgtaagtt acatgaactg gtatcagcag aaaccaggga agcccctaa gagatggatt    1380
tatgactcat ccaaactggc ttctggggtc ccatcaaggt tcagcggcag tggatctggg    1440
acagaattca ctctcaccat cagcagcctg cagcctgatg attttgcaac ttattactgc    1500
caacagtgga gtcgtaaccc acccactttt ggcggaggga ccaaggtgga gatcaaacgg    1560
tcctccagct aa                                                        1572
(SEQ ID NO: 47)
Signal sequence is residue 1 to 60
```

Mature protein sequence of TSC371:

```
EPKSSDKTHT CPPCPAPEAA GAPSVFLFPP KPKDTLMISR TPEVTCVVVD VSHEDPEVKF      60
NWYVDGVEVH NAKTKPREEQ YNSTYRVVSV LTVLHQDWLN GKAYACAVSN KALPAPIEKT     120
ISKAKGQPRE PQVYTLPPSR DELTKNQVSL TCLVKGFYPS DIAVEWESNG QPENNYKTTP     180
PVLDSDGSFF LYSKLTVDKS RWQQGNVFSC SVMHEALHNH YTQKSLSLSP GQRHNNSSLN     240
TGTQMAGHSP NSQVQLVQSG AEVKKPGSSV KVSCKASGGT FSRSTMHWVR QAPGQGLEWI     300
GYINPSSAYT NYNQKFKDRV TITADKSTST AYMELSSLRS EDTAVYYCAR PQVHYDYNGF     360
PYWGQGTLVT VSSGGGGSGG GGSGGGGSGG GGSDIQMTQS PSTLSASVGD RVTITCSASS     420
SVSYMNWYQQ KPGKAPKRWI YDSSKLASGV PSRFSGSGSG TEFTLTISSL QPDDFATYYC     480
QQWSRNPPTF GGGTKVEIKR SSS                                             503
(SEQ ID NO: 48)
```

DNA sequence of TSC372:

```
atggaagcac cagcgcagct tctcttcctc ctgctactct ggctcccaga taccaccggt      60
gagcccaaat cttctgacaa aactcacaca tgcccaccgt gcccagcacc tgaagccgcg     120
ggtgcaccgt cagtcttcct cttcccccca aacccaagg acaccctcat gatctcccgg      180
accccctgagg tcacatgcgt ggtggtggac gtgagccacg aagaccctga ggtcaagttc    240
aactggtacg tggacggcgt ggaggtgcat aatgccaaga caaagccgcg ggaggagcag     300
tacaacagca cgtaccgtgt ggtcagcgtc ctcaccgtcc tgcaccagga ctggctgaat     360
ggcaaggcat acgcatgcgc ggtctccaac aaagcccctcc cagcccccat cgagaaaacc   420
atctccaaag ccaaagggca gccccgagaa ccacaggtgt acaccctgcc cccatcccgg    480
gatgagctga ccaagaacca ggtcagcctg acctgcctgg tcaaaggctt ctatccaagc    540
gacatcgccg tggagtggga gagcaatggg cagccggaga acaactacaa gaccacgcct    600
cccgtgctgg actccgacgg ctccttcttc ctctacagca agctcaccgt ggacaagagc    660
aggtggcagc aggggaacgt cttctcatgc tccgtgatgc atgaggctct gcacaaccac    720
tacacgcaga agagcctctc cctgtctccg ggtcagaggc acaacaattc ttccctgaat    780
acaggaactc agatggcagg tcattctccg aattctcagg tccagctggt gcaatctggg    840
gctgaggtga agaagcctgg gtcctcggtg aaggtctcct gcaaggcttc tggaggcacc    900
ttcagcagat ctacgatgca ctgggtgcga caggcccctg gacaagggct tgagtggatg    960
ggatacatta atcctagcag tgcttatact aattacaatc agaaattcaa ggacagagtc   1020
acgattaccg cggacaaatc cacgagcaca gcctacatgg agctgagcag cctgagatct   1080
gaggacacgg ccgtgtatta ctgtgcgaga ccccaagtcc actatgatta caacgggttt   1140
ccttactggg gccaaggaac cctggtcacc gtctcctcag gtggaggcgg ttcaggcgga   1200
ggtggatccg gcggtggcgg atcgggtggc ggcggatctg acatccagat gacccagtct   1260
ccttccaccc tgtctgcatc tgtaggagac agagtcacca tcacttgcag tgccagctca   1320
agtgtaagtt acatgaactg gtatcagcag aaaccaggga agcccctaa gagatggatt    1380
tatgactcat ccaaactggc ttctggggtc ccatcaaggt tcagcggcag tggatctggg   1440
acagaattca ctctcaccat cagcagcctg cagcctgatg attttgcaac ttattactgc   1500
caacagtgga gtcgtaaccc acccactttt ggcggaggga ccaaggtgga gatcaaacgg   1560
tcctccagct aa                                                        1572
(SEQ ID NO: 49)
Signal sequence is residue 1 to 60
```

TABLE 14-continued

Binding Domain and Polypeptide Sequences and Components

Mature protein sequence of TSC372:

```
EPKSSDKTHT CPPCPAPEAA GAPSVFLFPP KPKDTLMISR TPEVTCVVVD VSHEDPEVKF    60
NWYVDGVEVH NAKTKPREEQ YNSTYRVVSV LTVLHQDWLN GKAYACAVSN KALPAPIEKT   120
ISKAKGQPRE PQVYTLPPSR DELTKNQVSL TCLVKGFYPS DIAVEWESNG QPENNYKTTP   180
PVLDSDGSFF LYSKLTVDKS RWQQGNVFSC SVMHEALHNH YTQKSLSLSP GQRHNNSSLN   240
TGTQMAGHSP NSQVQLVQSG AEVKKPGSSV KVSCKASGGT FSRSTMHWVR QAPGQGLEWM   300
GYINPSSAYT NYNQKFKDRV TITADKSTST AYMELSSLRS EDTAVYYCAR PQVHYDYNGF   360
PYWGQGTLVT VSSGGGGSGG GGSGGGGSGG GGSDIQMTQS PSTLSASVGD RVTMTCSASS   420
SVSYMNWYQQ KPGKAPKRWI YDSSKLASGV PSRFSGSGSG TEFTLTISSL QPDDFATYYC   480
QQWSRNPPTF GGGTKVEIKR SSS                                          503
(SEQ ID NO: 50)
```

DNA sequence of TSC390:

```
atggaagcac cagcgcagct tatcttcctc ctgctactct ggctcccaga taccaccggt    60
gagcccaaat cttctgacaa aactcacaca tgcccaccgt gcccagcacc tgaagccgcg   120
ggtgcaccgt cagtcttcct cttccccca aacccaagg acaccctcat gatctcccgg    180
acccctgagg tcacatgcgt ggtggtggac gtgagccacg aagaccctga ggtcaagttc   240
aactggtacg tggacggcgt ggaggtgcat aatgccaaga caaagccgcg ggaggagcag   300
tacaacagca cgtaccgtgt ggtcagcgtc ctcaccgtcc tgcaccagga ctggctgaat   360
ggcaaggcat acgcatgcgc ggtctccaac aaagccctcc cagcccccat cgagaaaacc   420
atctccaaag ccaaagggca gccccgagaa ccacaggtgt acaccctgcc cccatcccgg   480
gatgagctga ccaagaacca ggtcagcctg acctgcctgg tcaaaggctt ctatccaagc   540
gacatcgccg tggagtggga gagcaatggg cagccggaga acaactacaa gaccacgcct   600
cccgtgctga actccgacgg ctccttcttc ctctacagca agctcaccgt ggacaagagc   660
aggtggcagc aggggaacgt cttctcatgc tccgtgatgc atgaggctct gcacaaccac   720
tacacgcaga gagcctctc cctgtctccg ggtcagaggc acaacaattc ttccctgaat   780
acaggaactc agatggcagg tcattctccg aattctcagg tccagctggt gcaatctggg   840
cctgaggtga agaagcctgg gtcctcggtg aaggtctcct gcaaggcttc tggatatacc   900
ttcagcagat ctacgatgca ctgggtgcga caggcccctg gacaagggct tgagtggatg   960
ggatacatta tcctagcag tgcttatact aattacaatc agaaattcaa ggacagagtc  1020
acgattaccg cggacaaatc cacgagcaca gcctacatgg agctgagcag cctgagatct  1080
gaggacacgg ccgtgtatta ctgtgcgaga ccccaagtcc actatgatta caacgggttt  1140
ccttactggg gccaaggaac cctggtcacc gtctcctcag gtggaggcgg ttcaggcgga  1200
ggtggatccg gcggtggcgg atcgggtggc ggcggatctg acatccagat gacccagtct  1260
ccttccaccc tgtctctgtc tgtaggagac agagtcacca tcacttgcag tgccagctca  1320
agtgtaagtt acatgaactg gtatcagcag aaaccaggga agcccctaa gagatggatt  1380
tatgactcat ccaaactggc ttctgggtc ccatcaaggt tcagcggcag tggatctggg  1440
acagagttca ctctcaccat cagcagcctg cagcctgatg attttgcaac ttattactgc  1500
caacagtgga gtcgtaaccc acccactttc ggcggaggga ccaaggtgga gatcaaacgg  1560
tcctccagct aa                                                     1572
(SEQ ID NO: 51)
Signal sequence is residue 1 to 60
```

Mature protein sequence of TSC390:

```
EPKSSDKTHT CPPCPAPEAA GAPSVFLFPP KPKDTLMISR TPEVTCVVVD VSHEDPEVKF    60
NWYVDGVEVH NAKTKPREEQ YNSTYRVVSV LTVLHQDWLN GKAYACAVSN KALPAPIEKT   120
ISKARGQPRE PQVYTLPPSR DELTKNQVSL TCLVKGFYPS DIAVEWESNG QPENNYKTTP   180
PVLDSDGSFF LYSKLTVDKS RWQQGNVFSC SVMHEALHNH YTQKSLSLSP GQRHNNSSLN   240
TGTQMAGHSP NSQVQLVQSG PEVKKPGSSV KVSCKASGGT FSRSTMHWVR QAPGQGLEWM   300
GYINPSSAYT NYNQKFKDRV TITADKSTST AYMELSSLRS EDTAVYYCAR PQVHYDYNGF   360
PYWGQGTLVT VSSGGGGSGG GGSGGGGSGG GGSDIQMTQS PSTLSASVGD RVTITCSASS   420
SVSYMNWYQQ KPGKAPKRWI YDSSKLASGV PSRFSGSGSG TEFTLTISSL QPDDFATYYC   480
QQWSRNPPTF GGGTKVEIKR SSS                                          503
(SEQ ID NO: 52)
```

DNA sequence of TSC391:

```
atggaagcac cagcgcagct tctcttcctc ctgctactct ggctcccaga taccaccggt    60
gagcccaaat cttctgacaa aactcacaca tgcccaccgt gcccagcacc tgaagccgcg   120
ggtgcaccgt cagtcttcct cttccccca aacccaagg acaccctcat gatctcccgg    180
acccctgagg tcacatgcgt ggtggtggac gtgagccacg aagaccctga ggtcaagttc   240
aactggtacg tggacggcgt ggaggtgcat aatgccaaga caaagccgcg ggaggagcag   300
tacaacagca cgtaccgtgt ggtcagcgtc ctcaccgtcc tgcaccagga ctggctgaat   360
ggcaaggcat acgcatgcgc ggtctccaac aaagccctcc cagcccccat cgagaaaacc   420
atctccaaag ccaaagggca gccccgagaa ccacaggtgt acaccctgcc cccatcccgg   480
gatgagctga ccaagaacca ggtcagcctg acctgcctgg tcaaaggctt ctatccaagc   540
gacatcgccg tggagtggga gagcaatggg cagccggaga acaactacaa gaccacgcct   600
cccgtgctga actccgacgg ctccttcttc ctctacagca agctcaccgt ggacaagagc   660
aggtggcagc aggggaacgt cttctcatgc tccgtgatgc atgaggctct gcacaaccac   720
tacacgcaga gagcctctc cctgtctccg ggtcagaggc acaacaattc ttccctgaat   780
acaggaactc agatggcagg tcattctccg aattctcagg tccagctggt gcaatctggg   840
cctgaggtga agaagcctgg gtcctcggtg aaggtctcct gcaaggcttc tggatatacc   900
ttcaggagat ctacgatgca ctgggtgcga caggcccctg gacaagggct tgagtggata  960
ggatacatta tcctagcag tgcttatact aattacaatc agaaattcaa ggacagagtc  1020
acgattaccg cggacaaatc cacgagcaca gcctacatgg agctgagcag cctgagatct  1080
```

TABLE 14-continued

Binding Domain and Polypeptide Sequences and Components

```
gaggacacgg ccgtgtatta ctgtgcgaga ccccaagtcc actatgatta caacgggttt      1140
ccttactggg gccaaggaac cctggtcacc gtctcctcag gtggaggcgg ttcaggcgga      1200
ggtggatccg gcggtggcgg atcgggtggc ggcggatctg acatccagat gacccagtct      1260
ccttccaccc tgtctgcatc tgtaggagac agagtcacca tcacttgcag tgccagctca      1320
agtgtaagtt acatgaactg gtatcagcag aaaccaggga agcccctaa gagatggatt       1380
tatgactcat ccaaactggc ttctggggtc ccatcaaggt tcagcggcag tggatctggg      1440
acagagttca ctctcaccat cagcagcctg cagcctgatg attttgcaac ttattactgc      1500
caacagtgga gtcgtaaccc acccactttc ggcggaggga ccaaggtgga gatcaaacgg      1560
tcctccagct aa                                                          1572
(SEQ ID NO: 53)
Signal sequence is residue 1 to 60
```

Mature protein sequence of TSC391:

```
EPKSSDKTHT CPPCPAPEAA GAPSVFLFPP KPKDTLMISR TPEVTCVVVD VSHEDPEVKF       60
NWYVDGVEVH NAKTKPREEQ YNSTYRVVSV LTVLHQDWLN GKAYACAVSN KALPAPIEKT      120
ISKAKGQPRE PQVYTLPPSR DELTKNQVSL TCLVKGFYPS DIAVEWESNG QPENNYKTTP      180
PVLDSDGSFF LYSKLTVDKS RWQQGNVFSC SVMHEALHNH YTQKSLSLSP GQRHNNSSLN      240
TGTQMAGHSP NSQVQLVQSG PEVKKPGSSV KVSCKASGYT FSRSTMHWVR APGQGLEWI       300
GYINPSSAYT NYNQKFKDRV TITADKSTST AYMELSSLRS EDTAVYYCAR PQVHYDYNGF      360
PYWGQGTLVT VSSGGGGSGG GGSGGGGSGG GGSDIQMTQS PSTLSASVGD RVTITCSASS      420
SVSYMNWYQQ KPGKAPKRWI YDSSKLASGV PSRFSGSGSG TEFTLTISSL QPDDFATYYC      480
QQWSRNPPTF GGGTKVEIKR SSS                                              503
(SEQ ID NO: 54)
```

DNA sequence of TSC392:

```
atggaagcac cagcgcagct tctcttcctc ctgctactct ggctcccaga taccaccggt       60
gagcccaaat cttctgacaa aactcacaca tgcccaccgt gcccagcacc tgaagccgcg      120
ggtgcaccgt cagtcttcct cttccccca aaacccaagg acaccctcat gatctcccgg       180
accccctgagg tcacatgcgt ggtggtggac gtgagccacg aagaccctga ggtcaagttc     240
aactggtacg tggacggcgt ggaggtgcat aatgccaaga caaagccgcg ggaggagcag      300
tacaacagca cgtaccgtgt ggtcagcgtc ctcaccgtcc tgcaccagga ctggctgaat      360
ggcaaggcat acgcatgcgc ggtctccaac aaagcccctcc cagcccccat cgagaaaacc     420
atctccaaag ccaaagggca gccccgagaa ccacaggtgt acaccctgcc cccatcccgg      480
gatgagctga ccaagaacca ggtcagcctg acctgcctgg tcaaaggctt ctatcccagc      540
gacatcgccg tggagtggga gagcaatggg cagccggaga caactacaa gaccacgcct       600
cccgtgctgg actccgacgg ctccttcttc ctctacagca agctcaccgt ggacaagagc      660
aggtggcagc aggggaacgt cttctcatgc tccgtgatgc atgaggctct gcacaaccac      720
tacacgcaga gagcctctc cctgtctccg ggtcagaggc acaacaattc ttccctgaat       780
acaggaactc agatggcagg tcattctccg aattctcagg tccagctggt gcaatctggg      840
cctgaggtga agaagcctgg gtcctcggtg aaggtctcct gcaaggcttc tggatatacc      900
ttcagcagat ctacgatgca ctgggtgcga caggcccctg gacaagggct tgagtggatg      960
ggatacatta tgcttatact aattacaatc agaaattcaa agcttaagcttaagcaaagctt     1020
...
```

(abbreviated — see DNA sequence)

```
acgattaccg cggacaaatc cacgagcaca gcctacatgg agctgagcag cctgagatct      1080
gaggacacgg ccgtgtatta ctgtgcgaga ccccaagtcc actatgatta caacgggttt     1140
ccttactggg gccaaggaac cctggtcacc gtctcctcag gtggaggcgg ttcaggcgga     1200
ggtggatccg gcggtggcgg atcgggtggc ggcggatctg acatccagat gacccagtct     1260
ccttccaccc tgtctgcatc tgtaggagac agagtcacca tgacttgcag tgccagctca     1320
agtgtaagtt acatgaactg gtatcagcag aaaccaggga agcccctaa gagatggatt      1380
tatgactcat ccaaactggc ttctggggtc ccatcaaggt tcagcggcag tggatctggg     1440
acagagttca ctctcaccat cagcagcctg cagcctgatg attttgcaac ttattactgc     1500
caacagtgga gtcgtaaccc acccactttc ggcggaggga ccaaggtgga gatcaaacgg     1560
tcctccagct aa                                                         1572
(SEQ ID NO: 55)
Signal sequence is residue 1 to 60
```

Mature protein sequence of TSC392:

```
EPKSSDKTHT CPPCPAPEAA GAPSVFLFPP KPKDTLMISR TPEVTCVVVD VSHEDPEVKF       60
NWYVDGVEVH NAKTKPREEQ YNSTYRVVSV LTVLHQDWLN GKAYACAVSN KALPAPIEKT      120
ISKAKGQPRE PQVYTLPPSR DELTKNQVSL TCLVKGFYPS DIAVEWESNG QPENNYKTTP      180
PVLDSDGSFF LYSKLTVDKS RWQQGNVFSC SVMHEALHNH YTQKSLSLSP GQRHNNSSLN      240
TGTQMAGHSP NSQVQLVQSG PEVKKPGSSV KVSCKASGYT FSRSTMHWVR QAPGQGLEWM      300
GYINPSSAYT NYNQKFKDRV TITADKSTST AYMELSSLRS EDTAVYYCAR PQVHYDYNGF      360
PYWGQGTLVT VSSGGGGSGG GGSGGGGSGG GGSDIQMTQS PSTLSASVGD RVTMTCSASS      420
SVSYMNWYQQ KPGKAPKRWI YDSSKLASGV PSRFSGSGSG TEFTLTISSL QPDDFATYYC      480
QQWSRNPPTF GGGTKVEIKR SSS                                              503
(SEQ ID NO: 56)
```

DNA sequence of TSC393:

```
atggaagcac cagcgcagct tctcttcctc ctgctactct ggctcccaga taccaccggt       60
gagcccaaat cttctgacaa aactcacaca tgcccaccgt gcccagcacc tgaagccgcg      120
ggtgcaccgt cagtcttcct cttccccca aaacccaagg acaccctcat gatctcccgg       180
accccctgagg tcacatgcgt ggtggtggac gtgagccacg aagaccctga ggtcaagttc     240
aactggtacg tggacggcgt ggaggtgcat aatgccaaga caaagccgcg ggaggagcag      300
tacaacagca cgtaccgtgt ggtcagcgtc ctcaccgtcc tgcaccagga ctggctgaat      360
```

TABLE 14-continued

Binding Domain and Polypeptide Sequences and Components

```
ggcaaggcat acgcatgcgc ggtctccaac aaagcccctcc cagcccccat cgagaaaacc      420
atctccaaag ccaaagggca gccccgagaa ccacaggtgt acaccctgcc cccatcccgg      480
gatgagctga ccaagaacca ggtcagcctg acctgcctgg tcaaaggctt ctatccaagc      540
gacatcgccg tggagtggga gagcaatggg cagccggaga caactacaa gaccacgcct       600
cccgtgctgg actccgacgg ctccttcttc tctacagca agctcaccgt ggacaagagc      660
aggtggcagc aggggaacgt cttctcatgc tccgtgatgc atgaggctct gcacaaccac      720
tacacgcaga agagcctctc cctgtctccg ggtcagaggc acaacaattc ttccctgaat      780
acaggaactc agatggcagg tcattctccg aattctcagg tccagctggt gcaatctggg      840
gctgaggtga agaagcctgg gtcctcggtg aaggtctcct gcaaggcttc tggatatacc      900
ttcagcagat ctacgatgca ctgggtgcga caggcccctg gacaagggct tgagtggata      960
ggatacatta atcctagcag tgcttatact aattacaatc agaaattcaa ggacagagtc     1020
acgattaccg cggacaaatc cacgagcaca gcctacatgg agctgagcag cctgagatct     1080
gaggacacgg ccgtgtatta ctgtgcgaga ccccaagtcc actatgatta acgggttt       1140
ccttactggg gccaaggaac cctggtcacc gtctcctcag gtggaggcgg ttcaggcgga     1200
ggtggatccg acggtggcgg atcgggtggc ggcggatctg acatccagat gacccagtct     1260
ccttccaccc tgtctgcatc tgtaggagac agagtcacca tgacttgcag tgccagctca     1320
agtgtaagtt acatgaactg gtatcagcag aaaccaggga agcccctaa gagatggatt      1380
tatgactcat ccaaactggc ttctggggtc ccatcaaggt tcagcggcag tggatctggg     1440
acagagttca ctctcaccat cagcagcctg cagcctgatg attttgcaac ttattactgc     1500
caacagtgga gtcgtaaccc acccactttc ggcggaggga ccaaggtgga gatcaaacgg     1560
tcctccagct aa                                                         1572
(SEQ ID NO: 57)
```
Signal sequence is residue 1 to 60

Mature protein sequence of TSC393:

```
EPKSSDKTHT CPPCPAPEAA GAPSVFLFPP KPKDTLMISR TPEVTCVVVD VSHEDPEVKF       60
NWYVDGVEVH NAKTKPREEQ YNSTYRVVSV LTVLHQDWLN GKAYACAVSN KALPAPIEKT      120
ISKAKGQPRE PQVYTLPPSR DELTKNQVSL TCLVKGFYPS DIAVEWESNG QPENNYKTTP      180
PVLDSDGSFF LYSKLTVDKS RWQQGNVFSC SVMHEALHNH YTQKSLSLSP GQRHNNSSLN      240
TGTQMAGHSP NSQVQLVQSG AEVKKPGSSV KVSCKASGYT FSRSTMHWVR QAPGQGLEWI      300
GYINPSSAYT NYNQKFKDRV TITADKSTST AYMELSSLRS EDTAVYYCAR PQVHYDYNGF      360
PYWGQGTLVT VSSGGGGSGG GGSGGGGSGG GGSDIQMTQS PSTLSASVGD RVTMTCSASS      420
SVSYMNWYQQ KPGKAPKRWI YDSSKLASGV PSRFSGSGSG TEFTLTISSL QPDDFATYYC      480
QQWSRNPPTF GGGTKVEIKR SSS                                             503
(SEQ ID NO: 58)
```

DNA sequence of TSC394:

```
atggaagcac cagcgcagct tctcttcctc ctgctactct ggctcccaga taccaccggt       60
gagcccaaat cttctgacaa aactcacaca tgcccaccgt gcccagcacc tgaagccgcg      120
ggtgcaccgt cagtcttcct cttccccca aaacccaagg acaccctcat gatctcccgg      180
accccctgagg tcacatgcgt ggtggtggac gtgagccacg aagaccctga ggtcaagttc      240
aactggtacg tggacggcgt ggaggtgcat aatgccaaga caaagccgcg ggaggagcag      300
tacaacagca cgtaccgtgt ggtcagcgtc ctcaccgtcc tgcaccagga ctggctgaat      360
ggcaaggcat acgcatgcgc ggtctccaac aaagcccctcc cagcccccat cgagaaaacc     420
atctccaaag ccaaagggca gccccgagaa ccacaggtgt acaccctgcc cccatcccgg      480
gatgagctga ccaagaacca ggtcagcctg acctgcctgg tcaaaggctt ctatccaagc      540
gacatcgccg tggagtggga gagcaatggg cagccggaga caactacaa gaccacgcct       600
cccgtgctgg actccgacgg ctccttcttc tctacagca agctcaccgt ggacaagagc      660
aggtggcagc aggggaacgt cttctcatgc tccgtgatgc atgaggctct gcacaaccac      720
tacacgcaga agagcctctc cctgtctccg ggtcagaggc acaacaattc ttccctgaat      780
acaggaactc agatggcagg tcattctccg aattctcagg tccagctggt gcaatctggg      840
cctgaggtga agaagcctgg gtcctcggtg aaggtctcct gcaaggcttc tggatatacc      900
ttcagcagat ctacgatgca ctgggtgcga caggcccctg gacaagggct tgagtggata      960
ggatacatta atcctagcag tgcttatact aattacaatc agaaattcaa ggacagagtc     1020
acgattaccg cggacaaatc cacgagcaca gcctacatgg agctgagcag cctgagatct     1080
gaggacacgg ccgtgtatta ctgtgcgaga ccccaagtcc actatgatta acgggttt       1140
ccttactggg gccaaggaac cctggtcacc gtctcctcag gtggaggcgg ttcaggcgga     1200
ggtggatccg gcggtggcgg atcgggtggc ggcggatctg acatccagat gacccagtct     1260
ccttccaccc tgtctgcatc tgtaggagac agagtcacca tgacttgcag tgccagctca     1320
agtgtaagtt acatgaactg gtatcagcag aaaccaggga agcccctaa gagatggatt      1380
tatgactcat ccaaactggc ttctggggtc ccatcaaggt tcagcggcag tggatctggg     1440
acagagttca ctctcaccat cagcagcctg cagcctgatg attttgcaac ttattactgc     1500
caacagtgga gtcgtaaccc acccactttc ggcggaggga ccaaggtgga gatcaaacgg     1560
tcctccagct aa                                                         1572
(SEQ ID NO: 59)
```
Signal sequence is residue 1 to 60

Mature protein sequence of TSC394:

```
EPKSSDKTHT CPPCPAPEAA GAPSVFLFPP KPKDTLMISR TPEVTCVVVD VSHEDPEVKF       60
NWYVDGVEVH NAKTKPREEQ YNSTYRVVSV LTVLHQDWLN GKAYACAVSN KALPAPIEKT      120
ISKAKGQPRE PQVYTLPPSR DELTKNQVSL TCLVKGFYPS DIAVEWESNG QPENNYKTTP      180
PVLDSDGSFF LYSKLTVDKS RWQQGNVFSC SVMHEALHNH YTQKSLSLSP GQRHNNSSLN      240
TGTQMAGHSP PEVKKPGSSV KVSCKASGYT FSRSTMHWVR QAPGQGLEWI                 300
GYINPSSAYT NYNQKFKDRV TITADKSTST AYMELSSLRS EDTAVYYCAR PQVHYDYNGF      360
PYWGQGTLVT VSSGGGGSGG GGSGGGGSGG GGSDIQMTQS PSTLSASVGD RVTMTCSASS      420
```

TABLE 14-continued

Binding Domain and Polypeptide Sequences and Components

| | |
|---|---|
| SVSYMNWYQQ KPGKAPKRWI YDSSKLASGV PSRFSGSGSG TEFTLTISSL QPDDFATYYC | 480 |
| QQWSRNPPTF GGGTKVEIKR SSS | 503 |
| (SEQ ID NO: 60) | |

DNA sequence of TSC408:

| | |
|---|---|
| atggaagcac cagcgcagct tctcttcctc ctgctactct ggctcccaga taccaccggt | 60 |
| gatatccaga tgacccagtc tccatccgcc atgtctgcat ctgtaggaga cagagtcacc | 120 |
| atcacttgcc gggcgagtaa gagcattagc aaatatttag cctggtttca gcagaaacca | 180 |
| gggaaagttc ctaagctccg catccattct ggatctactt tgcaatcagg gtcccatct | 240 |
| cggttcagtg gcagtggatc tgggacagaa tttactctca ccatcagcag cctgcagcct | 300 |
| gaagattttg caacttatta ctgtcaacag catattgaat acccgtggac gttcggccaa | 360 |
| gggaccaagg tggaaatcaa acgaggtggc ggagggtctg ggggtggcgg atccggaggt | 420 |
| ggtggctctc aggtccagct ggtacagtct ggggctgagg tgaagaagcc tggggcttca | 480 |
| gtgaaggtct cctgcaaggc ttctggatac acattcactg actactacat gcactgggtg | 540 |
| cgacaggccc ctggacaagg gcttgagtgg atgggatatt ttaatcctta taatgattat | 600 |
| actagatacg cacagaagtt ccagggcaga gtcaccatga ccagggacac gtctatcagc | 660 |
| acagcctaca tggagctgag cagcctgaga tctgacgaca cggccgtgta ttactgtgca | 720 |
| agatcggatg gttactacga tgctatggac tactgggtc aaggaaccac agtcaccgtc | 780 |
| tcctcgagtg agcccaaatc ttctgacaaa actcacacat gcccaccgtg cccagcacct | 840 |
| gaagccgcgg gtgcaccgtc agtcttcctc ttccccccaa aacccaagga caccctcatg | 900 |
| atctcccgga cccctgaggt cacatgcgtg gtggtggacg tgagccacga agaccctgag | 960 |
| gtcaagttca actggtacgt ggacggcgtg gaggtgcata atgccaagac aaagccgcgg | 1020 |
| gaggagcagt acaacagcac gtaccgtgtg gtcagcgtcc tcaccgtcct gcaccaggac | 1080 |
| tggctgaatg gcaaggcgta cgcgtgcgcg gtctccaaca aagcccctcc cagccccatc | 1140 |
| gagaaaacca tctccaaagc caaagggcag ccccgagaac cacaggtgta caccctgccc | 1200 |
| ccatcccggg atgagctgac caagaaccag gtcagcctga cctgcctggt caaaggcttc | 1260 |
| tatccaagcg acatcgccgt ggagtgggag agcaatgggc agccggagaa caactacaag | 1320 |
| accacgcctc ccgtgctgga ctccgacggc tccttcttcc tctacagcaa gctcaccgtg | 1380 |
| gacaagagca ggtggcagca ggggaacgtc ttctcatgct ccgtgatgca tgaggctctg | 1440 |
| cacaaccact acacgcagaa gagcctctcc ctgtctccgg gtcagaggca acaattct | 1500 |
| tccctgaata caggaactca gatgcaggct cattctccga attctcaggt ccagctggtg | 1560 |
| caatctgggc ctgaggtgaa gaagcctggg tcctcggtga aggtctcctg caaggcttct | 1620 |
| ggatatacct tcagcagatc tacgatgcac tgggtgcgac aggcccctgg acagggctt | 1680 |
| gagtggatag gatacattaa tcctagcagt gcttatacta attacaatca gaaattcaag | 1740 |
| gacagagtca cgattaccgc ggacaaatcc acgagcacag cctacatgga gctgagcagc | 1800 |
| ctgagatctg aggacacggc cgtgtattac tgtgcgagac cccaagtcca ctatgattac | 1860 |
| aacgggtttc cttactgggg ccaaggaacc ctggtcaccg tctcctcagg tggaggcggt | 1920 |
| tcaggcggag gtggatccgg cggtggcgga tcgggtggcg gcggatcga catccagatg | 1980 |
| acccagtctc cttccaccct gtctgcatct gtaggagaca gagtcaccat cacttgcagt | 2040 |
| gccagctcaa gtgtaagtta catgaactgg tatcagcaga aaccaggaa agcccctaag | 2100 |
| agatggattt atgactcatc caactggct tctggggtcc catccaggtt cagcggcagt | 2160 |
| ggatctggga cagagttcac tctcaccatc agcagcctgc agcctgatga ttttgcaact | 2220 |
| tactactgcc aacagtggag tcgtaaccca cccacttctcg gcggagggac caaggtggag | 2280 |
| atcaaacggt cctccagcta a | 2301 |
| (SEQ ID NO: 61) | |
| Signal sequence is residue 1 to 60 | |

Mature protein sequence of TSC408:

| | |
|---|---|
| DIQMTQSPSA MSASVGDRVT ITCRASKSIS KYLAWFQQKP GKVPKLRIHS GSTLQSGVPS | 60 |
| RFSGSGSGTE FTLTISSLQP EDFATYYCQQ HIEYPWTFGQ GTKVEIKRGG GGSGGGGSGG | 120 |
| GGSQVQLVQS GAEVKKTGAS VKVSCKAEGY TFTDYYMHWV RQAPGQGLEW MGYFNPYNDY | 180 |
| TRYAQKFQGR VTMTRDTSIS TAYMELSSLR SDDTAVYYCA RSDGYYDAMD YWGQGTTVTV | 240 |
| SSSEPKSSDK THTCPPCPAP EAAGAPSVFL FPPKPKDTLM ISRTPEVTCV VVDVSHEDPE | 300 |
| VKFNWYVDGV EVHNAKTKPR EEQYNSTYRV VSVLTVLHQD WLNGKAYACA VSNKALPAPI | 360 |
| EKTISKAKGQ PREPQVYTLP PSRDELTKNQ VSLTCLVKGF YPSDIAVEWE SNGQPENNYK | 420 |
| TTPPVLDSDG SFFLYSKLTV DKSRWQQGNV FSCSVMHEAL HNHYTQKSLS LSPGQRHNNS | 480 |
| SLNTGTQMAG HSPNSQVQLV QSGPEVKKPG SSVKVSCKAS GYTFSRSTMH WVRQAPGQGL | 540 |
| EWIGYINPSS AYTNYNQKFK DRVTITADKS TSTAYMELSS LRSEDTAVYY CARPQVHYDY | 600 |
| NGFPYWGQGT LVTVSSGGGG SGGGGSGGGG SGGGGSDIQM TQSPSTLSAS VGDRVTITCS | 660 |
| ASSSVSYMNW YQQKPGKAPK RWIYDSSKLA SGVPSRFSGS GSGTEFTLTI SSLQPDDFAT | 720 |
| YYCQQWSRNP PTFGGGTKVE IKRSSS | 746 |
| (SEQ ID NO: 62) | |

DNA sequence of TSC409:

| | |
|---|---|
| atggaagcac cagcgcagct tctcttcctc ctgctactct ggctcccaga taccaccggt | 60 |
| gatatccaga tgacccagtc tccatccgcc atgtctgcat ctgtaggaga cagagtcacc | 120 |
| atcacttgcc gggcgagtaa gagcattagc aaatatttag cctggtttca gcagaaacca | 180 |
| gggaaagttc ctaagctccg catccattct ggatctactt tgcaatcagg gtcccatct | 240 |
| cggttcagtg gcagtggatc tgggacagaa tttactctca ccatcagcag cctgcagcct | 300 |
| gaagattttg caacttatta ctgtcaacag catattgaat acccgtggac gttcggccaa | 360 |
| gggaccaagg tggaaatcaa acgaggtggc ggagggtctg ggggtggcgg atccggaggt | 420 |
| ggtggctctc aggtccagct ggtacagtct ggggctgagg tgaagaagcc tggggcttca | 480 |
| gtgaaggtct cctgcaaggc ttctggatac acattcactg actactacat gcactgggtg | 540 |
| cgacaggccc ctggacaagg gcttgagtgg atgggatatt ttaatcctta taatgattat | 600 |
| actagatacg cacagaagtt ccagggcaga gtcaccatga ccagggacac gtctatcagc | 660 |

TABLE 14-continued

Binding Domain and Polypeptide Sequences and Components

```
acagcctaca tggagctgag cagcctgaga tctgacgaca cggccgtgta ttactgtgca      720
agatcggatg gttactacga tgctatggac tactggggtc aaggaaccac agtcaccgtc      780
tcctcgagtg agcccaaatc ttctgacaaa actcacacat gcccaccgtg cccagcacct      840
gaagccgcgg gtgcaccgtc agtcttcctc ttccccccaa aacccaagga cacccctcatg     900
atctcccgga cccctgaggt cacatgcgtg gtggtggacg tgagccacga agaccctgag      960
gtcaagttca actggtacgt ggacggcgtg gaggtgcata atgccaagac aaagccgcgg     1020
gaggagcagt acaacagcac gtaccgtgtg gtcagcgtcc tcaccgtcct gcaccaggac     1080
tggctgaatg gcaaggcgta cgcgtgcgcg gtctccaaca aagccctccc agccccatc      1140
gagaaaacca tctccaaagc caaagggcag ccccgagaac cacaggtgta caccctgccc     1200
ccatcccggg atgagctgac caagaaccag gtcagcctga cctgcctggt caaaggcttc     1260
tatccaagcg acatcgccgt ggagtgggag agcaatgggc agccggagaa caactacaag     1320
accacgcctc ccgtgctgga ctccgacggc tccttcttcc tctacagcaa gctcaccgtg     1380
gacaagagca ggtggcagca ggggaacgtc ttctcatgct ccgtgatgca tgaggctctg     1440
cacaaccact acacgcagaa gagcctctcc ctgtctccgg gtcagaggca acaattct       1500
tccctgaata caggaactca gatggcaggt cattctccga attctcaggt ccagctggtg     1560
caatctgggc ctgaggtgaa gaagcctggg tcctcggtga aggtctcctg caaggcttct     1620
ggatatacct tcagcagatc tacgatgcac tgggtgcgac aggcccctgg acaagggctt     1680
gagtggatgg gatacattaa tcctagcagt gcttatacta attacaatca gaaattcaag     1740
gacagagtca cgattaccgc ggacaaatcc acgagccaca cctacatgga gctgagcagc     1800
ctgagatctg aggacacggc cgtgtattac tgtgcgagac cccaagtcca ctatgattac     1860
aacgggtttc cttactgggg ccaaggaacc ctggtcaccg tctcctcagg tgaggcggt      1920
tcaggcggag gtggatccgg cggtggcgga tcgggtggcg gcggatctga catccagatg     1980
acccagtctc cttccaccct gtctgcatct gtaggagaca gagtcaccat gacttgcagt     2040
gccagctcaa gtgtaagtta catgaactgg tatcagcaga aaccagggaa agcccctaag     2100
agatggattt atgactcatc caaactggct tctggggtcc catcaaggtt cagcggcagt     2160
ggatctggga cagagttcac tctcaccatc agcagcctgc agcctgatga ttttgcaact     2220
tattactgcc aacagtggag tcgtaaccca cccactttcg gcggagggac caaggtggag     2280
atcaaacggt cctccagcta a                                               2301
(SEQ ID NO: 63)
Signal sequence is residue 1 to 60
```

Mature protein sequence of TSC409:

```
DIQMTQSPSA MSASVGDPVT ITCPASKSIS KYLAWFQQKP GKVPKLRIHS GSTLQSGVPS       60
RFSGSGSGTE FTLTISSLQP EDFATYYCQQ HIEYPWTFGQ GTKVEIKRGG GGSGGGGSGG      120
GGSGVQLVQS GAEVKKTGAS VKVSCKASGY TFTDYYMHWV RQAPGQGLEW MGYFNPYNDY     180
TRYAQKFQGR VTMTRDTSIS TAYMELSSLR SDDTAVYYCA RSDGYYDAMD YWGQGTTVTV      240
SSSEPKSSDK THTCPPCPAP EAAGAPSVFL FPPKPKDTLM ISRTPEVTCV VVDVSHEDPE      300
VKFNWYVDGV EVHNAKTKPR EEQYNSTYRV VSVLTVLHQD WLNGKAYACA VSNKALPAPI      360
EKTISKAKGQ PREPQVYTLP PSRDELTKNQ VSLTCLVKGF YPSDIAVEWE SNGQPENNYK      420
TTPPVLDSDG SFFLYSKLTV DKSRWQQGNV FSCSVMHEAL HNHYTQKSLS LSPGQRHNNS      480
SLNTGTQMAG HSPNSQVQLV QSGPEVKKPG SSVKVSCKAS GYTFSRSTMH WVRQAPGQGL      540
EWMGYINPSS AYTNYNQKFK DRVTITADKS TSTAYMELSS LRSEDTAVYY CARPQVHYDY      600
NGFPYWGQGT LVTVSSGGGG SGGGGSGGGG SGGGGSDIQM TQSPSTLSAS VGDRVTMTCS      660
ASSSVSYMNW YQQKPGKAPK RWIYDSSKLA SGVPSRFSGS GSGTEFTLTI SSLQPDDFAT      720
YYCQQNSRNP PTFGGGTKVE IKRSSS                                           746
(SEQ ID NO: 64)
```

DNA sequence of TSC410:

```
atggaagcac cagcgcagct tctcttcctc ctgctactct ggctcccaga taccaccggt       60
gatatccaga tgacccagtc tccatccgcc atgtctgcat ctgtaggaga cagagtcacc      120
atcacttgcc gggcgagtaa gagcattagc aaatatttag cctggtttca gcagaaacca     180
gggaaagttc ctaagctccg catccattct ggatctactt tgcaatcagg ggtcccatct      240
cggttcagtg gcagtggatc tgggacagaa tttactctca ccatcagcag cctgcagcct      300
gaagattttg caacttatta ctgtcaacag catattgaat acccgtggac gttcggccaa      360
gggaccaagg tggaaatcaa acgaggtggc ggaggttctg gggtggcgg atccggaggt      420
ggtggctctc aggtccagct ggtacagtct ggggctgagg tgaagaagcc tggggcttca     480
gtgaaggtct cctgcaaggc ttctggatac acattcactg actactacat gcactgggtg      540
cgacaggccc ctggacaagg gcttgagtgg atgggatatt ttaatcctta taatgattat      600
actagatacg cacagaagtt ccagggcaga gtcaccatga ccagggacac gtctatcagc     660
acagcctaca tggagctgag cagcctgaga tctgacgaca cggccgtgta ttactgtgca      720
agatcggatg gttactacga tgctatggac tactggggtc aaggaaccac agtcaccgtc     780
tcctcgagtg agcccaaatc ttctgacaaa actcacacat gcccaccgtg cccagcacct      840
gaagccgcgg gtgcaccgtc agtcttcctc ttccccccaa aacccaagga cacccctcatg     900
atctcccgga cccctgaggt cacatgcgtg gtggtggacg tgagccacga agaccctgag      960
gtcaagttca actggtacgt ggacggcgtg gaggtgcata atgccaagac aaagccgcgg     1020
gaggagcagt acaacagcac gtaccgtgtg gtcagcgtcc tcaccgtcct gcaccaggac     1080
tggctgaatg gcaaggcgta cgcgtgcgcg gtctccaaca aagccctccc agccccatc      1140
gagaaaacca tctccaaagc caaagggcag ccccgagaac cacaggtgta caccctgccc     1200
ccatcccggg atgagctgac caagaaccag gtcagcctga cctgcctggt caaaggcttc     1260
tatccaagcg acatcgccgt ggagtgggag agcaatgggc agccggagaa caactacaag     1320
accacgcctc ccgtgctgga ctccgacggc tccttcttcc tctacagcaa gctcaccgtg     1380
gacaagagca ggtggcagca ggggaacgtc ttctcatgct ccgtgatgca tgaggctctg     1440
cacaaccact acacgcagaa gagcctctcc ctgtctccgg gtcagaggca acaattct       1500
tccctgaata caggaactca gatggcaggt cattctccga attctcaggt ccagctggtg     1560
caatctgggc ctgaggtgaa gaagcctggg tcctcggtga aggtctcctg caaggcttct     1620
ggatatacct tcagcagatc tacgatgcac tgggtgcgac aggcccctgg acaagggctt     1680
```

TABLE 14-continued

Binding Domain and Polypeptide Sequences and Components

```
gagtggatag gatacattaa tcctagcagt gcttatacta attacaatca gaaattcaag      1740
gacagagtca cgattaccgc ggacaaatcc acgagcacag cctacatgga gctgagcagc      1800
ctgagatctg aggacacggc cgtgtattac tgtgcgagac cccaagtcca ctatgattac      1860
aacgggtttc cttactgggg ccaaggaacc ctggtcaccg tctcctcagg tggaggcggt      1920
tcaggcggag gtggatccgg cggtggcgga tcgggtggcg gcggatctga catccagatg      1980
acccagtctc cttccaccct gtctgcatct gtaggagaca gagtcaccat gacttgcagt      2040
gccagctcaa gtgtaagtta catgaactgg tatcagcaga aaccaggaa agcccctaag      2100
agatggattt atgactcatc caaactggct tctggggtcc catcaaggtt cagcggcagt      2160
ggatctggga cagagttcac tctcaccatc agcagcctgc agcctgatga ttttgcaact      2220
tattactgcc aacagtggag tcgtaaccca cccactttcg gcggagggac caaggtggag      2280
atcaaacggt cctccagcta a                                                2301
(SEQ ID NO: 65)
Signal sequence is residue 1 to 60
```

Mature protein sequence of TSC410:

```
DIQMTQSPSA MSASVGDRVT ITCRASKSIS KYLAWFQQKP GKVPKLRIHS GSTLQSGVPS       60
RFSGSGSGTE FTLTISSLQP EDFATYYCQQ HIEYPWTFGQ GTKVEIKRGG GGSGGGGSGG      120
GGSQVQLVQS GAEVKKPGAS VKVSCKASGY TFTDYYMHWV PQAPGQGLEW MGYFNPYNDY      180
TRYAQKFQGR VTMTRDTSIS TAYMELSSLR SDDTAVYYCA RSDGYYDAMD YWGQGTTVTV      240
SSSEPKSSDK THTCPPCPAP EAAGAPSVFL FPPKPKDTLM ISRTPEVTCV VVDVSHEDPE      300
VKFNWYVDGV EVHNAKTKPR EEQYNSTYRV VSVLTVLHQD WLNGKAYACA VSNKALPAPI      360
EKTISKAKGQ PREPQVYTLP PSRDELTKNQ VSLTCLVKGF YPSDIAVEWE SNGQPENNYK      420
TTPPVLDSDG SFFLYSKLTV DKSRWQQGNV FSCSVMHEAL HNHYTQKSLS LSPGQRHNNS      480
SLNTGTQMAG HSPNSQVQLV QSGAEVKKPG SSVKVSCKAS GYTFSRSTMH WVRQAPGQGL      540
EWIGYINPSS AYTNYNQKFK DRVTITADKS TSTAYMELSS LRSEDTAVYY CARPQVHYDY      600
NGFPYWGQGT LVTVSSGGGG SGGGGSGGGG SGGGGSDIQM TQSPSTLSAS VGDRVTMTCS      660
ASSSVSYMNW YQQKPGKAPK RWIYDSSKLA SGVPSRFSGS GSGTEFTLTI SSLQPDDFAT      720
YYCQQWSRNP PTFGGGTKVE IKRSSS                                           746
(SEQ ID NO: 66)
```

DNA sequence of TSC411:

```
atggaagcac cagcgcagct tctcttcctc ctgctactct ggctcccaga taccaccggt       60
gatatccaga tgacccagtc tccatccgcc atgtctgcat ctgtaggaga cagagtcacc      120
atcacttgcc gggcgagtaa gagcattagc aaatatttag cctggtttca gcagaaacca      180
gggaaagttc ctaagctccg catccattct ggatctactt tgcaatcagg ggtcccatct      240
cggttcagtg gcagtggatc tgggacagaa tttactctca ccatcagcag cctgcagcct      300
gaagattttg caacttatta ctgtcaacag catattgaat acccgtggac gttcggccaa      360
gggaccaagg tggaaatcaa acgaggtggc ggagggtctg gggtggcgg atccggaggt      420
ggtggctctc aggtccagct ggtacagtct ggggctgagg tgaagaagcc tggggcttca      480
gtgaaggtct cctgcaaggc ttctggatac acattcactg actactacat gcactgggtg      540
cgacaggccc ctggacaagg gcttgagtgg atgggatatt ttaatcctta taatgattat      600
actagatacg cacagaagtt ccagggcaga gtcaccatga ccagggacac gtctatcagc      660
acagcctaca tggagctgag cagcctgaga tctgacgaca cggccgtgta ttactgtgca      720
agatcggatg gttactacga tgctatggac tactggggtc aaggaaccac agtcaccgtc      780
tcctcgagtg agcccaaatc ttctgacaaa actcacacat gcccaccgtg cccagcacct      840
gaagccgcgg gtgcaccgtc agtcttcctc ttccccccaa aacccaagga caccctcatg      900
atctcccgga cccctgaggt cacatgcgtg gtggtggacg tgagccacga agaccctgag      960
gtcaagttca actggtacgt ggacggcgtg gaggtgcata atgccaagac aaagccgcgg     1020
gaggagcagt acaacagcac gtaccgtgtg gtcagcgtcc tcaccgtcct gcaccaggac     1080
tggctgaatg gcaaggcgta cgcgtgcgcg gtctccaaca aagcccccc agccccccatc     1140
gagaaaacca tctccaaagc caaagggcag ccccgagaaa cacaggtgta caccctgccc     1200
ccatcccggg atgagctgac caagaaccag gtcagcctga cctgcctggt caaaggcttc     1260
tatcccagcg acatcgccgt ggagtgggag agcaatgggc agccggagaa caactacaag     1320
accacgcctc ccgtgctgga ctccgacggc tccttcttcc tctacagcaa gctcaccgtg     1380
gacaagagca ggtggcagca ggggaacgtc ttctcatgct ccgtgatgca tgaggctctg     1440
cacaaccact acacgcagaa gagcctctcc ctgtctccgg gtcagaggca caacattct     1500
tccctgaata caggaactca gatggcaggt cattctcaga attctcaggt ccagctggtg     1560
caatctgggc ctgaggtgaa gaagcctggg tcctcggtga aggtctcctg caaggcttct     1620
ggatatacct tcagcagatc tacgatgcac tgggtgcgac aggcccctgg acagggcttt     1680
gagtggatag gatacattaa tcctagcagt gcttatacta attacaatca gaaattcaag     1740
gacagagtca cgattaccgc ggacaaatcc acgagcacag cctacatgga gctgagcagc     1800
ctgagatctg aggacacggc cgtgtattac tgtgcgagac cccaagtcca ctatgattac     1860
aacgggtttc cttactgggg ccaaggaacc ctggtcaccg tctcctcagg tggaggcggt     1920
tcaggcggag gtggatccgg cggtggcgga tcgggtggcg gcggatctga catccagatg     1980
acccagtctc cttccaccct gtctgcatct gtaggagaca gagtcaccat gacttgcagt     2040
gccagctcaa gtgtaagtta catgaactgg tatcagcaga aaccaggaa agcccctaag     2100
agatggattt atgactcatc caaactggct tctggggtcc catcaaggtt cagcggcagt     2160
ggatctggga cagagttcac tctcaccatc agcagcctgc agcctgatga ttttgcaact     2220
tattactgcc aacagtggag tcgtaaccca cccactttcg gcggagggac caaggtggag     2280
atcaaacggt cctccagcta a                                               2301
(SEQ ID NO: 67)
Signal sequence is residue 1 to 60
```

TABLE 14-continued

Binding Domain and Polypeptide Sequences and Components

Mature protein sequence of TSC411:

```
DIQMTQSPSA MSASVGDRVT ITCRASKSIS KYLAWFQQKP GKVPKLRIHS GSTLQSGVPS         60
RFSGSGSGTE FTLTISSLQP EDFATYYCQQ HIEYPWTFGQ GTKVEIKRGG GGSGGGGSGG        120
GGSGVQLVQS GAEVKKTGAS VKVSCKASGY TFTDYYMHWV RQAPGQGLEW MGYFNPYNDY        180
TRYAQKFQGR VTMTRDTSIS TAYMELSSLR SDDTAVYYCA RSDGYYDAMD YWGQGTTVTV        240
SSSEPKSSDK THTCPPCPAP EAAGAPSVFL FPPKPKDTLM ISRTPEVTCV VVDVSHEDPE        300
VKFNWYVDGV EVHNAKTKPR EEQYNSTYRV VSVLTVLHQD WLNGKAYACA VSNKALPAPI        360
EKTISKAKGQ PREPQVYTLP PSRDELTKNQ VSLTCLVKGF YTSDIAVEWE SNGQPENNYK        420
TTPPVLDSDG SFFLYSKLTV DKSRWQQGNV FSCSVMHEAL HNHYTQKSLS LSPGQRHNNS        480
SLNTGTQMAG HSPNSQVQLV QSGPEVKKPG SSVKVSCKAS GYTFSRSTMH WVRQAPGQGL        540
EWIGYINPSS AYTNYNQKFK DRVTITADKS TSTAYMELSS LRSEDTAVYY CARPQVHYDY        600
NGFPYWGQGT LVTVSSGGGG SGGGGSGGGG SGGGGSDIQM TQSPSTLSAS VGDRVTMTCS        660
ASSSVSYMNW YQQKPGKAPK RWIYDSSKLA SGVPSRFSGS GSGTEFTLTI SSLQPDDFAT        720
YYCQQWSRNP PTFGGGTKVE IKRSSS                                            746
(SEQ ID NO: 68)
```

DNA sequence of CAS105:

```
atggaagcac cagcgcagct tctcttcctc ctgctactct ggctcccaga taccaccggt         60
gaggtgcagc tggtgcagtc tggagcagag gtgaaaaagc ccggagagtc tctgaagatt        120
tcctgtaagg gctccggtta ctcattcact ggctacaata tgaactgggt gcgccagatg        180
cccgggaaag gcctggagtg gatgggcaat attgatcctt attatggtgg tactacctac        240
aaccggaagt tcaagggcca ggtcactatc tccgccgaca agtccatcag caccgcctac        300
ctgcaatgga gcagcctgaa ggcctcggac accgccatgt attactgtgc acgctcagtc        360
ggccctttcg actcctgggg ccaggtgacc ctggtcactg tctcctctgg gggtggaggc        420
tctggtggcg gtggctctgg cggaggtgga tccggtggcg gcgggtggc                   480
tctgaaattg tgttgacaca gtctccagcc accctgtctt tgtctccagg cgaaagagcc        540
accctctcct gccgagcaag tgaaaatgtt tacagctact tagcctggta ccaacagaaa        600
cctggccagg ctcctaggct cctcatctat tttgcaaaaa ccttagcaga aggtattcca        660
gccaggttca gtggcagtgg ctccgggaca gacttcactc tcaccatcag cagcctagag        720
cctgaagatt ttgcagttta ttactgtcaa catcattccg ataatccgtg gacattcggc        780
caagggacca aggtggaaat caatcctcg agtgagccca atcttctga caaaactcac         840
acatgcccac cgtgcccagc acctgaagcc gcgggtcacg agtcagtctt cctcttcccc        900
ccaaaaccca aggaccct catgatctcc ggaccccctg aggtcacatg cgtggtggtg         960
gacgtgagcc acgaagaccc tgaggtcaag ttcaactggt acgtggacgg cgtggaggtg       1020
cataatgcca agacaaagcc gcgggaggag cagtacaaca gcacgtaccg tgtggtcagc       1080
gtcctcaccg tcctgcacca ggactggctg aatggcaagg catacgcgtg cgcggtctcc       1140
aacaaagccc tcccagcccc catcgagaaa accatctcca aagccaaagg gcagccccga       1200
gaaccacagg tgtacaccct gccccccatcc cgggatgagc tgaccaagaa ccaggtcagc       1260
ctgacctgcc tggtcaaagg cttctatcca agcgacatcg ccgtggagtg ggagagcaat       1320
gggcagccgg agaacaacta caagaccacg cctcccgtgc tggactccga cggctccttc       1380
ttcctctaca gcaagctcac ggtggacaag agcaggtggc agcaggggaa cgtcttctca       1440
tgctccgtga tgcatgaggc tctgcacaac cactacacgc agaagagcct ctccctgtct       1500
ccgggtcaga ggcacaacaa ttcttccctg aatacaggaa ctcagatggc aggtcattct       1560
ccgaattctc aggtccagct ggtggagtct ggggcggag tggtgcagcc tgggcggtca       1620
ctgaggctgt cctgcaaggc ttctggctac accttttacta gatctacgat gcactgggta       1680
aggcaggccc ctggacaagg tctggaatgg attggataca ttaatcctag cagtgcttat       1740
actaattaca atcagaaatt caaggacagg ttcacaatca gcgcagacaa atccaagagc       1800
acagccttcc tgcagatgga cagcctgagg cccgaggaca ccggcgtcta tttctgtgca       1860
cggccccaag tccactatga ttacaacggg ttttccttact ggggccaagg gactcccgtc       1920
actgtctcta gcggtggcgg agggtctggg ggtggcggat ccggagggtg tggctctgca       1980
caagacatcc agatgaccca gtctccaagc agccgtctg caagcgtggg gacagggtc         2040
accatgacct gcagtgccag ctcaagtgta agttacatga actggtacca gcagaagccg       2100
ggcaaggccc ccaaaagatg gatttatgac tcatccaaac tggcttctgg agtccctgct       2160
cgcttcagtg gcagtgggtc tgggaccgac tataccctca caatcagcag cctgcagccc       2220
gaagatttcg ccacttatta ctgccagcag tggagtcgta acccacccac gttcggaggg       2280
gggaccaagc tacaaattac atcctccagc taa                                    2313
(SEQ ID NO: 69)
Signal sequence is residue 1 to 60
```

Mature protein sequence of CAS105:

```
EVQLVQSGAE VKKPGESLKI SCKGSGYSFT GYNMNWVRQM PGKGLEWMGN IDPYYGGTTY         60
NRKFKGQVTI SADKSISTAY LQWSSLKASD TAMYYCARSV GPFDSWGQGT LVTVSSGGGG        120
SGGGGSGGGG SGGGGSGGGG SEIVLTQSPA TLSLSPGERA TLSCRASENV YSYLAWYQQK        180
PGQAPRLLIY FAKTLAEGIP ARFSGSGSGT DFTLTISSLE PEDFAVYYCQ HHSDNPWTFG        240
QGTKVEIKSS SEPKSSDKTH TCPPCPAPEA AGAPSVFLFP PKPKDTLMIS RTPEVTCVVV        300
DVSHEDPEVK FNWYVDGVEV HNAKTKPREE QYNSTYRVVS VLTVLHQDWL NGKAYACAVS        360
NKALPAPIEK TISKAKGQPR EPQVYTLPPS RDELTKNQVS LTCLVKGFYP SDIAVEWESN        420
GQPENNYKTT PPVLDSDGSF FLYSKLTVDK SRWQQGNVFS CSVMHEALHN HYTQKELSLS        480
PGQRHNNSSL NTGTQMAGHS PNSQVQLVES GGGVVQPGRS LRLSCKASGY TFTRSTMHWV        540
RQAPGQGLEW IGYINPSSAY TNYNQKFKDR FTISADKSKS TAFLQMDSLR PEDTGVYFCA        600
RPQVHYDYNG FPYWGQGTPV TVSSGGGGSG GGGSGGGGSA QDIQMTQSPS SLSASVGDRV        660
TMTCSASSSV SYMNWYQQKP GKAPKRWIYD SSKLASGVPA RFSGSGSGTD YTLTISSLQP        720
EDFATYYCQQ WSRNPPTFGG GTKLQITSSS                                        750
(SEQ ID NO: 70)
```

TABLE 14-continued

Binding Domain and Polypeptide Sequences and Components

DNA sequence of Anti-CD37 X TSC445:

```
atggaagcac cagcgcagct tctcttcctc ctgctactct ggctcccaga taccaccggt      60
gaggtgcagc tggtgcagtc tggagcagag gtgaaaaagc ccggagagtc tctgaagatt     120
tcctgtaagg gctccggtta ctcattcact ggctacaata tgaactgggt gcgccagatg     180
cccgggaaag gcctggagtg gatgggcaat attgatcctt attatggtgg tactacctac     240
aaccggaagt tcaagggcca ggtcactatc tccgccgaca agtccatcag caccgcctac     300
ctgcaatgga gcagcctgaa ggcctcggac accgccatgt attactgtgc acgctcagtc     360
ggcccttcg actcctgggg ccagggcacc ctggtcactg tctcctctgg gggtggaggc     420
tctggtggcg gtggctctgg cggaggtgga tccggtggcg gcggatctag cggggtggc      480
tctgaaattg tgttgacaca gtctccagcc accctgtctt tgtatccagg cgaaagagcc     540
accctctcct gccgagcaag tgaaaatgtt tacagctact tagcctggta ccaacagaaa     600
cctggccagg ctcctaggct cctcatctat tttgcaaaaa ccttagcaga aggtattcca     660
gccaggttca gtggcagtgg ctccgggaca gacttcactc tcaccatcag cagcctagag     720
cctgaagatt ttgcagttta ttactgtcaa catcattccg ataatccgtg gacattcggc     780
caagggacca aggtggaaat caaatcctcg agtgagccca atcttctga caaaactcac     840
acatgcccac cgtgcccagc acctgaagcc gcgggtgcac cgtcagtctt cctcttcccc     900
ccaaaaccca aggacaccct catgatctcc cggacccctg aggtcacatg cgtggtggtg     960
gacgtgagcc acgaagaccc tgaggtcaag ttcaactggt acgtggacgg cgtggaggtg    1020
cataatgcca agacaaagcc gcgggaggag cagtacaaca gcacgtaccg tgtggtcagc    1080
gtcctcaccg tcctgcacca ggactggctg aatggcaagg catacgcgtg cgcggtctcc    1140
aacaaagccc tcccagcccc catcgagaaa accatctcca aagccaaagg gcagccccga    1200
gaaccacagg tgtacaccct gcccccatcc cgggatgagc tgaccaagaa ccaggtcagc    1260
ctgacctgcc tggtcaaagg cttctatcca agcgacatcg ccgtggagtg ggagagcaat    1320
gggcagccgg agaacaacta caagaccacg cctcccgtgc tggactccga cggctccttc    1380
ttcctctaca gcaagctcac cgtggacaag agcaggtggc agcaggggaa cgtcttctca    1440
tgctccgtga tgcatgaggc tctgcacaac cactacacgc agaagagcct ctccctgtct    1500
ccgggtcaga ggcacaacaa ttcttccctg aatacaggaa ctcagatggc aggtcattct    1560
ccgaattctc aggtccagct ggtgcaatct gggcctgagg tgaagaagcc tgggtcctcg    1620
gtgaaggtct cctgcaaggc ttctggatat accttcagca gatctacgat gcactgggtg    1680
cgacaggccc ctggacaagg gcttgagtgg ataggataca ttaatcctag cagtgcttat    1740
actaattaca atcagaaatt caaggacaga gtcacgatta ccgcggacaa atccacgagc    1800
acagcctaca tggagctgag cagcctgaga tctgaggaca cggccgtgta ttactgtgcg    1860
agaccccaag tccactatga ttacaacggg tttccttact ggggccaagg aaccctggtc    1920
accgtctcct caggtggagg cggttcaggc ggaggtggat ctggcggtgg cggatcggat    1980
ggcggcggat ctgacatcca gatgacccag tctccttcca ccctgtctgc atctgtagga    2040
gacagagtca ccatgacttg cagtgccagc tcaagtgtaa gttacatgaa ctggtatcag    2100
cagaaaccag ggaaagcccc taagagatgg atttatgact catccaaact ggcttctggg    2160
gtcccatcaa ggttcagcgg cagtggatct gggacagagt tcactctcac catcagcagc    2220
ctgcagcctg atgattttgc aacttattac tgccaacagt ggagtcgtaa cccacccact    2280
ttcggcggag ggaccaaggt ggagatcaaa cggtcctcca gctaa              2325
(SEQ ID NO: 71)
Signal sequence is residue 1 to 60
```

Mature protein sequence of Anti-CD37 X TSC445:

```
EVQLVQSGAE VKKPGESLKI SCKGSGYSFT GYNMNWVRQM PGKGLEWMGN IDPYYGGTTY       60
NRKFKGQVTI SADKSISTAY LQWSSLKASD TAMYYCARSV GPFDSWGQGT LVTVSSGGGG      120
SGGGGSGGGG SGGGGSGGGG SEIVLTQSPA TLSLSPGERA TLSCRASENV YSYLAWYQQK      180
PGQAPRLLIY FAKTLAEGIP ARFSGSGSGT DFTLTISSLE PEDFAVYYCQ HHSDNPWTFG      240
QGTKVEIKSS SEPKSSDKTH TCPPCPAPEA AGAPSVFLFP PKPKDTLMIS RTPEVTCVVV      300
DVSHEDPEVK FNWYVDGVEV HNAKTKPREE QYNSTYRVVS VLTVLHQDWL NGKAYACAVS      360
NKALPAPIEK TISKAKGQPR EPQVYTLPPS RDELTKNQVS LTCLVKGFYP SDIAVEWESN      420
GQPENNYKTT PPVLDSDGSF FLYSKLTVDK SRWQQGNVFS CSVMHEALHN HYTQKSLSLS      480
PGQRHNNSSL NTGTQMAGHS PNSQVQLVQS GPEVKKPGSS VKVSCKASGY TFSRSTMHWV      540
RQAPGQGLEW IGYINPSSAY TNYNQKFKDR VTITADKSTS TAYMELSSLR SEDTAVYYCA      600
RPQVHYDYNG FPYWGQGTLV TVSSGGGGSG GGGSGGGGSG GGGSDIQMTQ SPSTLSASVG      660
DRVTMTCSAS SSVSYMNWYQ QKPGKAPKRW IYDSSKLASG VPSRFSGSGS GTEFTLTISS      720
LQPDDFATYY CQQWSRNPPT FGGGTKVEIK RSSS                                 754
(SEQ ID NO: 72)
```

DNA sequence of Anti-CD37 X TSC452:

```
atggaagcac cagcgcagct tctcttcctc ctgctactct ggctcccaga taccaccggt      60
gaggtgcagc tggtgcagtc tggagcagag gtgaaaaagc ccggagagtc tctgaagatt     120
tcctgtaagg gctccggtta ctcattcact ggctacaata tgaactgggt gcgccagatg     180
cccgggaaag gcctggagtg gatgggcaat attgatcctt attatggtgg tactacctac     240
aaccggaagt tcaagggcca ggtcactatc tccgccgaca agtccatcag caccgcctac     300
ctgcaatgga gcagcctgaa ggcctcggac accgccatgt attactgtgc acgctcagtc     360
ggcccttcg actcctgggg ccagggcacc ctggtcactg tctcctctgg gggtggaggc     420
tctggtggcg gtggctctgg cggaggtgga tccggtggcg gcggatctag cggggtggc      480
tctgaaattg tgttgacaca gtctccagcc accctgtctt tgtatccagg cgaaagagcc     540
accctctcct gccgagcaag tgaaaatgtt tacagctact tagcctggta ccaacagaaa     600
cctggccagg ctcctaggct cctcatctat tttgcaaaaa ccttagcaga aggtattcca     660
gccaggttca gtggcagtgg ctccgggaca gacttcactc tcaccatcag cagcctagag     720
cctgaagatt ttgcagttta ttactgtcaa catcattccg ataatccgtg gacattcggc     780
caagggacca aggtggaaat caaatcctcg agtgagccca atcttctga caaaactcac     840
```

TABLE 14-continued

Binding Domain and Polypeptide Sequences and Components

```
acatgcccac cgtgcccagc acctgaagcc gcgggtgcac cgtcagtctt cctcttcccc      900
ccaaaaccca aggacaccct catgatctcc cggacccctg aggtcacatg cgtggtggtg      960
gacgtgagcc acgaagaccc tgaggtcaag ttcaactggt acgtggacgg cgtggaggtg     1020
cataatgcca agacaaagcc gcgggaggag cagtacaaca gcacgtaccg tgtggtcagc     1080
gtcctcaccg tcctgcacca ggactggctg aatggcaagg catacgcgtg cgcggtctcc     1140
aacaaagccc tcccagcccc catcgagaaa accatctcca agccaaagg gcagccccga      1200
gaaccacagg tgtacaccct gcccccatcc cgggatgagc tgaccaagaa ccaggtcagc     1260
ctgacctgcc tggtcaaagg cttctatcca agcgacatcg ccgtggagtg ggagagcaat     1320
gggcagccgg agaacaacta caagaccacg cctcccgtgc tggactccga cggctccttc     1380
ttcctctaca gcaagctcac cgtggacaag agcaggtggc agcaggggaa cgtcttctca     1440
tgctccgtga tgcatgaggc tctgcacaac cactacacgc agaagagcct ctccctgtct     1500
ccgggtcaga ggcacaacaa ttcttccctg aatacaggaa ctcagatggc aggtcattct     1560
ccgaattctc aggtccagct ggtggagtct ggggcggag tggtgcagcc tgggcggtca     1620
ctgaggctgt cctgcaaggc ttctggctac acctttacta gatctacgat gcactgggta     1680
aggcaggccc ctggacaagg tctggaatgg attgatacta ttaatcctag cagtgcttat     1740
actaattaca atcagaaatt caaggacagg ttcacaatca gcgcagacaa atccaagagc     1800
acagccttcc tgcagatgga cagcctgagg cccgaggaca ccggcgtcta tttctgtgca     1860
cggcccaag tccactatga ttacaacggg tttccttact ggggccaagg gactcccgtc     1920
actgtctcta gcggtggcgg agggtctggg ggtggcggat ccggcggtga cggatcggat     1980
ggcggcggat ctgacatcca gatgacccag tctccttcca ccctgtctgc atctgtagga     2040
gacagagtca ccatgacttg cagtgccagc tcaagtgtaa gttacatgaa ctggtatcag     2100
cagaaaccag gaaagccccc taagagatgg atttatgact catccaaact ggcttctggg     2160
gtcccatcaa ggttcagcgg cagtggatct gggacagagt tcactctcac catcagcagc     2220
ctgcagcctg atgattttgc aacttattac tgccaacagt ggagtcgtaa cccacccact     2280
ttcggcggag ggaccaaggt ggagatcaaa cggtcctcca gctaa                     2325
(SEQ ID NO: 73)
Signal sequence is residue 1 to 60

Mature protein sequence of Anti-CD37 X TSC452:

EVQLVQSGAE VKKPGESLKI SCKGSGYSFT GYNMNWVRQM PGKGLEWMGN IDPYYGGTTY       60
NRKFKGQVTI SADKSISTAY LQWSSLKASD TAMYYCARSV GPFDSWGQGT LVTVSSGGGG      120
SGGGGSGGGG SGGGGSGGGG SEIVLTQSPA TLSLSPGERA TLSCRASENV YSYLAWYQQK      180
PGQAPRLLIY FAKTLAEGIP ARFSGSGSGT DFTLTISSLE PEDFAVYYCQ HHSDNPWTFG      240
QGTKVEIKSS SEPKSSDKTH TCPPCPAPEA AGAPSVFLFP PKPKDTLMIS RTPEVTCVVV      300
DVSHEDPEVK FNWYVDGVEV HNAKTKPREE QYNSTYRVVS VLTVLHQDWL NGKAYACAVS      360
NKALPAPIEK TISKAKGQPR EPQVYTLPPS RDELTKNQVS LTCLVKGFYP SDIAVEWESN      420
GQPENNYKTT PPVLDSDGSF FLYSKLTVDK SRWQQGNVFS CSVMHEALHN HYTQKSLSLS      480
PGQRHNNSSL NTGTQMAGHS PNSQVQLVES GGGVVQPGRS LRLSCKASGY TFTRSTMHWV      540
RQAPGQGLEW IGYINPSSAY TNYNQKFKDR FTISADKSKS TAFLQMDSLR PEDTGVYFCA      600
RPQVHYDYNG FPYWGQGTPV TVSSGGGGSG GGGSGGGGSG GGGSDIQMTQ SPSTLSASVG      660
DRVTMTCSAS SSVSYMNWYQ QKPGKAPKRW IYDSSKLASG VPSRFSGSGS GTEFTLTISS      720
LQPDDFATYY CQQWSRNPPT FGGGTKVEIK RSSS                                 754
(SEQ ID NO: 74)

DNA sequence of Anti-CD37 X TSC453:

atggaagcac cagcgcagct tctcttcctc ctgctactct ggctcccaga taccaccggt       60
gaggtgcagc tggtgcagtc tggagcagag gtgaaaaagc ccggagagtc tctgaagatt      120
tcctgtaagg gctccggtta ctcattcact ggctacaata tgaactgggt gcgccagatg      180
cccgggaaag gcctggagtg gatgggcaat attgatcctt attatggtgg tactacctac      240
aaccggaagt tcaagggcca ggtcactatc tccgcgacaa agtccatcag caccgcctac      300
ctgcaatgga gcagcctgaa ggcctcggac accgccatgt attactgtgc acgcgtcagtc     360
ggcccttttcg actcctgggg ccagggcacc ctggtcactg tctcctctgg gggtggaggc     420
tctggtggcg gtggctctgg cggaggtgga tccggtggcg gcggatcggg ggggtggc        480
tctgaaattg tgttgacaca gtctccagcc accctgtctt tgtatccagg cgaaagagcc     540
accctctcct gccgagcaag tgaaaatgtt tacagctact tagcctggta ccaacagaaa     600
cctggccagg ctcctaggct cctcatctat tttgcaaaaa ccttagcaga aggtattcca     660
gccaggttca gtggcagtgg ctccgggaca gacttcactc tcaccatcag cagcctagag     720
cctgaagatt ttgcagttta ttactgtcaa catcattccg ataatccgtg gacattcggc      780
caagggacca aagttggaaat caaatcctcg agtgagccca aatcttctga caaaactcac    840
acatgcccac cgtgcccagc acctgaagcc gcgggtgcac cgtcagtctt cctcttcccc      900
ccaaaaccca aggacaccct catgatctcc cggacccctg aggtcacatg cgtggtggtg      960
gacgtgagcc acgaagaccc tgaggtcaag ttcaactggt acgtggacgg cgtggaggtg     1020
cataatgcca agacaaagcc gcgggaggag cagtacaaca gcacgtaccg tgtggtcagc     1080
gtcctcaccg tcctgcacca ggactggctg aatggcaagg catacgcgtg cgcggtctcc     1140
aacaaagccc tcccagcccc catcgagaaa accatctcca agccaaagg gcagccccga      1200
gaaccacagg tgtacaccct gcccccatcc cgggatgagc tgaccaagaa ccaggtcagc     1260
ctgacctgcc tggtcaaagg cttctatcca agcgacatcg ccgtggagtg ggagagcaat     1320
gggcagccgg agaacaacta caagaccacg cctcccgtgc tggactccga cggctccttc     1380
ttcctctaca gcaagctcac cgtggacaag agcaggtggc agcaggggaa cgtcttctca     1440
tgctccgtga tgcatgaggc tctgcacaac cactacacgc agaagagcct ctccctgtct     1500
ccgggtcaga ggcacaacaa ttcttccctg aatacaggaa ctcagatggc aggtcattct     1560
ccgaattctc aggtccagct ggtgcaatct gggcctgagg tgaagactgg tgggtcctcg     1620
gtgaaggtct cctgcaaggc ttctggatat accttcagca gatctacgat gcactgggtg     1680
cgacaggccc ctggacaagg gcttgagtgg ataggataca ttaatcctag cagtgcttat     1740
actaattaca atcagaaatt caaggacaga gtcacgatta ccgcggacaa atccacgagc     1800
acagcctaca tggagctgag cagcctgaga tatgaggaca cggccgtgta ttactgtgcg     1860
```

TABLE 14-continued

Binding Domain and Polypeptide Sequences and Components

```
agaccccaag tccactatga ttacaacggg tttccttact ggggccaagg aaccctggtc      1920
accgtctcct caggtggagg cggttcaggc ggaggtggat ccggaggtgg tggctctggt      1980
ggcggeggat ctgacatcca gatgacccag tctccaagca gcctgtctgc aagcgtgggg      2040
gacagggtca ccatgacctg cagtgccagc tcaagtgtaa gttacatgaa ctggtaccag      2100
cagaagccgg gcaaggcccc caaaagatgg atttatgact catccaaact ggcttctgga      2160
gtccctgctc gcttcagtgg cagtgggtct gggaccgact ataccctcac aatcagcagc      2220
ctgcagcccg aagatttcgc cacttattac tgccagcagt ggagtcgtaa cccacccacg      2280
ttcggagggg ggaccaagct acaaattaca tcctccagct aa                        2322
(SEQ ID NO: 75)
```

Signal sequence is residue 1 to 60
Mature protein sequence of Anti-CD37 X TSC453:

```
EVQLVQSGAE VKKPGESLKI SCKGSGYSFT GYNMNWVRQM PGKGLEWMGN IDPYYGGTTY       60
NRKFKGQVTI SADKEISTAY LQWSSLKASD TAMYYCARSV GPFDSWGQGT LVTVSSGGGG      120
SGGGGSGGGG SGGGGSGGGG SEIVLTQSPA TLSLSPGERA TLSCRASENV YSYLAWYQQK      180
PGQAPRLLIY FAKTLAEGIP ARFSGSGSGT DFTLTISSLE PEDFAVYYCQ HHSDNPWTFG      240
QGTKVEIKSS SEPKSSDKTH TCPPCPAPEA AGAPSVFLFP PKPKDTLMIS RTPEVTCVVV      300
DVSHEDPEVK FNWYVDGVEV HNAKTKPREE QYNSTYRVVS VLTVLHQDWL NGKAYACAVS      360
NKALPAPIEK TISKAKGQPR EPQMYTLPPS RDELTKNQVS LTCLVKGFYP SDIAMEWESN      420
GQPENNYKTT PPVLDSDGSF FLYSKLTVDK SRWQQGNVFS CSVMHEALHN HYTQKSLSLS      480
PGQRHNNSSL NTGTQMAGHS PNSQVQLVQS GPEVKKPGSS VKVSCKASGY TFSRSTMHWV      540
RQAPGQGLEW IGYINPSSAY TNYNQKEKDR VTITADKSTS TAYMELSSLR SEDTAVYYCA      600
RPQVHYDYNG FPYWGQGTLV TVSSGGGGSG GGGSGGGGSG GGGSDIQMTQ SPSSLSASVG      660
DRVTMTCSAS SSVSYMNWYQ QKPGKAPKRW IYDSSKLASG VPARFSGSGS GTDYTLTISS      720
LQPEDFATYY CQQWSRNPPT FGGGTKLQIT SSS                                  753
(SEQ ID NO: 76)
```

DNA sequence of Anti-CD37 X TSC454:

```
atggaagcac cagcgcagct tctcttcctc ctgctactct ggctcccaga taccaccggt       60
gaggtgcagc tggtgcagtc tggagcagag gtgaaaaagc ccggagagtc tctgaagatt      120
tcctgtaagg gctccggtta ctcattcact ggctacaata tgaactgggt gcgccagatg      180
cccgggaaag gcctggagtg gatgggcaat attgatcctt attatggtgg tactacctac      240
aaccggaagt tcaagggcca ggtcactatc tccgccgaca gtccatcag caccgcctac      300
ctgcaatgga gcagcctgaa ggcctcggac accgccactt attactgtgc acgctagtcg      360
ggcccttttcg actcctgggg ccagggcacc ctggtcactg tctcctctgg ggtggaggc      420
tctggtggcg gtggctctgg cggaggtgga tccgtggcg gcggatctgg cggggtggc      480
tctgaaattg tgttgacaca gtctccagcc accctgtctt tgtatccagg cgaaagagcc      540
accctctcct gccagcaag tgaaaatgtt tacagctact tagcctggta ccaacagaaa      600
cctggccagg ctcctaggct cctcatctat tttgcaaaaa ccttagcaga aggtattcca      660
gccaggttca gtgcagtgg ctccgggaca gacttcactc tcaccatcag cagcctagag      720
cctgaagatt ttgcagttta ttactgtcaa catcattccg ataatccgtg gacattcggc      780
caagggacca aggtggaaat caaatcctcg agtgagccas aatcttctga caaactcac      840
acatgcccac cgtgcccagc acctgaagcc gcggtgcac cgtcagtctt cctcttcccc      900
ccaaaaccca aggacaccct catgatctcc cggacccctg aggtcacatg cgtggtggtg      960
gacgtgagcc acgaagaccc tgaggtcaag ttcaactggt acgtggacgg cgtggaggtg     1020
cataatgcca agacaaagcc gcgggaggag cagtacaaca gcacgtaccg tgtggtcagc     1080
gtcctcaccg tcctgcacca ggactggctg aatggcaagg catacgcgtg cgcggtctcc     1140
aacaaagccc tcccagcccc catcgagaaa accatctcca aagccaaagg gcagccccga     1200
gaaccacagg tgtacaccct gcccccatcc cgggatgagc tgaccaagaa ccaggtcagc     1260
ctgacctgcc tggtcaaagg cttctatccc agcgacatcg ccgtggagtg ggagagcaat     1320
gggcagccgg agaacaacta caagaccacg cctcccgtgc tggactccga cggctccttc     1380
ttcctctaca gcaagctcac cgtggacaag agcaggtggc agcaggggaa cgtcttctca     1440
tgctccgtga tgcatgaggc tctgcacaac cactacacgc agaagagcct ctccctgtct     1500
ccgggtcaga ggcacaacaa ttcttccctg aatacaggaa ctcagatggc aggtcattct     1560
ccgaattctc aggtccagct ggtgcaatct gggcctgagg tgaagaagcc tgggtcctcg     1620
gtgaaggtct cctgcaaggc ttctggatat accttcagca gatctacgat ggcactgggtg    1680
cgacaggccc ctggacaagg gcttgagtgg ataggataca ttaatcctag cagtgcttat     1740
actaattaca atcagaaatt caaggacaga gtcacgatta ccgcggacaa atccacgagc     1800
acagcctaca tggagctgag cagcctgaga tctgaggaca cggccgtgta ttactgtgcg     1860
agaccccaag tccactatga ttacaacggg tttccttact ggggccaagg aaccctggtc     1920
accgtctcct caggtggagg cggttcaggc ggaggtggat ccggcggtgg cggatcgggt     1980
ggcggcggat ctgacatcca gatgacccag tctccttcca cctgtctgc atctgtagga     2040
gacagagtca ccatgacttg cagtgccagc tcaagtgtaa gttacatgaa ctggtatcag     2100
cagaaaccag gaaagccccc taagagatgg atttatgact catccaaact ggcttctggg     2160
gtcccatcaa ggttcagcgg cagtggatct gggacagatt tcactctcac catcagcagc     2220
ctgcagcctg atgatttttgc aacttattac tgccaacagt ggagtcgtaa cccacccact     2280
ttcggcggag ggaccaaggt ggagatcaaa cggtcctcca gctaa                     2325
(SEQ ID NO: 77)
```
Signal sequence is residue 1 to 60

Mature protein sequence of Anti-CD37 X TSC454:

```
EVQLVQSGAE VKKPGESLKI SCKGSGYSFT GYNMNWVRQM PGKGLEWMGN IDPYYGGTTY       60
NRKFKGQVTI SADKSISTAY LQWSSLKASD TAMYYCARSV GPFDSWGQGT LVTVSSGGGG      120
SGGGGSGGGG SGGGGSGGGG SEIVLTQSPA TLSLSPGERA TLSCRASENV YSYLAWYQQK      180
PGQAPRLLIY FAKTLAEGIP ARFSGSGSGT DFTLTISSLE PEDFAVYYCQ HHSDNPWTFG      240
```

TABLE 14-continued

Binding Domain and Polypeptide Sequences and Components

```
QGTKVEIKSS SEPKSSDKTH TCPPCPAPEA AGAPSVFLFP PKPKDTLMIS RTPEVTCVVV      300
DVSHEDPEVK FNWYVDGVEV HNAKTKPREE QYNSTYRVVS VLTVLHQDWL NGKAYACAVS      360
NKALPAPIEK TISKAKGQPR EPQMYTLPPS RDELTKNQVS LTCLMKGFYP SDIAVEWESN      420
GQPENNYKTT PPVLDSDGSF FLYSKLTVDK SRWQQGNVFS CSVMHEALHN HYTQKSLSLS      480
PGQRHNNSSL NTGTQMAGHS PNSQVQLVQS GPEVKKPGSS VKVSCKASGY TFSRSTMHWV      540
RQAPGQGLEW IGYINPSSAY TNYNQKFKDR VTITADKSTS TAYMELSSLR SEDTAVYYCA      600
RPQVHYDYNG FPYWGQGTLV TVSSGGGGSG GGGSGGGGSG GGGSDIQMTQ SPSTLSASVG      660
DRVTMTCSAS SSVSYMNWYQ QKPGKAPKRW IYDSSKLASG VPSRFSGSGS GTDFTLTISS      720
LQPDDFATYY CQQWSRNPPT FGGGTKVEIK RSSS                                 754
(SEQ ID NO: 78)
```

DNA sequence of Anti-CD37 X TSC455:

```
atggaagcac cagcgcagct tctcttcctc ctgctactct ggctcccaga taccaccggt       60
gaggtgcagc tggtgcagtc tggagcagag gtgaaaaagc ccggagagtc tctgaagatt      120
tcctgtaagg gctccggtta ctcattcact ggctacaata tgaactgggt gcgccagatg      180
cccgggaaag gcctggagtg gatgggcaat attgatcctt attatggtgg tactacctac      240
aaccggaagt tcaagggcca ggtcactatc tccgccgaca gtccatcagc accgcctac       300
ctgcaatgga gcagcctgaa ggcctcggac accgccatgt attactgtgc acgctcagtc      360
ggcccttttcg actcctgggg ccagggcacc ctggtcactg tctcctctgg gggtggaggc      420
tctggtggcg gtggctctgg cggaggtgga tccggtggcg gcggatctgg cggggtggc       480
tctgaaattg tgttgacaca gtctccagcc accctgtctt tgtatccagg cgaaagagcc      540
accctctcct gccagcaag tgaaaatgtt tacagctact tagcctggta acaacgaaa        600
cctggccagg ctcctaggct cctcatctat tttgcaaaaa ccttagcagg aggtattcca      660
gccaggttca gtgcagtgg ctccgggaca gacttcactc tcaccatcag cagcctagag       720
cctgaagatt ttgcagttta ttactgtcaa catcattccg ataatccgtg acattcggc       780
caagggacca aggtggaaat caaatcctcg agtgagccca aatcttctga caaactcac       840
acatgcccac cgtgcccagc acctgaagcc gcgggtgcac cgtcagtctt cctcttcccc      900
ccaaaaccca aggacaccct catgatctcc cggaccctg aggtcacatg cgtggtggtg       960
gacgtgagcc acgaagaccc tgaggtcaag ttcaactggt acgtgacgg cgtggaggtg      1020
cataatgcca agacaaagcc gcgggaggag cagtacaaca gcacgtaccg tgtggtcagc     1080
gtcctcaccg tcctgcacca ggactggctg aatggcaagg catacgcgtg cgcggtctcc     1140
aacaaagccc tcccagcccc catcgagaaa accatctcca aagccaaagg cagccccga      1200
gaaccacagg tgtacaccct gcccccatcc cgggatgagc tgaccaagaa ccaggtcagc     1260
ctgacctgcc tggtcaaagg cttctatcca agcgacatcg ccgtggagtg ggagagcaat     1320
gggcagccgg agaacaacta caagaccacg cctcccgtgc tggactccga cggctcttcc     1380
ttcctctaca gcaagctcac cgtggacaag agcaggtggc agcaggggaa cgtcttctca     1440
tgctccgtga tgcatgaggc tctgcacaac cactacacgc agaagagcct ctccctgtct     1500
ccgggtcaga ggcacaacaa ttcttcctg aatacaggaa ctcagatggc aggtcattct     1560
ccgaattctc aggtccagct ggtgcaatct gggcctgagg tgaagaagcc tgggtcctcg     1620
gtgaaggtct cctgcaaggc ttctggatat accttcagca gatctacgat gcactgggtg     1680
cgacaggccc ctggacaagg gcttgagtgg ataggataca ttaatccag cagtgcttat     1740
actaattaca atcagaaatt caaggacaga gtcacgatta ccgcggacaa atccacgagc     1800
acagcctaca tggagctgag cagcctgaga tctgaggaca cggccgtgta ttactgtgcg     1860
agacccaag tccactatga ttacaacggg tttccttact ggggccaagg aaccctggtc     1920
accgtctcct caggtggagg cggttcaggc ggaggtggat ccggcggtgg cggatcgggt     1980
ggcggcggat ctgacatcca gatgacccag tctccttcca cctgtctgc atctgtagga     2040
gacagagtca ccatgacttg cagtgccagc tcaagtgtaa gttacatgaa ctggtatcag     2100
cagaaaccag ggaaagcccc taagagatgg atttatgact catccaaact ggcttctggg     2160
gtcccatcaa ggttcagcgg cagtggatct gggacagagt atactctcac catcagcagc     2220
ctgcagcctg atgattttgc aacttattac tgccaacagt ggagtcgtaa cccacccact     2280
ttcggcggag ggaccaaggt ggagatcaaa cggtcctcca gctaa                    2325
(SEQ ID NO: 79)
Signal sequence is residue 1 to 60
```

Mature protein sequence of Anti-CD37 X TSC455:

```
EVQLVQSGAE VKKPGESLKI SCKGSGYSFT GYNMNWVRQM PGKGLEWMGN IDPYYGGTTY       60
NRKFKGQVTI SADKSISTAY LQWSSLKASD TAMYYCARSV GPFDSWGQGT LVTVSSGGGG      120
SGGGGSGGGG SGGGGSGGGG SEIVLTQSPA TLSLSPGERA TLSCRASENV YSYLAWYQQK      180
PGQAPRLLIY FAKTLAEGIP ARFSGSGSGT DFTLTISSLE PEDFAVYYCQ HHSDNPWTFG      240
QGTKVEIKSS SEPKSSDKTH TCPPCPAPEA AGAPSVFLFP PKPKDTLMIS RTPEVTCVVV      300
DVSHEDPEVK FNWYVDGVEV HNAKTKPREE QYNSTYRVVS VLTVLHQDWL NGKAYACAVS      360
NKALPAPIEK TISKAKGQPR EPQVYTLPPS RDELTKNQVS LTCLVKGFYP SDIAVEWESN      420
GQPENNYKTT PPVLDSDGSF FLYSKLTVDK SRWQQGNVFS CSVMHEALHN HYTQKSLSLS      480
PGQRHNNSSL NTGTQMAGHS PNSQVQLVQS GPEVKKPGSS VKVSCKASGY TFSRSTMHWV      540
RQAPGQGLEW IGYINPSSAY TNYNQKFKDR VTITADKSTS TAYMELSSLR SEDTAVYYCA      600
RPQVHYDYNG FPYWGQGTLV TVSSGGGGSG GGGSGGGGSG GGGSDIQMTQ SPSTLSASVG      660
DRVTMTCSAS SSVSYMNWYQ QKPGKAPKRW IYDSSKLASG VPSRFSGSGS GTEYTLTISS      720
LQPDDFATYY CQQWSRNPPT FGGGTKVEIK RSSS                                 754
(SEQ ID NO: 80)
```

DNA sequence of Anti-CD37 X TSC456:

```
atggaagcac cagcgcagct tctcttcctc ctgctactct ggctcccaga taccaccggt       60
gaggtgcagc tggtgcagtc tggagcagag gtgaaaaagc ccggagagtc tctgaagatt      120
tcctgtaagg gctccggtta ctcattcact ggctacaata tgaactgggt gcgccagatg      180
cccgggaaag gcctggagtg gatgggcaat attgatcctt attatggtgg tactacctac      240
```

TABLE 14-continued

Binding Domain and Polypeptide Sequences and Components

```
aaccggaagt tcaagggcca ggtcactatc tccgccgaca agtccatcag caccgcctac    300
ctgcaatgga gcagcctgaa ggcctcggac accgccagt attactgtgc acgctcagtc    360
ggcccttcg actcctgggg ccagggcacc ctggtcactg tctcctctgg gggtggagtc    420
tctggtggcg gtggctctgg cggaggtgga tccggtggcg gcggatctgg cggggggtggc    480
tctgaaattg tgttgacaca gtctccagcc acctgtctt tgtatccagg cgaaagagcc    540
accctctcct gccgagcaag tgaaaatgtt tacagctact tagcctggta ccaacagaaa    600
cctgccagg ctcctaggct cctcatctat tttgcaaaaa cctagcaga aggtattca      660
gccaggttca gtggcagtgg ctccgggaca gacttcactc tcaccatcag cagcctagag    720
cctgaagatt ttgcagttta ttactgtcaa catcattccg ataatccgtg gacattcggc    780
caagggacca aggtggaaat caatcctcg agtgagccca atcttctga caaaactcac      840
acatgcccac cgtgcccagc acctgaagcc gcgggtgcac cgtcagtctt cctcttcccc     900
ccaaaaccca aggacaccct catgatctcc cggacccctg aggtcacatg cgtggtggtg     960
gacgtgagcc acgaagaccc tgaggtcaag ttcaactggt acgtggacgg cgtggaggtg   1020
cataatgcca agacaaagcc gcgggaggag cagtacaaca gcacgtaccg tgtggtcagc   1080
gtcctcaccg tcctgcacca ggactggctg aatggcaagg agtacgcgtg cgcggtctcc   1140
aacaaagccc tcccagcccc catcgagaaa accatctcca aagccaaagg gcagccccga   1200
gaaccacagg tgtacaccct gcccccatcc cgggatgagc tgaccaagaa ccaggtcagc   1260
ctgacctgcc tggtcaaagg cttctatcca agcgacatcg ccgtggagtg ggagagcaat   1320
gggcagccgg agaacaacta caagaccacg cctcccgtgc tggactccga cggctccttc   1380
ttcctctaca gcaagctcac cgtggacaag agcaggtggc agcaggggaa cgtcttctca   1440
tgctccgtga tgcatgaggc tatgcacaac cactacacgc agaagagcct ctccctgtct   1500
ccgggtcaga ggcacaacaa ttcttccctg aatacaggaa ctcagatggc aggtcattct   1560
ccgaattctc aggtccagct ggtgcaatct gggcctgagg tggaaagcc tgggtcctcg   1620
gtgaaggtct cctgcaaggc ttctggatat accttcagca gatctacgat gcactgggtg   1680
cgacaggccc ctggacaagg gcttgagtgg ataggataca ttaatcctag cagtgcttat   1740
actaattaca atcagaaatt caaggacaga gtcacgatta ccgcggacaa atccacgagc   1800
acagcctaca tggagctgag cagcctgaga tatgaggaca cggccgtgta ttactgtgcg   1860
agacccaag tccactatga ttacaacggg tttccttact ggggccaagg aaccctggtc   1920
accgtctcct caggtggagg cggttcaggc ggaggtggat ccggcggtgg cggatcgggt   1980
ggcggcggat ctgacatcca gatgacccag tctccttcca ccctgtctgc atctgtagga   2040
gacagagtca ccatgacttg cagtgccagc tcaagtgtaa gttacatgaa ctggtatcag   2100
cagaaaccag ggaaagcccc taagagatgg atttatgact catccaaact ggcttctggg   2160
gtcccatcaa ggttcagcgg cagtggatct gggacagatt atactatcac catcagcagc   2220
ctgcagcctg atgattttgc aacttattac tgccaacagt ggagtcgtaa cccacccact   2280
ttcggcggag ggaccaaggt ggagatcaaa cggtcctcca gctaa                   2325
(SEQ ID NO: 81)
```
Signal sequence is residue 1 to 60

Mature protein sequence of Anti-CD37 X TSC456:

```
EVQLVQSGAE VKKPGESLKI SCKGSGYSFT GYNMNWVRQM PGKGLEWMGN IDPYYGGTTY    60
NRKFKGQVTI SADKSISTAY LQWSSLKASD TAMYYCARSV GPPDSWGQGT LVTVSSGGGG   120
SGGGGSGGGG SGGGGSGGGG SEIVLTQSPA TLSLSPGERA TLSCRASENV YSYLAWYQQK   180
PGQAPRLLIY FAKTLAEGIP ARFSGSGSGT DFTLTISSLE PEDFAVYYCQ HHSDNPWTFG   240
QGTKVEIKSS SEPKSSDKTH TCPPCPAPEA AGAPSVFLFP PKPKDTLMIS RTPEVTCVVV   300
DVSHEDPEVK FNWYVDGVEV HNAKTKPREE QYNSTYRVVS VLTVLHQDWL NGKAYACAVS   360
NKALPAPIEK TISKAKGQPR EPQVYTLPPS RDELTKNQVS LTCLVKGFYP SDIAVEWESN   420
GQPENNYKTT PPVLDSDGSF FLYSKLTVDK SRWQQGNVFS CSVMHEALHN HYTQKSLSLS   480
PGQRHNNSSL NTGTQMAGHS PNSQVQLVQS GPEVKKPGSS VKVSCKASGY TFSRSTMHWV   540
RQAPGQGLEW IGYINPSSAY TNYNQKFKDR VTITADKSTS TAYMELSSLR SEDTAVYYCA   600
RPQVHYDYNG FPYWGQGTLV TVSSGGGGSG GGGSGGGGSG GGGSDIQMTQ SPSTLSASVG   660
DRVTMTCSAS SSVSYMNWYQ QKPGKAPKRW IYDSSKLASG VPSRFSGSGS GTDYTLTISS   720
LQPDDFATYY CQQWSRNPPT FGGGTKVEIK RSSS                                754
(SEQ ID NO: 82)
```

Protein sequence of TSC455 anti-CD3 scFv

```
QVQLVQSGPEVKKPGSSVKVSCKASGYTFSRSTMHWVRQAPGQGLEWIGYINPSSAYTNYNQKFKDRVTITADK
STSTAYMELSSLRSEDTAVYYCARPQVHYDYNGFPYWGQGTLVTVSSGGGGSGGGGSGGGGSGGGGSDIQMTQS
PSTLSASVGDRVTMTCSASSSVSYMNWYQQKPGKAPKRWIYDSSKLASGVPSRFSGSGSGTEYTLTISSLQPDD
FATYYCQQWSRNPPTFGGGTKVEIKRSSS
(SEQ ID NO: 83)
```

Protein sequence of TSC456 anti-CD3 scFv

```
QVQLVQSGPEVKKPGSSVKVSCKASGYTFSRSTMHWVRQAPGQGLEWIGYINPSSAYTNYNQKFKDRVTITADK
STSTAYMELSSLRSEDTAVYYCARPQVHYDYNGFPYWGQGTLVTVSSGGGGSGGGGSGGGGSGGGGSDIQMTQS
PSTLSASVGDRVTMTCSASSSVSYMNWIQQKPGKAPKRWIYDSSKLASGVPSRFSGSGSGTDYTLTISSLQPDD
FATYYCQQWSRNPPTFGGGTKVEIKRSSS
(SEQ ID NO: 84)
```

Protein sequence of DRA222 anti-CD3 scFv

```
QVQLVESGGGVVQPGRSLRLSCKASGYFTTRSTMHWVRQAPGQGLEWIGYINPSSAYTNYNQKFKDRFTISADK
SKSTAFLQMDSLRPEDTGVYFCARPQVHYDYNGFPYWGQTPVTVSSGGGGSGGGGSGGGGSAQDIQMTQSPSS
LSASVGDRVTMTCSASSSVSYMNWYQQNPGKAPKRWIYDSSKLASGVPARFSGSGSGTDYTLTISSLQPEDFAT
YYCQQWSRNPPTFGGGTKLQITSSS
(SEQ ID NO: 85)
```

TABLE 14-continued

Binding Domain and Polypeptide Sequences and Components

Protein sequence of TSC455 and TSC456 variable heavy domain

QVQLVQSGPEVKKPGSSVKVSCKASGYTFSRSTMHWVRQAPGQGLEWIGYINPSSAYTNYNQKFKDRVTITADK
STSTAYMELSSLRSEDTAVYYCARPQVHYDYNGFPYWGQGTLVTVSS
(SEQ ID NO: 86)

Protein sequence of DRA222 variable heavy domain

QVQLVESGGGVVQPGRSLRLSCKASGYTFTRSTMHWVRQAPGQGLEWIGYINPSSAYTNYNQKFKDRFTISADK
SKSTAFLQMDSLRPEDTGVYFCARPQVHYDYNGFPYWGQGTPVTVSS
(SEQ ID NO: 87)

Protein sequence of TSC455 variable light domain

DIQMTQSPSTLSASVGDRVTMTCSASSSVSYMNWYQQKPGKAPKRWIYDSSKLASGVPSRFSGSGSGTEYTLTI
SSLQPDDFATYYCQQWSRNPPTFGGGTKVEIKRS
(SEQ ID NO: 88)

Protein sequence of TSC456 variable light domain

DIQMTQSPSTLSASVGDRVTMTCSASSSVSYMNWYQQKPGKAPKRWIYDSSKLASGVPSRFSGSGSGTDYTLTI
SSLQPDDFATYYCQQWSRNPPTFGGGTKVEIKRS
(SEQ ID NO: 89)

Protein sequence of DRA222 variable light domain

DIQMTQSPSSLSASVGDRVTMTCSASSSVSYMNWYQQKPGKAPKRWIYDSSKLASGVPARFSGSGSGTDYTLTI
SSLQPEDFATYYCQQWSRNPPTFGGGTKLQITS
(SEQ ID NO: 90)

Cris7 and DRA222 VH CDR1 (Kabat)

RSTMH (SEQ ID NO: 91)

Cris7 and DRA222 VH CDR2 (Kabat)

YINPSSAYTNYNQKFK (SEQ ID NO: 92)

Cris7 and DRA222 VH CDR3 (Kabat)

QVHYDYNGFPY (SEQ ID NO: 93)

Cris7 and DRA222 VL CDR1 (Kabat)

SASSSVSYMN (SEQ ID NO: 94)

Cris7 and DRA222 VL CDR2 (Kabat)

DSSKLAS (SEQ ID NO: 95)

Cris7 and DRA222 VL CDR3 (Kabat)

QQWSRNPPT (SEQ ID NO: 96)

Cris7 and DRA222 VH CDR1 (IMGT)

GYTFTRST (SEQ ID NO: 199)

Cris7 and DRA222 VH CDR2 (IMGT)

INPSSAYT (SEQ ID NO: 200)

Cris7 and DRA222 VH CDR3 (IMGT)

QQWSRNPPT (SEQ ID NO: 201)

Cris7 and DRA222 VL CDR1 (IMGT)

ASSSVSY (SEQ ID NO: 202)

Cris7 and DRA222 VL CDR2 (IMGT)

DSS (SEQ ID NO: 203)

Cris7 and DRA222 VL CDR3 (IMGT)

QQWSRNPPT (SEQ ID NO: 204)

TABLE 14-continued

Binding Domain and Polypeptide Sequences and Components

DNA sequence of ROR133:

```
atggaagcaccagcgcagcttctcttcctcctgctactctggctcccagataccaccggtgacatccagatgacccagtcccccctc
ctccctgtccgcctccgtgggcgacccgggtgaccatcaactgccaggcctcccagtccatcgactccaacctggcctggttccagc
agaagcccggccaagccccccaagctgctgatctaccgggcctccaacctggcctccggcgtgccctcccggttctccggctccggc
tccggcaccgacttcaccctgaccatctcctccctgcagcccgaggacgtggccacctactactgcctgggcggcgtgggcgccgt
gtcctaccggacctccttcggcggcggcaccaaggtggagatcaagggtggaggcggttcaggcggaggtggatccggcggtggcg
gctccggtggcggcggatctgaggtgcagctggtggagtccggcggcggcctggtgcagcccggccggtccctcgggctgtcctgc
accgcctccggctccgacatcaacgactaccccatctcctgggtgcggcaggcccccggcaagggcctggagtggatcggcttcat
caactccggcggctccacctggtacgcctcctgggtgaaggggccggttcaccatctcccgggacgactccaagtccatcgcctacc
tgcagatgaactccctgaagaccaaggacaccgccgtgtactattgcgcccggggctactccacctactacggcgacttcaacatc
tggggccagggcaccctggtaaccgtgtcctgagtgagcccaaatcttctgacaaaactcacacatgcccaccgtgcccagcacc
taaagccgcgggtgcaccgtcagtcttcctcttccccccaaaacccaaggacaccctcatgatctcccggacccctgaggtcacat
gcgtggtggtggacgtgagccacgaagaccctgaggtcaagttcaactggtacgtggacggcgtggaggtgcataatgccaagaca
aagccgcgggaggagcagtacaacagcacgtaccgtgtggtcagcgtcctcaccgtcctgcaccaggactggctgaatggcaagga
atacaagtgcgcggtctccaacaaagccctcccagccccatcgagaaaaccatctccaaagccaaagggcagccccgagaaccac
aggtgtacaccctgcccccatcccgggatgagctgaccaagaaccaggtcagcctgacctgcctggtcaaaggcttctatccaagc
gacatcgccgtggagtgggagagcaatgggcagccggagaacaactacaagaccacgcctcccgtgctggactccgacggctcctt
cttcctctacagcaagctcaccgtggacaagagcaggtggcagcaggggaacgtcttctcatgctccgtgatgcatgaggctctgc
acaaccactacacgcagaagagcctctccctgtctccggttctggtggaggcggttcaggcggaggtggctccggcggtggcgga
tcgccgggctctcaggtccagctggtggagtctaggggcggagtggtgcagcctgggcggtcactgaggctgtcctgcaaggcttc
tggctacacctttactagatctacgatgcactgggtaaggcaggccccctggacaaggtctggaatggattggatacattaatccta
gcagtgcttatactaattacaatcagaaattcaaggacaggttcacaatcagcagagacaaatccaagagcacagccttcctgcag
atggacagcctgaggcccgaggacaccggcgtctatttctgtgcacggccccaagtccactatgattacaacgggtttccttactg
gggccaagggactcccgtcactgtctctagcggtggcggagggtctgggggtggcggatccggaggtggtggctctgcacaagaca
tccagatgacccagtctccaagcagcctgtctgcaagcgtggggacagggtcaccatgacctgcagtgccagctcaagtgtaagt
tacatgaactggtaccagcagaagccgggcaaggcccccaaaagatggatttatgactcatccaaactggcttctggagtccctgc
tcgcttcagtggcagtgggtctgggaccgactataccctcacaatcagcagcctgcagcccgaagatttcgccacttattactgcc
agcagtggagtcgtaacccacccacgttcggaggggggaccaagctacaaattacatcctccagctaa
(SEQ ID NO: 97)
```

Mature protein sequence of ROR133:

```
diqmtqspsslsasvgdrvtincqasqsidsnlawfqqkpgkppklliyrasnlasgvpsrfsgsgsgtdftltisslqpedvaty
yclggvgavsyrtsfgggtkveikggggsggggsggggsggggsevqlvesgggglvqpgrslrlsctasgsdindypiswvrqapg
kglewigfinsggstwyaswvkgrftisrddsksiaylqmnslktedtavyycargystyygdfniwgqgtlvtvsssepkssdkt
htcppcpapeaagapsvflfppkpkdtlmisrtpevtcvvvdvshedpevkfnwyvdgvevhnaktkpreeqynstyrvvsvltvl
hqdwlngkeykcavsnkalpapiektiskakgqprepqvytlppsrdeltknqvsltclvkgfypsdiavewesngqpennykttp
pvldsdgsfflyskltvdksrwqqgtvfscsvmhealhnhytqkslslspgsggggsggggsggggspgsqvqlvesgggvvqpgr
slrlsckasgytftrstmhwvrqapgqglewigyinpssaytnynqkfkdrftisadkskstaflqmdslrpedtgvyfcarpqvh
ydyngfpywgqgtpvtvssggggsggggsggggsaqdiqmtqspsslsasvgdrvtmtcsasssvsymnwyqqkpgkapkrwiyds
sklasgvparfsgsgsgtdytltisslqpedfatyycqqwsrnpptfgggtklqitsss
(SEQ ID NO: 98)
```

DNA sequence of ROR193:

```
atggaagcaccagcgcagcttctcttcctcctgctactctggctcccagataccaccggtgacatccagatgacccagtcccccctc
ctccctgtccgcctccgtgggcgacccgggtgaccatcaactgccaggcctcccagtccatcgactccaacctggcctggttccagc
agaagcccggccaagccccccaagctgctgatctaccgggcctccaacctggcctccggcgtgccctcccggttctccggctccggc
tccggcaccgacttcaccctgaccatctcctccctgcagcccgaggacgtggccacctactactgcctgggcggcgtgggcgccgt
gtcctaccggacctccttcggcggcggcaccaaggtggagatcaagggtggaggcggttcaggcggaggtggatccagcggtggcg
gctccggtggcggcggatctgaggtgcagctggtggagtccggcggcggcctggtgcagcccggccggtccctcgggctgtcctgc
accgcctccggctccgacatcaacgactaccccatctcctgggtgcggcaggcccccggcaagggcctggagtggatcggcttcat
caactccggcggctccacctggtacgcctcctgggtgaagggccggttcaccatctcccgggacgactccaagtccatcgcctacc
tgcagatgaactccctgaagaccgaggacaccgccgtgtactattgcgcccggggctactccacctactacggcgacttcaacatc
tggggccagggcaccctggtgaccgtgtcctgagtgagcccaaatcttctgacaaaactcacacatgcccaccgtgcccagcacc
tgaaaccgcgggtacaccgtcagtcttcctcttccccccaaaacccaaggacaccctcatgatctcccggacccctgaggtcacat
gcgtggtggtggacgtgagccacgaagaccctgaggtcaagttcaactggtacgtggacagcgtggaggtgcataatgccaagaca
aagccgcgggaggagcagtacaacagcacgtaccgtgtggtcagcgtcctcaccgtcctgcaccaggactggctgaatggcaagga
atacaagtgcgcggtctccaacaaagccctcccagccccatcgagaaaaccatctccaaagccaaagggcagccccgagaaccac
aggtgtacaccctgcccccatcccgggatgagctgaccaagaaccaggtcagcctgacctgcctggtcaaaggcttctatccaagc
gacatcgccgtggagtgggagagcaatgggcagccggagaacaactacaagaccacgcctcccgtgctggactccgacggctcctt
cttcctctacagcaagctcaccgtggacaagagcaggtggcagcaggggaacgtcttctcatgctccgtgatgcatgaggctctgc
acaaccactacacgcagaagagcctctccctgtctccgggttctggtggaggcggttcaggcggaggtggctccggcggtggcgga
tcgccgggctctcaggtccagctggtgcaatctgggcctgaggtgaagaagcctgggtcctcggtgaaggtctcctgcaaggcttc
tggatataccttcaacagatctacgatacactgggtgcgacaggcccctggacaaggcttgagtggataggatacattaatccta
gcagtgcttatactaattacaatcagaaattcaaggacagagtcacgattaccgcggacaaatccacgagcacagcctacatggag
ctgagcagcctgagatctgaggacacggccgtgtattactgtgcgagaccccaagtccactatgattacaacgggtttccttactg
gggccaagggaccctggtcaccgtctcctcaggtggaggcggttcaggcggaggtggctccggcggtggcggcg
gatctgacatccagatgacccagtctccttccaccctgtctgcatctgtaggagacagagtcaccatgacttgcagtgccagctca
agtgtaagttacatgaactggtatcagcagaaacagggaaagcccctaagatgatttatgactcatccaaactggcttctgg
ggtcccatcaaggttcagcggcagtggatctgggacagagtataactcaccatcagcagcctgcagcctgatgatttttgcaactta
ttactgccaacagtggagtcgtaacccacccactttcggcggagggaccaaggtggagatcaaacggtcctccagctaa
(SEQ ID NO: 99)
```

TABLE 14-continued

Binding Domain and Polypeptide Sequences and Components

Mature protein sequence of ROR193:

Diqmtqspsslsasvgdrvtincqasqsidsnlawfqqkpgkppklliyrasnlasgvpsrfsgsgsgtdftltisslqpedvaty
yclggvgavsyrtsfgggtkveikggggsggggsggggsggggsevqlvesgggglvqpgrslrlsctasgsdindypiswvrqpag
kglewigfinsggstwyaswvkgrftisrddsksiaylqmnslktedtavyycargystyygdfniwgqgtlvtvsssepkssdkt
htcppcpapeaagapsvflfppkpkdtlmisrtpevtcvvvdvshedpevkfnwyvdgvevhnaktkpreeqynstyrvvsvltvl
hqdwlngkeykcavsnkalpapiektiskakgqprepqvytlppsrdeltknqvsltclvkgfypsdiavewesngqpennykttp
pvldsdgsfflyskltvdksrwqqgnvfscsvmhealhnhytqkslslspgsggggsggggsggggspgsqvqlvqsgpevkkpgs
svkvsckasgytfsrstmhwvrqapgqglewigyinpssaytnynqkfkdrvtitadkststaymelsslrsedtavyycarpqvh
ydyngfpywgqgtlvtvssggggsggggsggggsggggsdiqmtqspstlsasvgdrvtmtcsasssvsytmnwyqqkpgkapkrw
iydssklasgvpsrfsgsgsgteytltisslqpddfatyycqqwsrnpptfgggtkveikrsss
(SEQ ID NO: 100)

DNA sequence of ROR134:

atggaagcaccagcgcagcttctcttcctcctgctactctggctcccagataccaccggtgacatccagatgacccagtcccctc
ctccctgtccgcctccgtgggcgaccgggtgaccatcaactgccaggcctcccagtccatcgactccaacctggcctggttccagc
agaagcccggcaagcccccccaagctgctgatctaccgggcctccaacctggcctccggcgtgccctcccggttctctcggctccggc
tccggcaccgacttcaccctgaccatctcctccctgcagcccgaggacgtggccacctactactgcctgggcggcgtgggcgccgt
gtcctaccggacctccttcggcggcggcaccaaggtggagatcaagggtggaggcggttcaggcggaggtggatccggcggtggcg
gctccggtggcggcggatctgaggtgcagctggtggagtccggcggcggcctggtgcagcccggcggctccctgcggctgtcctgc
accgcctccggctccgacatcaacgactaccccatctcctgggtgcggcaggccccggcaagggcctggagtggatcggcttcat
caactccggcggctccacctggtacgccgactcggtgaagggccggttcaccatctcccggcactcctccaagaacaccctgtacc
tgcagatgaactccctgcgggccgaggacaccgccgtgtacttctgcgcccggggctactccacctactacggcgacttcaacatc
tggggccagggcaccctggtgaccgtgtcctcgagtgagcccaaatcttctgacaaaactcacacatgcccaccgtgcccagcacc
tgaaccgcgggtgcaccgtcagtcttcctcttccccccaaaaccaaggacacccctcatgatctcccggacccctgaggtcacat
gcgtggtggtggacgtgagccacgaagaccctgaggtcaagttcaactggtacgtggacaacgtggaggtgcataatgccaagaca
aagccgcgggaggagcagtacaacagcacgtaccgtgtggtcagcgtcctcaccgtcctgcaccaggactggctgaatggcaagga
atacaagtgcgcggtctccaacaaagcctcccagccccccatcgagaaaaccatctccaaagccaaaaggcagccccgagaaccac
aggtgtacaccctgcccccatcccgggatgagctaaccaagaaccaggtcagcctgacctgcctggtcaaaggcttctatccaagc
gacatcgccgtggagtgggagagcaatgggcagccggagaacaactacaagaccacgcctcccgtgctggactccgacggctcctt
cttcctctacagcaagctcaccgtggacaagagcaggtggcagcaggggaacgtcttctcatgctccgtgatgcatgaggctctgc
acaaccactacacgcagaagagcctctccctgtctccgggttctggtggaggcggttcaggcggaggtggctccggcggtggcgga
tcgccggctctcaggtccagctggtggagtctggggcggagtggtgcagcctgggcggtcactgaggctgtcctgcaaggcttc
tggctacacctttactagatctacgatgcactgggtaaggcaggccccctggacaaggtctggaatggattggatacattaatccta
gcagtgcttatactaattacaatcagaaattcaaggacaggttcacaatcagcgcagacaaatccaagagcacagccttcctgcag
atggacagcctgaggcccgaggacaccggcgtctatttctgtgcacggccccaagtccactatgattacaacgggtttccttactg
gggccaagggactcccgtcactgtctctagcggtggcggagggtctggggtgggatccggaggtggtggctctgcacaagaca
tccagatgacccagtctccaagcagcctgtccgcaagcgtgggcgaccggtgaccatgacctgcagtgccagcaagtgattaagtt
acatgaactggtaccagcagaagccgggcaaggcccccaaaagatggattatgactcatccaaactggcttctggagtccctgct
cgcttcagtggcagtgggtctgggaccgactatacctcacaatcagcgctgcagcccgaagatttcgccacttattactgcca
gcagtggagtcgtaacccacccacgttcggaggggggaccaagctacaaattacatcctccagctaa
(SEQ ID NO: 101)

Mature protein sequence of ROR134:

Diqmtqspsslsasvgdrvtincqasqsidsnlawfqqkpgkppklliyrasnlasgvpsrfsgsgsgtdftltisslqpedvaty
yclggvgavsyrtsfgggtkveikggggsggggsggggsggggsevqlvesgggglvqpggslrlsctasgsdindypiswyrqapg
kglewigfinsggstwyadsvkgrftisrhsskntlylqmnslraedtavyfcargystyygdfniwgqgtlvtvsssepkssdkt
htcppcpapeaagapsvflfppkpkdtlmisrtpevtcvvvdvshedpevkfnwyvdgvevhnaktkpreeqynstyrvvsvltvl
hqdwlngkeykcavsnkalpapiektiskakgqprepqvytlppsrdeltknqvsltclvkgfypsdiavewesngqpennykttp
pvldsdgsfflyskltvdksrwqqgnvfscsvmhealhnhytqkslslspgsggggsggggsggggspgsqvqlvqsgpvvqpgr
slrlsckasgytftrstmhwvrqapgqglewigyinpssaytnynqkfkdrftisadkskstaflqmdslrpedtgvyfcarpqvh
ydyngfpywgqgtpvtvssggggsggggsggggsaqdiqmtqspsslsasvgdrytmtcsasssvsymnwyqqkpgkapkrwiyds
sklasgvparfsgsgsgtdytltisslqpedfatyycqqwsrnpptfgggtklqitsss
(SEQ ID NO: 102)

DNA sequence of ROR189:

atggaagcaccagcgcagcttctcttcctcctgctactctggctcccagataccaccggtgacatccagatgacccagtcccctc
ctccctgtccgcctccgtgggcgaccgggtgaccatcaactgccaggcctcccagtccatcgactccaacctggcctggttccagc
agaagcccggcaagcccccccaagctgctgatctaccgggcctccaacctggcctccggcgtgccctcccggttctctcggctccggc
tccggcaccgacttcaccctgaccatctcctccctgcagcccgaggacgtggccacctactactgcctgggcggcgtgggcgccgt
gtcctaccggacctccttcggcggcggcaccaaggtggagatcaagggtggaggcggttcaggcggaggtggatccggcggtggcg
gctccggtggcggcggatctgaggtgcagctggtggagtccggcggcggcctggtgcagcccggcggctccctgcggctgtcctgc
accgcctccggctccgacatcaacgactaccccatacctgggtgcggcaggccccggcaagggcctggagtggatcggcttcatc
aactccggcggctccacctggtacgccgactcggtgaagggccggttcaccatctcccggcactcctccaagaacaccctgtacct
gcagatgaactccctgcgggccgaggacaccgccgtgtacttctgcgcccggggctactccacctactacggcgacttcaacatct
ggggccagggcaccctggtgaccgtgtcctcgagtgagcccaaatcttctgacaaaactcacacatgcccaccgtgcccagcacct
gaaccgcgggtgcaccgtcagtcttcctcttccccccaaaaccaaggacacccctcatgatctcccggacccctgaggtcacatg
cgtggtggtggacgtgagccacgaagaccctgaggtcaagttcaactggtacgtggacggcgtggaggtgcataatgccaagacaa
agccgcgggaggagcagtacaacagcacgtaccgtgtggtcagcgtcctcaccgtcctgcaccaggactggctgaatggcaaggaa
tacaagtgcgcggtctccaacaaagcctcccagccccccatcgagaaaaccatctccaaagccaaaaggcagccccgagaaccaca
ggtgtacaccctgcccccatcccgggatgagctgaccaagaaccaggtcagcctgacctgcctggtcaaaggcttctatccaagcg
acatcgccgtggagtgggagagcaatgggcagccggagaacaactacaagaccacgcctcccgtgctggactccgacggctcctte
ttcctctacagcaagctcaccgtggacaagagcaggtggcagcaggggaacgtcttctcatgctccgtgatgcatgaggctctgca
caaccactacacgcagaagagcctctccctgtctccgggttctggtggaggcggttcaggcggaggtggctccggcggtggcggat TABLE 14-continued Binding Domain and Polypeptide Sequences and Components cgccgggctctcaggtccagctggtgcaatctgggcctgaggtgaagaagcctggg tcctcggtgaaggtctcctgcaaggcttct
ggatataccttcagcagatctacgatgcactgggtgcgacaggcccctggacaagggcttgagtggataggatacattaatcctag
cagtgcttatactaattacaatcagaaattcaaggacagagtcacgattaccgcggacaaatccacgagcacagcctacatggagc
tgagcagcctgagatctgaggacacggccgtgtattactgtgcgagaccccaagtccactatgattacaacgggtttccttactgg
ggccaaggaaccctggtcaccgtctcctcaggtggaggcggttcaggcggaggtggatccggcggtggcggatcgggtggcggcgg
atctgacatccagatgacccagtcctccttccaccctgtctgcatctgtaggagacagagtcaccatgacttgcagtgccagctcaa
gtgtaagttacatgaactggtatcagcagaaaccagggaaagccccctaaggagtggatttatgactcatccaaactggcttctggg
gtcccatcaaggttcagcggcagtggatctgggacagattatactctcaccatcagcagcctgcagcctgatgattttgcaactta
ttactgccaacagtggagtcgtaacccacccactttcggcggagggaccaaggtggagatcaaacggtcctccagctaa
(SEQ ID NO: 103)

Mature protein sequence of ROR189:

diqmtqspsslsasvgdrvtincqasqsidsnlawfqqkpgkppklliyrasnlasgvpsrfsgsgsgtdftltisslqpedvaty
yclggvgavsyrtsfgggtkveikgggsggggsggggsggggsevqlvesgglvqpgslrlsctasgsdindypiswvrqapg
kglewigfinsggstwtadsvkgrftisrhssknt1ylqmns1raedtavyfcargystyygdfniwgqgtlvtvsssepkssdkt
htcppcpapeaagapsvflfppkpkdtlmisrtpevtcvvvdvshedpevkfnwyvdgvevhnakt kpreeqynstyrvvsvltvl
hqdwlngkeykcavsnkalpapiektiskakgqprepqvytlppsrdeltknqvsltclvkgfypsdiavewesngqpennykttp
pvldsdgsfflyskltvdksrwqqgnvfscsvmhealhnhytqkslslspgsggggsggggsggggspgsqvqlvqsgpevkkpgs
svkvsckasgytfsrstmhwvrqapgqglewigyinpssaytnynqkfkdrvtitadkststaymelssIrsedtavyycarpqvh
ydyngfpywgqgtlvtvssggggsggggsggggsggggsdiqmtqspstlsasvgdrvtmtcsasssvsymnwyqqkpgkapkrwi
ydssklasgvpsrfsgsgsgtdytltisslqpddfatyycqqwsrnpptfgggtkveikrsss
(SEQ ID NO: 104)

DNA sequence of ROR154:

atggaagcaccagcgcagcttctcttcctcctgctactctggctcccagataccaccggtgacatccagatgacccagtcccctc
ctccctgtccgcctccgtgggcgaccgggtgaccatcaactgccaggcctcccagtccatcgactccaacctggcctggttccagc
agaagcccggcaagccccccaagctgctgatctaccgggcctccaacctggcctccggcgtgccctcccggttctccggctccggc
tccggcaccgacttcaccctgaccatctctcctgcagcccgaggacgtggccacctactactgcctgggcggcgtgggcgccgt
gtcctaccgggacctccttcggcggcggcaccaaggtggagatcaaggg tggaggcggttcaggcggaggtggatccggcggtggcg
gctccggtggcggcggatctgaggtgcagctggtggagtccggcggcggcctggtgcagcccggccggtccctgcggctgtcctgc
accgcctccggctccgacatcaacgactaccccatcacctgggtgcggcaggcccccggcaagggcctggagtggatcggcttcat
caactccggcggctccacctggtacgcctccgggtgaagggccggttcaccatctcccgggacgactccaagtccatcgcctacct
gcagatgaactccctgaagaccgaggacaccgccgtgtactattgcgcccggggctactccacctactaccgggacttcaacatct
ggggccagggcaccctggtgaccgtgtcctcgagcagccaaatcttctgacaaaactcacacatgcccaccgtgcccagcacct
gaagccgcgggtgcaccgtcagtcttcctcttccccccaaaacccaaggacaccctcatgatctcccggacccctgaggtcacatg
cgtggtggtggacgtgagccacgaagaccctgaggtcaagttcaactggtacgtggacggcgtggaggtgcataatgccaagacaa
agccgcgggaggagcagtacaacagcacgtaccgtgtggtcagcgtcctcaccgtcctgcaccaggactggctgaatggcaaggaa
tacaagtgcgcggtctccaacaaagccctcccagcccccatcgagaaaaccatctccaaagccaaagggcaagcccgagaaccaca
ggtgtacaccctgcccccatcccgggatgagctgaccaagaaccaggtcagcctgacctgcctggtcaaaggcttctatccaagcg
acatcgccgtggagtgggagagcaatgggcagccggagaacaactacaagaccacgcctcccgtgctggactccgacggctccttc
ttcctctacagcaagctcaccgtggacaagagcaggtggcagcaggggaacgtcttctcatgctccgtgatgcatgaggctctgca
caaccactacacgcagaagagcctctccctgtctccgggtctgtggaggcggttcaggcggaggtggctccggcggtggcggat
cgccgggctctcaggtccagctggtggagtctggggcgagtggtgcagcctgggcggtcactgaggcgtcctgcaaggcttct
ggctacacctttactagatctacgatgcactgggtaaggcaggcccctggacaaggtctggaatggattggatacattaatcctag
cagtgcttatactaattacaatcagaaattcaaggacaggttcacaatcagcgcagacaaatccaagagcacagcctcctgcaga
tggacagcctgaggcccgaggacaccggcgtctatttctgtgcacggccccaagtccactatgattacaacgggtttccttactgg
ggccaagggactcccgtcactgtctctagcggtggcgaggtctggggtggcggatccggaggtggtgcctctgcacaagacat
ccagatgacccagtctccaagcagcctgtctgcaagcgtggggacaggtcaccatgacctgcagtgccagctcaagtgtaagtta
catgaactggtaccagcagaagcccggcaaggccccaaagatggatttgactcatccaaactggcttctggagtccctgctc
gcttcagtggcagtgggtctgggaccgactatacccctcacaatcagcagcctgcagcccgaagatttcgccacttattactgccag
cagtggagtcgtaacccacccacgttcggaggggggaccaagctacaaattacatcctccagctaa
(SEQ ID NO: 105)

Mature protein sequence of ROR154:

diqmtqspsslsasvgdrvtincqasqsidsnlawfqqkpgkppklliyrasnlasgvpsrfsgsgsgtdftltisslqpedvaty
yclggvgavsyrtsfgggtkveikgggsggggsggggsggggsevqlvesgggvqpgrslrlsctasgsdindypitwvrqapg
kglewigfinsggstwyaswvkgrftisrddsksiaylqmnslktedtavyycargystyyrdfniwgqgtlvtvsssepkssdkt
htcppcpapeaagapsvflfppkpkdtlmisrtpevtcvvvdvshedpevkfnwyvdgvevhnakt kpreeqynstyrvvsvltvl
hqdwlngkeykcavsnkalpapiektiskakgqprepqvytlppsrdeltknqvsltclvkgfypsdiavewesngqpennykttp
pvldsdgsfflyskltvdksrwqqgnvfscsvmhealhnhytqkslslspgsggggsggggsggggspgsqvqlvesgggvvqpgr
slrlsckasgyftfrstmhwvrqapgqglewigyinpssaytnynqkfkdrftisadkskstaflqmdslrpedtgvyfcarpqvh
ydyngfpywgqgtpvtvssggggsggggsggggsaqdiqmtqspsslsasvgdrvtmtcsasssvsymnwyqqkpgkapkrwiyds
sklasgvparfsgsgsgtdytltisslqpedfatyycqqwsrnpptfgggtklqitsss
(SEQ ID NO: 106)

DNA sequence of ROR185:

atggaagcaccagcgcagcttctcttcctcctgctactctggctcccagataccaccggtgacatccagatgacccagtcccctc
ctccctgtccgcctccgtgggcgaccgggtgaccatcaactgccaggcctcccagtccatcgactccaacctggcctggttccagc
agaagcccggcaagccccccaagctgctgatctaccgggcctccaacctggcctccggcgtgccctcccggttctccggctccggc
tccggcaccgacttcaccctgaccatctctcctgcagcccgaggacgtggccacctactactgcctgggcggcgtgggcgccgt
gtcctaccgggacctccttcggcggcggcaccaaggtggagatcaaggg tggaggcggttcaggcggaggtggatccggcggtggcg
gctccggtggcggcggatctgaggtgcagctggtggagtccggcggcggcctggtgcagcccggccggtccctgcggctgtcctgc
accgcctccggctccgacatcaacgactaccccatcacctgggtgcggcaggcccccggcaagggcctggagtggatcggcttcat
caactccggcggctccacctggtacgcctccgggtgaagggccggttcaccatctcccgggacgactccaagtccatcgcctacc

TABLE 14-continued

Binding Domain and Polypeptide Sequences and Components

```
tgcagatgaactccctgaagaccgaggacaccgccgtgtactattgcgcccggggctactccacctactaccgggacttcaacatc
tggggccagggcaccctggtgaccgtgtcctcgagtgagcccaaatcttctgacaaaactcacacatgcccaccgtgcccagcacc
tgaagccgcggtgcaccgtcagtcttcctcttccccccaaaacccaaggacaccctcatgatctcccggacccctgaggtcacatg
cgtggtggtggacgtgagccacgaagaccctgaggtcaagttcaactggtacgtggacggcgtggaggtgcataatgccaagacaa
agccgcgggaggagcagtacaacagcacgtaccgtgtggtcagcgtcctcaccgtcctgcaccaggactggctgaatggcaaggaa
tacaagtgcgcggtctccaacaaagccctcccagcccccatcgagaaaaccatctccaaagccaaagggcagccccgagaaccaca
ggtgtacaccctgcccccatcccgggatgagctgaccaagaaccaggtcagcctgacctgcctggtcaaaggcttctatcccagcg
acatcgccgtggagtgggagagcaatgggcagccggagaacaactacaagaccacgcctcccgtgctggactccgacggctccttc
ttcctctacagcaagctcaccgtggacaagagcaggtggcagcaggggaacgtcttctcatgctccgtgatgcatgaggctctgca
caaccactacacgcagaagagcctctccctgtctccgggtctggtggaggcggttcaggcggaggtggctccggcggtggcggat
cgccgggctctcaggtccagctggtgcaatctggggctgaggtgaagaagcctgggtcctcggtgaaggtctcctgcaaggcttct
ggatataccttcagcagatctacgatgcactgggtgcgacaggccctggacaagggcttgagtggataggatacattaatcctag
cagtgcttatactaattacaatcagaaattcaaggacagagtcacgattaccgcggacaaatccacgagcacagcctacatggagc
tgagcagcctgagatctgaggacacggccgtgtattactgtgcgagaccccaagtccactatgattacaacgggtttccttactgg
ggccaaggaacccctggtcaccgtctcctcaggtggaggcggttcaggcggaggtggatccggcggtggcggatcggatatccagat
gacccagtctccatcctccctgtctgcatctgtaggagacagagtcaccatgacttgcagtgccagccaa
gtgtaagttacatgaactggtatcagcagaaaccagggaaagcccctaagagatggatttatgactcatccaaactggcttctggg
gtcccatcaaggttcagcggcagtggatctgggacagattatactctcaccatcagcagcctgcagcctgatgatttacaactta
ttactgccaacagtggagtcgtaacccacccacttttcggcggagggaccaaggtggagatcaaacggtcctccagctaa
(SEQ ID NO: 107)
```

Mature protein sequence of ROR185:

```
diqmtqspsslsasvgdrvtincqasqsidsnlawfqqkpgkppklliyrasnlasgvpsrfsgsgsgtdftltisslqpedvaty
yclggvgavsyrtsfgggtkveikgggsgggsgggsgggsevqlvesgglvqpgrslrlsctasgsdindypitwvrqapg
kglewigfinsggstwyaswvkgrftisrddsksiaylqmnslktedtavyycargystyyrdfniwgqgtlvtvsssepkssdkt
htcppcpapeaagapsvflfppkpkdtlmisrtpevtcvvvdvshedpevkfnwyvdgvevhnaktkpreeqynstyrvvsvltvl
hqdwlngkeykcavsnkalpapiektiskakgqprepqvytlppsrdeltknqvsltclvkgfypsdiavewesngqpennykttp
pvldsdgsfflyskltvdksrwqqgnvfscsvmhealhnhytqkslslspgsgggsgggsgggsgpgsqvqlvqsgpevkkpgs
svkvsckasgytfsrstmhwvrqapgqglewigyinpssaytnynqkfkdrvtitadkststaymelsslrsedtavyycarpqvh
ydyngfpywgqgtlvtvssggggsggggsggggsggggsdiqmtqspstlsasvgdrvtmtcsasssvsymnwyqqkpgkapkrwi
ydssklasgvpsrfsgsgsgtdytltisskqpddfatyycqqwsrnpptfgggtkveikrsss
(SEQ ID NO: 108)
```

DNA sequence of ROR179:

```
atggaagcaccagcgcagcttctcttcctcctgctactctggctcccagataccaccggtgacatccagatgacccagtcccccctc
ctccctgtccgcctccgtgggcgaccgggtgaccatcaactgccaggcctcccagtccatcgactccaacctggcctggttccagc
agaagcccggcaagccccccaagctgctgatctaccgggcctccaacctggcctccgcgtgccctcccggttctcccggctccggc
tccggcaccgacttcaccctgaccatctcctccctgcagccggacgtggccactactgccgtctgcctgggcggcgtggggcgt
gtcctactggacccttcggcggcggcaccaaggtggagatcaaggtgaggcggttcaggcggaggtggatccggcggtggc
gctccggtggcggcggatctgaggtgcagctggtggagtccggcggcggcctggtgcagcccggccgtccctcgcggctgtcctgc
accgcctccggctccgacatcaacgactaccccatcacctgggtgcggcaggcccccggcaagggcctggagtggatcggcttcat
caactccggcggctccacctggtacgcctcctgggtgaagggccggttcaccatctccccgggacgactccaagtccatcgcctacc
tgcagatgaactccctgaagaccgaggacaccgccgtgtactattgcgcccggggctactccacctactaccgggacttcaacatc
tggggccagggcaccctggtgaccgtgtcctcgagtgagcccaaatcttctgacaaaactcacacatgcccaccgtgcccagcacc
tgaagccgcgggtgcaccgtcagtcttcctcttccccccaaaacccaaggacaccctcatgatctcccggacccctgaggtcacat
gcgtggtggtggacgtgagccacgaagaccctgaggtcaagttcaactggtacgtggacggcgtggaggtgcataatgccaagaca
aagccgcgggaggagcagtacaacagcacgtaccgtgtggtcagcgtcctcaccgtcctgcaccaggactggctgaatggcaagga
atacaagtgcgcggtctccaacaaagccctcccagcccccatcgagaaaaccatctccaaagccaaagggcagccccgagaaccac
aggtgtacaccctgcccccatcccgggatgagctgaccaagaaccaggtcagcctgacctgcctggtcaaaggcttctatcccagc
gacatcgccgtggagtgggagagcaatgggcagccggagaacaactacaagaccacgcctcccgtgctggactccgacggctcctt
cttcctctacagcaagctcaccgtggacaagagcaggtggcagcaggggaacgtcttctcatgctccgtgatgcatgaggctctgc
acaaccactacacgcagaagagcctctccctgtctccgggtctggtggaggcggttcaggcggaggtggctccggcggtggcgga
tcgccgggctctcaggtccagctggtggagtctggggcggagtggtgcagcctgggcggtcactgaggctgtcctgcaaggcttc
tggctacacctttactagatctacgatgcactgggtaaggcaggcccctggacaaggtctggaatggattggatacattaatccta
gcagtgcttatactaattacaatcagaaattcaaggacaggttcaccatcagcgacagcaagagcacggcctccttgcag
atggacagcctgaggcccgaggacaccggcgtctatttctgtgcacggccccaagtccactatgattacaacgggtttccttactg
gggccaagggactcccgtcactgtctctagcggtggcggagggtctgggggtggcggatccggaggtggtggctctgcacaagaca
tccagatgacccagtctccaagcagcctgtctgcaagcgtggggacagggtcaccatgacctgcagtgccagctcaagtgtaagt
tacatgaactggtaccagcagaagccgggcaaggccccccaaaagatggatttatgactcatccaaactggcttctggagtccctgc
tcgcttcagtggcagtgggtctgggaccgactataccctcacaatcagcagcctgcagcccgaagattttcgccacttattactgcc
agcagtggagtcgtaacccacccacgttcggaggggggaccaagctacaaattacatcctccagctaa
(SEQ ID NO: 109)
```

Mature protein sequence of ROR179:

```
diqmtqspsslsasvgdrvtincqasqsidsnlawfqqkpgkppklliyrasnlasgvpsrfsgsgsgtdftltisslqpedvaty
yclggvgavsywtsfgggtkveikgggsgggsgggsgggsevqlvesgglvqpgrslrlsctasgsdindypitwvrqapg
kglewigfinsggstwyaswvkgrftisrddsksiaylqmnslktedtavyycargystyyrdfniwgqgtlvtvsssepkssdkt
htcppcpapeaapagsvflfppkpkdtlmisrtpevtcvvvdvshedpevkfnwyvdgvevhnaktkpreeqynstyrvvsvltvl
hqdwlngkeykcavsnkalpapiektiskakgqprepqvytlppsrdeltknqvsltclvkgfypsdiavewesngqpennykttp
pvldsdgsfflyskltvdksrwqqgnvfscsvmhealhnhytqkslslspgsggggsggggsggggspgsqvqlvqsgvvqpgr
slrlsckasgyftfrstmhwvrqapgqglewigyinpssaytnynqkfkdrftisadkskstaflqmdslrpedtgvyfcarpqvh
ydyngfpywgqgtpvtvssggggsggggsggggsaqdiqmtqspsslsasvgdrvtmtcsasssvsymnwyqqkpgkapkrwiyds
sklasgvparfsgsgsgtdytltisslqpedfatyycqqwsrnpptfgggtlkqitsss
(SEQ ID NO: 110)
```

TABLE 14-continued

Binding Domain and Polypeptide Sequences and Components

DNA sequence of ROR186:

atggaagcaccagcgcagcttctcttcctcctgctactctggctcccagataccaccggtgacatccagatgacccagtccccctc
ctccctgtccgcctccgtgggcgacgggtgaccatcaactgccaggctcccagtccatcgactccaacctggcctggttccagc
agaagcccggcaagcccccaagctgctgatctaccgggcctccaacctggcctccggcgtgccctcccggttctccggctccggc
tccggcaccgacttcaccctgaccatctcctccctgcagcccgaggacgtggccacctactactgctgggcggcgtgggcgccgt
gtcctactggacctccttcggcggcggcaccaaggtggagatcaagggtggaggcggttcaggcggaggtggatccggcggtggcg
gctccggtggcggcggatctgaggtgcagctggtggagtccggcggcggcctggtgcagcccggccggtccctcgggctgtcctgc
accgcctccggctccgacatcaacgactaccccatcacctgggtgcggcaggccccggcaagggcctggagtggatcggcttcat
caactccggcggctccacctggtacgcctcctgggtgaagggccggttccaccatctcccgggacgactccaagtccatcgcctacc
tgcagatgaactccctgaagaccgaggacaccgccgtgtactattgcgcccggggctactccacctactaccgggacttcaacatc
tggggccagggcaccctggtgaccgtgtcctcgagtgagcccaaatcttctgacaaaactcacacatgcccaccgtgcccagcacc
tgaagccgcgggtgcaccgtcagtcttcctcttccccccaaaacccaaggacaccctcatgatctcccggacccctgaggtcacat
gcgtggtggtggacgtgagccacgaagaccctgaggtcaagttcaactggtacgtggacggcgtggaggtgcataatgccaagaca
aagccgcgggaggagcagtacaacagcacgtaccgtgtggtcagcgtcctcaccgtcctgcaccaggactggctgaatggcaagga
atacaagtgcgcggtctccaacaaagccctcccagccccatcgagaaaaccatctccaaagccaaagggcagccccgagaaccac
aggtgtacaccctgcccccatcccgggatgagctgaccaagaaccaggtcagcctgacctgcctggtcaaaggcttctatcccaagc
gacatcgccgtggagtgggagagcaatgggcagccggagaacaactacaagaccacgcctcccgtgctggactccgacggctcctt
cttcctctacagcaagctcaccgtggacaagagcaggtggcagcaggggaacgtcttctcatgctccgtgatgcatgaggctctgc
acaaccactacacgcagaagagcctctccctgtctccgggttctggtggaggcggttcaggcggaggtggctccggcggtggcgga
tcgccgggctctcaggtccagctggtgcaatctgggcctgaggtgaagaagcctgggtcctcggtgaaggtctcctgcaaggcttc
tggatataccttcagcagatctacgatgcactgggtgcgacaggccccctggacaagggcttgagtggataggatacattaatccta
gcagtgcttatactaattacaatcagaaattcaaggacagagtcacgattaccgcggacaaatccacgagcacagcctacatggag
ctgagcagcctgagatctgaggacacggccgtgtattactgtgcgagaccccaagtccactatgattacaacgggtttccttactg
gggccaaggaaccctggtcaccgtctcctcaggtggaggcggttcaggcggaggtggatccggcggtggcggatcgggtggcggcg
gatctgacatccagatgacccagtctcctccaccctgtctgcatctgtaggagacagagtcaccatgacttgcagtgccagctca
agtgtaagttacatgaactggtatcagcagaaaccagggaaagccctaagagatggatttatgactcatccaaactggcttctgg
ggtcccatcaaggttcagcggcagtggatctgggacagattatactctcaccatcagcagcctgcagcctgatgattttgcaactt
attactgccaacagtggagtcgtaacccacccactttcggcggagggaccaaggtggagatcaaacggtcctccagctaa
(SEQ ID NO: 111)

Mature protein sequence of ROR186:

diqmtqspsslsasvgdrvtincqasqsidsnlawfqqkpgkppkllyrasnlasgvpsrfsgsgsgtdftltisslqpedvaty
yclggvgavsywtsfgggtkveikggggsggggsggggsggggsevqlvesgggvlvqpgrslrlsctasgsdindypitwvrqapg
kglewigfinsggstwyaswvkgrftisrddsksiaylqmnslktedtavyycargystyyrdfniwgqgtlvtvsssepkssdkt
htcppcpapeaagapsvflfppkpkdtlmisrtpevtcvvvdvshedpevkfnwyvdgvevhnaktkpreeqynstyrvvsvltvl
hqdwlngkeykcavsnkalpapiektiskakgqprepqvytlppsrdeltknqvsltclvkgfypsdiavewesngqpennyktptp
pvldsdgsfflyskltvdksrwqqgnvfscsvmhealhnhytqkslslspgsggggsggggsggggspgsqvqlvqsgpevkkpgs
svkvsckasgytfsrstmhwvrqapgqglewigyinpssaytnynqkfkdrvtitadkststaymelsslrsedtavyycarpqvh
ydyngfpywgqgtlvtvssggggsggggsggggsggggsdiqmtqspstlsasvgdrvtmtcsasssvsymnwyqqkpgkapkrwi
ydssklasgvpsrfsgsgsgtdytltisslqpddfatyycqqwsrnpptfgggtkveikrsss
(SEQ ID NO: 112)

DNA sequence of ROR181:

atggaagcaccagcgcagcttctcttcctcctgctactctggctcccagataccaccggtgacatccagatgacccagtccccctc
ctccctgtccgcctccgtgggcgacgggtgaccatcaactgccaggctcccagtccatcgactccaacctggcctggttccagc
agaagcccggcaagcccccaagctgctgatctaccgggcctccaacctggcctccggcgtgccctcccggttctccggctccggc
tccggcaccgacttcaccctgaccatctcctccctgcagcccgaggacgtggccacctactactgctgggcggcgtgggcgccgt
gtcctaccggacctccttcggcggcggcaccaaggtggagatcaagggtggaggcggttcaggcggaggtggatccggcggtggcg
gctccggtggcggcggatctgaggtgcagctggtggagtccggcggcggcctggtgcagcccggccggtccctcgggctgtcctgc
accgtgtccggcaccgacatcaacgactaccccatctcctgggtgcggcaggccccggcaagggcctggagtggatcggcttcat
caactccggcggctccacctggtacgccgactcggtgaagggccggttccaccatctcccggcactcctccaagaacaccctgtacc
tgcagatgaactccctgcgggccgaggacaccgccgtgtacttctgcgcccggggctactccacctactaccgggacttcaacatc
tggggccagggcaccctggtgaccgtgtcctcgagtgagcccaaatcttctgacaaaactcacacatgcccaccgtgcccagcacc
tgaagccgcgggtgcaccgtcagtcttcctcttccccccaaaacccaaggacaccctcatgatctcccggacccctgaggtcacat
gcgtggtggtggacgtgagccacgaagaccctgaggtcaagttcaactggtacgtggacggcgtggaggtgcataatgccaagaca
aagccgcgggaggagcagtacaacagcacgtaccgtgtggtcagcgtcctcaccgtcctgcaccaggactggctgaatggcaagga
atacaagtgcgcggtctccaacaaagccctcccagccccatcgagaaaaccatctccaaagccaaagggcagccccgagaaccac
aggtgtacaccctgcccccatcccgggatgagctgaccaagaaccaggtcagcctgacctgcctggtcaaaggcttctatcccaagc
gacatcgccgtggagtgggagagcaatgggcagccggagaacaactacaagaccacgcctcccgtgctggactccgacggctcctt
cttcctctacagcaagctcaccgtggacaagagcaggtggcagcaggggaacgtcttctcatgctccgtgatgcatgaggctctgc
acaaccactacacgcagaagagcctctccctgtctccgggttctggtggaggcggttcaggcggaggtggctccggcggtggcgga
tcgccgggctctcaggtccagctggtgagtctgggggaggcggttggtgcagcctgggcggtcactgaggctgtcctgcaaggcttc
tggctacacctttactagatctacgatgcactgggtaaggcaggcccctggacaaggtctggaatggattggatacattaatccta
gcagtgcttatactaattacaatcagaaattcaaggacaggttcacaatcagcgcagacaaatccaagagcacagccttcctgcag
atggacagcctgagggccgaggacaccggcgtctatttctgtgcacggccccaagtccactatgattacaacgggtttccttactg
gggccaagggactcccgtcactgtctctagcggtggcggaggttctggcggtggcggatccggaggtggtggctctgcacaagaca
tccagatgacccagtccaagcagcctgtctgcaagcgtggggacagggtccaccatgacctgcagtgccagctcaagtgtaagt
tacatgaactggtaccagcagaagccgggcaaggccccaaaagatggatttatgactcatccaaactggcttctggagtccctg
ctcgcttcagtggcagtgggtctgggaccgactatacccctcacaatcagcagcctgcagcccgaagatttcgccacttattactgc
cagcagtggagtcgtaacccacccacgttcggagggggaccaagctacaaattacatcctccagctaa
(SEQ ID NO: 113)

TABLE 14-continued

Binding Domain and Polypeptide Sequences and Components

Mature protein sequence of ROR181:

diqmtqspsslsasvgdrvtincqasqsidsnlawfqqkpgkppklliyrasnlasgvpsrfsgsgsgtdftltisslqpedvaty
yclggvgavsyrtsfgggtkveikggggsggggsggggsggggsevqlvesgggglvqpggslrlsctvsgtdindypiswvrqapg
kglewigfinsggstwyadsvkgrftisrhsskntlylqmnslraedtavyfcargystyyrdfniwgpgtlvtvsssepkssdkt
htcppcpapeaagapsvflfppkpkdtlmisrtpevtcvvvdvshedpevkfnwyvdgvevhnaktkpreeqynstyrvvsvltvl
hqdwlngkeykcavsnkalpapiektiskakgqprepqvytlppsrdeltknqvsltclvkgfypsdiavewesngqpennykttp
pvldgdgsfflyskltvdksrwqqgnvfscsvmhealhnhytqkslslspgsggggsggggsggggspgsqvqlvesgggvvqpgr
slrlsckasgytftrstmhwvrqapgqglewigyinpssaytnynqkfkdrftisadkskstaflqmdslrpedtgvyfcarpqvh
ydyngfpywgqgtpvtvssggggsggggsggggsaqdiqmtqspsslsasvgdrvtmtcsasssvsymnwyqqkpgkapkrwiyds
sklasgvparfsgsgsgtdytltisslqpedfatyycqqwsrnpptfgggtklqitsss
(SEQ ID NO: 114)

DNA sequence of ROR191:

atggaagcaccagcgcagcttctcttcctcctgctactctggctcccagataccaccggtgacatccagatgacccagtcccctc
ctccctgtccgcctccgtgggcgaccgggtgaccatcaactgccaggcctcccagtccatcgactccaacctggcctggttccagc
agaagcccggcaagccccccaagctgctgatctaccgggcctccaacctggcctccggcgtgccctccggttctctcggctccggc
tccggcaccgacttcaccctgaccatctcctccctgcagcccgaggacgtggccacctactactgcctgggcggcgtgggcgccgt
gtcctaccggacctccttcggcggcggcaccaaggtggagatcaagggtggaggcggttcaggcggaggtggatccggcggtggcg
gctccggtggcggcggatctgaggtgcagctggtggagtccggcggcggcctggtgcagcccggcggctccctgcggctgtcctgc
accgtgtccggcaccgacatcaacgactaccccatctcctgggtgcggcaggcccccggcaaggggcctggagtggatcggcttcatc
aactccggcggctccacctggtacgccgactcggtgaagggccggttcaccatctcccggcactcctccaagaacaccctgtacct
gcagatgaactccctgcgggccgaggacaccgccgtgtacttctgcgcccggggctactccacctactacgggacttcaacatct
ggggccagggcaccctggtgaccgtgtcctcgagtgagcccaaatcttctgacaaaactcacacatgcccaccgtgcccagcacct
gaagccgcgggtgcaccgtcagtcttcctcttcccccaaaacccaaggacacccctcatgatctcccggacccctgaggtcacatg
cgtggtggtggacgtgagccacgaagaccctgaggtcaagttcaactggtacgtggacggcgtggaggtgcataatgccaagacaa
agccgcgggaggagcagtacaacagcacgtaccgtgtggtcagcgtcctcaccgtcctgcaccaggactggctgaatggcaaggaa
tacaagtgcgcggtctccaacaaagcctcccagcccccatcgagaaaaccatctccaaagccaaagggcagccccgagaaccaca
ggtgtacaccctgcccccatcccgggatgagctgaccaagaaccaggtcagcctgacctgcctggtcaaaggcttctatccaagcga
catcgccgtggagtgggagagcaatgggcagccggagaacaactacaagaccacgcctcccgtgctggactccgacggctccttct
tcctctacagcaagctcaccgtggacaagagcaggtggcagcaggggaacgtcttctcatgctccgtgatgcatgaggctctgcac
aaccactacacgcagaagagcctctccctgtctccgggttctggtggaggcggttcaggcggaggtggctccggcggtggcggatc
gccgggctctcaggtccagctggtgcaatctgggcctgaggtgaagaagcctgggtcctcggtgaaggtctcctgcaaggcttctg
gatataccttcagcagatctacgatgcactgggtgcgacaggcccctggacaaggcttgagtggataggatacattaatcctagc
agtgcttatactaattacaatcagaaattcaaggacagagtcacgattaccgcggacaaatccacgagcacagcctacatggagct
gagcagcctgagatctgaggacacggccgtgtattactgtgcgagacccaagtccactatgattacaacgggtttccttactggg
gccaaggaaccctggtcaccgtctcctcaggtggaggcggttcaggcggaggtggatccggcggtggcggatcgggtggcggcgga
tctgacatccagatgacccagtccttccaccctgtctgcatctgtaggagacagagtcaccatcagttgcagtgcaagtcaag
tgtaagttacatgaactggtatcagcagaaaccagggaaagcccctaagagactggtttatgactcatccaaactggcttctgggg
tcccatcaaggttcagcggcagtggatctgggacagattatactctcaccatcagcagcctgcagcctgatgattttgcaacttat
tactgccaacagtggagtcgtaacccacccactttcggcggagggaccaaggtggagatcaaacggtcctccagctaa
(SEQ ID NO: 115)

Mature protein sequence of ROR191:

diqmtqspsslsasvgdrvtincqasqsidsnlawfqqkpgkppklliyrasnlasgvpsrfsgsgsgtdftltisslqpedvaty
yclggvgavsyrtsfgggtkveikggggsggggsggggsggggsevqlvesgggglvqpggslrlsctvsgtdindypiswvrqapg
kglewigfinsggstwyadsvkgrftisrhsskntlylqmnslraedtavyfcargystyyrdfniwgqgtlvtvsssepkssdkt
htcppcpapeaagapsvflfppkpkdtlmisrtpevtcvvvdvshedpevkfnwyvdgvevhnaktkpreeqynstyrvvsvltvl
hqdwlngkeykcavsnkalpapiektiskakgqprepqvytlppsrdeltknqvsltclvkgfypsdiavewesngqpennykttp
pvldsdgsfflyskltvdksrwqqgnvfscsvmhealhnhytqkslslspgsggggsggggsggggspgsqvqlvqsgpevkkpgs
svkvsckasgytfsrstmhwvrqapgqglewigyinpssaytnynqkfkdrvtitadkststaymelsslrsedtavyycarpqvh
ydyngfpywgqgtlvtvssggggsggggsggggsggggsdiqmtqspstlsasvgdrvtmtcsasssvsymnwyqqkpgkapkrwi
ydssklasgvpsrfsgsgsgtdytltisslqpddfatyycqqwsrnpptfgggtkveikrsss
(SEQ ID NO: 116)

DNA sequence of ROR182:

atggaagcaccagcgcagcttctcttcctcctgctactctggctcccagataccaccggtgacatccagatgacccagtcccctc
ctccctgtccgcctccgtgggcgaccgggtgaccatcaactgccaggcctcccagtccatcgactccaacctggcctggttccagc
agaagcccggccagccccccaagctgctgatctaccgggcctccaacctggcctccggcgtgcccgaccggttctccggctccggc
tccggcaccgacttcaccctgaccatctcctccctgcaggccgaggacgtggccacctactactgcctgggcggcgtgggcgccgt
gtcctaccggacctccttcggcggcggcaccaaggtggagatcaagggtggaggcggttcaggcggaggtggatccggcggtggcg
gctccggtggcggcggatctgaggtgcagctggtggagtccggcggcggcctggtgcagcccggccggtccctgcggctgtcctgc
accgcctccggctccgacatcaacgactaccccatcacctgggtgcggcaggcccccggccagggcctggagtggatcggcttcat
caactccggcggctccacctggtacgcctcctgggtgaagggccggttcaccatctcccgggacgactccaagtccatcgcctacc
tgcagatgaactccctgaagaccgaggacaccgccgtgtactattgcgcccgaggcttctccacctactacgggacttcaacatc
tggggccagggcaccctggtgaccgtgtcctcgagtgagcccaaatcttctgacaaaactcacacatgcccaccgtgcccagcacc
tgaagccgcgggtgcaccgtcagtcttcctcttcccccaaaacccaaggacacccctcatgatctcccggacccctgaggtcacat
gcgtggtggtggacgtgagccacgaagaccctgaggtcaagttcaactggtacgtggacggcgtggaggtgcataatgccaagaca
aagccgcgggaggagcagtacaacagcacgtaccgtgtggtcagcgtcctcaccgtcctgcaccaggactggctgaatggcaagga
atacaagtgcgcggtctccaacaaagcctcccagcccccatcgagaaaaccatctccaaagccaaagggcagccccgagaaccac
aggtgtacaccctgcccccatcccgggatgagctgaccaagaaccaggtcagcctgacctgcctggtcaaaggcttctatccaagc
gacatcgccgtggagtgggagagcaatgggcagccggagaacaactacaagaccacgcctcccgtgctggactccgacggctcctt
cttcctctacagcaagctcaccgtggacaagagcaggtggcagcaggggaacgtcttctcatgctccgtgatgcatgaggctctgc
acaaccactacacgcagaagagcctctccctgtctccgggttctggtggaggcggttcaggcggaggtggctccggcggtggcgga

TABLE 14-continued

Binding Domain and Polypeptide Sequences and Components

```
tcgccgggctctcaggtccagctggtggagtctgggggcggagtggtgcagcctgggcggtcactgaggctgtcctgcaaggcttc
tggctacaccctttactagatctacgatgcactgggtaaggcaggccccctggacaaggtctggaatggattggatacattaatccta
gcagtgcttatactaattacaatcagaaattcaaggacaggttcacaatcagcgcagacgaaatccaagagcacagccttcctgcag
atggacagcctgagcccgaggacaccggcgtctatttctgtgcacggccccaagtccactatgattacaacggggtttccttactg
gggccaagggactcccgtcactgtctctagcggtggcggagggtctgggggtggcggatccggaggtggtggctctgcacaagaca
tccagatgacccagtctccaagcagcctgtctgcaagcgtggggacagggtcaccatgacctgcagtgccagctcaagtgtaagt
tacatgaactggtaccagcagaagccgggcaaggcccccaaaagatggatttatgactcatccaaactggcttctggagtccctgc
tcgcttcagtggcagtgggtctgggaccgactataccctcacaatcagcagcctgcagcccgaagatttcgccacttattactgcc
agcagtggagtcgtaacccacccacgttcggaggggggaccaagctacaaattacatcctccagctaa
(SEQ ID NO: 117)
```

Mature protein sequence of ROR182:

```
diqmtqspsslsasvgdrvtincqasqsidsnlawfqqkpgqppklliyrasnlasgvpdrfsgsgsgtdftltissleaedvaty
yclggvgavsyrtsfgggtlveikgggsgggsgggsgggsevqlvesgggvqpgrslrlsctasgsdindypitwvrqapg
qglewigfinsggstwyaswvkgrftisrddsksiaylqmnslktedtavyycargystyyrdfniwgqgtlvtvsssepkssdkt
htcppcpapeaagapsvflfppkpkdtlmisrtpevtcvvvdvshedpevkfnwyvdgvevhnaktkpreeqynstyrvvsvltvl
hqdwlngkeykcavsnkalpapiektiskakgqprepqvytlppsrdeltknqvsltclvkgfypsdiavewesngqpennykttp
pvldsdgsfflyskltvdksrwqqgnvfscsvmhealhnhytqkslslspgsgggsgggsgggspgsqvqlvesgggvqpgrs
lrlsckasgytftrstmhwvrqapgqglewigyinpssaytnynqkfkdrftisadkskstaflqmdslrpedtgvyfcarpqvhy
dyngfpywgqgtpvtvssgggsgggsgggsaqdiqmtqspsslsasvgdrvtmtcsasssvsymnwyqqkpgkapkrwiydss
klasgvparfsgsgsgtdytltisslqpedfatyycqqwsrnpptfgggtklqitsss
(SEQ ID NO: 118)
```

DNA sequence of ROR192:

```
atggaagcaccagcgcagcttctcttcctcctgctactctggctcccagataccaccggtgacatccagatgacccagtcccccctc
ctccctgtccgcctccgtgggcgaccgggtgaccatcaactgccaggcctcccagtccatcgactccaacctggcctggttccagc
agaagcccggccagcccccaagctgctgatctaccgggcctccaacctggcctccggcgtgcccgaccggttctccggctccggc
tccggcaccgacttcaccctgaccatctctcctcccctggaggccgaggacgtggccacctactactgcctgggcggcgtgggcgccgt
gtcctaccgggacctccttcggcggcggcaccaaggtggagatcaagggtggaggcggttcaggcggaggtggatccggcggtggcg
gctccggtggcggcggatctgaggtgcagctggtggagtccgggggcctggtgcagcccgccggtcctcggctgtcctgc
accgcctccggctccgacatcaacgactaccccatcacctgggtgcggcaggcccccggccagggcctggagtggatcggcttcat
caactccggcggctccacctggtacgcctcctgggtgaagggccggttcaccatctcccgggacgactccaagtccatcgcctacc
tgcagatgaactccctgaagaccgaggacaccgccgtgtactattgcgcccggggctactccacctactaccgggacttcaacatc
tggggccagggcaccctggtgaccgtgtcctcgagtgagcccaaatcttctgacaaaactcacacatgcccaccgtgcccagcacc
tgaagccgcgggtgcaccgtcagtcttcctatccccccaaaacccaaggacaccctcatgatctcccggacccctgaggtcacatg
cgtggtggtggacgtgagccacgaagacccctgaggtcaagttcaactggtacgtggacggcgtggaggtgcataatgccaagacaa
agccgcgggaggagcagtacaacagcacgtaccgtgtggtcagcgtcctcaccgtcctgcaccaggactggctgaatggcaaggaa
tacaagtgcgcggtctccaacaaagccctcccagccccatcgagaaaaccatctccaaagccaaagggcagccccgagaaccaca
ggtgtacaccctgcccccatcccgggatgagctgaccaagaaccaggtcagcctgacctgcctggtcaaaggcttctatccaagcg
acatcgccgtggagtgggagagcaatgggcagccggagaacaactacaagaccacgcctcccgtgctggactccgacggctccttc
ttcctctacagcaagctcaccgtggacaagagcaggtggcagcaggggaacgtcttctcatgctccgtgatgcatgaggctctgca
caaccactacacgcagaagagcctctccctgtctccgggtctgtggaggcggttcaggcggaggtggatccggcggtggcggat
cgccgggctctcaggtccagctggtgcaatctgggcctgaggtgaagaagcctgggtcctcggtgaaggtctcctgcaaggcttct
ggatatacctttcagcagatctacgatgcactgggtgcgacaggcccctggacaagggcttgagtggataggatacattaatcctag
cagtgcttatactaattacaatcagaaattcaaggacagagtcacgattaccgcggacaaatccacgagcacagcctacatggagc
tgagcagcctgagatctgaggacacggccgtgtattactgtgcgagacccaagtccactatgattacaacgggtttccttactgg
ggccaaggaaccctggtcaccgtctcctcaggtggaggcggttcaggcggaggtggatccggcggtggcggatcgggtggcggcgg
atctgacatccagatgacccagtctccttccaccctgtctgcatctgtaggagacagagtcaccatgacttgcagtgccagctcaa
gtgtaagttacatgaactggtatcagcagaaaccagggaaagcccctaagagatggatttatgactcatccaaactggcttctggg
gtcccatcaaggttcagcggcagtggatctgggacagattatactctcaccatcagcagcctgcagcctgatgatttgcaacttta
ttactgccaacagtggagtcgtaacccacccactttcggcggagggaccaaggtggagatcaaacggtcctccagctaa
(SEQ ID NO: 119)
```

Mature protein sequence of ROR192:

```
diqmtqspsslsasvgdrvtincqasqsidsnlawfqqkpgqppklliyrasnlasgvpdrfsgsgsgtdftltissleaedvaty
yclggvgavsyrtsfgggtkveikgggsgggsgggsgggsevqlvesgggvqpgrslrlsctasgsdindypitwvrqapg
qglewigfinsggstwyaswvkgrftisrddsksiaylqmnslktedtavyycargystyyrdfniwgqgtlvtvsssepkssdkt
htcppcpapeaagapsvflfppkpkdtlmisrtpevtcvvvdvshedpevkfnwyvdgvevhnaktkpreeqynstyrvvsvltvl
hqdwlngkeykcavsnkalpapiektiskakgqprepqvytlppsrdeltknqvsltclvkgfypsdiavewesngqpennykttp
pvldsdgsfflyskltvdksrwqqgnvfscsvmhealhnhytqkslslspgsgggsgggsgggspgsqvqlvqsgpevkkpgs
svkvsckasgytfsrstmhwvrqapgqglewigyinpssaytnynqkfkdrvtitadkststaymelsslrsedtavyycarpqvh
ydyngfpywgqgtlvtvssgggsgggsgggsgggsdiqmtqspstlsasvgdrvtmtcsasssvsymnwyqqkpgkapkrwi
ydssklasgvpsrfsgsgsgtdytltisslqpddfatyycqqwsrnpptfgggtkveikrsss
(SEQ ID NO: 120)
```

Chimeric bispecific anti-CD123 (VLVH) x anti-CD3 (TSC456) scFv-Fc-scFv

```
Dimmsqspsslavsvgekftmtckssqslffgstqknylawyqqkpgqspkliiywastresgvpdrftgsgsgtdftlaissvmp
edlavyycqqyynypwtfgggtkleikgggsgggsgggsgggsvqlqesgpglvkpsqslsltcsvtdysitsgyywnwirq
fpgnklewmgyisydgsnnynpslknrisitrdtsknqfflklssvttedtayycsrgegfyfdswgqgttlvsssepkssdlt
htcppcpapeaagapsvflfppkpkdtlmisrtpevtcvvvdvshedpevkfnwyvdgvevhnaktkpreeqynstyrvvsvltvl
hqdwlngkeykcavsnkalpapiektiskakgqprepqvytlppsrdeltknqvsltclvkgfypsdiavewesngqpennykttp
pvldsdgsfflyskltvdksrwqqgnvfscsvmhealhnhytqkslslspgsgggsgggsgggspgsqvqlvqsgpevkkpgs
svkvsckasgytfsrstmhwvrqapgqglewigyinpssaytnynqkfkdrvtitadkststaymelsslrsedtavyycarpqvhy
dyngfpywgqgtlvtvssgggsgggsgggsgggsdiqmtqspstlsasvgdrvtmtcsasssvsymnwyqqkpgkapkrwiy
```

TABLE 14-continued

Binding Domain and Polypeptide Sequences and Components dssklasgvpsrfsgsgsatdytltisslqpddfatyycqqwsrnpptfgggtkveikrsss
(SEQ ID NO: 197)

Chimeric bispecific anti-CD123 (VHVL) x anti-CD3 (TSC456) sc-Fv-Fc-scFv

Vqlqesgpglvkpsqslsltcsvtdysitsgyywnwirqfpgnklewmgyisydgsnnynpslknrisitrdtsknqfflklssvt
tedtatyycsrgegfyfdswgqgttltvssggggsggggsggggsggggsdimmsqspsslavsvgekftmtckssqslffgstqk
nylawyqqkpgqspklliywastresgvpdrftgsgsgtdftlaissvmpedlavyycqqyynypwtfggtkleiksssepkssd
kthtcppcpapeaagapsvflfppkpkdtlmisrtpevtcvvvdvshedpevkfnwyvdgvevhnaktkpreeqynstyrvvsvlt
vlhqdwlngkeykcavsnkalpapiektiskakgqprepqvytlppsrdeltknqvsltclvkgfypsdiavewesngqpennykt
tppvldsdgsfflyskltvdksrwqqgnvfscsvmhealhnhytqkslslspgsggggsggggsggggspgsqvqlvqsgpevkkp
gssvkvsckasgytfsrstmhwvrqapgqglewigyinpssaytnynqkfkdrvtitadkststaymelsslrsedtavyycarpq
vhydyngfpywgqgtlvtvssggggsggggsggggsggggsdiqmtqspstlsasvgdrvtmtcsasssvsymnwyqqkpgkapkr
wiydssklasgvpsrfsgsgsgtdytltisslqpddfatyycqqwsrnpptfgggtkveikrsss
(SEQ ID NO: 198)

DNA sequence of TSC471:

atggaagcaccagcgcagcttctcttcctcctgctactctggctcccagataccaccggtgatatccagatgacccagtctccatc
cgccatgtctgcatctgtaggagacagagtcaccatcacttgccgggcgagtaagagcattagcaaatatttagcctggtttcagc
agaaaccagggaaagttcctaagctccgcatccattctggatctactttgcaatcaggggtcccatctcggttcagtggcagtgga
tctgggacagaattactctcaccatcagcagcctgcagcctgaagattttgcaacttattactgtcaacagcatattgaataccc
gtggacgttcggccaagggaccaaggtggaaatcaaacgaggtggcggaggtctggggtggcggatccggaggttggtggctctc
aggtccagctggtacagtctggggctgaggtgaagaagcctggggcttcagtgaaggtctcctgcaaggcttctggatacacattc
actgactactacatgcactgggtgcgacaggcccctggacaaggcttgagtggatgggatattttaatccttataatgattatac
tagatacgcacagaagttccagggcagagtcaccatgaccagggacacgtctatcagcacagcctacatggagctgagcagcctga
gatctgacgacacggccgtgtattactgtgcaagatcggatggttactacgatgctatggactactggggtcaaggaaccacagtc
accgtctcctcgagtgagcccaaatcttctgacaaaactcacacatgcccaccgtgcccagcacctgaagccgcgggtgcaccgtc
agtcttcctcttccccccaaaaccccaaggacaccctcatgatctcccgacccctgaggtcacatgcgtggtggtggacgtgagcc
acgaagaccctgaggtcaagttcaactggtacgtggacggcgtggaggtgcataatgccaagacaaagccgcgggaggagcagtac
aacagcacgtaccgtgtggtcagcgtcctcaccgtcctgcaccaggactggctgaatggcaaggaatacaagtgcgcggtctccaa
caaagccctcccagccccccatcgagaaaaccatctccaaagccaaagggcagccccgagaaccacaggtgtacaccctgcccccat
cccgggatgagctgaccaagaaccaggtcagcctgacctgcctggtcaaaggcttctatcccagcgacatcgccgtggagtgggag
agcaatgggcagccggagaacaactacaagaccacgcctcccgtgctggactccgacggctccttcttcctctacagcaagctcac
cgtggacaagagcaggtggcagcaggggaacgtcttctcatgctccgtgatgcatgaggctctgcacaaccactacacgcagaaga
acctctccctgtaccgggttccggagagtggcggttcggagaggtggcggtcaggaggtggggctctccttcacaggtgcagctgg
tgcagtctggtcctgaggtgaaaaagcctggctccagcgtgaaggtgtcctgcaaggccagcggatacaccttagccggtccacc
atgcattgggtgaggcaggctcctggacagggcctggagtggatcggctacatcaaccccagcagcgcttataccaactacaatca
gaagtttaaggaccgggtgaccatcaccgccgataagtccaccagcaccgcctacatggagctgtccagcctgaggagcgaggata
ccgccgtgtactattgcgcccggcccaggtccattacgactacaacggcttcccctattggggccagggaaccctggtgaccgtg
tccagcggtggcggtggcagcagcggcggcggctctggcggaggtggcagcggcgagggggctccgacattcagatgacccagtc
ccctccaccctgtccgctaacgtgggcgatcgggtgaccatgacctgcaacgccagcagctccatgtcctacatgaactggtacc
agcagaagcccggcaaggctcccaaaaggtggatttacgactccaacaagctggcctaggtgtcccaacaggttctctggtagcg
acagcggcacaaactacacccctaaccatcctcctgcagcccgacgatttcgccacctactattgccagcagtggtccggaat
ccccctaccatggcgacggcaccaaggtggagatcaagaggagctaa
(SEQ ID NO: 205)

Mature protein sequence of TSC471:

Diqmtqspspsamsasvgdrvtitcrasksiskylawfqqkpgkvpklrihsgstlqsgvpsrfsgsgsgteftltisslqpedfaty
ycqqhieypwtfgqgtkveikrggggsggggsggggsqvqlvqsgaevkkpgasvkvsckasgytftdyymhwvrqapgqglewmg
yfnpyndytryaqkfqgrvtmtrdtsistaymelsslrsddtavyycarsdgyydamdywgqgttvtvsssepkssdkthtcppcp
apeaagapsvflfppkpkdtlmisrtpevtcvvvdvshedpevkfnwyvdgvevhnaktkpreeqynstyrvvsvltvlhqdwlng
keykcavsnkalpapiektiskakgqprepqvytlppsrdeltknqvsltclvkgfypsdiavewesngqpennykttppvldsdg
sfflyskltvdksrwqqgnvfscsvmhealhnhytqkslslspgsggggsggggsggggspsqvqlvqsgpevkkpgssvkvscka
sgytfsrstmhwvrqapgqglewigyinpssaytnynqkfkdrvtitadkststaymelsslrsedtavyycarpqvhydyngfpy
wgqgtlvtvssggggsggggsggggsggggsdiqmtqspstlsasvgdrvtmtcsasssvsymnwyqqkpgkapkrwiydssklas
gvpsrfsgsgsgtdytltisslqpddfatyycqqwsrnpptfgggtkveikrs
(SEQ ID NO: 206)

DNA sequence of ROR243:

atggaggctcccgctcagctgctgttcctcctgctgctctggctgcccgacaccacaggcgacatccagatgacccagtcccttc
ctccctgtccgctagcgtgggcgatagggtgaccatcaactgccaggcctcccagtccattgactccaatctggcctggttccagc
agaagcccggacagccccccaagctgctgatttacagggcctccaacctggctccggcgtgcctgacaggttctccggatccggc
agcggcaccgacttcacccctgaccatctcctccctggaggccgaggatgtcgccacctactactgtcgggcggcgtgggcgctgtg
agctatcggaccctcctcggcggcggcaccaaggtggagatcaagggcggcggcggcagcggcggcggcggcagcggcggcggagg
ctccggcggcggcggcagcgaggtgcagctggtggaaagcggaggaggcctggtgcagcctggaaggtccctgaggctgtcctgca
cagccagcggctccgacatcaacgactacccccatcacctgggtgaggcaggctcctggccagggcctggaatggatcggctttatc
aacagcggcggcagcacctggtatgctcctgggtgaaggggccggttcaccattagcagggacgactccaagtccattgcctact
gcagatgaactccctgaagaccgaggacaccgccgtgtactactgcgccaggggctacagcacctattaccgggactttaacatct
ggggccagggcacactggtcaccgtgtcctcgagtgagcccaaatcttctgacaaaactcacacatgcccaccgtgcccagcacct
gaaccgcgggtgcaccgtcagtcttcctcttccccccaaaaccccaaggacaccctcatgatctcccgacccctgaggtcacatg
cgtggtggtggacgtgagccacgaagaccctgaggtcaagttcaactggtacgtggacggcgtggaggtgcataatgccaagacaa
agccgcgggaggagcagtacaacagcacgtaccgtgtggtcagcgtcctcaccgtcctgcaccaggactggctgaatggcaaggaa
tacaagtgcgcggtctccaacaaagccctcccagccccatcgagaaaaccatctccaaagccaaagggcagccccgagaaccaca
ggtgtacaccctgcccccatcccgggatgagctgaccaagaaccaggtcagcctgacctgcctggtcaaaggcttctatccaagcg
acatcgccgtggagtgggagagcaatgggcagccggagaacaactacaagaccacgcctcccgtgctggactccgacggctccttc

TABLE 14-continued

Binding Domain and Polypeptide Sequences and Components

```
ttcctctacagcaagctcaccgtggacaagagcaggtggcagcagggggaacgtcttctcatgctccgtgatgcatgaggctctgca
caaccactacacgcagaagagcctctccctgtctccgggttccggaggaggggggttcaggtggggaggttctggcggcgggggaa
gcccttcacaggtgcaactggtgcagagtggaccccgaggttaaaaaaccagggtcctccgttaaggttagctgcaaagcctctggc
tacacattttccaggagtacaatgcactgggtgaggcaggctcctggacagggactcgagtggatcgggtatatcaacccatctag
cgcctataccaattacaaccaaaagtttaaggaccgagttaccattaccgctgacaaatccaccagtacagcttatatggagctgt
catctcttaggtccgaggacactgctgtttattactgcgctcgtcctcaggttcactatgactataatggttttccctactgggt
cagggaaccctggtgactgtctcttctagcggtggaggcagcggtggggtgggtctggaggcggtggcagtggcggcgagggctc
tgatattcagatgactcagtctcctagcactctcagcgccaacgtggggatcgtgtgacaatgacttgctccgctagcaatagtg
tgtcttacatgaattggtatcagcagaagcccgggaaagcacctaagcactggatctatgactcttccaagctggcaagtggtgtc
ccctcacggttctctggctcaggttctggtactgactatactttgactatctcctccctccagcccgatgatttcgctacctatta
ttgtcagcagtgaagccgtaacccacccacttcggaggcgataccaaagtggagatcaaaaggtcatga
(SEQ ID NO: 207)
```

Mature protein sequence of ROR243:

```
Diqmtqspsslsasvgdrvtincqasqsidsnlawfqqkpgqppkklliyrasnlasgvpdrfsgsgsgtdftltissleaedvaty
yclggvgavsyrtsfgggtkveikgggsgggsgggsgggsevqlvesgglvqpgrslrlsctasgsdindypitwvrqapg
qglewigfinsggstwyaswvkgrftisrddsksiaylqmnslktedtavyycargystyyrdfniwgqgtlvtvsssepkssdkt
htcppcpapeaagapsvflfppkpkdtlmisrtpevtcvvvdvshedpevkfnwyvdgvevhnaktkpreeqynstyrvvsvltvl
hqdwlngkeykcavsnkalpapiektiskakgqprepqvytlppsrdeltknqvsltclvkgfypsdiavewesngqpennykttp
pvldsdgsfflyskltvdksrwqqgnvfscsvmhealhnhytqkslslspgsgggsgggsgggspsqvqlvqsgpevkkpgss
vkvsckasgytfsrstmhwvrqapgqglewigyinpssaytnynqkfkdrvtitadkststaymelsslrsedtavyycarpqvhy
dyngfpywgqgtlvtvssgggsgggsgggsgggsdiqmtqspstlsasvgdrvtmtcsasssvsymnwyqqkpgkapkrwiy
dssklasgvpsrfsgsgsgtdytltisslqpddfatyycqqwsrnpptfgggtkveikrs
(SEQ ID NO: 208)
```

DNA sequence of TSC266:

```
atggaagcaccagcgcagcttctcttcctcctgctactctggctcccagataccaccggtgatatccagatgacccagtctccatc
cgccatgtctgcatctgtaggagacagagtcaccatcacttgccgggcgagtaagagcattagcaaatatttagcctggtttcagc
agaaaccagggaaagttcctaagctccgcatccattctggatctactttgcaatcaggggtcccatctcggttcagtggcagtgga
tctgggacagaatttactctcaccatcagcagcctgcagcctgaagattttgcaacttattactgtcaacagcatattgaataccc
gtggacgttcggccaagggaccaaggtggaaatcaaacgaggtggcggaggtctgggggtggcggatccggaggtggtggctctc
aggtccagctggtacagtctggggctgaggtgaagaagcctggggcttcagtgaaggtctcctgcaaggcttctggatacacattc
actgactactacatgcactgggtgcgacaggcccctggacaagggcttgagtggatgggatattttaatccttataatgattatac
tagatacgcacagaagttccagggcagatcaccatgaccagggacacgtctatcagcacagcctacatggagctgagcagcctga
gatctgacgacacggccgtgtattactgtgcaagatcggatggttactacgatgctatggactactgggtcaaggaaccacagtc
accgtctcctcgagtgagcccaaatcttctgacaaaactcacacatgccaccgtgcccagcacctgaagccgcgggtgcaccgtc
agtcttcctcttcccccaaaacccaaggacaccctcatgatctcccggacccctgaggtcacatgcgtggtggtggacgtgagcc
acgaagaccctgaggtcaagttcaactggtacgtggacggcgtggaggtgcataatgccaagacaaagccgcgggaggagcagtac
aacagcacgtaccgtgtggtcagcgtcctcaccgtcctgcaccaggactggctgaatggcaaggcgtacgcgtgcgcggtctccaa
caaagccctcccagcccccatcgagaaaaccatctccaaagccaaagggcagccccgagaaccacaggtgtacaccctgcccccat
cccgggatgagctgaccaagaaccaggtcagcctgacctgcctggtcaaaggcttctatccaagcgacatcgccgtggagtgggag
agcaatgggcagccggagaacaactacaagaccacgcctcccgtgctggactcctccttcttcctctacagcaagctcac
cgtggacaagagcaggtggcagcaggggaacgtcttctcatgctccgtgatgcatgaggctctgcacaaccactacacgcagaaga
gcctctccctgtctccgggtcagaggcacaacaattcttccctgaatacaggaactcagatggcaggtcattctccgaattctcag
gtccagctggtggagtctgggggcggagtggtgcagcctgggcggtcactgaggctgtcctgcaaggcttctggctacacctttac
tagatctacgatgcactgggtaaggcaggcccctggacaaggtctggaatggattggatacattaatcctagcagtgcttatacta
attacaatcagaaattcaaggacaggttcacaatcagcgcagacaaatccaagagcacagccttcctgcagatggacagcctgagg
cccgaggacaccggcgtctatttctgtgcacggccccaagtccactatgattacaacgggtttccttactgggccaagggactcc
cgtcactgtctctagcggtggcggagggtctgggggtggcggatccggaggtggtggctctgcacaagacatccagatgacccagt
ctccaagcagcctgtctgcaagcgtggggggacagggtcaccatgacctgcagtgccagctcaagtgtaagttacatgaactggtac
cagcagaagccgggcaaggccccccaaaagatggatttatgactcatccaaactggcttctggagtccctgctcgcttcagtggcag
tgggtctgggaccgactataccaccacaatcagcagcctgacgcccgaagatttcgccacttattactgccagcagtggagtcgtaa
cccacccacgttcggaggggggaccaagctacaaattacatcctccagctaa
(SEQ ID NO: 209)
```

Proten sequence of TSC266:

```
Diqmtqspspsamsasvadrvtitcrasksiskylawfqqkpgkvpklrihsgstlqsgvpsrfsgsgsgteftltisslqpedfaty
ycqqhieypwtfgqgtkveikrgggsgggsgggsgggsvqlvqsgaevkkpgasvkvsckasgytftdyymhwvrqapgqglewmg
yfnpyndytryaqkfqgrvtmtrdtsistaymelsslrsddtavyycarsdgyydamdywgqgtvtvsssepkssdkthtcppcp
apeaagapsvflfppkpkdtlmisrtpevtcvvvdvshedpevkfnwyvdgvevhnaktkpreegynstyrvvsvltvlhqdwlng
kayacavsnkalpapiektiskakgqprepqvytlppsrdeltknqvsltclvkgfypsdiavewesngqpennykttppvldsdg
sfflyskltvdksrwqqgnvfscsvmhealhnhytqkslslspgqrhnnsslntgtqmaghspnsqvqlvesgggvvqpgrslrls
ckasgytftrstmhwvrqapgqglewigyinpssaytnynqkfkdrftisadkskstaflqmdslrpedtgvyfcarpqvhydyng
fpywgqgtpvtvssgggsgggsgggsaqdiqmtqspsslsasvadrvtmtcsasssvsymnwyqqkpgkapkrwiydssklas
gvparfsgsgsgtdytltisslqpedfatyycqqwsrnpptfgggtklqitsss
(SEQ ID NO: 210)
```

DNA sequence of ROR206:

```
atggaagcaccagcgcagcttctcttcctcctgctactctggctcccagataccaccggtgacatccagatgacccagtcccctc
ctccctgtccgcctccgtgggcgaccgggtgaccatcaactgccaggcctccagtccatcgactccaacctggcctggttccagc
agaagcccggcaagcccccaagctgctgatctaccggcctccaacctggcctccggcgtgcctcccggttctccggctccggc
tccggcaccgacttcaccctgaccatctcctcccctgcagcccgaggacgtggccacctactactgctgggcggcgtgggcgccgt
gtcctaccgacctccttcggcggcggcaccaaggtggagatcaaggtggaggcggttcaggcggaggtggatccggcggtggcg
gctccggtggcggcggatctgaggtgcagctggtggagtccggcggcggcctggtgcagcccggccggtccctgcggctgtcctgc
```

TABLE 14-continued

Binding Domain and Polypeptide Sequences and Components accgcctccggctccgacatcaacgactaccccatcacctgggtgcggcaggccccggcaagggcctggagtggatcggcttcat
caactccggcggctccacctggtacgcctcctgggtgaagggccggttcaccatctcccgggacgactccaagtccatcgcctacc
tgcagatgaactccctgaagaccgaggacaccgccgtgtactattgcgcccggggctactccacctactaccgggacttcaacatc
tgggcaggcaccctggtgaccgtgtcctcgagtgagcccaaatcttctgacaaaactcacacatgcccaccgtgcccagcacc
tgaagcgcgggtgcaccgtcagtcttcctcttcccccaaaacccaaggacaccctcatgatctcccggacccctgaggtcacat
gcgtggtggtggacgtgagccacgaagaccctgaggtcaagttcaactggtacgtggacggcgtggaggtgcataatgccaagaca
aagccgcgggaggagcagtacaacagcacgtaccgtgtggtcagcgtcctcaccgtcctgcaccaggactggctgaatggcaagga
atacaagtgcgcggtctccaacaaagcctcccagccccatcgagaaaaccatctccaaagccaaagggcagccccgagaaccac
aggtgtacaccctgcccccatcccgggatgagctgaccaagaaccaggtcagcctgacctgcctggtcaaaggcttctatccaagc
gacatcgccgtggagtgggagagcaatgggcagccggagaacaactacaagaccacgcctcccgtgctggactccgacggctcctt
cttcctctacagcaagctcaccgtggacaagagcaggtggcagcaggggaacgtcttctcatgctccgtgatgcatgaggctctgc
acaaccactacacgcagaagagcctctccctgtctccgggttctggtggaggcggttcaggcggaggtggctccggcggtggcgga
tcgccgggctctcaggtccagctggtggagtctgggggcggagtggtgcagcctgggcggtcactgaggctgtcctgcaaggcttc
tggctacacctttactagatctacgatgcactgggtaaggcaggcccctggacaaggtctggaatggattggatacattaatccta
gcagtgcttatactaattacaatcagaaattcaaggacaggttcacaatcagcgcagacaaatccaagagcacagccttcctgcag
atggacagcctgaggcccgaggacaccggcgtctatttctgtgcacggcccaagtccactatgattacaacgggtttccttactg
gggccaagggactcccgtcactgtctctagcggtggcggagggtctgggggtggcggatccggaggtggtggctctgcacaagaca
tccagatgacccagtctccaagcagcctgtctgcaagcgtgggggacagggtcaccatgacctgcagtgccagctcaagtgtaagt
tacatgaactggtaccagcagaagccgggcaaggcccccaaaagatggatttatgactcatccaaactggcttctggagtccctgc
tcgcttcagtggcagtgggtctgggaccgactatacccctcacaatcagcagcctgcagcccgaagatttcgccacttattactgcc
agcagtggagtcgtaacccacccacgttcggaggggggaccaagctacaaattacatcctccagc
(SEQ ID NO: 211)

Proten sequence of ROR206:

MEAPAQLLFLLLLWLPDTTGDIQMTQSPSSLSASVGDRVTINCQASQSIDSNLAWFQQKP
GKPPKLLIYRASNLASGVPSRFSGSGSGTDFTLTISSLQPEDVATYYCLGGVGAVSYRTSF
GGGTKVEIKGGGGSGGGGSGGGGSGGGGSEVQLVESGGGLVQPGRSLRLSCTASGSDI
NDYPITWVRQAPGKGLEWIGFINSGGSTWYASWVKGRFTISRDDSKSIAYLQMNSLKTE
DTAVYYCARGYSTYYRDFNIWGQGTLVTVSSSEPKSSDKTHTCPPCPAPEAAGAPSVFL
FPPKPKDTLMISRTPEVTCVVVDVSHEDPEVKFNWYVDGVEVHNAKTKPREEQYNSTY
RVVSVLTVLHQDWLNGKEYKCAVSNKALPAPIEKTISKAKGQPREPQVYTLPPSRDELT
KNQVSLTCLVKGFYPSDIAVEWESNGQPENNYKTTPPVLDSDGSFFLYSKLTVDKSRWQ
QGNVFSCSVMHEALHNHYTQKSLSLSPGSGGGGSGGGGSGGGGSPGSQVQLVESGGGV
VQPGRSLRLSCKASGYTFTRSTMHWVRQAPGQGLEWIGYINPSSAYTNYNQKFKDRFTI
SADKSKSTAFLQMDSLRPEDTGVYFCARPQVHYDYNGFPYWGQGTPVTVSSGGGGSG
GGGSGGGGSAQDIQMTQSPSSLSASVGDRVTMTCSASSSVSYMNWYQQKPGKAPKRWI
YDSSKLASGVPARFSGSGSGTDYLTISSLQPEDFATYYCQQWSRNPPTFGGGTKLQITS
SS (SEQ ID NO: 212)

DNA sequence of ROR207:

atggaagcaccagcacagcttctcttcctcctgctactctggctcccagataccaccggtgacatccagatgacccagtcccctc
ctccctgtccgcctccgtgggcgaccgggtgaccatcaactgccagcctccagtccatcgactccaactctggcctggttccagc
agaagcccggcaagcccccaagctgctgatctaccgggcctccaacctggcctccggcgtgcctcccggttctccggctccggc
tccggcaccgacttcaccctgaccatctcctccctgcagcccgaggacgtggccacctactactgcctgggcggcgtgggcgccgt
gtcctaccggacctccttcggcggcggcaccaaggtggagatcaagggtggaggcggttcaggcggaggtggatccggcggtggcg
gctccggtggcggcggatctgaggtgcagctggtggagtccgggggcggcctggtgcagccgggccggtccctgcggctgtcctgc
accgcctccggctccgacatcaacgactaccccatcacctgggtgcggcaggccccggcaaaaacctggagtggatcggcttcat
caactccggcggctccacctggtacgcctcctgggtgaagggccggttcaccatctcccgggacaactccaagtccatcgcctacc
tgcagatgaactccctgaagaccgaggacaccgccgtgtactattgcgcccggggctactccacctactaccgggacttcaacatc
tggggccaaaacaccctggtaacgtgtcctcgagtgagcccaaatcttctgacaaaactcacacatgcccaccgtgcccagcacc
tgaagcgcgggtgcaccgtcagtcttcctcttcccccaaaacccaaggacaccctcatgatctcccggacccctgaggtcacat
gcgtggtggtggacgtgagccacgaagaccctgaggtcaagttcaactggtacgtggacggcgtggaggtgcataatgccaagaca
aagccgcgggaggagcagtacaacagcacgtaccgtgtggtcagcgtcctcaccgtcctgcaccaggactggctgaatggcaagga
atacaagtgcgcggtctccaacaaagcctcccagccccatcgagaaaaccatctccaaagccaaagggcagccccgagaaccac
aggtgtacaccctgcccccatcccgggatgagctgaccaagaaccaggtcagcctgacctgcctggtcaaaggcttctatccaagc
gacatcgccgtggagtgggagagcaatgggcagccggagaacaactacaagaccacgcctcccgtgctggactccgacggctcctt
cttcctctacagcaagctcaccgtggacaagagcaggtggcagcaggggaacgtcttctcatgctccgtgatgcatgaggctctgc
acaaccactacacgcagaagagcctctccctgtctccgggttctggtggaggcggttcaggcggaggtggctccggcggtggcgga
tcgccgggctctcaggtccagctggtgcaatctgggcctgaggtgaagaagcctgggtcctgcaaggtctcctgcaaggcttc
tggatataccttcagcagatctacgatgcactgggtgcgacaggcccctggacaagggcttgagtggataggatacattaatccta
gcagtgcttatactaattacaatcagaaattcaaggacagagtcacgattaccgcggacaaatccacgagcacagcctacatggag
ctgagcagcctgagatctgaggacacggccgtgtattactgtgcgagaccccaagtccactatgattacaacgggtttccttactg
gggccaaggaaccctggtcaccgtctcctcaggtggaggcggttcaggcggaggtggctccggcggtggcggatcggaggtggcg
gatctgacatccagatgacccagtctccttccacccctgtctgcatctgtaggagacagagtcaccatcacttgcagtgccagctca
agtgtaagttacatgaactggtatcagcagaaaccagggaaagccccctaagagatggatttatgactcatccaaactggcttctgg
ggtcccatcaaggttcagcggcagtggatctgggacagattatactctcaccatcagcagcctgcagcctgatgattttgcaactt
attactgccaacagtggagtcgtaacccacccactttcggcggagggaccaaggtggagatcaaacggtcctccagc
(SEQ ID NO: 213)

Protein sequence of ROR207:

MEAPAQLLFLLLLWLPDTTGDIQMTQSPSSLSASVGDRVTINCQASQSIDSNLAWFQQKP
GKPPHLLIYRASNLASGVPSRFSGSGSGTDFTLTISSLQPEDVATYYCLGGVGAVSYRTSF
GGGTKVEIKGGGGSGGGGSGGGGSGGGGSEVQLVESGGGLVQPGRSLRLSCTASGSDI
NDYPITWVRQAPGKGLEWIGFINSGGSTWYASWVKGRFTISRDDSKSIAYLQMNSLKTE
DTAVYYCARGYSTYYRDFNIWGQGTLVTVSSSEPKSSDKTHTCPPCPAPEAAGAPSVFL

TABLE 14-continued

Binding Domain and Polypeptide Sequences and Components

FPPKPKDTLMISRTPEVTCVVVDVSHEDPEVKFNWYVDGVEVHNAKTKPREEQYNSTY
RVVSVLTVLHQDWLNGKEYKCAVSNKALPAPIEKTISKAKGQPREPQVYTLPPSRDELT
KNQVSLTCLVKGFYPSDIAVEWENSGQPENNYKTTPPVLDSDGSFFLYSKLTVDKSRWQ
QGNVFSCSVMHEALHNHYTQKSLSLSPGSGGGGSGGGGSGGGGSPGSQVQLVQSGPEV
KKPGSSVKVSCKASGYFTSRSTMHWVRQAPGQGLEWIGYINPSSAYTNYNQKFKDRVT
ITADKSTSTAYMELSSLRSEDTAVYYCARPQVHYDYNGFPYWGQGTLVTVSSGGGGSG
GGGSGGGGSGGGGSDIQMTQSPSTLSASVGDRVTMTCSASSSVSYMNWYQQKPGKAP
KRWIYDSSKLASGVPSRFSGSGSGTDYTLTISSLQPDDFATYYCQQWSRNPPTFGGGTKV
EIKRSSS
(SEQ ID NO: 214)

DNA sequence of ROR208:

atggaagcaccagcgcagcttctcttcctcctgctactctggctcccagataccaccggtgacatccagatgacccagtccccctc
ctccctgtccgcctccgtgggcgacgggtgaccatcaactgccaggcctcccagtccatcgactccaacctggcctggttccagc
agaagcccggccagcccccaagctgctgatctaccgggcctccaacctggcctccggcgtgcccgaccggttctccggctccggc
tccggcaccgacttcaccctgaccatctcctccctggaggccgaggacgtggccacctactactgcctgggcggcgtgggcgccgt
gtcctaccgggacctccttcggcggcggcaccaaggtggagatcaagggtggaggcggttcaggcggaggtggatccggcggtggcg
gctccggtggcggcggatctgaggtgcagctggtggagtccggcggcggcctggtgcagcccggccggtccctgcggctgtcctgc
accgcctccggctccgacatcaacgactaccccatcacctgggtgcggcaggcccccggccagggcctggagtggatcggcttcat
caactccggcggctccacctggtacgcctcctgggtgaagggccggttcaccatctcccgggacgactccaagtccatcgcctacc
tgcagatgaactccctgaagaccgaggacaccgccgtgtactattgcgcccggggctactccacctactaccggggacttcaacatc
tggggccagggcaccctggtgaccgtgtcctcgagtgagcccaaatcttctgacaaaactcacacatgcccaccgtgcccagcacc
tgaagccgcgggtgcaccgtcagtcttcctcttccccccaaaacccaaggacaccctcatgatctcccggaccctgaggtcacat
gcgtggtggtggacgtgagccacgaagaccctgaggtcaagttcaactggtacgtggacggcgtggaggtgcataatgccaagaca
aagccgcgggaggagcagtacaacagcacgtaccgtgtggtcagcgtcctcaccgtcctgcaccaggactggctgaatggcaagga
atacaagtgcgcggtctccaacaaagccctcccagcccccatcgagaaaaccatctccaaagccaaagggcagccccgagaaccac
aggtgtacaccctgcccccatcccgggatgagctgaccaagaaccaggtcagcctgacctgcctggtcaaaggcttctatccaagc
gacatcgccgtggagtgggagagcaatgggcagccggagaacaactacaagaccacgcctcccgtgctggactccgacggctcctt
cttcctctacagcaagctcaccgtggacaagagcaggtggcagcaggggaacgtcttctcatgctccgtgatgcatgaggctctgc
acaaccactacacgcagaagagcctctccctgtctccgggttctggtggaggcggttcaggcggaggtggctccggcggtggcgga
tcgccgggctctcaggtccagctggtggagtctggggggggaggtggtcgccagcctgggcggtcactgaggctgtcctgcaaggcttc
tggctacaccttactagatctacgatgcactgggtaaggcaggcccctggacaaggtctggaatggattggatacattaatccta
gcagtgcttatactaattacaatcagaaattcaaggacaggttcacaatcagcgcagacaaatccaagagcacagccttcctgcag
atggacagcctgaggcccgaggacaccggcgtctatttctgtgcacggccccaagtccactatgattacaacggtttccttactgg
ggccaagggactcccgtcactgtctctagcggtggcggaggttctggaggtggaggcggatccggaggtggtggctctgcacaagacat
ccagatgacccagtctccaagcagcctgtctgcaagcgtgggagacagggtcaccatgacctgcagtgccagctcaagtgtaagtt
acatgaactggtaccagcagaagccgggcaaggcccccaaaagatggatttatgactcatccaaactggcttctggagtccctgct
cgcttcagtggcagtgggtctgggaccgactatacctcacaatcagcagcctgcagcccgaagatttcgccacttattactgcca
gcagtggagtcgtaacccacccacgttcggaggggggaccaagctacaaattacatcctccagc
(SEQ ID NO: 215)

Protein sequence of ROR208:

MEAPAQLLFLLLLWLPDTTGDIQMTQSPSSLSASVGDRVTINCQASQSIDSNLAWFQQKP
GQPPKLLIYRASNLASGVPDRFSGSGSGTDFTLTISSLEAEDVATYYCLGGVGAVSYRTS
FGGGTKVEIKGGGGSGGGGSGGGGSGGGGSEVQLVESGGGLVQPGRSLRLSCTASGSDI
NDYPITWVRQAPGQGLEWIGFINSGGSTWYASWVKGRFTISRDDSKSIAYLQMNSLKTE
DTAVYYCAGYSTYYRDFNIWQGTLVTVSSSEPKSSDKTHTCPPCPAPEAAGAPSVFL
FPPKPKDTLMISRTPEVTCVVVDVSHEDPEVKFNWYVDGVEVHNAKTKPREEQYNSTY
RVVSVLTVLHQDWLNGHEYKCAVSNKALPAPIEKTISKAKGQPREPQVYTLPPSRDELT
KNQVSLTCLVKGFYPSDIAVEWESNGQPENNYKTTPPVLDGSFFLYSKLTVDKSRWQ
QGNVFSCSVMHEALHNHYTQKSLSLSPGSGGGGSGGGGSGGGGSPGSQVQLVESGGGV
VQPGRSLRLSCKASGYTFTRSTMHWVRQAPGQGLEWIGYINPSSAYTNYNQKFKDRFTI
SADKSKSTAFLQMDSLRPEDTGVYFCARPQVHYDYNGFPYWGQGTPVTVSSGGGGSG
GGGSGGGGSAWDIQMTQSPSSLSASVGDRVTMTCSASSSVSYMNWYQQKPGKAPKRWI
YDSSKLASGVPARFSGSGSGTDYTLTISSLQPEDFATYYCQQWSRNPPTFGGGTKLQITS
SS
(SEQ ID NO: 216)

DNA sequence of ROR209:

atggaagcaccagcgcagcttctcttcctcctgctactctggctcccagataccaccggtgacatccagatgacccagtccccctc
ctccctgtccgcctccgtgggcgacgggtgaccatcaactgccaggcctcccagtccatcgactccaacctggcctggttccagc
agaagcccggccagcccccaagctgctgatctaccgggcctccaacctggcctccggcgtgcccgaccggttctccggctccggc
tccggcaccgacttcaccctgaccatctcctccctggaggccgaggacgtggccacctactactgcctgggcggcgtgggcgccgt
gtcctaccgggacctccttcggcggcggcaccaaggtggagatcaagggtggaggcggttcaggcggaggtggatccggcggtggcg
gctccggtggcggcggatctgaggtacagctggtggagtccggcggcggcctggtgcagcccggccggtccctgcggctgtcctgc
accgcctccggctccgacatcaacgactaccccatcacctgggtgcggcaggcccccggccagggcctggagtggatcggcttcat
caactccggcggctccacctggtacgcctcctgggtgaagggccggttcaccatctcccgggacgactccaagtccatcgcctacc
tgcagatgaactccctgaagaccgaggacaccgccgtgtactattgcgcccggggctactccacctactaccggggacttcaacatc
tggggccagggcaccctggtgaccgtgtcctcgagtgagcccaaatcttctgacaaaactcacacatgcccaccgtgcccagcacc
taaagccgcgggtgcaccgtcagtcttcctcttccccccaaaacccaaggacaccctcatgatctcccgaaccctgaggtcacat
gcgtggtggtggacgtgagccacgaagaccctgaggtcaagttcaactggtacgtggacggcgtggaggtgcataatgccaagaca
aagccgcgggaggagcagtacaacagcacgtaccgtgtggtcagcgtcctcaccgtcctgcaccaggactggctgaatggcaagga
atacaagtgcgcggtctccaacaaagccctcccagcccccatcgagaaaaccatctccaaagccaaagggcagccccgagaaccac
aggtgtacaccctgcccccatcccgggatgagctgaccaagaaccaggtcagcctgacctgcctggtcaaaggcttctatccaagc
gacatcgccgtggagtgggagagcaatgggcagccggagaacaactacaagaccacgcctcccgtgctggactccgacggctcctt TABLE 14-continued Binding Domain and Polypeptide Sequences and Components cttcctctacagcaagctcaccgtggacaagagcaggtggcagcaggggaacgtcttctcatgctccgtgatgcatgaggctctgc
acaaccactacacgcagaagagcctctccctgtctccggttctggtggaggcggttcaggcggaggtggctccggcggtggcgga
tcgccgggctctcaggtccagctggtgcaatctggggcctgaggtgaagaagcctgggtcctcggtgaaggtctcctgcaaggcttc
tggatataccttcagcagatctacgatgcactgggtgcgacaggcccctggacaagggcttgagtggataggatacattaatccta
gcagtgcttatactaattacaatcagaaattcaaggacagagtcacgattaccgcggacaaatccacgagcacagcctacatggag
ctgagcagcctgagatctgaggacacggccgtgtattactgtgcgagaccccaagtccactatgattacaacgggttccttactg
gggccaaggaaccctggtcaccgtctcctcaggtggaggcggttcaggcggaggtggatccggcggtggcggatcgggtggcgcg
gatctgacatccagatgacccagtctccttccaccctgtctgcatctgtaggagacagagtcaccatgacttgcagtgccagctca
agtgtaagttacatgaactggtatcagcagaaacagggaaagcccctaagagatggatttatgactcatccaaactggcttctgg
ggtcccatcaaggttcagcggcagtggatctgggacagattatactacaccatcagcagcctgcagcctgatgattttgcaactta
ttactgccaacagtggagtcgtaacccacccactttcggcggagggaccaaggtggagatcaaacggtcctccagc
(SEQ ID NO: 217)

Protein sequence of ROR209:

MEAPAQLLFLLLLWLPDTTGDIQMTQSPSSLSASVGDRVTINCQASQSIDSNLAWFQQKP
GQPPKLLIYRASNLASGVPDRFSGSGSGTDFTLTISSLEAEDVATYYCLGGVGAVSYRTS
FGGGTKVEIKGGGGSGGGGSGGGGSGGGGSEVQLVESGGGLVQPGRSLRLSCTASGSDI
NDYPITWVRQAPGQGLEWIGFINSGGSTWYASWVKGRFTISRDDSKSIAYLQMNSLKTE
DTAVYYCARGYSTYYRDFNIWGQGTLVTVSSSEPKSSDKTHTCPPCPAPEAAGAPSVFL
FPPKPKDTLMISRTPEVTCVVVDVSHEDPEVKFNWYVDGVEVHNAKTKPREEQYNSTY
RVVSVLTVLHQDWLNGKEYKCAVSNKALPAPIEKTISKAKGQPREPQVYTLPPSRDELT
KNQVSLTCLVKGFYPSDIAVEWESNGQPENNYKTTPPVLDSDGSFFLYSKLTVDKSRWQ
QGNVFSCSVMHEALHNHYTQKSLSLSPGSGGGGSGGGGSGGGGSPGSQVQLVQSGPEV
KKPGSSVKVSCKASGYTFSRSTMHWVRQAPGQGLEWIGYINPSSAYTNYNQKFKDRVT
ITADKSTSTAYMELSSLRSEDTAVYYCARPQVHYDYNGFPYWGQGTLVTVSSGGGGSG
GGGSGGGGSGGGGSDIQMTQSPSTLSASVGDRVTMTCSASSSVSYMNWYQQKPGKAP
KRWIYDSSKLASGVPSRFSGSGSGTDYTLTISSLQPDDFATYYCQQWSRNPPTFGGGTKV
EIKRSSS
(SEQ ID NO: 218)

DNA sequence of ROR231:

atggaggcacccgcccagctgctgttcttgttgctgctgtggctccctgataccaccggagacatccagatgacccaatcccttc
tagtctctccgctagcgtcggagaccgcgtgaccatcaattgtcaagcatctcagagtattgacagcaatctcgcctggtttcagc
agaagccagggaaagccacccaagctcctgatttatagggctagcaacctggcttctggtgtccctagtagttcagcggctctggga
gtggcacagacttcaccctgaccattagtagtctgcagcccgaagatgtcgctacctattactgcctcggaggagtgggtgccgtt
tcttatcgcacctcatttggaggtggcaccaaagtggagatcaaaggtggtggcggctccggggtggcgggtcaggggggaggg
gtctggaggcggcggatcagaagttcagctggtggaatctggaggaggtctggtgcagccaggcaggtccctccggctgagctgca
ctgcatccggctctgacattaatgactacccctatcacctggggcgacaggccgcccccggtaaaggcctggagttggatcgggttcatc
aattctggtggatctacttggtacgaagctgggtgaaaggacgcttcacaattagtagagacgactctaagtctatcgcatatct
gcagatgaatagcttgaagacagaggacaccgccgtgtactattgtgcaagaggatactccacttactaccgcgatttcaatatct
ggggccagggaaccctggtgacagtgtcctcgagtgagcccaaatcttctgacaaaactcacacatgcccaccgtgcccagcacct
gaagccgcgggtgcaccgtcagtcttcctcttcccccaaaaccaaggacaccctcatgatctcccggacccctgaggtcacatg
cgtggtggtggacgtgagccacgaagaccctgaggtcaagttcaactggtacgtggacggcgtggaggtgcataatgccaagacaa
agccgcgggaggagcagtacaacagcacgtaccgtgtggtcagcgtcctcaccgtcctgcaccaggactggctgaatgcaaggaa
tacaagtgcgcggtctccaacaaagccctcccagcccccatcgagaaaaccatctccaaagccaaagggcagccccgagaaccaca
ggtgtacaccctgcccccatcccgggatgagctgaccaagaaccaggtcagcctgacctgcctggtcaaaggcttctatccaagcg
acatcgccgtggagtgggagagcaatgggcagccggagaacaactacaagaccacgcctcccgtgtctggactccgacggctcctt
cttcctctacagcaagctcaccgtggacaagagcaggtggcagcaggggaacgtcttctcatgctccgtgatgcatgaggctctgc
acaaccactacacgcagaagagcctctccctgtctccggttctccggaggcggcggctccggcggcggcagcggcggcggcggc
agccccggatcccaggtgcagctggtgcagtctggtcctgaggtgaaaaagcctggctccagcgtgaaggtgtcctgcaaggccag
cggatacacctttagccggtccaccatgcattgggtgaggcaggctcctggacagggcctggagtggatcggctacatcaaccca
gcagcgcttataccaactacaatcagaagtttaaggaccgggtgaccatcaccgccgataagtccaccagcaccgcctacatggag
ctgtccagcctgaggagcgaggataccgccgtgtactattgcgcccggccccaggtccattacgactacaacggcttccccctattg
gggccagggaaccctggtgaccgtgtccagcgagggcggcggcagcggcggcggcagcggcggaggagccagcggcgaggag
gctccgacattcagatgacccagtcccctccacccctgtccgctagcgtgggcgatcggtgaccatgacctgcagcgccagcagc
tccgtgtcctacatgaactggtaccagcagaagcccggcaaggctcccaagaggtggatttacgactccagcaagctggcctctgg
tgtcccagcaggttctctggtagcggcagcggcacagactacaccctgaccatctcctccctgcagcccgacgatttcgccacct
actattgccagcagtggtcccggaatcccctacctttggcggcggcaccaaggtggagatcaagaggagctccagc
(SEQ ID NO: 219)

Protein sequence of ROR231:

MEAPAQLLFLLLLWLPDTTGDIQMTQSPSSLSASVGDRVTINCQASQSIDSNLAWFQQKP
GKPPKLLIYRASNLASGVPSRFSGSGSGTDFTLTISSLQPEDVATYYCLGGVGAVSYRTSF
GGGTKVEIKGGGGSGGGGSGGGGSGGGGSEVQLVESGGGLVQPGRSLRLSCTASGSDI
NDYPITWVRQAPGKGLEWIGFINSGGSTWYASWVKGRFTISRDDSKSIAYLQMNSLKTE
DTAVYYCARGYSTYYRDFNIWGQGTLVTVSSSEPKSSDKTHTCPPCPAPEAAGAPSVFL
FPPKPKDTLMISRTPEVTCVVVDVSHEDPEVKFNWYVDGVEVHNAKTKPREEQYNSTY
RVVSVLTVLHQDWLNGKEYKCAVSNKALPAPIEKTISKAKGQPREPQVYTLPPSRDELT
KNQVSLTCLVKGFYPSDIAVEWESNGQPENNYKTTPPVLDSDGSFFLYSKLTVDKSRWQ
QGNVFSCSVMHEALHNHYTQKSLSLSPGSGGGGSGGGGSGGGGSPGSQVQLVQSGPEV
KKPGSSVKVSCKASGYTFSRSTMHWVRQAPGQGLEWIGYINPSSAYTNYNQKFKDRVT
ITADKSTSTAYMELSSLRSEDTAVYYCARPQVHYDYNGFPYWGQGTLVTVSSGGGGSG
GGGSGGGGSGGGGSDIQMTQSPSTLSASVGDRVTMTCSASSSVSYMNWYQQKPGKAP

TABLE 14-continued

Binding Domain and Polypeptide Sequences and Components

KRWIYDSSKLASGVPSRFSGSGSGTDYTLTISSLQPDDFATYYCQQWSRNPPTFGGGTKV
EIKRSSS
(SEQ ID NO: 220)

DNA sequence of ROR233:

atggaggctcccgctcagctgctgttcctcctgctgctctggctgcccgacaccacaggcgacatccagatgacccagtccccttc
ctccctgtccgctagcgtgggcgatagggtgaccatcaactgccaggcctcccagtccattgactccaatctggcctggttccagc
agaagcccggacagccccccaagctgctgatttacagggcctccaacctggcttccggcgtgcctgacaggttctccggatccggc
agcggcaccgacttcacctgaccatctcctccctggaggccgaggatgtcgccacctactactgtctgggcggcgtgggcgctgt
gagctatcggacctccttcggcggcggcaccaaggtggagatcaagggcggcggcggcggcggcggcagcggcggcggag
gctccggcggcggcggcagcgaggtgcagctggtggaaagcggaggaggcctggtgcagcctggaaggtccctgaggctgtcctgc
acagccagcggctccgacatcaacgactaccccatcacctgggtgaggcaggctcctggccagggcctggaatggatcggctttat
caacagcggcggcagcacctggtatgcttcctgggtgaagggccggttcaccattagcagggacgactccaagtccattgcctacc
tgcagatgaactccctgaagaccgaggacaccgccgtgtactactgcgccaggggctacagcacctattaccgggactttaacatc
tggggccagggcacactggtcaccgtgtcctcgagtgagcccaaatcttctgacaaaactcacacatgcccaccgtgcccagcacc
tgaagccgcgggtgcaccgtcagtcttcctcttccccaaaacccaaggacaccctcatgatctcccggacccctgaggtcacat
gcgtggtggtggacgtgagccacgaagaccctgaggtcaagttcaactggtacgtggacggcgtggaggtgcataatgccaagaca
aagccgcgggaggagcagtacaacagcacgtaccgtgtggtcagcgtcctcaccgtcctgcaccaggactggctgaatggcaagga
atacaagtgcgcggtctccaacaaagcccccagccccatcgagaaaaccatctccaaagccaaagggcagccccgagaaccac
aaggtgtacaccctgccccatcccgggatgagctgaccaagaaccaggtcagcctgacctgcctggtcaaaggcttctatcccag
cgacatcgccgtggagtgggagagcaatgggcagccggagaacaactacaagaccacgcctcccgtgctggactccgacggctcct
tcttcctctacagcaagctcaccgtggacaagagcaggtggcagcaggggaacgtcttctcatgctccgtgatgcatgaggctctg
cacaaccactacacgcagaagagcctctccctgtctccgggtccggaggcggcggctccggcggcggcggcagcggcggcggcgg
cagccccggatcccaggtcagctggtgcagtctggtcctgaggtgaaaaagcctggctccagcgtgaaggtgtcctgcaaggcca
gcggatacacctttagccggtccaccatgcattgggaggcaggctcctggacagggcctggagtggatcggctacatcaaccc
cagcagcgcttataccaactacaatcagaagtttaaggaccgggtgaccatcaccgccgataagtccaccagcaccgcctacatgga
gctgtccagcctgaggagcgaggataccgccgtgtactattgcgcccgccaggtccattacgactacaaccggctttccctatt
ggggccagggaaccctggtgaccgtgtccagcggaggcggcggcagcggcggcagcggcagcggcggaggaggcagcggcggagga
ggctccgacattcagatgacccagtccccccacctgtccgctagcgtgggcgatcgggtgaccatgacctgcagcgccagcagc
tccgtgtcctacatgaactggtaccagcagaagcccggcaaggctcccaagaggtggatttacgactccagcaagctggcctctgg
tgtccccagcaggttctctggtagcggcagcggcacagactacaccctgaccatctcctccctgcagcccgacgatttcgccacct
actattgccagcagtggtcccggaatccccctacctttggcggcggcaccaaggtggagatcaagaggagctccagc
(SEQ ID NO: 221)

Protein sequence of ROR233:

MEAPAQLLFLLLLWLPDTTGDIQMTQSPSSLSASVGDRVTINCQASQSIDSNLAWFQQKP
GQPPKLLIYRASNLASGVPDRFSGSGSGTDFTLTISSLEAEDVATYYCLGGVGAVSYRTS
FGGGTKVEIKGGGSGGGGSGGGGSGGGSEVQLVESGGGLVQPGRSLRLSCTASGSDI
NDYPITWVRQAPGQGLEWIGFINSGGSTWYASWVKGRFTISRDDSKSIAYLQMNSLKTE
DTAVYYCARGYSTYYRDFNIWGQGTLVTVSSSEPKSSDKTHTCPPCPAPEAAGAPSVFL
FPPKPKDTLMISRTPEVTCVVVDVSHEDPEVKFNWYVDGVEVHNAKTKPREEQYNSTY
RVVSVLTVLHQDWLNGKEKCAVSNKALPAPIEKTISKAKGQPREPQVYTLPPSRDELT
KNQVSLTCLVKGFYPSDIAVEWESNGQPENNYKTTPPVLDSGSFFLYSKLTVDKSRWQ
QGNVFSCSVMHEALHNHYTQKSLSLSPGSGGGGSGGGGSGGGGSPGSQVQLVQSGPEV
KKPGSSVKVSCKASGYTFSRSTMHWVRQAPGQGLEWIGYINPSSAYTNYNQKFKDRVT
ITADKSTSTAYMELSSLRSEDTAVYYCARPQVHYDYNGFPYWGQGTLVTVSSGGGGSG
GGGSGGGGSGGGGSDIQMTQSPSTLSASVGDRVTMTCSASSSVSYMNWYPPKPGKAP
KRWIYDSSKLASGVPSRFSGSGSGTDYTLTISSLQPDDFATYYCQQWSRNPPTFGGGTKV
EIKRSSS
(SEQ ID NO: 222)

TABLE 15

Summary of SEQ ID NOs

| Designation | Description | DNA SEQ ID NO | Protein SEQ ID NO |
|---|---|---|---|
| TSC311 or TSC312 | Fc DRA222 | 1 | 2 |
| TSC313 | Fc H7L1 | 3 | 4 |
| TSC314 | Fc H7L4 | 5 | 6 |
| TSC315 | Fc H7L5 | 7 | 8 |
| TSC316 | Fc H8L1 | 9 | 10 |
| TSC317 | Fc H8L4 | 11 | 12 |
| TSC318 | Fc H8L5 | 13 | 14 |
| TSC319 | Fc H9L1 | 15 | 16 |
| TSC320 | Fc H9L4 | 17 | 18 |
| TSC321 | Fc H9L5 | 19 | 20 |
| TSC322 | Fc H10L1 | 21 | 22 |
| TSC323 | Fc H10L4 | 23 | 24 |
| TSC324 | Fc H10L5 | 25 | 26 |

TABLE 15-continued

Summary of SEQ ID NOs

| Designation | Description | DNA SEQ ID NO | Protein SEQ ID NO |
|---|---|---|---|
| TSC334 | Fc H7L6 | 27 | 28 |
| TSC335 | Fc H7L7 | 29 | 30 |
| TSC336 | Fc H7L8 | 31 | 32 |
| TSC337 | Fc H8L6 | 33 | 34 |
| TSC338 | Fc H8L7 | 35 | 36 |
| TSC339 | Fc H8L8 | 37 | 38 |
| TSC340 | Fc H10L6 | 39 | 40 |
| TSC341 | Fc H10L7 | 41 | 42 |
| TSC342 | Fc H10L8 | 43 | 44 |
| TSC370 | TSC342 G27Y | 45 | 46 |
| TSC371 | TSC342 M53I | 47 | 48 |
| TSC372 | TSC342 I21M | 49 | 50 |
| TSC390 | TSC370 A9P | 51 | 52 |
| TSC391 | TSC370 A9P M53I | 53 | 54 |

TABLE 15-continued

Summary of SEQ ID NOs

| Designation | Description | DNA SEQ ID NO | Protein SEQ ID NO |
|---|---|---|---|
| TSC392 | TSC370 A9P I21M | 55 | 56 |
| TSC393 | TSC370 M53I I21M | 57 | 58 |
| TSC394 | TSC370 A9P M53I I21M | 59 | 60 |
| TSC408 | Anti-PSMA × TSC391 | 61 | 62 |
| TSC409 | Anti-PSMA × TSC392 | 63 | 64 |
| TSC410 | Anti-PSMA × TSC393 | 65 | 66 |
| TSC411 | Anti-PSMA × TSC394 | 67 | 68 |
| TSC471 | Anti-PSMA × TSC456 | 205 | 206 |
| TSC266 | Anti-PSMA × DRA222 (huVL-VH 107- 1A4 scFv-Fc-DRA222 scFv) | 209 | 210 |
| CAS105 | Anti-CD37 × DRA222 | 69 | 70 |
| Anti-CD37 × TSC445 | Anti-CD37 × TSC394 | 71 | 72 |
| Anti-CD37 × TSC452 | Anti-CD37 × (TSC394 VL + DRA222 VH) | 73 | 74 |
| Anti-CD37 × TSC453 | Anti-CD37 × (TSC394 VH + DRA222 VL) | 75 | 76 |
| Anti-CD37 × TSC454 | Anti-CD37 × TSC394 E86D | 77 | 78 |
| Anti-CD37 × TSC455 | Anti-CD37 × TSC394 F87Y | 79 | 80 |
| Anti-CD37 × TSC456 | Anti-CD37 × TSC394 ES6D F87Y | 81 | 82 |
| TSC455 | TSC394 F87Y scFv (anti-CD3 scFv) | | 83 |
| TSC456 | TSC394 E86D F87Y scFv (anti-CD3 scFv) | | 84 |
| DRA222 | Anti-CD3 scFv | | 85 |
| TSC455 and TSC456 VH | TSC455 and TSC456 variable heavy domain | | 86 |
| DRA222 VH | DRA222 variable heavy domain | | 87 |
| TSC455 VL | TSC455 variable light domain | | 88 |
| TSC456 VL | TSC456 variable light domain | | 89 |
| DRA222 VL | DRA222 variable light domain | | 90 |
| Cris7 and DRA222 VH CDR1 (Kabat) | Anti-CD3 VH CDR1 | | 91 |
| Cris7 and DRA222 VH CDR2 (Kabat) | Anti-CD3 VH CDR2 | | 92 |
| Cris7 and DRA222 VH CDR3 (Kabat) | Anti-CD3 VH CDR3 | | 93 |
| Cris7 and DRA222 VL CDR1 (Kabat) | Anti-CD3 VL CDR1 | | 94 |
| Cris7 and DRA222 VL CDR2 (Kabat) | Anti-CD3 VL CDR2 | | 95 |
| Cris7 and DRA222 VL CDR3 (Kabat) | Anti-CD3 VL CDR3 | | 96 |
| Cris7 and DRA222 VH CDR1 (IMGT) | Anti-CD3 VH CDR1 | | 199 |
| Cris7 and DRA222 VH CDR2 (IMGT) | Anti-CD3 VH CDR2 | | 200 |
| Cris7 and DRA222 VH CDR3 (IMGT) | Anti-CD3 VH CDR3 | | 201 |
| Cris7 and DRA222 VL CDR1 (IMGT) | Anti-CD3 VL CDR1 | | 202 |
| Cris7 and DRA222 VL CDR2 (IMGT) | Anti-CD3 VL CDR2 | | 203 |
| Cris7 and DRA222 VL CDR3 (IMGT) | Anti-CD3 VL CDR3 | | 204 |
| ROR133 | Anti-ROR1 (R11 L7H15) × DRA222 | 97 | 98 |
| ROR193 | Anti-ROR1 (R11 L7H15) × TSC394 F87Y | 99 | 100 |
| ROR134 | Anti-ROR1 (R11 L7H10) × DRA222 | 101 | 102 |
| ROR189 | Anti-ROR1 (R11 L7H10) × TSC394 E86D F87Y | 103 | 104 |
| ROR154 | Anti-ROR1 (R11 L7H16) × DRA222 | 105 | 106 |
| ROR185 | Anti-ROR1 (R11 L7H15) × TSC394 E86D F87Y | 107 | 108 |
| ROR179 | Anti-ROR1 (R11 L8H16) × DRA222 | 109 | 110 |
| ROR186 | Anti-ROR1 (R11 L8H16) × TSC394 E86D F87Y | 111 | 112 |
| ROR181 | Anti-ROR1 (R11 L7H17) × DRA222 | 113 | 114 |
| ROR191 | Anti-ROR1 (R11 L7H17) × TSC394 E86D F87Y | 115 | 116 |
| ROR182 | Anti-ROR1 (R11 L9H18) × DRA222 | 117 | 118 |
| ROR192 | Anti-ROR1 (R11 L9H18) × TSC394 E86D F87Y | 119 | 120 |
| ROR243 | Humanized, codon optimized anti-ROR1 × anti-CD3 (parent anti-ROR1 molecule is ROR192) scFv-Fc-scFv | 207 | 208 |
| ROR206 | ROR133 S40T G113R × DRA222 Fc ADCC- K322A-H111 in pEE12.4 | 211 | 212 |
| ROR207 | ROR133 S40T G113R × TSC456 Fc ADCC- K322A-H111 in pEE12.4 | 213 | 214 |
| ROR208 | ROR174 S40T G113R × DRA222 Fc ADCC- K322A-H111 in pEE12.4 | 215 | 216 |
| ROR209 | ROR174 S40T G113R × TSC456 Fc ADCC- K322A-H111 in pEE12.4 | 217 | 218 |
| ROR231 | Anti-ROR1 × anti-CD3 | 219 | 220 |
| ROR233 | Anti-ROR1 × anti-CD3 | 221 | 222 |
| | Chimeric bispecific anti-CD123 (VLVH) × anti-CD3 (TSC456) scFv-Fc-scFv | | 197 |
| | Chimeric bispecific anti-CD123 (VHVL) × anti-CD3 (TSC456) scFv-Fc-scFv | | 198 |

The invention claimed is:

1. A CD3-binding protein comprising a CD3-binding domain that binds specifically to human CD3 and that comprises a humanized immunoglobulin light chain variable region and a humanized immunoglobulin heavy chain variable region wherein the immunoglobulin light chain variable region comprises
an LCDR1 amino acid sequence of SEQ ID NO:94, an LCDR2 amino acid sequence of SEQ ID NO:95, and an LCDR3 amino acid sequence of SEQ ID NO:96 and wherein the immunoglobulin heavy chain variable region comprises an HCDR1 amino acid sequence of SEQ ID NO:91, an HCDR2 amino acid sequence of SEQ ID NO:92, and an HCDR3 amino acid sequence of SEQ ID NO:93;
wherein the amino acid residue at position 9 according to the IMGT numbering system of the immunoglobulin heavy chain variable region is proline; and
wherein the amino acid residue at position 21 according to the IMGT numbering system of the immunoglobulin light chain variable region is methionine; and
wherein the amino acid residue at position 87 according to the IMGT numbering system of the immunoglobulin light chain variable region is tyrosine.

2. The CD3-binding protein of claim 1, wherein the immunoglobulin light chain variable region comprises framework regions based on the human IGKV3D-20*1 germline amino acid sequence.

3. The CD3-binding protein of claim 1, wherein the immunoglobulin heavy chain variable region comprises framework regions based on the human IGHV1-69*02 germline amino acid sequence.

4. The CD3-binding protein of claim 1, wherein the amino acid residue at position 52 according to the IMGT numbering system of the immunoglobulin light chain variable region is arginine and/or the amino acid residue at position 53 according to the IMGT numbering system of the immunoglobulin light chain variable region is tryptophan.

5. The CD3-binding protein of claim 1, wherein the amino acid residue at position 27 according to the IMGT numbering system of the immunoglobulin heavy chain variable region is tyrosine.

6. The CD3-binding protein of claim 1, wherein the amino acid residue at position 53 according to the IMGT numbering system of the immunoglobulin heavy chain variable region is isoleucine.

7. The CD3-binding protein of claim 1, wherein the amino acid residue at position 86 according to the IMGT numbering system of the immunoglobulin light chain variable region is aspartic acid.

8. The CD3-binding protein of claim 1, wherein the CD3-binding domain comprises SEQ ID NO:83 or SEQ ID NO:84.

9. The CD3-binding protein of claim 1, wherein the CD3-binding domain is a single chain variable fragment (scFv).

10. The CD3-binding protein of claim 9, wherein said scFv comprises a linker between the heavy chain variable region and the light chain variable region of said scFv and wherein said linker comprises the amino acid sequence QRHNNSSLNTGTQMAGHSPNS (SEQ ID NO:148).

11. The CD3-binding protein of claim 9, wherein the heavy chain variable region of said scFv is amino-terminal to the light chain variable region of said scFv.

12. The CD3-binding protein of claim 1, wherein the CD3-binding protein binds specifically to cynomolgus CD3.

13. The CD3-binding protein of claim 1, wherein the CD3-binding protein comprises an immunoglobulin constant region.

14. The CD3-binding protein of claim 1, further comprising a second binding domain.

15. The CD3-binding protein of claim 14, wherein said CD3-binding protein is a single chain molecule comprising, in order from amino-terminus to carboxyl-terminus, (i) the second binding domain, (ii) a hinge region, (iii) an immunoglobulin constant region, (iv) a carboxyl-terminus linker, and (v) the CD3-binding domain.

16. The CD3-binding protein of claim 14, wherein the second binding domain comprises (a) an immunoglobulin light chain variable region comprising LCDR1, LCDR2, and LCDR3, and (b) an immunoglobulin heavy chain variable region comprising HCDR1, HCDR2, and HCDR3.

17. The CD3-binding protein of claim 15, wherein the hinge region is derived from an immunoglobulin hinge region.

18. The CD3-binding protein of claim 15, wherein the carboxyl-terminus linker comprises or consists of SEQ ID NO:196.

19. The CD3-binding protein of claim 13, wherein the immunoglobulin constant region comprises immunoglobulin CH2 and CH3 domains of IgG1, IgG2, IgG3, IgG4, IgA1, IgA2 or IgD.

20. The CD3-binding protein of claim 19, wherein the immunoglobulin constant region comprises a human IgG1 CH2 domain comprising the substitutions L234A, L235A, G237A, and K322A, according to the EU numbering system.

21. The CD3-binding protein of claim 14, wherein the CD3-binding protein induces redirected T-cell cytotoxicity (RTCC).

22. The CD3-binding protein of claim 14, wherein the second binding domain is a single chain variable fragment (scFv).

23. The CD3-binding protein of claim 14, wherein the second binding domain binds a tumor associated antigen.

24. The CD3-binding protein of claim 23, wherein said CD3-binding protein induces T-cell-dependent lysis of cells expressing the tumor associated antigen.

25. The CD3-binding protein of claim 23, wherein the tumor associated antigen is selected from the group consisting of PSMA, CD19, CD20, CD37, CD38, CD123, Her2, ROR1, RON, glycoprotein A33 antigen (gpA33), and CEA.

26. The CD3-binding protein of claim 1, wherein said CD3-binding protein further comprises an immunoglobulin heterodimerization domain.

27. The CD3-binding protein of claim 26, wherein the immunoglobulin heterodimerization domain comprises an immunoglobulin CH1 domain or an immunoglobulin CL domain.

28. The CD3-binding protein of claim 1, wherein said CD3-binding protein is a bispecific single chain antibody molecule comprising a CD3-binding domain and a second binding domain, wherein the binding domains are arranged in the order VH CD3-VL CD3-VH second binding domain-VL second binding domain, VL CD3-VH CD3-VH second binding domain-VL second binding domain, VH second binding domain-VL second binding domain-VH CD3-VL CD3 or VH second binding domain-VL second binding domain-VL CD3-VH CD3.

29. A pharmaceutical composition comprising the CD3-binding protein of claim 3 and a pharmaceutically acceptable carrier, diluent, or excipient.

30. A method for inducing redirected T-cell cytotoxicity (RTCC) against a cell expressing a tumor associated antigen, the method comprising: contacting said tumor associated antigen-expressing cell with the CD3-binding protein of claim 23, wherein said contacting is under conditions whereby RTCC against the tumor associated antigen-expressing cell is induced.

31. A method for inhibiting tumor growth in a subject in need thereof, comprising administering a therapeutically effective amount of the CD3-binding protein of claim 23 to the subject.

32. A method for treating cancer in a subject in need thereof, comprising administering a therapeutically effective amount of the CD3-binding protein of claim 23 to the subject.

33. The method of claim 32, wherein the cancer is prostate cancer, colorectal cancer, renal cell carcinoma, bladder cancer, salivary gland cancer, pancreatic cancer, ovarian cancer, non-small cell lung cancer, breast cancer, melanoma, adrenal cancer, mantle cell lymphoma, acute lymphoblastic leukemia, chronic lymphocytic leukemia, Non-Hodgkin's lymphoma, acute myeloid leukemia (AML), B-lymphoid leukemia, blastic plasmocytoid dendritic neoplasm (BPDCN), or hairy cell leukemia.

34. A CD3-binding protein that is a dimer of two identical proteins, wherein each protein is the CD3-binding protein of claim 15.

35. The CD3-binding protein of claim 1, wherein
   (a) the immunoglobulin light chain variable region comprises SEQ ID NO:88 and the immunoglobulin heavy chain variable region comprises SEQ ID NO:86; or
   (b) the immunoglobulin light chain variable region comprises SEQ ID NO:89 and the immunoglobulin heavy chain variable region comprises SEQ ID NO:86.

36. The CD3-binding protein of claim 1, wherein
   (a) the immunoglobulin light chain variable region comprises an amino acid sequence that is at least 96% identical to SEQ ID NO:88 and the immunoglobulin heavy chain variable region comprises an amino acid sequence that is at least 96% identical to SEQ ID NO:86; or
   (b) the immunoglobulin light chain variable region comprises an amino acid sequence that is at least 96% identical to SEQ ID NO:89 and the immunoglobulin heavy chain variable region comprises an amino acid sequence that is at least 96% identical to SEQ ID NO:86.

37. The method of claim 33, wherein the breast cancer is triple negative breast cancer.

* * * * *

UNITED STATES PATENT AND TRADEMARK OFFICE
CERTIFICATE OF CORRECTION

PATENT NO. : 11,352,426 B2
APPLICATION NO. : 15/761499
DATED : June 7, 2022
INVENTOR(S) : Philip Tan et al.

Page 1 of 1

It is certified that error appears in the above-identified patent and that said Letters Patent is hereby corrected as shown below:

In the Claims

At Column 521, Claim number 29, Line number 45:
"29. A pharmaceutical composition comprising the CD3-binding protein of claim 3 and a pharmaceutically acceptable carrier, diluent, or excipient."

Should read:
--29. A pharmaceutical composition comprising the CD3-binding protein of claim 1 and a pharmaceutically acceptable carrier, diluent, or excipient.--

Signed and Sealed this
Twenty-seventh Day of September, 2022

Katherine Kelly Vidal
*Director of the United States Patent and Trademark Office*